United States Patent
Sumi et al.

(10) Patent No.: US 11,125,866 B2
(45) Date of Patent: Sep. 21, 2021

(54) MEASUREMENT AND IMAGING INSTRUMENTS AND BEAMFORMING METHOD

(71) Applicant: Chikayoshi Sumi, Saitama (JP)

(72) Inventors: Chikayoshi Sumi, Saitama (JP); Naoto Yamazaki, Kanagawa-ken (JP)

(73) Assignee: Chikayoshi Sumi, Saitama (JP)

( * ) Notice: Subject to any disclaimer, the term of this patent is extended or adjusted under 35 U.S.C. 154(b) by 231 days.

(21) Appl. No.: 15/951,459

(22) Filed: Apr. 12, 2018

(65) Prior Publication Data

US 2019/0129026 A1 May 2, 2019

Related U.S. Application Data

(63) Continuation-in-part of application No. 14/730,583, filed on Jun. 4, 2015, now Pat. No. 10,624,612.

(30) Foreign Application Priority Data

May 22, 2017 (JP) .............................. JP2017-100947
Jun. 22, 2017 (JP) .............................. JP2017-122554
(Continued)

(51) Int. Cl.
*G01S 7/52* (2006.01)
*A61B 6/00* (2006.01)
(Continued)

(52) U.S. Cl.
CPC ............ *G01S 7/52039* (2013.01); *A61B 6/00* (2013.01); *A61B 8/00* (2013.01); *G01S 7/52019* (2013.01);
(Continued)

(58) Field of Classification Search
CPC .......................... G01N 29/0654; G01S 7/52039
See application file for complete search history.

(56) References Cited

U.S. PATENT DOCUMENTS

| | | |
|---|---|---|
| 5,720,708 A | 2/1998 | Lu et al. |
| 6,215,730 B1 | 4/2001 | Pinto |

(Continued)

FOREIGN PATENT DOCUMENTS

| | | |
|---|---|---|
| JP | 5-63509 | 8/1993 |
| JP | 2005-278892 | 10/2005 |

(Continued)

OTHER PUBLICATIONS

Japanese Office Action dated Oct. 30, 2018 in Japanese Patent Application No. 2014-116949 with partial English translation.

(Continued)

*Primary Examiner* — John E Breene
*Assistant Examiner* — Jeffrey C Morgan
(74) *Attorney, Agent, or Firm* — Wenderoth, Lind & Ponack, L.L.P.

(57) ABSTRACT

A measurement and imaging instrument capable of beamforming with high speed and high accuracy without approximate calculation. The instrument includes a reception unit which receives a wave arriving from a measurement object to generate a reception signal; and an instrument main body which performs a lateral modulation while superposing two waves in a two-dimensional case and three or four waves in a three-dimensional case in beamforming processing of the reception signal in which at least one wave arriving from the measurement object is processed as being transmitted or received in the axial direction or directions symmetric with respect to the axial direction to generate a multi-dimensional reception signal, performs Hilbert transform with respect to the multi-dimensional reception signal, and performs partial (Continued)

derivative processing or one-dimensional Fourier transform to generate analytic signals of the multi-dimensional reception signals of the two waves or the three or four waves.

30 Claims, 55 Drawing Sheets

(30) Foreign Application Priority Data

| | | | |
|---|---|---|---|
| Jul. 13, 2017 | (JP) | | JP2017-137185 |
| Jul. 26, 2017 | (JP) | | JP2017-144588 |
| Aug. 16, 2017 | (JP) | | JP2017-157256 |
| Aug. 17, 2017 | (JP) | | JP2017-157590 |
| Oct. 26, 2017 | (JP) | | JP2017-207592 |
| Nov. 24, 2017 | (JP) | | JP2017-225982 |
| Dec. 18, 2017 | (JP) | | JP2017-0242013 |
| Dec. 21, 2017 | (JP) | | JP2017-245377 |

(51) Int. Cl.
  *G01S 15/89* (2006.01)
  *A61B 8/00* (2006.01)
  *G01S 17/90* (2020.01)

(52) U.S. Cl.
  CPC ...... *G01S 7/52023* (2013.01); *G01S 7/52025* (2013.01); *G01S 7/52033* (2013.01); *G01S 7/52038* (2013.01); *G01S 7/52041* (2013.01); *G01S 7/52046* (2013.01); *G01S 7/52047* (2013.01); *G01S 15/89* (2013.01); *G01S 15/8915* (2013.01); *G01S 15/8997* (2013.01); *G01S 17/90* (2020.01); *A61B 8/4488* (2013.01)

(56) References Cited

U.S. PATENT DOCUMENTS

| | | |
|---|---|---|
| 6,685,641 B2 | 2/2004 | Liu |
| 7,690,838 B2 | 4/2010 | Sumi |
| 7,775,980 B2 | 8/2010 | Sumi |
| 7,868,824 B2 | 1/2011 | Sumi |
| 7,957,609 B2 | 6/2011 | Lu et al. |
| 8,211,019 B2 | 7/2012 | Sumi |
| 9,084,559 B2 | 7/2015 | Sumi |
| 9,326,748 B2 | 5/2016 | Sumi |
| 2005/0273265 A1 | 12/2005 | Ren |
| 2007/0150232 A1 | 6/2007 | Szeto |
| 2009/0036772 A1 | 2/2009 | Lu |
| 2011/0172538 A1 | 7/2011 | Sumi |
| 2013/0046175 A1 | 12/2013 | Sumi |

FOREIGN PATENT DOCUMENTS

| | | |
|---|---|---|
| JP | 2007152074 | 6/2007 |
| JP | 2011-521204 | 7/2011 |
| JP | 5441292 | 12/2013 |
| WO | 03/079047 | 9/2003 |
| WO | 2008-010375 | 1/2008 |

OTHER PUBLICATIONS

Partial Translation of Office Action dated Nov. 12, 2019 in corresponding Japanese Patent Application No. 2016-013287.
Partial Translation of Office Action to Counterpart Japanese Patent Application No. 2014-116949 dated Aug. 7, 2018.
J. W. Goodman, "Introduction to Fourier Optics" 2nd ed., McGraw-Hill Co, Inc., 1996.
L. J. Busse, "Three-Dimensional Imaging Using a Frequency-Domain Synthetic Aperture Focusing Technique", IEEE Trans. UFFC, vol. 39, No. 2, pp. 174-179, 1992.
J. Cheng, J.-y. Lu, "Extended High-Frame Rate Imaging Method with Limited-Diffraction Beams", IEEE Trans. UFFC, vol. 53, No. 5, pp. 880-899, 2006.
H. Peng, J.-y. Lu, X. Han, "High frame rate ultrasonic imaging system based on the angular spectrum principle", Ultrasonics 44, e97-e99, 2006.
P. Kruizinga et al., "Plane-Wave Ultrasound Beamforming Using a Nonuniform Fast Fourier Transform", IEEE Trans. UFFC, vol. 59, No. 12, pp. 2684-2691, 2012.
M. A. Haun, D. L. Jones, W. D. O'Brien, Jr., "Efficient Three-Dimensional Imaging from a Small Cylindrical Aperture", IEEE Trans. UFFC, vol. 49, pp. 861-870, 2002.
C. Sumi et al., "Effective Lateral Modulations With Applications to Shear Modulus Reconstruction Using Displacement Vector Measurement", IEEE Trans. on Ultrasonics, Ferroelectrics, and Frequency Control, vol. 55, No. 12, pp. 2607-2625, Dec. 2008.
C. Sumi, S. Uga, "Effective ultrasonic virtual sources which can be positioned independently of physical aperture focus positions", Rep. Med. Imag., vol. 3, pp. 45-59, 2010.
M. Soumekh, "Fourier Array Imaging", PTR Prentice Hall, Englewood Cliffs, New Jersey 07632, 1994.
S. Haykin, A. Steinhardt ed. "Adaptive R A D E R Detection and Estimation", John Wiley & Sons, inc. New York, 1992.
K. W. Hollman, K. W. Rigby, M. O'Donnell, "Coherence Factor of Speckle from a Multi-Row Probe", Proc. of IEEE Ultrasonics Symp, pp. 1257-1260, 1999.
D. Garcia, L. L. Tarnec, S. Muth, E. Montagnon, J. Poree, G. Cloutier, "Stolt's f-k Migration for Plane Wave Ultrasound Imaging", IEEE Trans. UFFC , vol. 60, No. 9, pp. 1853-1867, 2013.
C. Sumi, "Displacement Vector Measurement Using Instantaneous Ultrasound Signal Phase—Multidimensional Autocorrelation and Doppler Methods", IEEE Trans. on Ultrasonics, Ferroelectrics, and Frequency Control, vol. 55, No. 1, pp. 24-43, Jan. 2008.
C. Sumi, Y. Ishii, "Ultrasonic lateral modulation imaging, speckle reduction, and displacement vector measurements using simple single-beam scanning or plural crossed-beam scanning with new spectra frequency division processing methods", Rep. Med. Imag., vol. 5, pp. 57-101, 2012.
C. Sumi, "Fine Elasticity Imaging Utilizing the Iterative RF-echo Phase Matching Method", IEEE Trans. on Ultrasonics, Ferroelectrics, and Frequency Control, vol. 46, No. 1, pp. 158-166, Jan. 1999.
S. Srinivasan, F. Kallel, J. Ophir, "Estimating the Elastographic Signal-To-Noise Ratio Using Correlation Coefficients", Ultrasound Med. Biol., vol. 28, pp. 359-368, 2002.
C. Sumi, "Regularization of Tissue Shear Modulus Reconstruction Using Strain Variance", IEEE Trans. UFFC, vol. 55, pp. 297-307, 2008.
C. Sumi, K. Sato, "Regularization for Ultrasonic Measurements of Tissue Displacement Vector and Strain Tensor", IEEE Trans. UFFC, vol. 55, pp. 787-799, 2008.
C. Sumi, Y. Takanashi, K. Ichimaru, "Consideration of generated beam angles increases the accuracy of ultrasonic displacement measurements", Rep. Med. Imag., vol. 5, pp. 23-50, 2012.
C. Kasai, K. Namekawa, A. Koyano, R. Omoto, "Real-Time Two-Dimensional Blood Flow Imaging Using an Autocorrelation Technique", IEEE Trans. On Sonics and Ultrasonics, vol. 32, pp. 458-464, 1985.
J. A. Jensen, "Field: A Program for Simulating Ultrasound Systems," Med, Biol, Eng, Comp, 10th Nordic-Baltic Conference on Biomedical Imaging, vol. 34, Supplement 1, Part 1, pp. 351-353, 1996.
B. Schrope, V. L. Newhouse, V. Uhlendorf, "Simulated Capillary Blood Flow Measurement Using a Nonlinear Ultrasonic Contrast Agent", Ultrason. Imag., vol. 14, pp. 134-158, 1992.
P. N. Burns, S. R. Wilson, D. H. Simpson, "Pulse Inversion Imaging of Liver Blood Flow: Improved Method for Characterizing Focal Masses with Microbubble Contrast", Investigative Radiology, vol. 35, No. 1, pp. 58-71, 2000.
M. A. Averkiou, D. N. Roundhill, J. E. Powers, "A New Imaging Technique Based on the Nonlinear Properties of Tissues", 1997 IEEE Ultrasonics symp, pp. 1561-1566, 1997.

(56) References Cited

OTHER PUBLICATIONS

B. Haider, R. Y. Chiao, "Higher Order Nonlinear Ultrasonic Imaging", 1999 IEEE Ultrasonics symp., pp. 1527-1531, 1999.

A. Needles, M. Arditi, N. G. Rognin, J. Mehi, T. Coulthard, C. Bilan-Tracey, E. Gaud, P. Frinking, D. Hirson, F. S. Foster, "Nonlinear Contrast Imaging With an Array-Based Micro-Ultrasound System", Ultrasound Med. Biol., vol. 36, No. 12, pp. 2097-2106, 2010.

J. R. Doherty, G. E. Trahey, K. R. Nightingale, M. L. Palmeri, "Acoustic Radiation Force Elasticity Imaging in Diagnostic Ultrasound", IEEE Trans. on UFFC, vol. 60, No. 4, pp. 685-701, Apr. 2013.

K. Hynynen, "Demonstration of Enhanced Temperature Elevation Due To Nonlinear Propagation of Focussed Ultrasound in Dog's Thigh In Vivo", Ultrasound Med. Biol. vol. 13, No. 2, pp. 85-91, 1987.

Y. Huang, N. I. Vykhodtseva, K. Hynynen, "Creating Brain Lesions With Low-Intensity Focused Ultrasound With Microbubbles: a Rat Study At Half a Megahertz", Ultrasound Med. Biol., vol. 39, No. 8, pp. 1420-1428, 2013.

C. Sumi, "Utilization of an ultrasound beam steering angle for measurements of tissue displacement vector and lateral displacement", Rep. in Med. Imag., vol. 3, pp. 61-81, 2010.

A. K. Katsaggelos, K. T. Lay, "Maximum Likelihood Blur Identification and Image Restoration Using the EM Algorithm", IEEE Trans. Signal Processing, vol. 39, No. 3, pp. 729-733, 1991.

R. Molina, A. K. Katsaggelos, J. Mateos, "Bayesian and Regularization Methods for Hyperparameter Estimation in Image Restoration", IEEE Trans. Image Processing, vol. 8, No. 2, pp. 231-246, 1999.

M. Nikolova, "Markovian Reconstruction Using a GNC Approach", IEEE Trans. Image Processing, vol. 8, No. 9, pp. 1204-1220, 1999.

R. Molina, J. Mateos, A. K. Katsaggelos, M. Vega, "Bayesian Multichannel Image Restoration Using Compound Gauss-Markov Random Fields", IEEE Trans. Image Processing, vol. 12, No. 12, pp. 1642-1654, 2003.

H. Kokubo, S. Yagi, K. Nakayama, "High resolution ultrasonic imaging using 2-D echo filtering", Journal of Acoustical Society of Japan, vol. 47, No. 7, pp. 443-450, 1991 with partial English translation.

T. Morohoshi, K. Nakayama, S. Yagi, A. Suzuki, "High Resolution Ultrasonic Imaging Utilizing AR-Estimated Point Spread Function", Journal of The Institute of Electronics, Information and Communication Engineers, vol. J76-D-II, No. 2, pp. 233-240, 1993 with partial English translation.

C. L. Chan, A. K. Katsaggelos, "Iterative Maximum Likelihood Displacement Field Estimation in Quantum-Limited Image Sequences", IEEE Trans. Image Processing, vol. 4, No. 6, pp. 743-751, 1995.

J. C. Brailean, A. K. Katsaggelos, "Simultaneous Recursive Displacement Estimation and Restoration of Noisy-Blurred Image Sequences", IEEE Trans. Image Processing, vol. 4, No. 9, pp. 1236-1251, 1995.

Y.-L. You, M. Kaveh, "Blind Image Restoration by Anisotropic Regularization", IEEE Trans. Image Processing, vol. 8, No. 3, pp. 396-407, 1999.

T. F. Chan, C.-K. Wong, "Total Variation Blind Deconvolution", IEEE Trans. Image Processing, vol. 7, No. 3, pp. 370-375, 1998.

F. Sroubek, J. Flusser, "Multichannel Blind Iterative Image Restoration", IEEE Trans. Image Processing, vol. 12, No. 9, pp. 1094-1106, 2003.

Miles N. Wernick et al., "Fast Spatio-Temporal Image Reconstiaction for Dynamic PET", IEEE Trans. on Medical Imaging, vol. 18, pp. 185-195, 1999.

A. K. Katsaggelos, J. Biemond, R. W. Schafer, R. M. Mersereau, "A Regularized Iterative Image Restoration Algorithm", IEEE Trans. Signal Processing, vol. 39, pp. 914-929, 1991.

C. Sumi, "Determination of Lateral Modulation Apodization Functions Using a Regularized, Weighted Least Squares Estimation", Int. J. Biomed. Imag, ID: 635294 (7 pages), 2010.

C. Sumi et al., "A Demonstration of Optimal Apodization Determination for Proper Lateral Modulation", Jpn, J. of Appl. Phys., vol. 48 (7B), 07GJ06, Jul. 2009.

Office Action dated May 29, 2018 in corresponding Japanese Patent Application No. 2014-116949 with partial English translation.

Office Action dated Apr. 14, 2020 in corresponding Japanese Patent Application No. 2019-077101 with Partial Translation.

Sato et al., "Ultrasonic Wave and Information Processing", Measurement Control, May 1989, vol. 28, No. 5, pp. 392-397 with Partial Translation.

Westervelt, "Parametric Acoustic Array", The Journal of the Acoustical Society of America, Apr. 1963, vol. 35, No. 4, pp. 535-537.

Notification of Reason(s) for Rejection dated Sep. 1, 2020 in Japanese Patent Application No. 2019-077101 with partial English Translation.

FIG.3
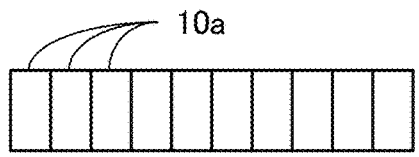
(a1) DENSE
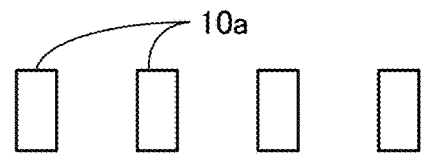
(b1) SPARSE
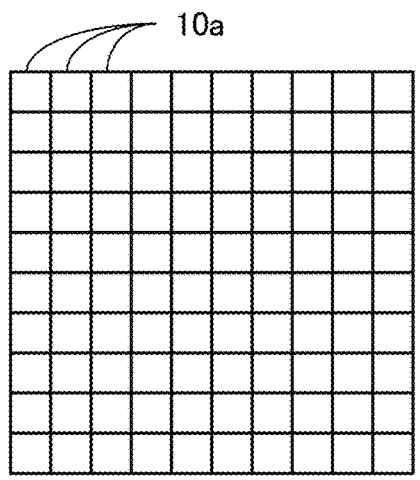
(a2) DENSE
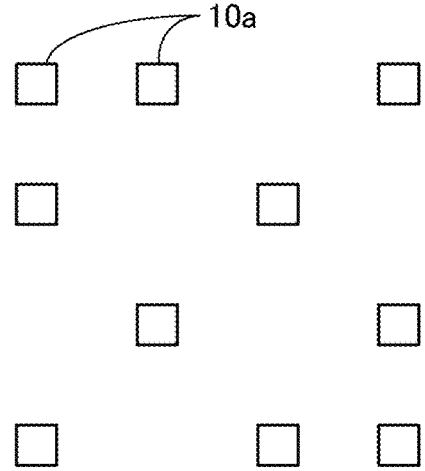
(b2) SPARSE
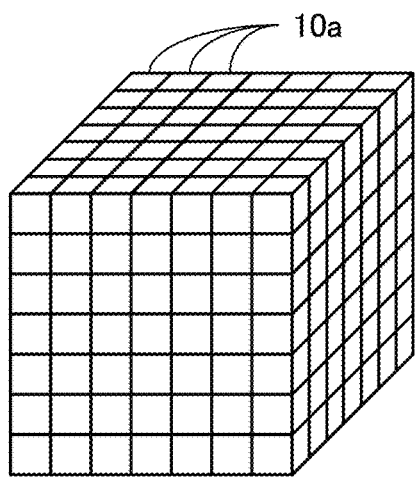
(a3) DENSE
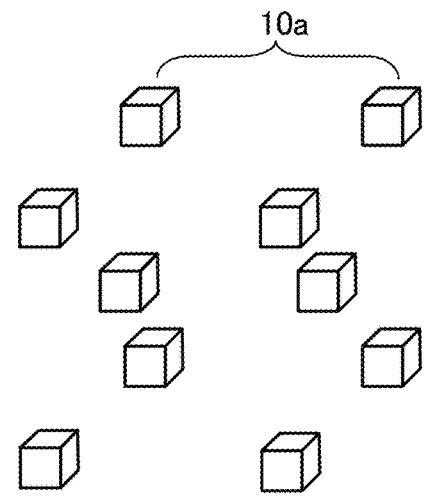
(b3) SPARSE

FIG. 7
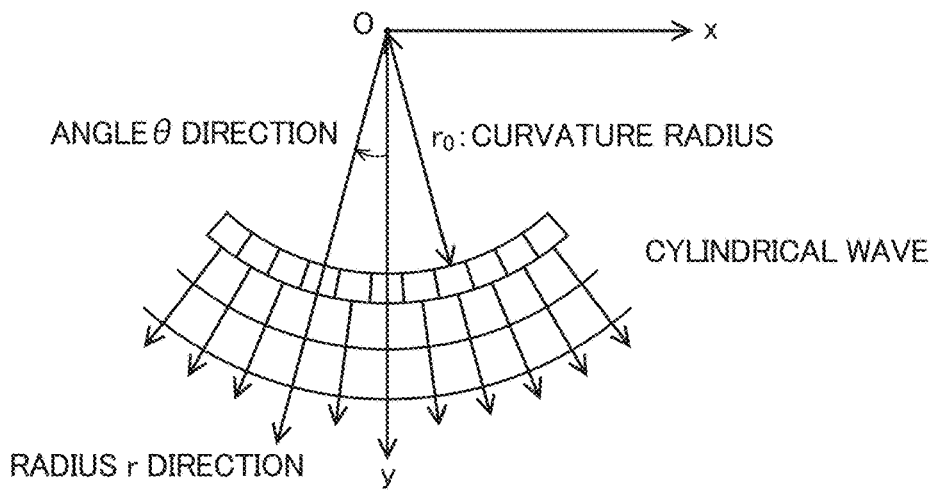
(a) CONVEX-TYPE APERTURE ELEMENT ARRAY
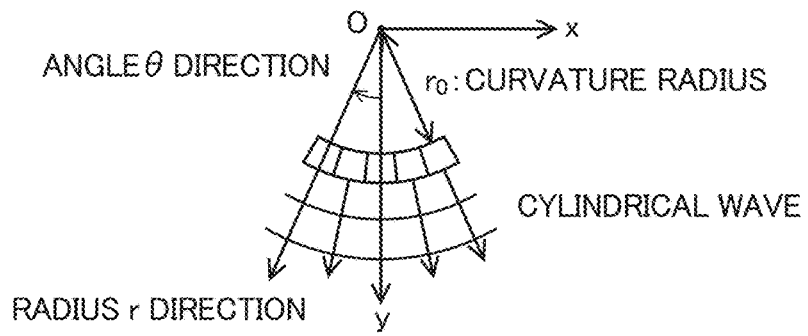
(b) SECTOR-TYPE APERTURE ELEMENT ARRAY
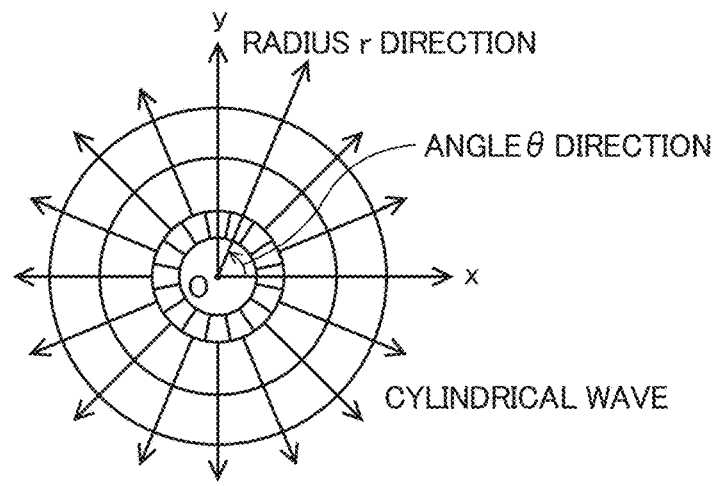
(c) IVUS(CIRCULAR-TYPE) APERTURE ELEMENT ARRAY

FIG.8A
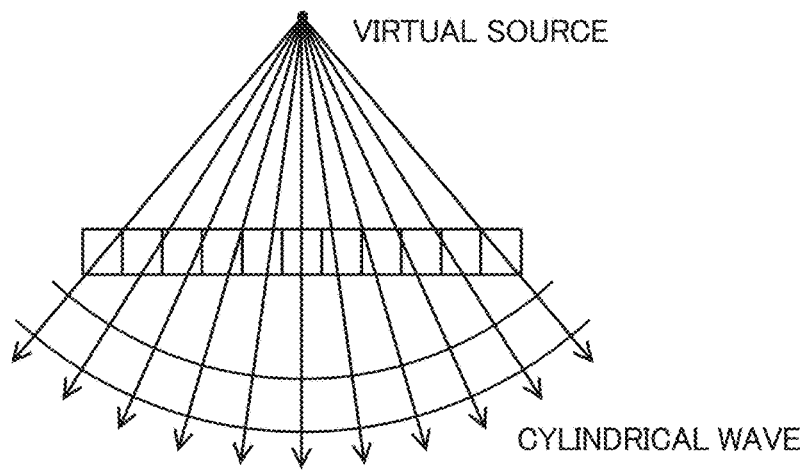
(a) LINEAR-TYPE APERTURE ELEMENT ARRAY
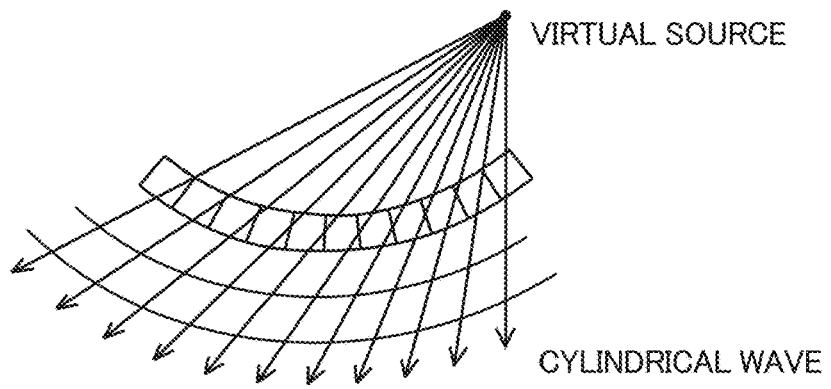
(b) CONVEX-TYPE APERTURE ELEMENT ARRAY
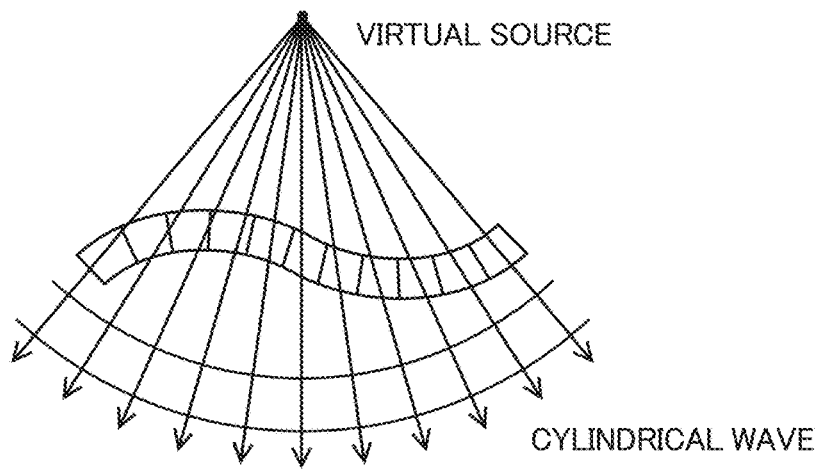
(c) ARBITRARY APERTURE ELEMENT ARRAY

FIG.8B
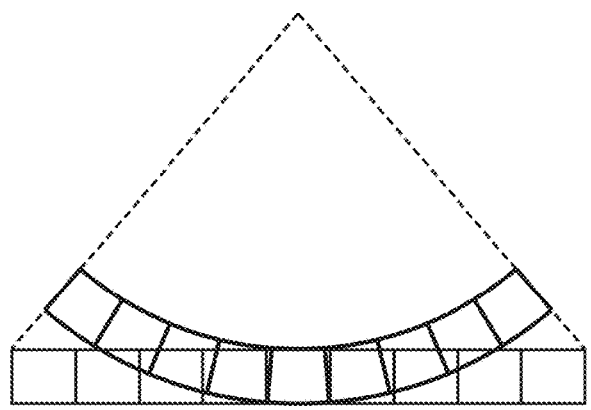
(d)
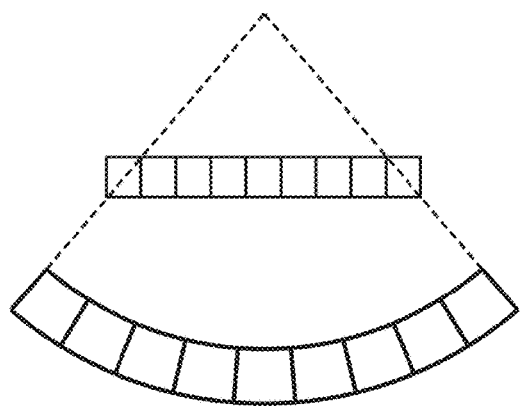
(e)
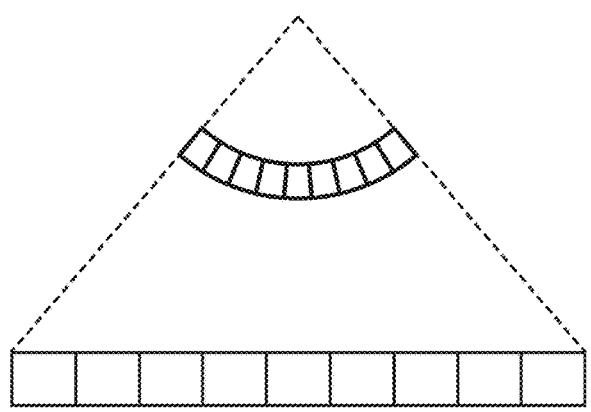
(f)
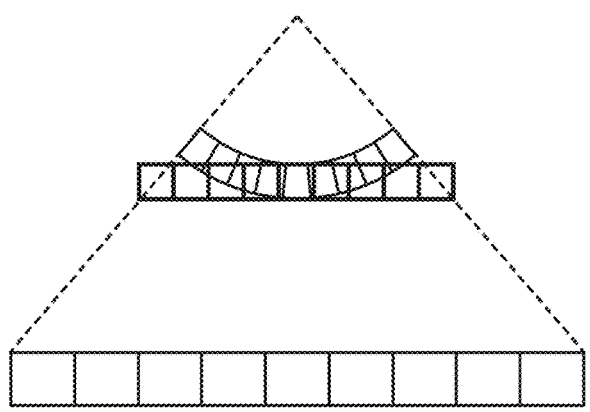
(g)

FIG.16
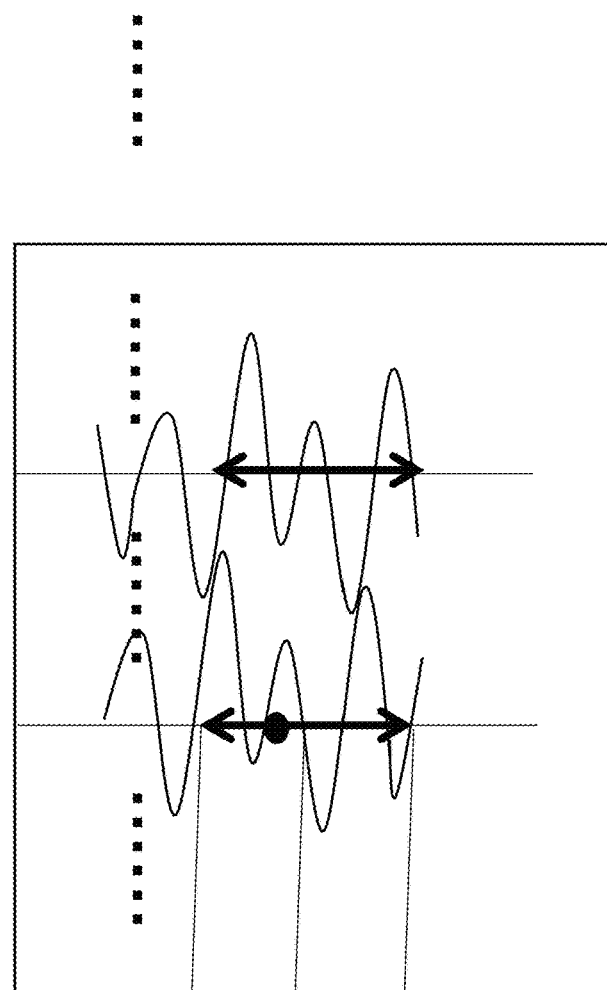
(b)
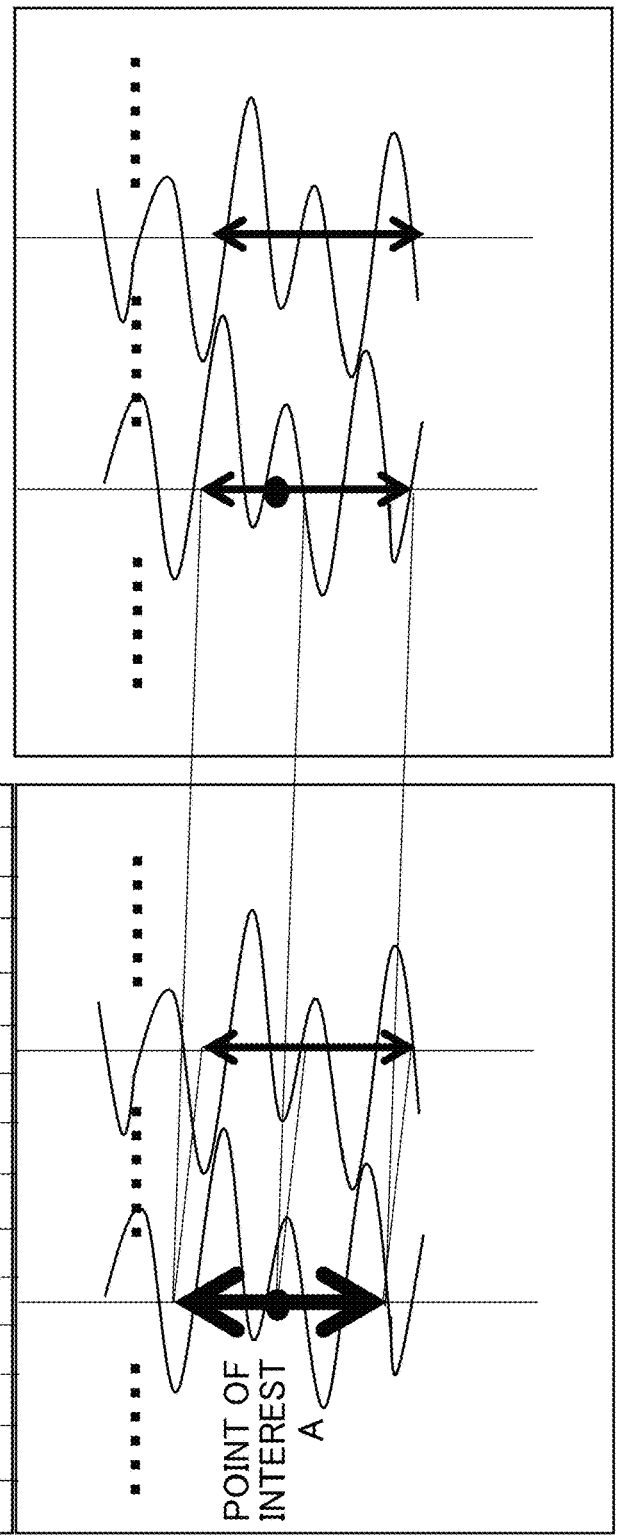
(a)

FIG. 17
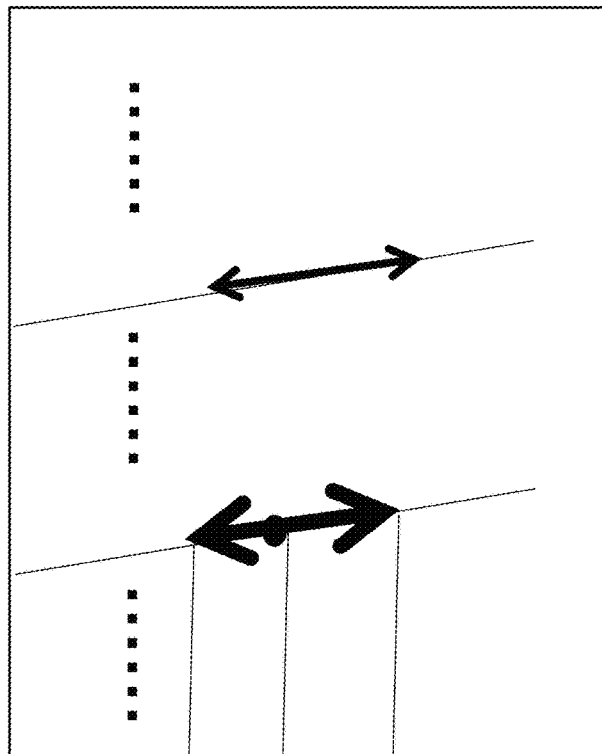
(b)
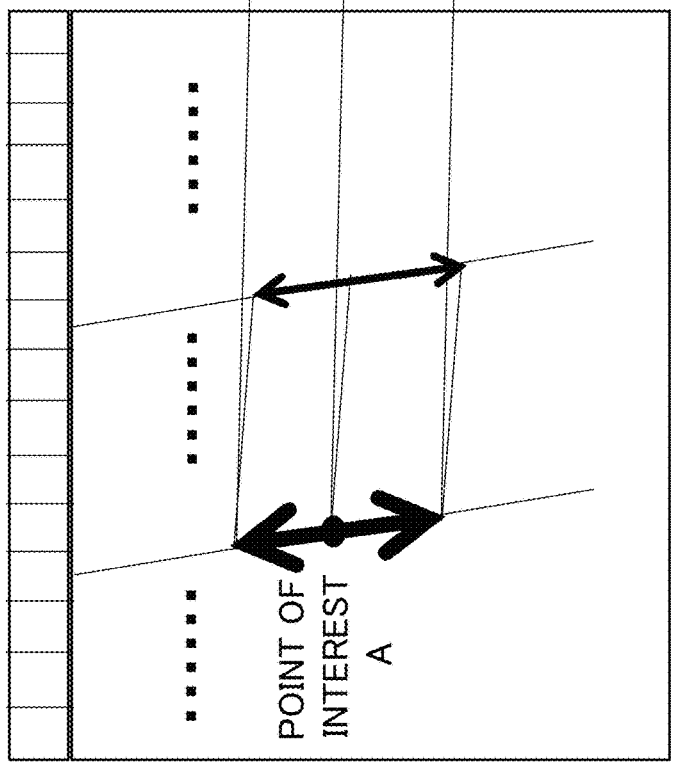
(a)

FIG.19
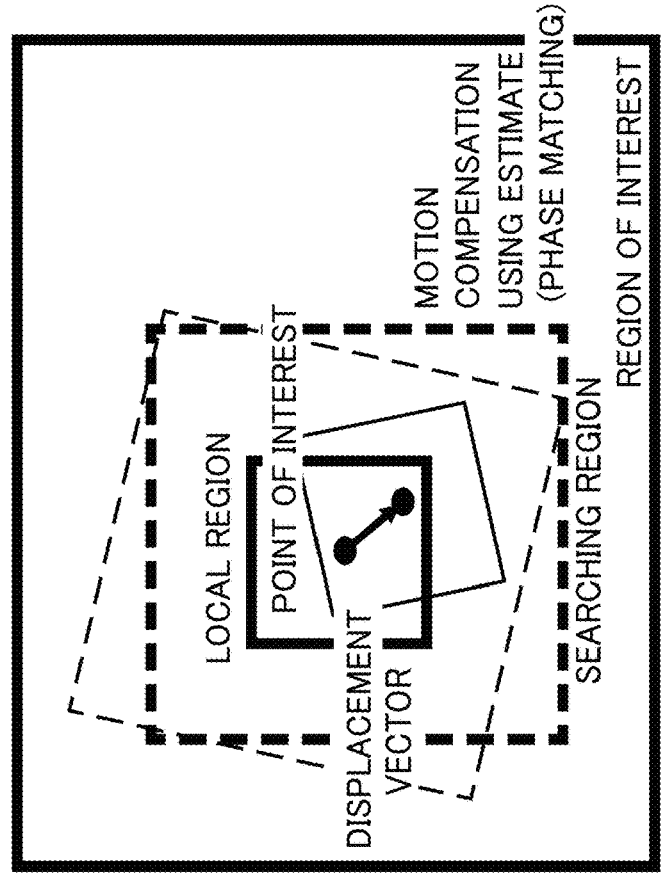
(b) MOTION COMPENSATION FOR TRANSLATION AND ROTATION
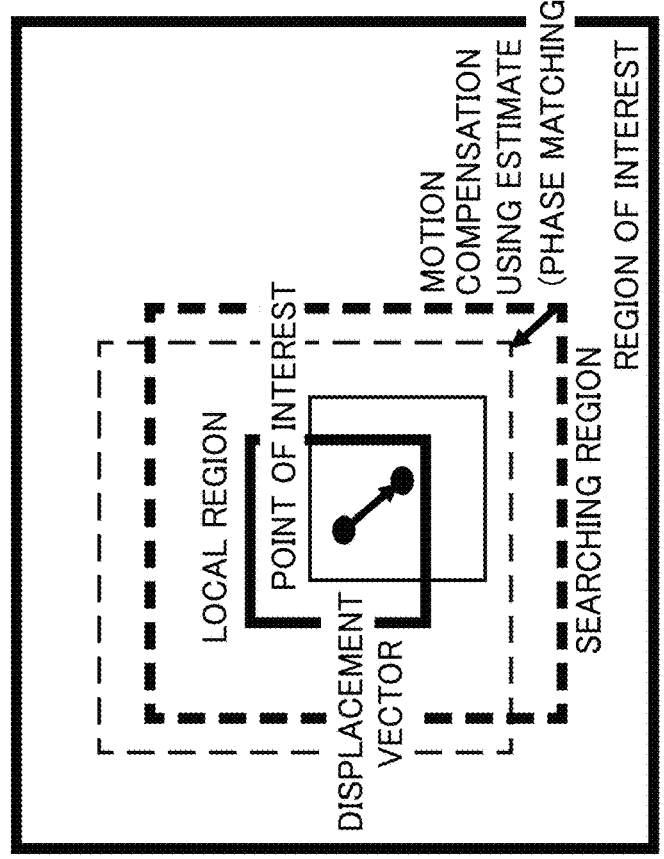
(a) MOTION COMPENSATION FOR TRANSLATION

FIG.23A
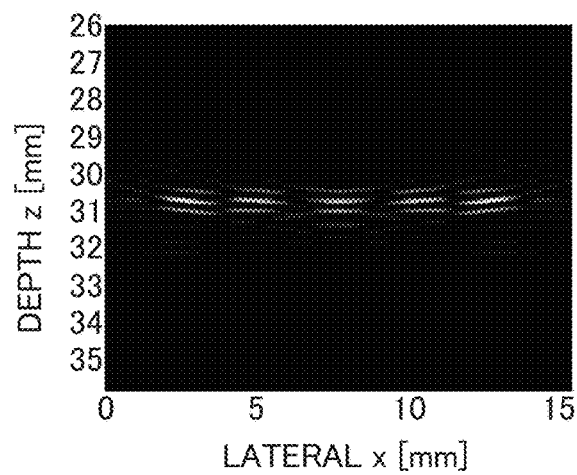
(a) $\theta = 0°$
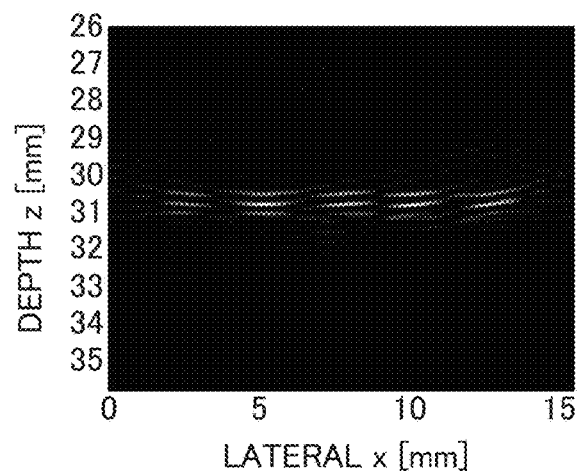
(b) $\theta = 5°$
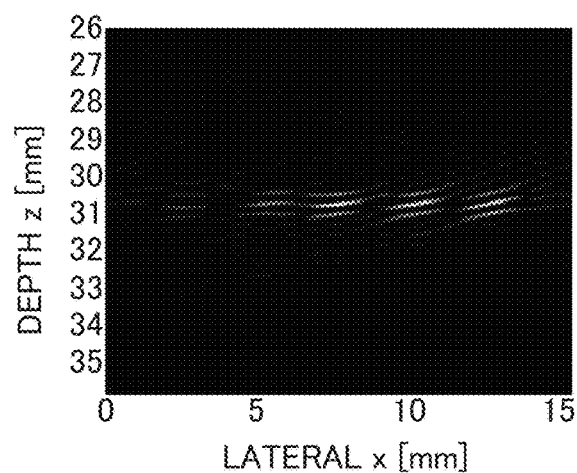
(c) $\theta = 10°$
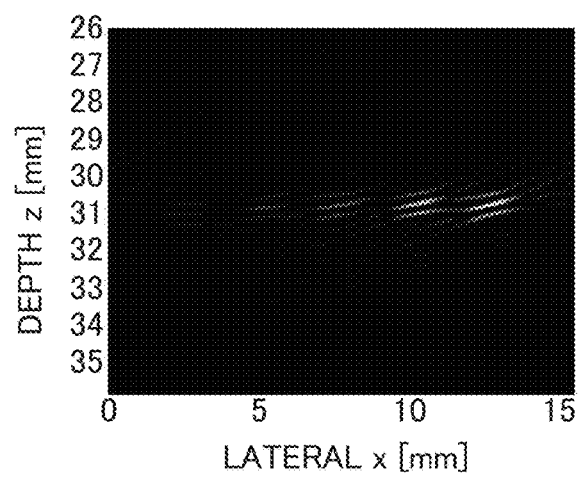
(d) $\theta = 15°$

FIG.23B
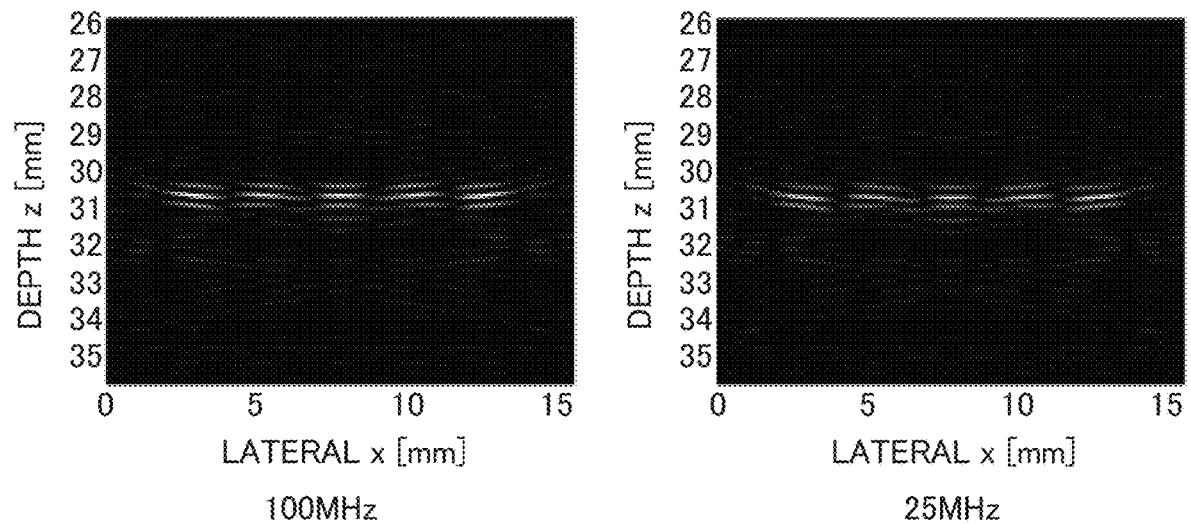
(e) $\theta = 0°$, APPROXIMATE INTERPOLATIONS USING NEIGHBORING SPECTRA
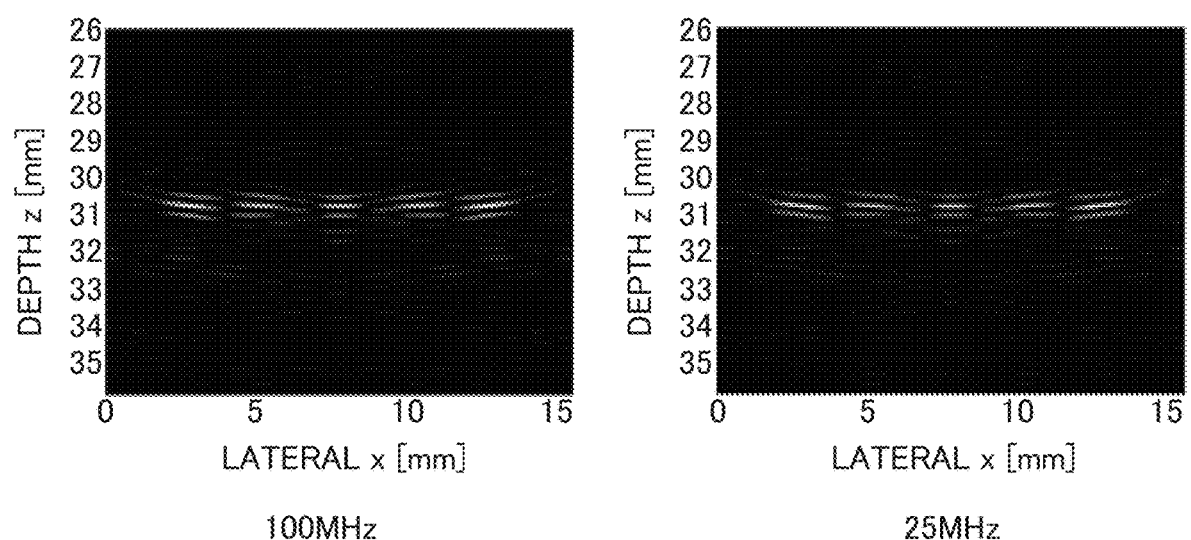
(f) $\theta = 0°$, LINEAR APPROXIMATE INTERPOLATIONS

| SET ANGLE (DEGREE) | 0 | 5 | 10 | 15 | 20 |
|---|---|---|---|---|---|
| OBTAINED STEERING ANGLE (DEGREE) | −0.7853 | 5.6048 | 9.4149 | 14.5036 | 19.1852 |
| ERROR (DEGREE) | −0.7853 | 0.6048 | −0.5851 | −0.4964 | −0.8148 |

FIG.26
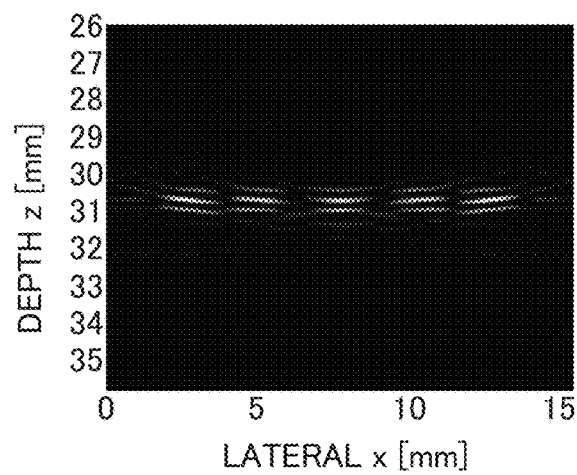
(a) 1 WAVE (0°)
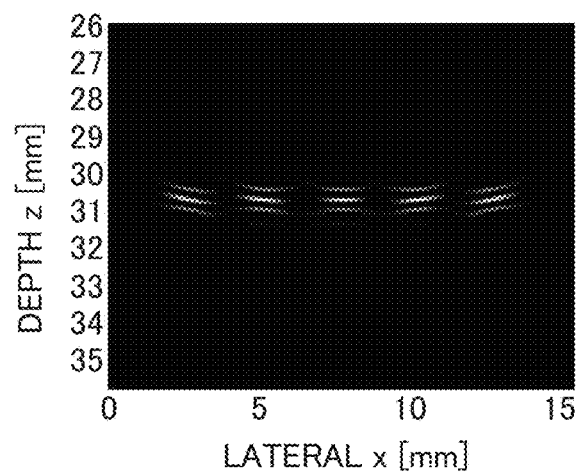
(b) 11 WAVES (−5° TO 5°)
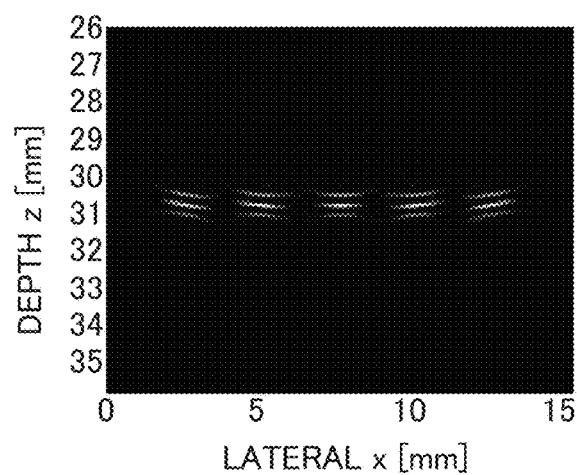
(c) 21 WAVES (−10° TO 10°)
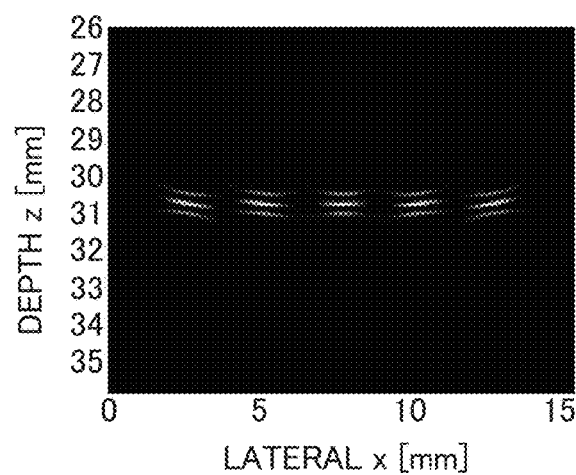
(d) 41 WAVES (−20° TO 20°)

*FIG.28*
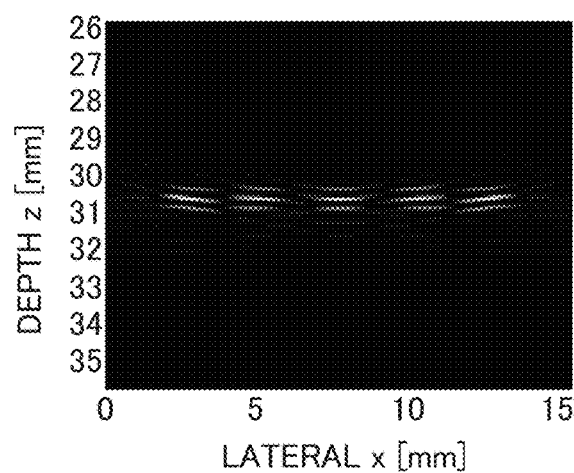
(a) $\theta = 0°$
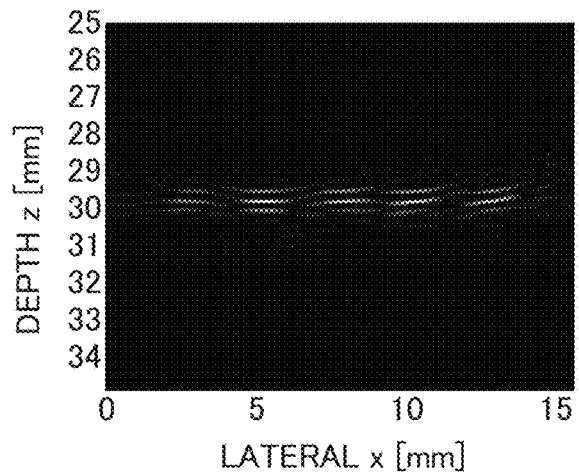
(b) $\theta = 5°$
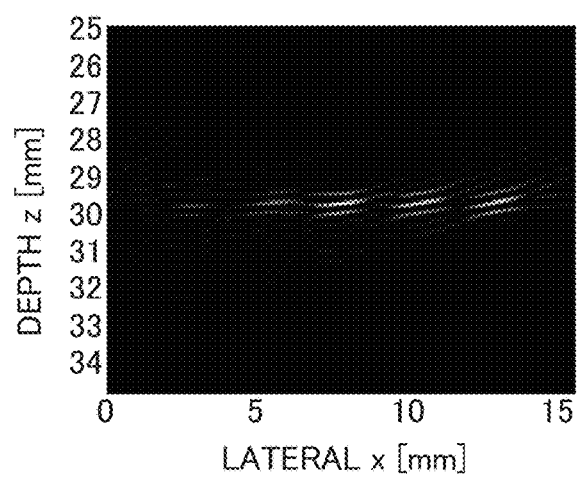
(c) $\theta = 10°$
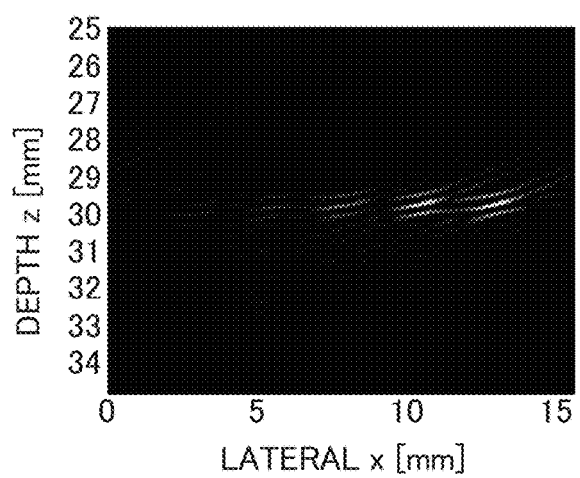
(d) $\theta = 15°$

FIG.29
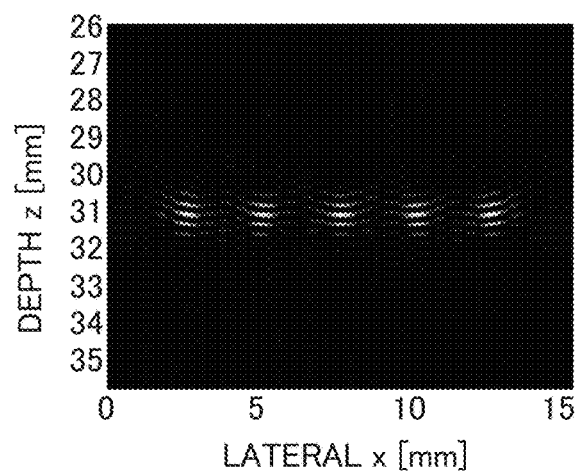
(a) $\theta = 0°$
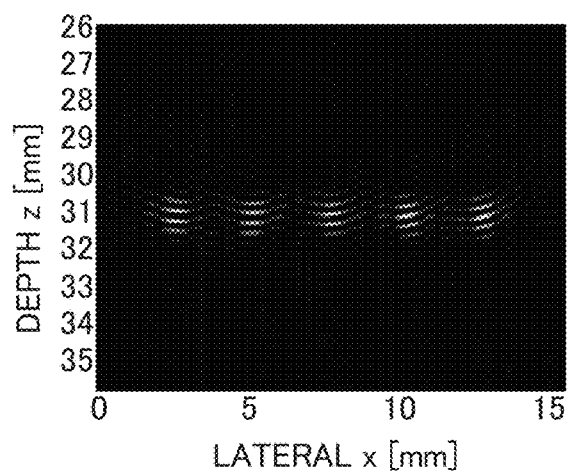
(b) $\theta = 5°$
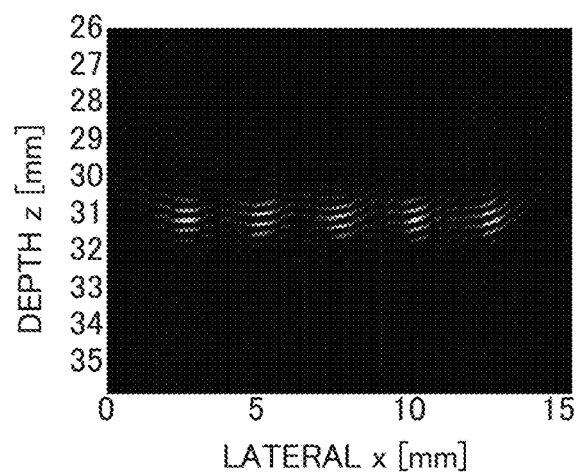
(c) $\theta = 10°$
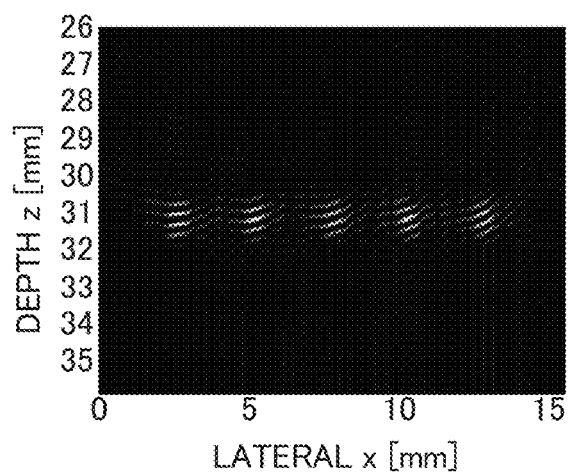
(d) $\theta = 15°$

FIG.30
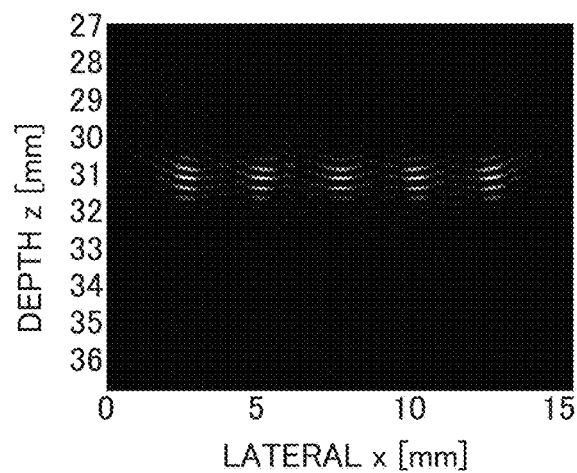
(a) 1 ELEMENT
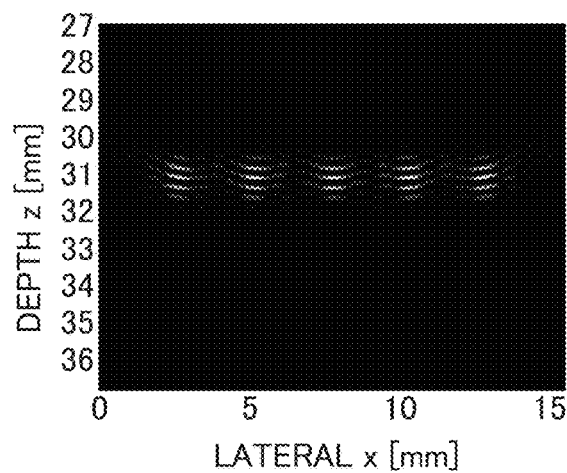
(b) 33 ELEMENTS
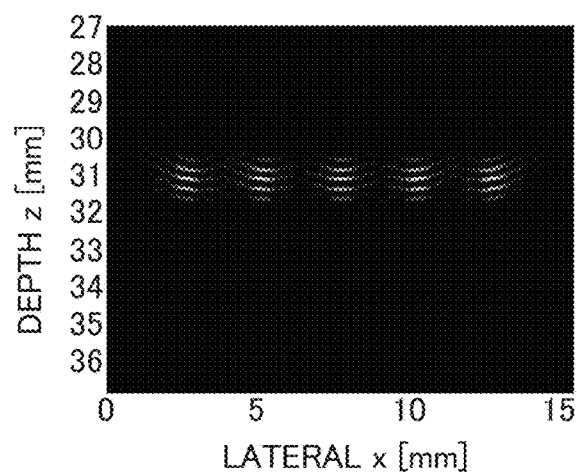
(c) 65 ELEMENTS
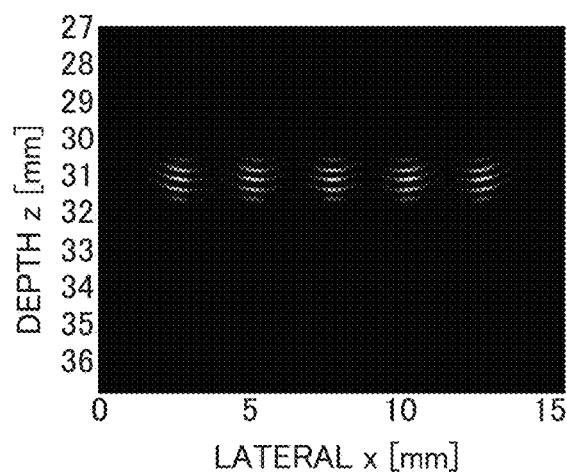
(d) 129 ELEMENTS FIG.32
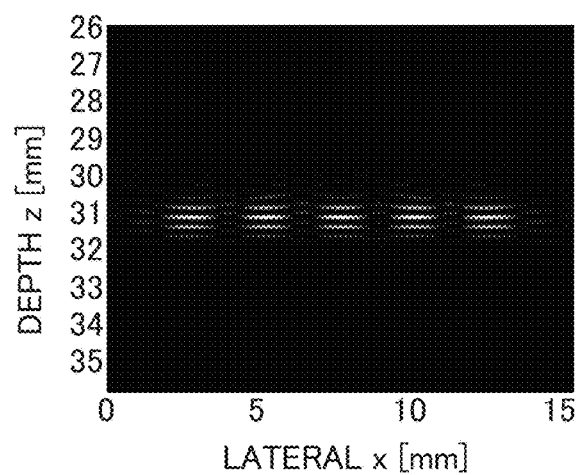
(a) METHOD(1)
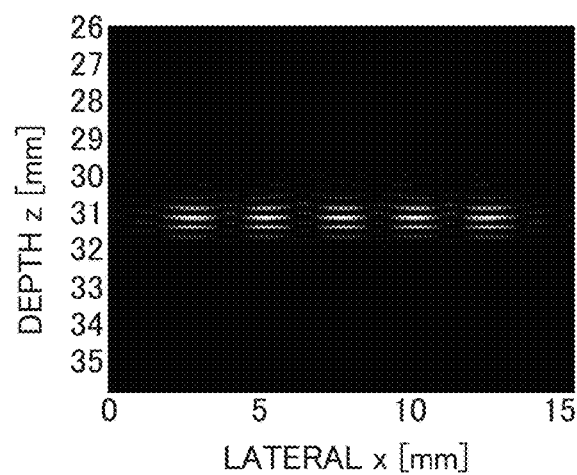
(b) METHOD(2)
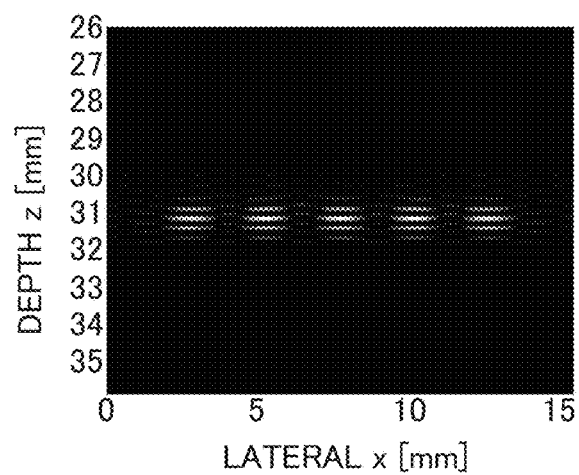
(c) METHOD(3)

FIG.33
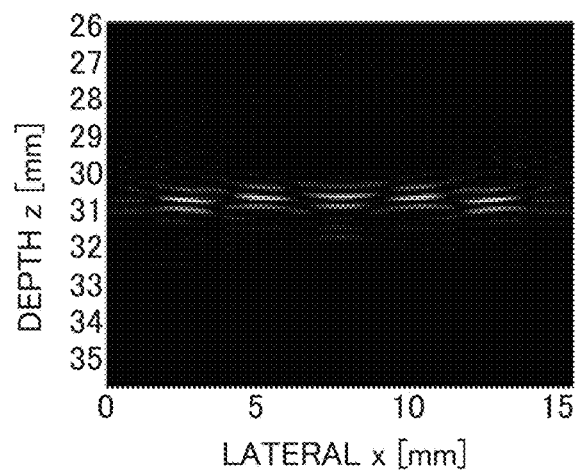
(a)
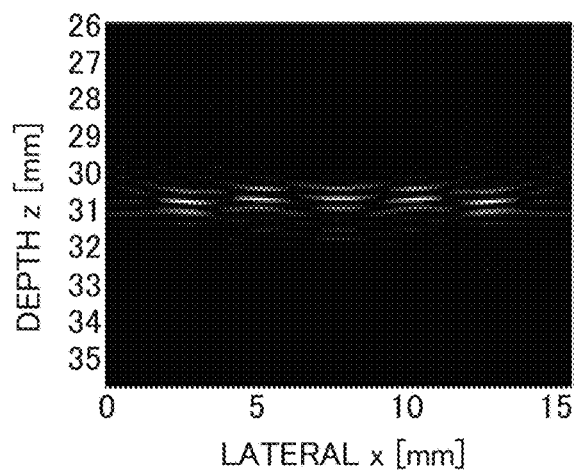
(b)
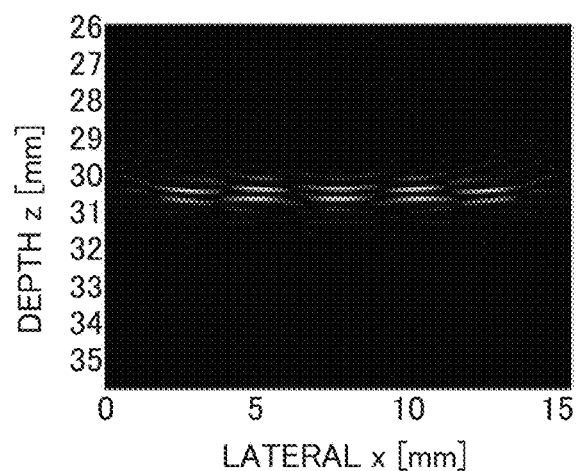
(c)
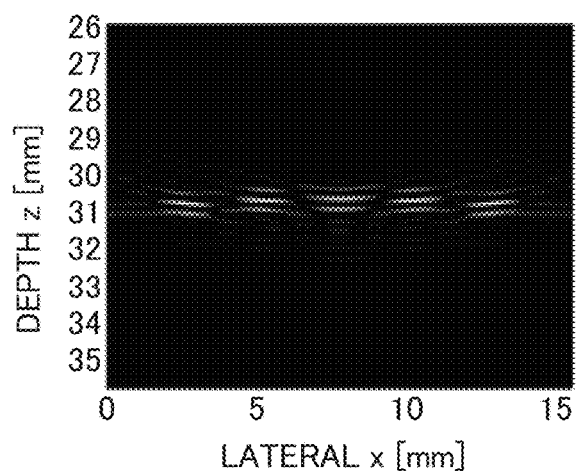
(d)

FIG.34
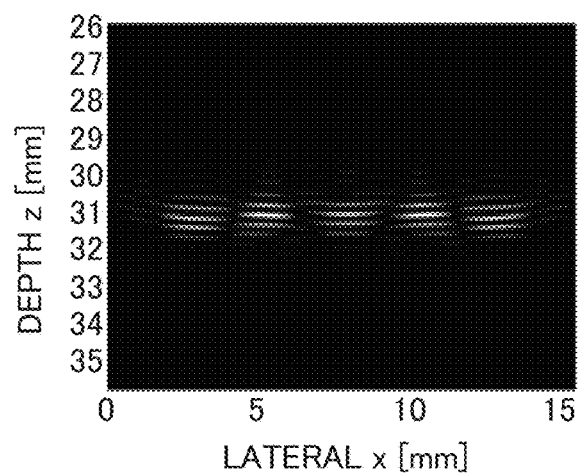
(a)
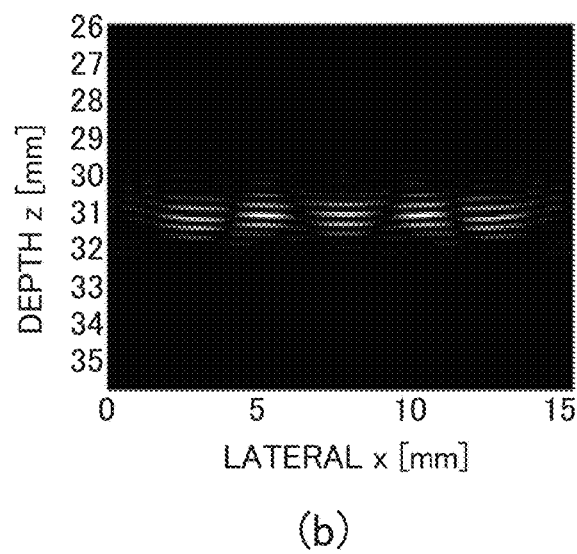
(b)
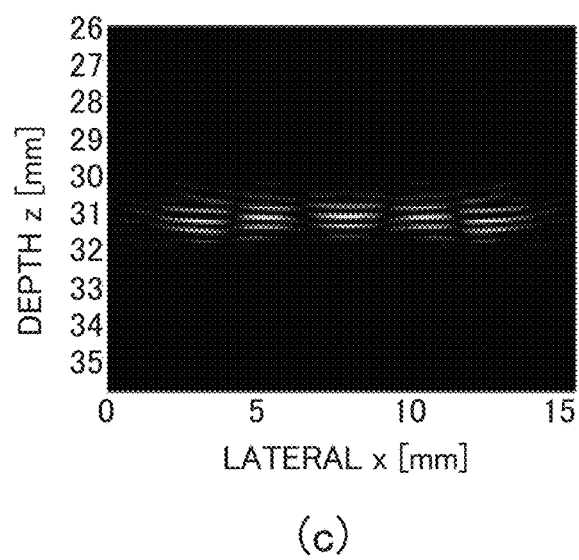
(c)

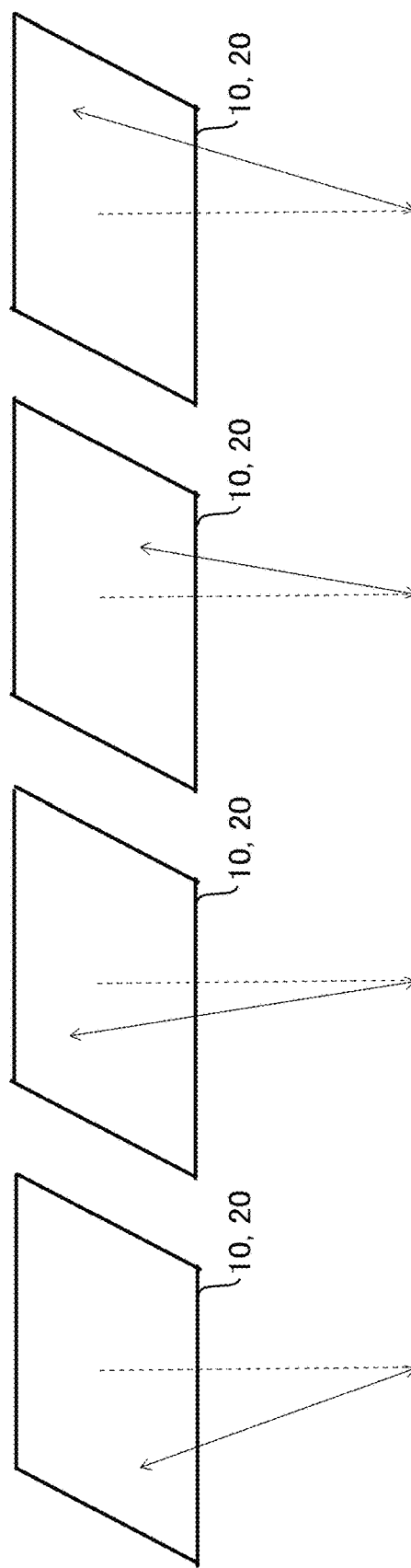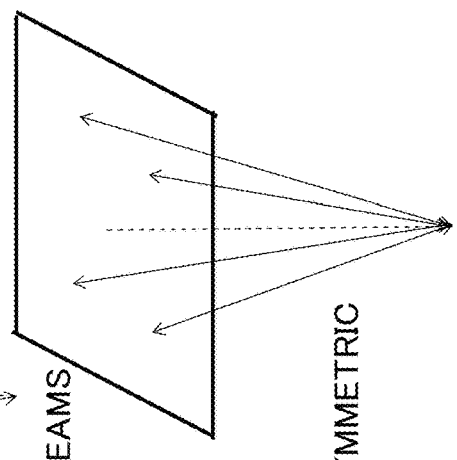
FIG.36
EXAMPLE OF SYMMETRIC STEERING BEAMS
SUPERPOSITION OF SYMMETRIC STEERING BEAMS

FIG.39
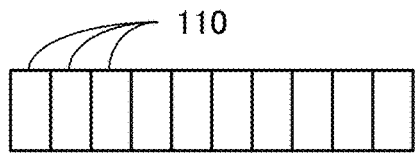
(a1) DENSE
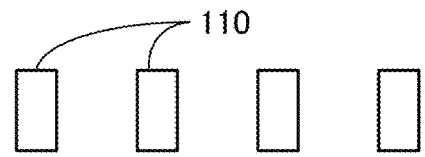
(b1) SPARSE
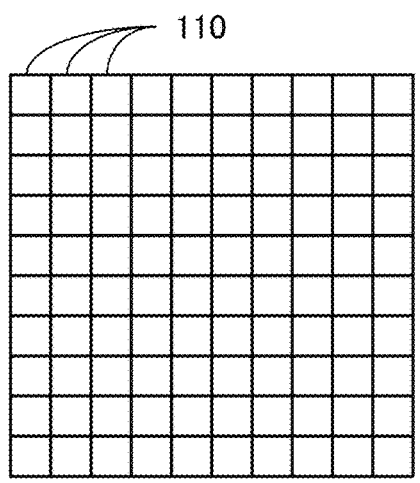
(a2) DENSE
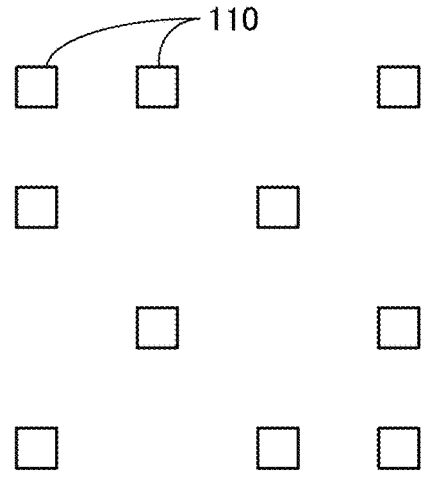
(b2) SPARSE
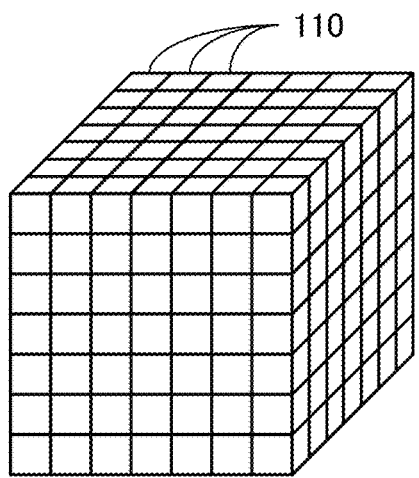
(a3) DENSE
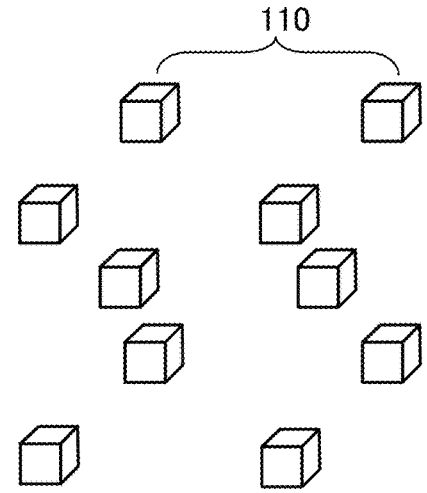
(b3) SPARSE

FIG. 40
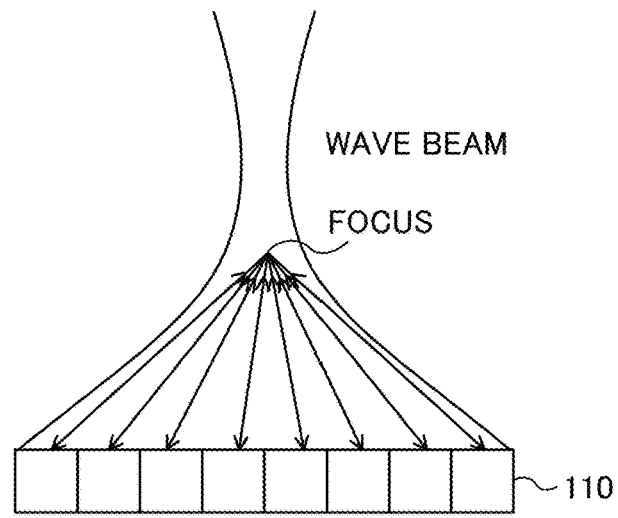
(a) TRANSMISSION OR RECEPTION FOCUSING
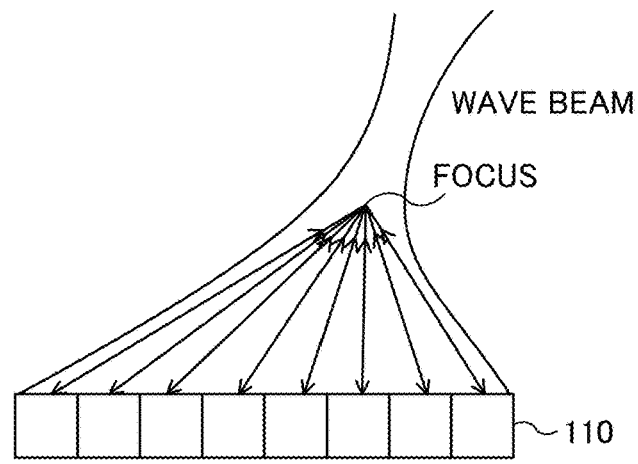
(b) TRANSMISSION OR RECEPTION STEERING
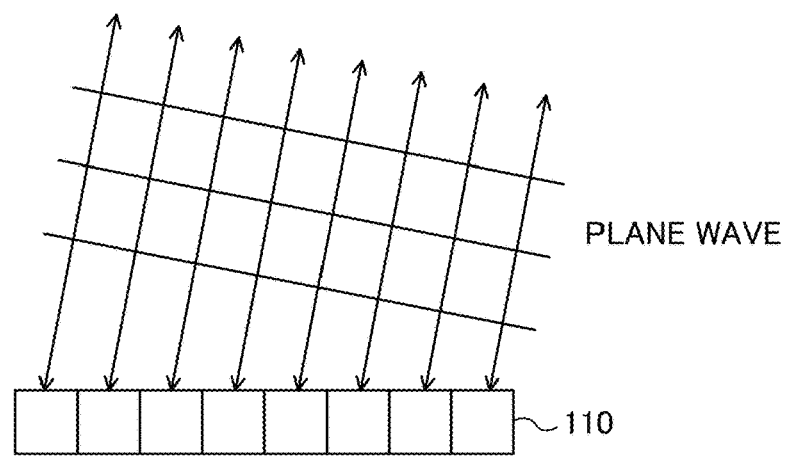
(c) TRANSMISSION OR RECEPTION OF PLANE WAVE

FIG.41
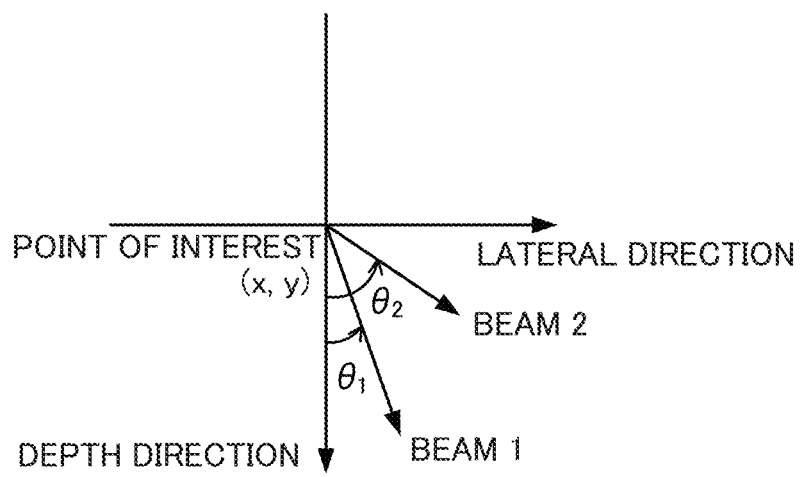
(a) SPATIAL DOMAIN
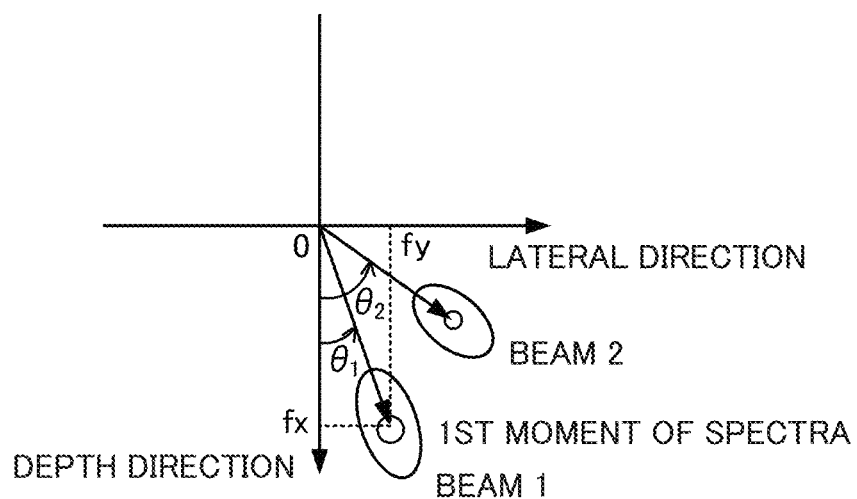
(b) FREQUENCY DOMAIN

FIG. 49
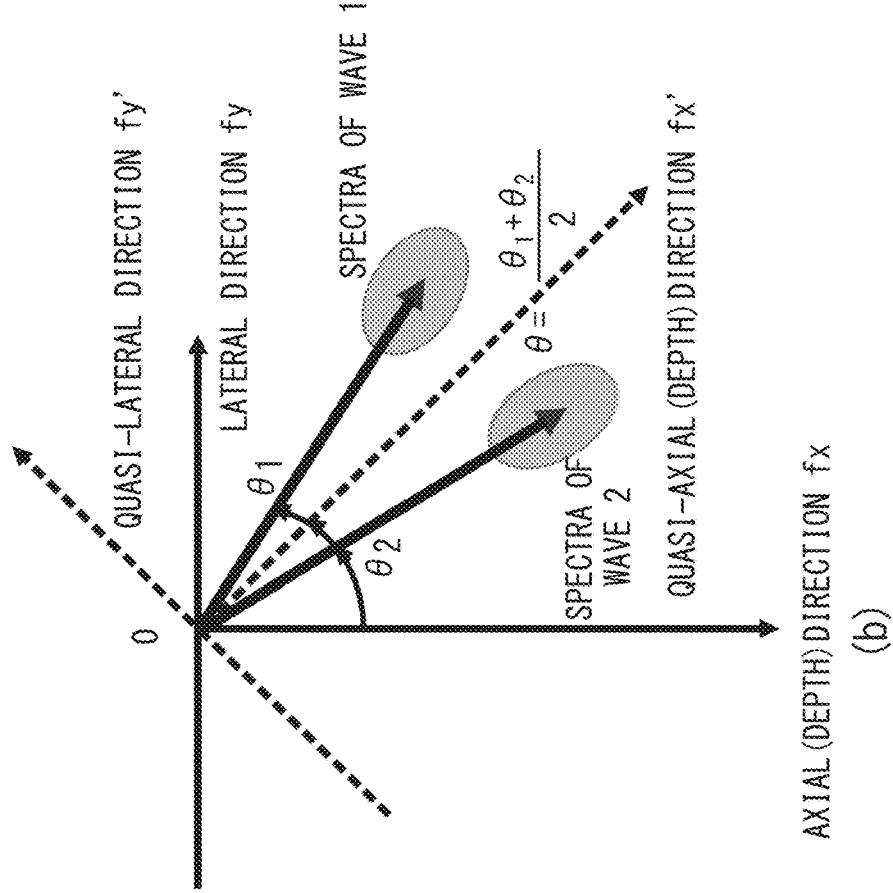
(b)
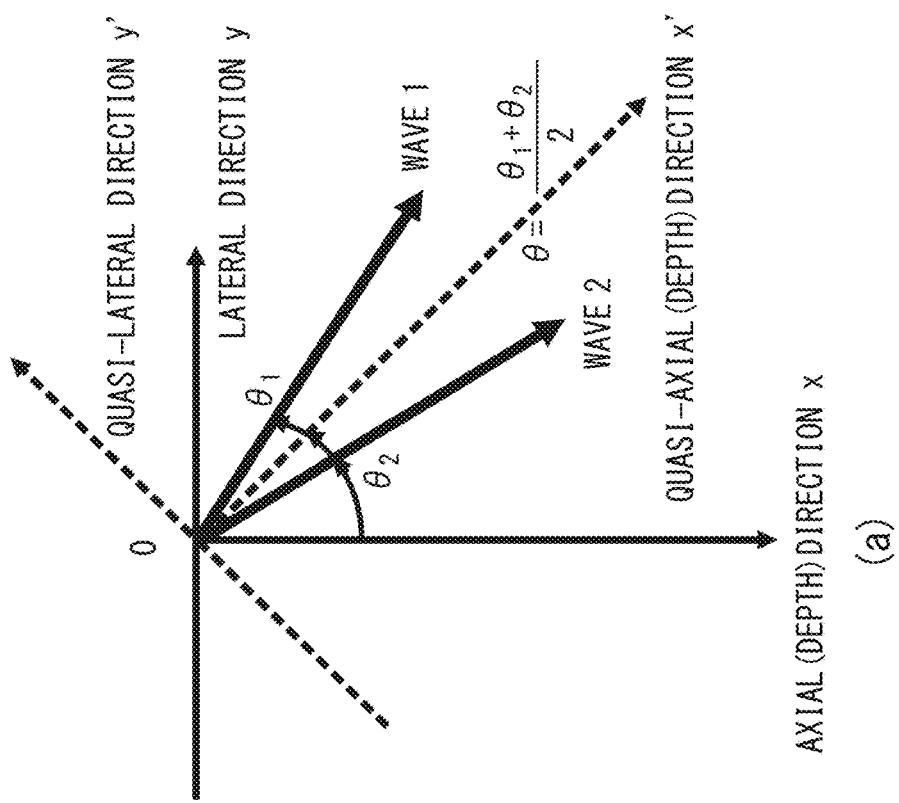
(a)

FIG.53
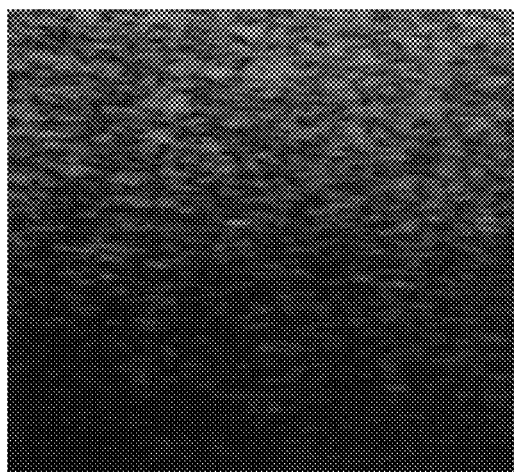
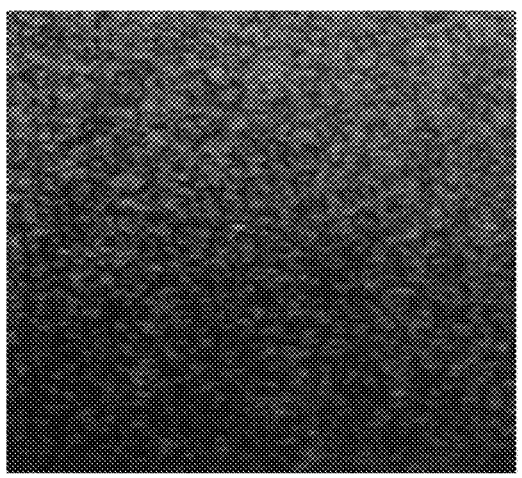
(a1) ENVELOPE DETECTION AND SQUARE DETECTION
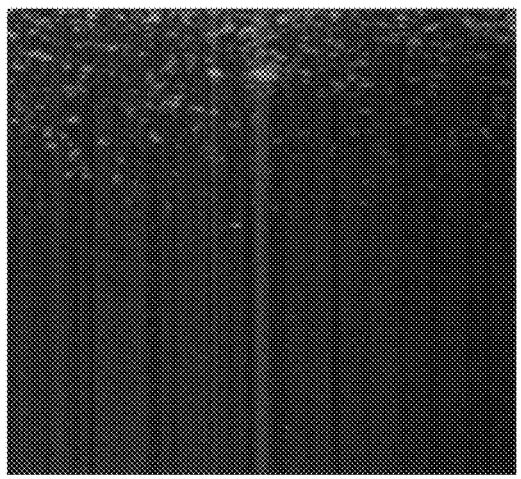
(a2) ENVELOPE DETECTION
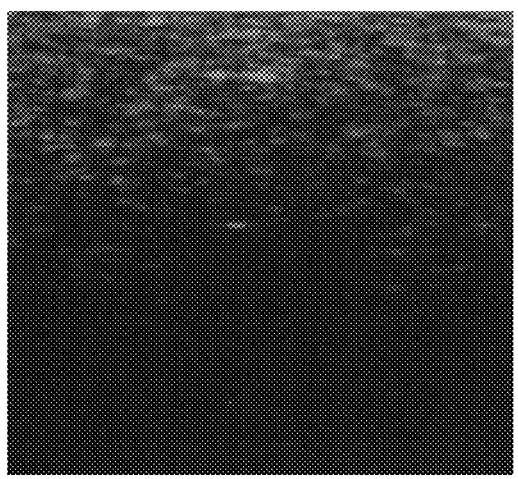
(a3) ENVELOPE DETECTION AND SQUARE DETECTION

FIG.54
 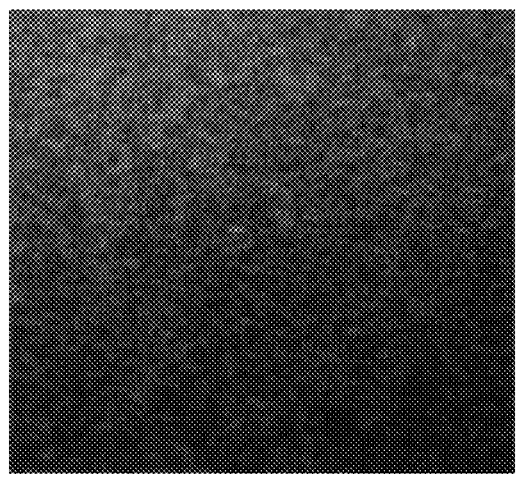
(b1) ENVELOPE DETECTION AND SQUARE DETECTION
(b2) ENVELOPE DETECTION
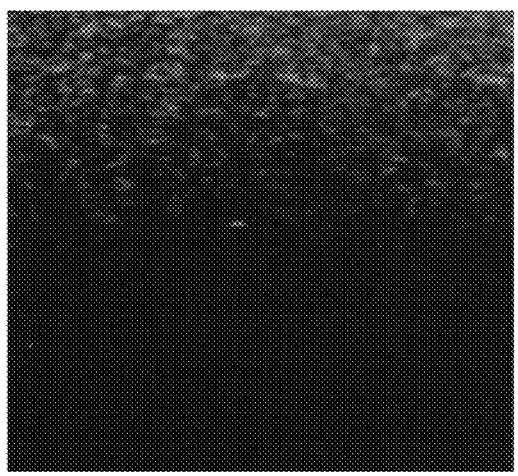 
(b3) ENVELOPE DETECTION AND SQUARE DETECTION

FIG.55
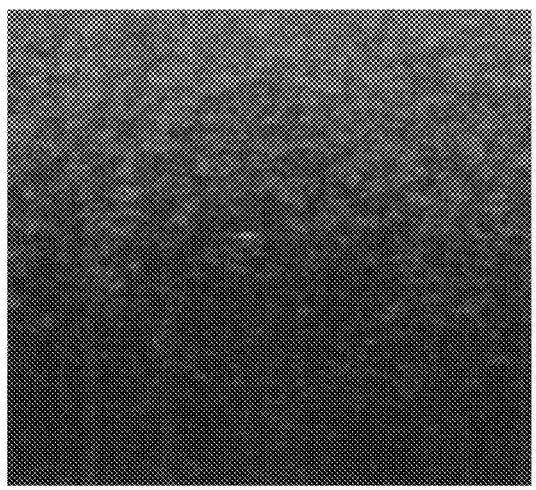
(b4) SQUARE DETECTION
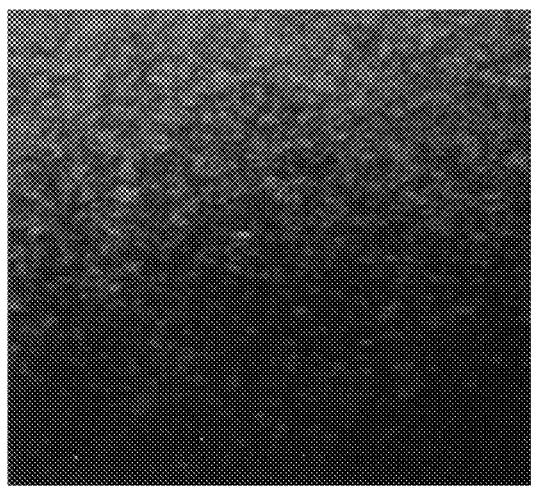
(b5) SQUARE DETECTION
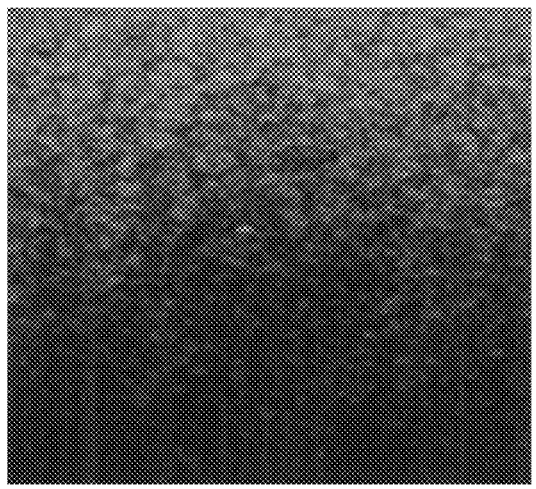
(c1) SQUARE DETECTION
(c2) SQUARE DETECTION

FIG.57
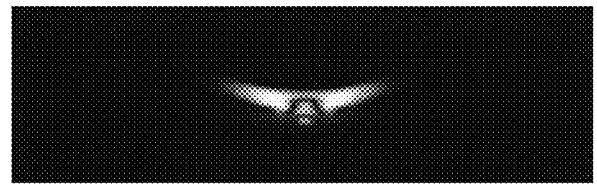
(a1)
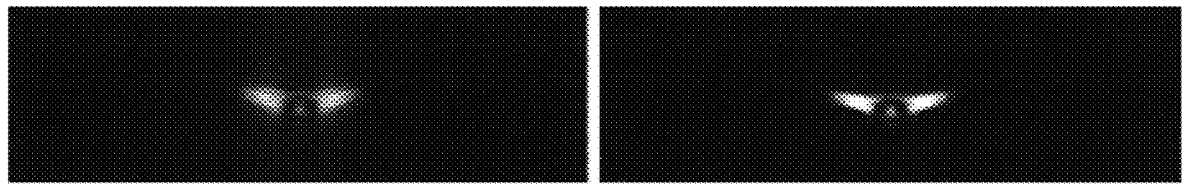
(a2)
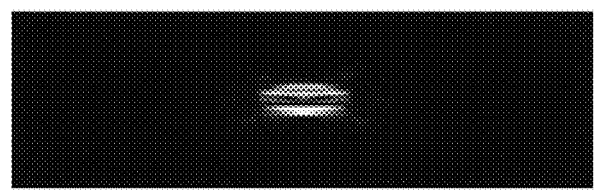
(b1)
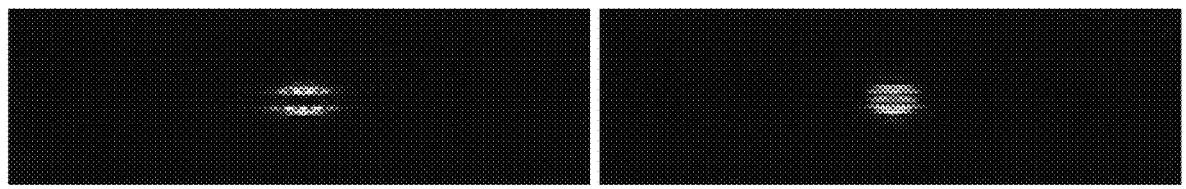
(b2)

MEASUREMENT AND IMAGING INSTRUMENTS AND BEAMFORMING METHOD

CROSS-REFERENCE TO RELATED APPLICATION

The present application is a Continuation-In-Part of U.S. patent application Ser. No. 14/730,583 filed on Jun. 4, 2015 (inventors: Dr. Chikayoshi Sumi, an associate professor of Sophia University, Tokyo Japan and Mr. Naoto Yamazaki, a master student of Chikayoshi Sumi's laboratory). The disclosure of that application is incorporated herein by reference.

Further, the present application claims priority from Japanese Patent Applications No. 2017-100947 filed on May 22, 2017, No. 2017-122554 filed on Jun. 22, 2017, No. 2017-137185 filed on Jul. 13, 2017, No. 2017-144588 filed on Jul. 26, 2017, No. 2017-157256 filed on Aug. 16, 2017, No. 2017-157590 filed on Aug. 17, 2017, No. 2017-207592 filed on Oct. 26, 2017, No. 2017-225982 filed on Nov. 24, 2017, No. 2017-242013 filed on Dec. 18, 2017, and No. 2017-245377 filed on Dec. 21, 2017 (inventor: Dr. Chikayoshi Sumi, an associate professor of Sophia University), the contents of which are incorporated herein by reference in their entirety.

BACKGROUND OF THE INVENTION

Field of the Invention

The present invention relates to measurement and imaging methods that are used for performing measurements of measurement objects by performing beamformings for arbitrary waves that arrive from the measurement objects.

Furthermore, the present invention relates to beamforming methods that perform, based on arbitrary waves such as electromagnetic waves, lights, mechanical vibrations, acoustic waves, thermal waves, etc. that arrive from measurement objects, imaging of the objects, or non-destructively measuring and imaging of physical quantities such as temperatures, displacements, etc., compositions and structures, etc. of the objects. The measurement objects are various such as organic and inorganic substances or matters, solids, liquids, gases, rheology matters, living things, celestial objects, an earth, environments, etc., and the application range is prominently widespread.

The present invention relates to nondestructive evaluations, diagnoses, resource explorations, growth and manufacturing of substances and structures, monitoring of physical and chemical restorations and treatments, applications of clarified functions and physical properties, etc., where a high measurement accuracy can be required to be achieved without generating turbulences under the conditions of a noninvasiveness, a low invasiveness, no observable blood, etc. Ideally, the measurement objects should be observed at their original positions in situ.

Measurement objects can also be treated or restored owing to the actions of the waves themselves. Simultaneously, the processes can also be observed by performing the beamforming using the responses from the objects.

Beamforming is also performed on satellite communications, radars, sonars, etc. to perform accurate communications under saving energies by realizing informationally safe environments. In ad hoc communication instruments and mobile instruments, beamforming has also been used. When the objects are dynamic, real time characteristics is demanded and therefore, the beamforming is required to be completed in a short time.

Description of a Related Art

Behaviors of waves such as electromagnetic waves, lights, mechanical vibrations, acoustic waves, thermal waves, etc. are different on their frequencies, bandwidths, intensities, modes, etc. Many transducers of various waves are developed so far, and imaging with the transmission waves, reflection waves, refraction waves, diffraction waves or scattered waves (forward or back scattered waves), etc. is performed.

For instance, it is well known that a higher frequency acoustic wave categorized into an ultrasound is used for non-destructive evaluations, a medicine and sonars. For radars, proper frequency electromagnetic waves such as a radio wave, an FM wave, a micro wave, a terahertz wave, an infrared wave, a visible wave, a violet wave, a radioactive ray such as an X-ray, etc. are used. Also, for other waves, the behavior is different and dependent on the frequency and therefore it has a specific name, which is used for various sensing and communications properly with respect to measurement objects, media and bandwidths (polarization can also be performed on electromagnetic waves).

By those applications, the measurement objects are often scanned with a transducer mechanically. Also, the same transducer is often used plural times, or plural transducers aligned in an array form beforehand are often used to perform a beamforming processing. It is well known that when the earth and land, the ocean, weather are observed by the radar of a satellite and an airplane, a synthetic aperture processing, etc. is performed. Particularly when imaging the measurement objects, an appropriate directivity is kept, and the beamforming is often intended that a high spatial resolution and a high contrast are achieved in a region of interest or at a point of interest.

As a result, a reflection and transmission generated by a spatial change of the impedance, various scattering (Rayleigh scattering, Mie scattering, and others), attenuation, refraction, diffraction or those frequency variance, etc. acting on a wave in the measurement object can be observed, and the inside and surface structures and compositions can be observed in addition to what the measurement object is. The measurement object can also be observed in a various spatial resolution. At various levels of the structure and composition (e.g., an individual level, a molecular level, an atom level, a nuclear level, etc.), characteristic evaluations (characterization) can be performed.

For the purpose of highly accuracy, high-spatial resolution imaging, the signal compression technique such as a chirp technology and an encoding technique have been representatively used for a long time. In ISAR (inverse synthetic aperture radar), etc., the inversion of beam properties is implemented on an observed signal to generate a super-resolution (e.g., when performing SA or others). Alternatively, a spatial resolution may also be reduced positively. For their processing, the singular value decomposition (SVD), the regularization, the Wiener filtering, etc. are effective.

In addition, the encoding technology is also used for separating the simultaneously received signals into the respective signals, e.g., for a reception signal with respect to plural transmitted signals with different transmission positions. The waves to come from the different directions can be separated, and a signal source can be separated or identified. For both active and passive cases, the signal source can also be dealt with a diffracting object. In such cases, matched filtering that achieves a high signal detection is great. However, when signal energy is obtained, but on the other hand, the object movement with the deformation, and the object displacement and strain, etc. decrease the spatial resolution of signals, and therefore, the measurement accuracy is decreased as well. For the separation of waves and signals, the use of a frequency and a bandwidth or multi-dimensional spectra is also useful.

For imagings with the waves mentioned above, the distribution of amplitude data provided through a quadrature detection and an envelope detection or a square detection is displayed as a gray image and a color image in one dimension, two dimensions or three dimensions, and the imaging often provides morphologic images. In addition, the functional observation is also possible, and for instance, a raw coherent signal is processed in the Doppler measurement using those waves (ultrasound Doppler, Radar Doppler, Laser Doppler, etc.).

In addition, for instance, there is no information of a tissue displacement direction, but the power Doppler used in the medical ultrasound field can detect a tissue with the movement, which is a useful technique. In addition, when using a microwave, a terahertz wave or far infrared rays, the temperature distribution of object can be observed. Those measured physical quantities can be displayed with superposing them on morphologic images. In the field of the image measurement, observation of the movement can also be performed using the incoherent signal obtained through detection of a coherent signal (cross-correlation processing or optical flow, etc.). On a medical ultrasound and a sonar, imaging using harmonic waves, and chord and different tone waves generated physically are also carried out. Particularly when a measurement object is dynamic, real time characteristics are demanded for beamforming processing.

In addition, in satellite communications, radars, sonars, etc., beamforming is also performed to realize an informationally safe environment under the energy saving, and accurate communication is performed. In the ad hoc communication instruments and for mobile communications, beamforming has also been applied. Beamforming is also effective for an authorized person and a specific signal outbreak source, the specific communication with the position. In communications, information is put on a wave at the transmission side and sent to the reception side from the transmission side, which can be a purpose, the reception side can also reply to the transmission side by a result of the communication, and can also reply for the transmitted information and communicate again, but, of course, communications are not limited to these examples. When contents are dynamic, depending on a communication object and an observation object, real time characteristics are demanded, and it is demanded that the beamforming in that case is completed in a short time.

In such communication and medical fields, for instance, the present inventor develops ultrasonic imaging techniques for a differential diagnosis of lesions such as cancerous diseases, sclerosis, etc. of human tissues. The present inventor increases a spatial resolution in echo imaging and an accuracy in measurement and imaging of a tissue displacement; and the present inventor also increases a spatial resolution and an efficiency of HIFU (High Intensity Focus Ultrasound) treatment; and the present inventor also promotes those imagings based on the reception of the echo with respect to the HIFU radiation. Those imagings are based on performing appropriate beamforming at high speed and therefore, the present inventor develops and discloses appropriate, high-speed detection methods, tissue displacement measurement methods and shear wave propagation measurement methods, etc.

The medical ultrasound diagnosis imaging instrument passed more than 20 years after it was digitized. In old times, mechanical scanning was performed using a single aperture transducer (a single element); and subsequently electronic scanning using plural transducers (elements) and the array type devices consisting of them was performed, and the device which processed a signal changed from an analog device to a digital device afterwards. Actually, the classical synthetic aperture processing itself has been digital beamforming since those days when it came to be used in a radar carried by a satellite and an airborne, but it was rare to be used in a medical ultrasound instrument by the reason of the strength of the reception signal (echo intensity) being weak.

In contrast, in late years the present inventor invented the multidirectional synthetic aperture method and achieved multidirectional beamforming by using a reception echo data set for a conventional synthetic aperture method. As a result, lateral modulation imaging with a carrier frequency in the lateral direction orthogonal to an axial direction and with a higher spatial resolution than conventional imaging was enabled by becoming able to obtain multidirectional-steered image signals at the frame rate that was the same as that by the conventional electronic scanning, and the coherent superposition (compounding). The conventional focused beams, etc. can also be crossed, and non-focused waves such as a plane or spherical wave, etc. determined by a geometry of aperture or waves generated by virtual sources or receivers mentioned later can also be crossed. For achieving 2-dimensional (2D) lateral modulation imaging, usually 2 steered waves are crossed such that the waves become symmetric with respect to the axial or lateral coordinate used for the observation. For 3-dimensional (3D) lateral modulation imaging, 3 or 4 steered waves are crossed such that the waves become symmetric with respect to areas including both the axial coordinate and the lateral direction orthogonal to the axial axis of the coordinate system used for the observation (that is, the crossed waves are made symmetric with respect to the axial coordinate). Usually, the axial coordinate is set in the frontal direction of the aperture of an element of arrays or a physical aperture. Other axial coordinates can also be used. The wave can be generated in the positive or negative direction of the axial coordinate. The lateral coordinate can also be used as an axial coordinate for the sake of convenience.

Besides, a real time measurement was enabled for the displacement vector distribution by using the multi-dimensional autocorrelation method, the multi-dimensional Doppler method, the multi-dimensional cross-spectrum method, or the demodulation method that the present inventor invented together. In addition, speckle reduction was also enabled by performing incoherent superposition (compounding). Although conventionally transmission beams in different directions were used for the speckle reduction, the invented multidirectional synthetic aperture achieved a higher frame rate speckle reduction. In other sensing devices which use the waves such as a microwave, a terahertz wave, radioactive rays such as an X-ray, etc., other electromagnetic waves, vibration waves including a sound, a thermal wave, etc. for non-destructive evaluations other than those in ultrasound fields, digitization is pushed forward.

For instance, the synthetic aperture performed in those sensing instruments is an active beamforming, and the wave to be targeted for processing is a transmission wave, a reflection wave, a refraction wave, a diffraction wave or a scattered wave (forward or backward scattered wave, etc.) with respect to those waves generated by a transducer. As the diffraction waves, a wave generated by a transducer (a signal source) or others generated by a signal source can be processed. On the other hand, for instance, in a passive beamforming, a transmission wave, a reflection wave, a refraction wave or a scattered wave (forward or backward scattered wave, etc.) become targets under the assumption that all the waves are generated from a wave emitted from the signal source which is by oneself a divergence targeted for a measurement (self-emanating), so that a case to measure a temperature distribution based on the far infrared observation mentioned above and an electrical activity source by the brain magnetic field of the creature is also. Similarly to the active beamforming, a diffraction wave can also be processed. The examples corresponding to them exist much elsewhere. But recently photoacoustics is also targeted for a measurement of living things, and a laser is irradiated to an ultrasound creature as a measurement object (ultrasound source), i.e., a volume change caused by heat absorption with the laser frequency dependence generates an ultrasound, by which peripheral blood vessels can be distinguished as a result of reception beamforming, i.e., arteries or veins, for instance.

The digital instrument needs a lot of processing time in comparison with an analog instrument, but there are many advantages such as it being easy to implement high level calculation processing, being cheap and downsized including data storage medium, which improves calculation processing capacity and flexibility markedly. Actually, the high-speed analog processing performed immediately after having a received signal is extremely important, and it should be implemented with post-digital processing after AD conversion (Analogue-to-Digital conversion) relatively considered to be in around of the sensing device appropriately even if the instrument is called as a digital system.

In the analog instrument, the beamformings of the transmission and reception are carried out by analog processing. On the other hand, in the digital instrument, the transmission beamforming can be carried out by analog processing or digital processing, and the reception beamforming is carried out by digital processing. Thus, in the present invention, a beamformer performing reception beamforming by digital processing by all means is referred to as a digital beamformer.

After having received the waves from a measurement object through plural transducers (elements), an array type device consisting of them or mechanical scanning with one or more transducers (elements); DAS (Delay and Summation: phasing and summing) that is so-called synthetic aperture processing is carried out. For transmission, plural elements are excited to perform transmission beamforming, or a classical synthetic aperture processing is performed on the basis of one element transmission, whereas for reception beamforming, the DAS processing is performed commonly.

In other words, the transmission beamforming is carried out by analog processing or digital processing. On the other hand, in the reception beamforming, a reception signal is generated by each element in the array or by each element of the different position; and is AD converted into a digital reception signal after level adjustment of signal amplitude by the analogue amplification or attenuation, or analog filtering, etc.; and the digital reception signal of each element is stored into a storage. Afterwards a device or computer, PLD (Programmable Logic Device), FPGA (Field-Programmable Gate Array), DSP (Digital Signal Processor), GPU (Graphical processing Unit) or microprocessor, etc. with the general-purpose calculation processing capacity, or a dedicated computer, a dedicated digital circuit or a dedicated device, the digital processing is performed on the stored reception signals.

The device performing these digital processing can comprise those analog devices or AD converter, memory, etc. The device or computer with computing capacity can be multi-cores. These make it possible to carry out a dynamic focusing that is almost impossible with an analog device at the reception. The parallel computations can also be carried out. A transmission line (e.g., multilayer circuit, etc.) or a broadband wireless line is important on speeding up the analog processing and digital processing.

The dynamic focusing improves the spatial resolutions of generated image signals in a range direction or a depth direction for a measurement object. Alternatively, it is possible to perform a transmission dynamic focusing only when performing a classical synthetic aperture using one element transmission. In order to generate energy of a transmitted wave, a fixed focus transmission is often performed using plural excited elements instead of the synthetic aperture using the one element transmission.

The present inventor developed a high frame rate echo imaging that allowed interrogating a large region using one transmission by using a lateral wide wave such as a plane wave, etc. Moreover, the present inventor realized lateral modulation and increasing a lateral bandwidth (a lateral spatial resolution) by performing coherent compounding (superposition) of plural waves with different steering angles. Particularly when using the above-mentioned autocorrelation method, etc., the following displacement vector measurements are enabled, a shear wave propagation, a rapid blood flow in a carotid, a complex flow in a heart, etc. When performing the multidirectional synthetic aperture or the transmission beamforming, similarly the imaging and measurement can be achieved. Or, superposing plural waves with different carrier frequencies can also realize increasing an axial bandwidth (an axial spatial resolution).

For an active beamforming, these processings are performed, whereas for a passive beamforming, a transmitter is not used. Thus, a digital beamformer is comprised of a transmitter (an active beamforming case), a receiver and a DAS processing device, which is realized by building up them. Recently, they are packaged into a small size and can be used.

Phasing in the DAS processing can performed with a high speed by implementing delays onto a received echo signals via spatial approximate interpolations in a spatial domain, whereas the delays can also be implemented with a high accuracy, but with vast time, on the basis of the Nyquist theorem via phase rotations using multiplications of complex exponential functions in a frequency domain (a present inventor's past invention). After the phasing, the received signals are summed in a spatial domain (phasing and summing). In a digital instrument, for instance, a command signal generated by a control unit and used for transmitter's generating a transmission signal sent to an element to be driven can be used as a trigger signal for digital sampling of an analogue received signal (AD conversion).

When driving plural elements with transmission delays for a beamforming, one of analogue or digital transmission delay patterns set on a transmit unit in advance can be used for realizing a transmission focus position or a direction of steering, etc. to be chosen by an operator. Moreover, in a received digital processing, a command signal used for driving an element at first, at last or other can be used as a trigger signal for starting the sampling of received signals; and the digital delays can be implemented on the digitized, received signals. The command signals can be generated on the basis of a command signal used for starting beamformings for a frame.

When implementing a digital delay for a transmission delay, an error determined by a clock frequency that generates a digital control signal, which is different from when performing an analogue delay. Thus, for a transmission delay, an analogue delay should be implemented. Alternatively, because for performing a reception dynamic focusing, when implementing a digital delay on to a received signal, an error is caused by the above-mentioned interpolation approximation, the sampling frequency of an AD converter is made sufficiently high with a high cost, or the above-mentioned high accuracy digital delay (phase rotation processing) must be implemented, which leads a low speed beamforming.

The phasing and summing performed with the interpolation approximations can be achieved by simply adding echo signals of positions including the position of which an echo signal is synthesized, or by performing interpolations such as a bi-linear or a polynomial fitting, etc. to increase the accuracy of the synthesized echo signal. Such beamformings are much faster than the high accuracy phasing and summing using complex exponential functions, but the accuracy is lower than that of the high accuracy phasing and summing. The high accuracy phasing and summing is much slower. The phasing and summing are performed under the condition that the wave propagation speed is known or under using of an assumed wave propagation speed, for instance, a constant speed in a region of interest (ROI). Alternatively, phase aberration correction can also be performed via measuring of the wave propagation speed. For instance, the phase aberration can be calculated via estimating a cross-correlation function between adjacent beam signals or beam signals with different steering angles. When the wave propagation speed is homogeneous, interferometry analysis is achieved.

When the aperture elements exist in a 2D region or a 3D space, or a 2D or 3D array is comprised of the aperture elements, the further more processings are required for the beamforming and many processors are used for parallel processing, etc. than when the aperture elements exist in a 1D region or a 1D array is comprised of the aperture elements. For the beamforming performed at positions that yield less interferences of transmission waves, the transmission beamforming of plural different directions (different steering angles), a transmission beamforming solo, parallel reception beamforming can be performed.

For the control of communication, being dependent on a kind of communication data and the data amount, and medium properties, a proper wave should be generated, and an optimized communication should be performed under the observation of them. Interfered waves can also be separated using an analogue device, or analogue or digital signal processing. Waves with controlled propagation directions, encodings, frequencies and/or bandwidths are important.

The present inventor's another invent similarly to the above-mentioned multidirectional synthetic aperture processing is to perform reception beamformings with plural directions with respect to one transmission beamforming; yielding a high frame rate. Also, for the beamforming, apodization can be important. For instance, the respective transmission and reception apodizations can be performed to decrease sidelobes; properly the apodizations should be performed because they have a relation of trade-off with a lateral resolution. Alternatively, a simple beamformer with no apodization can also be used not to decrease the spatial resolution. However, the present inventor has been reporting that for the steering beamforming, proper apodizations are required to yield a high lateral resolution as well as suppressed sidelobes. The present inventor's previous invents include an approach that removing the sidelobes in a frequency domain.

Agents can be used to use nonlinear properties of waves propagating in an object. For instance, in a medical ultrasound field, microbubbles can be used. The present inventor invented imaging with a high spatial resolution and a high contrast by suppressing the sidelobes via transmitting high intensity waves or waves including harmonic waves, or implementing nonlinear processing onto received coherent signals or phased and summed coherent signals. The present inventor also invented a high accuracy tissue displacement (vector) measurement on the basis of the nonlinear processing.

Also imaging signals can also be generated using virtual sources. Regarding virtual sources, a virtual source set behind a physical aperture and a virtual source set at a focus position were reported previously. The present inventor also reported a virtual detector as well as a virtual source that is set at an arbitrary position, i.e., including not a focus position, and a proper scatter and a proper diffraction grid with an arbitrary position to be used as a physical wave source or a physical detector, etc. A high spatial resolution and a large field of vision (FOV) can be obtained.

For performing imaging, a quadrature detection, an envelope detection, or a square detection can be used. The present inventor makes much of the using of phase information, e.g., by displaying a waveform itself in a color or gray image. Thus, toward various purposes, various multi-dimensional systems using various waves are developed.

As far, several digital beamforming methods using the Fourier transform were disclosed. One of them is the digitized, analogue processing via the Fourier transform that is an analytic solution of a classical monostatic synthetic aperture (SA) (nonpatent document 1), i.e., the beamforming that performs the classical synthetic aperture with a high speed and a high accuracy by using the fast Fourier transform (FFT) (nonpatent document 2). In the processing, any approximate interpolation processing is not required. However, any digital processing for steering and a multistatic SA (receptions using plural elements, generally, including a transmission element and the surrounding elements) has not been disclosed yet.

All other digital beamforming methods disclosed perform approximate interpolation processings, and then yield low accuracies. For instance, for a plane wave transmission including a steered case, in which a wavenumber matching (mapping) via the FFT (nonpatent documents 3-5) and a non-flat aperture of an array (e.g., the array aperture geometry is an arc (nonpatent document 6)), the calculation and displaying require approximate interpolation processings, and yield low accuracies. The beamformings using the FFT for a plane wave transmission is also disclosed in patent documents 1-4, all of which perform the wavenumber matching via approximate interpolations. Multidimensional spectra are calculated on a wavenumber coordinate system with constant intervals via the approximate interpolations from directly calculated angular spectra, and the beamforming is completed by implementing the inverse FFT (IFFT).

In recently published nonpatent document 5, the non-uniform IFFT to be implemented on spectra with non-constant intervals is disclosed, which is also based on an approximate interpolation processing. As mentioned above, although such digital beamforming has already had a long history, because in a case where a real-time processing up to displaying an image is made much of, approximate interpolations are often performed, the highest accuracy is not always provided. Moreover, for the popular beamformings such as a fixed focus processing and steering, etc. known to be performed via the DAS processing, any processing method using the digital FFT has not been disclosed yet.

Also, the migration method is also reported (for instance, nonpatent document 7), which also requires approximate interpolation on the wavenumber matching. In order to achieve a high accuracy for these processings with approximate interpolations, sufficient over-samplings are performed by setting the analogue-to-digital (AD) sampling frequency high.

PATENT DOCUMENT LIST

[PATENT DOCUMENT 1] U.S. Pat. No. 5,720,708
[PATENT DOCUMENT 2] U.S. Pat. No. 6,685,641
[PATENT DOCUMENT 3] U.S. Pat. No. 7,957,609
[PATENT DOCUMENT 4] US patent applicant publication 2009/0036772
[PATENT DOCUMENT 5] U.S. Pat. No. 8,211,019
[PATENT DOCUMENT 6] U.S. Pat. No. 7,775,980
[PATENT DOCUMENT 7] US patent applicant publication 2011/0172538
[PATENT DOCUMENT 8] JP patent 5,441,292
[PATENT DOCUMENT 9] U.S. Pat. No. 9,326,748
[PATENT DOCUMENT 10] U.S. Pat. No. 7,690,838
[PATENT DOCUMENT 11] U.S. Pat. No. 9,084,559
[PATENT DOCUMENT 12] U.S. Pat. No. 7,868,824

NONPATENT DOCUMENT LIST

[NONPATENT DOCUMENT 1] J. W. Goodman, "Introduction to Fourier Optics" $2^{nd}$ ed., McGraw-Hill Co, Inc., 1996
[NONPATENT DOCUMENT 2] L. J. Busse, IEEE Trans. UFFC, vol. 39, no. 2, pp. 174-179, 1992
[NONPATENT DOCUMENT 3] J. Cheng, J.-y. Lu, IEEE Trans. UFFC, vol. 53, no. 5, pp. 880-899, 2006
[NONPATENT DOCUMENT 4] H. Peng, J.-y. Lu, X. Han, Ultrasonics, 44, e97-e99, 2006
[NONPATENT DOCUMENT 5] P. Kruizinga et al, IEEE Trans. UFFC, vol. 59, no. 12, pp. 2684-2691, 2012
[NONPATENT DOCUMENT 6] M. A. Haun, D. L. Jones, W. D. O'Brien, Jr., IEEE Trans. UFFC, vol. 49, pp. 861-870, 2002
[NONPATENT DOCUMENT 7] C. Sumi, IEEE Trans. UFFC, vol. 55, pp. 2607-2625, 2008
[NONPATENT DOCUMENT 8] C. Sumi, S. Uga, "Effective ultrasonic virtual sources which can be positioned independently of physical aperture focus positions," Rep. Med. Imag., vol. 3, pp. 45-59, 2010
[NONPATENT DOCUMENT 9] M. Soumekh, "Fourier Array Imaging," PTR Prentice Hall, Englewood Cliffs, N.J. 07632, 1994
[NONPATENT DOCUMENT 10] S. Haykin, A. Steinhardt ed. "ADAPTIVE RADAR DETECTION AND ESTIMATION," John Wiley & Sons, inc. New York. 1992
[NONPATENT DOCUMENT 11] K. W. Hollman, K. W. Rigby, M. O'Donnell, "Coherence Factor of Speckle from a Multi-Row Probe," Proc. of IEEE Ultrasonics Symp, pp. 1257-1260, 1999
[NONPATENT DOCUMENT 12] D. Garcia, L. L. Tarnec, S. Muth, E. Montagnon, J. Poree, G. Cloutier, IEEE Trans. UFFC, vol. 60, no. 9, pp. 1853-1867, 2013
[NONPATENT DOCUMENT 13] C. Sumi, IEEE Trans. UFFC, vol. 55, pp. 24-43, 2008
[NONPATENT DOCUMENT 14] C. Sumi, Y. Ishii, Rep. Med. Imag., vol. 5, pp. 57-101, 2012
[NONPATENT DOCUMENT 15] C. Sumi, IEEE Trans. UFFC, vol. 46, pp. 158-166, 1999
[NONPATENT DOCUMENT 16] S. Srinivasan, F. Kallel, and J. Ophir, Ultrasound Med. Biol., vol. 28, pp. 359-368, 2002
[NONPATENT DOCUMENT 17] C. Sumi, IEEE Trans. UFFC, vol. 55, pp. 297-307, 2008
[NONPATENT DOCUMENT 18] C. Sumi and K. Sato, IEEE Trans. UFFC, vol. 55, pp. 787-799, 2008
[NONPATENT DOCUMENT 19] C. Sumi, Y. Takanashi, K. Ichimaru, Rep. Med. Imag., vol. 5, pp. 23-50, 2012
[NONPATENT DOCUMENT 20] C. Kasai, K. Namekawa, A. Koyano, R. Omoto, "Real-Time Two-Dimensional Blood Flow Imaging Using an Autocorrelation Technique," IEEE Trans. On Sonics and Ultrasonics, vol. 32, pp. 458-464, 1985
[NONPATENT DOCUMENT 21] J. A. Jensen, "FIELD: A Program for Simulating Ultrasound Systems," Med, Biol, Eng, Comp, $10^{th}$ Nordic-Baltic Conference on Biomedical Imaging, Vol. 34, Supplement 1, Part 1, pp. 351-353, 1996
[NONPATENT DOCUMENT 22] B. Schrope, V. L. Newhouse, V. Uhlendorf, "SIMULATED CAPILLARY BLOOD FLOW MEASUREMENT USING A NONLINEAR ULTRASONIC CONTRAST AGENT," Ultrason. Imag., vol. 14, pp. 134-158, 1992
[NONPATENT DOCUMENT 23] P. N. Burns, S. R. Wilson, D. H. Simpson, "Pulse Inversion Imaging of Liver Blood Flow: Improved Method for Characterizing Focal Masses with Microbubble Contrast," Investigative Radiology, vol. 35, no. 1, pp. 58-71, 2000
[NONPATENT DOCUMENT 24] M. A. Averkiou, D. N. Roundhill, J. E. Powers, "A NEW IMAGING TECHNIQUE BASED ON THE NONLINEAR PROPERTIES OF TISSUES," 1997 IEEE Ultrasonics symp, pp. 1561-1566, 1997
[NONPATENT DOCUMENT 25] B. Haider, R. Y. Chiao, "Higher Order Nonlinear Ultrasonic Imaging," 1999 IEEE Ultrasonics symp., pp. 1527-1531, 1999
[NONPATENT DOCUMENT 26] A. Needles, M. Arditi, N. G. Rognin, J. Mehi, T. Coulthard, C. Bilan-Tracey, E. Gaud, P. Frinking, D. Hirson, F. S. Foster, "NONLINEAR CONTRAST IMAGING WITH AN ARRAY-BASED MICRO-ULTRASOUND SYSTEM," Ultrasound Med. Biol., vol. 36, no. 12, pp. 2097-2106, 2010
[NONPATENT DOCUMENT 27] J. R. Doherty, G. E. Trahey, K. R. Nightingale, M. L. Palmeri, "Acoustic Radiation Force Elasticity Imaging in Diagnostic Ultrasound," IEEE Trans. on UFFC, vol. 60, no. 4, pp. 685-701, April 2013
[NONPATENT DOCUMENT 28] K. Hynynen, "DEMONSTRATION OF ENHANCED TEMPERATURE ELEVATION DUE TO NONLINEAR PROPAGATION OF FOCUSED ULTRASOUND IN DOG'S THIGH IN VIVO," Ultrasound Med. Biol. vol. 13, no. 2, pp. 85-91, 1987
[NONPATENT DOCUMENT 29] Y. Huang, N. I. Vykhodtseva, K. Hynynen, "CREATING BRAIN LESIONS WITH LOW-INTENSITY FOCUSED ULTRASOUND WITH MICROBUBBLES: A RAT STUDY AT HALF A MEGAHERTZ," Ultrasound Med. Biol., vol. 39, no. 8, pp. 1420-1428, 2013

[NONPATENT DOCUMENT 30] C. Sumi, "Utilization of an ultrasound beam steering angle for measurements of tissue displacement vector and lateral displacement," Reports in Medical Imaging, vol. 3, pp. 61-81, 2010

[NONPATENT DOCUMENT 31] A. K. Katsaggelos, K. T. Lay, "Maximum Likelihood Blur Identification and Image Restoration Using the EM Algorithm," IEEE Trans. Signal Processing, vol. 39, no. 3, pp. 729-733, 1991

[NONPATENT DOCUMENT 32] R. Molina, A. K. Katsaggelos, J. Mateos, "Bayesian and Regularization Methods for Hyperparameter Estimation in Image Restoration," IEEE Trans. Image Processing, vol. 8, no. 2, pp. 231-246, 1999

[NONPATENT DOCUMENT 33] M. Nikolovia, "Markovian Reconstruction Using a GNC Approach," IEEE Trans. Image Processing, vol. 8, no. 9, pp. 1204-1220, 1999

[NONPATENT DOCUMENT 34] R. Molina, Javier Mateos, A. K. Katsaggelos, M. Vega, "Bayesian Multichannel Image Restoration Using Compound Gauss-Markov Random Fields," IEEE Trans. Image Processing, vol. 12, no. 12, pp. 1642-1654, 2003

[NONPATENT DOCUMENT 35] H. Kokubo, S. Yagi, K. Nakayama, "High resolution ultrasonic imaging using 2-D echo filtering," J. of ASJ, vol. 47, no. 7, pp. 443-450, 1991

[NONPATENT DOCUMENT 36] T. Morohoshi, K. Nakayama, S. Yagi, A. Suzuki, "High Resolution Ultrasonic Imaging Utilizing AR-Estimated Point Spread Function," IEICE, vol. J76, no. 2, pp. 233-240, 1993

[NONPATENT DOCUMENT 37] C. L. Chan, A. K. Katsaggelos, "Iterative Maximum Likelihood Displacement Field Estimation in Quantum-Limited Image Sequences," IEEE Trans. Image Processing, vol. 4, no. 6, pp. 743-751, 1995

[NONPATENT DOCUMENT 38] J. C. Brailean, A. K. Katsaggelos, "Simultaneous Recursive Displacement Estimation and Restoration of Noisy-Blurred Image Sequences," IEEE Trans. Image Processing, vol. 4, no. 9, pp. 1236-1251, 1995

[NONPATENT DOCUMENT 39] Y.-L. You, M. Kaveh, "Blind Image Restoration by Anisotropic Regularization," IEEE Trans. Image Processing, vol. 8, no. 3, pp. 396-407, 1999

[NONPATENT DOCUMENT 40] T. Chan, C.-K. Wong, "Total Variation Blind Deconvolution," IEEE Trans. Image Processing, vol. 7, no. 3, pp. 370-375, 1998

[NONPATENT DOCUMENT 41] F. Sroubek, J. Flusser, "Multichannel Blind Iterative Image Restoration," IEEE Trans. Image Processing, vol. 12, no. 9, pp. 1094-1106, 2003

[NONPATENT DOCUMENT 42] Miles N. Wernick et al, "Fast Spatio-Temporal Image Reconstruction for Dynamic PET," IEEE Trans on Medical Imaging, vol. 18, pp. 185-195, 1999

[NONPATENT DOCUMENT 43] A. K. Katsaggelos, J. Biemond, R. W. Schafer, R. M. Mersereau, "A Regularized Iterative Image Restoration Algorithm," IEEE Trans Signal Processing, vol. 39, pp. 914-929, 1991

[NONPATENT DOCUMENT 44] C. Sumi, "Determination of Lateral Modulation Apodization Functions Using a Regularized, Weighted Least Squares Estimation," Int. J. Biomed. Imag, ID: 635294 (7 pages), 2010

[NONPATENT DOCUMENT 45] C. Sumi, Y. Komiya, S. Uga, "A Demonstration of Optimal Apodization Determination for Proper Lateral Modulation," Jpn J. of Appl. Phys., vol. 48(7B), ID: 07GJ06 (10 pages), 2009

SUMMARY OF THE INVENTION

Technical Problem

As explained above, because when performing the reception dynamic focusing by implementing the digital delays at the reception, errors occurs due to the above-mentioned approximate interpolations, the AD sampling frequency is made high with a high cost, or the low speed beamforming must be performed by implementing the above-mentioned high accuracy digital delays on signals (phase rotation processing).

As far, for waves such as electromagnetic waves, vibration (mechanical) waves such as acoustic waves (compressible waves), shear waves and surface waves, etc., and thermal waves, etc., disclosed digital beamforming methods on waves such as reflection and transmission waves, scattering waves (forward and backward scattering, etc.), refractions, diffraction waves, surface waves, ballistic waves, or waves generated by self-emanating sources are limited to the monostatic SA with no steering, the plane wave transmission including a steering case, and the migration method as mentioned above. Also, except for the monostatic SA, all the digital beamforming methods require approximate interpolations; yielding low accuracies.

In contrast to these, when using a transmission or reception transducer array device with an arbitrary aperture geometry (the transducer can also be used for both transmission and reception; different waves can be respectively dealt with for the transmission and reception), or when using only the reception transducer for the passive beamforming, regardless the using the transmission and reception focusing or steering, and for the cases where the coordinate systems are different for the transmissions and receptions of beams and the displaying images, an arbitrary beamforming should be realized with a high speed and a high accuracy with no approximate interpolate calculations.

For the active beamforming, array-type transmission and reception transducer devices with arbitrary aperture geometries are used (one device may be used for both transmission and reception). For the passive beamforming, only an array-type reception transducer device with an arbitrary aperture geometry is used. For the beamforming, arbitrary beamforming is desired to be performed with a high speed and with a high accuracy via digital processing. In practice, arbitrary focusings and arbitrary steerings are desired to be performed using array-type transducer devices with arbitrary aperture geometries.

After beamforming with phasing and summing, linear or nonlinear signal processing is implemented on plural beams with at least one different wave parameter among a frequency, a bandwidth, a pulse shape, a beam shape, etc. in each direction in order to yield a new beam with at least one different wave parameter (in various fashions such as frequency modulation, widebanding, multi-focusing, etc.). In beamformings like these, focusing, steering and apodization can be performed via the DAS processing using arbitrary array-type transducer devices with arbitrary aperture geometries. Or, as mentioned later, linear or nonlinear phenomena generated in media can yield a new beam with at least one different wave parameter among the wave parameters and the new wave can also be used.

Because the propagation speed of a wave is determined by the properties of a medium under physical conditions, when the multi-dimensional array comprising of 2D or 3D distribution of aperture elements is used for multi-dimensional space imaging, due to increasing the number of beams and data required for generating one beam, it takes much longer time to complete beamforming. Thus, a real-time processing instrument or an instrument that displays results in a short time should be used by obtaining a high speediness in beamforming.

As far, regarding digital beamformings using Fourier transform, mainly the beamformings to be achieved via approximate interpolations on the Cartesian coordinate system using a 1D or 2D linear array-type transducer is disclosed. However, including the cases where coordinate systems are different for transmission, reception and display, digital beamformings are desired to be performed not with approximate interpolations at all.

Also, the methods disclosed for cases where the geometry of an array aperture is not flat (for instance, the geometry of an array aperture is an arc) requires approximate interpolations. For instance, as typical cases, for using a convex-type transducer, an electric or mechanical sector scan or an IVUS scan (intravascular ultrasound), beamformed data are required to be generated directly on arbitrary display coordinate systems such as the Cartesian coordinate system by implementing digital processings on signals received on arbitrary coordinate systems such as the polar coordinate system.

Although recently a memory and an AD convertor became remarkably cheap, by sampling a wave on the basis of the Nyquist theorem, however, without over-sampling of data, the beamforming is desired to be completed with a higher speed than the beamforming with the DAS processing. The apodization is also required to be performed properly.

By solving these problems, it is desired to achieve a high spatial resolution and a high contrast including the effects of suppressing sidelobes in image signals obtained in a real-time or in a short time. Moreover, it is desired to achieve high accuracy measurements of target's motion (displacement) or deformation, or temperature, etc. from the obtained signals. For instance, recently in a medical ultrasound field, after measuring a tissue displacement or velocity by applying the Doppler method to echo signals, by applying temporal or spatial derivatives to these measurements, a tissue acceleration or strain, etc. is calculated and displayed. Since the temporal or spatial derivative is a processing that amplifies high frequency measurement errors and decreases an SNR (Signal-to-Noise ratio), the displacement measurement accuracy must be made high by using the signal phase. As far, as the high accuracy beamforming, the dynamic focusing on the basis of the so-called DAS processing was used. The 3D imaging instrument using a 2D or 3D array tends to spread. Thus, it is desired to achieve arbitrary beamformings including the dynamic focusing with high speeds and high accuracies without approximate interpolations.

Recently, the present inventor realized high accuracy measurement methods of a rather high-speed tissue motion or shear wave propagation on the basis of high-speed beamformings using steered plane wave transmissions (high-speed transmission and reception of signals from an ROI). Also, for such beamformings with no focusing, it is desired to complete the beamformings with high speeds and high accuracies with no approximate interpolations. By performing high-speed beamformings with changing a steering angle and coherent superposition of them, it is made possible to yield almost the same image qualities (a spatial resolution and a contrast) as those of conventional focused beamforming, however, with a higher speed. Such high-speed beamformings are also effective for the multi-dimensional imaging using a multi-dimensional array.

Also, it is desired to achieve the steering using a classical SA (monostatic type) on the basis of scanning with driving each one transmission element and the multistatic SA with high speeds and high accuracies without approximate interpolations. Also, when using so-called migration processing, similarly it is desired to perform arbitrary beamformings on arbitrary coordinate systems with high speeds and high accuracies with no approximate interpolations. Other concrete examples of beamformings to be realized are described in other parts of the present patent document, similarly which are also desired to be performed with high speeds and high accuracies.

One of the purposes of the present invention is that it is made possible, while using instruments with digital operational functions as digital beamformers, to perform arbitrary beamformings with high speeds and high accuracies with no approximate calculations. According to the invention, for instance, the below-described various applications of waves including superresolution imaging using nonlinear processing, etc. can be made performable. The applications also include various others such as imagings, displacement measurements, temperature measurements, etc. In order to make it possible to perform such applications with high speeds, new processings with much higher speeds and much simpler calculations than the high accuracy and high speed Hilbert transform processing using the multi-dimensional Fourier transform (nonpatent document 13: the method for performing the multi-dimensional inverse Fourier transform with respect to the octant and quadrant spectra in the 3D and 2D cases, respectively, obtained by padding zero spectra in the frequency domains to the spectra obtained by performing the multi-dimensional Fourier transform for the multi-dimensional reception signals.).

Particularly, for the displacement measurement, as displacement vector observation methods, the multi-dimensional autocorrelation method, the multi-dimensional Doppler method (nonpatent document 13), the multi-dimensional cross-spectrum phase gradient method (patent document 6 and nonpatent document 15, etc.), the usual demodulation method (patent documents 7 and 8), the nonlinear processing method, the spectral division method, the multi-dimensional phase matching method, the method for increasing a bandwidth via coherent superposing, the over-determined method, etc. have been developed, in which particularly the usual demodulation method to be performed with the lateral modulation is required to be improved for increasing the measurement accuracy much. Actually, the demodulation disclosed in the patent documents 7 and 8 has a problem that the measurement accuracy decreases in a practice since the waves do not become symmetric strictly in a practice even if waves are generated to be symmetrically crossed by steerings (beamforming) with respect to the axes of an axial direction or the lateral direction orthogonal to the axial direction of the orthogonal coordinate system to be used for the observation (i.e., axial and lateral axes, respectively) and areas including the axial axis and the lateral direction orthogonal to the axial axis (i.e., All waves are to be symmetric with respect to the axial direction.) in the 2D and 3D lateral modulation cases, respectively. Moreover, it becomes impossible to perform the observations when performing the steering the central axis of the steered waves from the frontal direction of the aperture. Furthermore, a measurement error also occurs when the instantaneous frequencies or the local spectral 1st moments (center frequencies) in the propagation directions of generated, steered waves (the waves themselves' frequencies) differ each other.

Solution to Problem

The present invention has been achieved to solve at least one portion of the above-mentioned problem. A measurement and imaging instrument according to the first aspect of the present invention includes: reception means configured to receive, when at least one wave is transmitted from at least one wave source positioned in an arbitrary direction to a measurement object, a wave arriving from the measurement object by using at least one reception aperture element to generate at least one reception signal; and an instrument main body configured to perform a lateral modulation in beamforming processing of the at least one reception signal generated by the reception means to generate a multi-dimensional reception signal, and perform a Hilbert transform with respect to the generated multi-dimensional reception signal, wherein the instrument main body performs the lateral modulation while superposing two waves in a two-dimensional case and three or four waves in a three-dimensional case in an orthogonal coordinate system using coordinates of an axial direction determined by a direction of an aperture of an arbitrary reception aperture element array and at least one lateral direction orthogonal to the axial direction in the beamforming processing in which at least one wave arriving from the measurement object is processed as being transmitted or received in the axial direction or directions symmetric with respect to the axial direction, and performs a partial derivative processing or a one-dimensional Fourier transform in the axial or lateral direction to generate analytic signals of the respective multi-dimensional reception signals of the two waves in the two-dimensional case and the three or four waves in the three-dimensional case.

Further, a beamforming method according to the second aspect of the present invention includes the steps of: (a) receiving, when at least one wave is transmitted from at least one wave source positioned in an arbitrary direction to a measurement object, a wave arriving from the measurement object by using at least one reception aperture element to generate at least one reception signal; (b) performing a lateral modulation in beamforming processing of the at least one reception signal generated at step (a) to generate a multi-dimensional reception signal; and (c) performing a Hilbert transform with respect to the multi-dimensional reception signal generated at step (b), wherein step (b) includes performing the lateral modulation while superposing two waves in a two-dimensional case and three or four waves in a three-dimensional case in an orthogonal coordinate system using coordinates of an axial direction determined by a direction of an aperture of an arbitrary reception aperture element array and at least one lateral direction orthogonal to the axial direction in the beamforming processing in which at least one wave arriving from the measurement object is processed as being transmitted or received in the axial direction or directions symmetric with respect to the axial direction, and step (c) includes performing a partial derivative processing or a one-dimensional Fourier transform in the axial or lateral direction to generate analytic signals of the respective multi-dimensional reception signals of the two waves in the two-dimensional case and the three or four waves in the three-dimensional case.

Furthermore, a beamforming method according to the third aspect of the present invention is a method for an arbitrary orthogonal coordinate system such as a Cartesian coordinate system using an axial direction x determined by a direction of an aperture of a reception aperture element array and a lateral direction x orthogonal to the axial direction x, in a case where an arbitrary wave is transmitted form a wave source positioned in an arbitrary direction to a measurement object and a wave arrival from the measurement object is processed as a transmission beamforming with a steering angle θ defined with respect to the axial direction being zero or nonzero degree, and the wave arrival from the measurement object is reception-dynamic-focused with a steering angle φ defined with respect to the axial direction being zero or nonzero degree, and the beamforming method includes the steps of: (a) where the wave arrival from the measurement object is received at least by a reception aperture element to generate a reception signal; and (b) where beamforming processing is performed at least by implementing Fourier transform and wavenumber matching with respect to the reception signal generated in step (a), wherein step (b) includes without performing wavenumber matching including approximate interpolation processings in a wavenumber domain or in a frequency domain with respect to the reception signal, and the reception signal is Fourier transformed in the axial direction y and the calculated Fourier transform is multiplied to a complex exponential function (101) expressed using a wavenumber k of the wave and a wave number $k_0$ expressed by a carrier frequency $\omega_0$ as $k_0$ ($=\omega_0/c$) and imaginary unit i to perform wavenumber matching in the lateral direction x, $$\exp\{i(k \sin \theta + k_0 \sin \phi)x\} \quad (101)$$

and further, the product is Fourier transformed in the lateral direction x and the calculated result is multiplied to a complex exponential (102), from which an effect of the lateral wavenumber matching is removed, to yield a spatial resolution in the axial direction y and simultaneously multiplied to a complex exponential function (103) as well to perform wavenumber matching in the axial direction y, and the lateral wavenumber is expressed as $k_x$, $$\exp(i\sqrt{k^2-(k_x-k\sin\theta-k_0\sin\phi)^2}y) \quad (102)$$

$$\exp[i\{k \cos \theta + k_0(-1+\cos \phi)\}y] \quad (103)$$

by which the wavenumber matching is performed with no approximate interpolations, and an image signal is generated on the Cartesian coordinate system directly.

The present invention includes instruments and methods that are used for performing arbitrary beamformings on arbitrary coordinate systems with a high speed and a high accuracy, and without approximate calculations required for general digital processings, on the basis of properly using the FFT, the multiplications of complex exponential functions and the Jacobi operation. In order to solve the problem, With respect to the waves such as the electromagnetic waves, vibration waves (mechanical waves) such as sounds (compressible waves), shear wave, surface wave, etc., or the thermal wave, etc., for the reflection waves, the transmission waves, the scattering waves (forward or backward scatterings, etc.), the refraction waves, the diffraction waves, the surface waves, the ballistic waves, the waves generated by self-emanating wave sources, the waves transmitted from moving bodies, or the waves arrived from unknown wave sources, etc., to be observed, proper digital processing algorithms implemented on digital circuits or softwares, or analogue or digital hardwares are used.

The hardware includes an instrument that equips an operational function that allows digital wave signal processing as well as a phasing and summing device that is used in a general beamformer of each wave instrument, in which the softwares of the present invention can be implemented, or digital circuits that performing the operations can be used. As mentioned later, other required devices are, at least, transducers, transmitters, receivers, and storage devices of received signals, etc., which are used in general. Waves such as harmonic waves can also be dealt with. Beamformings using virtual sources and virtual receives can also be performed. Parallel processing can also be performed for generating plural beams simultaneously.

The present invention uses analogue devices such as the above-mentioned analogue amplifiers or attenuators for controlling a signal level, analogue filters, etc., and effective applications of analogue signal processing devices (linear and specific nonlinear devices for modifying a wave shape by such as enhancing or decreasing of wave properties of a driving signal), and for performing digital processing on stored signals, the above-mentioned devices or calculators, PLDs (Programmable Logic Devices), FPGAs (Field-Programmable Gate Arrays), DSPs (Digital Signal Processors), GPUs (Graphical Processing Units), microprocessors, etc. that equip general calculation capabilities, and also exclusive calculators and exclusive digital circuits, or exclusive devices.

It is important that not only such analogue devices, AD convertors, memories, devices that perform digital signal processing (multi-cores, etc.) are highly efficient but also the number of communication channels between devices, channel capacities, wirings, wideband wireless communications. In particular, in the present invention, it is desired that such functional devices are installed into a chip or a circuit board (the devices may be detachable), or the devices are directly implemented into a chip or a circuit board (including a multilayer type). Parallel processings are also important. When a calculator also plays a role of a controller unit, if the device is not detachable, a remarkably higher security can be achieved than that obtained under a general programmed control. In a contrary, under the existing legislation, cases where disclosing of processing contents is demanded will increase.

Advantageous Effects of Invention

According to some aspect of the present invention, overcome can be the problem of the usual demodulation method (patent documents 7 and 8), for a displacement vector observation with a 2D or 3D lateral modulations, that the measurement accuracy decreases in a practice since the waves do not become symmetric strictly in a practice even if waves are generated to be symmetrically crossed by steerings (beamforming) with respect to the axes of an axial direction or the lateral direction orthogonal to the axial direction of the orthogonal coordinate system to be used for the observation (i.e., axial and lateral axes, respectively) and areas including the axial axis and the lateral direction orthogonal to the axial axis (i.e., All waves are to be symmetric with respect to the axial direction.). That is, the measurement accuracy increases much. Moreover, overcome can also be the problem that it becomes impossible to perform the observations when performing the steering the central axis of the steered waves from the frontal direction of the aperture. That is, various beamformings can be used for the displacement vector measurement with the demodulation processing. Furthermore, overcome can also be the problem that a measurement error also occurs when the instantaneous frequencies or the local spectral 1st moments (center frequencies) in the propagation directions of generated, steered waves (i.e., the waves themselves' frequencies) differ each other. The measurement accuracy increases.

In addition, according to some aspect of the present invention, by performing new Hilbert transforms using the (partial) differential processing or the (fast) Fourier transform, it becomes possible to perform various applications with a high speed such as the imaging of waves, the displacement (vector) measurement, the temperature measurement, etc. (The former is faster than the latter.).

When generating plural beams or waves with different wave parameters such as an ultrasound, etc. or beamforming parameters at every temporal phase, since the number of performing beamformings and Hilbert transforms due to increasing the reception signals received by the reception transducer, the new Hilbert transforms are effective. The new Hilbert transforms are also effective when a beamforming is performed at once for a superposition of reception echo signals received by the reception transducer. The high speediness of new Hilbert transforms becomes further effective in a case where the physical aperture element comprises a 2D or 3D distribution or a multi-dimensional array since the new transforms efficiently overcomes the problem that much longer processing time is required.

In addition, it is made possible, by using a fast Fourier transform while using instruments with digital operational functions as digital beamformers, to perform arbitrary beamformings with high speeds and high accuracies with no approximate calculations (Fourier beamforming). As explained later in detail, the present invention realizes, on the basis of proper using of the multiplications of complex exponential functions and the Jacobi operation, arbitrary beamformings on arbitrary orthogonal coordinate systems including a curvilinear coordinate system with high speeds and high accuracies with no approximate interpolations. When generating plural beams or waves with different wave parameters such as an ultrasound, etc. or beamforming parameters, a beamforming can be performed at once for a superposition of reception echo signals received by a reception transducer.

Although the DAS (Delay and Summation) processing also realizes arbitrary beamformings including conventional beamformings, when using a 1D array-type physical aperture and a general PC (personal computer), at least the present invention makes the calculation speeds 100 times as high as those achieved using the DAS processing. When the aperture elements distribute in a 2D or 3D space or comprise a multi-dimensional array, the present invention efficiently solve the problem that it takes more processing times in the multi-dimensional cases than in the 1D case, i.e., the increasing the speediness of beamforming becomes more efficient. Off course, the DAS processing can also be used.

That is, the present invention uses a transmission or reception transducer array device with an arbitrary aperture geometry (it may be used for both transmission and reception) or a sensor array device, and allows arbitrary beamformings with high speeds and high accuracies and with no approximate interpolations via digital processing. In practical, arbitrary focusings, arbitrary steerings, arbitrary apodizations can be performed with array devices with arbitrary aperture geometries.

For instance, in a field of medical ultrasound imaging, according to observation targets, a coordinate system on which physical transmission and reception and digital sampling are performed is selected such as a Cartesian coordinate system for a linear array-type transducer and a polar coordinate system popular for a convex type transducer, a sector scan, or an IVUS (intravascular ultrasound). For instance, for observing heart dynamics between ribs, the sector scan is performed generally. An aperture of not a transducer with an array-type aperture geometry but a PVFD (polyvinylidene fluoride) based transducer may be deformable. That is, the present invention allows obtaining signals directly beamformed on arbitrary coordinate systems such as image displays, etc. with no approximate interpolations by processing digital signals obtained from waves transmitted and received on arbitrary coordinate systems. Composite transducer comprising of PVDF that allows generating a high frequency ultrasound and PZT (Pb (lead) zirconate titanate) that allows generating a high power ultrasound (however, with a low frequency) can also be used as a wide-band transducer or a transducer that allows generating plural frequency ultrasounds. As transducers that allows generating plural frequency ultrasounds, an array with elements of different dimensions, kerfs or thicknesses, or a lamination layer of array comprised variously can also be used.

For the multistatic SA, echo data frames with the number of reception elements are made from echo signals received at a same position within plural reception positions with respect to a transmission position, each of which echo data frame are processed by the monostatic SA of the present invention and finally the IFFT is implemented on the superposition of all the monostatic SA results. That is, echo data can be generated by performing the monostatic SA processings with the same number as that of received channels. Thus, it takes shorter time to complete the beamforming (a higher speed) than the DAS method, known as the general multistatic type method, that yields high spatial resolution image signals by generating low spatial resolution image signals to be superposed.

And on the basis of the multistatic processing of the present invention, the reception dynamic focusing and steering can also be performed, with respect to the popular fixed transmission focusing, with a high speed and a high accuracy. All the beamformings can be achieved by implementing the proper phase rotation processings using the multiplications of complex exponential functions.

Also, regarding a coordinate system, the present invention also allows, on the basis of performing the Jacobi operation on the Fourier transform, generating echo data directly on a Cartesian coordinate system used for the display with a high speed and a high accuracy with no approximate interpolations, for instance, for performing the signal processing on the convex or sector scan, IVUS.

Using the present invention, when using the so-called migration processing, similarly arbitrary beamformings can be performed on arbitrary coordinate systems with high speeds and high accuracies with no approximate interpolations. The present invention also allows the uses of virtual sources for performing high SNR and high spatial resolution imagings with high speeds. Moreover, the present invention also allows with high speeds and high accuracies, on the basis of digital signal processing, frequency modulating and widebanding of beams via linear or nonlinear processing, multi-focusing, parallel processing, virtual sources or receivers, etc. The present invention is also effective for optimizing beamformings that require much calculations.

The beamforming methods according to other aspects of the present invention includes various beamformings such as the Fourier beamformings, DAS processings, etc., and among others, with using plural elements positioned adjacently or positioned far in array-type effective aperture elements (The respective elements have independent transmission or reception channels such that the respective elements can be driven independently, and can also be used for independently receiving reception signals.) as one aperture (element) by setting the same transmission and/or reception delay and/or the same transmission and/or reception apodization onto the plural elements (channels). For the transmission and reception beamformings, this processing allows using larger magnitude waves than those generated by one element. For instance, for a 1D array-type transducer, when the element width and/or the element pitch is shortened to increase the spatial resolutions in the axial and lateral directions, the magnitudes of transmission and reception waves become small. For a medical ultrasound, an element pitch (synthesized or physical one) approximately to 0.1 mm or the smaller pitch realizes a high accuracy displacement vector measurement. This is also when using a 2D or the higher dimensional transducer (The element widths and pitches of all dimensional directions become short.). For an ultrasound, when making the frequency to be generated higher by making the element thickness thin or when using a PVDF, etc. which yields a smaller transmission intensity than the PZT, etc., the intensities of the waves to be generated become small. In these cases, the processing is effective. When the element pitch is large, and the beamforming becomes to be performed with respect to aliased reception signals in the element array direction (originally, a digital space), the aliased bandwidth signals must be filtering out for spectra of reception raw signals (angular spectra) or those of beamformed signals. By making the element pitch small with making the element width small as mentioned above, the lateral bandwidth increases as confirmed for the angular spectra, the beamforming yields laterally large bandwidth signals. However, if an aliasing occurs, the processing is required to be performed similarly. These processings are required for all beamformings. Since the beamformed signals are generated within a bandwidth that can be confirmed for the angular spectra of raw reception signals, the maximum steering angle to be generated using the element array can also be confirmed form the angular spectra.

As mentioned above, regardless performing the transmission and reception focusing, and transmission and reception apodizations or not, the present invention allows, for waves such as electromagnetic waves, vibration (mechanical) waves such as acoustic waves (compressible waves), shear waves, ballistic waves, surface waves, etc., thermal waves, etc., arbitrary beamformings with high accuracies and high speeds on the basis of digital processings, even if the coordinate systems of transmissions/receptions and generations of beamformed signals are different each other.

Thus, not only the frame rates for displaying the images of beamformed signals increase but also, regarding image qualities, high spatial resolutions and high contrasts can be yielded. Moreover, using the beamformed signals, measurement accuracies on displacements, deformations, temperatures, etc. can also increase. The increase in a processing speediness yields a remarkable effect on the multi-dimensional imaging using a multi-dimensional array. The present invention relates to mathematical algorithms regarding wave propagations, which was obtained as products by leading to solutions with no approximate calculations even via performing the digital processings. These cannot be achieved simply.

BRIEF DESCRIPTION OF THE DRAWINGS

FIG. 3 shows illustrations of configurations of plural transmission aperture elements used in a transmission transducer;

FIG. 7 shows illustrations of cylindrical wave transmissions on polar coordinate system (r,θ) (transmissions of waves, in a radial (r) direction, widely spread in an angle direction (θ));

FIG. 8A shows illustrations of cylindrical wave transmissions on polar coordinate system (r,θ) (transmissions of waves, in a radial (r) direction, widely spread in an angle direction (θ)) from virtual sources set behind physical apertures with arbitrary aperture geometries; and FIG. 8B shows illustrations of positions of physical apertures with arbitrary aperture geometries, or other apertures or waves generated in front of or behind the physical apertures;

FIG. 16 shows a schematic for explaining an illustration of the phase aberration correction when not performing a steering with a 1D linear-array-type transducer;

FIG. 17 shows a schematic for explaining an illustration of the phase aberration correction when performing a steering with a 1D linear-array-type transducer;

FIG. 19 shows for a 2D case a schematic of a motion compensation performed by moving a searching region set in the next frame with respect to a frame of interest by a displacement vector estimate obtained for a point of interest or a local region including a point of interest;

FIGS. 23A and 23B show images obtained using method (1) for steered plane wave transmissions;

FIG. 26 shows images obtained for steered plane wave transmissions with method (1) together with a compounding method;

FIG. 28 shows images obtained for steered plane wave transmissions with method (6), i.e., the migration method;

FIG. 29 shows images obtained using method (2), i.e., monostatic SA;

FIG. 30 shows images obtained using method (3), i.e., multistatic SA;

FIG. 32 shows images obtained using method (4), i.e., fixed focusing transmissions;

FIG. 33 shows images obtained for a cylindrical wave transmission using a convex-type array with method (5-1), and for a cylindrical wave transmission using a linear-type array with method (5-1');

FIG. 34 shows images obtained using a convex-type array with method (5-2), i.e., fixed focusing transmissions;

FIG. 36 shows an illustration in a 3D case, four steering beams and a lateral modulation yielded by superposing the four steering beams;

FIG. 39 shows illustrations of configurations of plural transducers;

FIG. 40 shows figures that explain various wave formations obtained using 1D transducer array;

FIG. 41 shows illustrations of a beam direction, an angle of a direction of arriving wave and the first moments of spectra in spatial and frequency domains in a 2D measurement case;

FIG. 49 shows for schematics of an original 2D orthogonal coordinate system of axial direction and lateral direction orthogonal to the axial direction a quasi-axial direction and a quasi-lateral direction orthogonal to the quasi-axial direction generated in different directions from those of the original coordinate system;

FIG. 53 shows varieties of B-mode echo images obtained via an embodiment of the present invention;

FIG. 54 shows varieties of B-mode echo images obtained via an embodiment of the present invention;

FIG. 55 shows varieties of B-mode echo images obtained via an embodiment of the present invention;

FIG. 57 shows varieties of acoustic pressures obtained using a concave HIFU applicator via an embodiment of the present invention.

DESCRIPTION OF THE PREFERRED EMBODIMENTS

Below, embodiments of the present invention will be explained in detail with referring to figures. The same compositions of instruments are referred to using the same codes or numbers by which overlapped explanations are omitted. The instruments according to the present invention can be used as a measurement and imaging instrument as well as a communication instrument (Hereafter, it can be simply referred to as the imaging instrument.). Below explained are mainly about generations of image signals of transmission waves, refraction waves, reflection waves, scattering waves (forward and backward scatterings, etc.), diffraction waves such as of an acoustic pressure and a particle (medium) velocity for an acoustic wave such as an ultrasound, etc., a stress wave or a strain wave for a compressible wave (longitudinal wave) or a shear wave (transverse wave), a ballistic wave, a surface wave, etc., an electric field wave or a magnetic wave for an electromagnetic wave, a temperature or a thermal flux for a thermal wave.

The 1st Embodiment

Figure 1:
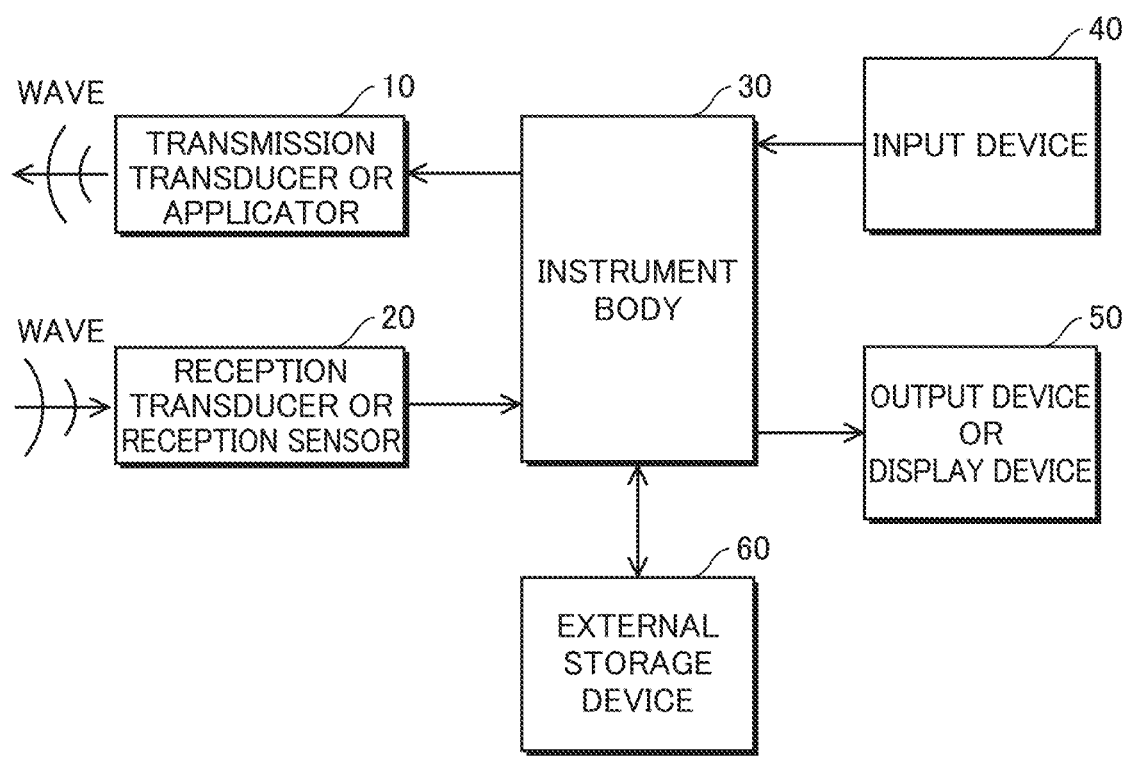
FIG. 1 shows schematic representation (block map) of compositions of a measurement and imaging instrument according to the first embodiment of the present invention.

At first, the compositions of the measurement and imaging instrument according to the first embodiment of the present invention are explained. FIG. 1 shows a schematic representation (block map) of compositions of the measurement and imaging instrument according to the first embodiment of the present invention. As shown in FIG. 1, the measurement and imaging instrument is equipped with a transmission transducer (or an applicator) 10, a reception transducer (or a reception sensor) 20, an instrument body 30, an input device 40, an output device (or a display device) 50, and an external storage (memory) device 60. Here, the transmission transducer 10 and the reception transducer 20 can also be installed into one body or combined to realize a transmission and reception sensor.

Figure 2:
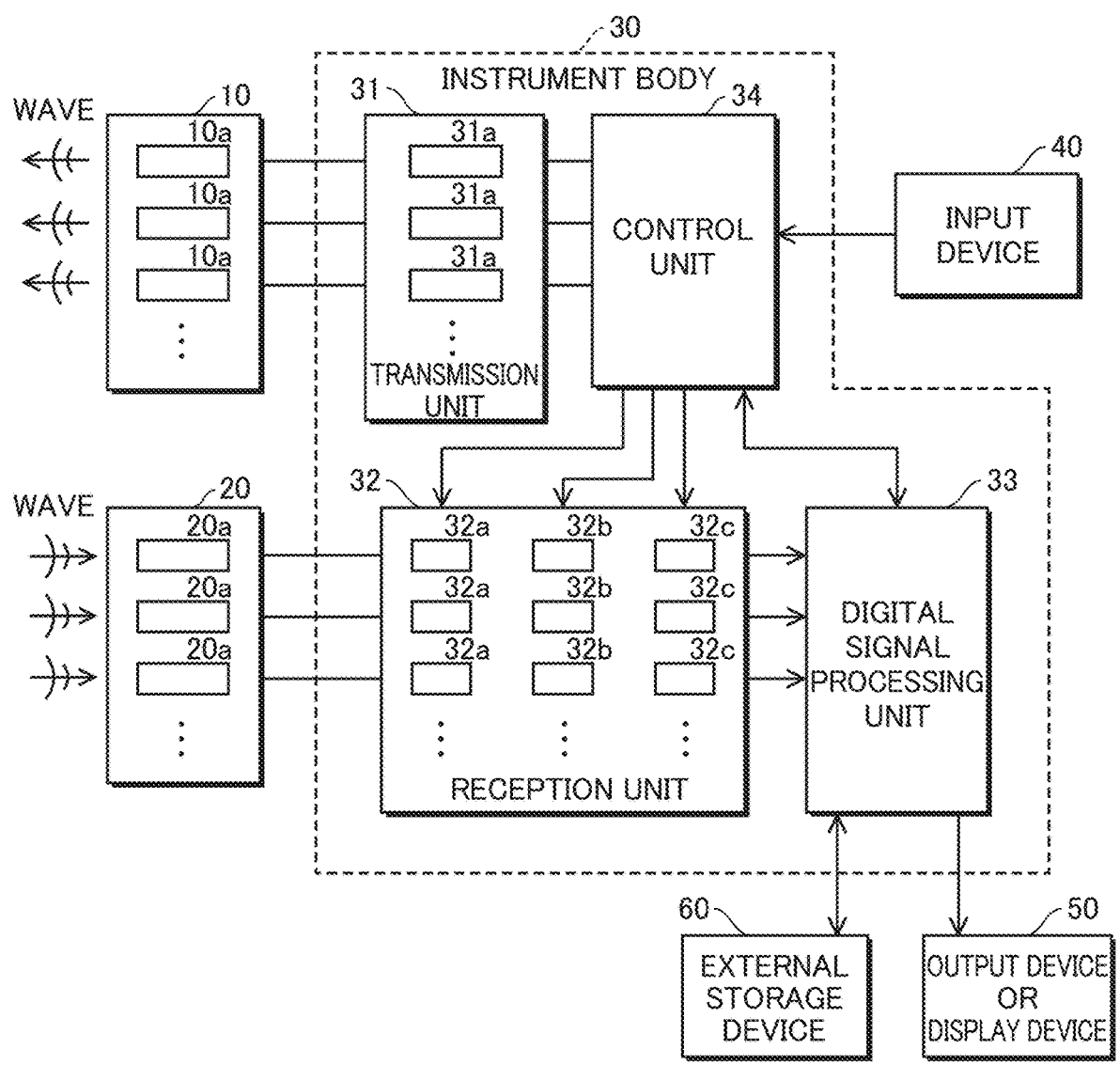
FIG. 2 shows the specific schematic representation (block map) of compositions of a body of instrument shown in FIG. 1.

FIG. 2 shows the specific schematic representation (block map) of compositions of a body of instrument shown in FIG. 1. Mainly, the body of instrument 30 is equipped with a transmission unit 31, a reception unit 32, a digital signal processing unit 33 and a control unit 34. Here, the transmission unit 31 and reception unit 32 can respectively generate at least one driving signal and process at least one reception signal to realize a signal processing unit for generating wave data. The digital signal processing unit 33 realizes a data processing unit for calculating a displacement vector by performing a displacement measurement method for wave signal data generated at least two different temporal phases. The control unit 34 realizes a measurement control unit for controlling the transmission unit 31 and the reception unit 32 for generating at least one steered wave electrically or mechanically (referred to as "steering beam") and scanning the measurement object in a lateral direction for generating the wave signal data at least at the two different temporal phases. The reception unit 32 can include the digital signal processing unit 33. FIG. 1 and FIG. 2 show a properly simplified block map, to which the present embodiment is not limited, and the detail of the present embodiment is explained below. For instance, communications between the above-mentioned instruments, or between the units in the body of instrument 30 or in the units are properly performed on the basis of a wire or wireless technology, and they can also be set at different positions. One comprised of such plural units is conventionally referred to as the body of instrument 30.

<Transmission Transducers>

The transmission transducer (or the applicator) 10 shown in FIG. 2 generates and transmits waves using drive signals provided from the transmission unit 31 in the body of instrument 30. On the present embodiment, plural transmission aperture elements 10a of the transmission transducer 10 comprise an array.

FIG. 3 shows illustrations of configurations of plural transmission aperture elements used in a transmission transducer. FIG. 3($a$1) shows plural transmission aperture elements 10a arrayed densely in a 1D array state; FIG. 3($b$1) shows plural transmission aperture elements 10a arrayed sparsely in a 1D array state; FIG. 3($a$2) shows plural transmission aperture elements 10a arrayed densely in a 2D array state; FIG. 3($b$2) shows plural transmission aperture elements 10a arrayed sparsely in a 2D array state; FIG. 3($a$3) shows plural transmission aperture elements 10a arrayed densely in a 3D array state; FIG. 3($b$3) shows plural transmission aperture elements 10a arrayed sparsely in a 3D array state.

The respective transmission aperture elements 10a have shapes of a rectangular, a circle, a hexagon or others, and a flat, a concave or a convex, etc., and an array is 1D, 2D or 3D state. The directivity of a transmission aperture element 10a is determined by the frequency or bandwidth of a generated wave, and the geometry of transmission aperture element 10a. Generally, the directivity is exhibited in a 2D or 3D space. When the element is comprised of two apertures that respectively have directivities in orthogonal two directions, or three apertures that respectively have directivities in orthogonal three directions, the element can also be counted to be one. Also, an element can also be comprised of larger than three apertures that have directivities in larger than three directions. The number of apertures in an element may be different at positions and also, they can be mixed in with.

Although the transmission aperture element 10a can exist spatially densely or sparsely (at far positions), the present embodiment is explained with no distinguish with 1D to 3D array types. According to objects (communication) in which the waves propagate or the observation is performed, the aperture element arrays have various formations such as a linear type (the alignment of elements is flat), a convex type (a convex, an arc alignment), a focus type (a concave, an arc alignment), a circular type (for instance, an IVUS in a medical ultrasound, etc.), a spherical type, a convex or concave spherical kernel type, a convex or concave other geometry types, etc. The types are not limited to these. Proper driving these aperture element arrays generates the above-mentioned waves that widely spread in a lateral direction such as plane waves, the steering, the synthetic aperture, fixed transmission focusing, etc., i.e., a transmission beam or a transmission wave with a wave-front.

For electric scanning, as mentioned in detail later, in order to a transmission beam or a transmission wave with a wave-front, by using independent drive signals generated by plural transmission channels equipped in the transmission unit 31 shown in FIG. 2, the transmission aperture elements 10a with the same number as that of the drive signals are independently driven. The transmission aperture element array that is used for generating a transmission beam or a transmission wave with a wave-front is referred to as a transmission effective aperture. Or, all the aperture elements are totally referred to as a physical aperture element array, from which the transmission aperture that is realized by the transmission aperture element 10a driven simultaneously is referred to as a transmission subaperture element array or simply a transmission subaperture.

When the object in which waves propagate (communication object) are large or over a region of interest (ROI) is observed at once, the instrument may have transmission channels with the same number as that of the aperture elements existing in a physical aperture element array, and all the channels may always be used. However, in order to make the instrument cheaper, by translating the transmission subaperture element array by switching the transmission channels electrically, or by performing a mechanical scan with a physical aperture element array, waves can be transmitted to over the ROI with the minimum number of transmission channels. When the object in which waves propagate (communication object) is large or the size of object to be observed is large, both the electric and mechanical scanning can also be performed.

When performing sector scanning, a spatially fixed aperture element array of the above-mentioned type can be electrically driven to perform the scanning (electric scanning), or the aperture element array itself can be used to perform the mechanically scanning, or both can be performed together. As classical SAs, there are two types using electric scanning in which the respective elements in an aperture element array are individually driven or using mechanical scanning using one aperture element. That is, a transmission aperture array is composed by performing transmissions at different positions. For the electric scanning, the transmission unit 31 is equipped with transmission channels with the same number as that of transmission elements in a physical aperture array and then, the transmission channel number can be decreased by using a switching device and at least one channel is required similarly to the mechanical scanning. For transmitting polarized waves, at least the channel number expressed by the multiplication of the element number to be driven simultaneously and the number of polarized waves is required for the transmission unit 31.

<Reception Transducers>

The reception transducer (or the reception sensor) 20 shown in FIG. 2 can also be used as the transmission transducer 10 or an exclusive reception array-type sensor another one from the transmission transducer 10. Thus, the reception transducer 20 can also be set at a different position from that of the transmission transducer 10. Or, the reception transducer 20 can be one that allows detecting a different type wave from that generated by the transmission transducer 10. Such a reception transducer 20 can be set at the same position as that of the transmission transducer 10 and can also be installed into a body.

The reception transducer 20 used in the present embodiment has an array comprised of at least one reception aperture element 20a, and the signals received by the respective elements are independently transmitted to the reception unit 32 (FIG. 2) in the body of instrument. The respective reception aperture elements 20a have shapes of a rectangular, a circle, a hexagon or others, and a flat, a concave or a convex, etc., and an array is 1D, 2D or 3D state. The directivity of a reception aperture element 20a is determined by the frequency or bandwidth of a received wave, and the geometry of reception aperture element 20a. When the element comprised of plural apertures can also be counted to be one. The number of apertures in such an element may be different at positions and also, they can be mixed in with. The reception aperture elements 20a can be spatially dense or sparse (there at far positions) and here, both are similarly used (FIG. 3 shows examples of transmission arrays.).

According to objects (communication) in which the waves propagate or the observation is performed, similarly to the transmission transducer 10, the aperture element arrays have various formations such as a linear type (the alignment of elements is flat), a convex type (a convex, an arc alignment), a focus type (a concave, an arc alignment), a circular type (for instance, an IVUS in a medical ultrasound, etc.), a spherical type, a convex or concave spherical kernel type, a convex or concave other geometry types, etc. The types are not limited to these. Receiving waves using these aperture element arrays, the above-mentioned waves that widely spread in a lateral direction such as plane waves, the steering, the synthetic aperture, fixed transmission focusing, dynamic focusing, etc. are performed, i.e., a reception beam or a reception wave with a wave-front is generated.

The transducer aperture (element) can also spatially exist not densely but sparsely (at far positions); or transmission and reception can also be performed by mechanically scanning the measurement object; or no array-type transducer generally referred to as can also be used to perform almost same processings of received signals; and the present embodiment is explained with no distinguish about them particularly by mentioning mainly about cases using array-type devices. For instance, when radar apertures exist at different positions of lands, the respective apertures can be comprised as arrays or not.

Not only for radars carried by a satellite or an airborne but also a transducer to be used for performing mechanical scanning of a measurement target, also in such cases, the transducers can also have an array or not; transmissions and receptions of signals can also be performed at spatially continuously or densely, or at far positions or sparsely. Thus, not only the classical SAs (transmission from one element) but also receptions of signals with respect to transmission beamformings are performed. The aperture element can exist in a 1D, 2D or 3D state. In addition to electric scanning, mechanical scanning can also be performed together.

Regarding with the electric scanning, as mentioned later, in order to realize a reception beam or a received wave with a generated wave-front, received signals can be detected simultaneously via aperture elements with the same number as that of reception channels equipped with the reception unit 32 (a reception effective aperture). The reception effective aperture can be different from the transmission effective aperture. Such a reception effective aperture is distinguished with the total aperture elements referred to as the physical aperture element array, and the reception aperture realized by the reception aperture elements 20a simultaneously used is referred to as a reception subaperture element array or only a reception subaperture.

When the object in which waves propagate (communication object) are large or over a region of interest (ROI) is observed at once, the reception unit 32 may have reception channels with the same number as that of the aperture elements existing in a physical aperture element array, and all the channels may always be used. However, in order to make the instrument cheaper, by translating the reception subaperture element array by switching the reception channels electrically (electric scanning), or by performing a mechanical scan with a physical aperture element array, waves can be received from over the ROI with the minimum number of reception channels.

When the object in which waves propagate (communication object) is large or the size of object to be observed is large, both the electric and mechanical scanning can also be performed. When performing sector scanning, a spatially fixed aperture element array of the above-mentioned type can be electrically driven to perform the scanning (electric scanning), or the aperture element array itself can be used to perform the mechanically scanning, or both can be performed together. As classical SAs, there are two types using electric scanning in which the respective elements in an aperture element array are individually driven or using mechanical scanning using one aperture element. That is, a transmission aperture array is composed by performing transmissions at different positions. For the electric scanning, the transmission unit 31 is equipped with transmission channels with the same number as that of transmission elements in a physical aperture array and then, the transmission channel number can be decreased by using a switching device and at least one channel is required similarly to the mechanical scanning.

Alternatively, regarding the reception in the case, in a monostatic type where the receptions are performed by the same elements as those of the active transmission elements, the reception unit 32 is equipped with the reception channels with the same number as that of the transmission channels at least. Alternatively, in a multistatic type where plural elements around the active transmission elements to be used in almost cases, for electric scanning, the reception unit 32 is equipped with reception channels with the same number as that of reception elements in a physical aperture array, whereas both for electric and mechanical scanning, the reception unit 32 is equipped with the reception channels with the same number as that of the elements of a reception effective aperture at least. For receiving polarized waves, at least the channel number expressed by the multiplication of the element number to be used for the receiving simultaneously and the number of polarized waves is required for the reception unit 32.

<Concrete Examples of Transducers>

Transducers 10 or 20 to be used include various ones that allow generating or receiving arbitrary waves such as electromagnetic waves, lights, mechanical waves, acoustic waves or thermal waves, etc. For instance, there are transducers 10 that allow transmitting arbitrary waves to the measurement target and receiving reflected waves, refracted waves, back or forward scattered waves or diffracted waves, etc. generated in the measurement target (also used as the transducers 20). For instance, when the arbitrary wave is an ultrasound, an ultrasound transducer can be used, which allows transmitting ultrasounds using drive signals provided and generating received signals by receiving ultrasounds. It is well known that according to the applications, ultrasound elements (PZT (Pb (lead) zirconate titanate), PVDF (polyvinylidene fluoride) piezoelectric element, etc.) are different as well as the structures of the transducers.

In the medical applications, for blood flow measurement, a narrowband ultrasound is used historically. First in the world, the inventor of present invention has been realizing to use a wideband echo imaging transducer for measurements of soft tissues' displacement or strain (including static cases), shear wave propagation (speed), etc. Also, for HIFU treatment, although a continuous wave can be used, in order to realize a high spatial resolution treatment, the inventor of the present patent has been developing new applicators using devices in a high frequency type or in a wideband type. As one of applications of a high intensity ultrasound, as mentioned above, tissues are stimulated by generating mechanical sources in measurement targets with no thermal effects, for which echo imaging transducer can also be used. In addition to the thermal treatments and generations of mechanical sources, echo imagings can also be performed simultaneously. This is also for using of other wave sources and transducers.

The digital signal processing unit 33 allows controlling the shear wave propagation direction by superposing plural shear waves generated by respective mechanical sources generated temporally or spatially, by which anisotropies of a visco-shear modulus or a shear wave propagation speed. Because shear waves generated almost simultaneously are superposed physically, after observing the shear waves via ultrasonic displacement measurement, the shear waves can be separated. When the shear waves are not superposed physically, after shear waves generated by respective mechanical sources are observed by analyzing and observing ultrasound signals, the results are superposed in order to calculate regarding the synthesized shear wave (superposed shear waves), the propagation direction, the propagation velocity, the visco-shear modulus in the propagation direction (patent document 11, etc.). Alternatively, ultrasounds obtained when the respective mechanical sources are generated are superposed, and the synthesized shear wave (superposed shear waves respectively generated by the respectively mechanical sources) is observed to calculate them similarly. These are also in cases where thermal waves generated by thermal sources are observed to calculate thermal properties. As mentioned below, various other processings are performed.

It is possible to realize a desired thermal source or a desired mechanical source, and a desired sound pressure by performing optimizations of transmission and reception apodizations or delays, and a radiation intensity that control the shapes of a thermal source or a mechanical source, and a sound pressure by detecting a transmission wave or a reflection wave. The wave shapes can also be observed with a high sensitivity using a hydrophone, or the shapes can also be estimated by calculating the autocorrelation functions of the signals detected by sensors, etc. (patent document 11, etc.); on the basis of such processings, linear or nonlinear optimization is performed. Particularly when the reception is performed using an array-type detector (each array element), a high sensitivity is required. An object for performing a test an also be used, and they can also be performed for the observation object itself. By using more than two effective apertures being far from each other within various physical apertures, plural waves or beams can also be used (Although simultaneous transmissions are desired to be performed, if required, the respective waves or beams can also be transmitted.). Under some constraint about the geometry, size and position of a device body, a physical aperture and an effective aperture, the optimization can also be performed (e.g., cases where obstacles such as a bone, etc, exist, and an endoscope or a laparoscope is used, and not limited to these). Various isotropic finite lengths of waves can also be generated in the range and lateral directions (e.g., a spherical geometry, and among others), a wave with an arbitrary specified geometry can also be generated. The propagation directions of shear waves and thermal waves can also be optimized. In the respective cases, estimation results of mechanical properties and thermal properties are desired to be used. The waves to be used for the sensing are not limited to the mechanical ones, and the waves can be lights, electromagnetic waves, thermal waves. Thus, a proper transmitter and a proper receiver are used.

For instance, when using a concave applicator, it is possible to focus at a focus position an ultrasound with a high intensity and thus, a wide bandwidth is yielded in a lateral direction. But the sound pressure shape has feet growing from the focus position. Then, processings such as filtering, weighting, etc. are performed on spectra calculated after receiving reflection or reflection waves to shaping the shape to be an ellipse (nonpatent document 7). The fact that the spectra of waves or beams propagating in the respective directions exist in the same directions in a frequency domain can be used. Consequently, an image quality as well as the accuracy of displacement measurement increases.

Such processing can also be perform to yield the same effects in cases where beams or waves with new properties that cannot be generated by generation of one wave or one beamforming on the basis of one transmission and one reception (for instance, cases where lateral modulation or increasing a lateral bandwidth is performed by superposing crossed waves or beams, multi-focusing is performed, etc.) are yielded by superposing plural reception signals respectively generated by performing plural transmissions, plural receptions or the both with at least a different wave or beamforming parameter, i.e., one of a transmission focus position when transmission focusing is performed, a plane wave, a cylindrical wave, a spherical wave, etc. when transmission focusing is not performed, a steering angle (including zero degree with no steering), using or not of apodization, an F-number, a transmission ultrasound frequency or a transmission bandwidth, a reception frequency or a reception bandwidth, a pulse shape, a beam geometry, etc. The superposition can also be performed in a real-time (at the same time with the transmissions and receptions) regarding with the received signals at the measurement objects' same phase, however, at different times. The respective signals to be superposed can also be reception-beamformed ones, or the superposed raw signals can also be reception-beamformed.

The received signals obtained from the single wave or beam, or the superposed waves or beams can be weighted in a frequency domain to increase a bandwidth and perform superresolution (increasing a spatial resolution). The so-called inverse filtering or deconvolution can be performed. Also, the methods, etc. described in the paragraph 0009, the observed waves are multiplied by the conjugate or reciprocal of a frequency response of beam properties as the inversion of beam properties. Alternatively, the conjugate of observed wave or the frequency response can also be implemented newly (These are detection processings, i.e., the former yields a square of envelope; the later yields auto-spectra or an autocorrelation function). The beamformed (SA), received signals can also be superresolution-processed, and received signals non-reception-beamformed or not beamformed at all (received signals for SA) can also be beamformed after performing superresolution processings.

Regarding displacement (vector) measurement, in order to increase the accuracies of displacement components, the frequency in the direction of displacement components can be increased. If increasing a spatial resolution is also required, increasing a bandwidth is also performed. For instance, by increasing the frequency via decreasing low spectra, the displacement measurement accuracy can be increased. The calculation amounts can also be decreased. High accuracy displacement measurement, etc. can also be performed by generating over-determined systems via generating plural waves or beams physically or dividing spectra on the basis of signal processing (Since the spectral division performed for the angular spectra before performing a beamforming requires to perform the beamformings for respective divided angular spectra, in many cases, the spectral division should be performed after performing the beamforming.). For performing imaging, envelop detection, square detection or absolute detection is implemented, and by superposing the detected waves or beams, speckles can be decreased, and specular reflections can be enhanced.

Similarly, these processings can be performed in various fields using electromagnetic waves as well as using ultrasound or in the medical field. For instance, audible sounds can be observed using ultrasounds (Doppler effect), acoustic sounds or thermal waves can be observed using electromagnetic waves or lights, or earthquake waves can be observed using such waves. In conjunction, physical properties (distributions) related to the waves can also be observed.

For a transducer, there are contact and contactless types. Every time, impedance matching is properly performed with respect to each measurement object by putting an impedance matcher such as a gel or water, etc. for an ultrasound between the measurement target and the transducer. Such an impedance matcher can also be installed into the transducer in advance (impedance layers for an ultrasound). Thus, impedances of waves are performed properly with respect to measurement targets. A power or a carrier frequency, a bandwidth (wide or narrow ones that determines the axial resolution, etc.), a wave shape, a size of element (determining a lateral resolution), a directivity, etc. designed on the basis of both the aperture element level and the array capability (detail omitted) are used. As an ultrasonic transducer, there is a combined type using layered PZTs and PVDFs, which is equipped with both a transmission acoustic power and a wideband When performing forcedly vibrating using a drive signal, by controlling the drive signal, the generated ultrasound frequency or bandwidth can be adjusted, or the ultrasound can be encoded (On reception, a bandwidth is selected from signal with a bandwidth determined by the used transducer using an analogue or digital filter). Occasionally, aperture elements with different properties such as a frequency and a sensitivity, etc. can be arrayed. Originally, the ultrasound transducer is a handy type and with a favorable usability. Recently, a non-cable type transducer can be used with a handy body of instrument. For a low frequency sound such as an audible sound, there as a speaker and a microphone. With a viewpoint similarly to the ultrasound, transducers for other waves can be realized and however, they are not limited to the case.

Alternatively, as a transducer 10, transmission transducers that generate arbitrary waves, and as a transducer 20, reception transducers (sensors) that receive arbitrary waves can be used. In the cases, the transmission transducers allow transmitting arbitrary waves to the measurement targets and the sensors allows receiving reflected or back forward scattered waves generated in the measurement targets, or transmission, forward scattered, refracted or diffracted waves, etc. in the measurement targets.

For instance, when the arbitrary wave is a thermal wave, a sunlight or illumination, a metabolism, etc. that is a thermal source not made intentionally, and alternatively, an infrared warmer or heater, etc. that is rather stationary, or an ultrasound transducer that transmits an ultrasound for heating (that may also be used for generating a mechanical source in the measurement object) or an electromagnetic wave transducer, laser, etc. can also be used, which are controlled according to drive signals. For receptions of thermal waves for generating reception signals, an infrared sensor, a pyroelectric sensor, detectors of a microwave or a terahertz wave, a temperature sensor such as an optical fiber, an ultrasound transducer (detection of a temperature change using the dependency of a sound speed and a volume change on a temperature), a magnetic resonance signal detector (detection of a temperature using a chemical shift of magnetic resonance frequency), etc. can be used. For the respective waves, transducers that properly performing the receptions can be used.

For an optical digital camera or a digital mammography, the Charge-Coupled Device (CCD) technology is used, and an integrated circuit (IC) and a sensor can be installed into one body. The same technology is also used in an ultrasound 2D array, and a real-time 3D imaging can be made possible. For detection of an X-ray, the combination of a scintillator and a photocoupler is used, and observation of the X-ray wave has been able to be made possible. When performing digital sampling of high frequency signals, it is effective to perform analogue detection or modulation as preprocessings, i.e., it is effective to store signals into a memory or storage device (storage media) via AD conversion after reception signals is made the low frequency signals. Or, digital detection can also be performed. These can be installed into one body, a chip or a circuit board together with a transmitter or a receiver.

Or, for instance, when radars exist at far positions, etc., the respective apertures can be comprised of array elements, and there are also other cases. A wide directivity can also be obtained by performing mechanical scanning with various apertures. Apertures can exist spatially continuously or densely, or at far positions or sparsely, or with some regularity such as an equal interval, or with an irregularity under physical limitations. For instance, in sea or building, indoor, etc., apertures to be used can be spatially fixed with respect to objects in which waves propagate (communication object) or positions to be observed. Or, the respective apertures can also be used for transmissions and receptions, which can receive waves that are responses with respect to transmission from other apertures as well as the reception apertures themselves. In a medicine or biology, ultrasounds generated by radiating lasers to objects can be observed, referred to as photoacoustics (plural wave transducers can be installed into one body). The present invention allows performing photoacoustics that is realized by combining an ultrasound diagnosis instrument and OCT, for instance, for differentiating an artery and a vein, and measuring the respective blood flow velocity (The superresolutions can also be performed). Or, by applying vibrations or ultrasounds to cancerously diseased parts after performing intravenous injection of magnetic substrates having an affinity for the cancerous diseases, generated electromagnetic waves can also be observed. It is possible to use electromagnetic waves to perform communications with various moving bodies.

Transducers (arrays) used for passive observations such as earthquakes (seismograph), brain waves (EEG, electroencephalograph), MEGs (magnetoencephalograph), ECGs (electrocardiography), biological neural networks (electrode array), electromagnetic waves (antenna), radars, etc. are also various, and they can also be used for observing the wave sources. It is possible to estimate the directions of arriving waves on the basis of spectra analysis (one of past achievements of the present patent's inventor). Moreover, when information regarding propagation times cannot also be obtained (generally, positions of wave sources are calculated using times of observed waves at plural positions), particularly using the instruments of the present invention with plural transducers equipped with different positions or reception effective apertures, positions of wave sources, etc. can be calculated geometrically. Even if the waves are not pulsed waves nor burst waves, continuous waves can also be used to observe such wave sources. Via any processings, at once the directions of arriving waves are known, the wave sources can be observed in detail by steering or focusing plural types of beams. In the processings, transmissions are steered, and receptions are selectively performed in very probable directions, and the image, spatial resolution, contrast, signal intensity, etc. are observed, or the directions of wave sources are specified via spectral analysis. Thus, the transducer used in the instrument of the present invention is used for steering, with which the mechanisms of electric scanning, mechanical scanning, or both scannings can be equipped with.

As the transducers that allows demonstrating the effectiveness of the present invention, typical transducers being rather familiar with or some special transducers are enumerated and, however, the transducers used or applied in the present patent are not limited to them and include various transducers that allow generating and receiving arbitrary waves such as electromagnetic waves, lights, mechanical vibrations, sound waves, or thermal waves.

<Beamformings>

At the same time, the same phase of the observation objects in which waves are propagated (communication object) or conditions being identical or almost identical, other time or other phase, plural beamformings, transmissions or receptions can be performed using each aperture. Similarly, plural beamformings, transmissions or receptions can be performed at a pair of apertures. Similarly, plural beamformings, transmissions or receptions can be performed at respective pairs of apertures. In cases including the cases where plural results of beamformings and receptions are obtained using such apertures, new data can also be generated via linear or nonlinear operations. The reception signals to be processed can be superposed ones originally or processed to be superposed.

For radars, etc. carried by spatially moving bodies such as a satellite or an airborne, the arrays can have an array or not, and mechanical scannings can also be performed to obtain wide directivities. Transmissions and receptions of signals can also be performed at spatially continuously or densely, or at far positions or sparsely, or with some regularity such as an equal interval, or with an irregularity if necessary. The moving bodies are various and also include cars, ships, electric trains, submarines, moving robots, etc. Others are circulation goods, etc., living things, etc., bodies moving regularly or randomly, etc. In such cases, mobile communication instruments can be used. RFID (Radio Frequency Identification) tag or IC card, etc. can also be used.

In such cases, reception beamformings can be performed with performing transmission beamformings in addition to classical SA (SA on the basis of transmission of each element). Mechanical scannings can also be performed in a regular fashion or irregularly with performing electric scannings to properly propagate waves in spatially large regions (communications) or properly observe large regions. Needless to say that using a multi-dimensional array allows properly propagating waves in spatially large regions (communications) or properly observing large regions (permitting multi-directional steering as well as increasing the size of physical aperture).

Apertures carried can also be used for both transmission and reception apertures, only transmission apertures, or only reception apertures that receive responses not with respect to the transmissions by the reception apertures themselves but with respect to the transmissions by other apertures. Plural moving bodies can be equipped with apertures. At the same time, the same phase of the observation objects in which waves are propagated (communication object) or conditions being identical or almost identical, other time or other phase, plural beamformings, transmissions or receptions can be performed using each aperture.

Similarly, plural beamformings, transmissions or receptions can be performed at a pair of apertures. Similarly, plural beamformings, transmissions or receptions can be performed at respective pairs of apertures. In cases including the cases where plural results of beamformings and receptions are obtained using such apertures, new data can also be generated via linear or nonlinear operations. In applications mentioned above, according to the objects in which waves are propagated (communication objects) or observation objects, combinations of the apertures of moving bodies and the fixed apertures can also be used.

Thus, in the present embodiment, using plural transmission aperture elements $10a$ and plural reception aperture elements $20a$ (respective elements can work as both the transmission aperture elements $10a$ and the reception aperture elements $20a$), active beamformings are performed. In the active beamformings, arbitrary beamformings can be performed via digital processing including FFT with high speeds and with no approximate interpolations. In practical, arbitrary focusings and arbitrary steerings can be performed using transducer array devices with arbitrary aperture geometries.

Since the directions of the faces of respective aperture elements are made much account of, generally orthogonal coordinate systems determined by the geometries of physical aperture element arrays (virtual sources are explained separately) are used. The features of the present invention are to generate signals expressing waves directly on the coordinate systems used for displaying the signals mainly via performing reception digital beamformings with no approximate interpolations; and also, to perform the reception beamformings on the coordinate systems used for performing transmission beamformings derivatively. Virtual sources or virtual receptors, etc. can also be used, and the beamformings can be performed similarly to using the physical aperture element arrays.

<Transmission Unit>

Next, the transmission unit 31 (FIG. 2) equipped with the bogy of instrument 30 is explained. The transmission unit 31 includes the transmitters $31a$ with plural transmission channels. The transmission channel number is the number of communication lines that are used for performing one beamforming, to send different drive signals to the respective aperture elements. For instance, as mentioned below, the formations of transmission channels are various. The generated waves on the respective transmission aperture elements $10a$ have frequencies, bandwidths, wave shapes, and directivities that are determined by the transmission aperture elements $10a$ and the transmission unit 31.

Applying impulse signals to the transmission aperture elements $10a$ generates waves determined by the geometries of the transmission aperture elements $10a$ (thickness or aperture size and shape) and materials (a single crystal is representative type of ultrasound element), and additionally using drive signals with frequencies, bandwidths and wave shapes (including an encoded case), generated at the transmission unit 31, can also be used for performing forcedly vibrating the transmission aperture elements $10a$ to control the frequencies, bandwidths, wave shapes and directivities of the waves to be generated. The properties of drive signals to be generated are set as parameters under the control by the control unit 34. Desired parameters can also be set automatically via the control unit 34's distinguishing the transducers set on, and the parameter settings or adjustings can also be performed using the input device 40.

Generally, in order to perform one beamforming every time, plural aperture elements are excited using drive signals with different delays. That is, the transmission unit 31 is equipped with analogue or digital delay patterns, and for instance, delay patterns that realize transmission focusings or steering directions, etc. can be used according to the operator's selection using the input device 40. The patterns can be programmable and according to the purposes, the pattern to be used or selective can also be installed via various media such as CD-ROMs, floppy disks, or MOs, etc. After running programs, using the input device 40, the patterns can also be selected interactively, and the delays (patterns) can also be directly input. Or, there various cases including the case where the patterns are set by reading out files in which data are recorded, etc. Particularly, when the delays to be used are analogue, the delays can also be changed in an analogue or digital manner, the delay circuit or the delay patterns themselves are exchanged by others or switched to others.

In the body of instrument 30 (FIG. 2), the command signals are sent to the transmitters $31a$ with plural channels from the control unit 34 to generate drive signals (including an encoded case) for exciting the corresponding transmission aperture elements $10a$. Such command signals can be generated on the basis of the command signals for starting the beamformings for generating one frame. When the transmission delays are digital, for instance, digital delays can be implemented on the respective command signals sent to the plural transmitters $31a$ using, as the trigger signal, the command signal for the transmission aperture element to be excited first. For implementing the digital delays, digital devices to be used in a digital circuit can also be used.

Or, after a drive signal generated in the transmitter 31a for exciting an element first is implemented with analogue delays for exciting the respective aperture elements, drive signals are sent to the respective aperture elements. When such analogue delays are used, synchronizations required for using digital circuits are not required, and at least a transmitter 31a can be used to excite transmission aperture elements 10a. Thus, transmission analogue delays can be set at several timings, i.e., in front of, behind or in the transmitters 31a, or in the control unit 34, whereas transmission digital delays can be set at in front of or in the transmitters 31a, or in the control unit 34.

The delay patterns can also be selected by switching analogue circuits or analogue devices and digital circuits or digital devices, and the delays set on the delay devices can be changed under the controls by the control unit 34 or programmable via installing or setting using inputting, etc. Delay devices can also be set in the control unit 34. Moreover, when the control unit 34 is made using a calculator, etc. as mentioned below, the control unit 34 can directly output command signals that are delayed under software controls.

The control unit 34 or digital delay can be realized using devices, calculators, PLD (Programmable Logic Device), FPGA (Field-Programmable Gate Array), DSP (Digital Signal Processor), GPU (Graphical Processing Unit), microprocessor, etc. with general calculation capabilities, or an exclusive digital circuit and an exclusive device. The devices are desired to exhibit high performance (multicores, etc.), and also devices used for analogue devices, AD convertors 32b, memories 32c and/or digital signal processing unit 33 performing transmission or reception beamforming processings.

Important are the number of communication channels between devices, channel capacities, wirings, wideband wireless communications. In particular, in the present invention, it is desirable that such functional devices are installed into a chip or a circuit board (the devices may be detachable), or the devices are directly implemented into a chip or a circuit board (including a multilayer type). Parallel processings are also important. When the calculator also plays a role of the controller unit 34, if the device is not detachable, a remarkably higher security can be achieved than that obtained under a general programmed control. In a contrary, under the existing legislation, cases where disclosing of processing contents is demanded will increase.

The control software or delays can also be directly encoded, input or installed. The ways how to implement digital delays are not limited to these. When implementing digital delays for transmission delays, being different from implementing analogue delays, errors determined by the clock frequency for generating the digital control signals occurs; thus, in the viewpoints of an accuracy, the analogue delay had better be implemented for the transmission delays. Basically, the errors can be reduced by using a high clock frequency with a high cost. Alternatively, the analogue delays can also be changed in an analogue manner, the delay can also be programmable, and the digital control can be made possible. However, the analogue processing has a lower degree of freedom than the digital delay processing, and if the cost is required to decrease, the delay pattern realized using an analogue circuit can also be switched.

Transmission apodizations are performed using energies of drive signals provided to the respective aperture elements, or temporal changes of magnitudes, i.e., temporal changes in wave shapes (including an encoded case). On the basis of calibration data regarding the aperture elements' conversion efficiencies from the drive signals to waves, the drive signals are controlled. For other purposes such as calibrations, adjustments of the drive signals can also be performed. The command signals from the control unit 34 to the transmitters 31a can be signals that express, as temporal series, the information of wave shapes or phases of drive signals to be generated by the transmitters 31a, encoded signals which the transmitters 31a recognize to generate pre-determined drive signals, or only signals that convey commands to the transmitter 31 that generate pre-determined drive signals with respect to the respective aperture elements existing in an effective aperture.

Similarly to the delay setting, the transmitters 31a can be programmable such that pre-determined drive signals are generated with respect to the respective aperture elements in an effective aperture, and various formations can be generated. To generate drive signals, an electric power supplier or an amplifier can be used; electric power suppliers that can provide different electric powers or energies, or amplifiers with different amplification degrees can be switched or simultaneously used to generate a drive signal. Similarly to the transmission delay patterns, as mentioned above, the transmission apodizations are directly set or programmable. The delays and apodizations can be implemented in the transmission unit, which are realized at the same hierarchy level or at different hierarchy levels, and in the same or different formations.

The transmission channels used for driving aperture elements in a transmission effective aperture are switched using switching devices such as a shift-register, a multiplexer, etc., beamformings can be performed using other positioned effective apertures to scan the ROI. The delays of delay elements can also be changeable, the delay pattern (delay elements) can also be switched. Moreover, steering in plural directions can also be performed using an effective aperture, and occasionally the aperture position or the effective aperture width can also be changed. Moreover, steering directions can also be changed.

When switching high voltage signals, exclusive switching devices can be used. Apodizations set on apodization elements can be changeable in a temporal transmission direction or an array direction of aperture elements, or apodization patterns (apodization elements) can be switched on. Being dependent on the aperture position, range direction, or steering direction, the beam geometry can be controlled. Specifically, an apodization (value), zero, means the corresponding transmission element is not active and off. Thus, the apodization can also work as a switch of effective element and can also determine the effective aperture width (when apodization function in the aperture element array direction is a rectangular window, the switches of the effective elements are on; and when the apodization function is not constant, the switches are weighted on).

Regarding the delay pattern or apodization pattern, the body of instrument 30 can be equipped with plural patterns or can be programmable. Then, on the basis of the responses from the object or the results of beamformings performed by the reception unit 32 explained next, the digital signal processing unit 33 (FIG. 2), explained later, in the body of instrument 30 calculates waves' attenuations, scatterings (forward or back scatterings, etc.), transmissions, reflections, refractions, diffractions or propagation speeds such as sound speed's frequency variances or spatial distributions, etc., optimizations regarding the delays or intensities of waves transmitted from the respective apertures, steering directions of beams or wave-fronts, apodization patterns, etc. can be performed.

For classical SA, there are monostatic and multistatic types performed using transmissions from respective aperture elements (i.e., each 1 element), the active transmission aperture elements 10a are switched or switched using apodizations as mentioned above. There is a case where all the transmission elements are equipped with transmission channels including transmitters 31a. For SAs, it is required to generate waves with sufficient intensities or energies, and the transmission apodization functions are not always important themselves. In practical, generally, SAs are performed simultaneously with reception apodizations using the phasing and summation device. In the present invention, the digital signal processing unit 33 often performs SAs together with the reception apodization. Representative transmission units used in the present embodiment are above-explained, all allowing transmission beamforming can be arbitrarily used and they are not limited to the units above-explained.

<Reception Unit and Digital Signal Processing Unit>

Explained next is about the reception unit 32 and the digital signal processing unit 33 (FIG. 2) equipped with the body of instrument 30. The reception unit 32 includes the receivers 32a with plural channels, AD convertors 32b, and memories (or storage devices, storage media) 32c. The frequencies, bandwidths, wave shapes, directivities of the received signals generated by the respective reception elements are determined by the reception aperture elements 20a and reception unit 32. Arriving of waves to the reception aperture elements 20a generates the reception signals determined by the geometries of the reception aperture elements 20a (thickness or aperture size and shape) and materials (a single crystal is representative type of ultrasound element), and additionally performing filtering processings (analogue amplifiers can also work as the filters), the frequencies, bandwidths, wave shapes and directivities of the received signals to be generated are controlled. The properties of received signals to be generated are set on the basis of filter parameters (frequency properties such as a frequency, a bandwidth) under the control by the control unit 34. Desired parameters can also be set automatically via the control unit 34's distinguishing the transducers set on, and the parameter settings or adjustings can also be performed using the input device 40.

The general digital reception unit or digital reception device are equipped with the phasing and summing function in addition to like these functions. That is, the DAS processings performed in the digital reception unit or digital reception device perform phasing processings on plural reception signals and also sum the plural phased reception signals. As the phasing processings, the respective reception channels for plural reception apertures implement the AD conversions on the received signals and store the digitized signals in memories, storage devices or storage media, etc. that can be written and read out in high speeds basically. In order to perform the phasings at the respective positions of interest in an ROI, reception delays can be implemented on the received signals read out from the storages with high speeds with approximate interpolations in a spatial domain. Or, the reception delays can also be implemented on the received signals read out from the storages, with high accuracies on the basis of the Nyquist theorem, by performing the phase rotations with multiplications of complex exponential functions (the present inventor's past invention, patent document 6 and nonpatent document 15, etc.), how- ever, it takes much time to complete the processings. The respective signals received by reception apertures can be stored in the positions (addresses) in storages according to the reception delays, and the received signals can be read out and summed or summed after performing the above-mentioned processings as well.

Figure 4:
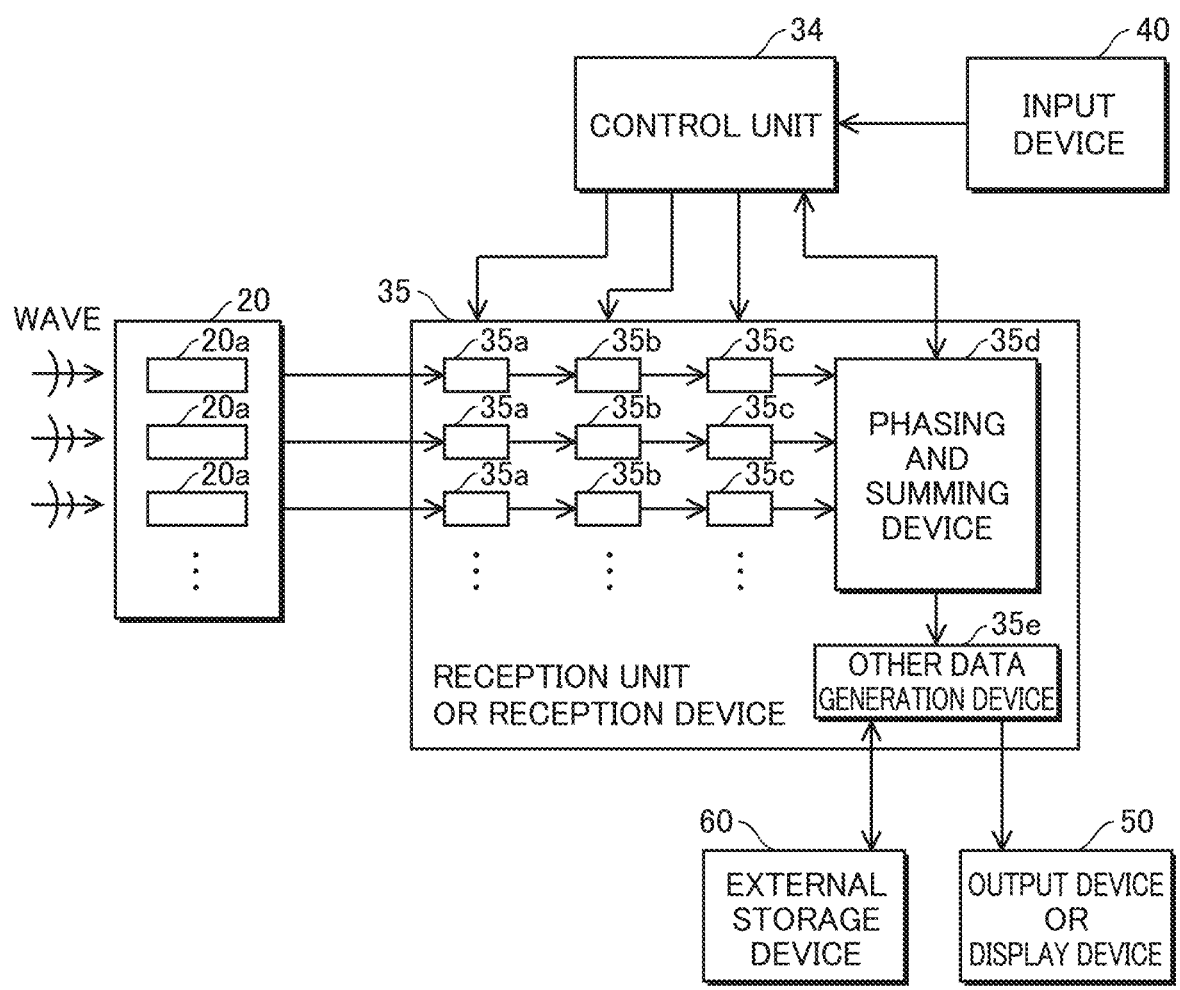
FIG. 4 shows illustrations of compositions of a reception unit including a phasing and summing device, and the peripheral devices.

FIG. 4 shows illustrations of compositions of the reception unit or reception device including the phasing and summing device that realizes the phasing and summing processings, and the peripheral devices. FIG. 4 shows the reception unit (or the reception device) 35 which is equipped with the phasing and summing device 35d that performs the phasing and summing processings, and other data generation device 35e that implements the digital signal processings on generated image signals, in addition to the receivers 35a with plural reception channels, AD convertors 35b and memories (or storage devices or storage media) 35c. For instance, "other data generation device 35e" generates image display data, and via high order calculations, for instance, "other data generation device 35e" performs the measurements of displacements on the basis of the Doppler method or temperatures and performs analyses about the object.

By performing the phasing and summing processings at the respective positions in an ROI, the dynamic focusing is performed. Originally, the dynamic focusing is a term that is used for the range direction with respect to the reception by an effective aperture. In practical, however, the reception digital beamformings performed by the present invention are not limited to this. The reception unit 32 used in the embodiment of the present invention shown in FIG. 2 allows performing high accuracy digital beamformings with high speeds and with no approximate processings, calculation processes of which DAS processings are different from the above-mentioned calculation processes which the term expresses. Thus, in the embodiment of the present invention, the digital signal processing unit 33 shown in FIG. 2 is used instead of the phasing and summing device 35d shown in FIG. 4. At the digital signal processing unit 33, based on the image signals, various data can also be generated such as ones described in the present patent document.

For instance, the digital signal processing unit 33 can perform a beamforming processing with respect to the reception signals generated by the reception means such as the transducer 20, etc., and can also perform the Hilbert transform and other processings such as the spectral frequency division, the superposition, etc. with respect to the generated multi-dimensional reception signals. Also, the digital signal processing unit 33 can also generate for the measurement object the compositions, the structures, various data of physical quantities and properties. The data to be generated by the digital signal processing unit 33 are not limited to ones described in the present patent document. As mentioned above, the reception unit 32 can include the digital signal processing unit 33, and vice versa. The control unit (the measurement control unit) 34 can also control the digital signal processing unit 33 and other units by sending command signals, and the control unit 34 can also work as the digital signal processing unit, and vice versa.

The general phasing and summing device can also be realized in the digital signal processing unit 33 used in the embodiment of the present invention. Particularly, the features of the reception unit 32 are that in order to realize high speed and high accuracy processings, preserving the signal intensities or reducing the noises is performed using analogue devices such as analogue amplifiers or attenuators, for signal level controls, of the received signals generated by the reception aperture elements 20a or analogue filters (programmable and works under frequency properties and parameters set via the control unit 34), etc. In addition, by considering an advantage that analogue signal processings are faster than digital signal processings, effective uses of devices for linear or particularly, nonlinear single processings, if required, are also features. The analogue signals obtained through such processings are digitized (AD-converted) and the generated digital signals are stored into memories (or memory devices, memory media) 32c that can be written or read out with high speeds.

The digital signal processing unit 33 equipped with can be realized using devices, calculators, PLD (Programmable Logic Device), FPGA (Field-Programmable Gate Array), DSP (Digital Signal Processor), GPU (Graphical Processing Unit), microprocessor, etc. with general calculation capabilities, or an exclusive calculator, an exclusive digital circuit and an exclusive device, and the digital wave signal processings of the present invention are performed on the stored digital signals.

The devices are desired to exhibit high performances, and also devices used for analogue devices, AD convertors 32b, memories (or stored devices, stored media) 32c, and digital signal processing unit 33 (multi-cores, etc.). Also important are the number of communication channels between devices, channel capacities, wirings, wideband wireless communications. In particular, in the present invention, it is desirable that such functional devices are installed into a chip or a circuit board (the devices may be detachable), or the devices are directly implemented into a chip or a circuit board (including a multilayer type). Parallel processings are also important.

When the calculator also plays a role of the controller unit 34, if the device is not detachable, a remarkably higher security can be achieved than that obtained under a general programmed control. In a contrary, under the existing legislation, cases where disclosing of processing contents is demanded will increase. The digital signal processing unit 33 can also work as the control unit 34 that controls other units by sending command signals.

In the reception unit 32 used in the present invention, the trigger signals for making the AD convertors 32b to start the samplings of the received signals generated by the reception transducer (or the reception sensor) 20 (i.e., command signals for starting the AD conversions and storings of the digital signals into memories, stored devices or stored media 32c) are the same as those used for a general reception unit. For instance, ones of the command signals, generated by the control unit 34, for making the transmitters 31 to generate transmission signals to the transmission aperture elements 10a to be excited, can be used. When performing receiving waves suing plural reception aperture elements 20a in an effective aperture, the command signal to be sent to the transmission element to be excited first, last or other elements can be used, and occasionally the predetermined digital delays can be implemented on the trigger signals for staring the AD conversions.

The command signals can be generated on the basis of a command signal used for starting beamformings for a frame. In other words, the generations of the transmission trigger signals are counted, and if the hardware or control program confirms that the counted number reaches to the predetermined number, or the number, to be a programmable parameter, set by inputting using the input device 40 etc., a command signal is generated to start beamformings for the next frame. Similarly to other parameters, the number can be installed via various media such as CD-ROMs, floppy disks, MOs, etc. After running programs, using the input device 40, the number can also be selected interactively, and numerical data can also be directly input. Or, there various cases including the case where the number is set by reading out files in which data are recorded, etc. The number can also be set using dipswitches, etc. Not so many reception delay patterns are not required, analogue delay patterns can also be implemented on the received signals, after which AD conversions can be performed on the delayed, received signals.

In order to perform the reception dynamic focusing with high speeds, performing not the present patent's inventor's past invention that multiplications of complex exponential functions are performed on signals in a frequency domain on the basis of the Nyquist theorem but general high-speed implementations of reception delays leads errors determined by the sampling interval of an AD convertor. Thus, the AD converter's (32b's) sampling frequency is made high with a high cost, or the low speed beamforming must be performed by implementing the high accuracy digital delays on signals (phase rotation processing). In contrast, the present invention allows that the received signals are digital-sampled with synchronizations as mentioned above, such types of approximate errors do not occur. Moreover, high speed reception digital beamformings can be performed. The reception digital beamformings are remarkably faster than the present patent's inventor's past invention that performs the multiplications of the complex exponential functions in a frequency domain.

In the present patent, and also generally, the reception channel number is the number of communication lines that are used for performing one beamforming, to send waves (signals) received by the respective reception aperture elements 20a to the reception unit 32. Thus, the reception unit 32 can be explained as below. The formations of reception channels are various. Generally, in order to perform one beamforming every time, received signals generated by plural reception aperture elements 20a are applied with different delays. That is, the reception unit 32 is equipped with analogue or digital delay patterns as mentioned above, and the delay patterns that realize reception focusings or steering directions, etc. can be used according to the operator's selection using the input device 40.

The patterns can be programmable and according to the purposes, the pattern to be used or selective can also be installed via various media such as CD-ROMs, floppy disks, or MOs, etc. After running programs, using the input device 40, the patterns can also be selected interactively, and the delays (patterns) can also be directly input. Or, there various cases including the case where the patterns are set by reading out files in which data are recorded, etc. Particularly, when the delays to be used are analogue, the delays can also be changed in an analogue or digital manner, the delay circuit or the delay patterns themselves are exchanged by others or switched to others.

When the reception delay is digital, the received signals stored in the memories (or storage devices, storage media) 32c are read out to perform the phasing and summing the signals. In the instrument of the embodiment, the digital signal processing unit can implement the reception delays on the digital received signals, the digital received signals can be passed into the delay devices of digital circuit, or the control signals for starting the acquisitions of received signals generated by the control unit 34 (i.e., signals for switching on AD convertors 32b and memories, storage devices, or storage media 32c) can be delayed. Thus, the digital delays can be implemented at arbitrary positions including the AD convertors 32*b* and the post-devices, or the control unit 34.

Also the analogue delays can also be implemented on the received signals at arbitrary positions following the generating of the received signals at the reception aperture elements 20*a*, or at the control unit 34. When using the analogue delay patterns, plural aperture elements' generated received signals can be received at least by one receiver 32*a*. Thus, in the storages of the received signals, the respective received signals of reception apertures can be stored at positions (addresses) according to the reception delays, or when the received signals cannot be delayed at all, the stored received signals are read out and the digital wave signal processings mentioned later can be performed by the digital signal processing unit 33 (the digital signal processing unit 33 can also perform general phasing and summing processings).

The delay patterns can also be selected by switching analogue circuits or analogue devices and digital circuits or digital devices, and the delays set on the delay devices can be changed under the controls by the control unit 34 or programmable via installing or setting using inputting, etc. Delay devices can also be set in the control unit 34. Moreover, when the control unit 34 is made using a calculator, etc. as mentioned above, the control unit 34 can directly output command signals that are delayed under software controls.

The control unit 34 or digital delay can be realized using devices, calculators, PLD (Programmable Logic Device), FPGA (Field-Programmable Gate Array), DSP (Digital Signal Processor), GPU (Graphical Processing Unit), microprocessor, etc. with general calculation capabilities, or an exclusive digital circuit and an exclusive device. The devices are desired to exhibit high performance (multi-cores, etc.), and also devices used for analogue devices, AD convertors 32*b*, memories 32*c* and/or digital signal processing unit 33 performing transmission or reception beamforming processings.

Important are the number of communication channels between devices, channel capacities, wirings, wideband wireless communications. In particular, in the present invention, it is desirable that such functional devices are installed into a chip or a circuit board (the devices may be detachable), or the devices are directly implemented into a chip or a circuit board (including a multilayer type). Parallel processings are also important. When the calculator also plays a role of the controller unit 34, if the device is not detachable, a remarkably higher security can be achieved than that obtained under a general programmed control. In a contrary, under the existing legislation, cases where disclosing of processing contents is demanded will increase. The control software or delays can also be directly encoded, input or installed. The ways how to implement digital delays are not limited to these.

In the present embodiment, on the basis of the above-mentioned trigger signals sent form the control unit 34 (FIG. 2) in the body of instrument 30, the respective trigger signals that are commands for staring the AD conversions are provided to the AD convertors 32*b* of the respective channels. According to the command signals, the AD conversions of analogue signals of respective channels and the storings of the digitized signals into the memories, storage devices or storage media 32*c* are started. Till one frame of received signals are stored, with changing the transmission aperture position, the transmission effective aperture width, or the transmission steering directions, etc. and every the transmissions of waves or beams, with changing the reception aperture position, the reception effective aperture width or the reception steering directions, the transmission unit 31, the reception unit 32 and the digital signal processing unit 33 iteratively perform the processings from the transmission to the storing under the controls by the control unit 34. Moreover, every one frame of received signals is stored, coherent signals are generated by performing the digital wave signal processing method (digital beamforming method) of the present invention on the received signals.

Thus, if the instrument of the present invention is equipped with the above-mentioned analogue or digital delays, the delays are not always used directly for the DAS beamformings, the delays can also be used for implementing the delays on the timing for starting AD conversions of the received signals and storings the signals into memories (or storage devices, storage media) 32*c* to save and effectively use the memories, storage devices or storage media, and shorten the access times. The implementation of reception delays used for the beamformings are mainly the digital wave signal processings performed in the digital signal processing unit 33 absolutely and then, the saving and shortening the access time are very meaningful. When performing the classical SA that does not perform the physical beamformings at the transmissions (for instance, physical processings such as using calculators, exclusive devices, etc. that are different form the software beamformings such as using calculators, exclusive devices, etc.: the transmission or reception focusings or steerings, or the apodizations, etc.), the transmission delays are implemented at the same timing as that for implementing the reception delays by the digital wave signal processings.

Thus, the reception unit 32 is absolutely equipped with independent devices with respect to the respective reception channels, i.e., analogue or digital delays, the receivers 32*a*, the AD convertors 32*b* and memories (or the storage devices, storage media) 32*c*. If required, level controls using analogue amplifiers or attenuators, filters and other analogue operational devices are equipped with. That is, in the present invention's instrument, when the delays are implemented by using the reception delays, if delays for the beamformings are not implemented, errors dependent on a clock frequency do not occur similarly to the implementation of analogue delays.

That is, since the transmission digital delays causes the errors determined by the clock frequency absolutely, it is required to use an expensive, high clock frequency for decreasing the errors. However, it is not required for implementing the reception digital delays. By implementing the digital delays for the reception delays, no decreasing the accuracy and a high degree of freedom about the settings of delay patterns can be obtained, and by further using the analogue delays for the transmission delays, a high accuracy can be obtained as well as the required clock can be made low. The analogue delays can also be possible for changing the delays in an analogue fashion and can also be made programmable and digital controllable. However, the analogue delays have a lower degree of freedom than the digital delays, and for decreasing the cost, the delay patterns implemented by an analogue circuit can be switched and used, or exchangeable with proper ones. If a high degree of freedom is required for the transmission delay patterns, the digital delays must work with a high clock frequency.

As mentioned below, the coherent signals generated by the present invention's beamformings are referred to as "image signals." The reception effective aperture elements or their positions are controlled similarly to the transmission effective aperture elements (mentioned later). The digital beamformings are not always performed every one frame of reception signals is stored. For instance, every the received signals with the number of hardware's channels or a programmable parameter determined or set by the effective aperture width, other numbers predetermined or input by the input devices 40 etc. are stored, the digital beamformings can also be performed (there exists various means of input as mentioned above). Also image signals partially beamformed can also be synthesized, to generate one frame image signals.

In the cases, the received signals to be processed at adjacent positions can also be overlapped, and for the synthesizing the received signals, simple superpositions can also be performed (spectra superposed in a frequency domain can also be Inverse Fourier transformed), properly weighted superposition can also be performed, or simple connections can also be performed. The number of stored reception signals can also be confirmed by counting the trigger signals for storing reception signals (command signals sent from the control unit 34) in a hardware or a control program, and as mentioned above the command signal, generated by the control unit 34 every one frame, for starting the digital wave signal processings for the one frame can also be confirmed similarly, and then the one frame image signals are properly generated.

The highest frame rate realizable depends on the beamforming formation to be implemented, and basically determined by the wave propagation speed. In practical applications, it is determined by the time required for performing the digital calculations of one frame image signals. Thus, it is useful that the above-mentioned partial generations of image signals are performed in a parallel fashion. As mentioned above, it is also useful to perform the multidirectional synthetic aperture (SA) that the inventor of present invention previously developed, to generate reception beams at plural positions or in plural directions with respect to one transmission beam or to perform multi-focusings. In order to perform such beamformings with high speeds, parallel processings are useful. For all the beamformings, on the basis of the transmissions and receptions mentioned above, after storing the received signals for one frame beamforming or partially, the present invention's digital wave signal processings below-mentioned in detail can be performed. When the image signals cannot be generated in a real-time, the frame rate can also be decreased, or off-line processings can also be performed.

The reception apodizations performs the weighting on the received signals on the respective reception channels of aperture elements and can be changeable in a range direction. Although it is not impossible to be changeable in an analogue fashion, it is simple to be changeable in a digital fashion. For almost general reception units, the apodizations are changeable at respective positions or respective range positions, etc. at the timings of the phasing and summing, whereas in the instrument of the present invention the apodizations can be performed in the digital signal processing unit 33. Alternatively, it is rare that nonchangeable apodizations are performed, in which the apodizations are performed at the timings of level controls of received signals, generated by aperture elements, by analogue amplifications or attenuations.

Being different from apodizations, on the basis of calibration data about conversion efficiencies of drive signals to waves, at least the calibrations of signal levels can be performed, and also the apodizations can be simultaneously performed together with the level calibrations. The processings can also be objects, the dynamic ranges of wave shapes of received analogue signals can also be nonlinearly extended or compressed, and other analogue devices such as nonlinear elements, etc. can also be used in respective reception channels. Including the amplifiers, etc., the analogue devices to be used can be programmable, and the setting methods can be various formations. Similarly to other parameters, they can be directly set using the various types of input devices. Generally, the delays and apodizations can be implemented in the reception unit 32, which are realized at the same hierarchy level or at different hierarchy levels, and in the same or different formations, and then the phasing and summing devices can be used. In the digital signal processing unit 33 of the present invention, they can be carried out with a high degree of freedom.

The reception channels used for driving aperture elements in a reception effective aperture are switched using switching devices such as a shift-register, a multiplexer, etc., beamformings can be performed using other positioned effective apertures to scan the ROI. The delays of delay elements can also be changeable, the delay pattern (delay elements) can also be switched. Moreover, steering in plural directions can also be performed using an effective aperture, and occasionally the aperture position or the effective aperture width can also be changed. Moreover, steering directions can also be changed. Simple memories, storage devices, or storage media can be saved, and the access time can also be shortened. It is effective that the data to be frequently used are stored into small size memories that are simply written and read out.

In the present invention, the saving and shortening the access time are meaningful. The apodization patterns comprised of apodization elements can also be switched. Depending on the aperture position, the range direction and the steering direction, the beam shape can also be controlled. Specifically, an apodization (value), zero, means the corresponding reception element is not active and off. Thus, the apodization can also work as a switch of effective element and can also determine the effective aperture width (when apodization function in the aperture element array direction is a rectangular window, the switches of the effective elements are on; and when the apodization function is not constant, the switches are weighted on). Thus, the apodization elements are the same levels as those of switches.

When the delays or apodization patterns are equipped with plural patterns or programmable, the digital signal processing unit 33 in the body of instrument 30 calculates for waves propagating in media, on the basis of the responses from the transmission objects or the results of beamformings, the attenuations, scatterings (forward scattering or backscattering), transmissions, reflections, refractions, diffractions, impedances, or propagation speeds such as sound speed's frequency variances, or the spatial distributions, etc., and the delays or intensities of waves transmitted from or received by respective apertures, steering directions of beams or waves, or apodization patterns, etc. can also be optimized. The frequency properties (responses) of medium properties can also be calculated by dividing the frequency response of reception wave(s) by that of transmission wave(s) at each frequency instead of using the instantaneous frequency or phase of the reception wave(s) with respect to the transmission wave(s) such as a pulse wave, etc. and then, it is effective to calculate the spatiotemporal distribution of the medium properties by performing the inverse Fourier transform with respect to the frequency properties of medium properties. For the calculations, it is effective to correct the wave distortions generated by the observation instruments in advance as described in the paragraphs 0363 and 0371. Similarly to in the case of a superresolution using the division, since the division by a small spectrum leads a serious large error due to increasing a noise, it is effective to perform the regularization or the Wiener filtering, etc. The Maximum likelihood (ML) can also be effective and the MAP (Maximum a posteriori) can also be performed. The integration/fusion can also be performed. The processings can also be performed with respect to the plural echo data acquired at the same position. Or, similarly to other superresolution, it is also effective to perform a conjugate multiplication of frequency responses instead of the division. Various superresolutions including the superresolutions are also described in the present invention. In the cases using the above-mentioned instantaneous frequencies or instantaneous phases, or performing various other imagings (including a reflection method such as a fundamental, conventional echo imaging, etc. and transmission method, for instance), it is effective to correct the wave distortions generated by the observation instruments (devices) in advance.

Or, instead of the frequency response of the transmission wave(s), the division can also be performed by the frequency response of the reception wave(s) obtained with respect to the same transmission wave transmitted to a reference material (A simple reference material is, for instance, homogeneous in propagation properties such as a random scattering medium, or a reflector or a scatter set at a representative position, etc.; and an elaborated reference material is, for instance, an inhomogeneous in that the accumulations of changes in wave spectra due to the medium properties when the wave propagating in a homogeneous medium such as frequency-dependent, propagation speed, impedance, scattering, attenuation, etc., can be compensated, etc.). Or, instead of the division, the maximum likelihood (ML) estimation or the conjugate multiplication of the frequency responses is also effective and the relative properties can be calculated with respect to the reference material as the result (i.e., applications of a linear system). The reference material can also be one generating a diffraction(s).

The above-described calculations can also be performed at once for over the region of interest; and according to the spatial inhomogeneity in a point spread function (PSF) expressed by the propagation properties of the wave(s) itself, a local region or each local region can also be processed (The former calculation is simple). The latter local processing has a precent for the superresolution processing, in which the division is performed by the frequency response of a point spread function locally estimated for a reference material (a random scatter distribution or a scatter set at a representative position, etc., nonpatent documents 35 and 36). Also for other superresolution processings, it is effective to perform the respective processings for over a region of interest at once or every local region similarly.

In the classical synthetic aperture (SA), all the reception elements can be equipped with the reception channels including the receivers 32a. Generally, SA can be performed, in the phasing and summing device, together with the reception apodizations, and in the present invention, SA can be implemented, in the digital signal processing unit 33, together with the reception apodizations.

The parameters used in the transmission unit 31 or reception unit 32 mentioned above can effective by installing the parameters into respective functional devices in the units via various media such as CD-ROMs, DVDs, floppy disks, or MOs, etc., i.e., an ultrasound frequency, a bandwidth, a code, a delay pattern, an apodization pattern, an analogue device used for the signal processing, an effective aperture, a focus position, a steering angle, and times to perform the transmissions and receptions required.

After running programs, using the input device 40, the number can also be selected interactively, and numerical data can also be directly input. Or, there various cases including the case where the number is set by reading out files in which data are recorded, etc. The number can also be set using dipswitches, etc. The units can also be exchanged or switched. By selecting the measurement objects, or setting the transducers on the instrument, the instrument can recognize them and can automatically operate under the desired parameters. It is possible to post-control the parameters. In addition, by installing the functional devices of a general reception unit, the comparison between the image signals obtained using the present invention's instrument and those obtained using the general phasings and summings, particularly including approximate interpolations, can be performed.

<Input Devices>

The input devices 40 are used, for instance, for setting various types of parameters as mentioned above. The input devices are various devices such as a keyboard, a mouse, buttons, panel switches, a touch command screen, a footswitch or a tacking ball, etc., and not limited to these. Using storage media such as general memories, USB memories, hard disks, flexible disks, CD-ROMs, DVD-ROMs, floppy disks or MOs, etc., the operation system (OS) or the device software can be installed or versioned up, various types of parameters can be set up or updated. The input devices 40 are equipped with various types of devices that can read out data from the storage media, or the input devices 40 are equipped with interfaces such that various type devices are installed to be used, if required.

The input device 40 can be used for setting the parameters of various types of operational modes according to the present embodiment as well as controlling and switching of the operational modes. When the operator is a human, the input device 40 is a so-called man-machine interface, and however the input device 40 is not always controlled by a human. The same inputting operation can also be achieved by receiving the parameters, data, or control signals from other devices via various types of communication standards and connectors, or by using wire or wireless communication (at least communication devices equipped with reception functions) and not limited to the above-mentioned examples. Exclusive or general networks can be used.

The input data are stored into the internal or external memories with respect to the instrument, stored devices, or stored media, and the functional devices equipped in the instrument operate with referring to the stored data. Or, when the functional devices in the instrument are equipped with the exclusive memories, the data are written into the memories or updated to determine the operational setting in a software fashion, or set or updated in a hardware fashion. Operation of the calculation function considers the resource of the instrument occasionally on the basis of the input data, and the optimized setting parameters can be calculated to be used. The operation modes can also be set by commands. Additional information about the waves of measurement objects (kinds, features and properties of waves, intensities, frequencies, bandwidths, codes, wave sources, diffractions, etc.) or objects or media in which waves propagate (propagation velocities, physical properties according to waves, attenuations, forward scatterings, backward scatterings, transmissions, reflections, refractions, diffractions, etc. or their frequency variances, etc.) are given, the instrument can also perform analogue or digital processings properly.

<Output Devices>

As a representative output device 50 is a display device, which can display the generated image signals, and others such as various results measured on the basis of the image signals as numerical data or images, etc. The image signals can be converted to display images, or dynamic images or static images in formats (scan converted) and graphic-accelerators can be also used. The images are displayed in a gray (brightness) or color scale, and the means of the brightness or color can be displayed with a scale or a logo. Or, the results can also be displayed using a bird'-eye view, graphs, and not limited to these.

When the results are displayed, the respective operation modes and various types of parameters or patterns (patterns' names) can also be displayed simultaneously using logos and characters. Also complementary information or various types of data about the measurement objects input by operators or other instruments can be displayed. The display instrument can also be used for displaying the GUI (Graphical User Interface) to be used for setting the respective parameters or patterns using the input instrument 40, or by using an attach command screen, drawn images of arbitrary positions or of arbitrary areas specified can be extended to be displayed largely, and can be used to display the respective numerical data for partially working as an input device 40.

As the display devices, various ones such as a CRT, a liquid crystal or an LED can be used. Exclusive 3D display devices, etc. can also be used, etc., and not limited to these. The output data are not always interpreted or read directly, and the body of instrument (calculator) interprets, on the basis of the predetermined calibration data or calculations, the output data and displays the results (for instance, the measurement objects' compositions and structures are understood form the spectral analysis of received signals, etc.). The output data can also be output on other instruments, of which output data can also be interpreted. Moreover, the same instruments (for instance, robots, etc.) or other instruments can put the output data to practical use.

One instrument can receive plural waves and can generate image signals, and further the data mining or unification (fusion), etc. can also be performed. Other instruments can also be used to perform processings of the kind. The properties or features of generated image signals (intensities, frequencies, bandwidths, or codes, etc.) can also be analyzed. Thus, the data acquired by the instruments according to the present embodiment can also be used in other instruments, and in practical the communication instruments with a transmission function at least can also be used as one of the output devices 50. Exclusive or general networks can also be used.

<Storage Devices>

The generated image signals or the various results (numerical data or images, etc.) measured on the basis of image signals are stored into internal or external memories with respect to the instruments, storage instruments or storage media that can become the out devices 50. Here, these are distinguished with the display devices, and referred to as "storage devices." In FIG. 2 etc., the external storage device 60 is also shown. When storing the image signals, the operation modes or parameters set, complementary information or various types of data about the measurement objects input by operators or other instruments can be stored together with the image signals. As the storage devices, general or special memories, USB memories, hard disks, flexible disks, CD-R (W), DVD-R (W), a video recorder, or image data storage devices, etc. can be used, and not limited to these. The storage devices are properly used according to the applications, data amount to be stored or times required for writing in or reading out, etc.

Past stored image signals or other data are read out from the storage devices and replayed. The storage devices are important in that an OS or a device software, or parameters set are stored mainly. The respective functional devices can also be equipped with exclusive storage devices. Detachable storage devices can also be used in other instruments.

The body of instrument 30 reads out image signals stored in the storage devices and implements the high order digital signal processings. Resynthesized image signals (frequency modulations, increasing bandwidths or multi-focusings, etc. performed by linear or nonlinear processings) can be generated, image analyses of image signals (superresolutions, enhancings, smoothings, separations, extractings, or CGs, etc.) can be performed, various types of measurements such as displacements and deformations of objects or various other temporal changes, etc. can be performed; and images or measurement results can be output and can also be displayed onto display devices.

The measurement results to be stored include the waves themselves, waves' attenuations, scatterings (forward scatterings, backscatterings, etc.), transmissions, reflections, refractions, diffractions, etc. The stored results are read out and used to optimize various types of parameters for generating image signals. Thus, the storing results can be used. The optimizations can be performed using the calculation functions equipped with the control unit 34 or the digital signal processing unit 33.

<Control Unit>

The control unit 34 controls all the operations of the instrument. The control unit 34 can be comprised of various types of calculators or exclusive digital circuits, etc., and can work as the digital signal processing unit 33. Basically, according to various types of demands input via the input device 40, the control unit 34 controls, on the basis of various types of control programs or various types of data read out from the storage devices, the transmission unit 31, the reception unit 32 and the digital signal processing unit 33 such that the image signals are generated by performing the transmissions and receptions of waves and performing the wave digital signal processings.

When the control unit 34 is comprised of the exclusive digital circuits, the parameters can be changeable and however, only the determined operations can be realized even including the cases where the operations are switched. When the control unit 34 uses the calculators, including performing the version up, the degree of freedom is high. In addition to the controls for the realizing the above-mentioned various types of operations, the basis of the control unit 34 is to perform the controls of scannings and image signal generations by providing a repetition frequency or information about the transmission and reception positions, etc. to the transmission unit 31 and the reception unit 32 according to the transmission and reception aperture number to be used (the respective channels) or the beam number to be generated, the frame number to be generated (the operations may be continued unless the number is not set or not stopped), the frame rate to be realized. Various interfaces are equipped with and various devices can also be used simultaneously.

The instrument according to the present embodiment can be used as one of devices used for general networks or sensor networks, etc., and may be controlled by the controller of the network systems or may be used as a controller for controlling locally comprised networks. For the uses, interfaces can also be equipped with.

<Beamforming Methods>

Next, effective and fast digital beamforming methods using digital Fourier transforms, performed by the digital signal processing unit 33 in the body of instrument 30 (FIG. 2), for plural transmission and reception aperture elements (including arrayed elements) are explained. In the digital signal processings, occasionally, the middle of data generated in the calculation process or data to be iteratively used can be stored into the memories equipped with or storage devices. For generating plural image signals with the same phases of the objects, the storage devices can be used effectively. The small size memories can also be useful.

The generated image signals can also be displayed as a static image by the output device 50 such as a display device, etc., or can also be stored into the external storage devices 60 using storage media such as hard disks, etc. When the digital signal processing unit 33 is a calculator, various programming languages can be used. Although the assembler is useful, when the calculator is run using high-level language programs such as C-language or Fortran, etc., high speed operations can also be performed by implementing the optimizations or parallel processings at the compiling the languages. Softwares for performing general operations such as MatLab or various types of control softwares, ones with graphic interfaces, etc. can also be used, or special ones can also be used.

Below, by using cases where the waves are ultrasounds, the beamforming methods for used for the present invention's instruments are explained. The beamforming methods used for the present embodiments are the following methods (1) to (7). On the methods (7), in addition to various types of beamforming methods, the representative observation data generated by the digital signal processing unit 33 are disclosed.

The method (1) is a method used for the reception beamformings with respect to transmissions and/or receptions of plane waves including cases where the transmission direction is steered, in which wavenumber matching (mapping) is performed in a Fourier domain with no approximate interpolation required for the past Fourier beamforming methods. The method (1) includes an invention performed on the wavenumber matching when the steering is performed, i.e., performing multiplications of the complex exponential functions related to the respective cosine and sine of a steering angle to received signals to perform the wavenumber matchings in the axial and lateral directions. Similarly to the classical monostatic SA, the accuracies of measurement results are increased. Moreover, the method (2) is also disclosed, i.e., a high speed digital processing method about steered dynamic focusings to be performed on the basis of the monostatic SA.

Moreover, the method (3) is also disclosed, i.e., a high speed digital processing method on the basis of the multistatic SA. The method (2) performing the digital monostatic SA with steering can be achieved with a high accuracy such that the 1st moments of multi-dimensional spectra or the instantaneous frequencies of generated image signals can be expressed ideally using the steering angle and the carrier frequency (as mentioned later, a wavenumber vector has components expressed by the multiplications of sine and cosine of the steering angle with respect to the carrier frequency) by performing wavenumber matching with no approximate interpolations similarly to the method (1). Alternatively, the method (3) performing the multistatic SA can be achieved by generating echo data frames, with the same number as that of reception elements, comprised of echo signals received at the same position in plural reception position with respect to the transmission position. Moreover, the above-mentioned monostatic digital SA is implemented on the respective echo data frames in a Fourier domain, and the superposed, processed results are inverse-Fourier transformed to accomplish the multistatic SA with a high accuracy. Consequently, the method (3) can generate echo data with the same number of digital SA processings as that of the reception aperture channels, and with a remarkably higher speed than the so-called conventional DAS (Delay and Summation) method generates a high spatial resolution image signal frame by superposing the generated low spatial resolution image signal frame.

By the way, the DAS method can be realized by implementing delays (phasing) onto the received signals with a high speed via performing approximate interpolations in a spatial domain or by implementing delays in a Fourier domain (a past achievement of the present invention's inventor), after which the phased, received signals are summed in a spatial domain. The former yields a high speed, but low accuracy, beamforming; the latter yields a high accuracy, but low speed beamforming.

The method (4) realized on the basis of the method (1) or (3) is also disclosed, i.e., a high accuracy digital dynamic focusing reception beamforming method for a transmission fixed focusing. Moreover, the method (5) is also disclosed, i.e., for allowing the echo data generations using the convex, sector scanning or IVUS, from echo data received on the polar coordinate system, directly on the Cartesian coordinate system used for displaying the echo data to be generated with a high accuracy with no approximate interpolations by performing processing via the Jacobi operation.

The method (6) is also disclosed, i.e., the migration method using the present inventions that allows high speed processings with high accuracies and with no approximate interpolations. All the beamforming processings of methods (1) to (5) can also be performed by using the migration method. At last, the applications on the basis of these methods (1) to (5) are disclosed as method (7). Using these methods, it is possible to demonstrate that arbitrary beamformings on the basis of focusings and steerings can be performed.

Method (1): Transmission and/or Reception Beamforming of Plane Wave (i) Echo Signal with Respect to Plane Wave Transmission (Image Signal)

Figure 5:
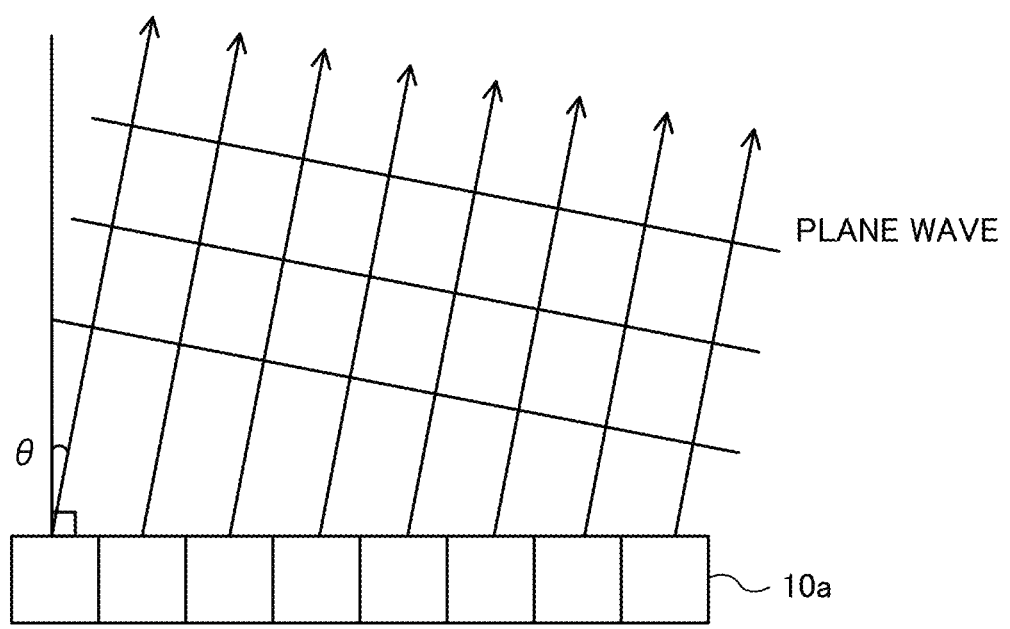
FIG. 5 shows an illustration of steered plane wave transmission.

FIG. 5 shows illustrations for a steered plane wave transmission. The plane wave transmission can be performed using a linear array-type transducer by using all the effective array elements simultaneously to transmit ultrasounds. When the wavenumber is k, and when the plane wave with the wavenumber vector expressed as eq. (0) is transmitted (x and y respectively expresses the orthogonal directions of scanning and an axial (depth) of the Cartesian coordinate system, of which zeros of y-axis exist on the position of reception effective aperture element array), the acoustic pressure of position (x,y) is expressed as eq. (1).

$$(k_x^t, k_y^t) \tag{0}$$

$$p(x,y;k) = A(k)e^{ik_x^t x + ik_y^t y} \tag{1}$$

Here, A(k) is frequency spectra of a transmitted pulse, and eq. (2) holds.

$$k_y^t = \sqrt{k^2 - (k_x^t)^2} \tag{2}$$

Each echo signal form a scatter with a reflection coefficient $f(x,y_i)$, positioned at a depth $y=y_i$, is expressed as eq. (3).

$$s(x, y_i, k) = f(x, y_i) p(x, y_i, k) \qquad (3)$$

The angular spectrum of the eq. (3) is expressed by eq. (4).

$$S(k_x, k, y_i) = \int_x s(x, y_i, k) e^{ik_x x} dx \qquad (4)$$
$$= \int_x f(x, y_i) A(k) e^{ik_x^t x + ik_y^t y_i} e^{ik_x x} dx$$

Expressing the frequency response of the transducer by $T(k)$, the angular spectra, at the aperture plane ($y=0$), of the echo signals from the depth $y=y_i$ are expressed by eq. (5).

$$R(k_x, k, y_i) = T(k) S(k_x, k, y_i) e^{ik_y y_i} = T(k) S(k_x, k, y_i) e^{i\sqrt{k^2 - k_x^2}\, y_i} \qquad (5)$$

Thus, adding the angular spectra from the respective depths yields the angular spectra of echo signals expressed by eq. (6).

$$R'(k_x, k) = \int_y R(k_x, k, y) dy = \int_{x,y} f(x,y) A(k) T(k) e^{ik'_x x + ik'_y y} dx dt \qquad (6)$$

Thus, the echo signals (image signals) are expressed by eq. (9) by implementing IFFT on the spectra via performing the wavenumber matching expressed by eqs. (7) and (8).

$$F(k'_x, k'_y) = R'(k_x, k) \qquad (7)$$

$$\begin{cases} k'_x = k_x + k_x^t = k_x + k\sin\theta \\ k'_y = k_y + k_y^t = \sqrt{k^2 - k_x^2} + k\cos\theta \end{cases} \qquad (8)$$

$$f(x,y) = F^{-1}(F(k'_x, k'_y)) \qquad (9)$$

Considering the transmission and reception inversely, arbitrary transmission beamformings (for instance, steered plane wave, steered fixed focusing beam, steering dynamic focusing using SA, non-steered waves or beams, and various others, etc.) are performed with respect to the measurement object, a wave arriving from the measurement object can be used as a received plane wave with the steering angle θ (including a case of zero degree). The way how to interpret the transmission and reception was not disclosed. Similarly, when arbitrary waves or beams transmitted with arbitrary steering angles (zero or non-zero degree) are performed, it is possible to receive the waves with the same or different steering angles θ (zero or non-zero degree). Moreover, reception beamformings can be performed on the coordinate system determined by the reception aperture with respect to arbitrary waves transmitted from arbitrary wave sources or arbitrary transmission effective aperture array (for instance, the same one as that of the reception effective aperture array or a different one with an arbitrary geometry and an arbitrary direction, other positioned one from the reception effective aperture or in the same physical aperture, etc.).

When physically performing the plane wave transmission with a steering angle α (including a case of zero degree), implementing the steering with a steering angle θ (including a case of zero degree) in a software fashion yields the transmission of a steered plane wave with a steering angle (α+θ) (finally, generated transmission steering angle is the mean of α and θ). The software steering (steering angle θ) can be performed for reinforcing the physically performed steering (steering angle α) or for realizing a steering of a plane wave transmission in a software fashion purely or can be interpret that reception steering of a plane wave is performed in a software fashion.

When performing the transmissions with a physical steering angle α, a software steering angle θ or both steerings α+θ are performed, reception dynamic focusing with a steering angle φ can be realized by performing the steering angle used in the method (2) next explained (finally, generated transmission steering angle is the mean of transmission and reception steering angles) The software steering (steering angle θ) can be performed for reinforcing the physically performed steering (steering angle α) or for realizing a steering of a plane wave transmission in a software fashion purely, or can be interpret that reception steering of a plane wave is performed in a software fashion in addition to the reception dynamic focusing (including a case where the steering angle φ is zero degree).

In these cases, the software transmission and reception beamformings can be considered inversely. Performing the exchanging of the software steered plane wave transmission (including a case where the steering angle is zero degree) and the software steered dynamic focusing reception (including a case where the steering angle is zero degree) has the same processings as those of the original beamforming (equivalent). Generated, beamformed signals can also be interpreted as ones beamformed with respect to the physically received, steered plane wave. Generally, regardless performing the steering or not, it is not reasonable to physically perform dynamic focusing transmission and however, it is also possible to interpret that a wave is physically received as a steered plane wave.

Also using this method allows performing arbitrary transmission beamformings (for instance, steered plane wave, steered fixed focusing beam, steering dynamic focusing using SA, non-steered waves or beams, and various others, etc.). That is, performing the same processings as those for this plane wave transmission allows dealing with arbitrary waves or beams (for instance, the above-mentioned examples, etc.) generated by physical beamformings. In other words, even if arbitrary transmissions are performed, reception beamformings (dynamic focusing, etc.) can be performed. Particularly when performing plural transmissions, simultaneous processings can be performed. In addition to a transmission steerings (the angles including a case of zero degree), the transmission or reception steerings of a plane wave or a dynamic focused beam can be performed (the angles including a case of zero degree). The finally generated steering angles are means of the transmission and reception angles. Also similarly to the above mentioned beamformings, the transmission and reception can be considered inversely and then, various combinations of beamformings can be performed. The respective transmission and reception beamformings are performed and plane wave processing can also be performed for both the transmission and reception in a software fashion. As explained later, these are also for the 3D beamformings using a 2D array.

On the basis of the above explained theory, the calculation method disclosed by J.-y. Lu (nonpatent documents 3 and 4) implements, in order to calculate $R(k_x, k)$, the 2D FFT on the received signals with respect to the time and space at first, the wavenumber matching using eq. (7) next, and the 2D IFFT finally (also described in the paragraph 0354). The wavenumber matching is performed using approximations such as a linear interpolation or using the most neighborhood data. Thus, to increase the approximation accuracy, over sampling of received signals is required. High order approximate interpolations or a sinc function can also be used. In 3D cases, similarly, 3D FFT and 3D IFFT are performed. One of features of the present intention is to perform the wavenumber matching with no approximate interpolations and however, when the processings are applied to various beamformings as likely disclosed in the paragraphs 0192 to 0196, the corresponding approximate interpolations can also be performed to yield approximate solutions with high speeds.

(ii) The Present Invention's Calculation Procedure of Echo Signal (Image Signal) with Respect to Transmission and/or Reception Beamforming of Plane Wave The case where the transmission and/or reception of a plane wave with a steering angle θ is explained. Using the present invention, the wavenumber matching is performed as follows: at first, the wavenumber matching is performed in the lateral direction x by multiplying the complex exponential function (eq. (9a)) to the received signal before performing the FFT in the lateral direction (a spatial direction), and subsequently in the depth direction by multiplying the complex exponential function (eq. (9c)) in addition to the complex exponential function (eq. (9b)) with removed the performed lateral matching processing for simultaneously yielding a spatial resolution in the depth direction y. The steering angle θ can be zero degree as well as non-zero degree. This processing is not disclosed in prior art documents.

$$\exp(ik_x'x) = \exp(ik \sin \theta x) \tag{9a}$$

$$\exp(i\sqrt{k^2-(k_x-k_x^t)^2}y) = \exp(i\sqrt{k^2-(k_x-k\sin\theta)^2}y) \tag{9b}$$

$$\exp(ik_y'y) = \exp(ik \cos \theta y) \tag{9c}$$

Figure 6:
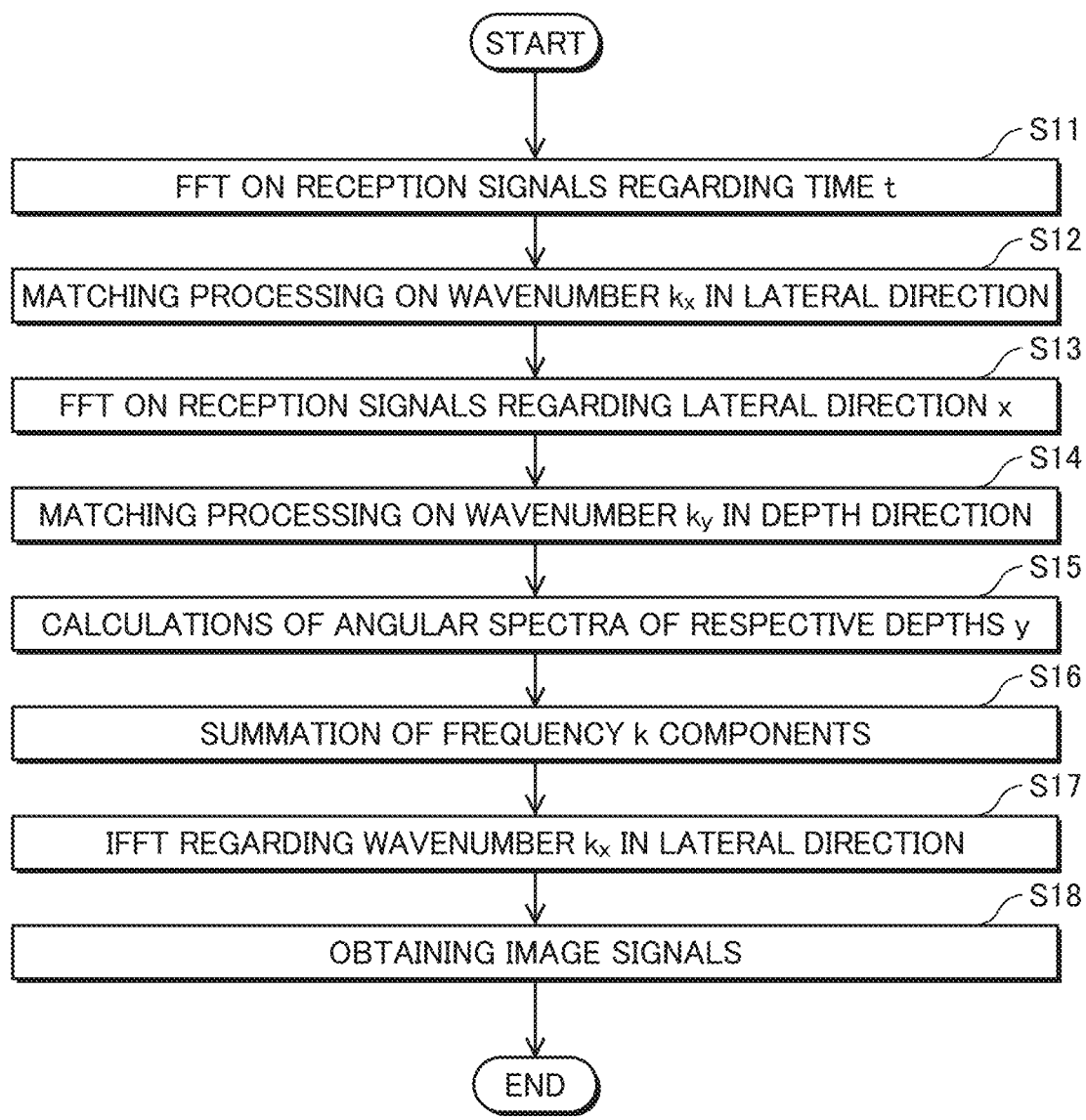
FIG. 6 shows a flowchart about the digital signal processing for steered plane wave transmission.

FIG. 6 shows the flowchart explaining the digital signal processing for the steered plane wave transmission. The calculation procedure follows. At the step S11, as shown in eq. (10), the received signals are Fourier transformed with respect to the time t (FFT should be performed):

$$R'(x,k) = \int r(x,t)\exp(i\omega t)dt \tag{10}$$

where k is a wavenumber expressed using the angular frequency ω and an ultrasound propagation speed c as k=ω/c, form which analytic signals are obtained. Here, although according to the above-explanation, the processing is performed using the plus signed kernel of the complex exponential function for the Fourier transform referred to as, according to the usual Fourier transform, the processing can also be performed using the minus signed kernel of the complex exponential function. Anyway, when the processing to be performed later as the inverse Fourier transformed referred to as, absolutely a kernel of which sign being inverted is used in the complex exponential function (That is, for the transforms at the first and last, the signs of kernels of complex exponential functions are being inverted and then, the inverse Fourier transform and Fourier transform generally referred to as can be respectively performed for the first and last transformations: the order of transforms can be inverted.). This is also for other methods (2) to (7).

Next, at the step S12, the matching processing is performed with respect to the wavenumber $k_x$ for steering by multiplying eq. (11) to eq. (10) and at the step S13, Fourier transform is performed on the signals in the lateral direction x (FFT should be performed) to yield signals expressed by eq. (12). When performing the multiplication of eq. (10) (the results of FFT performed on time t) and eq. (11) (the complex exponential function), exclusive FFT can also be useful to yield the multiplication results directly.

$$\exp(ik_x'x) = \exp(ik \sin \theta x) \tag{11}$$

$$R'(k_x,k) = \int R(x,k)\exp[i(k_x+k \sin \theta)x]dx \tag{12}$$

The results of eq. (12) can also be obtained by performing the calculation of eq. (12) directly.

This twice Fourier transforms (2D Fourier transform) analyze the received signals into plane wave components. The angular spectra of an arbitrary depth position y generated by the respective plane waves can be calculated by shifting the phase via performing of multiplication of eq. (13).

$$B(k_x, k, y) = \exp(i\sqrt{k^2-(k_x-k_x^t)^2}\, y)$$
$$= \exp(i\sqrt{k^2-(k_x-k\sin\theta)^2}\, y) \tag{13}$$

At the step S14, the matching processing is also performed on the wavenumber $k_y$ by simultaneously multiplying eq. (14).

$$\exp(ik_y'y) = \exp(ik \cos \theta y) \tag{14}$$

At the step S15, the angular spectra of the respective depths y are calculated. That is, by multiplying eq. (15), eq. (16) can be obtained.

$$B'(k_x,k,y) = \exp(i(\sqrt{k^2-(k_x-k\sin\theta)^2}+k \cos \theta)y) \tag{15}$$

$$R(k_x,k,y) = R'(k_x,k)B'(k_x,k,y) \tag{16}$$

The acoustic pressure field generated at a depth y by the respective plane wave components can be calculated by performing the inverse Fourier transform (IFFT) on the lateral direction x as eq. (17).

$$f(x,y,k) = \int R(k_x,k,y)\exp(-ik_xx)dx \tag{17}$$

Finally, the image signals can be obtained by summing up the plural wavenumber k (or frequency) components.

Here, the order of integral calculations regarding the wavenumber k (or the frequency) and spatial frequency $k_x$ are exchangeable. Thus, summing up k components of angular spectra at the step S16 and performing the IFFT with respect to the wavenumber $k_x$ at the step S17 can also yield the same image signals at the step 18. In this case, the calculations can be accomplished by one-time inverse Fourier transform at each depth position and then, the high-speed calculation can be achieved. This is also for all methods (1) to (6).

The wavenumber matching for steering is performed on the basis of eqs. (11) and (14). Being different from the wavenumber matching method performed via approximate interpolations in a Fourier domain (nonpatent documents 3 and 4), since such approximations are not performed, the present invention allows the high accuracy calculation.

Physically or mathematically, the wavenumber matching can also be performed at the first Fourier transforms or at the last inverse Fourier transforms. These are also for other methods (1) to (6). As described in the paragraph 199, similarly to the above explanations, a positive sign is used in the complex exponential's kernel for the Fourier transform and however, the minus sign can be used instead as that of the usual Fourier transform. Regardless the sign, the inverse Fourier transform to be performed at the last absolutely uses the inverted sign in the kernel (That is, for the transforms at the first and last, the signs of kernels of complex exponential functions are being inverted and then, the inverse Fourier transform and Fourier transform generally referred to as can be respectively performed for the first and last transformations: the order of transforms can be inverted). When performing the wavenumber matching with the first Fourier transform, to achieve eq. (8), with respect to the reception signal r(x,y) (here, being different from eq. (10), the depth distance y is used instead of the wave propagation time t.), using eq. (11) together to perform the Fourier transform in the lateral direction x as expressed in eq. (12), eq. (15) with eqs. (13) and (14) expressed for the Fourier transform in the depth direction y is used, where the correction to be performed in eq. (15) about k sin θ is not performed since the phase matching is performed in 2 directions simultaneously, i.e., $$R'(k_x,k_y)=\int r(x,y)\exp[i(k_x+k\sin\theta)x+i(\sqrt{k^2-k_x^2}+k\cos\theta)y]dxdy \quad (16')$$

(the results of usual inverse Fourier transform). When the steering angle θ is zero, the 1D Fourier transform can be performed in the lateral direction x, which should be the fast Fourier transform (FFT) (When performing calculations similarly to the above equation, the usual inverse Fourier transform is performed.). And, to perform the Fourier transform in the depth direction y with respect to the calculated R'(kx,y) together with the wavenumber matching, the following 1D processing can be performed.

$$R'(k_x,k_y)=\int R'(k_x,y)\exp[i(\sqrt{k^2-k_x^2}+k)y]dy \quad (16'')$$

Totally, the calculations are faster than the respective calculations R'(kx,ky) according to eq. (16'). And finally, the inverse 2D Fourier transform in the x and y directions are performed for eq. (16') or (16") to yield the image signal f(x,y). The 1D inverse Fourier transforms can also be performed in the respective directions x and y, for which the inverse fast Fourier transforms (IFFT) are effective (When performing calculations similarly to the above equations, the usual 2D Fourier transform is performed.).

Or, when performing the wavenumber matching with the last Fourier transform reversely, the 2D Fourier transform is performed for the reception signal r(x,y) at first to yield R(kx,k) and at the last inverse Fourier transform, to achieve eq. (8), using eq. (11) together to perform the inverse Fourier transform in the lateral direction x, eq. (15) expressed with eqs. (13) and (14) for the inverse Fourier transform in the depth direction y is used, where the correction to be performed in eq. (15) about k sin θ is not performed since the phase matching is performed in the 2 directions simultaneously, the image signal is calculated as follows:

$$f(x,y)=\int R(k_x,k)\exp[i(k_x+k\sin\theta)x+i(\sqrt{k^2-k_x^2}+k\cos\theta)y]dk_xdk. \quad (16''')$$

Here, when the steering angle θ is zero, at first, the following 1D processing is performed to achieve the inverse Fourier transform in the depth direction y with performing wavenumber matching:

$$R'(k_x,y)=\int R(k_x,k)\exp[i(\sqrt{k^2-k_x^2}+k)y]dk \quad (16'''')$$

and next, the 1D inverse Fourier transform can be performed in the lateral direction x, which should be the inverse fast Fourier transform (IFFT). Totally, the calculations are faster than the respective calculations of f(x,y) according to eq. (16''').

Instead, for these, the wavenumber matchings corresponding to eqs. (11) and (14) can also be performed by performing the frequency modulations about kx and ky, i.e., by multiplying the complex exponential functions to spatiotemporal signals and performing the summation. In this case, at first, the 1D transform can be performed in the lateral direction x, which should be performed by the fast transform, and next the 1D processing using eq. (13) can be performed to achieve the phase matching together with the transform in the depth direction y, which can increase the calculation speed.

In the 3D cases, similarly, the 3D Fourier transform, and the 3D inverse Fourier transform can be performed. This is also for other methods (1) to (6).

Also when using a 2D aperture element array, arbitrary waves are transmitted from wave sources positioned in arbitrary directions to the measurement object and then, the waves arriving from the measurement object are received as a plane wave and processed by 3D wave digital signal processing, 3D Fourier transform is performed regarding an axial (or depth, y) and lateral directions (x and z) on the 3D Cartesian orthogonal coordinate system (x,y,z) expressed by an axial direction y determined by the direction of a flat reception aperture element array and lateral directions x and z, for instance. When the steering angle being an angle between the reception direction as a plane wave and the axial direction (y) is expressed using zero or non-zero elevation and azimuth angles, similarly to when performing the 2D wave digital signal processing explained above, the following wavenumber matching is performed on the 3D Fourier transform R'(k_x,k,k_z) of the received signals with no approximate interpolations.

$$F(k'_x, k'_y, k'_z) = R'(k_x, k, k_z) \quad (7')$$

$$\begin{cases} k'_x = k_x + k_x^t = k_x + k\sin\theta\cos\varphi \\ k'_y = k_y + k_y^t = \sqrt{k^2 - k_x^2 - k_z^2} + k\cos\theta \\ k'_z = k_z + k_z^t = k_z + k\sin\theta\sin\varphi \end{cases} \quad (8')$$

Similarly to the 2D case, when the processings are applied to various beamformings as likely disclosed in the paragraphs 0192 to 0196, according to eqs. (7') and (8'), the corresponding approximate interpolations can also be performed to yield approximate solutions with high speeds and in the case, the 3D inverse Fourier transform is performed on F(k_x',k_y',k_z').

When not implementing the approximate interpolations on the wavenumber matching, at first the wavenumber matching in lateral directions x and z by multiplying the complex exponential function eq. (C21) expressed by the wavenumber k and an imaginary unit i to the Fourier transforms of the received signals in the axial direction y.

$$\exp\{ik\sin\theta(\cos\varphi x+\sin\varphi z)\} \quad (C21)$$

And the wavenumber matching is subsequently performed in the axial direction by multiplying, to the angular spectra obtained by performing Fourier transforms on the multiplications in the lateral directions x and z (2D Fourier transform or 2D FFT), the complex exponential function (eq. (C23)) in addition to the complex exponential function (eq. (C22)) with removed the performed lateral matching processings for simultaneously yielding a spatial resolution in the depth direction y. Here, the wavenumbers in the lateral directions are expressed as $k_x$ and $k_z$.

$$\exp(i\sqrt{k^2-(k_x-k\sin\theta\cos\phi)^2-(k_z-k\sin\theta\sin\phi)^2}y) \quad (C22)$$

$$\exp(ik\cos\theta y) \quad (C23)$$

The performing wavenumber matching with no approximate interpolations allows generating image signals on the Cartesian coordinate system directly. That is, the sound pressure field at each depth y generated by the respective plane waves can be obtained as image signals by performing the 2D IFFT with respect to the lateral directions x and z and summing up the plural wave number k components (or frequency components). Off course, even when the steering angle or either elevation or azimuth degree is zero, the processings can be performed.

In the above explained calculations, the bandwidth determined by the transmission signals or the SN ratio of the received signals considered is used to set the bandwidth to be processed. For instance, when generating analytic signals on the basis of eq. (10), those with the required band-limited are generated and stored (corresponding to the down-sampling). Although the method or instrument of the present invention does not perform the approximate interpolations when performing the wavenumber matching, the over-sampling of echo signals in the depth and lateral directions also yield the effects for yielding image signals robust to noises contaminated in received echo signals. These are also for other methods (1) to (6).

On eqs. (13) to (15) or eqs. (C22) and (C23), by setting the position (coordinate) y in a depth direction or the range, the interval of data in the direction, image signals with an arbitrary depth position or depth range, or an arbitrary interval or density in the depth direction can be generated with no approximate interpolations. Regardless performing the down-sampling explained in the paragraph 0208 or not, up-sampling can be performed. The down-sampling is effective within the Nyquist theorem holds. Intentionally, high frequency signal components can also be filtered out (processed to be outside the bandwidth). Regardless performing the down-sampling explained in the paragraph 0208 or not, the down-sampling can be performed within the Nyquist theorem holds. In addition, on the inverse Fourier transform such as eq. (17), etc., by setting the lateral position (coordinate) x or the range (if required, spatial shifting is performed in an analogue fashion by using the past invention of the present invention's inventor, i.e., the phase rotation via multiplication of a complex exponential function), image signals with an arbitrary lateral position or range can be generated with no approximate interpolations; and also on the inverse Fourier transform, by making the lateral bandwidth narrower with removed the lateral high frequency components (if required) to make the lateral density of data lower, or by making the lateral bandwidth wider with padded zero spectra in the angular spectra to make the lateral density of data higher, image signals with an arbitrary lateral interval or density can be generated with no approximate interpolations.

Thus, the image signals can be generated with the desired arbitrary positions, ranges, intervals, densities. That is, image signals with the shorter intervals than the sampling interval of the received signals and the pitch of the reception aperture elements can be generated. Or, coarse intervals of image signals can also be generated in the respective directions (it is cautious that the Nyquist theorem holds). Similarly to in the 2D case (paragraph 0205), physically or mathematically, the wavenumber matching can also be performed at the first Fourier transform or at the last inverse Fourier transform. When not performing the steerings, for the transform with the phase matching, similarly at first the transform can be performed in the lateral direction x or z and finally, the transform can be performed in the depth direction y, which can increase the calculation speed. Instead, for these, the wavenumber matchings corresponding to eqs. (C21) and (C23) can also be performed by performing the frequency modulations, i.e., by multiplying the complex exponential functions to spatio-temporal signals and performing the summation. In this case, at first, the 1D transform can be performed in the lateral direction x or z, which should be performed by the fast transform, and next the 1D processing using eq. (C22) can be performed to achieve the phase matching together with the transform in the depth direction y, which can increase the calculation speed. When performing the wavenumber matching with approximate interpolations, however with high accuracies, on the basis of eqs. (7) and (8) or (7') and (8'), the approximations are required to be performed with proper over-samplings of data in return an increased calculation amount. In the case, being different from in the case where image signals of arbitrary positions can be generated when no approximate interpolations are performed, it is cautious that the number of data to be used for the Fourier transforms increases. These are also for other methods (1) to (6).

When a convex-type transducer, a sector scanning or an IVUS being used, waves spread widely in the angle direction θ (cylindrical waves) can also be transmitted or received in the radial direction r on the polar coordinate system (FIG. 7); or virtual sources set behind the apertures with arbitrary geometries being used, the same beamformings (cylindrical waves) can also be performed (see FIGS. 8A(a) to (c), patent document 7 or nonpatent document 8 etc.). In such cases, the above-explained methods can be implemented with the polar orthogonal coordinate system (r,θ) instead of the Cartesian orthogonal coordinate system (x,y) (the depth y and lateral x coordinates are replaced by r and θ, respectively) and image signals can be directly generated on the polar coordinate system (r,θ). These are also for spherical waves expressed on the spherical coordinate system. Also as shown in FIGS. 8B(d) to (f), when using the physical aperture element arrays expressed by the polar system or the physical apertures with arbitrary aperture geometries as explained above, the beamformings can also be performed similarly to generate, at an arbitrary distance position, the transmission or reception, or both of plane waves. Performing such beamformings is equivalent to make a formation of a virtual linear-type aperture array (or a plane wave) at the distance position and then, setting the distance position zero corresponds to the case where a linear-type aperture array is used at the position virtually. The distance position can be set behind as well as in the front of the physical aperture and then, the virtual linear-type aperture array (or a plane wave) can be generated at the distance positions. The virtual linear-type aperture array can also be used not as the virtual sources but the virtual receivers, or both virtual sources and receivers.

FIG. 7 shows the illustrations of cylindrical wave transmissions or receptions on the polar coordinate system (r,θ) (transmissions or receptions, in a radial (r) direction, of waves widely spread in an angle direction (θ)). FIG. 7(a) shows the cylindrical wave transmission using a convex-type aperture element array; FIG. 7(b) shows the cylindrical wave transmission using a sector-type aperture element array; FIG. 7(c) shows the cylindrical wave transmission using an IVUS (a circular-type) aperture element array. Although FIG. 7(b) shows an aperture of which geometry is an arc, a flat aperture can also be used for the sector scanning. Also using these apertures, focused beams can also be generated.

FIG. 8A shows the illustrations of the cylindrical wave transmissions on the polar coordinate system (r,θ) (transmissions of waves, in a radial (r) direction, widely spread in an angle direction (θ)) from virtual sources set behind physical apertures with arbitrary aperture geometries. FIG. 8A(a) shows the cylindrical wave transmission using a linear-type aperture element array; FIG. 8A(b) shows the cylindrical wave transmission using a convex-type aperture element array; FIG. 8A(c) shows the cylindrical wave transmission using an arbitrary aperture element array. Receptions can also be performed similarly. FIGS. 8B(d) to (f) show, when using the physical aperture element arrays expressed by the polar system or the physical apertures with arbitrary aperture geometries, the beamformings can also be performed to generate, at an arbitrary distance position, the transmission of a plane wave (In the figures, the cases where a convex-type aperture element array is physically used are shown). Setting the distance position zero corresponds to the case where a linear-type aperture array is used at the position virtually (FIG. 8B(d)). The distance position can be set in the front of (FIG. 8B(f)) as well as behind (FIG. 8B(e)) the physical aperture and then, the virtual linear-type aperture array (or a plane wave) can be generated at the distance positions. Reception can be also performed similarly. FIG. 8B(g) shows a special case, for instance, a case where physically using a linear-type array transducer, and a cylindrical wave is generated using a virtual source set behind the physical aperture is applied to generate, at an arbitrary distance position, a pane wave widely spread in a lateral direction or a large virtual linear-type array transducer. Reception can also be performed similarly. The virtual linear-type aperture array can also be used not as the virtual sources but the virtual receivers, or both virtual sources and receivers.

Nonpatent document 6 discloses performing of transmission focusing and similarly, the result can be obtained on the polar coordinate system (r,θ). For instance, a large FOV can be obtained. As another method from that disclosed in the nonpatent document 6, the method (1) is used for the beamformings and obtaining steered beams with steering angles on the polar coordinate system (r,θ) (one of features of the present invention). These are also when using the methods (2) to (4) and (6). For the cases, the polar coordinate system (r,θ) is used instead of the Cartesian coordinate system (x,y) (the axial x and lateral y coordinates are replaced by r and e coordinates, respectively). However, when performing these beamformings, to obtain the signals at the positions of the discrete Cartesian coordinate system used for the display, interpolations are required to be performed. The interpolations are strictly performed in a Fourier domain by performing the phase rotations via implementing the multiplications of complex exponential functions, however, with consuming long time; or alternatively performed by approximate interpolations with consuming short time, however, with approximate errors. These are also for using the spherical coordinate system.

Also in these cases where the beamformings are performed on the polar coordinate system, the displacement measurements can also be performed, for instance, measurements of a displacement in the radial (r) or angle (θ) direction or a displacement vector comprised of both the displacements. To obtain the measurement results at the positions of the discrete Cartesian coordinate system used for the display, interpolations are required to be performed. Similarly to the interpolations for the echo signals, the interpolations are strictly performed in a Fourier domain by performing the phase rotations via implementing the multiplications of complex exponential functions, however, with consuming long time; or alternatively performed by approximate interpolations with consuming short time, however, with approximate errors. These are also for using the spherical coordinate system.

From the results of displacements, a strain (tensor) or a strain rate (tensor), a velocity (vector) or an acceleration (vector) can be calculated via calculating the partial derivatives using differential filterings and further, mechanical properties (for instance, a bulk modulus or a shear modulus (for instance, nonpatent document 7), elastic modulus tensor of an anisotropic media, etc.), a temperature, etc. can be calculated via numerical operations. When performing the approximate interpolations, the calculations performed on the Cartesian coordinate system with approximations allow shortening the total calculation time in many cases. Alternatively, performing the numerical operations on the polar coordinate system to obtain the results, of which approximations on the Cartesian coordinate system can be performed with small error propagations. That is, the errors generated in the processes after the displacement measurement are caused only by the approximate interpolations for obtaining final data to be displayed (There is a case where plural data to be displayed can be obtained from same displacement data).

As mentioned above, after implementing the interpolation processings on the echo signals to express the echo data on the Cartesian coordinate system, the displacement and the subsequent measurements can also be performed. When the approximate processings are performed on the interpolation processings, errors are led to and however, the total calculation time can be shortened. When measurements are performed on the basis of other echo data processings, as mentioned above, such processings can be performed similarly. These are also when the 3D beamformings are performed using a 2D array.

For all the above-mentioned beamformings, such processings can also be performed using arbitrary orthogonal coordinate systems except for the polar coordinate system.

Alternatively, in the same way, when performing cylindrical wave transmissions or receptions on the polar coordinate system (r,θ) (transmissions or receptions, in a radial (r) direction, of waves widely spread in an angle direction (θ)) using a convex-type transducer or a sector scan, or an IVUS, etc. (FIG. 7) and using virtual sources set behind physical apertures with arbitrary aperture geometries (FIGS. 8A(a) to (c)), the methods for generating image signals directly on the Cartesian coordinate system can be explained as the methods (5), (5-1), (5-1'), etc. When using the physical aperture element arrays expressed by the polar system or the physical apertures with arbitrary aperture geometries as explained above, the beamformings can also be performed similarly to generate, at an arbitrary distance position, the transmission or reception, or both of plane waves (FIGS. 8B (d) to (f)). Performing such beamformings is equivalent to make a formation of a virtual linear-type aperture array (or a plane wave) at the distance position and then, setting the distance position zero corresponds to the case where a linear-type aperture array is used at the position virtually. The distance position can be set in front of as well as behind the physical aperture and then, the virtual linear-type aperture array (or a plane wave) can be generated at the distance positions. The virtual linear-type aperture array can also be used not as the virtual sources but the virtual receivers, or both virtual sources and receivers. Alternatively, in the same way, the beamforming methods can be explained as the methods (5), (5-1), (5-1'), etc. In these cases, the imagings of echo signals and displacement measurements, etc. can be performed on the same Cartesian coordinate system consistently. These are also for the polar coordinate system. In such cases, it is also possible to transform the echo signals or measurements on the Cartesian coordinate system to those on the polar coordinate system via interpolations. These are also when using 2D arrays for the 3D beamformings. Transmission focusings may also be performed. Alternatively, in the same way, For all the above-mentioned beamformings, such processings can also be performed using arbitrary orthogonal coordinate systems except for the polar coordinate system. As mentioned above, the virtual source or the virtual receiver are not always positioned behind the physical aperture and can also be set in front of the aperture. Regardless the geometry of a physical aperture, they can be positioned arbitrarily (patent document 7 or nonpatent document 8). Thus, the present inventions are not limited to these. On the wavenumber matching in these beamformings, approximate solutions can also be calculated with approximate interpolations. All these can be processed similarly using the methods (1) to (7).

On the present methods (1) to (7), for these received signals, apodizations for the transmission or reception, or the both can be performed at various timings, because the processings are linear. That is, the apodizations can be performed in a hardware fashion when performing the receivings or in a software fashion after performing the receivings. As mentioned above, the apodizations can also be performed at transmissions physically. These are also for the following beamformings.

It is natural that when performing the beamformings not with respect to the received echo signals but transmission waves, the coordinate y is not the half round trip distance (expressed as ct/2 using the propagation time t) but the distance (ct) from the aperture element on the coordinate system determined by the reception aperture element.

Next, the cases where synthetic apertures (SAs) are performed. Two types SAs exist, i.e., a monostatic and multistatic types.

Method (2): Monostatic Type SA

Figure 9:
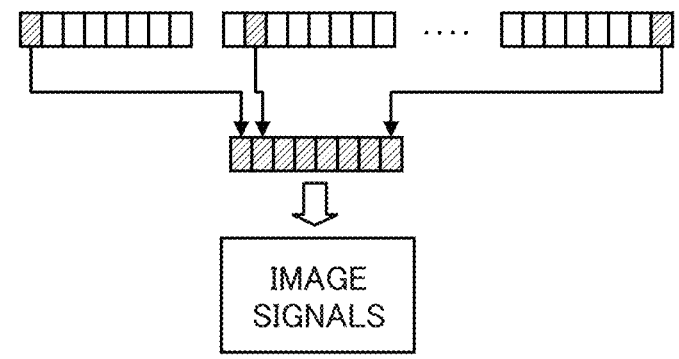
FIG. 9 shows an illustration of a monostatic synthetic aperture (SA)

FIG. 9 shows an illustration of a monostatic type SA. For the SA, an ultrasound is transmitted from one element in an array, and echo is received by the element itself. Also for the SA, by performing the wavenumber matching using the procedure shown in FIG. 6, echo signals (image signals) can be calculated.

Since the monostatic type SA performs the transmission and reception using the same elements, the propagation paths of ultrasounds to scatters at transmissions are same as those of ultrasounds from the scatters at receptions. Therefore, on the Cartesian coordinate system, of which zeros of y-axis exist on the position of reception effective aperture element array, when performing no steering (θ is zero), as shown in eq. (18a), the wavenumber matching expressed by eqs. (7) and (8) are performed with the twice wavenumber k (i.e., s=2, 2k for reflection waves). This is also for the following SAs. For transmission waves, not 2k but k is used (s=1). This is also for the following SAs.

$$\begin{cases} k'_x = k_x \\ k'_y = k_y = \sqrt{(sk)^2 - k_x^2} \end{cases} \quad (18a)$$

Figure 10:
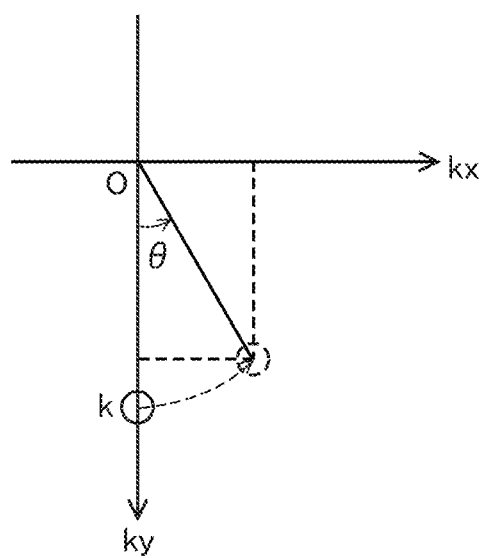
FIG. 10 shows an illustration of spectra (θ, steering angle) generated by performing steering on a monostatic SA.

When the steering angle θ is not zero, image signals having the wavenumber vector $(sk_0 \sin\theta, sk_0 \cos\theta)$ expressed using the wavenumber vector $(0,k_0)$ with a wavenumber $k_0$ $(=\omega_0/c)$ expressed using the carrier frequency $\omega_0$ of ultrasound signals as the 1st moments (centers) of the multi-dimensional spectra or the instantaneous frequencies are generated by performing the beamforming, in which the shifting of spectra is performed (FIG. 10). That is, on eqs. (7) and (8), the wavenumber matching expressed by eq. (18b) is performed.

$$\begin{cases} k'_x = k_x + k_x^t = k_x + sk_0\sin\theta \\ k'_y = k_y + k_y^t = \sqrt{(sk)^2 - k_x^2} + sk_0(-1 + \cos\theta) \end{cases} \quad (18b)$$

The signal processing is performed similarly to the method (1). Particularly, the wavenumber matching is performed, at first, for the spatial (lateral) direction, by multiplying the complex exponential function eq. (19a) expressed using the carrier frequency $\omega_0$ of the ultrasound signals instead of the complex exponential function eq. (9a) prior to performing the Fourier transform with respect the spatial (lateral) direction and next for the depth direction y, by multiplying the complex exponential function eq. (19c), instead of the complex exponential function eq. (9c), together with the complex exponential function eq. (19b) with removed the performed lateral matching processing eq. (19a) to yield the spatial resolution in the depth direction y instead of the complex exponential function eq. (9b). This processing can be performed when the steering angle is zero degree. This processing is not disclosed in the prior art documents.

$$\exp(ik_x'x) = \exp(isk_0 \sin\theta x) \quad (19a)$$

$$\exp(i\sqrt{(sk)^2 - (k_x - k_x^t)^2}\,y) = \exp(i\sqrt{(sk)^2 - (k_x - sk_0\sin\theta)^2}\,y) \quad (19b)$$

$$\exp(ik_y'y) = \exp\{isk_0(-1 + \cos\theta)y\} \quad (19c)$$

For instance, when using an echo technique (a reflection method), there are cases where the steering angles of transmission and reception beams are different. When the steering angles of the transmission and reception beams are respectively $\theta_t$ and $\theta_r$, the wavenumber matching expressed by eq. (18c) with s=2 is performed on eqs. (7) and (8).

$$\begin{cases} k'_x = k_x + k_x^t = k_x + k_0(\sin\theta_t + \sin\theta_r) \\ k'_y = k_y + k_y^t = \sqrt{(sk^2) - k_x^2} + k_0(-2 + \cos\theta_t + \cos\theta_r) \end{cases} \quad (18c)$$

The signal processing is performed similarly to the cases where the steering angles of transmission and reception beams are same. Particularly, the wavenumber matching is performed, at first, for the spatial (lateral) direction, by multiplying the complex exponential function eq. (19d) expressed using the carrier frequency $\omega_0$ of the ultrasound signals instead of the complex exponential function eq. (19a) prior to performing the Fourier transform with respect the spatial (lateral) direction and next for the depth direction y, by multiplying the complex exponential function eq. (19f), instead of the complex exponential function eq. (19c), together with the complex exponential function eq. (19e) with removed the performed lateral matching processing eq. (19d) to yield the spatial resolution in the depth direction y instead of the complex exponential function eq. (19b). This processing can be performed when the steering angles $\theta_t$ and $\theta_r$ are zero degree. This processing is not disclosed in the prior art documents.

$$\exp(ik_x'x) = \exp\{ik_0(\sin\theta_t + \sin\theta_r)x\} \tag{19d}$$

$$\exp(i\sqrt{(sk)^2 - (k_x - k_x')^2}\, y) = \exp(i\sqrt{(sk)^2 - \{k_x - k_0(\sin\theta_t + \sin\theta_r)\}^2}\, y) \tag{19e}$$

$$\exp(ik_y'y) = \exp\{ik_0(-2 + \cos\theta_t + \cos\theta_r)y\} \tag{19f}$$

Using the respective eqs. (19a) to (19c) and eqs. (19d) to (19f), the wavenumber matchings expressed by eqs. (18b) and (18c) can be performed on the 2D Fourier transform $R'(k_x,k)$ with no approximate interpolations similarly to the combinations of eqs. (7) and (8). Alternatively, the beamformings can also be performed with approximate interpolations and with a high speed, in which $F(k_x',k_y')$ is 2D inverse-Fourier transformed. Similarly to the method (1), regarding eqs. (18a) to (18c), physically or mathematically, the wavenumber matching can also be performed at the first Fourier transform or at the last inverse Fourier transform (paragraphs 205 and 210). When also performing the steerings in these cases, for the transform with the phase matching, similarly at first the transform can be performed in the lateral direction x and finally, the transform can be performed in the depth direction y (Since this processing is performed after performing the wavenumber matching in the x direction, eq. (19b) or eq. (19e) is used.), which can increase the calculation speed. The wavenumber matchings corresponding to eqs. (19a) and (19c) or eqs. (19d) and (19f) can also be performed by performing the frequency modulations instead, i.e., by multiplying the complex exponential functions to spatio-temporal signals and performing the summation. Or, regarding eqs. (18b) and (18c), also the approximate wavenumber matching about eq (18a), corresponding to the case where steering angles are zero degree, is not disclosed in the prior art documents.

Also when performing 3D wave digital signal processing using a 2D aperture element array, the 3D Cartesian orthogonal coordinate system (x,y,z) expressed by an axial direction y determined by the direction of a flat reception aperture element array (zeros of y-axis exist on the position of reception effective aperture element array) and lateral directions x and z can be used, for instance. When the steering angle being an angle between the beam direction to be generated and the axial direction (y) is expressed using zero or non-zero elevation and azimuth angles, similarly to when performing the 2D wave digital signal processing explained above, the following wavenumber matching is performed on the 3D Fourier transform of the received signals with respect to the depth (y) and lateral directions (x and z), where $(k_x,k_y,k_z)$ is the wavenumber domain expressed using the wavenumbers $k_x$, $k_y$ and $k_z$ of the depth (y) and lateral directions (x and z).

Image signals having the wavenumber vector ($sk_0 \sin\theta \cos\varphi$, $sk_0 \cos\theta$, $sk_0 \sin\theta \sin\varphi$) expressed using the wavenumber vector $(0,k_0,0)$ with a wavenumber $k_0$ ($=\omega_0/c$) expressed using the carrier frequency $\omega_0$ of waves as the 1st moments (centers) of the multi-dimensional spectra or the instantaneous frequencies are generated by performing transmission and reception dynamic focusings, in which the shifting of spectra is performed by multiplying the complex exponential function eq. (C41), being expressed using the parameter s being 2 and 1 respectively for the y coordinates of the transmission aperture elements being zero and non-zero, the wavenumber $k_0$ and an imaginary unit i, to the Fourier transforms of the received signals in the axial direction y to perform the wavenumber matchings in the lateral directions x and z at fast; and further by multiplying the complex exponential function eq. (C43) to 2D Fourier transform (2D FFT) of the signals multiplied with eq. C(41) in order to perform the wavenumber matching in the axial direction together with the complex exponential function eq. (C42) with removed the wavenumber matchings performed in the lateral directions x and z. Thus, by performing the wavenumber matching with no approximate interpolations, image signals can be generated on the Cartesian coordinate system directly.

$$\exp\{isk_0 \sin\theta(\cos\varphi x + \sin\varphi z)\} \tag{C41}$$

$$\exp(i\sqrt{(sk)^2 - (k_x - sk_0\sin\theta\cos\varphi)^2 - (k_z - sk_0\sin\theta\sin\varphi)^2}\, y) \tag{C42}$$

$$\exp\{isk_0(-1 + \cos\theta)y\} \tag{C43}$$

That is, the acoustic pressure fields generated by the respective plane wave components at the depth y can also be calculated as image signals by summing, with respect to the plural wavenumber k, the 2D inverse Fourier transform (IFFT) performed with respect to the lateral directions x and z. The calculations can also be performed for a zero-steering angle (i.e., the elevation and azimuth angles are zeros) or either angle is zero at least.

By the processing, the following wavenumber matching [eq. (C44)] can be performed with respect to the 3D Fourier transform $R'(k_x,k,k_z)$ similarly to eqs. (7') and (8'). Similarly to the 2D case, for eq. (C44), the wavenumber matching can be performed. Physically or mathematically, the wavenumber matching can also be performed at the first Fourier transform or at the last inverse Fourier transform (paragraph 229). When also performing the steerings, for the transform with the phase matching, similarly at first the transform can be performed in the lateral direction x or z and finally, the transform can be performed in the depth direction y (Since this processing is performed after performing the wavenumber matching in the x and z direction, eqs. (C42) and (C43) are used.), which can increase the calculation speed. The wavenumber matchings corresponding to eqs. (C41) and (C43) can also be performed by performing the frequency modulations instead, i.e., by multiplying the complex exponential functions to spatio-temporal signals (respective frequency modulations about kx, kz and ky). The above-disclosed processing achieves this wavenumber matching with no approximate interpolations, whereas according to eq. (C44) the wavenumber matching can also be performed with approximate interpolations and with a high speed, in which $F(k_x',k_y',k_z')$ is 3D inverse-Fourier transformed. The processing is not disclosed in the prior art documents.

$$\begin{cases} k_x' = k_x + k_x^t = k_x + sk_0\sin\theta\cos\varphi \\ k_y' = k_y + k_y^t = \sqrt{k^2 - k_x^2 - k_z^2} + sk_0(-1 + \cos\theta) \\ k_z' = k_z + k_z^t = k_z + sk_0\sin\theta\sin\varphi \end{cases} \tag{C44}$$

For instance, when using an echo technique (a reflection method), there are cases where the steering angles of transmission and reception beams are different. When the steering angles of the transmission and reception beams are respectively (an elevation angle, an azimuth angle)=$(\theta_t,\varphi_t)$ and $(\theta_r,\varphi_r)$, the signal processing is performed with s=2 similarly to the above-mentioned cases where the angles of transmission and reception beams are same. Particularly, the wavenumber matching is performed, at first, for the spatial (lateral) directions, by multiplying the complex exponential function eq. (D41) expressed using the carrier frequency $\omega_0$ of the ultrasound signals instead of the complex exponential function eq. (C41) prior to performing the Fourier transform with respect the spatial (lateral) directions and next for the depth direction y, by multiplying the complex exponential function eq. (D43), instead of the complex exponential function eq. (C43), together with the complex exponential function eq. (D42) with removed the performed lateral matching processing eq. (D41) to yield the spatial resolution in the depth direction y instead of the complex exponential function eq. (C42). This processing can also be performed when the steering angles of transmission and reception beams are zero degree (i.e., $\theta_t$, $\varphi_t$, $\theta_r$ and $\varphi_r$ are zero degree). This processing is not disclosed in the prior art documents.

$$\exp[ik_0\{\sin\theta_t(\cos\varphi_t x + \sin\varphi_t z) + \sin\theta_r(\cos\varphi_r x + \sin\varphi_r z)\}] \quad (D41)$$

$$\exp\left(i\sqrt{\begin{array}{c}(sk)^2 - \{k_x - k_0(\sin\theta_t\cos\varphi_t + \sin\theta_r\cos\varphi_r)\}^2 - \\ \{k_z - k_0(\sin\theta_t\sin\varphi_t + \sin\theta_r\sin\varphi_r)\}^2\end{array}}\, y\right) \quad (D42)$$

$$\exp(ik_y^t y) = \exp\{ik_0(-2 + \cos\theta_t + \cos\theta_r)y\} \quad (D43)$$

For the SA that performs both the transmission and reception beamformings in a software fashion, the exchange of transmission and reception is the same processing.

By the processing, the following wavenumber matching [eq. (D44)] can be performed with respect to the 3D Fourier transform R'($k_x$,$k_y$,$k_z$) similarly to eqs. (7') and (8'). Similarly, regarding eq. (D44), physically or mathematically, the wavenumber matching can also be performed at the first Fourier transform or at the last inverse Fourier transform (paragraph 232). When also performing the steerings, for the transform with the phase matching, similarly at first the transform can be performed in the lateral direction x or z and finally, the transform can be performed in the depth direction y (Since this processing is performed after performing the wavenumber matching in the x and z direction, eqs. (D42) and (D43) are used.), which can increase the calculation speed. The wavenumber matchings corresponding to eqs. (D41) and (D43) can also be performed by performing the frequency modulations instead, i.e., by multiplying the complex exponential functions to spatio-temporal signals (respective frequency modulations about kx, kz and ky). The above-disclosed processing achieves this wavenumber matching with no approximate interpolations, whereas according to eq. (D44) the wavenumber matching can also be performed with approximate interpolations and with a high speed, in which F($k_x'$,$k_y'$,$k_z'$) is 3D inverse-Fourier transformed. The processing is not disclosed in the prior art documents.

$$\begin{cases} k_x' = k_x + k_x^t = k_x + k_0(\sin\theta_t\cos\varphi_t + \sin\theta_r\cos\varphi_r) \\ k_y' = k_y + k_y^t = \sqrt{k^2 - k_x^2 - k_z^2} + k_0(-2 + \cos\theta_t + \cos\theta_r) \\ k_z' = k_z + k_z^t = k_z + k_0(\sin\theta_t\sin\varphi_t + \sin\theta_r\sin\varphi_r) \end{cases} \quad (D44)$$

Using the SAs (the method (3), i.e., multistatic SA as well as the method (2), i.e., monostatic SA) with respect to the acquired echo signal data for the SAs, arbitrary beamformings can be performed (actually, the processings disclosed in the method (1) or (4) to (7) can yield image signals from the data). Also in the processings for plane wave transmissions (method (1)), by using coding, the SAs can be performed. That is, the signal data for SAs can be obtained by implementing the decoding on the received signals with respect to transmissions of encoded plane waves.

As also disclosed in the method (1), the steering can be performed on the dynamic focusing. In the method (1), when the physical steering with a steering angle $\alpha$ (including a case of zero degree) is performed at the transmission of plane wave, and the steering with a steering angle $\theta$ (including a case of zero degree) is performed of the method (1) is performed as well, it can be interpreted that the pane wave is steered with a transmission steering ($\alpha$+9) [the finally generated steering angle is the mean]. Therefore, in the method (1), a plane wave is steered at the transmission with the steering angle $\alpha$, $\theta$ or $\alpha$+$\theta$ and at the reception dynamic focusing, the steering with a reception steering angle $\varphi$ (including a case of zero degree) can be achieved by performing the reception steering of the method (2); then the finally generated steering angle is a mean of all the transmission and the reception steering angles. The steering of plane wave in a software fashion (steering angle $\theta$) is, as mentioned in the method (1), used for reinforcing the physical transmission steering (steering angle $\alpha$), for purely generating the steering of plane wave in a software fashion, or for performing, in a software fashion, the steering of plane wave at the reception in addition to the reception dynamic focusing (including a case of the steering angle $\varphi$ is zero degree).

That is, in a 2D case, eqs. (F41), (F42) and (F43) being respective combinations of eqs. (9a) and (19a), eqs. (9b) and (19b) and eqs. (9c) and (19c) are used to similarly perform the beamforming.

$$\exp(ik_x'x) = \exp\{i(k\sin\theta + k_0\sin\phi)x\} \quad (F41)$$

$$\exp(i\sqrt{k^2 - (k_x - k_x')^2}\, y) = \exp(i\sqrt{k^2 - (k_x - k\sin\theta - k_0\sin\phi)^2}\, y) \quad (F42)$$

$$\exp(ik_y'y) = \exp[i\{k\cos\theta + k_0(-1+\cos\phi)\}y] \quad (F43)$$

Also in a 3D case, that is, when the plane wave is physically transmitted with elevational ($\alpha$) and azimuth ($\beta$) steering angles ($\alpha$,$\beta$), or at least either steering angle is zero degree, to perform the steering of the plane wave with a steering angle ($\theta_1$,$\varphi_1$) and the steered dynamic focusing with a steering angle ($\theta_2$,$\varphi_2$) in a software fashion (including a case where at least one steering angle is zero degree), eqs. (G41), (G42) and (G43) being respective combinations of eqs. (C21) and (C41), eqs. (C22) and (C42) and eqs. (C23) and (C43) are used to similarly perform the beamforming. The finally generated steering angle is a mean of all the transmission and the reception steering angles.

$$\exp[i\{k\sin\theta_1(\cos\varphi_1 x + \sin\varphi_1 z)\} + i\{k_0\sin\theta_2(\cos\varphi_2 x + \sin\varphi_2 z)\}] \quad (G41)$$

$$\exp\left(i\sqrt{\begin{array}{c}k^2 - (k_x - k\sin\theta_1\cos\varphi_1 - k_0\sin\theta_2\cos\varphi_2)^2 - \\ (k_z - k\sin\theta_1\sin\varphi_1 - k_0\sin\theta_2\sin\varphi_2)^2\end{array}}\, y\right) \quad (G42)$$

$$\exp[i\{k\cos\theta_1 + k_0(-1+\cos\theta_2)\}y] \quad (G43)$$

As mentioned in the method (1), performing the exchanging of the software transmission and reception has the same processings as those of the original beamforming (equivalent). That is, also in these cases, the software transmission and reception can be considered inversely. Also beamformings of various combinations can be performed in a software fashion with respect to arbitrary physical transmission beamformings (for instance, a steered plane wave, a steered fixed focusing beam, a steered dynamic focusing on the basis of SA, a non-steered wave or beam, various others). It is possible to perform, in a software fashion, the steerings of a plane wave or a dynamic focusing at the transmission or reception (including a case where at least one steering angle is zero degree) in addition to the physical steering of a generated arbitrary wave or beam (for instance, the above examples including a case where at least one steering angle is zero degree). Particularly, the software plane wave steering is used for reinforcing the physical transmission steering, for purely performing the steering of the physically transmitted arbitrary waves or beams or for performing, in a software fashion, the reception steering in addition to the reception dynamic focusing (including a case where the steering angle φ is zero degree). These are also for 3D beamforming using a 2D array. Others mentioned in the method (1) hold.

Similarly to the methods (1) and (2), physically or mathematically, the wavenumber matching can also be performed at the first Fourier transform or at the last inverse Fourier transform. Being dependent on the steering, for the transform with the phase matchings, the 1D processings can be performed in the respective directions, which can increase the calculation speed. The wavenumber matchings corresponding to eqs. (F41) and (F43) or eqs. (G41) and (G43) can also be performed by performing the frequency modulations instead, i.e., by multiplying the complex exponential functions to spatio-temporal signals (respective frequency modulations about kx, kz and ky).

For the beamformings in the 2D case with eqs. (F41), (F42) and (F43) and in the 3D case with eqs. (G41), (G42) and (G43), the wavenumber matchings can also be performed with approximate interpolations and with high speeds.

In the 2D case, according to eqs. (7) and (8), the wavenumber matching expressed by eqs. (18b) and (18c) is performed with respect to the 2D Fourier transform R'($k_x$,k) with approximate interpolations [eq. (F44)] and F(kx',ky') is 2D inverse-Fourier transformed. The approximate processings are not disclosed in the prior art documents.

$$\begin{cases} k'_x = k_x + k^t_x = k_x + k \sin\theta + k_0 \sin\phi \\ k'_y = k_y + k^t_y = \sqrt{(sk^2) - k_x^2} + k\cos\theta + k_0(-1 + \cos\phi) \end{cases} \quad (F44)$$

In the 3D case, according to eqs. (7') and (8'), the wavenumber matching expressed by eqs. (C44) and (D44) is performed with respect to the 3D Fourier transform R'($k_x$, k,$k_z$) with approximate interpolations [eq. (G44)] and F($k_x$', $k_y$',$k_z$') is 3D inverse-Fourier transformed. The approximate processings are not disclosed in the prior art documents.

$$\begin{cases} k'_x = k_x + k^t_x = k_x + k\sin\theta_1 \cos\varphi_1 + k_0 \sin\theta_2 \cos\varphi_2 \\ k'_y = k_y + k^t_y = \sqrt{k^2 - k_x^2 - k_z^2} + k\cos\theta_1 + k_0(-1 + \cos\theta_2) \\ k'_z = k_z + k^t_z = k_z + k\sin\theta_1 \sin\varphi_1 + k_0 \sin\theta_2 \sin\varphi_2 \end{cases} \quad (G44)$$

When performing cylindrical wave transmissions or receptions on the polar coordinate system (r,θ) (transmissions or receptions, in a radial (r) direction, of waves widely spread in an angle direction (θ)) using a convex-type transducer or a sector scan, or an IVUS, etc. (FIG. 7) or using virtual sources set behind physical apertures with arbitrary aperture geometries (FIGS. 8A(a) to (c)), or acquiring echo data for the SAs on the polar coordinate system, similarly to in the method (1), the processing can also be performed with the polar orthogonal coordinate system (r,θ) instead of the Cartesian orthogonal coordinate system (x,y) (the depth y and lateral x coordinates are replaced by r and θ, respectively) and then, image signals can be directly generated on the Cartesian coordinate system (x,y) or the polar coordinate system (r,θ). When using the physical aperture element arrays expressed by the polar system or the physical apertures with arbitrary aperture geometries as explained above, the beamformings can also be performed similarly to generate, at an arbitrary distance position, the transmission or reception, or both of plane waves (FIGS. 8B (d) to (f)). Performing such beamformings is equivalent to make a formation of a virtual linear-type aperture array (or a plane wave) at the distance position and then, setting the distance position zero corresponds to the case where a linear-type aperture array is used at the position virtually. The distance position can be set in front of as well as behind the physical aperture and then, the virtual linear-type aperture array (or a plane wave) can be generated at the distance positions. The virtual linear-type aperture array can also be used not as the virtual sources but the virtual receivers, or both virtual sources and receivers. These are also when performing other transmission beamformings or performing beamformings on the spherical coordinate system. Alternatively, in the same way, when performing cylindrical wave transmissions or receptions on the polar coordinate system (r,θ) (transmissions or receptions, in a radial (r) direction, of waves widely spread in an angle direction (θ)) using a convex-type transducer or a sector scan, or an IVUS, etc. (FIG. 7) and using virtual sources set behind physical apertures with arbitrary aperture geometries (FIGS. 8A(a) to (c)), image signals can be directly generated on the Cartesian coordinate system using the method (5). When using the physical aperture element arrays expressed by the polar system or the physical apertures with arbitrary aperture geometries as explained above, the beamformings can also be performed similarly to generate, at an arbitrary distance position, the transmission or reception, or both of plane waves (FIGS. 8B(d) to (f)). Performing such beamformings is equivalent to make a formation of a virtual linear-type aperture array (or a plane wave) at the distance position and then, setting the distance position zero corresponds to the case where a linear-type aperture array is used at the position virtually. The distance position can be set in front of as well as behind the physical aperture and then, the virtual linear-type aperture array (or a plane wave) can be generated at the distance positions. The virtual linear-type aperture array can also be used not as the virtual sources but the virtual receivers, or both virtual sources and receivers. In these cases, the imagings of echo signals and displacement measurements, etc. can be performed on the same Cartesian coordinate system consistently. These are also for the polar coordinate system. In these cases, similarly to the method (1), it is possible to perform the processings on arbitrary orthogonal coordinate systems or via transforming the echo signals or measurements to those on other orthogonal coordinate systems. These are also when using 2D arrays for the 3D beamformings. Transmission focusings may also be performed. In these processings, transmission focusing can also be performed. As mentioned above, the virtual source or the virtual receiver are not always positioned behind the physical aperture and can also be set in front of the aperture. Regardless the geometry of a physical aperture, they can be positioned arbitrarily (patent document 7 or nonpatent document 8). Thus, the present inventions are not limited to these.

On the wavenumber matching in these beamformings, approximate solutions can also be calculated with approximate interpolations.

With respect to the received signals, apodizations for the transmission or reception, or the both can be performed at various timings, because the processings are linear. That is, the apodizations can be performed in a hardware fashion when performing the receivings or in a software fashion after performing the receivings. As mentioned above, the apodizations can also be performed at transmissions physically. When performing the wavenumber matching with approximate interpolations, however with high accuracies, on the basis of eqs. (7) and (7'), the approximations are required to be performed with proper over-samplings of data in return an increased calculation amount. In the case, being different from in the case where image signals of arbitrary positions can be generated when no approximate interpolations are performed, it is cautious that the number of data to be used for the Fourier transforms increases. These processings can be performed similarly to the method (1), and these are also for other methods (3) to (7).

Method (3): Multistatic Type SA

Figure 11:
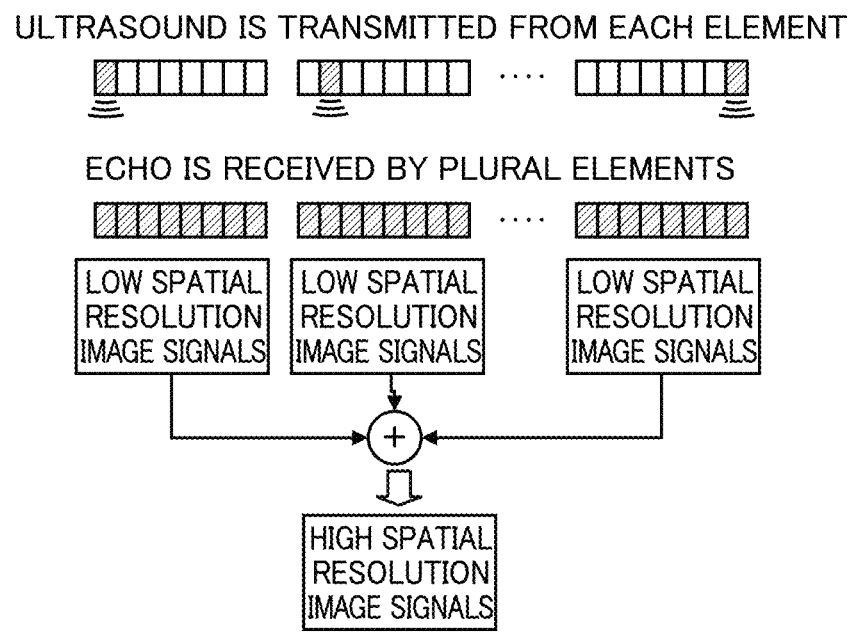
FIG. 11 shows an illustration of a multistatic SA.

FIG. 11 shows an illustration of a multistatic type SA. For the multistatic type SA, an ultrasound is transmitted from one element in an array, and echo is received by the plural elements around the transmission element (generally, including the transmission element). Low-resolution image signals are generated every one transmission; and generated plural low-resolution image signals are superposed to generate high-resolution image signals. To generate the low-resolution image signals, the present invention can also be used.

As mentioned above, generally and traditionally the low-resolution echo signals are generated from the echo signals received every the transmissions are performed by the respective transmission elements; and the generated low-resolution echo signals are superposed. In contrast, the present invention generates plural sets, respective of which are comprised of signals received at the same positions with respect to the transmission positions; and respective of which are processed by the digital monostatic SA methods to generate plural low-resolution image signals and superpose them. In practice, the linear superposition can be performed in a frequency domain prior to the lateral inverse Fourier transform, which yields a high speed. Specifically, when performing the superposition in the frequency domain, the lateral positions of plural low-resolution image signals are adjusted by performing the lateral shifting processings, i.e., by performing the phase rotations in the lateral direction via multiplying the complex exponential functions to data, and then with no approximate interpolations and with high speeds the image signals are generated. The inverse Fourier transform is performed using IFFT once. To generate the respective low-resolution echo signals to be superposed in a spatial domain, the multiplications of complex exponential functions for rotating the phases in the lateral direction (the lateral shifting processings) can also be performed simultaneously when performing the lateral inverse Fourier transform. In this case, exclusive IFFT can be performed.

Important is that when using the program of monostatic type SA, if s=2, the distance of propagation path with respect to the point of interest, to which distance is y (coordinate y), between the transmission and the reception element positions, which are positioned at y=0 and have the distance between the elements Δx in the x-direction, is converted to y' and further when the steering angle is zero degree, the converted distance y' is expressed by eq. (20a). Also, if s=1, when the steering angle is zero degree, the converted distance about the point of interest, to which distance is y (coordinate y), is expressed by eq. (20b) with respect to the transmission element positioned at y=Y (non-zero) and the reception element positioned at y=0 with the element distance Δx in the x-direction. The coordinates y of the transmission and reception positions can be considered inversely.

$$y'=(y+\sqrt{y^2+\Delta x^2})\div 2 \quad (20a)$$

$$y'=y+\sqrt{(Y-y)^2+\Delta x^2} \quad (20b)$$

When the steering angle is θ (including non-zero degree), the beams are generated by the multistatic SA, to which at least the reception dynamic focusing is implemented (when s=2, the transmission dynamic focusing can also be realized). Waves are transmitted from the respective transmission aperture elements in the transmission effective aperture element array and the waves arriving from the measurement object are received at least by one reception aperture element, in plural reception aperture elements, existing at a different position from that of the transmission element to generate the reception signals (even when one element is used, the instrument of the present invention can also perform the processing). To generate waves that are at least reflected or backscattered waves (s=2), or at least transmission, forward scattered or refracted waves (s=1), the transmission aperture elements are used such that the position has arbitrary x coordinates regardless the x coordinates of reception aperture elements that generate the received signals. The transmission element can also be, positioned at a constant zero y-coordinate, i.e., one of the reception aperture elements in the reception effective aperture element or different element from the reception aperture elements, or positioned at a constant non-zero y-coordinate, i.e., one of the plural transmission aperture elements in the transmission effective aperture element array faced to the reception effective aperture element array (when s=1, the y coordinates of transmission and reception can be considered inversely).

That is, when performing the steering, the above-mentioned data for the monostatic SA processing, comprised of data generated by the combination of the transmission and the reception elements with same distances, are respectively processed using the steering disclosed in the method (2) and similarly, the processing can be performed. These are also when the transmission and the reception steering angles are different. When the steering angle is non-zero and the program of the monostatic SA processing is used, similarly to the case where steering angles are zero degree, the converted distances expressed by eqs. (20a) and (20b) are respectively used for s=2 and 1 with respect to the distance y (y coordinate) to the point of interest. Thus, similarly to the methods (1) and (2), the processing can be performed using zero or non-zero steering angles on the programs that allow steerings.

For the transmission, the plane wave transmission of the method (1) can also be performed, and arbitrary transmission beamformings such as a fixed focusing, etc. can also be performed, etc.

As other methods, when the y coordinates of the transmission and reception elements are zero, with respect to the same sets of received signals obtained for the same distances Δx in the lateral coordinate for the positions of transmission and reception, using the half distance between the transmission and the reception aperture elements via the point of interest (eq. (20c)) expressed using the steering angle θ, the y coordinate of the point of interest and the distance Δx for s=2, or the distance between the transmission and the reception aperture elements via the point of interest (eq. (20d)) expressed using the steering angle θ, the y coordinate of the point of interest, the y coordinate of the transmission aperture element (y=Y, i.e., non-zero y) and the distance Δx for s=1 (the y coordinates of transmission and reception can also be considered inversely) for the above-disclosed monostatic SA allows generating image signals via spatial corrections of the lateral positions in a frequency domain with respect to the steered image signals and superposition of the corrected image signals, with no approximate interpolations. Although the spatial resolution in the depth direction decreases, a large steering angle can be generated.

$$y'=(y/\cos\theta+\sqrt{y^2+(y\tan\theta-\Delta x)^2})\div 2 \quad (20c)$$

$$y'=y/\cos\theta+\sqrt{(y\tan\theta-\Delta x)^2+(y-Y)^2} \quad (20d)$$

When performing the 3D wave digital signal processing is performed using the 2D aperture element array, for instance, on the Cartesian coordinate system of which y-axis is determined by the direction of a face of flat reception aperture element array and the lateral coordinates x and z are determined such that the axes are orthogonal to the y-axis, similarly to the 2D processing case, the zero or non-zero steering elevational and azimuth angles can be generated regarding the beam direction generated and the axial direction. Waves are transmitted from the respective transmission aperture elements in the transmission effective aperture element array and the waves arriving from the measurement object are received at least by one reception aperture element, in plural reception aperture elements, existing at a different position from that of the transmission element to generate the reception signals. To generate waves that are at least reflected or backscattered waves (s=2), or at least transmission, forward scattered or refracted waves (s=1), the transmission aperture elements are used such that the position has arbitrary x and z coordinates regardless the x and z coordinates of reception aperture elements that generate the received signals. The transmission element can also be, positioned at a constant zero y-coordinate (s=2), i.e., one of the reception aperture elements in the reception effective aperture element or different element from the reception aperture elements, or positioned at a constant non-zero y-coordinate (s=1), i.e., one of the plural transmission aperture elements in the transmission effective aperture element array faced to the reception effective aperture element array (when s=1, the y coordinates of transmission and reception can be considered inversely).

$$y'=(y+\sqrt{y^2+\Delta x^2+\Delta z^2})\div 2 \quad (20e)$$

$$y'=y+\sqrt{(Y-y)^2+\Delta x^2+\Delta z^2} \quad (20f)$$

For the transmission, the plane wave transmission of the method (1) can also be performed, and arbitrary transmission beamformings such as a fixed focusing, etc. can also be performed, etc.

As other methods, when the y coordinates of the transmission and reception elements are zero, with respect to the same sets of received signals obtained for the same distances Δx and Δz in the lateral coordinates for the positions of transmission and reception, using the half distance between the transmission and the reception aperture elements via the point of interest expressed using the steering elevational and azimuth angles θ and φ, the y coordinate of the point of interest and the distances Δx and Δz for s=2, or the distance between the transmission and the reception aperture elements via the point of interest expressed using the steering elevational and azimuth angles θ and φ, the y coordinate of the point of interest, the y coordinate of the transmission aperture element (y=Y, i.e., non-zero y) and the distances Δx and Δz for s=1 (the y coordinates of transmission and reception can also be considered inversely) for the above-disclosed monostatic SA allows generating image signals via spatial corrections of the lateral positions in a frequency domain with respect to the steered image signals and superposition of the corrected image signals, with no approximate interpolations. Although the spatial resolution in the depth direction decreases, a large steering angle can be generated.

To generate image signals that expresses unknown wave sources, or the wave propagations generated by the unknown sources (passive mode), the beamformings can also be performed via setting estimates of y coordinates of the unknown sources at the y coordinates of the transmission aperture elements. It is also effective to perform the observing with changing the setting of y-coordinates of transmission elements by trial and error. For instance, it is better that the image is to be formed, the spatial resolution increases, the signal amplitude increases, the contrast increases, etc., and using these as criteria for the judgement, the series of processings can also be performed automatically.

As mentioned later, as information about the wave source positions or the transmission aperture elements, the positions with respect to the reception aperture elements, the directions of positions or distances to the positions, the direction of aperture or the propagation directions of generated waves can also be given occasionally. The time when waves are generated by arbitrary wave sources can also be given. The wave sources can also be observed using other instruments. Or, the received signals can also convey the information or other waves can be generated, propagating with higher speeds, and can also convey the information, etc.

The beamformings can also be performed by calculating the directions of wave source positions or the wave propagation directions via estimating the 1st moment (center) frequencies of the multi-dimensional spectra or the instantaneous frequencies with respect to the received signals; and also by regulating the transmission or reception steering angle. Alternatively, with respect to the generated image signals, the beamformings can also be performed by calculating the directions of wave source positions or the wave propagation directions via estimating the 1st moment (center) frequencies of the multi-dimensional spectra or the instantaneous frequencies; and also by regulating the transmission or reception steering angle. These processings can also be performed using plural reception apertures or plural reception effective apertures, the positions and directions of the wave sources can also be calculated geometrically. These processings are useful and can also be applied to other beamformings.

As explained in the monostatic SA (method (2)), using the multistatic SA (method (3)) allows performing arbitrary beamformings by using the echo data acquired for the multistatic SA (In fact, the image signals can be generated by implementing the method (1) or (4) to (7) on the data). Although the larger amount of data to be used for the multistatic SA than that for the monostatic SA can be effective, the calculation amount increases. For plane wave processing (method (1)), the SAs can also be performed using the coding. When performing cylindrical wave transmissions or receptions on the polar coordinate system (r,θ) (transmissions or receptions, in a radial (r) direction, of waves widely spread in an angle direction (θ)) using a convex-type transducer or a sector scan, or an IVUS, etc.

(FIG. 7) or using virtual sources set behind physical apertures with arbitrary aperture geometries (FIGS. 8A(a) to (c)), or acquiring echo data for the SAs on the polar coordinate system, similarly to in the method (1), the processing can also be performed with the polar orthogonal coordinate system (r,θ) instead of the Cartesian orthogonal coordinate system (x,y) (the depth y and lateral x coordinates are replaced by r and θ, respectively) and then, image signals can be directly generated on the Cartesian coordinate system (x,y) or the polar coordinate system (r,θ). These can also be performed when performing other transmission beamformings or performing beamformings on the spherical coordinate system. Alternatively, in the same way, when using a convex-type transducer or a sector scan, or an IVUS, etc. and using virtual sources set behind physical apertures with arbitrary aperture geometries, image signals can be directly generated on the Cartesian coordinate system using the method (5). In the case, the imagings of echo signals and displacement measurements, etc. can be performed on the same Cartesian coordinate system consistently. In these cases, similarly to the method (1), it is possible to perform the processings on arbitrary orthogonal coordinate systems or via transforming the echo signals or measurements to those on other orthogonal coordinate systems. Or, the beamformings disclosed in the paragraphs 0211 to 0222 etc. in the method (1) and in the paragraphs 0240 etc. in the method (2) can be performed in the same ways and for instance, virtual sources or virtual receivers can be used at arbitrary positions regardless the geometry of physical aperture (patent document 7 and nonpatent document 8). The inventions are not also limited to these (also below).

Also as disclosed above, although the depth resolution decreases, large steering angles can also be generated using other steering methods. In the cases, different transmission and reception steerings can also be generated. The converted distances expressed using the lateral distances between the transmission and the reception elements, the transmission and reception steering angles and for the transmission cases, the distances between the transmission and the reception elements can be calculated and used.

Basically, the steerings to be performed using the method (3) are also performed in a software fashion. The apodizations can also be performed at the transmissions or are not performed. The reception apodizations are linear processings and then can be performed at various timings (in a hardware or software fashion). For instance, when performing the software apodizations, the calculation amounts being dependent on the effective aperture width, etc. that determines the number of low-resolution echo signals to be generated are considered to allow performing the apodizations simply at a proper timing. For instance, the apodizations can be performed with respect to the respective sets for generating the low-resolution echo signals, or the generated low-resolution signals in a frequency or spatial domain.

Also for the application of the monostatic SA (method (2)), physically or mathematically, the wavenumber matching can also be performed at the first Fourier transform or at the last inverse Fourier transform. And, the wavenumber matching can also be performed with above-disclosed approximate interpolations and with high speeds. For the approximate interpolations, the linear interpolations or using the most neighborhood data themselves approximately can also be performed, or high order approximate interpolations or using the sinc functions can also be performed. To increase the accuracies of the wavenumber matchings to be performed with approximate interpolations, proper over-samplings of data are required in return an increased calculation amount. In the case, being different from in the case where image signals of arbitrary positions can be generated when no approximate interpolations are performed, it is cautious that the number of data to be used for the Fourier transforms increases.

Also for the adjusting the lateral positions of the low-resolution image signals to be superposed (disclosed in the paragraphs 0243, 0247 and 0250), instead of the high accuracy processing that the complex exponential functions are multiplied in a frequency domain to rotate the phase in the lateral direction, spatial shifting processing can also be performed with approximate interpolations to achieve the higher speed processings. For the approximate interpolations, the linear interpolations or using the most neighborhood data themselves approximately can also be performed, or high order approximate interpolations or suing the sinc functions can also be performed. Also in the cases, to increase the accuracies of approximate interpolations, proper over-samplings of data are required in return an increased calculation amount.

Method (4); Fixed Focusing

Figure 12:
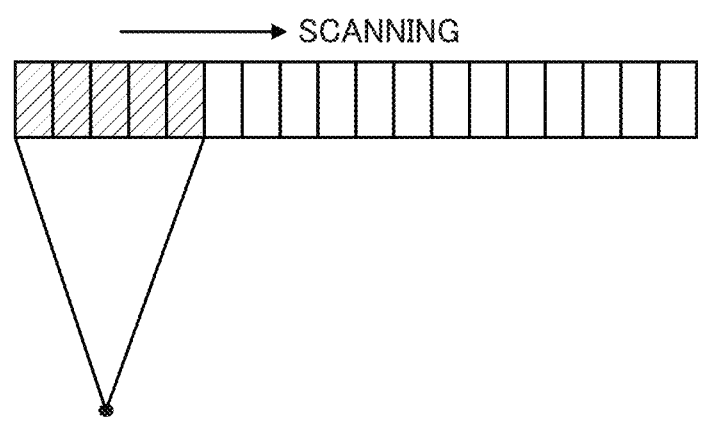
FIG. 12 shows an illustration of a fixed focusing performed using a linear array-type transducer.

FIG. 12 shows an illustration of a fixed focusing performed using a linear array-type transducer. The fixed focusing is to make ultrasound waves transmitted from the respective transmission elements to arrive at the focusing position at the same time by setting delays for the transmissions on the respective transmission elements (channels). The measurement object is scanned by receiving waves using the partial or whole physical aperture of the array type transducer as an effective aperture. Off course, the steering can also be performed. The angles of transmission and reception steerings can also be different.

The fixed focusing can be performed to generate image signals using the method (1), i.e., beamforming for plane wave transmission or the method (3), i.e., the multistatic type SA, or the combinations of the method (1) for the beamforming for plane wave transmission and the method (2) or (3) for the reception dynamic focusing. In the cases, the following three methods can be performed.

(i) Implementing image signal generation processing once on superposing of the respective reception signals obtained at the effective aperture width.
(ii) Superposing of general low-resolution image signals generated using reception signals obtained with respect to the respective transmissions.
(iii) Superposing of low-resolution image signals generated performing the same processings as those of the multistatic SA, i.e., the respective low-resolution image signals are generated with respect to the respective data sets comprised of data with same position relationships between the transmissions and the receptions.

When performing cylindrical wave transmissions or receptions on the polar coordinate system (r,θ) using a convex-type transducer or a sector scan, or an IVUS, etc. or using virtual sources set behind physical apertures with arbitrary aperture geometries, the processing can also be performed with the polar orthogonal coordinate system (r,θ) instead of the Cartesian orthogonal coordinate system (x,y) (the depth y and lateral x coordinates are replaced by r and θ, respectively) and then, image signals can be directly generated on the polar coordinate system (r,θ). As mentioned above, approximate interpolations are required after generating the image signals. These are also when performing the transmission and the reception beamformings on the spherical coordinate system. In the nonpatent document 6, a beamforming method for the transmission focusing with approximate processings is disclosed and similarly, the results are obtained on the polar coordinate system (r,θ). The inventor of the present invention also invented the beamforming methods (5), (5-1), (5-1') and (5-2) for generating image signals directly on the Cartesian coordinate system as the results of beamformings with respect to transmissions and receptions performed on the polar coordinate system, the spherical coordinate system or arbitrary orthogonal curvilinear coordinate systems. In the case, the imagings of transmission waves, reflected waves, scattered waves or attenuated waves, etc. and displacement measurements, etc. can be performed on the same Cartesian coordinate system consistently. In these cases, similarly to the method (1), it is possible to perform the processings on arbitrary orthogonal coordinate systems or via transforming the echo signals or measurements to those on other orthogonal coordinate systems. Or, the beamformings disclosed in the paragraphs 0211 to 0222 etc. in the method (1) and in the paragraphs 0240 etc. in the method (2) can be performed in the same ways and for instance, virtual sources or virtual receivers can be used at arbitrary positions regardless the geometry of physical aperture (patent document 7 and nonpatent document 8). The inventions are not also limited to these (also below). Also, as mentioned above, the steering can also be performed. The cases where the steering angles of physical transmission beamforming and software reception beamforming are different can also be realized. In addition, software transmission steering can also be implemented. In the cases, the steering angle can also be different from other steering angles. For the reception, physical beamformings can also be performed. It is possible to interpret the transmission and reception inversely. The apodizations can also be performed at the transmissions and with respect to the received signals, the reception apodization processings can also be performed (in a hardware fashion at the receptions or in a software fashion after the receptions). The software apodizations can be performed according to the method (1) or (3). Similarly, the apodizations can also be performed when the combination of the method (1) for the plane wave transmission beamforming and the method (2) or (3) for the reception dynamic focusing.

Theoretically and in practice, the method (4) using the method (1) for processing the plane wave allows arbitrary physical transmissions or the reception beamformings. By performing the processings as mentioned above, various combinations of beamformings can be performed (For instance, for the plane wave transmission and the reception dynamic focusing, the proceedings such as focusings, steerings, apodizations, etc. that can be performed physically, at transmissions and receptions, by using calculators or exclusive devices, etc. others from those performed in software beamformings using calculators or exclusive devices, etc., can be respectively performed, or both the physical and software processings can be performed. Also the transmissions and receptions can be considered inversely as mentioned above). For instance, as mentioned in the paragraphs 0109, 0112, 0365, 0367, 0368 etc., regardless the physical focuses (subaperture widths, distances or depths, positions, etc.) being same or not, or the physical transmission steering angles being same or not, the above-mentioned processings mentioned in the method (4) is effective for simultaneous transmissions of plural beams including physically steered or non-steered ones, or occurrences of interferences of beams or not, such transmissions, however, at different timings, but, on the same phase of the object, or the mixed transmissions. Particularly, the method (i) that performs the processing once for generating image signals with respect to the superposition of the respective reception signals obtained at effective aperture widths yields a high frame rate. Using the method (4) does not always require beamformings to be performed at positions where the interferences of beams do not occur (mentioned in the paragraphs 0030, 0364, etc.). Even if over-lapped subapertures are simultaneously used, etc. or the interferences occur, the same processings realize the high frame rate. At the time, if respective the software transmission steering angles and the software reception steering angles to be implemented on the plural focused beams are same, the above-mentioned processings can be performed. When plural transmissions such as plural positioned focusings or transmission dynamic focusing are performed on the same phase of the object, the superposition of received signals can also be processed similarly. Regarding the received signals obtained at the same phase of the object, if the received signals are superposed such that the positions (time) of signals are adjusted on the basis of the transmission element position or the timing, all the cases can be processed by the method.

When either the software transmission steering angles or the software reception steering angles to be implemented on the plural focused beams include at least a different angle, the received signals are separated into those with same steering angles, and the respective separated, received signals with the same steering angles are processed, after which the processed results are superposed in a frequency domain to generate the final result. With respect to one physical transmission beam (steered or non-steered one), plural steered reception beams (a zero steering angle can be included) can also be generated and similarly processed. Also when performing plural different physical steerings, the received signals are separated into those with same steering angles, and the respective separated, received signals are processed to generate the results, or the received signals are also processed without performing the separation. When performing the separations, the superpositions can also be performed in a spatial or frequency domain.

When physically performing the transmitting in plural directions, specific transmission and reception steerings can also be implemented on the respective physical transmission steerings. In the cases, the signals generated by the respective transmitted beams can be separated in a frequency domain or the independent component analysis (ICA, many literatures exist such as a rather classical one, Te-Won Lee, Independent Component Analysis: Theory and Applications, Springer, 1998 as well as others) and the processing can be performed. Analogue devices can also be used. For instance, the same steering angles can be set on the software transmission or reception steering angle as that of the physical steering angle used. Other signal separation methods are also mentioned (for instance, the paragraph 0370).

Here, mentioned is the using of these methods on various fixed focusing processings. These methods are not limited to these and can also be used for other transmission beamformings. Similarly, the beamformings with new properties that cannot be achieved by a single beamforming by performing plural transmissions or receptions of waves or ultrasounds with different parameters such as a focusing (multi-focusings that generate plural different focusing positions with respect to the effective aperture) or a non-focusing, a steering (plural steerings with different steering angles) or a non-steering, an apodization (changeable with positions) or a non-apodization, an F-number, a transmission ultrasound frequency or a transmission bandwidth, a reception frequency or a reception bandwidth, a pulse shape, a beam shape, etc. For instance, it is known that the superposing yields plural focusings or wide bandwidths in the depth and lateral directions (high spatial resolutions). These processings can be speeded up. To obtain the harmonic waves, the so-called pulse inversion method (transmissions of pulses with inverse polarities as an ultrasound parameters), etc. can be performed by superposing the received signals and similarly, the high-speed processing can be performed. Off course, after performing the beamformings, the received signals can also be superposed. More than two plural beams can also be superposed.

On the basis of the considerations of the transmissions and receptions in an inverse fashion, the above-mentioned processings can also be performed simultaneously on the reception beamforming(s). Or, the above-mentioned processings can also be performed on both transmission(s) and reception(s).

When the separated beamformings are performed, parallel processings can also be performed. The separations can be performed the position in an ROI as well as the above-mentioned various parameters of waves or ultrasounds such as a steering angle, etc. One reception signal can also be used for various purposes such as imaging, measurement, treatment, etc. via generating, by performing beamformings, informative waves (including much information) such as transmission signals, reflection signals, scattering signals, attenuation signals, etc. with high accuracies and high spatial resolutions and performing post-processings such as filtering to yield signals adapted for the respective purposes. According to the respective purposes, proper beamformings can also be performed and the processings can also be performed in a parallel fashion.

The present invention allows performing beamformings for such as arbitrary beam transmissions such as fixed, focused beams, etc., arbitrary wave transmissions (including non-beamformed waves), superposition of transmissions of plural beams or waves and simultaneous transmissions of plural beams or waves. That is, whenever any single or plural transmissions are performed, "the reception beamformings" (dynamic focusing, etc.) can be performed at once. Plural beamformings can also be performed by using the multi-directional synthetic aperture (SA) method (past invention of the inventor of the present invention) and in the cases, similarly the processings can be performed with high speeds. The present inventions are not limited to these.

Physically or mathematically, the wavenumber matching can also be performed at the first Fourier transform or at the last inverse Fourier transform. One of the features of present invention is to perform the wavenumber matchings with no approximate interpolations. However, also in the method (4) using the above-mentioned methods (1) to (3), similarly to the methods (1) to (3), approximate interpolations can be performed on the wavenumber matchings (approximate wavenumber matchings mentioned for the respective beamformings) and the beamformings can also be completed with high speeds. To increase the accuracies of the wavenumber matchings to be performed with approximate interpolations, proper over-samplings of data are required in return an increased calculation amount. In the case, being different from in the case where image signals of arbitrary positions can be generated when no approximate interpolations are performed, it is cautious that the number of data to be used for the Fourier transforms increases.

Method (5): Image Signal Generation on Polar Coordinate System

Method (5) is used to generate image signals on the Cartesian coordinate system when performing, by using the convex-type array or sector scanning, IVUS, etc., the transmissions and receptions of ultrasound cylindrical waves (or the partial waves) on the 2D polar coordinate system (r,θ) (FIG. 7). The methods (1) to (4) and (6) can be performed.

Below explained are the expression of Fourier transform using the polar coordinate system. The 2D Fourier transform is expressed by eq. (22).

$$F(k_x,k_y)=\iint f(r,\theta)e^{-i(k_x x+k_y y)}dxdy \tag{22}$$

The reception signals are expressed as $f(r,\theta)$ on the polar coordinate system and then, eq. (23) holds.

$$x=r\sin\theta,\ y=r\cos\theta \tag{23}$$

Then, eq. (24) can be obtained via the Jacobi operation. Thus, the wave expressed on the polar coordinate system can be decomposed into plane wave components $(k_x,k_y)$ on the Cartesian coordinate system. Waves expressed on arbitrary orthogonal curvilinear coordinate systems can also be decomposed into the plane wave components $(k_x,k_y)$ similarly.

$$F(k_x,k_y)=\iint f(r,\theta)|r|e^{-i(k_x r\sin\theta+k_y r\cos\theta)}drd\theta \tag{24}$$

Figure 13:
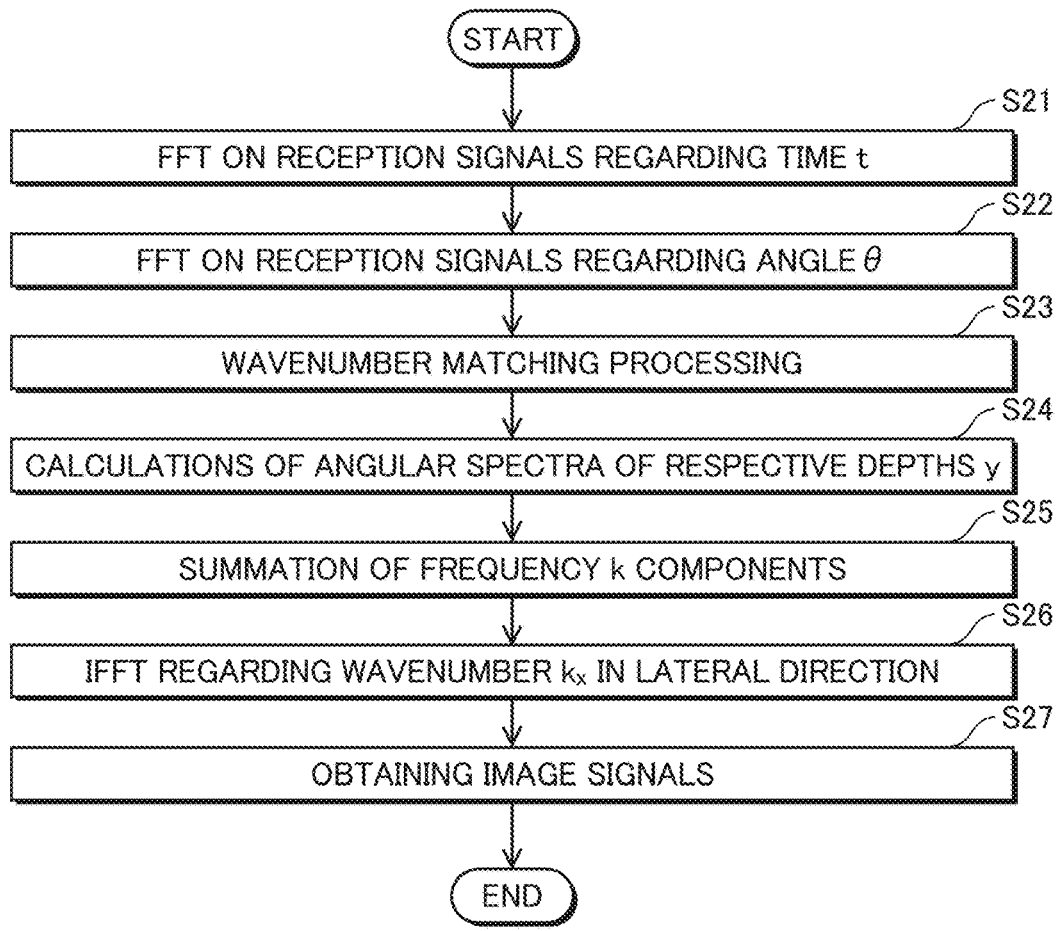
FIG. 13 shows a flowchart about the digital signal processing for a cylindrical wave transmission.

Method (5-1): Image Signal Generation of Cylindrical Wave Transmission or Reception FIG. 13 shows a flowchart about the digital signal processing for a cylindrical wave transmission. According to eq. (24), the Fourier transform along the aperture in the angle direction θ is expressed as eq. (25).

$$U(k_x,k_y)=\int u(k,\theta)r_0 e^{-i(k_x r_0\sin\theta+k_y r_0\cos\theta)}d\theta \tag{25}$$

or $$U(k_x,k_y)=\int u(k,\theta)r_0 e^{-i(k_x x_0+k_y y_0)}d\theta \tag{25'}$$

Here, $r_0$ is a curvature radius of the convex-type transducer; $x_0$ and $y_0$ are x and y coordinates expressing the array element positions (those of convex-type array transducer). At the step S21, the received signals are Fourier transformed (FFT) regarding the time t and at the step S22, the received signals are Fourier transformed (FFT) regarding the angle θ; achieving the decomposition of the signals received on the polar coordinate system into the plane wave components $(k_x,k_y)$ on the Cartesian coordinate system.

Thus, for instance, the wavenumber matching expressed by eq. (26) is implemented on the spectra at the step S23 and by subsequently performing the inverse Fourier transforms on the space (x,y), the image signals are generated.

$$U'(k_x,k_y)=U(k_x,k_y)e^{-ik(r-r_0)} \tag{26a}$$

Moreover, at the step S24, the following complex exponential function is multiplied to the 2D spectra to calculate the angular spectra at the respective depths.

$$\exp(i\sqrt{k^2-k_x^2}\,y) \tag{26b}$$

Or, the calculations of the steps 23 and 24 can be performed inversely.

Or, without using eqs. (26a) and (26b), according to the method (5), the following complex exponential function is straightforwardly multiplied to yield the angular spectra at the respective depths y as well as to perform the wavenumber matching.

$$\exp\{i(\sqrt{k^2-k_x^2}+k)y\} \tag{26c}$$

Moreover, for instance, at the step S25, summing of the angular spectra is performed with respect to the frequency (k) components and at the step S26, the inverse Fourier transform (IFFT) is performed in the lateral direction $k_x$ and at the step S27, the image signals are generated. Purely, the 2D inverse Fourier transform can also be implemented.

When performing the steering, according to eqs. (9a) to (9c) of the method (1), with performing the wavenumber matchings in the x and y directions, the spatial resolutions can be obtained. As mentioned later, when the calculations are performed on the polar coordinate system (r,θ), the steering angle is set on the polar coordinate system (an angle between the steered direction and the radius direction) and similarly, steering can also be performed. Similarly to the method (1), etc. and other methods, physical steering can also be performed, software steerings of transmission, reception or both the transmission and reception can also be performed, the combinations of the physical and software steerings can also be performed.

This method is used for performing beamformings to directly generate image signals on the Cartesian coordinate system (x,y) from the signals acquired on the polar coordinate system (r,θ) via no approximate wavenumber matchings and the coordinate conversion and with high speeds and with high accuracies. Similarly to the plane wave transmission performed using a linear array-type transducer, steering can also be performed with respect to the cylindrical wave on the polar coordinate system. Similarly, the cases where steering angles of the transmission and reception beamformings are different, etc. can also be processed. The steerings can also be performed in a software fashion. Apodizations can also be performed. When using the cylindrical wave, at plural positions on the z axis orthogonal to the 2D polar coordinate system (i.e., the z-axis of the cylindrical coordinate system (r,θ,z)), the above-mentioned transmissions can be performed simultaneously and reception can be performed, or the above-mentioned transmissions can be performed at different times, however, at the same phase of the object, and reception performed can be superposed. For these, the above-mentioned processings can also be performed. In the z-axis, focusing can also be performed using an analogue device (lens), or arbitrary processings can also be performed using the digital signal processing of the present invention. When the wave propagation directions point to an origin of the polar coordinate system, the beamformings can be performed similarly (For instance, useful for a HIFU treatment, various type imagings using circular array-type transducers that encircles the objects or a CT, etc.). Off course, in the cases, only the reception beamformings can also be performed and similarly can be processed. With respect to the received signals expressed on the polar coordinate system (r,θ), the processings mentioned in the method (1), however, with exchanging the Cartesian coordinate system by the polar coordinate system (r,θ), can also be performed to generate image signals on the polar coordinate system (r,θ) as mentioned above. When generating the image signals on the Cartesian coordinate system from the results, approximate interpolations are performed as post-processings. In these, steering can also be performed similarly. The methods (2) to (4) and (6) can also be performed similarly.

Also when the received signals are expressed as digital signals on the Cartesian coordinate system (x,y), inversely to eq. (22), f(x,y) is Fourier transformed with respect to the radius r and the angle θ, and image signals can also be generated on the polar coordinate system (r,θ) after all. Or, using the respective methods also allows generating image signals on the Cartesian coordinate system (x,y). Steering and apodization can also be performed similarly.

As shown in FIGS. 8B(d) to (f), when using the physical aperture element arrays expressed by the polar system or the physical apertures with arbitrary aperture geometries as explained above, the beamformings can also be performed similarly to generate, at an arbitrary distance position, the transmission or reception, or both of plane waves. The image signals can be generated on the Cartesian coordinate system, the polar coordinate system or orthogonal curvilinear coordinate system set according to the physical aperture geometry. Performing such beamformings are equivalent to make a formation of a virtual linear-type aperture array (or a plane wave) at the distance position and then, setting the distance position zero corresponds to the case where a linear-type aperture array is used at the position virtually. The distance position can be set in the front of as well as behind the physical aperture and then, the virtual linear-type aperture array (or a plane wave) can be generated at the distance positions. Virtually, the plane wave can also be steered, or the linear-type aperture array can also be slanted (Virtually, the mechanical steering can also be performed). Off course, if required, the physical aperture can also be mechanically steered. The transmissions or the receptions of such plane waves can be performed on the basis of the transmissions and the receptions of the cylindrical waves, respectively, and occasionally, other beamformings can also be performed.

Method (5-1'): Image Signal Generation Using Virtual Source and Aperture Array with Other Arbitrary Geometries In cases where waves are transmitted from arbitrary aperture geometries such as a linear-type array transducer as well as the circular aperture arrays and specifically, generations of partial cylindrical waves using virtual sources set behind the physical apertures are explained (FIGS. 8A(a) to (c)).

(i) When using the reception signals acquired for monostatic SAs, the reception signals stored in memories, etc., i.e., the reception signals received by the respective transmission elements themselves, are Fourier transformed and if necessary, the calculated spectra are multiplied with complex exponential functions to express the responses with respect to the waves transmitted from the virtual source as the digital signals on the polar coordinate system (r,θ), and the method (5) or (5-1) can be used to generate image signals on the Cartesian coordinate system (x,y) directly. Alternatively, after the received signals are expressed as the digital signals on the polar coordinate system (r,θ) in the same way, the processings mentioned in the method (1), however, with exchanging the Cartesian coordinate system by the polar coordinate system (r,θ), can also be performed to generate image signals on the polar coordinate system (r,θ). Off course, the monostatic processings in the method (2) can be also performed on the polar coordinate system (r,θ).

(ii) When using the reception signals acquired for multistatic SAs, the reception signals stored in memories, etc., i.e., the reception signals received at the surrounding reception elements of the respective transmission elements, are Fourier transformed and if necessary, the calculated spectra are multiplied with complex exponential functions to express the responses with respect to the waves transmitted from the virtual source as the digital signals on the polar coordinate system (r,θ), and the method (3) can be used to perform the multistatic SA. Alternatively, the method (5) can be used, or after superposing the digital reception signals at the respective reception elements, the method (5-1) can be used to generate image signals on the Cartesian coordinate system (x,y) directly. Or, after superposing the digital reception signals at the respective reception elements in the same way, the processings mentioned in the method (1), however, with exchanging the Cartesian coordinate system by the polar coordinate system (r,θ), can also be performed to generate image signals on the polar coordinate system (r,θ). Off course, without performing the superposition, the multistatic processings in the method (3) can also performed on the polar coordinate system (r,θ).

(iii) In these processings, to omit the processings for rewriting the reception signals, received at the physical aperture array, by the digital signals on the polar coordinate system (r,θ), delay patterns for the elements with respect to the transmissions or the receptions are used to perform the transmissions and the receptions such that the reception samplings of the received signals are performed on the polar coordinate system originally. And, using the method (2) or (3), which is on the basis of the method (5) or (5-1), can generate image signals directly on the Cartesian coordinate system (x,y). Alternatively, after obtaining the digital signals on the polar coordinate system (r,θ) in the same way, the processings mentioned in the methods (1) to (3), however, with exchanging the Cartesian coordinate system by the polar coordinate system (r,θ), can also be performed to generate image signals on the polar coordinate system (r,θ).

(iv) Also, in the same way, on the above-mentioned (i) to (iii) in the cases where the partial cylindrical wave is generated using the virtual source behind the arbitrary aperture geometry (FIGS. 8A(a) to (c)), the reception signals stored in memories, etc., i.e., the reception signals received by the respective elements, are Fourier transformed; and the calculated spectra are multiplied with complex exponential functions (times required) or approximate interpolations are performed to rewrite the reception signals by the digital signals on the Cartesian coordinate system (x,y); and f(x,y) is Fourier transformed in the directions of a radius r and an angle θ (inversely to eq. (22) in the method (5-1)) to generate image signals on the polar coordinate system (r,θ) after all, or using the respective methods can also generate image signals on the Cartesian coordinate system (x,y). When using orthogonal curvilinear coordinate systems (curvilinear coordinate systems) set according to the aperture geometry, image signals can be generated similarly.

Or, on (i) to (iv), various beamformings, etc. mentioned in the method (5-1) can be performed.

As mentioned in the method (1), etc., when a cylindrical wave is transmitted (transmission delays can be used) using the virtual source set behind arbitrary aperture (one of apertures of a linear-type array transducer or other types, or quasi-array apertures generated by mechanical scanning, etc.) (FIGS. 8A(a) to (c)), the transmission is encoded by implementing the coding on the signals of the respective transmission elements (channels) similarly to the cases of a plane wave transmission; and the received signals are decoded for generating the reception signals for SA processings. Then, by using the above-mentioned processings, image signals are generated directly on the Cartesian coordinate system or arbitrary orthogonal curvilinear coordinate systems such as the polar coordinate system, etc. Also, not virtual sources but virtual receivers can also be set, and the virtual receivers can also work as the virtual sources.

Also, as mentioned in the method (1), etc., when a cylindrical wave is transmitted (transmission delays can be used) using the virtual source set behind arbitrary aperture (one of apertures of a linear-type array transducer or other types, or quasi-array apertures generated by mechanical scanning, etc.) (FIGS. 8A(a) to (c)), using the above-mentioned methods allows the following processings.

(A) With respect to the reception signals expressed on the Cartesian coordinate system (x,y), obtained using the linear-type array transducer or the mechanical scanning, the method (1) itself is used to generate image signals on the Cartesian coordinate system.

(B) With respect to the reception signals received at the reception positions by using the linear-type array transducer or the mechanical scanning, the spectra calculated by (fast) Fourier transform in the y direction are multiplied with complex exponential functions to perform the spatial shiftings of the signals in the y direction such that on the polar coordinate system (r,θ) having the origin at the position of virtual source, the positions of signals are corrected to the r positions under θ determined by the reception positions; and the method (5) or (5-1) is implemented to the data to generate image signals on the Cartesian coordinate system (x,y) or the polar coordinate system (r,θ). Although not the spatial shiftings using the complex exponential functions but approximate spatial shiftings by zero padding in the signal values in the r coordinates can also be performed, to increase the accuracies of the approximations, proper over-samplings of the received signals are required, i.e., AD convertors with high sampling rates or many memories are required. It is cautious that the number of data to be used prior to the Fourier transforms increases.

(C) With respect to the reception signals received by arbitrary aperture geometries except for a linear-type array transducer and quasi-linear type array apertures generated by mechanical scanning, etc., the method (5) or (5-1) is implemented and in the same way, image signals are generated on the Cartesian coordinate system (x,y), the polar coordinate system (r,θ), the orthogonal curvilinear coordinate system (curvilinear coordinate system) set according to the aperture geometry.

(D) Not virtual sources but virtual receivers can also be used, or the virtual receivers can also work as the virtual sources.

As the results of these methods (5-1'), for instance, using other type transducers or other mechanical scanning such as a convex-type or sector-type transducer as shown in FIG. 7 (figures of the corresponding mechanical scanning are omitted) can also generate image signals on the Cartesian coordinate system (x,y), the polar coordinate system (r,θ), the orthogonal curvilinear coordinate system (curvilinear coordinate system) set according to the aperture geometry.

Or, when the virtual linear-type array transducer is realized using the physically other type array transducers inversely (for instance, a physical convex-type array transducer is used, as shown in FIGS. 8B(d) to (f), when the virtual source or the virtual receiver is set at the position of physical aperture, or behind or in front of the physical aperture), image signals can also be generated in the same way on the Cartesian coordinate system (x,y), the polar coordinate system (r,θ), the orthogonal curvilinear coordinate system (curvilinear coordinate system) set according to the aperture geometry.

Also, in special cases, for instance, when using the linear-type array transducer physically, applications of the generations of cylindrical waves using virtual sources or virtual receivers set behind the physical aperture allows the generations of image signals in the cases where at arbitrary distance positions, a plane wave widely spread in a lateral direction or a virtual linear-type array transducer is generated (FIG. 8B(G)).

In these cases, the transmissions to be generated or wave receptions can also be steered, or the apertures can also be slanted virtually (mechanical scanning is virtually performed). Off course, if required, physical apertures can also be mechanically scanned.

Figure 14:
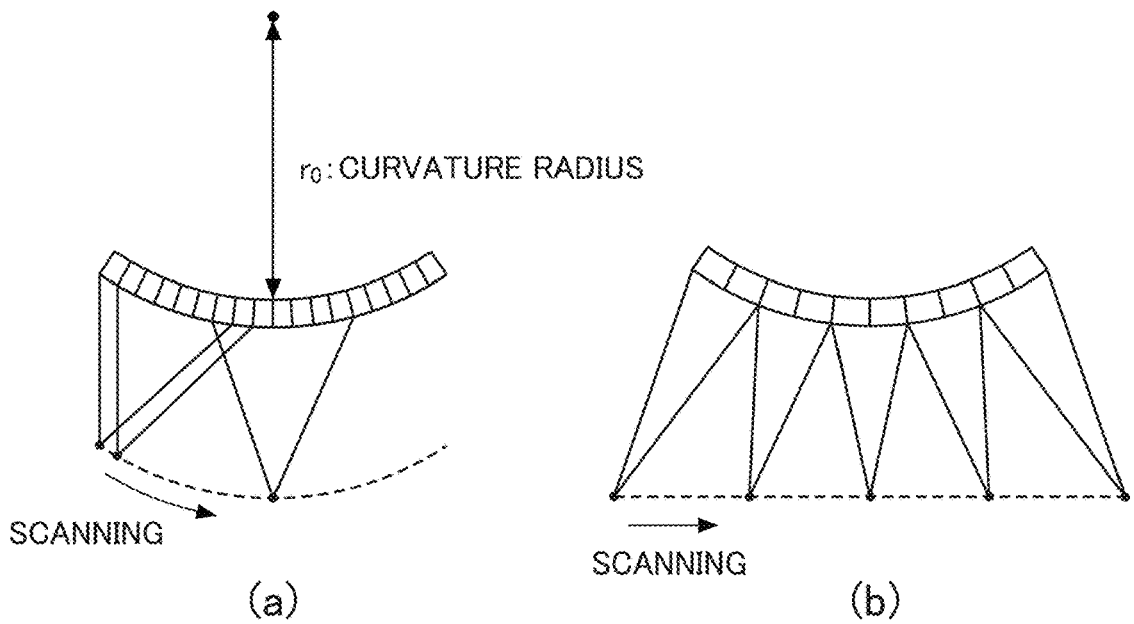
FIG. 14 shows an illustration of a fixed focusing performed using a convex-type transducer.

Method (5-2): Image Signal Generation Using Fixed Focusing FIG. 14 shows an illustration of a fixed focusing performed using a convex-type transducer. Also when using a convex-type transducer, the fixed focusing can be performed. For instance, FIGS. 14(a) and (b) respectively shows cases where the fixed focus positions are equal from the respective effective aperture and arbitrarily set. Similarly to when using a linear-type array transducer (method (4)), image signals can be generated using the same calculations as those performed when the cylindrical wave is transmitted. That is, on the basis of the processings of the method (1) or (3), the following three methods can be performed.

(i) Implementing image signal generation processing once on superposing of the respective reception signals obtained at the effective aperture width.

(ii) Superposing of general low-resolution image signals generated using reception signals obtained with respect to the respective transmissions.

(iii) Superposing of low-resolution image signals generated performing the same processings as those of the multistatic SA, i.e., the respective low-resolution image signals are generated with respect to the respective data sets comprised of data with same position relationships between the transmissions and the receptions.

By performing the above-mentioned processings, image signals can be generated directly on the Cartesian coordinate system. And, it is also possible to generate image signals on the polar coordinate system by implementing the method (4) with the axes of the polar coordinate system. Similarly, steering and apodization can also be performed. Regarding the direction of z-axis, similar processings to those of the method (5-1) can be performed.

Also when the received signals are expressed as digital signals on the Cartesian coordinate system (x,y), by implementing Fourier transforms on f(x,y) regarding the radius r and the angle θ, image signals can be generated on the polar coordinate system (r,θ) after all or image signals can also be generated on the Cartesian coordinate system (x,y) using the respective methods. Steering, apodization and processing in the z-axis can also be performed similarly.

When performing the steering, according to the method (4), the spatial resolution can be obtained together with performing the wavenumber matchings in the x and y directions. As mentioned later, when performing the calculations on the polar coordinate system (r,θ), similarly the steering can also be performed by setting the steering angle (an angle between the steered direction and the radius direction) on the polar coordinate system similarly. Similarly to the method (1), etc. and other methods, physical steering can also be performed, software steerings of transmission, reception or both the transmission and reception can also be performed, the combinations of the physical and software steerings can also be performed.

Also, when using virtual sources or virtual receivers, by setting virtual apertures in front of or behind the physical apertures, etc. mentioned in the method (5-1'), the above-mentioned, transmission fixed focusing can be performed. For instance, a linear-type array transducer can be realized virtually. Or, transducers with arbitrary aperture geometries can also be realized. Image signals are generated on the Cartesian coordinate system, the polar coordinate system or the orthogonal curvilinear coordinate system. Similarly to the method (1), etc. and other methods, physical steering can also be performed, software steerings of transmission, reception or both the transmission and reception can also be performed, the combinations of the physical and software steerings can also be performed. In these cases, the transmissions to be generated or wave receptions can also be steered, or the apertures can also be slanted virtually (mechanical scanning is virtually performed). Off course, if required, physical apertures can also be mechanically scanned.

As mentioned above, the beamformings of the methods (1) to (4) can be performed, however, not limited to these. The adaptions of these approaches to arbitrary beamformings yield the same effects. Particularly, when using the method (4), the reception beamforming can be performed with respect to any transmission beams or waves in addition to the transmission fixed focusing. Off course, similarly the beamformings can also be performed on the simultaneous reception signals received with respect to the simultaneous transmissions of plural different beams or waves, or the superposition of reception signals with respect to the respective transmissions.

Method (5-3): Image Signal Generation Using Signal Reception on Spherical Coordinate System When using the wave aperture element array with a spherical kernel geometry, 3D digital wave signal processing can be performed. For instance, when using the type reception aperture element array, receptions of waves are performed on the spherical coordinate system $(r,\theta,\varphi)$ and then, the reception signals of received waves are expressed by $f(r,\theta,\varphi)$. In this case, similarly to using the 2D polar coordinate system $(r,\theta)$, various beamformings can be implemented using the Jacobi operation.

Concretely, to decompose the received waves into plane waves on the Cartesian coordinate system (x,y,z), 3D Fourier transform is implemented on the reception signal $f(r,\theta,\varphi)$, expressed by eq. (27) expressed in the wavelength or frequency domain $(k_x,k_y,k_z)$ with respect to the Cartesian coordinate system (x,y,z). Moreover, the calculation of eq. (28) using the Jacobi operation using $x=r\sin\theta\cos\varphi$, $y=r\cos\theta$ and $z=r\sin\theta\sin\varphi$ on the eq. (27) can generate image signals directly on the Cartesian coordinate system with no approximate interpolations. Off course, the beamformings of the methods (1) to (4) and (6) can be performed, however, not limited to these. The adaptions of these approaches to arbitrary beamformings yield the same effects. Particularly, when using the method (4), similarly to in the 2D case, the reception beamforming can be performed with respect to any transmission beams or waves in addition to the transmission fixed focusing. Off course, similarly the beamformings can also be performed on the simultaneous reception signals received with respect to the simultaneous transmissions of plural different beams or waves, or the superposition of reception signals with respect to the respective transmissions. Also, when using the virtual sources or virtual receivers or performing the steering, etc., the all can be performed similarly to in the 2D case and image signals can be generated on the Cartesian coordinate system, the polar coordinate system or the orthogonal curvilinear coordinate system set according to the physical aperture geometry.

$$F(k_x,k_y,k_z)=\iiint f(r,\theta,\varphi)\exp\{-i(k_xx+k_yy+k_zz)\}dxdydz \quad (27)$$

$$F(k_x,k_y,k_z)=\iiint f(r,\theta,\varphi)\times r^2\sin\theta\exp\{-i(k_x\sin\theta\cos\varphi+k_y\cos\theta+k_z\sin\theta\sin\varphi)r\}drd\theta d\varphi \quad (28)$$

Method (5"): Image Signal Generation on Arbitrary Orthogonal Curvilinear Coordinate System when Transmission or Reception is Performed on Cartesian Coordinate System Inversely to the above-mentioned series of methods, however, with the similar calculations, image signals can be generated directly on the 2D polar coordinate system or the spherical coordinate system with no approximate interpolations from reception signals obtained by performing transmissions and receptions on the Cartesian coordinate system. For instance, when the reception signals are expressed by f(x,y,z), by implementing Fourier transforms on f(x,y,z) regarding the directions of r, θ and φ via the Jacobi operation, the reception signals f(x,y,z) are decomposed into the circular waves or spherical waves corresponding to plane waves decomposed into on the Cartesian coordinate system. These methods can also be used for changing FOV (for instance, there is a case where a larger FOV can be obtained). Using the Jacobi operation, image signals can also be obtained on arbitrary orthogonal coordinate systems similarly and whenever transmissions and receptions are performed on arbitrary coordinate systems, image signals can also be generated on arbitrary orthogonal coordinate systems (including different orthogonal coordinate systems such as the Cartesian orthogonal coordinate system, various curvilinear orthogonal coordinates, the same or different orthogonal coordinate systems with different origins or rotated). Similarly to other methods mentioned in the method (5), any transmission beams or waves can also be processed; steering can also be implemented similarly; the virtual sources or the virtual receivers can also be used.

And, physically or mathematically, the wavenumber matching can also be performed at the first Fourier transform or at the last inverse Fourier transform. One of the features of method (5) is to perform the beamformings on arbitrary coordinate systems with no approximate interpolations on the wavenumber matchings. However, when using the method (5) for the methods (1) to (4), the method (5), the method (6) and the method (7) to perform the beamformings with high speeds on arbitrary coordinate systems, approximate interpolations can also be performed on the wavenumber matchings (the respectively mentioned approximate wavenumber matchings). To increase the accuracies of the wavenumber matchings to be performed with approximate interpolations, proper over-samplings of data are required in return an increased calculation amount. In the case, being different from in the case where image signals of arbitrary positions can be generated when no approximate interpolations are performed, it is cautious that the number of data to be used for the Fourier transforms increases.

Method (6): Migration Method

Using the instrument of present invention allows performing for the migration methods no approximate interpolations for the wavenumber matchings. The expression of the migration (below mentioned eq. (M6')) is well known and the derivation is also well known and then, the derivation is omitted here.

In the nonpatent document 12, the disclosed method is that the difference in a propagation time from an arbitrary transmission aperture element to the reception aperture element (i.e., the transmission aperture element itself) via an arbitrary same position of interest (i.e., the object position) with respect to the plane wave transmission and/or reception with the steering or no steering (i.e., corresponding to the method (1)) from that on the general migration using one element reception by the one element transmission (i.e., corresponding to the non-steering processing using the method (2) on the transmission and reception data for monostatic SA) is used for performing the calculation of the same type expression of the migration (eq. (M6)), of which the propagation speed and the coordinate of the position of interest (the object position) are modified (i.e., below mentioned eq. (M1)).

However, regarding the processings of other methods (2) to (5), nothing is disclosed in the nonpatent document 12 (Specifically for the method (2), steering processing is not disclosed). Moreover, for calculating eq. (M6'), approximate interpolations are performed on the wavenumber matching traditionally (eqs. (M4) and (M4')). In contrast, the instrument of present invention allows performing the wavenumber matching with no approximate interpolations (eqs. (M7) and (M7')).

A 2D coordinate system is set with the lateral (x) and depth (y) directions (axes), and the temporal axis is set as t. Concretely, the propagation time required for the round trip between an arbitrary aperture element (x,0) and an arbitrary position of interest $(x_s,y_s)$ is expressed as eq. (M0).

$$T(x) = \frac{2}{c}\sqrt{(x_s - x)^2 + y_s^2} \tag{M0}$$

Alternatively, in the case of a plane wave transmission with a steering angle θ (it can be 0 degree), the corresponding propagation time is expressed as eq. (M0').

$$T(x) = \frac{1}{\alpha c}\sqrt{(x_s + \gamma y_s - x)^2 + (\beta y_s)^2} \tag{M0'}$$

where $$\alpha = \frac{1}{\sqrt{1 + \cos\theta + \sin^2\theta}},$$

$$\beta = \frac{(1 + \cos\theta)^{\frac{3}{2}}}{1 + \cos\theta + \sin^2\theta},$$

$$\gamma = \frac{\sin\theta}{2 - \cos\theta}.$$

Thus, when performing the beamforming for the steered plane wave transmission of the method (1) by using the migration method, the general migration expressions (eqs. (M4) and (M5)) are calculated by modifying the propagation speed c and the coordinate system $(x_s,y_s)$ expressing the object position by eq. (M1).

$$\hat{c} = \alpha c$$

$$(\widehat{x_s}, \widehat{y_s}) = (x_s + \gamma y_s, \beta y_s) \tag{M1}$$

Summarizing, all the methods (1) to (5) except for the method (2) performing the non-steering monostatic SA using the transmission and reception SA data (i.e., a general migration method) can also be performed using migration processing similarly. For instance, the migration calculation procedure is explained mainly for the steered plane wave transmission (the steering angle can be 0 degree).

Figure 15:
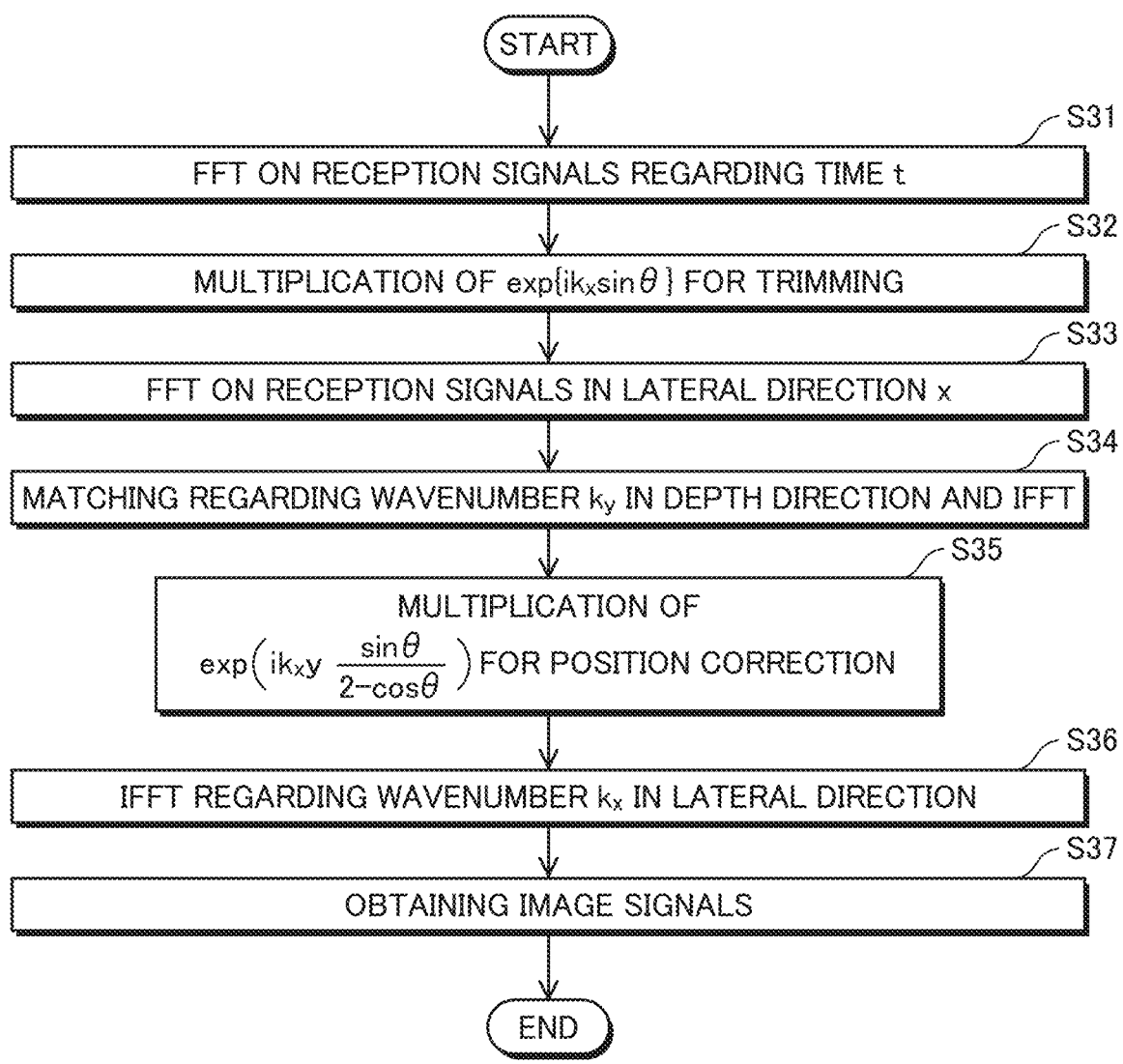
FIG. 15 shows a flowchart about the migration processing for a steered plane wave transmission.

FIG. 15 shows a flowchart about the migration processing for the steered plane wave transmission. When the received signals are expressed by r(x,y,t), the received signals are expressed by r(x,y=0,t) at the aperture element array positions.

At first, as expressed by eq. (M2), the received signals are 2D Fourier transformed regarding the time t and the lateral direction x (2D FFT can be used).

$$R(k_x, y=0, k) = \iint r(x, y=0, t)\exp\{-i(k_x x + \omega t)\}dxdt \tag{M2}$$

Here, k=ω/c, the wavenumber k and the angular frequency ω are related using the proportional coefficient 1/c (one-to-one correspondence) and then, w can be used instead of k to express the equations and to perform the calculations.

As mentioned above, special 2D FFT method can also be used and however, as a general (popular) method, at step 31, at first, the spectra of analytic signals are obtained by implementing FFT on the received signals regarding the time t at respective lateral coordinates x at the step S31. Besides, FFT is performed regarding the lateral direction x at the respective frequency coordinates within the bandwidth k (It is faster to calculate 2D spectra than the using eq. (M2) for calculating the respective 2D spectra).

When not performing the steered transmission of a plane wave, the above-mentioned calculations are performed and however, when performing the steering, the trimming is performed at the step S32, the results of the above-mentioned FFT on the time t (R'(x,0,k)) are multiplied with the complex exponential function (M3) (Similarly to the complex exponential function (11) used in the method (1), the multiplication of the FFT results on the time t and the complex exponential function can be performed at once and for such calculations, the exclusive FFT is also useful).

$$\text{Exp}\{ikx \sin\theta\} \tag{M3}$$

Besides, at the step S33, FFT is implemented on the received signals in the lateral direction x. Here, the results are expressed as R''($k_x$,0,k). Even if the trimming is programmed to be performed, a non-steered plane wave transmission can be processed (The steering angle can be set to zero degree).

In general, the wavenumber matching (or mapping) is performed next. When the beamforming to be performed is one of the methods (1) to (5) except for the general migration (the method (2) with no steering), similarly to using the modifications (conversions) about the propagation speed c and the coordinate ($x_s$,$y_s$) as likely expressed in eq. (M11) for the plane wave transmission, the respective modifications (conversions) of the propagation speed c and the coordinate system ($x_s$,$y_s$) for the respective beamformings into eqs. (E1) and (E2) are performed.

$$\hat{c} \tag{E1}$$

$$(\widehat{x_s}, \widehat{y_s}) \tag{E2}$$

On the 2D Fourier transform R''($k_x$,0,k) calculated for the methods including the method (1), however, except for the general migration (the method (2) with no steering) or the above-mentioned R($k_x$,0,k) calculated for the general migration, approximate interpolations (using the most neighborhood angular spectra at the digital frequency coordinate or bi-linear interpolations, etc.) are used to perform the wavenumber matchings respectively expressed by eqs. (M4) or (M4').

$$F''(k_x, 0, K(\overline{k_y})) = R''(k_x, 0, k), \tag{M4}$$

where $K(\overline{k_y}) = \hat{c}\ \text{sgn}(\overline{k_y})\sqrt{k_x^2 + \overline{k_y}^2}$, $\overline{k_y} = \sqrt{\hat{k}^2 - k_x^2} = \sqrt{\left(\frac{\omega}{\hat{c}}\right)^2 - k_x^2}$ or $\sqrt{\left(\frac{k}{\alpha}\right)^2 - k_x^2}$, $$F(k_x, 0, K(k_y)) = R(k_x, 0, sk), \tag{M4'}$$

where $K(k_y) = c\ \text{sgn}(k_y)\sqrt{k_x^2 + k_y^2}$, $k_y = \sqrt{(sk)^2 - k_x^2} = \sqrt{\left(s\frac{\omega}{c}\right)^2 - k_x^2}$, when the received signals are reflected ones, s=2; and when transmission signals, s=1.

When the approximate interpolations are not performed on the wavenumber matchings expressed by eqs. (M4) and (M4'), the wavenumbers in the depth direction respectively expressed in the supplementary explanations of equations are used, whereas when the approximate interpolations are performed, the wavenumbers in the depth direction are respectively ones obtained by dividing the angular frequency ω by the converted propagation speed (E1) and c. These are also below.

The wavenumber matchings are performed in these ways, and the next function (M4") is calculated.

$$F''(k_x,0,K(\overline{k_y}))\ \text{or}\ F(k_x,0,K(k_y)) \tag{M4''}$$

Besides, using the function (M4"), the next eqs. (M5) and (M5') are calculated.

$$\frac{\partial \overline{k_y}}{\sqrt{k_x^2 + \overline{k_y}^2}} F''(k_x, 0, K(\overline{k_y})) \tag{M5}$$

$$\frac{Ck_y}{\sqrt{k_x^2 + k_y^2}} F(k_x, 0, K(k_y)) \tag{M5'}$$

With respect to the respective eqs. (M5) and (M5'), by implementing 2D inverse Fourier transforms regarding the wavenumber $k_x$ and the wavenumbers (E3) as expressed by eq. (M6) and (M6'), image signal f(x,y) is generated.

$$\overline{K_y}\ \text{or}\ k_y \tag{E3}$$

$$F(x, y) = \tag{M6}$$
$$\int\int \frac{\partial \overline{K_y}}{\sqrt{k_x^2 + \overline{K_y}^2}} F''(k_x, 0, K(\overline{K_y}))\exp\{i(k_x x + \overline{K_y} y_s)\}d\overline{K_y}\, dk_x$$

$$F(x, y) = \int\int \frac{ck_y}{\sqrt{k_x^2 + k_y^2}} F(k_x, 0, K(k_y))\exp\{i(k_x x + k_y y)\}dk_y dk_x \tag{M6'}$$

The 2D inverse Fourier transform of eqs. (M6) and (M6') can be performed using 2D IFFT. Special 2D IFFT can also be used and however, as general (popular) methods for calculating eqs. (M6) and (M6'), with respect to the respective wavenumbers of $k_x$ within the bandwidths of signals, IFFT can be performed regarding another respective wavenumbers of (E3) within the bandwidths of signals; and further with respect to the respective spatial coordinates y generated, IFFT can be performed regarding the respective wavenumbers of $k_x$ within the bandwidths of signals (It is faster to calculate 2D image signals than the using eq. (M6) or (M6') for calculating the respective 2D image signals).

In the nonpatent document 12, eq. (M6) using $y_s$ in the equation is not disclosed and instead, it is disclosed that not $y_s$ but y is used for the calculation and after the calculation, correction of the coordinate is performed. For the correction of coordinate, approximate interpolations are performed, or no approximation interpolations are performed by performing the multiplications of complex exponential functions (a past invention of the inventor of present invention). Eq. (M6) can also be used when the steering angle is zero degree.

The instrument of present invention performs the wavenumber matchings together with the 2D inverse Fourier transform or together with the inverse Fourier transform in the depth direction, with no approximate interpolations. That is, on the 2D Fourier transform R''($k_x$,0,k) calculated for the methods including the method (1), however, except for the general migration (the method (2) with no steering), or the above-mentioned $R(k_x,0,k)$ calculated for the general migration, as expressed by eqs. (M7) or (M7'), the integration regarding k is implemented with respect to the respective wavenumbers of $k_x$ within the bandwidths of signals to simultaneously perform the wavenumber matching on the wavenumber (E3) and the inverse Fourier transform (IFFT possible) in the depth direction (step S34) and after the integrations, the lateral (x) IFFT is performed.

$$F(x,y)=\iint R''(k_x,0,k)\exp\{i(k_x x+\widehat{k_y}y_s)\}dkdk_x \quad (M7)$$

$$F(x,y)=\iint R(k_x,0,k)\exp\{i(k_x x+k_y y)\}dkdk_x \quad (M7')$$

In nonpatent document 12, eq. (M7) using $y_s$ in the equation is not disclosed. Eq. (M7) can also be used when the steering angle is zero degree. Similarly to the methods (1) to (6), after summing the spectral k components, the inverse Fourier transform (IFFT) can be performed on the lateral wavenumber $k_x$ and then, the inverse Fourier transform is performed once, and the total calculations are high speed.

Moreover, the migrations to be performed being different from the general migration (corresponding to the processing of non-steering of the method (2)), corrections of the lateral positions can be performed during performing the calculations of eq. (M6) or (M7). For instance, when performing the transmission of a steered plane wave of the method (1), at the step S34, at first, the calculation about the wavenumber (E3); at the step S35, the function (M8) calculated as each result is multiplied with complex exponential function (M9) for the position correction; at the step S36, IFFT is implemented on the wavenumber $k_x$ in the lateral direction. Alternatively, instead of the steps S35 and S36, eq. (M9) can also be multiplied together with the complex exponential function used for the inverse Fourier transform regarding the wavenumber $k_x$ in the lateral direction, or the exclusive IFFT can also be implemented. Eq. (M9) can also be used for the zero-steering angle. Thus, at the step S37, image signals f(x,y) are generated.

$$F'''(k_x, y) \text{ or } R'''(k_x, y) \quad (M8)$$

$$\mathrm{Exp}\left(ik_x y \frac{\sin\theta}{2-\cos\theta}\right) \quad (M9)$$

Summarizing, using eq. (M6), (M7) or (M7') yields a new processing for generating, with a high speed, image signal f(x,y) with no errors due to approximate interpolations.

Without performing the multiplication of eq. (M9) and with no approximate interpolations, to obtain the same results, eq. (M6) or (M7) is calculated using the next eq. (N4) instead of eq. (M4).

$$F''(k_x, 0, K(\widehat{k_y})) = R''(k_x, 0, k) \quad (N4)$$

where $K(\widehat{k_y}) = \hat{c}\ \mathrm{sgn}(\widehat{k_y})\sqrt{(k_x - k\sin\theta)^2 + \widehat{k_y}^2}$, $\widehat{k_y} = \sqrt{\hat{k}^2 - (k_x - k\sin\theta)^2} = $ $\sqrt{\left(\frac{\omega}{\hat{c}}\right)^2 - (k_x - k\sin\theta)^2}$ or $\sqrt{\left(\frac{k}{\alpha}\right)^2 - (k_x - k\sin\theta)^2}$.

That is, when the approximate interpolations are not performed on the wavenumber matching, the wavenumber in the depth direction expressed in the supplementary explanation of equation is used, whereas when the approximate interpolations are performed, the wavenumber in the depth direction is one obtained by dividing the angular frequency ω by the converted propagation speed (E1).

The equation of wavenumber in the depth direction in these equations is similar to eq. (13) of the method (1). To generate the same result using the method (1), however, with no use of −k sin θ in kx−k sin θ in eqs. (13) to (15) (i.e., use as zero), as in the method (6) the inverse Fourier transform being implemented on the multiplication with eq. (M9), eq. (16) can be multiplied with eq. (M9) prior to performing the processings mentioned in the paragraphs 0204 and 0203. However, note that the steering of the plane wave achieved by the above-mentioned method (6) is only realized under the approximate calculations and therefore, using eqs. (N4) and (M7) in the method (6) can perform the beamforming with no approximate interpolations and with a high accuracy, whereas the use of eq. (M9) decreases the accuracy of the method (1). Moreover, implementing the 2D IFFT for the last inverse Fourier transform (as mentioned later, 3D IFFT in a 3D case) increases the calculation speed for the method (6), however, decreases the speed for the method (1) (The processing mentioned in the paragraph 0204 is high speed).

On the respective modified methods (1) and (6), when performing approximate interpolations on the wavenumber matchings, to generate the same results using eqs. (M9) and (N4), the equations of approximate interpolations change correspondingly (mentioned later in the respective (A) and (B) in the paragraph 0354).

On the respective modified methods (1) and (6), when performing approximate interpolations on the wavenumber matchings, to generate the same results using eqs. (11) and (M3) (using the steering angle data θ) or not (the steering angle θ is set to zero degree), the equations of approximate interpolations change correspondingly (mentioned later in the respective (A') and (B') in the paragraph 0354).

Beamforming using the plane wave transmission is applied to various beamformings as mentioned before in the present invention document and instead the processings mentioned in this paragraph can also be used. It is cautious that when the reception dynamic focusing is performed using the method (6) on arbitrary transmission beamformings such as the transmission focusing, etc., as mentioned later, eq. (M3″), expressed using the wavenumber [eq. (M13)] expressed by the angular frequency ω and the converted propagation speed (E1), is used instead of eq. (M3) and then, for the wavenumber k in −k sin $θ_t$ in the expression of approximate interpolation, eq. (M13) is required to be used instead.

On the respective methods (1) and (6), the methods mentioned in this paragraph can also be combined and performed. For instance, similarly to J.-y. Ku's method that performs approximate interpolations for the method (1) (the paragraph 0197, expressions are described in (C') in the paragraph 0354), all the wavenumber matchings of the method (6) can be performed via approximate interpolations and accordingly, the first 2D Fourier transform and the last 2D inverse Fourier transform can be performed using 2D FFT and 2D IFFT, respectively (Described in (D') in the paragraph 0354. As mentioned later, in a 3D case, 3D FFT). In the respective these, eq. (11) can also be used (The steering angle data θ is used) and eq. (M3) can also be used (Described in (C) and (D) in the paragraph 0354). Off course, non-steering can also be used.

As mentioned above, the plane wave transmission on the basis of the methods (1) and (6) can be applied to various beamformings.

Here, mainly explained is the use of the migration method to the method (1), i.e., a high-speed beamforming with no approximate interpolations for a steered or non-steered plane wave transmission. All the beamformings described in other methods of the present invention, the method (2) (a monostatic SA method including a steering case), the method (3) (a multistatic SA method including a steering case), the method (4) (a transmission fixed focus with a steering or no steering), the method (5) (beamformings on the polar coordinate system or arbitrary orthogonal curvilinear coordinate systems) can also be performed similarly. On the transmission and the reception, different steering angles can also be processed similarly. Apodizations can also be performed similarly.

The 3D cases can also be processed similarly. When the received signals obtained using 2D aperture element array are expressed as r(x,y,z,t), the reception signals received at the position of aperture element array (y=0) are expressed as r(x,y=0,z,t).

At first, as shown in eq. (M'2), the reception signals are 3D Fourier transformed with respect to the time t, the lateral direction x and the elevational direction z (3D FFT can be performed).

$$R(k_x, y=0, k_z, k) = \iint r(x, y=0, z, t) \exp\{-i(k_x x + k_z z + \omega t)\} dx dt \quad (M'2)$$

where $k=\omega/c$.

In general, the spectra R(x,0,z,k) of analytic signals are obtained for the reception signals by performing FFT regarding the time t. Besides, for the respective frequency coordinates k within the bandwidth of signals, FFT is implemented regarding the lateral (x) and elevational (z) directions to generate $R(k_x,0,k_z,k)$ (It is faster to calculate 3D spectra than the using eq. (M'2) for calculating the respective 3D spectra).

When not performing the steered transmission of a plane wave, the above-mentioned calculations are performed and however, when performing the steering with the steering angle being an angle between the transmission direction as a plane wave and the axial direction (y) is expressed using zero or non-zero elevation (θ) and azimuth (φ) angles, the trimming is required to be performed, the results of the above-mentioned FFT on the time t (R'(x,0,z,k)) are multiplied with the complex exponential function (M'3) (The multiplication of the FFT results on the time t and the complex exponential function can be performed at once and for such calculations, the exclusive FFT is also useful).

$$\exp\{ik \sin \theta(\cos \varphi x + \sin \varphi z)\} \quad (M'3)$$

Besides, FFT is implemented on the received signals in the lateral direction x. Here, the results are expressed as $R''(k_x,0,z,k)$. Even if the trimming is programmed to be performed, a non-steered plane wave transmission can be processed (The steering angle can be set to zero degree).

Next, the wavenumber matching (or mapping) is performed. When the beamforming to be performed is one of the methods (1) to (5) except for the general migration (the method (2) with no steering), the respective modifications (conversions) of the propagation speed c and the coordinate system $(x_s, y_s, z_s)$ for the respective beamformings into eqs. (E'1) and (E'2) are performed.

$$\hat{c} \quad (E'1)$$

$$(\widehat{x_s}, \widehat{y_s}, \widehat{z_s}) \quad (E'2)$$

On the 3D Fourier transform R" $(k_x,0,z,k)$ calculated for the methods including the method (1), however, except for the general migration (the method (2) with no steering) or the above-mentioned $R(k_x,0,z,k)$ calculated for the general migration, approximate interpolations (using the most neighborhood angular spectra at the digital frequency coordinate or bi-linear interpolations, etc.) are used to perform the wavenumber matchings respectively expressed by eqs. (M'4) or (M'4').

$$F''(k_x, 0, k_z, K(\overline{k_y})) = R''(k_x, 0, k_z, k) \quad (M'4)$$

where $K(\overline{k_y}) = \hat{c} \operatorname{sgn}(\overline{k_y})\sqrt{k_x^2 + k_z^2 + \overline{k_y}^2}$, $$\overline{k_y} = \sqrt{\hat{k}^2 - k_x^2 - k_z^2} = \sqrt{\left(\frac{\omega}{\hat{c}}\right)^2 - k_x^2 - k_z^2} \text{ or } \sqrt{\left(\frac{k}{\alpha}\right)^2 - k_x^2 - k_z^2},$$

$$F(k_x, 0, k_z, K(k_y)) = R(k_x, 0, k_z, sk) \quad (M'4')$$

where $K(k_y) = c \operatorname{sgn}(K_y)\sqrt{k_x^2 + k_z^2 + K_y^2}$, $$k_y = \sqrt{(sk)^2 - k_x^2 - k_z^2} = \sqrt{\left(s\frac{\omega}{c}\right)^2 - k_x^2 - k_z^2},$$

when the received signals are reflected ones, s=2; and when transmission signals, s=1.

When the approximate interpolations are not performed on the wavenumber matchings expressed by eqs. (M'4) and (M'4'), the wavenumbers in the depth direction respectively expressed in the supplementary explanations of equations are used, whereas when the approximate interpolations are performed, the wavenumbers in the depth direction are respectively ones obtained by dividing the angular frequency ω by the converted propagation speed (E'1) and c. These are also below.

The phase matchings are performed in these ways, and the next function (M'4") is calculated.

$$F''(k_x,0,k_z,K(\widehat{k_y})) \text{ or } F(k_x,0,k_z,K(k_y)) \quad (M'4")$$

Besides, using the function (M'4"), the next eqs. (M'5) and (M'5') are calculated.

$$\frac{\hat{c}\overline{k_y}}{\sqrt{k_x^2 + k_z^2 + \overline{k_y}^2}} F''(k_x, 0, k_z, K(\overline{k_y})) \quad (M'5)$$

$$\frac{Ck_y}{\sqrt{k_x^2 + k_z^2 + k_y^2}} F(k_x, 0, k_z, K(k_y)) \quad (M'5')$$

With respect to the respective eqs. (M'5) and (M'5'), by implementing 3D inverse Fourier transforms regarding the wavenumber $k_x$ and $k_z$, and the wavenumbers (E'3) in the 3D case as expressed by eq. (M'6) and (M'6'), image signal f(x,y) is generated.

$$\overline{K_y} \text{ or } k_y \quad (E'3)$$

$$f(x, y, z) = \iiint \frac{\hat{c}\overline{k_y}}{\sqrt{k_x^2 + k_z^2 + \overline{k_y}^2}} \quad (M'6)$$

$$F''(k_x, 0, k_z, K(\overline{k_y})) \times \exp\{i(k_x x + k_z z + \overline{k_y} y_s)\} d\overline{k_y} dk_x dk_z$$

-continued $$f(x, y, z) = \iiint \frac{ck_y}{\sqrt{k_x^2 + k_z^2 + k_y^2}} \quad (M'6')$$

$$F(k_x, 0, k_z, K(k_y)) \times \exp\{i(k_x x + k_z z + k_y y)\} dk_y dk_x dk_z$$

The 3D inverse Fourier transform of eqs. (M'6) and (M'6') can be performed using 3D IFFT. Special 3D IFFT can also be used and however, as general (popular) methods for calculating eqs. (M'6) and (M'6'), with respect to the respective wavenumbers of $k_x$ and $k_z$ within the bandwidths of signals, IFFT can be performed regarding another respective wavenumbers of (E'3) within the bandwidths of signals; and further with respect to the respective spatial coordinates y generated, IFFT can be performed regarding the respective wavenumbers of $k_x$ and $k_z$ within the bandwidths of signals (It is faster to calculate 3D image signals than the using eq. (M'6) or (M'6') for calculating the respective 3D image signals).

The instrument of present invention performs the wavenumber matchings together with the 3D inverse Fourier transform or together with the inverse Fourier transform in the depth direction, with no approximate interpolations. That is, on the 3D Fourier transform R" $(k_x,0,k_z,k)$ calculated for the methods including the method (1), however, except for the general migration (the method (2) with no steering), or the above-mentioned $R(k_x,0,k_z,k)$ calculated for the general migration, as expressed by eqs. (M'7) or (M'7'), the integration regarding k is implemented with respect to the respective wavenumbers of $(k_x,k_z)$ within the bandwidths of signals to simultaneously perform the wavenumber matching on the wavenumber (E'3) and the inverse Fourier transform (IFFT possible) in the depth direction and after the integrations, the lateral (x) and elevation (z) IFFTs are performed.

$$f(x,y,z) = \iiint R''(k_x,0,k_z,k)\exp\{i(k_x x + k_z z + \widehat{k}_y y_s)\} dk dk_x dk_z \quad (M'7)$$

$$f(x,y,z) = \iiint R(k_x,0,k_z,k)\exp\{i(k_x x + k_z z + k_y y_s)\} dk dk_x dk_z \quad (M'7')$$

In nonpatent document 12, eqs. (M'6) and (M'7) using $y_s$ in the equation are not disclosed. Both equations can also be used when the steering angle is zero degree. Similarly to the methods (1) to (6), after summing the spectral k components, the inverse Fourier transforms (IFFTs) can be performed on the lateral $(k_x)$ and elevational $(k_z)$ wavenumbers and then, the inverse Fourier transform is performed once, and the total calculations are high speed.

Moreover, the migrations to be performed being different from the general migration (corresponding to the processing of non-steering of the method (2)), corrections of the lateral (x) and elevational (z) positions can be performed during performing the calculations of eq. (M'6) or (M'7). For instance, when performing the transmission of a steered plane wave of the method (1), at first, the calculation about the wavenumber (E'3); and next, the function (M'8) calculated as each result is multiplied with complex exponential function for the position correction; and finally, IFFTs are respectively implemented on the wavenumbers $k_x$ and $k_z$ in the lateral and elevational directions.

$$F'''(k_x,y) \text{ or } R'''(k_x,y) \quad (M'8)$$

Summarizing, using eq. (M'6), (M'6'), (M'7) or (M'7') yields a new processing for generating, with a high-speed, image signal f(x,y,z) with no errors due to approximate interpolations.

Without performing the multiplication of the complex exponential function corresponding to eq. (M9) and with no approximate interpolations, to obtain the same results, eq. (M6) or (M7) is calculated using the next eq. (N'4) instead of eq. (M'4).

$$F''(k_x, 0, k_z, K(\widehat{k}_y)) = R''(k_x, 0, k_z, k) \quad (N'4)$$

where $$K(\widehat{k}_y) = \hat{c}\ \mathrm{sgn}(\widehat{k}_y)\sqrt{(k_x - k\sin\theta\cos\varphi)^2 + (k_z - k\sin\theta\sin\varphi)^2 + \widehat{k}_y^2},$$

$$\widehat{k}_y = \sqrt{\hat{k}^2 - (k_x - k\sin\theta\cos\varphi)^2 - (k_z - k\sin\theta\sin\varphi)^2} =$$

$$\sqrt{\left(\frac{\omega}{\hat{c}}\right)^2 - (k_x - k\sin\theta\cos\varphi)^2 - (k_z - k\sin\theta\sin\varphi)^2}$$

$$\text{or } \sqrt{\left(\frac{k}{\alpha}\right)^2 - (k_x - k\sin\theta\cos\varphi)^2 - (k_z - k\sin\theta\sin\varphi)^2}.$$

That is, when the approximate interpolations are not performed on the wavenumber matching, the wavenumber in the depth direction expressed in the supplementary explanation of equation is used, whereas when the approximate interpolations are performed, the wavenumber in the depth direction is one obtained by dividing the angular frequency ω by the converted propagation speed (E'1).

The equation of wavenumber in the depth direction in these equations is similar to eq. (C22) of the method (1). To generate the same result using the method (1), however, with no use of –k sin θ cos φ and –k sin θ sin φ in respective kx–k sin θ cos φ and kz–k sin θ sin φ in eqs. (C22) and (C23) (i.e., uses as zero), as in the method (6) the inverse Fourier transform being implemented on the multiplication with the complex exponential function corresponding to eq. (M9) in the 2D case, the multiplication can be performed in the processings described in the paragraph 0207. However, note that the steering of the plane wave achieved by the method (6) is only realized under the approximate calculations and therefore, similarly to in the 2D case, using eqs. (N'4) and (M7) in the method (6) can perform the beamforming with no approximate interpolations and with a high accuracy, whereas the use of the complex exponential function corresponding to eq. (M9) in the 2D case decreases the accuracy of the method (1). Moreover, implementing the 3D IFFT for the last inverse Fourier transform increases the calculation speed for the method (6) similarly to in the 2D case, however, decreases the speed for the method (1) (The processing mentioned in the paragraph 0204 is high speed).

On the respective modified methods (1) and (6), when performing approximate interpolations on the wavenumber matchings, to generate the same results using the complex exponential function corresponding to eqs. (M9) in the 2D case and (N'4), the equations of approximate interpolations change correspondingly similarly to in the 2D case (mentioned in the respective (A) and (B) in the paragraph 0354).

On the respective modified methods (1) and (6), when performing approximate interpolations on the wavenumber matchings, to generate the same results using eqs. (C21) and (M'3) (using the steering angle data θ and φ) or not (the steering angles θ and φ are set to zero degree), the equations of approximate interpolations change correspondingly similarly to in the 2D case (mentioned in the respective (A') and (B') in the paragraph 0354).

Beamforming using the plane wave transmission is applied to various beamformings as mentioned before in the present invention document and instead the processings mentioned in this paragraph can also be used. Similarly in the 2D case, it is cautious that when the reception dynamic focusing is performed using the method (6) on arbitrary transmission beamformings such as the transmission focusing, etc., as mentioned later, eq. (M'3"), expressed using the wavenumber [eq. (M'13)] expressed by the angular frequency ω and the converted propagation speed (E'1), is used instead of eq. (M'3) and then for the wavenumber k in −k sin $\theta_1$(cos $\varphi_1$ x+sin $\varphi_1$z) in the expression of approximate interpolation, eq. (M'13) is required to be used instead.

On the respective methods (1) and (6), the methods mentioned in this paragraph can also be combined and performed. For instance, similarly to J.-y. Lu's method that performs approximate interpolations for the method (1) (the paragraph 0197, expressions are described in (C') in the paragraph 0354), all the wavenumber matchings of the method (6) can be performed via approximate interpolations and accordingly, the first 3D Fourier transform and the last 3D inverse Fourier transform can be performed using 3D FFT and 3D IFFT, respectively (Described in (D') in the paragraph 0354). In the respective these, eq. (C21) can also be used (The steering angle data θ is used) and eq. (M'3) can also be used (Described in (C') and (D') in the paragraph 0354). Off course, non-steering can also be used.

As mentioned above, the plane wave transmission on the basis of the methods (1) and (6) can be applied to various beamformings.

Also by using the migration method, similarly to the method (2) or (3), the monostatic or multistatic SA can be performed with no approximate interpolations.

In the case of monostatic SA, when the software transmission and reception steering angles are $\theta_t$ and $\theta_r$, instead of eq. (M3), similarly used can be $$\text{Exp}\{ixk_0(\sin\theta_t + \sin\theta_r)\} \tag{M3'}$$

expressed using the wavenumber, $$k_0 = \omega_0/c, \tag{M10}$$

expressed using the ultrasound angular frequency $\omega_0$ and the propagation speed c, and used in eq. (M7'), which does require no approximate interpolations on the wavenumber matching in the general migration processings, is $$k_y = \sqrt{(sk)^2 - (k_x - k_0\sin\theta_t - k_0\sin\theta_r)^2} + k_0(-2+\cos\theta_t + \cos\theta_r) \tag{M11}$$

when the received signals are reflected ones, s=2; and when transmission signals, s=1.

In the 3D case, when the steering angles of the transmission and reception beams are respectively (an elevation angle, an azimuth angle)=$(\theta_t,\varphi_t)$ and $(\theta_r,\varphi_r)$, similarly to the method (2), the wavenumber matching is performed, at first, for the spatial (lateral) directions, by multiplying the complex exponential function eq. (D41) expressed using the carrier frequency $\omega_0$ of the ultrasound signals and next for the depth direction y, by multiplying the complex exponential function eq. (D43) together with the complex exponential function eq. (D42) with removed the performed lateral matching processing eq. (D41). That is, eq. (D41) is used instead of eq. (M3') in the 2D case, and the multiplication of eqs. (D42) and (D43) is used instead of eq. (M11).

Thus, migration processings of the present invention, corresponding to the method (2) and the method (3) on the basis of the method (2), are equivalent to the methods (2) and (3), respectively.

Also in these cases, similarly to the general migration processings, the approximate wavenumber matching and the IFFT can be performed, in which not being equivalent to the method (2) and the method (3) on the basis of the method (2), after performing the above-mentioned processings using eq. (M3'), etc., instead of eq. (M4') with approximation wavenumber matching, eq. (M4") expressed by eq. (M4''') on the basis of eq. (M11) is calculated and the 2D inverse Fourier transform [eq. (M6')] of eq. (M5') expressed using the ky expressed in eq. (M4''') is performed.

$$F(k_x, 0, K(k_y)) = R(k_x, 0, sk) \tag{M4'''}$$

where $$K(k_y) = c \text{ sgn}(k_y) \times \sqrt{(k_x - k_0\sin\theta_t - k_0\sin\theta_r)^2 + \{k_y - k_0(-2+\cos\theta_t + \cos\theta_r)\}^2}$$

$$K_y \equiv \sqrt{(sk)^2 - (k_x - k_0\sin\theta_t - k_0\sin\theta_r)^2} + k_0(-2+\cos\theta_t + \cos\theta_r)$$

$$= \sqrt{\left(s\frac{\omega}{c}\right)^2 - (k_x - k_0\sin\theta_t - k_0\sin\theta_r)^2} + k_0(-2+\cos\theta_t + \cos\theta_r),$$

when the received signals are reflected ones, s=2 and when transmission signals, s=1; and the wavenumber in the depth direction obtained by dividing the angular frequency ω by the propagation speed c is used, whereas when not performing the approximate interpolations, the wavenumber in the depth direction expressed in the supplementary explanation of equation is used and similarly as below.

Alternatively, instead of eq. (M4'), eq. (M4"), which is used for approximate interpolations, expressed by eq. (M4''') is calculated and the 2D inverse Fourier transform [corresponding to eq. (M6')] is performed on the multiplication of eq. (M12) and eq. (M5') expressed using the ky expressed in eq. (M4''').

$$F(k_x, 0, K(k_y)) = R(k_x, 0, sk) \tag{M4'''}$$

where $$K(k_y) = c \text{ sgn}(k_y)\sqrt{(k_x - k_0\sin\theta_t - k_0\sin\theta_r)^2 + k_y^2},$$

$$k_y = \sqrt{(sk)^2 - (k_x - k_0\sin\theta_t - k_0\sin\theta_r)^2}$$

$$= \sqrt{\left(s\frac{\omega}{c}\right)^2 - (k_x - k_0\sin\theta_t - k_0\sin\theta_r)^2},$$

when the received signals are reflected ones, s=2 and when transmission signals, s=1; and the wavenumber in the depth direction obtained by dividing the angular frequency ω by the propagation speed c is used, whereas when not performing the approximate interpolations, the wavenumber in the depth direction expressed in the supplementary explanation of equation is used and similarly as below.

$$\text{Exp}\{ik_0(-2+\cos\theta_t + \cos\theta_r)y\} \tag{M12}$$

Also in these cases, the multistatic SAs can be performed using, instead of the method (2), the monostatic SAs on the basis of these migration methods, similarly to the case where the method (3) is performed using the method (2).

The 3D cases can also be processed similarly. That is, after performing the processing using eq. (M'3') in the 3D cases, instead of eq. (M'4') with approximation wavenumber matching, eq. (M'4") expressed by eq. (M'4''') on the basis of the multiplication of eq. (D42) and eq. (D43) [corresponding to eq. (M11) in the 2D cases] is calculated and the 3D inverse Fourier transform [eq. (M'6')] of eq. (M'5') expressed using the ky expressed in eq. (M'4''') is performed.

$$F(k_x, 0, k_z, K(k_y)) = R(k_x, 0, k_z, sk) \tag{M'4'''}$$

where $$K(k_y) = c \; \text{sgn}(k_y) \sqrt{\begin{array}{l}\{k_x - k_0(\sin\theta_t\cos\varphi_t + \sin\theta_r\cos\varphi_r)\}^2 + \\ \{k_z - k_0(\sin\theta_t\sin\varphi_t + \sin\theta_r\sin\varphi_r)\}^2 + \\ \{k_y - k_0(-2 + \cos\theta_t + \cos\theta_r)\}^2\end{array}},$$

$$k_y \equiv \sqrt{\begin{array}{l}(sk)^2 - \\ \{k_x - k_0(\sin\theta_t\cos\varphi_t + \sin\theta_r\cos\varphi_r)\}^2 - \\ \{k_z - k_0(\sin\theta_t\sin\varphi_t + \sin\theta_r\sin\varphi_r)\}^2 + \\ k_0(-2 + \cos\theta_t + \cos\theta_r)\end{array}} =$$

$$\sqrt{\begin{array}{l}\left(s\frac{\omega}{c}\right)^2 - \\ \{k_x - k_0(\sin\theta_t\cos\varphi_t + \sin\theta_r\cos\varphi_r)\}^2 - \\ \{k_z - k_0(\sin\theta_t\sin\varphi_t + \sin\theta_r\sin\varphi_r)\}^2 + \\ k_0(-2 + \cos\theta_t + \cos\theta_r)\end{array}},$$

when the received signals are reflected ones, s=2 and when transmission signals, s=1; and the wavenumber in the depth direction obtained by dividing the angular frequency a by the propagation speed c is used, whereas when not performing the approximate interpolations, the wavenumber in the depth direction expressed in the supplementary explanation of equation is used and similarly as below.

Alternatively, instead of eq. (M'4'), eq. (M'4"), which is used for approximate interpolations, expressed by eq. (M'4"") is calculated and the 3D inverse Fourier transform [corresponding to eq. (M'6')] is performed on the multiplication of eq. (M'12) and eq. (M'5') expressed using the ky expressed in eq. (M'4").

$$F(k_x, 0, k_z, K(k_y)) = R(k_x, 0, k_z, sk) \tag{M'4''''}$$

Where $$K(k_y) = c \; \text{sgn}(k_y) \sqrt{\begin{array}{l}\{k_x - k_0(\sin\theta_t\cos\varphi_t + \sin\theta_r\cos\varphi_r)\}^2 + \\ \{k_z - k_0(\sin\theta_t\sin\varphi_t + \sin\theta_r\sin\varphi_r)\}^2 + k_y^2\end{array}},$$

$$K_y = \sqrt{\begin{array}{l}(sk)^2 - \\ \{k_x - k_0(\sin\theta_t\cos\varphi_t + \sin\theta_r\cos\varphi_r)\}^2 - \\ \{k_z - k_0(\sin\theta_t\sin\varphi_t + \sin\theta_r\sin\varphi_r)\}^2\end{array}} =$$

$$\sqrt{\begin{array}{l}\left(s\frac{\omega}{c}\right)^2 - \\ \{k_x - k_0(\sin\theta_t\cos\varphi_t + \sin\theta_r\cos\varphi_r)\}^2 - \\ \{k_z - k_0(\sin\theta_t\sin\varphi_t + \sin\theta_r\sin\varphi_r)\}^2\end{array}},$$

when the received signals are reflected ones, s=2 and when transmission signals, s=1; and the wavenumber in the depth direction obtained by dividing the angular frequency ω by the propagation speed c is used, whereas when not performing the approximate interpolations, the wavenumber in the depth direction expressed in the supplementary explanation of equation is used and similarly as below.

$$\exp\{ik_0(-2+\cos\theta_t+\cos\theta_r)y\} \tag{m'12}$$

Also in these cases, the multistatic SAs can be performed using, instead of the method (2), the monostatic SAs on the basis of these migration methods, similarly to the case where the method (3) is performed using the method (2).

On the basis of these migration methods, all the beamformings mentioned in the methods (2) and (3) can be similarly performed.

Using the migration processing [eq. (M7), etc.] for the above-mentioned plane wave transmission corresponding to the method (1) allows performing beamformings for such as arbitrary beam transmissions such as fixed, focused beams, etc., arbitrary wave transmissions (including non-beamformed waves), superposition of transmissions of plural beams or waves and simultaneous transmissions of plural beams or waves. Plural beamformings can also be performed by using the multi-directional synthetic aperture (SA) method and in the cases, similarly the processings can be performed with high speeds. The present inventions are not limited to these. In these cases, similarly to the cases where the method (1) is used, the method (2) can be combined to perform the reception dynamic focusings with respect to arbitrary transmission beamformings.

When the physical transmission steering angle of a focused beam is A, if the respective software transmission and reception steering angles are θ (=θt) and θr, instead of eq. (M3), similarly used is $$\text{Exp}\{ix(\hat{k}\sin\theta_t + k_0\sin\theta_r)\}, \tag{M3'''}$$

which is expressed using the wavenumber $$\hat{k}=\omega/\hat{c}, \tag{M13}$$

where if $\theta=\theta_t=0°$, $\hat{k}=k=\omega/c$, which is expressed using the angular frequency $\omega_0$ and the modification (conversion) of propagation speed (E1) and when the physical transmission steering angle of a plane wave is A, if the respective software transmission and reception steering angles are θ (=θt) and θr, instead of eq. (M3), similarly used is $$\exp\{ix(k\sin\theta_t + k_0\sin\theta_r)\} \tag{M3''''}$$

and both when the transmissions are performed, the following wavenumber is used in eq. (M7).

$$\widehat{k_Y} = \sqrt{\hat{k}^2 - k_x - k_0\sin\theta_r)^2} + k_0(-1+\cos\theta_r) \tag{M11'''}$$

The 3D cases can also be processed similarly. When the physical transmission steering angle of a focused beam is expressed using an elevational angle A and an azimuth angle B (a case where at least either angle is zero can be included), if the software transmission steering is performed with a steering angle expressed by an elevational angle $\theta_1$ and an azimuth angle $\varphi_1$ and the software reception steered dynamic focusing is performed with a steering angle expressed using an elevational angle $\theta_2$ and an azimuth angle $\varphi_2$ (a case where at least one of the angles is zero can be included), instead of eq. (M'3), similarly used is $$\exp\{i\{\hat{k}\sin\theta_1(\cos\varphi_1 x+\sin\varphi_1 z)\}+i\{k_0\sin\theta_2(\cos\varphi_2 x+\sin\varphi_2 z)\} \tag{M'3''}$$

which is expressed using the wavenumber $$\hat{k}=\omega/\hat{c}, \tag{M'13}$$

where if θ=θt=0°, $\hat{k}=k=\omega/\hat{c}$, which is expressed using the angular frequency ω and the modification (conversion) of propagation speed (E'1) and when the physical transmission steering angle of a plane wave is expressed using an elevational angle A and an azimuth angle B (a case where at least either angle is zero can be included), if the software transmission steering is performed with a steering angle expressed by an elevational angle $\theta_1$ and an azimuth angle $\varphi_1$ and the software reception steered dynamic focusing is performed with a steering angle expressed using an elevational angle $\theta_2$ and an azimuth angle $\varphi_2$ (a case where at least one of the angles is zero can be included), instead of eq. (M'3), similarly used is $$\exp\{i\{k\sin\theta_1(\cos\varphi_1 x+\sin\varphi_1 z)\}+i\{k_0\sin\theta_2(\cos\varphi_2 x+\sin\varphi_2 z)\}\} \quad \text{(M'3''')}$$

and both when the transmissions are performed, the following wavenumber is used in eq. (M'7).

$$\widehat{k_y} = \sqrt{\hat{k}^2-(k_x-k_0\sin\theta_2\cos\varphi_2)^2-(k_z-k_0\sin\theta_2\sin\varphi_2)^2}+k_0(-1+\cos\theta_2) \quad \text{(M'11''')}$$

Also in these cases, similarly to the general migration processings, the approximate wavenumber matching and the IFFT can be performed, in which instead of eq. (M4) with approximation wavenumber matching, eq. (M4") expressed by eq. (M4'''') on the basis of eq. (M11''') is calculated and the 2D inverse Fourier transform [eq. (M6)] of eq. (M5) expressed using the ky expressed in eq. (M4'''') is performed.

$$F''(k_x, 0, K(\widehat{k_y})) = R''(k_x, 0, k), \quad \text{(M4''''')}$$

where $$K(\widehat{k_y}) = \hat{c}\ \text{sgn}(\widehat{k_y})\sqrt{(k_x-k_0\sin\theta_r)^2+\{\widehat{k_y}-k_0(-1+\cos\theta_r)\}^2},$$

$$\widehat{k_y} = \sqrt{\hat{k}^2-(k_x-k_0\sin\theta_r)^2}+k_0(-1+\cos\theta_r) = \sqrt{\left(\frac{\omega}{\hat{c}}\right)^2-(k_x-k_0\sin\theta_r)^2}+k_0(-1+\cos\theta_r)$$

or $$\sqrt{\left(\frac{k}{\alpha}\right)^2-(k_x-k_0\sin\theta_r)^2}+k_0(-1+\cos\theta_r),$$

when performing the approximate interpolations, the wavenumber in the depth direction obtained by dividing the angular frequency a by the modification (conversion) of propagation speed (E1) is used, whereas when not performing the approximate interpolations, the wavenumber in the depth direction expressed in the supplementary explanation of equation is used and similarly as below.

Alternatively, instead of eq. (M4), eq. (M4"), which is used for approximate interpolations, expressed by eq. (M4''''') is calculated and the 2D inverse Fourier transform [corresponding to eq. (M6)] is performed on the multiplication of eq. (M13) and eq. (M5) expressed using the ky expressed in eq. (M4''''').

$$F''(k_x, 0, K(\widehat{k_y})) = R''(k_x, 0, k), \quad \text{(M4'''''')}$$

where $K(\widehat{k_y}) = \hat{c}\ \text{sgn}(\widehat{k_y})\sqrt{(k_x-k_0\sin\theta_r)^2+\widehat{k_y}^2}$, $$\widehat{k_y} = \sqrt{\hat{k}^2-(k_x-k_0\sin\theta_r)^2} = \sqrt{\left(\frac{\omega}{\hat{c}}\right)^2-(k_x-k_0\sin\theta_r)^2}$$

or $\sqrt{\left(\frac{k}{\alpha}\right)^2-(k_x-k_0\sin\theta_r)^2}$, when performing the approximate interpolations, the wavenumber in the depth direction obtained by dividing the angular frequency $\omega$ by the modification (conversion) of propagation speed (E1) is used, whereas when not performing the approximate interpolations, the wavenumber in the depth direction expressed in the supplementary explanation of equation is used and similarly as below.

$$\text{Exp}\{ik_0(-1+\cos\theta_r)y\} \quad \text{(M13)}$$

In the above-mentioned processings, when the software transmission steering is performed (et is non-zero degree), exchanging of eqs. (M3") and (M3''') leads errors that the image formation position gets out of the true position. Also when the software reception steering is performed ($\theta r$ is non-zero degree), the using of, instead of the wavenumber eq. (M10) corresponding to the ultrasound frequency, the wavenumber expressed using the ultrasound angular frequency $\omega$ and the modification (conversion) propagation speed (E1), $$\widehat{K_0} = \omega_0/\hat{c}, \quad \text{(M14)}$$

where if $\theta=\theta_t=0°$, $\widehat{k_0}=k_0=\omega_0/c$, leads errors that the generated steering angle becomes larger than that generated using eq. (M10) (for instance, about 1 or 2 degrees when generating the steering angle 20 degrees), with which image formations can be obtained.

Also the 3D cases can also be processed similarly. That is, after performing the processings using eq. (M'3''') in the 3D cases, etc., instead of eq. (M'4) with approximation wavenumber matching, eq. (M'4") expressed by eq. (M'4''''') on the basis of eq. (M'11''') is calculated and the 3D inverse Fourier transform [eq. (M'6)] of eq. (M'5) expressed using the ky expressed in eq. (M'4''''') is performed.

$$F''(k_x, 0, k_z, K(\widehat{k_y})) = R''(k_x, 0, k_z, k) \quad \text{(M'4''''')}$$

where $$K(\widehat{k_y}) = \hat{c}\ \text{sgn}(\widehat{k_y})\sqrt{\begin{array}{l}(k_x-k_0\sin\theta_2\cos\varphi_2)^2+\\(k_z-k_0\sin\theta_2\sin\varphi_2)^2+\\\{\widehat{k_y}-k_0(-1+\cos\theta_2)\}^2\end{array}},$$

$$\widehat{k_y} = \sqrt{\hat{k}^2-(k_x-k_0\sin\theta_2\cos\varphi_2)^2-(k_z-k_0\sin\theta_2\sin\varphi_2)^2}+k_0(-1+\cos\theta_2)$$

$$= \sqrt{\left(\frac{\omega}{\hat{c}}\right)^2-(k_x-k_0\sin\theta_2\cos\varphi_2)^2-(k_z-k_0\sin\theta_2\sin\varphi_2)^2}+k_0(-1+\cos\theta_2)$$

or $\sqrt{\left(\frac{k}{\alpha}\right)^2-(k_x-k_0\sin\theta_2\cos\varphi_2)^2-(k_z-k_0\sin\theta_2\sin\varphi_2)^2}+k_0(-1+\cos\theta_2)$, when performing the approximate interpolations, the wavenumber in the depth direction obtained by dividing the angular frequency $\omega_0$ by the modification (conversion) of propagation speed (E'1) is used, whereas when not performing the approximate interpolations, the wavenumber in the depth direction expressed in the supplementary explanation of equation is used and similarly as below.

Alternatively, instead of eq. (M'4), eq. (M4"), which is used for approximate interpolations, expressed by eq. (M'4'''''') is calculated and the 3D inverse Fourier transform

[corresponding to eq. (M'6)] is performed on the multiplication of eq. (M'13) and eq. (M'5) expressed using the ky expressed in eq. (M'4"""').

$$F''(k_x, 0, k_z, K(\hat{k}_y^-)) = R''(k_x, 0, k_z, k) \quad (M'4'''')$$

where $$K(\hat{k}_y^-) = \hat{c}\ \text{sgn}(\hat{k}_y^-)\sqrt{(k_x - k_0\sin\theta_2\cos\varphi_2)^2 + (k_z - k_0\sin\theta_2\sin\varphi_2)^2 + k_y^{-2}},$$

$$k_y^- = \sqrt{\hat{k}^2 - (k_x - k_0\sin\theta_2\cos\varphi_2)^2 - (k_z - k_0\sin\theta_2\sin\varphi_2)^2}$$

$$= \sqrt{\left(\frac{\omega}{\hat{c}}\right)^2 - (k_x - k_0\sin\theta_2\cos\varphi_2)^2 - (k_z - k_0\sin\theta_2\sin\varphi_2)^2}$$

or $$\sqrt{\left(\frac{k}{\alpha}\right)^2 - (k_x - k_0\sin\theta_2\cos\varphi_2)^2 - (k_z - k_0\sin\theta_2\sin\varphi_2)^2},$$

when performing the approximate interpolations, the wavenumber in the depth direction obtained by dividing the angular frequency ω by the modification (conversion) of propagation speed (E'1) is used, whereas when not performing the approximate interpolations, the wavenumber in the depth direction expressed in the supplementary explanation of equation is used and similarly as below.

$$\text{Exp}\{ik_0(-1+\cos\theta_2)y\} \quad (M'13)$$

In the above-mentioned processings, when the software transmission steering is performed (the steering angle is non-zero degree), exchanging of eqs. (M'3") and (M'3'") leads errors that the image formation position gets out of the true position. Also when the software reception steering is performed (the steering angle is non-zero degree), the using of, instead of the wavenumber eq. (M'10) corresponding to the ultrasound frequency, the wavenumber expressed using the ultrasound angular frequency $\omega_0$ and the modification (conversion) propagation speed (E'1), $$\widehat{K_0} = \omega_0/\hat{c}, \quad (M'14)$$

where if $\theta=\theta_r=0°$, $\widehat{k_0}=k_0=\omega_0/c$,
leads errors that the generated steering angle becomes larger than that generated using eq. (M'10), with which image formations can be obtained.

Also when using the migrations on the basis of eq. (N4) mentioned in the paragraph 0316 and when the physical transmission steering angle of a focused beam is A, if the software transmission and reception steering angles are θ (=θ$_t$) and θ$_r$, respectively, instead of eq. (M3), similarly used is eq. (M3"), which is expressed using the wavenumber (M13), which is expressed using the angular frequency ω and the modification (conversion) of propagation speed (E1); and when the physical transmission steering angle of a plane wave is A, if the software transmission and reception steering angles are θ (=θ$_t$) and θ$_r$, respectively, instead of eq. (M3), similarly used is eq. (M3'"); and both when the transmissions are performed, instead of eq. (N4), the following eq. (N4') is similarly used for eq. (M6) or (M7).

$$F''(k_x, 0, K(\hat{k}_y^-)) = R''(k_x, 0, k), \quad (N4')$$

where $$K(\hat{k}_y^-) = \hat{c}\ \text{sgn}(\hat{k}_y^-)\sqrt{(k_x - k\sin\theta - k_0\sin\theta_r)^2 + k_y^{-2}},$$

$$k_y^- = \sqrt{\hat{k}^2 - (k_x - k\sin\theta - k_0\sin\theta_r)^2}$$

$$= \sqrt{\left(\frac{\omega}{\hat{c}}\right)^2 - (k_x - k\sin\theta - k_0\sin\theta_r)^2}$$

or $\sqrt{\left(\frac{k}{\alpha}\right)^2 - (k_x - k\sin\theta - k_0\sin\theta_r)^2}$ when performing the approximate interpolations, the wavenumber in the depth direction obtained by dividing the angular frequency ω by the modification (conversion) of propagation speed (E1) is used, whereas when not performing the approximate interpolations, the wavenumber in the depth direction expressed in the supplementary explanation of equation is used and similarly as below.

Also in the 3D cases when using the migrations on the basis of eq. (N'4) mentioned in the paragraph 0331 and when the physical transmission steering angle of a focused beam is expressed using an elevational angle A and an azimuth angle B (a case where at least either angle is zero can be included), if the software transmission steering is performed with a steering angle expressed by an elevational angle $\theta_1$ and an azimuth angle $\varphi_1$ and the software reception steered dynamic focusing is performed with a steering angle expressed using an elevational angle $\theta_2$ and an azimuth angle $\varphi_2$ (a case where at least one of the angles is zero can be included), instead of eq. (M'3), similarly used is eq. (M'3"), which is expressed using the wavenumber (M'13), which is expressed using the angular frequency ω and the modification (conversion) of propagation speed (E'1); and when the physical transmission steering angle of a plane wave is expressed using an elevational angle A and an azimuth angle B (a case where at least either angle is zero can be included), if the software transmission steering is performed with a steering angle expressed by an elevational angle $\theta_1$ and an azimuth angle $\varphi_1$ and the software reception steered dynamic focusing is performed with a steering angle expressed using an elevational angle $\theta_2$ and an azimuth angle $\varphi_2$ (a case where at least one of the angles is zero can be included), instead of eq. (M'3), similarly used is eq. (M'3'"); and both when the transmissions are performed, instead of eq. (N'4), the following eq. (N'4') is similarly used for eq. (M'6) or (M'7).

$$F''(k_x, 0, k_z, K(\hat{k}_y^-)) = R''(k_x, 0, k_z, k) \quad (N'4')$$

where $$K(\hat{k}_y^-) = \hat{c}\ \text{sgn}(\hat{k}_y^-)\sqrt{(k_x - k\sin\theta_1\cos\varphi_1 - k_0\sin\theta_2\cos\varphi_2)^2 + (k_z - k\sin\theta_1\sin\varphi_1 - k_0\sin\theta_2\sin\varphi_2)^2 + k_y^{-2}},$$

$$k_y^- = \sqrt{\hat{k}^2 - (k_x - k\sin\theta_1\cos\varphi_1 - k_0\sin\theta_2\cos\varphi_2)^2 - (k_z - k\sin\theta_1\sin\varphi_1 - k_0\sin\theta_2\sin\varphi_2)^2}$$

$$= \sqrt{\left(\frac{\omega}{\hat{c}}\right)^2 - (k_x - k\sin\theta_1\cos\varphi_1 - k_0\sin\theta_2\cos\varphi_2)^2 - (k_z - k\sin\theta_1\sin\varphi_1 - k_0\sin\theta_2\sin\varphi_2)^2}$$

-continued $$\text{or } \sqrt{\left(\frac{k}{\alpha}\right)^2 - (k_x - k\sin\theta_1\cos\varphi_1 - k_0\sin\theta_2\cos\varphi_2)^2 - (k_z - k\sin\theta_1\sin\varphi_1 - k_0\sin\theta_2\sin\varphi_2)^2},$$

when performing the approximate interpolations, the wavenumber in the depth direction obtained by dividing the angular frequency ω by the modification (conversion) of propagation speed (E'1) is used, whereas when not performing the approximate interpolations, the wavenumber in the depth direction expressed in the supplementary explanation of equation is used and similarly as below.

Thus, similarly to the methods mentioned in the paragraphs 0316 and 0331, the beamformings on the basis of these migration methods can also be performed with approximate interpolations or not on the wavenumber matchings.

The processings, regarding the method (1), mentioned in the paragraphs 0316 and 0331 can also be performed when being combined with the method (2) that performs the reception steered dynamic focusing, similarly to the original method (1) being combined with the method (2) as mentioned in the paragraphs 0235 to 0238. That is, in the 2D cases, to obtain the same results when performing the calculations of eqs. (F42) and (F43) with zero steering angles θ, similarly to the cases where eq. (M9) is multiplied and the inverse Fourier transform is performed in the method (6), eq. (M9) is multiplied to an equation corresponding to eq. (16) prior to performing the processings mentioned in the paragraph 0204. Also in the 3D cases, to obtain the same results when performing the calculations of eqs. (G22) and (G23) with zero steering angles θ and φ, similarly to the cases where complex exponential function corresponding to eq. (M9) in the 2D cases is multiplied and the inverse Fourier transform is performed in the method (6), the complex exponential equation is multiplied during the processings mentioned in the paragraph 0207.

These beamformings can also be performed with approximate interpolations or not on the wavenumber matchings as mentioned in the paragraphs 0316 and 0331. Others are also as mentioned in the same paragraphs.

On the basis of these migrations, all the beamformings mentioned in the method (4) can be performed similarly.

As likely mentioned in the method (5), all these migrations can be performed directly on the Cartesian coordinate system even when performing the transmissions and receptions on the orthogonal coordinate systems except for the Cartesian coordinate system such as the polar coordinate system, etc. That is, in the same ways, implementing the Jacobi operation onto the eqs. (M6), (M6'), (M7), and (M7') for the above-mentioned beamformings yields the results directly on the Cartesian coordinate system. Also in the 3D cases, the Jacobi operation can be implemented onto the eqs. (M6), (M6'), (M7), and (M7') in the same ways and similarly, the results can be obtained. All other beamformings mentioned in the method (5) can also be performed similarly.

One of purposes of the present inventions is to realize high speed and high accuracy beamformings. However, the above-mentioned methods (1) to (6) with no approximate interpolations can also be modified to methods with approximate interpolations in various fashions and can be used as further higher methods, however, with lower accuracies. The modifications can be performed by performing the approximate wavenumber matchings or the multiplications of complex exponential functions, etc. at least in one or two directions or all in the three directions in the lateral, elevational and depth directions. Performing the approximations increases the calculation speed, however, decreases the accuracy. The approximations include ones mentioned in the above-explanations. In the present paragraph, regarding the respective 2D and 3D cases, the 8 cases of (A), (A'), (B), (B'), (C), (C'), (D), (D') mentioned in the paragraphs 0316 and 0331 are explained, and the corresponding equations of approximate interpolations are described.

For instance, similarly the migration methods in the method (6) can also perform the processings for the cases where the steerings are performed, and the calculation speed becomes the fastest of all the migration processings similarly to the performing, on the wavenumber matchings, the approximate interpolations in all directions (corresponding to (D')) and the J.-y. Lu's method (the paragraph 0197, corresponding to (C')) performing the approximate interpolations being able to be used in the method (1). However, the accuracies are the lowest of all. Alternatively, when using the J.-y. Lu's method (the paragraph 0197, corresponding to (C')), for instance, when performing only the lateral wavenumber matching prior to performing the Fourier transform, the accuracy increases and however, the calculation speed decreases (corresponding to (C)). Others including cases of (A), (A'), (B) and (B'), the approximate processings (equations) in the 2D cases (mentioned in the paragraph 0316) are described (The 3D cases (the paragraph 0331) can also be similarly expressed and omitted). Regarding (A), (A'), (C) and (C'), the equations are expressed according to eqs. (7) and (8). And, on (B') and (D'), the lateral inverse Fourier transform is performed not on kx but kx'.

In (A) case, $$F(k'_x, k'_y) = R'(k_x, k), \quad (N5)$$

$$\text{where } k = \frac{k'^2_y + k'^2_x}{2k'_y},$$

$$k_x = k'_x,$$

$$K'_y = \frac{\omega}{c}.$$

When performing the approximate interpolations on the wavenumber matching, the wavenumber in the depth direction ky is one obtained by dividing the wavelength ω by the propagation speed c, whereas when not performing the approximate interpolations, the wavenumber matching can be performed as mentioned above.

In (A') case, $$F(k'_x, k'_y) = R'(k_x, k), \quad (N5')$$

$$\text{where } k = \frac{k'^2_y + k'^2_x}{2k'_y},$$

$$k_x = k'_x - k\sin\theta,$$

$$K'_y = \frac{\omega}{c}.$$

When performing the approximate interpolations on the wavenumber matching, the wavenumber in the depth direction ky is one obtained by dividing the wavelength ω by the propagation speed c, whereas when not performing the approximate interpolations, the wavenumber matching can be performed as mentioned above.

In (B) case (the same as eq. (N4)), $$F''(k_x, 0, K(\overline{k_y^-})) = R''(k_x, 0, k) \quad (N6)$$

where $K(\overline{k_y^-}) = \hat{c}\ \text{sgn}(k_y)\sqrt{(k_x - k\sin\theta)^2 + \overline{k_y}^2}$, $$\overline{k_y} = \sqrt{\hat{k}^2 - (k_x - k\sin\theta)^2} = \sqrt{\left(\frac{\omega}{\hat{c}}\right)^2 - (k_x - k\sin\theta)^2}$$

or $\sqrt{\left(\frac{k}{\alpha}\right)^2 - (k_x - k\sin\theta)^2}$.

When performing the approximate interpolations, the wavenumber in the depth direction obtained by dividing the angular frequency ω by the modification (conversion) of propagation speed (E1) is used, whereas when not performing the approximate interpolations, the wavenumber in the depth direction expressed in the supplementary explanation of equation is used.

In (B') case, $$F''(k_x', 0, K(\overline{k_y^-})) = R''(k_x, 0, k) \quad (N6')$$

where $k_x = k_x' - k\sin\theta$, $K(\overline{k_y}) = \hat{c}\ \text{sgn}(\overline{k_y})\sqrt{(k_x' - k\sin\theta)^2 + \overline{k_y}^2}$, $$\overline{k_y} = \sqrt{\hat{k}^2 - (k_x' - k\sin\theta)^2} = \sqrt{\left(\frac{\omega}{\hat{c}}\right)^2 - (k_x' - k\sin\theta)^2}$$

or $\sqrt{\left(\frac{k}{\alpha}\right)^2 - (k_x' - k\sin\theta)^2}$.

When performing the approximate interpolations, the wavenumber in the depth direction obtained by dividing the angular frequency ω by the modification (conversion) of propagation speed (E1) is used, whereas when not performing the approximate interpolations, the wavenumber in the depth direction expressed in the supplementary explanation of equation is used.

In (C) case, $$F(k_x', k_y') = R'(k_x, k) \quad (N7)$$

where $k = \dfrac{k_y'^2 + k_x'^2}{2k_y'\cos\theta + 2k_x'\sin\theta}$, $k_x = k_x'$, $K_y' = \dfrac{\omega}{c}$.

When performing the approximate interpolations on the wavenumber matching, the wavenumber in the depth direction ky is one obtained by dividing the wavelength ω by the propagation speed c, whereas when not performing the approximate interpolations, the wavenumber matching can be performed as mentioned above.

In (C') case (J.-y. Lu's method), $$F(k_x', k_y') = R'(k_x, k) \quad (N7')$$

where $k = \dfrac{k_y'^2 + k_x'^2}{2k_y'\cos\theta + 2k_x'\sin\theta}$, $k_x = k_x' - k\sin\theta$, $K_y' = \dfrac{\omega}{c}$.

When performing the approximate interpolations on the wavenumber matching, the wavenumber in the depth direction ky is one obtained by dividing the wavelength ω by the propagation speed c, whereas in one of the present inventions, when not performing the approximate interpolations, according to the method (1), the wavenumber matching can be performed as mentioned above.

In (D) case (the method disclosed in the nonpatent document 12), $$F''(k_x, 0, K(\overline{k_y})) = R''(k_x, 0, k) \quad (N8)$$

where $K(\overline{k_y}) = \hat{c}\ \text{sgn}(\overline{k_y})\sqrt{k_x^2 + \overline{k_y}^2}$, $$\overline{k_y} = \sqrt{\hat{k}^2 - k_x^2} = \sqrt{\left(\frac{\omega}{\hat{c}}\right)^2 - k_x^2}$$

or $\sqrt{\left(\frac{k}{\alpha}\right)^2 - k_x^2}$.

When performing the approximate interpolations on the wavenumber matching, the wavenumber in the depth direction ky is one obtained by dividing the wavelength ω by the modification (conversion) propagation speed (E1), whereas in one of the present inventions, when not performing the approximate interpolations, according to the method (6) (one of methods), the wavenumber in the depth direction expressed in the supplementary explanation of equation is used.

In (D') case, $$F''(k_x', 0, K(\overline{k_y})) = R''(k_x, 0, k) \quad (N8')$$

where $k_x = k_x' - k\sin\theta$, $K(\overline{k_y}) = \hat{c}\ \text{sgn}(\overline{k_y})\sqrt{k_x'^2 + \overline{k_y}^2}$, $$\overline{k_y} = \sqrt{\hat{k}^2 - k_x'^2} = \sqrt{\left(\frac{\omega}{\hat{c}}\right)^2 - k_x'^2}$$

or $\sqrt{\left(\frac{k}{\alpha}\right)^2 - k_x'^2}$.

When performing the approximate interpolations, the wavenumber in the depth direction obtained by dividing the angular frequency ω by the modification (conversion) of propagation speed (E1) is used, whereas when not performing the approximate interpolations, the wavenumber in the depth direction expressed in the supplementary explanation of equation is used.

Also in these cases, the method (2) can be used at the reception beamformings.

It is important to perform the multi-dimensional Fourier transform at first and the multi-dimensional inverse Fourier transform with high speeds and then, various types of fast Fourier transform (FFT) algorithms can be properly used. And, physically or mathematically, the wavenumber matching can also be performed at the first Fourier transform or at the last inverse Fourier transform. Also all other beamformings from ones mentioned in the present patent documentation (those of methods (1) to (6)) can also be performed with no approximate interpolations or with approximate interpolations similarly. To increase the accuracy in cases where approximate interpolations are performed, the sampling frequency can be set to be high and however, being different from in cases where image signals of arbitrary positions can be generated when no approximate interpolations are performed, it is cautious that the numbers of data to be used for the Fourier transforms increase. However, in the cases where approximate interpolation processings are not performed as well, it is important to realize the conditions that allow processing the signals with an increased SNR via performing proper over-samplings.

In these processings, the above-mentioned beamformings in the methods (1) to (5) (including cases of beamformings performed on the reception signals received at once with respect to the simultaneous transmissions of plural different beams or waves or superposing of received signals with respect to the respective transmissions, or using of virtual sources or receivers, etc.) can also be performed on the basis of the migration processings (method (6)) with approximate interpolations or not.

Method (7): Others

For the above-mentioned methods (1) to (6), the cases using the 1D array are explained mainly. In the cases using the respective 2D or 3D arrays, as mentioned above, the lateral processings are performed in other one or two directions as well. These can be performed on all orthogonal coordinate systems including orthogonal curvilinear coordinate systems. That is, the above-mentioned methods (1) to (6) are extended to those of higher dimensions simply. When direct currents or low frequency components in lateral or axial directions can be generated during processing the method (1) to (6) and (7) mentioned here. In such cases, zero-padding of spectra is effective to be performed prior to the last inverse Fourier transform. For performing the digital signal processing, analogue or digital processing can be performed to cut the direct currents off as pre-processings and also the zero-spectra-padding can also be performed with respect to the angular spectra.

For the digital Fourier beamforming, a periodicity (i.e., an itineracy or a circulatory) is assumed for the distributions of non-processed raw signals in a finite spatial domain and image signals to be obtained and then, the non-processed raw signals and the image signals to be obtained appears in a itineracy (circulatory) fashion at the upper and lower boundaries of a region of interest (mainly, a boundary parallel to the surface of a physical aperture element array, a boundary running in a direction of the so-called lateral or elevation direction, etc.) and other boundaries such as side areas or axial boundaries (mainly, a boundary orthogonal to the surface of a physical aperture element array, a boundary running in the axial direction, etc.) from them as centers, which can be a problem.

In both the cases where a reflection wave and a transmission wave are processed, getting more far from the surface of a transmission aperture, a propagating wave will have a small intensity due to phenomena of a divergence, an attenuation, a scattering, a reflection. Although when the region of interest (ROI) has such raw signals, the artifacts occurring at the upper and lower boundaries of ROI (mainly, a boundary parallel to the surface of a physical aperture element array, a boundary running in a direction of the so-called lateral or elevation direction, etc.) can be no problem, when the ROI has no small intensity of raw signals at upper and lower boundaries, the artifacts become serious problem.

When a reception aperture is different from a transmission aperture (i.e., when a transmission wave is processed), the signal intensity at the position of reception aperture can become a problem. In such a case, an ROI is extended in an axial direction toward far from a transmission and/or reception aperture by adding a region of zero signals, strictly, with the same length as the distance between the upper and lower boundaries of the original ROI, onto the original upper boundary toward the transmission aperture, or onto the original lower boundary toward far from the transmission aperture; and image signals obtained in the extended region are disregarded. Since the original raw signals have discontinuities, the raw signals can be windowed instead; and the image signals obtained at the around of window feet can also be disregarded.

On the other hand, other boundaries such as side areas or axial boundaries (mainly, a boundary orthogonal to the surface of a physical aperture element array, a boundary running in the axial direction, etc.), in almost cases, the artifacts occur, since the image signals are generated by synthesizing raw signals at spatially different positions and the signal intensities can be usually large. In such cases, an ROI is extended in a lateral direction toward far from at least one of original boundaries, i.e., a paired side areas or axial boundaries of the original ROI, by adding a region of zero signals, strictly, with the same length as the larger effective transmission or reception aperture width, onto the original boundary; and image signals obtained in the extended region are disregarded. Since the original raw signals have discontinuities, the raw signals can be windowed instead; and the image signals obtained at the around of window feet can also be disregarded. Since the original raw signals have discontinuities, the raw signals can be windowed in the lateral direction instead; and the image signals obtained at the around of window feet can also be disregarded. In a 3D case, the window is multi-dimensional including the lateral and elevational directions and the window is a so-called separable or non-separable type. The artifacts also occur when a steering is not performed; and the artifacts become more serious when a steering is performed. The above-mentioned processings are required.

The above-mentioned processings can also be performed simultaneously. When using a window, the window is multi-dimensional and a so-called separable or non-separable type. If image signals obtained without the processings have the signals with an itineracy (a circulatory), the region of the error signals can also be removed.

For other beamformings, disclosed in the nonpatent document 9, etc., using Fourier transforms, the methods disclosed in the methods (1) to (7) can also be used and the same effects can be obtained.

For instance, in the section 2.4 in the nonpatent document 9, a method is disclosed, i.e., a method using a general solution (Green function) of a wave equation for calculating arbitrary beams or waves. As examples of analytically performed calculations, spherical, cylindrical and plane waves are processed, respectively. As a feature of using the Green functions, signals to be calculated have, in the denominators in frequency domains, $$k_y = \sqrt{k^2 - k_x^2} \quad \text{(GR1)}$$

for using the 2D Cartesian coordinate system and $$k_y = \sqrt{k^2 - k_x^2 - k_z^2} \quad \text{(GR2)}$$

for using the 3D Cartesian coordinate system, respectively. Using the method, the calculations can be performed using the Green functions on arbitrary orthogonal coordinate systems such as a cylindrical coordinate system, a spherical coordinate system and among others.

That is, regarding the methods or mathematical expressions (both cases performing no approximate interpolations and performing approximate interpolations) disclosed in the methods (1) to (7), the calculations are performed such that the spectra of target signals have respective eqs. (GR1) and (GR2) in the denominators. The methods and the expressions disclosed in the methods (1) to (7) can also be applied to various other methods and beamformings.

In these cases using the Green functions, since a point source can be considered as a source, using the functions is proper for using a virtual source set in front of or behind a physical aperture (patent document 7 or nonpatent document 8). In the cases, it is important to perform the processings regarding actual radiation patterns of physical apertures (elements) as the next paragraph.

The methods (1) to (7) can also use the operations, disclosed in the section 3.2 in the nonpatent document 9, additionally considering the radiation patterns of apertures (elements), for instance. At the time, signal processings can also be performed via correcting the signal intensities properly using physical or software apodizations. As many mentioned in the present patent document, for instance, ISAR (including a version of using the target motion), nonlinear processings, adaptive beamformings (nonpatent document 10) and various other processings can be performed to increase the spatial resolution (particularly, directions orthogonal to the propagation direction) or increase the contrast by decreasing the sidelobes. The coherent factor, etc. disclosed in the nonpatent document 11, etc. can also be used. The processings are not limited to these. Apodizations can also be performed properly (For complex signals, the apodizations can also work as delays). The apodizations can also be changeable in the scanning directions as well as the propagation directions.

The methods (1) to (7) can also be used for various positions of the transmissions and receptions and various other beamformings. For instance, in the nonpatent document 9, various examples are disclosed. For instance, there are examples of the geophysical imaging in the section 7.3 (for instance, tale notice of the expression forms of eqs. (7.9) to (7.12)), the so-called X-ray CT (Computed Tomography), etc. In addition to these, the methods (1) to (7) can also be used for astronomical observations and among others. It is worthy of taking notice of FIG. 7.3 and eqs. (7.5) to (7.9) disclosed for the case of transmission imaging disclosed in the section 7.2 in the nonpatent document 9. For these examples can be processed with no approximate interpolations including for the wavenumber matchings, etc. (For these, approximate interpolations can also be performed).

These methods (1) to (7) have a feature that image signals can be directly and selectively generated on pre-specified bi-planes or multiple planes, desired planes or fault surfaces with spreading in arbitrary directions, etc. (not always flat and can be curvilinear) or not surfaces but lines (straight or curvilinear lines). For instance, when images can be displayed on the basis of 3D or 2D image signals, there are cases where the images can be displayed on the basis of the image signals, and the images are displayed solo. The image signals or images can also be displayed via approximate interpolations on the signal processings. Also measurement data such as a displacement or a strain, a temperature, etc. measured on the basis of the image signals or images can also be displayed solo or as superposed ones on the images.

As mentioned several times in the present patent document, the apodizations can be determined in various ways and can be performed. There are various adaptive beamformings, minimum-variance beamformings, Capon method, etc. as mentioned in the nonpatent document 10 etc. In these beamformings, when implementing the regularizations on the covariance matrices, the parameter to be used for controlling the degree of the regularization (the regularization parameter) can be properly determined on the basis of the SNR, etc. of the signal at each position and then the processing can be performed spatially variantly. As modified methods, not an identity matrix (i.e., diagonal matrices) but other positive-definite operators such as the gradient operator or the Laplacian operator, etc. can also be used for the regularization operator. It is possible to increase spatial resolutions in image signals (particularly, directions orthogonal to the propagation direction) and contrasts as well by decreasing sidelobes. On independent component analysis (independent signal separation), It is also effective to implement the regularization on the covariance matrix similarly. These regularizations have not been disclosed. Alternatively, in the both processings, it can also be performed to stabilize the processings by decreasing the rank via the singular value decomposition or the eigenvalue decomposition. These processings are also effective for other methods on beamformings similarly. As mentioned in other parts, it is also effective to use MIMO (Multiple-input and Multiple-output: a wireless communication technology increasing the bandwidth of transmission and reception signals using combinations of plural antennas at transmission and reception sides) and SIMO (Single-input and Multiple-output: a wireless communication technology increasing the bandwidth of transmission and reception signals using a single antenna at a transmission side and combinations of plural antennas at a reception side). The inventor of the present inventions has been using the absolute detection or the power (exponentiation) detection favorably since before, and the coherent factor is effective as mentioned in the nonpatent document 11 etc. The absolute detection or the power detection is effective for visualizing wave oscillations. Via considering the absolute value or implementing powers on signals, with yielding high frequency components using a high order powers, it is possible to assign brightness or colors to the magnitudes of wave (These can be considered as detections for adding biases to signals). In the nonpatent document 10, various other adaptive beamformings are mentioned, and also in the present patent document, various processings such as MUSIC (Multiple Signal Classification: a wireless communication technology using eigenvalues and eigen-vectors of correlation matrix calculated for reception signals), etc. are mentioned. Effective processings are not limited to these and there exist various processings. It is also possible to perform various processings such as these processings before, during or after the beamformings, and it is also possible to perform them by the processings at the level of the apodizations. For these processings, it is remarkably effective to perform the processings after temporal (time) and/or spatial (position) matchings on the basis of correlation processings as mentioned later.

In the present inventions, the SNR of signal can also be increased particularly by implementing integration (calculation) processing on acquired signals along the fast time axis (in a distance direction). The integration processing can be performed by analogue processings (using a so-called integrator) or by digital processings (integrator or integration calculation).

In the above-descriptions, for the apodizations, the methods performing the multiplications with weight values are explained, which realizes the small number of calculations and simplicities. The present inventions are not limited to these, and convolution integrations can also be performed on the basis of the relationship of a duality about the multiplication and the convolution integration in a spatial domain and a frequency domain. At the respective depths or at the respective same distances from the aperture elements to be used, proper apodizations can be performed.

Superposing the generated steered beams or waves generated by the instrument of the present embodiment using the methods (1) to (6) can generate the above-mentioned lateral modulation signals (image signals) or laterally, widely banded image signals (with an increased high lateral resolution). Similarly to the cases of single transmission, the physical steering or the software steering, or both the steerings can also be performed respectively, or the same combination of steerings (a non-steering can also be included) can also be performed on the all. Regarding the reception beamformings, it is mainly explained that the reception beamformings are performed in software fashions, if necessary, the reception beamformings using the reception delays or the reception apodizations can also be performed physically solo instead or together. Alternatively, regarding the transmission beamformings, it is mainly explained that the transmission beamformings are performed physically, and for instance, high frame rates can be achieved by transmitting a plane wave, or plural beams or waves, etc., while one transmission is performed every one element to perform SA (Multidirectional SA can also be performed by decoding the received signals with respect to the encoded transmission of a plane wave, a cylindrical wave, a spherical wave, etc.). As mentioned above, it is also possible to consider or perform the transmission and the reception inversely. The plane wave penetrates into a deeper position than the focused beams (With comparison, the echo can also be obtained from a deeper position). However, with comparison, the SNR of the wave or as a beam for the purpose of displacement measurement, etc. is lower. With comparison, the lateral resolution is also lower originally. Alternatively, superposing the plane waves steered in plural directions can yield almost the same lateral resolution regardless the depth position. In contrast, although using the focused beams steered in plural directions for the superposing at the same focus position is effective, multi-focusing or multi-focusings are required to be performed for generating high spatial resolutions at plural positions. Using the present invention, it is possible to achieve the beamformings with high speeds absolutely with respect to the reception signals received with respect to simultaneous transmissions of plural waves or beams, or superposition of reception signals respectively received with respect to transmissions performed at different times, however, at the same phase of the object. Also using plural waves having different carrier frequencies yields axially widely banded signals (image signals with an increased axial resolution). In these cases, the increasing of bandwidths can also be achieved by overlapping the spectra, by which the increasing of the spatial resolution can also be achieved. These plural beams can also be generated simultaneously in a parallel fashion, and can also at different times, however, at the same phase of the object. The waves of plural directions can also be generated by the above-mentioned multidirectional SA.

When making the steering angles large, the image formation position of a reflector or a strong scatter can get out of the original position. For instance, superposing the received signals with respect to the transmissions of plane waves with respective steering angles, with respect to the direction of a face of aperture element, increasing up to ±45° by changing the steering angle by a small angle (for instance, 1°) can make a quasi-SA in the frontal direction and a lateral bandwidth corresponding to that determined by the steering angles ±45° cannot be obtained (the laterally high frequency signals are canceled out at the superposition). It is straightforwardly possible to understand the results by considering a beamforming in a frontal direction to be decomposed into angular spectra as plane waves. To increase a lateral bandwidth by the superposing of signals in a temporal and/or spatial or frequency domain, regardless the plane wave transmitted or not, any steering beamformings should be performed such that the respectively generated spectra not overlapped in the frequency domain can be superposed. However, it is cautious that the errors in image formation positions (different positions from the original position) generated by the respective steered beams or waves lead the errors in the finally generated image formations. That is, errors occur in controlling a focus position and a propagation direction as a phase aberration due to a spatial inhomogeneity in a sound speed of a medium (dependent on a temperature and a pressure), and a directivity of an aperture particularly when performing a steering with a large steering angle. Thus, when performing the superposition of signals with large steering angles, it can be required to perform the corrections of signal positions at least at one timing of at the transmissions for the beamformings, at the receptions with respect to the received signals before performing the reception beamformings, during the reception beamformings and after beamformings (a phase aberration correction). When performing the superresolutions of these signals such as spectra processings (filtering or weighting, etc.) and nonlinear processings, because the errors (position errors, etc.) due to the simultaneous performing of the superposition processings (the affections due to the respective position errors) become more remarkable, the corrections of the respective signal positions become more important. For instance, superposing is performed, of which spectra are processed (filtered or weighted) or which is nonlinearly processed, or pre-processed (filtered or weighted) spectra or pre-nonlinearly processed signals are superposed and among others. In addition, the respective position errors can be caused by the frequency dependencies, etc. of the modified (conversion) propagation speeds or by superposing different frequency signals and can also be similarly coped with. A wave distortion can also be generated by a device due to frequency-dependent phase delay or phase change, etc. (for instance, a phase change generated at a sensor or a phase delay generated at an amplifier in the circuit, etc.), similarly the wave shapeform of the reception signal can be corrected by correcting the phase similarly (It is effective to perform the analogue-like spatial shifting of digital signals by multiplying a complex exponential function to every frequency signal component (spectrum) in a frequency domain, i.e., by rotating a phase of every frequency signal.). By measuring the phase change generated by the device(s) in advance, the sensor can also be electrically driven in a proper fashion to generate a wave with a desired waveform, a desired waveform at an observation position or a reception position. Thus, the measurement accuracy of observation target can increase (e.g., various observations using a phase, or frequency-dependent propagation speed, scattering or attenuation, etc.). Only the errors generated by the reception device(s) can also be corrected. Similarly, the above-mentioned other ones generating position errors can also be processed similarly. The corrections of positions are also mentioned in the paragraph 0371 etc. Various signal processing technologies can be used such as those of a motion compensation and a phase aberration correction. The corrections of signal intensity are also mentioned in the paragraph 0694 etc. Beamforming components of weak scattering signals or speckle components are different from such deterministic signals and can be used for imagings or displacement measurements without performing the corrections of positions as it was previously confirmed on the experiments using virtual sources or virtual receivers that are assumed as scatters, etc. (a past invention of the present invention's inventor: patent document 7 and nonpatent document 8). For instance, for the displacement measurement, the combination of the plane wave transmission(s) with the Gaussian type apodization(s) is effective and when performing the focusing, the exponentiation type apodization(s) such as the 2nd power is effective. The latter apodization also yields a high spatial resolution even when the single beamforming is performed.

To perform the multi-focusing (not limited to a general multi-focusing that generates plural foci at different positions along the direction of beam propagation and including a new multi-focusing that can generate plural foci at arbitrary different positions also including different lateral positions), plural waves respectively having different focus positions can be generated and the reception beamforming can be performed. With respect to one transmission beams, plural reception beams can also be generated at plural positions or in plural directions. Plural transmission beams with plural different steering angles can also be generated. Such beamformings can be performed at separate positions to be with little interferences between the beams to be generated, or the beamformings can be performed in the respective parts, i.e., divisions of one frame, on the basis of such transmissions and such receptions. Then, parallel beamformings can be performed to perform the beamformings of plural beams in a parallel fashion, and respectively in the parts the beamformed results can be superposed at respective positions in an ROI. The method (4) itself has a feature that when the waves propagate in an ROI, even if the waves have interferences each other, the corresponding reception signals can also be processed; the best use of which is made to realize a high frame rate (The method (4) allows performing reception beamformings with respect to arbitrary transmission beams or waves, or single or plural transmissions). Reception signals can also be implemented by various types of signal separation processings, the beamformings can be performed with respect to the signal components properly. Being dependent on the degree of interferences, the processings can also be performed with no removing processings on the waves that arrive from the outside of ROI or propagated to the outside of ROI.

The respective apertures of transmissions and receptions can be the exclusive ones and the apertures can work for both the transmissions and receptions. Thus, the apertures do not always perform the receiving of the responses with respect to the waves transmitted from the apertures themselves and the apertures can also receive waves generated by other apertures, and then parallel processings can be performed and the beamformed results can be superposed. Summarizing, the above-mentioned superposing can be performed with respect to the objects (communication media), in which the waves propagate, or the objects to be observed having the same time, the same or almost the same condition (same phase), at different times or at different phases, via performing one of at least one beamforming, one transmission and one reception at each aperture or using one combination of transmission and reception apertures. Similarly, the respective combinations of plural apertures can also perform one of at least one beamforming, one transmission and one reception. When performing such processings, the superposing the obtained plural, beamformed, transmitted or received results can be performed to yield new data.

Since the processings of superposing are linear processings, in the calculation processes of the above-mentioned methods (1) to (6), plural complex spectral signals having same frequencies can also be superposed in a frequency domain. In the case, the superposed spectra can be inverse-Fourier transformed at once; achieving a higher speed for completing the superposed beamforming than the above-mentioned superposing, in a spatial domain, of the plural respectively beamformed waves that requires to perform the same number of Fourier transforms as that of waves to be superposed. Such as arriving waves, however, not limited to this, of which angular spectra are superposed, can also be processed in a direction or in plural directions, for instance. For the processings, plural waves superposed in a spatial domain are Fourier transformed, and then the superposed angular spectra can be used (The effect can be yielded on performing the Fourier transform only one time) It can become to confirm the position of object, etc.

As mentioned above, when performing the transmissions of plural beamformed waves using the methods including the methods (1) to (6) except for the SAs of the methods (2) and (3) (predetermined transmission delays can be implemented at least and transmission apodizations can also be implemented), specifically for physically performed simultaneous transmissions (the aperture elements to be excited at first in effective apertures for generating the respective waves are simultaneously excited, etc.), the corresponding reception signals are stored into the memories or storage devices (storage media) in the condition of superposed. And then, using the respective methods, the processings for generating image signals for one frame can be performed (The parallel processing can also be performed on the respective processings to be performed in parts of one frame).

Alternatively, in the above-mentioned other cases in which the plural beamformings are performed at different times, since the instrument of the present invention can confirm the timings of performing transmissions at the aperture elements at first in the effective aperture arrays, the digital signal processing unit can similarly perform the processings via properly superposing the plural reception signals of the respective channels on the reception aperture elements such that the same reception signals can be obtained as those obtained by performing the simultaneous transmissions of the plural waves (The parallel processing can also be performed on the respective processings to be performed in parts of one frame). In these cases, in practical, Fourier transform to be performed at first can be one time (Note that the processings can also be performed at respective divisional parts).

In these active cases, the beamformings except for the SAs (methods (2) and (3)) can be achieved with higher speeds. However, note that if required, the transmission beamformings (predetermined transmission delays can be implemented at least and transmission apodizations can also be implemented) are implemented on the SA reception signals that are generally used for the methods (2) and (3), after which the processings are performed on superposed signals and similarly processed. Incidentally, when the reception signals obtained with no transmission delays are superposed, the reception signals with respect to the plane wave transmission with no steering can be generated. For SA processings, the calculation speeds can also be increased by performing the division(s) and parallel processing. Particularly, when performing the multidirectional SA (a past invention of the present invention's inventor), plural beams can be generated in different directions from same reception signals acquired at one phase of the object and when performing the processings using the instruments or the methods of the present invention, calculations are performed on the same angular spectra obtained by implementing the Fourier transform on the reception signals once and finally, image signals are generated with a high speed not via performing the inverse Fourier transforms plural times on the angular spectra obtained for the respective steering angles but via performing the inverse Fourier transform once on the superposed angular spectra (The processings can also be performed at respective divisional parts). However, whenever passive processings are performed using the SAs, reception fixed focusing or other beamformings, as mentioned above, it is effective to perform the processings in a direction or in plural different directions on the superposed reception signals (i.e., one set of angular spectra).

In these processings, in which the superposition of plural waves can be obtained, for instance, if the propagation directions or frequencies, or bandwidths are different, it is effective to perform the processings after separating the spectra. The superposed signals can also be separated in the digital signal processing unit by using coding, MIMO, SIMO, MUSIC, independent signal separation (independent component analysis), principle component analysis, coding or parametric methods, etc. Incidentally, the superposing processing can also be effective for other processings (For instance, using the plural signals obtained at the same phase of the object increases the SNRs of signals, etc.).

The independent signal separation (independent component analysis) is, for instance, effective for separating the specular reflection signals and scattering signals, i.e., if the frames larger than two including the same specular reflection signals have independent scattering signals or states that includes mixed, independent scattering signals, the processing can separate the commonly included specular reflection signals effectively. Such processing is effective for automatically detecting and/or separating (removing) high intensity signals from blood vessels when performing the measurements of tissue displacements such as blood flow, etc., or specifying (detecting) the region of blood flow. Or, it is effective for detecting or extracting the boundaries of organs or tumors, etc. and similarly, it is possible to detect, separate (or remove) the specular reflections (tissues) and also to specify (or detect) the region with properties or features. It is also possible to simultaneously separate the mixed independent scattering signals. The capability in detection of the specular reflection signals and that in separation of mixed signals using the independent component analysis (independent component separation) are higher than the detections of the signals using the sum (additional average) and the difference of frames, respectively. The detections (envelope detection, squared detection and absolute detection, etc.) can be performed as pre-processings to increase the capabilities. This can also be confirmed with quantitative evaluations in a deterministically or stochastically as well as visually. Corrections of signal positions can be performed to match the signal positions among the frames by performing the motion compensations regarding the translation, rotation and deformation, etc. via performing the measurements of a displacement or a strain, and the processing increases the capabilities (For instance, in simulations using a 3 MHz ultrasound pulse, the cross-correlation-based displacement measurement allows the motion compensation for the standard deviation (SD) of the scattering signals being 1.0 and the specular reflection coefficient distribution ranging from 0.1 to 0.5, even if the scattering signals with almost the same intensity are mixed). The processings having a spatial resolution are required to be performed. Performing the displacement measurement, etc. prior to the detections can yield a higher accuracy and however, after performing the detections, the measurement can also be performed. When performing the high accuracy displacement measurements using various types of measurement methods prior to the detections, the motion compensation using block matching (coarse phase matching) performed in a temporal and/or spatial domain via performing the over-samplings or up-samplings, or phase matching performed by implementing the phase rotation in a frequency domain is effective. When using a medical ultrasound transducer, the independent signals can be obtained by slanting the transducer and receiving from other angles the specular reflection signal generated at the same position or by receiving signals using other subapertures on the basis of the steering processing. Or, it is also effective to get out of the position of the scanning plane and receive the signal including the same specular reflection signal generated at the source of the same specular reflection signal (continua of the same structure or composition). This is an operational technique using a hand. It is also possible to positively use the object motions (when the scanning plane moves out, signals from other tissues are mixed) or the object deformations (can be considered that noises are included) when acquiring signals including the specular reflection signals. When using other waves from the medical ultrasound, such as an ultrasound for a sonar, etc. or an electromagnetic wave, reflection or transmission waves can be acquired and processed similarly, in which used are motions of a sensor, a signal source and a detector (the shakes of them or the disturbances of their holders, etc.), the steerings of waves or beams, the target motions or deformations, etc. Mixing of noises generated in circuits and the signals can also have similar effects and then, such noises can also be used by positively generating and mixing in analogue or digital fashions (including in a software fashion, where programs can also be used). These processings can also be used for obtaining the same effects on the common and mixed signals existing in signals as well as the separation of specular reflection signals and the scattering signals; and the applications are not limited to these. The differences in a time and/or in a space are not always caused by the displacement or strain, the directivity of an aperture (particularly, when performing a steering) and inhomogeneities of propagation speeds of media themselves or changes in the propagation speeds due to disturbances of media or changes in conditions (for instance, change in a pressure or a temperature, etc.), etc. can also cause the differences, which can be processed using the signal analysis purely. A wave distortion can also be generated by a device due to frequency-dependent phase delay or phase change, etc. (for instance, a phase change generated at a sensor or a phase delay generated at an amplifier in the circuit, etc.), similarly the wave shapeform of the reception signal can be corrected by correcting the phase similarly (It is effective to perform the analogue-like spatial shifting of digital signals by multiplying a complex exponential function to every frequency signal component (spectrum) in a frequency domain, i.e., by rotating a phase of every frequency signal.). By measuring the phase change generated by the device(s) in advance, the sensor can also be electrically driven in a proper fashion to generate a wave with a desired waveform, a desired waveform at an observation position or a reception position. Thus, the measurement accuracy of observation target can increase (e.g., various observations using a phase, or frequency-dependent propagation speed, scattering or attenuation, etc.). Only the errors generated by the reception device(s) can also be corrected. Similarly, the above-mentioned other ones generating position errors can also be processed similarly. Although the applications are mentioned on the frame signals, beamformed signals (including ones obtained by SAs), reception signals before performing the reception beamformings or reception signals with no beamformed signals (transmission and reception signals for SAs) can also be processed similarly and besides beamformings can be performed. That is, the processings can be performed at least before, during or after the beamformings. On the respective cases, the superresolution can also be performed. The above-mentioned motion compensation processings can effectively correct the temporal and spatial differences, etc. in addition to, for instance, the differences, etc. in signals with respect to the transmissions of focusing beams or plane waves, which are referred to with comparison (for instance, for performing the superresolutions). The above-mentioned motion compensation processings performed before or during the beamformings can also work as delay processings in DAS processings. The detections (absolute detection, square detection, envelope detection, etc.) or increasing a spatial resolution via linear or nonlinear processings mentioned later can also be implemented similarly on beamformed signals (including ones obtained by SAs), reception signals before performing the reception beamformings or reception signals with no beamformed signals (transmission and reception signals for SAs) and besides beamformings can be performed. That is, the processings can be performed at least before, during or after the beamformings. To increase the bandwidths during the processings, if required, over-samplings or up-samplings can be performed in a time and/or in a space, or zero spectra padding can also be performed in a frequency domain (implementing the inverse Fourier's transform on the spectra can yield the results of the over-samplings or up-samplings).

For the above-mentioned position correction or phase aberration correction, the cross-correlation method based on a correlation can be used; and other displacement measurement methods can also be used. The signals can be processed as multi-dimensional signals as well as a 1D signals. For instance, the (multi-dimensional) cross-spectrum phase gradient method, the (multi-dimensional) autocorrelation method, the (multi-dimensional) Doppler method, etc. The cross-spectrum phase gradient method and the autocorrelation method, etc. have an effect of matched filtering similarly to the cross-correlation method and then, the methods are robust to noises filled in wave signals as mentioned above. As mentioned above, it is effective to use the (iterative) phase matching method (a shifting in a spatio-temporal domain or a phase rotation in a frequency domain) together with these displacement measurement methods. Here, an automatic determination method for the phase aberration on a beamforming with an array-type aperture and an effective aperture width is illustrated. As described below, the judgement using a correlation value between the local signals (e.g., in an ultrasound case, a local echo signal or a local transmission signal) or the detection of estimation error for a delay time (a time difference) on the beamforming allows determining an effective aperture width and performing the beamforming. In the case, the iterative phase matching method is effective. For instance, as mentioned above, when performing the coherent compounding (superposition) of beamformings with different steering angles, an image formation can be obtained with effects of increasing the contrast and the spatial resolution. Or, as mentioned above, a MIMO, a SIMO, a MUSIC, an independent signal separation (independent component analysis), a principle component analysis, a parametric method, etc. or an adaptive beamforming, a minimum variance beamforming, a Capon method, etc. (nonpatent document 10) can also be performed effectively. Not only these accuracies can increase but also the calculations can decrease. The adaptivity depends on the measurement object's properties such as a reflection, a scattering or an attenuation, etc. and thus, the adaptivity is desired to have a spatial resolution.

Here, the explanation is performed using reception signals to which at least a reception beamforming is not performed (note, signals to which a reception beamforming was performed can also be processed as mentioned above.). For a transmission beamforming, a fixed, focused beamforming or a wave that spreads in the crossing direction with respect to the wave propagation direction such as a plane wave, a spherical wave, etc. can be used, and not limited to these. The latter beamforming allows generating a high frame rate as mentioned above. Or, when not performing the transmission beamforming, the so-called classical synthetic aperture such as a monostatic or multistatic type can be effectively performed.

Figure 18:
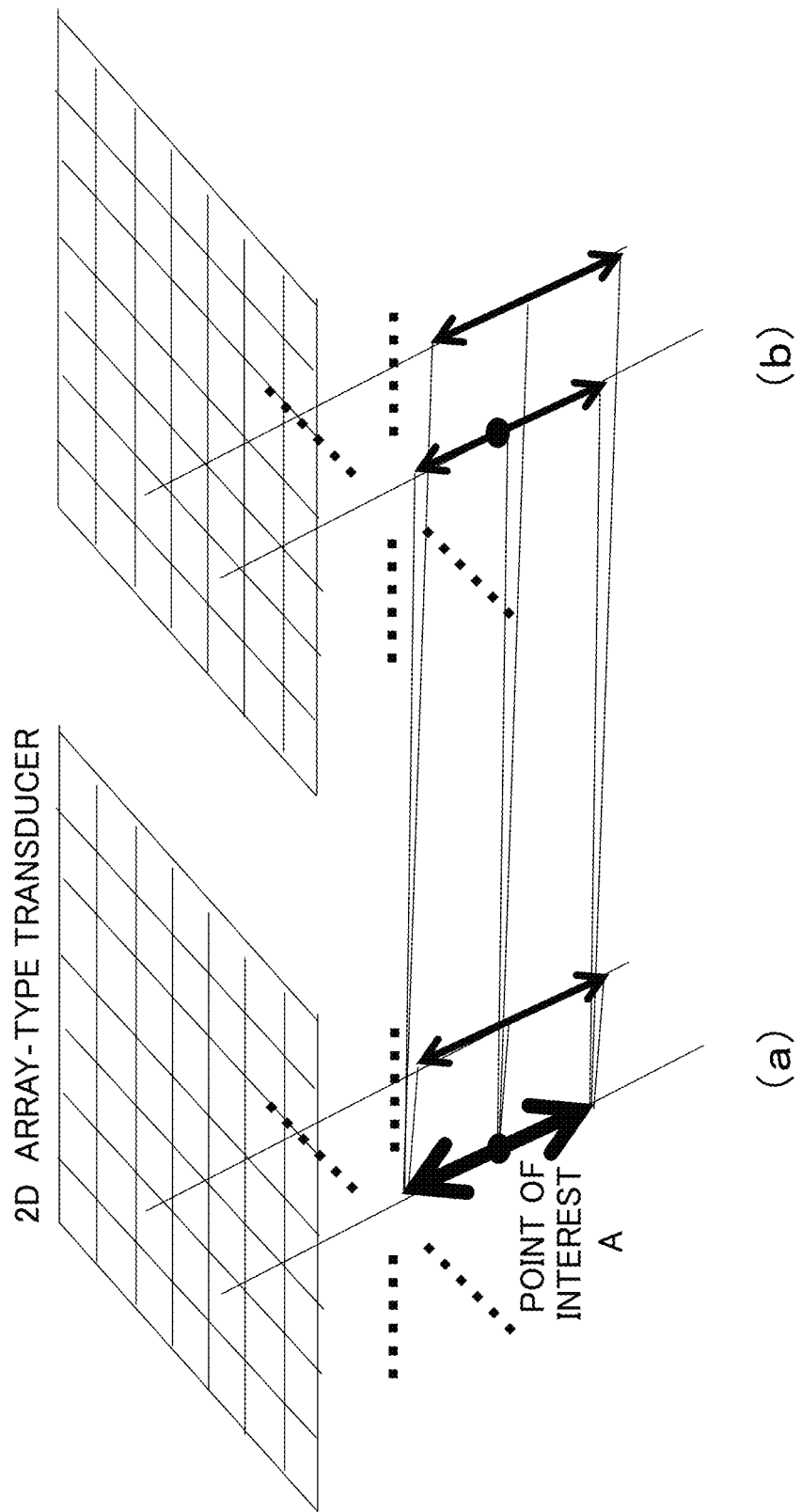
FIG. 18 shows a schematic for explaining an illustration of the phase aberration correction when performing a steering with a 2D linear-array-type transducer.

For the wave signals, with respect to a reception position, used for performing the beamforming, having the local signal including a signal of the observation position in a region of interest (ROI), the local signals with the highest correlation are searched for in the series signals received at the respective surrounding positions and their reception times are calculated (see FIG. 16 to 18). For searching for the local signals, the searching regions are set such that local signals with high correlations are included. The high accuracy phase rotation using the multiplication of a complex exponential function in a frequency domain is performed for the signal in the searching region. Then, the searching region is set properly larger than the local region such that the circulated signal does not appear in the local region of which signal is windowed for estimating the phase aberration (Setting the searching region too largely increases the calculations only and further the searching region is not always centered on the local region, and the size and position should be determined using the a priori estimate of the magnitude of phase aberration and the sign). When the phase aberration between the local signals is estimated as $\Delta t$, the signal of the searching region is spatially shifted by $-\Delta t$ to correct the phase aberration, i.e., the spectra of signal in the searching region $A(\omega)$ is multiplied by $\exp\{i\omega\Delta t\}$ and the inverse Fourier transform is performed (patent document 6, nonpatent document 15, etc.). Although the calculation time becomes longer, the iterative processing for the paired signals finally achieves the high precision estimation of the phase aberration with increasing the correlation between the paired local signals gradually (The iterative phase matching is described in detail in the patent document 6 and the nonpatent document 15, etc.).

FIG. 16 shows a schematic for explaining an illustration of the phase aberration correction when not performing a steering with a 1D linear-array-type transducer; FIG. 17 shows a schematic for explaining an illustration of the phase aberration correction when performing a steering with a 1D linear-array-type transducer. FIG. 16(a) and FIG. 16(b) show reception signal series groups obtained with different parameters; FIG. 17(a) and FIG. 17(b) also show reception signal series groups obtained with different parameters. As shown in FIG. 16(a) and FIG. 17(a), the processing can be performed only within the frame comprising of the reception signal series group including the signal of point of interest A to be beamformed; and Or, as shown in FIG. 16(b) and FIG. 17(b), the reception signal series group (frame) with different wave parameters or different beamforming parameters is obtained, for which the phase aberration correction can be performed with respect to the signal of the point of interest A shown in FIG. 16(a) and FIG. 17(a). The figures show the cases where plural frames obtained with different transmission or reception steering angles.

FIG. 18 shows a schematic for explaining an illustration of the phase aberration correction when performing a steering with a 2D linear-array-type transducer. FIG. 18(a) and FIG. 18(b) show reception signal series groups obtained with different parameters. The shown transducer is a linear-type one. Similarly to a 1D array type, a 2D array type is also various, for instance, an arc-type, a sector-scanning type (Using other type transducers from the linear-type, the steering can be performed with respect to the axial direction determined by the frontal direction of an element aperture.). Since the digital signals stored in the memory after the reception are to be processed, when using the cross-correlation method, the reception time of the local signal with a high correlation is estimated based on the sampling interval. Alternatively, the inventor of the present invention reported the cross-spectrum phase gradient method that allows performing an analogue-like estimation for the digital signals on the basis of the Nyquist theorem, which can be used for instance. Or, other displacement measurement methods can also be applied to the phase aberration correction as mentioned above; and if the SNRs of the reception signals are high, neither local estimations using the processing with a window (For the iterative phase matching described in the patent document 6 and nonpatent document 15, the window can often be rectangular and particularly at around the end of iterations, it is desired that the rectangular window is used.) nor the moving-average are required to be performed, i.e., it is possible to perform an estimation using a reception signal (instantaneous data) of the point of interest A shown in the figure. The reception signals to be processed here can also be ones that were processed by a transmission or reception beamforming.

This cross-spectrum phase gradient method requires a phase unwrapping if the time difference is large between the local signals due to the spectral phase's inversion. Thus, at first the cross-correlation method is used to perform a coarse estimation and a phase matching (spatial shift) including the effect of the phase unwrapping and next, the cross-spectrum phase gradient method is used to perform a fine estimation. In this fine estimation, the phase rotation using a complex exponential function is performed as the phase matching, which can be performed iteratively with increasing the correlation value to increase the accuracy (Although the signals to be processed are digital, the phase matching can be performed in an analogue-like fashion. This approach is based on the inventor's previously developed phase matching method as a displacement measurement method (patent document 6 and nonpatent document 15, etc.). In terms of the calculation speed, the cross-spectrum phase gradient method is faster than the cross-correlation method; the cross-spectrum phase gradient method that performs a phase unwrapping is also effective (Basically, the unwrapping determined by the distance between the point of interest and the element position is performed, which is simpler than when performing the observation of an object's motion in an arbitrary direction. When using the iterative phase matching, the window length can be made gradually smaller and finally, the result with a high spatial resolution can be obtained. The coarse estimation can be performed within the range physically determined by the propagation speed assumed in advance such that the range includes the corresponding signal, and the fine estimation can be performed. There can be a case where not the coarse estimation but only the fine estimation is required and even more the unwrapping processing cannot also be required.

The effective aperture width can be automatically determined as follows: with respect to a point of interest A for each element position to be beamformed within a physical aperture, the respective reception signals received at other positions in the direction getting far from the point of interest A (FIG. 16 and FIG. 17: the left and right direction in the 1D array case; FIG. 18: the surrounding directions in the 2D array case) are processed by the above-described processing; the edge of the effective aperture can be automatically determined as a former position with respect to a position where (i) the correlation value calculated by the inner product between the local signals becomes smaller than the threshold set in advance or (ii) the time difference with respect to the estimated corresponding local signal becomes larger than the threshold set in advance. During the processing, the estimated correlation value or time difference can also change discontinuously, the processing can be considered as the detection of an estimation error.

Although it is also effective to perform this processing for the beamforming only using the reception signals within the frame, for instance, it is also effective for the high-frame-rate coherent compounding (increasing a bandwidth) achieved using the plurally steered plane wave transmissions with different steering angles mentioned above because the single plane wave transmission yields only a laterally narrow-band wave. Also for the focused beamforming, it is effective in obtaining an effect, i.e., increasing the bandwidth. Reception signals obtained by different beamformings with other beamformings or wave parameters from the steering angle can also be processed similarly (see FIG. 16 and FIG. 17). The above-described processing can be performed with respect to the respective positions A within reception signal frames, specifically, the processings with the same or different reception steering angle with respect to the transmission steering angle can be performed, which can be compounded. However, the compounding performed with respect to ones with the largely different transmission or reception steering angles can fail in the image formation. Thus, a transmission steering angle of a wave to be generated is determined and the same or different reception steering angle is also chosen with respect to the transmission steering angle, and with respect to the respective positions A set within the reception signal frame correspondingly obtained with respect to the determined transmission steering angle, the processing is performed not only within the reception signal frame itself (when not performing the compounding, only the processing is performed within this frame) but also other reception signal frames obtained with respect to other transmission steering angles. When increasing the accuracy, the transmission and reception steering directions should be set in as strong directivity direction of an aperture as possible (i.e., a frontal direction of an aperture). Furthermore, it is possible to perform the processing for different combinations of transmission and reception steering angles, which can be used for further compounding. However, the compounding performed with respect to the largely different transmission or steering angles can fail in the image formation.

For the compounding, for instance, the following beamformings can also be used: plural signals can be generated with different reception steering angles with respect to a transmission steering angle such as a frontal or arbitrary direction, or plural different transmission and/or reception steerings can be performed using synthetic aperture data. These processings can also be applied to the above-described case of plural different transmission steerings.

In this processing, the local signal length (window length) is required to be set properly (The length for the iterative matching is the first window length). Using a smaller length yields a higher correlation value and the estimate of local signal has a high spatial resolution (i.e., the estimate of phase aberration) and however, another similar signal can be detected erroneously. Using a longer window length yields a lower correlation value and fails in searching for the corresponding signal. For instance, for an agar-graphite phantom ultrasonically mimicking a human soft tissue, when a transmission of a plane wave (a nominal frequency, 7.5 Mhz) is performed, 64 and 128 points under 30 MHz sampling are proper; and 32 and 256 points are improper. This is similar to the case of observing a displacement or a displacement vector. As described above, it is proper to perform the phase matching with a proper window length; and for the iterative phase matching, it is effective to decrease the window length gradually during the iterative phase matching (Finally, a high spatial resolution result can be obtained.). For instance, in the case where the synthetic aperture, etc. is performed, scattering signals which are not able to be formulated by a few times phase matching are to be successfully formulated by the more times phase matching: the iterative phase matching is effective. The above-described much accurate phase aberration correction or the iterative processings are proper for a precise examination, although it requires calculation times. Although a real-time processing is important in a medical ultrasound, the above-described processing will become a new medical ultrasound precise examination method. For the iterative phase matching, the upper limitation can also be set to the iteration times, and if the update value of phase aberration estimation becomes smaller than the value set in advance or sufficiently small, the iteration is terminated. Till the above-described condition (i) or (ii) is satisfied with, the same processing is continuously performed for the next laterally positioned reception signals. To shorten the calculation time, the estimate of phase aberration can be used for the initial estimate of the next position. In a case of 1D array, the processing can be performed in the left or right direction with respect to the position A (The effective aperture widths calculated by the processings (i) and (ii) do not always become laterally symmetric with respect to the positions A.). In a case of 2D array, it is possible to perform the processing toward the surrounding directions from the position A. Or, using the maximum effective aperture width including a position A determined in advance and the estimate of phase aberration is performed from the edge of the maximum width, the effective aperture width can also be determined based on the calculated correlation value of condition (i) becoming or being larger than the value set in advance or the estimate of phase aberration itself [(ii)]. Regardless the way of judgement, every estimate of phase aberration is obtained, the phase-aberration-correction local signal (delayed local signal) can also be obtained. Thus, the addition processing in DAS processing should be performed every final estimate is obtained (i.e., DAS processing using a phase aberration). In addition, the independent signal separation (independent component analysis) or the principle component analysis can be performed to separate the signal into a signal with the same component as that of a reference signal (a higher accuracy signal than the above-mentioned summation (additional average)) and a signal with the different component from that of the reference signal (a higher accuracy signal than the above-mentioned subtraction) and then it is useful to perform the summation for the former signal. The distinguish of the former and latter signals can be performed by calculating the correlation with respect to the reference signal; and the signal with a higher correlation can be regarded as the former signal and the signal with a lower correlation can be regarded as the latter signal. Also the latter signal can be used with a summation processing. Similarly, the phase aberration can be performed with respect to other positions A in a depth or lateral direction in an ROI. If the purpose of processing is only the estimation of phase aberration, the addition processing is not required. Also, for all phase-aberration-corrected signals within an effective aperture estimated with respect to each point of interest A, the processing for separating independent signals can be performed at once to separate a signal with the same component (a common signal) for all the signals (a signal with a high correlation) and other signals; then the former can also be used as the result of DAS processing.

When plural signals with different waves or beamforming parameters of transmission or reception are being superposed, the estimation or correction of phase aberration can also be performed for the superposed signals. Or, for instance, the signals are separated in a frequency domain or by other processings, after which the respective separated signals can also be processed by the above-described estimation or correction of phase aberration (For instance, the processings can be performed for the respective steering angle data.). Or, the estimation or correction of phase aberration can also be performed for waves newly generated by dividing spectra of similarly superposed or non-superposed signals in a frequency domain. When separating signals in a frequency domain, new waves or new beamforming parameters can be generated, for instance, quasi-steerings in various directions, new geometries of waves or beams, etc. (not limited to these). The respectively phase-aberration-corrected signals can also be superposed.

It has confirmed that the processing for a single frame yields a higher contrast and a higher spatial resolution in the formulated image than in that with no phase aberration correction; and also that the above-described compounding (superposing) of the processings for plural frames further increases the effects of phase aberration correction. This compounding is explained mainly for the coherent superposing of raw signals and however, the compounding can also be performed incoherently for detected signals (envelope detection, squared detection, absolute detection, etc.) to reduce speckles. That is, it is also effective for yielding an image with increased contrast and CNR (Contrast-to-noise ratio) by enhancing a deterministic signal such as a specular (reflection) signal or a scattering signal.

For the (multi-dimensional) autocorrelation method, the (multi-dimensional) Doppler method and other methods, the cross-correlation method is used for a coarse estimate of displacement; and then a fine estimation can be performed with no phase-unwrapping processing. Similarly to the cross-spectrum phase gradient method, the cross-correlation can also be used solo. Or, the unwrapping can also be performed.

The estimate of an effective aperture width or a phase aberration (above-described) can also be used for above-mentioned various applications such as the minimum variance beamforming, the independent component analysis, the principle component analysis, the superresolutions with nonlinear processings (performing a summation after performing a nonlinear processing or vice versa), etc. Here, as an approach, the beamforming can also be performed with no phase aberration correction using a database of a mean effective aperture width at each range position obtained based on the processing (i) or (ii). The above processings can also be performed for the passive case of the 2nd embodiment.

The signal separation can also be performed in a frequency domain with a high accuracy after performing the increasing frequencies and bandwidths using the exponentiation calculations (when the orders larger than 1) or the decreasing frequencies and bandwidths (when the orders smaller than 1). The restorations of the separated signals can be simply performed using the exponentiation calculations with the reciprocals of the used orders.

The above-mentioned phase aberration correction can yield various other effects. When the observed quantities are different (e.g., physical and chemical quantities, etc.) or the conditions or parameters for the same observed quantities are different, etc., the phase aberration can be implemented between various observed data or various processings described in the present invention can be performed with respect to the phase-aberration-corrected data. For instance, when performing the fusion/integration of an ultrasound (echo) and an OCT themselves and/or the observation data obtained from them, an accuracy about a characteristic position can be obtained from the OCT, which can also be used for the phase aberration correction of the ultrasound (echo) (Although the physical properties of a light and a sound are different, particularly the common positions of changing the properties or generating the scatterings can be used. The phase matching itself can also be performed between the coherent signals, the incoherent signals obtained by detections, or image data.). After performing the phase matching, as mentioned later, in addition to the ICA, etc., machine learnings, deep learnings, neural networks (a back-propagation type, a Hopfield type, deformed models based on the types and among others), or other processings can also be performed for the coherent signals, incoherent signals or image data).

The inventor of the present investigation is performing the fusion between the measurement techniques and the highly sophisticated information processings based on the information processings including innovative multi-dimensional digital signal processing techniques (including an electronics), inverse analyses or problems, or statistical processings (based on a mathematics) which are mainly developed for various wave applications in various fields such as a medical imaging, a remote sensing (various types of a radar such as a ground radar, a radar outside an earth or ones equipped with a star, a satellite or an airborne, various observations such as a weather, an earth, an environment, a resource, a space or a celestial body, or a sonar, etc.), a nondestructive evaluation (structures, materials, properties or functions, living things, etc.), etc. Particularly for the fields of a human tissues (including the applications of microscopes), a bio, a material, a structure, an environment, etc., comprehensive applications can be performed, which is expected to yield innovative scientific technologies that will provide us innovations of a society and an economy. For instance, being related to physical quantities, chemical quantities and properties for three fundamental physics of an electromagnetism, a mechanics and a thermology and other phenomena (a biology, a chemistry, a biochemistry, etc., various combinations and among others) that yields various applications widely, innovative nondestructive evaluations can be realized, which allows obtaining observed results as numerical values, graphs, imaging or visualizing, developing in the fields of a medicine, a life science (a healthy promotion of human, examinations of human tissues, generation, treatment, processing, application, an animal (small one), an organization, a cell, a medicine, etc.) or a material (electric, thermal, elasticity, or composite material, etc.), observing an environment (gas, liquid and solid), developing an energy, security (monitoring, observation of moving object, etc.) and various other high accuracy observings (a big or small object, a short or long-time phenomenon, an object located at a short or long distance, the first in silico measurement standard to be possible in the world), etc. By these, it is made possible to perform a measurement (examination or diagnosis), a restoration (or treatment, regeneration), a manufacturing (3D culture of tissues, growth of materials) and applications including yielding new functions and properties, etc. for the various fields. Thus, it is made possible to perform the in situ measurement of spatio-temporal distributions of fundamental physical quantities, chemical quantities, properties which cannot be observed as far, or perform the observations with no controlling the observation conditions. For instance, it is made possible to observe operating devices, or living things or cells in a condition bottom of nature or observe the growth process of materials in the condition bottom of the growth process. Furthermore, various potentiality factors (mechanism), new phenomena, new principles, etc. are elucidated in detail by a highly sophisticated fusions of a variety of simultaneous observation technologies/analysis technologies and the most advanced, information science or statistical mathematics, etc. This can contribute to the creation or the synthesis of new properties and functions, or new restorations. It is made possible not only to exceed the accuracy limitation achievable with a single observation by making the system over-determined (additional averaging or least squares estimation) but also to exceed drastically the accuracy limitation by the below-described an intelligent integration/fusion technology (highly accuracy multiplex of common information, separation of independent information, separation of independent signal sources), for instance. In order to increase the accuracy of the multiplex of common information, and the resolution of the independent information or the independent signal sources, performed are new applications of the ICA with high precision digital signal processings, integration learning and integration recognition, etc. as the new applications of the machine learning, the deep learning, the neural networks, etc. If necessary, the sensor is set in the neighborhood of the observation object for the high accuracy observation by dividing the object, and for a human, by opening the head or abdomen, or by using the laparoscope, the endoscope, the transoral or transnasal camera, the capsule type camera, the interstitial needle. Or, the phase aberration correction cannot be performed at all nor be with a high precision (For instance, the cross-correlation method, etc. can be used as with a small sampling interval as possible.). The signal source (which can also be processed as a diffraction source) can correspond to a physical signal source itself, a reflector, a scatter or a diffraction source. Particularly when the reception signals include those of multiple reflections or multiple scatterings, etc., and the signal to be observed is included at a different position or time, it is effective to directly perform the processings such as the ICA, etc. for the signal at the different position or time. Thus, with changing the position, etc., the processings can be performed and in this case, the processings include the signal detection processing (The correlation value can be used as an index for the accuracy or the confidence of the detected signal.). Thus, the signals of multiple reflections or multiple scatterings can be separated.

For instance, as described in the paragraph 0380, by realizing for the internal observation object the in situ imaging of the distributions of physical quantities of the electromagnetism, the mechanics or the thermology by using the wave sensings including the inverse analyses and based on the observations, it is possible to realize the reconstructions of related physical property distributions (inverse analyses). The sources of phenomena can also be reconstructed. In addition, using one physical quantity sensed and the reconstructions obtained, another physical quantity can also be calculated. Observation of an energy can also be performed through the calculation. In order to realize the high accuracy observation, the multi-dimensional observation (2D or 3D) can also be desired. For instance, there are:

(1) Reconstructions (imagings) of electric property distributions (a conductivity and a permittivity (dielectric constant), or one of them), electric current or voltage source distributions, or an electric voltage distribution based on an electric current density (vector) distribution measurement; or reconstructions of an electric property, an electric current density (vector), or an electric current source based on an electric voltage distribution measurement, etc.
(2) Reconstructions (imagings) of mechanical property distributions (a shear modulus, a visco-shear modulus, a compressibility (a Poisson's ratio), an incompressibility, a viscosity, a density, etc.) or a mechanical source distribution based on displacement (velocity, acceleration) vector or strain (rate) tensor distribution measurement. A mean normal stress (an internal pressure) distribution can also be observed simultaneously or independently. Observation of inertia vector or stress tensor distribution, etc.
(3) Reconstructions (imagings) of acoustic property distributions (a bulk modulus, a viscoelasticity, a density, a static pressure, specific heat, etc.), a sound source distribution, an acoustic pressure distribution, or a particle displacement/ velocity distribution, etc. based on a sound propagation measurement.
(4) Reconstructions (imagings) of thermal property distributions (a thermal conductivity, a thermal capacity, a thermal diffusivity, a perfusion, a convection), a thermal source distribution, a thermal flux distribution, etc.

The observations of them in the observation objects being the respective waves' media can be realized base on the magnetic resonance imaging (MRI), the superconducting quantum interference device (SQUID) (the observed waves: magnetic fields), terahertz (electric field), and others such as an electromagnetic waves (a direct current (DC, not a wave), an electric power, a radio wave, a microwave, an infrared ray, a visible light, an ultraviolet ray, a radioactive ray, a cosmic ray, etc.), the sound pressure measurement using the Doppler effect of a light pulse or a laser, the optical coherent tomography (OCT), the light microphone (the inventor, Dr. Yoshito Sonoda), the ultrasound echo (sound) instrument (modalities) and among others (patents of the inventor of the present invention). The reconstructions of property distributions (1) to (4) are referred to as the differential-type inverse problem/analysis by the inventor of the present invention, being different from a usual integral-type inverse problem/analysis. That is, partial differential equations or ordinary differential equations such as wave equations or diffuse equations, etc. are to be solved for performing the reconstructions of the relative property distributions from one physical quantity distribution, which are led by substituting the constitute equations into the governing equations, whereas in usual cases (e.g., X-ray CT, an electric impedance CT, etc.) integral equations are solved for observing within the object from physical quantities observed at the boundary position of the object. Providing a reference value or values (practical measurement data or typical values, etc.) of the target property at a proper position or region (a reference region), the absolute distribution can be determined. When some region can be considered to have a constant value (including an approximate case) and considered as the reference region, using a unity value for the reference value allows the determination of the relative value distribution. If required, the integral-type inverse problem can also be used.

In any case, a system of equations, $Ax=b$, holds for the unknown distribution, i.e., the unknown vector x (The numbers of unknowns (the dimension of x) and equations can also be same, or the system of equations can also be over-determined or fewer-determined.). In a case of a linear system, the unknown distribution x is often the target distribution itself, whereas in a case of a nonlinear system, since the target solution (estimate) is iteratively updated, the update distribution $\Delta x$ to be used for the updation is often the unknown (vector) in the system of equations instead the target x itself. The cases are not limited to these. In the nonlinear problem, the matrix A and/or the vector b depends on the unknown distribution x, at each step of the iterations, the matrix $A(x)$ and/or the vector $b(x)$ calculated using the last estimate of unknown distribution x is used in the system of equations to calculate the update distribution $\Delta x$. And, the last estimate x is update by $\Delta x$ to obtain the estimate at the step. This procedure is iteratively performed until the magnitude (norm) of $\Delta x$ becomes smaller than the pre-specified value. That is, the condition is used for judging the convergence of iterations.

Moreover, the fusion/integration of the sensings (electromagnetic and/or sonic ones) and inverse problems can be performed. For medical imagings, the fusion instruments of X-ray CT (geometrical information), MRI (geometrical and functional information) and PET (functional information) have been used in practice. Alternatively, as disclosed in the present invention, the fusions of the applications of electromagnetic waves, mechanical waves, and thermal waves can also be performed, for instance, in addition to the ultrasound (a longitudinal wave) and the shear phenomenon (a transverse wave), the MRI and the ultrasound, and the ultrasound, the terahertz, the OCT, and the laser, etc.

For instance, there are various applications for the fusion/ integration of (1) to (4), which is referred to as (5), as described in the paragraph 0380. For instance, in the field of a life science, based on the new measurements of the function or the property, the fusion/integration (5) can contribute to a highly efficient culture (particularly, a 3D culture), a controlling of the culture, a clarification of the disease outbreak mechanism, etc. (simultaneous observations of organic and inorganic objects, etc.). While the iPs cell attracts attention, for instance, the activity of a culture cardiac muscle cell being active naturally can be observed in situ as mechanical dynamics and electrical phenomena simultaneously (the multiplexing of new observations or fusions, etc.). Or, operating electric and electronic circuits can also be observed in situ (examinations of devices or joinings, etc.). Or, in processes of a growth and an operation of variously functional materials or various device developments, physical quantities and properties can be observed in situ (for instance, for an ultrasound element such as a piezoelectric PZT element, a polymer membrane, a PVDF, etc., simultaneous measurements from plural aspects about an electric and mechanical energy conversion efficiency, an electric impedance, a vibration mode, a thermal phenomenon; downsizing; speed up; increasing an energy efficiency (energy saving)), which yields contributions for generatings and synthesizings of new functions (electric materials, elastic materials, heat materials). Or, in various fields, such effective observations can be performed as described in the paragraph 0380.

For the inverse analyses and fusions, information science and statistical mathematics are effective. As described in the paragraph 0381, performed have been with the signal processings: various optimizations, the maximum likelihood, the Bayesian estimation, EM (Expectation-Maximization), the unbiased regularization using the partial derivative operator for a regularization term (a penalty term, e.g., the inventor's first spatio-temporal variant regularization in the world or for instance for the reconstruction of absolute or relative property reconstruction for a homogeneous material, the first in silico standard in the world to be realized possibly by decreasing the standard deviation and stabilizing as much as possible by setting the significantly large regularization parameter.), the singular value decomposition, the equalizer, the sparse modeling, the signal (source) separation or the feature analysis using the ICA or the MUSIC, the new superresolution (the inventor's patent applications such as in silico harmonic imaging, etc.), using an assumption of a stationary process, the Cramer-Rao Lower Bound (CRLB) or the Ziv-Zakai Lower Bound (ZZLB) for estimating the displacement (vector) measurement accuracy or applying to the a priori or a posteriori regularization). Established error models for the respective observation objects can also be applied to them. Or, for the integration and the fusion of the different kind information (including the observed different quantities or the quantities observed under different conditions or with different parameters), in addition to the KL information, the maximum likelihood, the mutual information minimization/maximization, the entropy minimization, particularly for improve the multiplexing of the common information and the separation ability of the independent information, the new application of ICA with high precision digital signal processings as mentioned above (Using the high precision spatio-temporal matching of plural digital signals (the analogue-like phase matching with no approximation for digital signals, etc.) together increases the extraction ability of the common component and makes the accuracy higher than the additional averaging, or increasing the separating ability of independent components.) or the new deep integration learning and integration judgement using the neural network (being approaches of integrating or analyzing the recognition or the multi-layered neural network, differential diagnosis/recognition of disease, etc. (The kind of diseases can be coded; and various recognition objects except for the medical diagnoses can also be coded.), mapping images to other kind images or other clinical data, some to desired purposes/targets or new functions, etc., which are not limited to the medical applications), etc. can be performed. It is also effective to integrate or perform the fusions of phenomena having different stochastic processes (For instance, the multiplexing or separating a noise with the Gaussian distribution and an ultrasound scattering signal with the Rayleigh distribution; multiplexing some with plural different stochastic processes, etc.). Since a terahertz signal or a SQUID signal has a low SNR, the signal processings such as the ICA (being more accurate than the additional averaging) or the MUSIC are also effective. Or, when performing the processing of the so-called big data such as sensing data of a 3-dimension or a spatio-temporal one, to increase the computation (calculation) speed (a degree of a real-time), the high precision and high-speed Fourier transform beamforming (including a data compression) or the parallel processings can also be performed at the timing of sensing. The so-called data mining can also be effective. Usual various compression methods or technologies can also be effective.

Such new observation technologies base on the parallel processings or the integrations/fusions will build the position as innovative non-destructive examination technique for each observation object in the future, and will open up new prospects (new engineerings, etc.) in various fields. It is thought to yield a rapid progress in scientific developments. In addition, it will be able to contribute to the international measurement standard of basic properties of matter, particularly, distributed constants (It will have a potential in becoming the first in silico international standard using the regularization.) and will bring a great effect in an industrial aspect (Realized will be approximately the same precision as the number of the effective digit of a computer.). The in situ remote sensing applications (approaches) mentioned above are not limited to these, and the ripple effects to other fields are immeasurable. As mentioned above, it will be returned to various fields and new fusion/integration fields, and a society.

The examples of applications realized by (1) to (4) mentioned above are enumerated below by items. The applications cannot be limited to these. In addition, reconstructions of the property distributions (a thermal conductivity or an electric conductivity) allows the observation the distribution of thickness change and there can also be a time when such apparent property observations become effective. Or, the distributions are not always observed and instead at least one value may be observed.

(1) Reconstructions (imagings) of electric property distributions (a conductivity and a permittivity (dielectric constant), or one of them), electric current or voltage source distributions, or an electric voltage distribution based on an electric current density (vector) distribution measurement; or reconstructions of an electric property, an electric current density (vector), or an electric current source based on an electric voltage distribution measurement, etc.

Platforms: MRI, terahertz, SQUID, electrode array (electroenchephalography, electrocardiography, etc.), capacitance-type potential sensor array, etc., and among others.

Observation objects: neural network of human or animals (mouse, etc.), electric circuit, electric material (resistance, permittivity (dielectric constant)), electric current field or electric field, electric potential field, etc., by the MRI, electrode array, capacitance-type potential sensor array; electric circuit, electric material (resistance, permittivity), piezoelectric element (PZT, PVDF), etc., by the terahertz; all the targets by SQUID, etc. When using the MRI or SQUID, the electric current density vector distribution can be determined by solving the inverse problem of Bio-Savart's law (integral-type inverse problem).

(2) Reconstructions (imagings) of mechanical property distributions (a shear modulus, a visco-shear modulus, a compressibility (a Poisson's ratio), an incompressibility, a viscosity, a density, etc.) or a mechanical source distribution based on displacement (velocity, acceleration) vector or strain (rate) tensor distribution measurement. A mean normal stress (an internal pressure) distribution can also be observed simultaneously or independently. Observation of inertia vector or stress tensor distribution, etc.

Platforms: MRI, terahertz, ultrasound, OCT, laser, light pulse, etc., and among others.

Observation objects: soft tissues (brain tumor, cancerous diseases such as a hepatocellular carcinoma, breast cancers, etc.) of human and animals (mouse, etc.), vascular disease models such as a sclerosis, heart and blood vessel, hemodynamics including the blood flows, particularly for the MRI, intracranial cancer lesion model of which the ultrasound and OCT have difficulties in observation); for the terahertz, the same animal lesion model, tooth and bone, inorganic solid body such as the piezoelectric body (PZT or PVDF), deformable/elasticity material such as the PVDF or a rubber, fluids such as a liquid (including the blood) or a gas including powders (tracer) such as a medicine or a metal (a conductor and magnetic body), etc., gas or waste fluid including a mine dust, etc.

(3) Reconstructions (imagings) of acoustic property distributions (a bulk modulus, a viscoelasticity, a density, a static pressure, specific heat, etc.), a sound source distribution, an acoustic pressure distribution, or a particle displacement/velocity distribution, etc. based on a sound propagation measurement.

Platforms: light pulse, light microphone, laser, MRI, ultrasound, OCT, etc., and among others.

Observation objects: In addition to the observation objects of organic ones mentioned above, gas (helium, oxygen, air, etc.) and liquid (pure liquid, mixture, water, salt solution, liquid or blood including the medicine, etc.), solids (including inorganic ones). Special environments (indoors, outdoors, altitude, mountain, deep depth, sea, small place, etc.), etc.

(4) Reconstructions (imagings) of thermal property distributions (a thermal conductivity, a thermal capacity, a thermal diffusivity, a perfusion, a convection), a thermal source distribution, a thermal flux distribution, etc.

Platforms: MRI, terahertz, ultrasound, light fiber, pyro sensor, etc., and among others.

Observation objects: thermal material, inorganic solid body such as the piezoelectric body (or terahertz material), etc., perfusion effects for neural networks of animals (mouse, etc.), metabolism, cancerous diseases or inflammation, blood (perfusion) model, piezoelectric material or PVDF, convection such as of gas or liquid, etc.

In addition to (1) to (4), as (5), the fusion/integration of (1) to (4) and other inverse analyses and the data mining can also be performed, for instance, (i) Using (1) to (4) with the same or different instruments allows the observation of the same object simultaneously or from plural aspects, or plural objects related to a phenomenon simultaneously or from plural aspects.

Medical in situ observation (In a health care diagnosis or a medical examination, a diagnosis of diseases, or a monitoring of various treatments, a same organ, a same tissue, or a same lesion can be observed at the same time or from plural aspects; a single disease or simultaneous diseases, or independent plural disease, related organs or tissues can be observed at the same time or from plural aspects; the observations can be performed with a fewer kind instruments (hardwares).).

In situ observation in a regenerative medicine and a life science (the highly efficient culture, particularly the 3D culture and the control, the outbreak mechanism of the lesion, the simultaneous observation of organic and inorganic objects, etc.).

Simultaneous in situ observations of the activity of a culture cardiac muscle cell (iPs cells, etc.) being active naturally as mechanical dynamics and electrical phenomena (the multiplexing of new observations.

Making the increasing of accuracy and the fusion possible.

Simultaneous observations of the (visco) elasticity (including the hemodynamics) and the thermal properties (or temperature) of lesion models of a human or animals (the brain tumor, the hepatocellular carcinoma, the breast cancer), the cardiac muscle cell, the blood vessel, the blood (including the medicine) in a cardiac cavity or a blood vessel.

Development of ultrasonic and/or terahertz observation of the drug delivery by the dynamics or the electromagnetic induction, or development of a new medicine.

Simultaneous observations of an electric activity and a heat generation (temperature) for a neural network and/or a metabolism of a human or animals, and a perfusion effect of the blood.

For a low invasive warming treatment (HIFU: High Intensity Focus Ultrasound) of a human cancer lesion or a Parkinson's disease, improving the treatment ability by performing the monitoring of treatment from plural aspects in a real time through the simultaneous observations of the treatment effect (a temperature rise or a denaturation such as a viscoelastic change) and the perfusion itself of lesion part, and the neural network control of the perfusion by MRI and/or an ultrasound, which allows performing the treatment (restoration) of only the abnormal part safely and efficiently without invading the normal part as well as with the diagnosis in a medical care. There also exists cases where various cells of a brain tissue, other tissues such as a nerve themselves can be treated.

Integrated medical case (general diagnosis, treatment, art of surgery, physiotherapy/chemotherapy, medication, etc.), theranosis (As a success example, the present inventor previously developed tissue shear modulus reconstruction methods based on an ultrasonic echo technique and succeeded for a hepatocellular carcinoma in the diagnosis and the monitoring before, during and after the thermal treatment with the one index consistently), observing a viscoelasticity or a temperature change due to the inflammation after the treatment (blood flow to be simultaneously observed).

Offering a high accuracy and cheap technique (e.g., the infrared camera can be used instead of the SQUID meter, etc.) through confirming the Wiedemann-Franz law about the electric conductivity and the thermal conductivity.

For a synthetic problem (composite material, etc.), optimizing the materials, structures, and a generation process, etc. with the desired characteristics as the targets For an ultrasound element such as a piezoelectric PZT element, a polymer membrane, a PVDF, etc., simultaneous measurements from plural aspects about an electric and mechanical energy conversion efficiency, an electric impedance, a vibration mode, a thermal phenomenon; contributions to the generations and syntheses of new functions (electric materials, elastic bodies such as the rubber, etc., thermal materials, etc.).

The voluntary operation of the robot by the integrated judgment in silico.

Realizing new measurements that have not been realized even by the conventional large-scale facilities with a lower cost (e.g., a fewer devices such as one can be used for many applications).

For instance, for a medical care, effective can be performing the diagnosis/differentiation of lesion by fusing the original images such as the ultrasonic echo technique, the MRI, the OCT, the laser and/or the light pulse with the reconstruction (observation) results of properties such as a (visco) shear modulus distribution obtained from observing the tissue displacement (vector)/deformation distributions, etc. (In addition to various fusions/integrations, the corresponding images thinned can be superposed onto others to display the plural observation data simultaneously); when carrying out some treatment (art of surgery and/or physiotherapy/chemotherapy), it is also effective to perform the diagnosis including the treatment effectiveness (mainly, degeneration) with the same index (an observed property), i.e., the diagnosis and monitoring before, during and after the treatment, and the progress after the treatment; particularly for the heating/warming treatment, using the temperature dependencies of the ultrasound speed and/or the volume change, the chemical shift of the Larmor frequency (nuclear magnetic resonance frequency) of MRI, the light (refractive index) of OCT, etc., the reconstruction (observation) of a (visco) shear modulus allows observing a temperature (change) distribution to monitor the treatment effectiveness; it is made possible to perform the estimation/prediction of a temperature distribution to be generated by the heating/warming by performing the reconstructions of thermal properties (distributions) and the thermal source from the observed temperature (distributions) data (The thermal source can be calculated based on the inverse problem; the shape of thermal source can be estimated by calculating the autocorrelation function of heating/warming waves to be sensed; the power of thermal source can be estimated using the transmission power and/or tissue properties; the shape data can be applied to the thermal reconstruction problem; the distributions of a wavelength and a propagation speed of heating/warming waves can also be observed using the above-mentioned autocorrelation function (patent document 11)); by performing the integrated judgement with observing them, it is possible to make a heating/warming plan one by one and to realize the minimum-invasive treatment. When the receiver can also receive a response wave with respect to the HIFU transmission, the received echo signals generated by the HIFU transmission can be processed and used, whereas when the reception is impossible, reception signals can be obtained by transmitting ultrasounds for observing the target. Both reception signals can be used for the imagings. As the former type, a large bandwidth one with a backing material, matching layers or a narrow bandwidth one with no backing material similarly to a conventional HIFU applicator can be used. For the large bandwidth one, although a pulse transmission can also be performed, since the transmission energy becomes small, a burst wave transmission or a forced vibration driving can also be performed or additionally for avoiding the decrease in a bandwidth, a chirp wave or a coded wave can also be used similarly to in imaging (The post signal processing increases the spatial resolution finally.). In a case with a narrow bandwidth, although the transmission can also be performed similarly, if the applicator has a fixed focus position determined by the aperture geometry, a continuous wave can also be used as a driving signal. The treatment can be performed not only via a skin or a bone but also under an opened head or abdomen, or with a laparoscope or an endoscope and then, if required, a small physical aperture is used. When the HIFU applicator also works as a sensor, the size can be made small. As the latter type often used, the sensor for observing is set at the central hole in a spherical HIFU aperture. Or, the respective physical aperture arrays for observing and treatment can be aligned, or the respective elements can also be aligned interchangeably or with some period. Particularly, by using a 2D array-type sensor as a sensor for observing, it is useful to perform the 3D treatment in a 3D space. The observation can be performed not only via a skin or a bone but also under an opened head or abdomen, or with a laparoscope or an endoscope and then, if required, a small physical aperture is used. As described in the paragraph 0095, the physical aperture width or the effective aperture width can be optimized. The optimizations can also be performed for a wave shape such as of a pulse wave, a burst wave, a chirp wave or a coded wave, or shapes of driving signals that generate the waves. For instance, they can also be optimized such that at least one of following conditions is satisfied with, the energy is larger than the prespecified value, the bandwidth is larger than the prespecified value, the length of a wave to be generated or a driving signal is shorter than the prespecified value. The kinds of a wave or a driving signal can also be the conditions. The optimization methods include various ones such as linear or nonlinear optimization methods, linear or nonlinear programming methods, etc., and not limited to these.

At least one of the above-mentioned reception signals can be used for calculating the phase aberration (due to the temperature dependency of a sound speed, the inhomogeneity of a sound speed, the directivity of a wave, etc.) for performing the phase aberration correction for the HIFU treatment and the observation imagings, which can increase the accuracy of a treatment position. Based on the observation and prediction results, successively the HIFU beam or the treatment parameter can also be determined via optimizations (Various linear or nonlinear optimizations can be used.). The linear or nonlinear programming can also be effective. With respect to the desired temperature distribution or thermal dose, or the tissue properties such as the (visco) elasticity, etc., or the tissue pressure, the optimizations can also be performed. In the optimizations, typical or practical measurement data of properties of tissues' heat receptions or degenerations, or the models can be used. To realize the minimum-invasive treatment, the present invention utilizes the HIFU exposure power, exposure intensity, exposure time, exposure interval, exposure position (focus position), exposure geometry (apodization), and the HIFU treatment interval, etc., for controlling the HIFU treatment electrically or mechanically, which can be determined on the basis of the above-mentioned observation, prediction, optimization achieved by the signal processings described in the present patent document. In addition to the exposure shape (apodization) and other ultrasound parameters (wave parameters), and the beamforming parameters, the desired wave geometry (1D, 2D or 3D shape) can be used as a target for an optimization (linear or nonlinear optimizations, linear programming, etc. and among others: patent document 12 and nonpatent documents 44 and 45, etc.). With respect to the lesion marked by a clinician or machinery diagnosed, the control of the treatment itself can also be performed by a clinician in a manual fashion with the clinician's judgements based on the observation results, predicted results or the optimized results. Or, the control can also be performed automatically. In the latter case, the treatment direction (or a plan) is always required to be changeable by the clinician. Also, the exchange by the manual control mode must be always possible. Reversibly the exchange from the manual to automatic mode can also be effective. The treatment can be performed not only via a skin or a bone but also under an opened head or abdomen, or with a laparoscope or an endoscope (A small physical aperture is desired.). In both cases, the tracking of lesion is important (The cross-correlation based methods such as the cross-correlation method or the cross-spectrum phase gradient method, etc., are robust to the changes (a noise source) in sequential ultrasound images due to the heating.). The interface can also be generated mainly for the PC and the surrounding instruments or for an exclusive instrument.

This means is one of means for realizing a theranosis. This has high spatial resolutions for a diagnosis as well as a treatment and realizes a proper treatment with as a minimum-invasiveness as possible under the differentiations of lesion tissues, nerves, blood (vessels), lymphs, niches. Properly, these are treated. It is also important for the microsurgery. In addition to an early or initial stage high precision diagnosis, an integration diagnosis (imaging) can be performed, which allows simultaneous and multiple diagnoses of a disease or diseases of a single or plural organs (a brain, a liver, a kidney, a breast, a prostate, a uterus, a heart, an eye, a thyroid, a blood vessel, a skin, etc.) by a single instrument. In addition, a high precision HIFU for the early or initial diseases, can also be performed together with the diagnosis imagings, the monitorings of the treatment effectiveness, follows-up after the treatment using the same indices such as mechanical and thermal quantities, tissue (visco) shear modulus, thermal properties, markers, etc. Since both the diagnosis and the treatment can be performed low-invasively but simply and in a short time, a lower cost medical care can be realized than other techniques. With the development of the medical technology that adapted to the super aging or aged society, a new clinical style (a short diagnosis and treatment, examination, etc.) will be opened up and the developed technology will be useful for a long time in the future. It is effective for the treatment of a pancreatic cancer and a metastasis cancer of the discovery often with much being late. In the meantime, a treatment precision is important. These means can also be effective the radioactive therapy or the heavy particle beam therapy as well as the HIFU therapy. Also effective for the medicine solo or the use together. Also, the wave for the observation is not limited to the ultrasound, various sensing waves such as the MRI, the OCT, the X-ray imagings, etc., can also be used (Others are also described in the patent application document.). These can also be fused or integrated and used simultaneously. When carrying out a diagnosis, a restoration and a manufacturing in a material engineering as well as a medical application, similar observation can be effective.

Elucidation of the function of brain of a human and animals: the processes of learning and recognition, and the effects of dosage of medicine, etc. for the culture neural network can be electrically observed in situ; the heart and the blood vessels of brain (viscoelastic), a blood flow (fluid), and the microflow, etc. can also be high-precisely measured; and the combinations of them can also be used for the developments of the external stimulation tool and processing technique to the tissues and cells.

(ii) Applications to the environment, biotechnology, energy saving and environmental conservation (the recycling, the observing of the air, soil, water, etc.). Various acoustic properties of matter (light pulse, optical microphone); gas including various mine dust (a flow observation by the terahertz), etc.

(iii) Exploring of new synthetic theory (material engineering) such as about an equivalent medium or a function substitute.

Next, the means of above-mentioned (1) to (4), other inverse analyses, (5, fusions/integrations) are enumerated below by items. They are technologies concerned with the information science and statistical mathematics and includes the inverse analyses. Basically, the purpose is to yields higher accuracy than conventional measurement limitations. For instance, the following processings are effective.

(A) Inverse Analyses: For Wave Sensings,

Increase in a processing speed and a stabilization, and data compression using the equalizer or sparse modeling of the system including the observation object (identifying, lowering the dimension, coarse sampling based on the down sampling (with a regularization effect for the inverse analysis), compressing the bandwidth in the Fourier beamforming).

Stabilizations of the solutions by performing the optimizations (a weighted least squares estimation, a Bayesian estimation, a maximum likelihood estimation (being MAP or not), a singular value decomposition, a linear/non-linear programming, a convex projection, etc.) for the inversions for the measurements/reconstructions (Inverse analysis of the Biot-Savart's law: the integral-type inverse problem that the electric current density (vector distribution) data or the electric current data (distribution) are reconstructed from the electromagnetic (vector distribution) data, etc.) or by performing optimizations for the physical property reconstructions (e.g., about the reference region (initial conditions), etc. of linear/non-linear differential-type inverse problem: the new initial-value problem with a partial differential equation, etc.) or the integral-type inverse problem (nonlinear inverse problem such as the impedance problem, etc.).

The existence and the adaptive stabilization of solution by performing the unbiased regularization for the inversion analysis (the spatially and temporally variant regularization which the inventor of the present invention used first in the world, the first in silico standard in the world by setting the regularization parameter much larger to decrease the standard deviation by stabilizing the observation object as much as possible, ones performed for the displacement (vector) observation or the shear modulus reconstruction, etc.).

The standard deviations or variances of the observation objects can be estimated by establishing the error model (standard deviation or variance) of the sensing signals themselves to be directly observed as well as the respective observation objects (strain tensor, temperature, current density vector, respective physical properties, etc.), which were used for increasing the measurement accuracies (For the displacement (vector components) measurement, those estimated under the assumption of a spatially and temporally local region, the Cramer-Rao Lower Bound (CRLB) or the Ziv-Zakai Lower Bound (ZZLB) for the estimation of measurement errors were used such that the a priori or a posteriori regularization parameter became proportional to the variances when performing the regularization for the system (thus, spatially and temporally variant).). Or, the reciprocals of standard deviations or variances were used for weighting the confidence of respective equations comprising a system of equations about the spatio-temporal distributions of various observation objects such as a displacement vector (a weighted least squares estimation). Or, simultaneously the regularization and the weighting onto equations can also be performed.

Super-resolution (the high-resolution, the first in silico harmonic imaging or instantaneous phase imaging in the world, known widely inverse synthetic aperture, inverse filtering, etc.), new minimum variance beamforming (the phase aberration correction is effective.), and high separation ability of signals or sources mentioned above, etc. The maximum likelihood, etc. has been used for a long time for image processings, for instance, the point spread function to be variously estimated, e.g., by estimating the autocorrelation function, etc. can be used (e.g., nonpatent document 31 to 34). Various other methods can also be used.

Linear or nonlinear processing for the wave signals in an analogue or digital fashion; generations and uses of new waves by linear or nonlinear phenomena during the propagation process (inside or outside the observation object); plural waves having the single or different parameters are processed including the cases where the observation objects (quantities such as physics or chemistry) are same or different.

Signal (source) separation or feature analysis (the independent component analysis (ICA), the principle component analysis (PCA), the MUSIC, and the above-mentioned applications of the regularization, the singular value composition, a machine learning, a neural network, and a deep learning, etc.
Not limited to these.
Or,
(B) Integrating and fusing different kind information, and multiplexing a same information and separating independent information (Exceeding the precision limit achievable by a single observation is achieved not by the additional averaging or the least squares estimation but by the high accuracy multiplexing common information and the high accuracy separating independent information.): to increase the precision drastically, multiplexing and separating, etc. by new integration/fusion in signal and image processings, particularly as such of the MRI (electromagnetic wave), the ultrasound (mechanical wave), the ultrasound and the terahertz (simultaneous observations of organic and inorganic ones), the ultrasound (longitudinal wave) and the shear wave (transverse wave), etc., in addition to the KL information, the maximum likelihood, the mutual information minimization/maximization, the entropy minimization, etc., novelly, ICA: For ultrasound echo signals (random signals), by performing the ICA for the high precision phase-matched plural data (phase rotated data, i.e., non-approximately processed digital signals, the extraction ability of common information exceeded that of the additional averaging or the separation ability increased.

Neural network (deep integration learning or integration judgement/recognition): approaches of integrating the learning and the recognition for multiply layered neural network with inputs of different feature vectors (information), which can be realized, for instance, by combining plural neural networks at the 3rd layer (a recognition layer) follows, i.e., after the respective neural networks learn the close data of respective feature vectors (information) to some extent (not deeply) and the networks physically combined as mentioned above learn the close data of all feature vectors (information). This achieves a much higher learning speed and improves a much higher successful recognition rate than an originally physically-combined neural network that learns close data of all feature vectors (information) from at the beginning. By applying the approach to a recognition of hand writing numeric numbers, the successful recognition rate drastically improved than the case using the single feature vector (information). For the analysis of the integration generated, novelly the comparison can be performed with respect to the connection weights of the single learned neural networks, the physically-combined network from at the beginning of learning, and the physically-combined network that deeply learns after the respective networks learned to some extent, for instance, via visualizing the connection weights, or interpreting the common and independent components by performing the ICA or the PCA for the weight distribution. For a differential diagnosis/recognition of disease, etc., novelly the recognition objects such as the kind of diseases or lesions can be coded (independent codes can be used), etc. and can be learned; Or, the mapping of data related to the recognition object, the same kind observed data, the different kind observed data, the related observed data, or the related recognition objects, etc. (for instance, disease or lesions), desired purposes or targets, new properties or new functions (in in silico, creation or generation, or syntheses, and the use; when there exists the difficulty in manufacturing the device or it is simple and cheap, working with other exclusive devices can also be performed.); in addition to various types of neural networks such as the backpropagation type, the Hopfield type (learning or recognition with an associate memory), and performable among others, for various optimizations and other processings such as in silico processings, etc. described in the present invention, similarly the processings can be performed.

For phenomena having different stochastic processes (For instance, an ultrasound scattering signal with the Rayleigh distribution and a noise with the Gaussian distribution), the multiplexing of common components and separating independent components, the elucidation about the translation of some stochastic process to others (changes of stochastic model, stochastic variables, etc.).
Or,
(c) Processing of big data A high-speed and highly precise Fourier beamforming or a parallel computation in a sensing in order to realize a high-speed operation in pursuit of a real time when the big data such as much sensing data (spatio-temporal data), etc. are processed.

Data mining (the above-mentioned statistical processings, correlation processing, ICA, PCA, neural network, etc., including the extractions of features).
Or,
(D) Increasing the SNR of observed signals: For instance, The SNRs of a generally observed terahertz signal, a SQUID signal, a light, etc. are low and then, the analogue correlation processing used in OCT can also be learned, digital processings can also be performed, and the technologies yielding a high precision based on the signal processings such as the ICA (being superior to the additional averaging), the MUSIC, the Wiener filter, the matched filter, the correlation processing, the signal detection, etc. (the signal can be a real or complex signal.) can also be used.

In the present invention, the above-mentioned processings, etc. can be performed, the purposes and the processing means of the present invention are not limited to these.

The measurements/inverse analyses (imagings) (1) to (4) or the fusion/integration (information science and statistical mathematics, etc.) of them carried out with a hardware (device, platform) and a computer becomes innovative technologies (measurement and analysis means) for realizing the in situ non-destructive examinations in a fusion/integration fashion such as of quantity and property distributions for the fundamental physics related to the electromagnetism, mechanics and thermology, and others such as a physics, a chemistry, biochemistry, etc. and in various fields, an innovative measurement (examination or diagnosis), restoration (repairing, treatment or reproduction), manufacturing or production (growths of materials or tissues, or 3D culture), application (new functions and/or properties generated by the syntheses, etc.). This development design to enable that physical quantities/material conditions that have not been caught, and the change and potentiality factors of them, etc. can be detected, and the observation object really working/functioning can be observed from plural aspects, etc. spreads to various fields such as a health promotion of human by a medical care and a life science, a exploring of new engineering based on a material development (including a synthesis), a food engineering (management of a freshness and a quality), a development of a highly efficient energy and a resource exploration, an energy saving, an environmental impact assessment and an environmental conservation (in the earth and the heavenly bodies as well), a weather prediction (weather prediction, precipitation, gas convection, ocean current, etc.), a national security, a satellite, a radar, a sonar, an international standard (the first in silico standard in the world), etc. Thus, the developments have ripple effects being economically and socially great including an industry and a society infrastructure. The developed techniques become the fundamental technologies contributing to the creation of technology innovation and new industry, and a society by all means.

Alternatively, in the beamforming methods (1) to (6), spectral division(s) is implemented on the reception signals stored in memories or storage devices (storage media), generally used for generating image signals for one frame, to yield plural waves with divisions, in a frequency domain, of spectra on which the wavenumber matchings are completed.

The states of angular spectra can also be divided and the respective divisions can also be processed. In both cases, the limited bandwidths of signal components can be processed. When plural waves are superposed, the spectral frequency division(s) can also be similarly performed. Correspondingly, these spectral frequency divisions can yield physically quasi-waves having new wave parameters such as frequencies, bandwidths, propagation directions, etc.). The divided spectra can also be processed in a parallel fashion. The superposing processings are also used for yielding new wave parameters; and to be performed in a spatial domain (corresponding to performing the superposing of angular spectra in a frequency domain) or spectra are superposed in a frequency domain before performing the inverse Fourier transform. If required, angular spectra obtained by Fourier transform can also be superposed, or signals obtained by inverse Fourier transform can also be superposed. Using a reversibility of Fourier transforms (i.e., Fourier and inverse Fourier transforms), the signals before the reception beamforming can be recovered from the generated signals (i.e., reception-beamformed ones). With respect to the signals obtained by a synthetic aperture processing, the signals before the transmission and reception beamformings can be recovered similarly. Using the recovered signals, other beamformings can also be performed, for instance, a beamforming with a different steering angle of transmission and/or reception, beamformings of plural waves with different steering angles with respect to one transmission, etc.

As superresolution processings, a spectral weighting processing (Neither the so-called inverse filtering nor the deconvolution but the filtering with such processings that yielding a desired point spread function simultaneously can be performed.), a nonlinear processing, an instantaneous phase imaging with removing a phase rotation are disclosed below, the DAS processing can also be performed in addition to the Fourier beamforming. For instance, for transmissions of laterally widely spreading waves such as plane waves, circular waves, cylindrical waves, spherical waves for a high-speed imaging mentioned above, and other beamformings, superposing of plural waves with different transmission and/or reception steering angles (i.e., a laterally wide-banded one) as mentioned above can be effectively used for the superresolutions, i.e., with enhancing the effects. The superposing of plane waves, etc. generates a focusing being independent of the depth position in terms of a phase. Thus, according to the spectral weighting processing mentioned above, for instance, a case using Gaussian-type apodizations can be effectively processed by compensating the obtained spectral magnitudes with the spectral magnitudes of a high spatial resolution image obtained by the synthetic aperture processing using a rectangular or power function as apodization functions. The superposing corresponds to the inverse calculations with respect to the angular spectra based on the plane wave separations for the Fourier beamforming. The superposing can also be performed on focused beams or synthetic aperture beams. It is important to control the steering angles of which waves are to be superposed. If the steering angle differences are small, the superposed signals are not widened laterally only in terms of the spectral magnitudes. However, note that the band with relatively small magnitude spectra has a high SNR, which can also be used as a laterally wide-banded one for the spectral weighting processing. Since the superposing is performed on spectra with different phases and the superposed signals have small magnitudes (intensities), precision calculations are required for the beamforming or the superresolutions, etc. if necessary. If there exist the steering angle differences to some extent for the signals to be superposed, the superposed signals having a laterally wide-banded with a large spectra can be obtained simply from a fewer beams/waves. It is effective to superpose waves via normalizations of the wave energies. Similarly, other two superresolutions can become more effective. Or, superposing of waves with different focus positions or ultrasound (wave) frequencies can also be effective for the superresolutions. Although the results of the superresolutions of respective waves can be superposed, calculations become a fewer and effectiveness of superresolution increases by performing the superresolution after superposing the waves. For the superpositions, the phase aberration correction (compensation of an inhomogeneity in an acoustic speed or a wave propagation speed) is important.

The inventor of the present invention has been reporting the cross-spectrum phase gradient method, the multi-dimensional autocorrelation method and among others for observing a displacement vector (a strain tensor) of an observation object based on the ultrasonic echo technique (i.e., a reflection method) or the transmission method. The methods can also be used when using other waves. To increase the measurement accuracy of the techniques, the generation of an over-determined system by using more waves than the lateral modulation (the extension) or by using the spectral frequency division method is effective in addition to the regularization (a priori or a posteriori, or cross-validation method) or the weighted least squares estimation (a priori or a posteriori). The maximum likelihood (e.g., nonpatent document 37, etc.) is also effective (being MAP or not). The fusion/integration or mixing is also effective. When using the standard deviation, it is possible to assume the locally stationary process, to use the Cramer-Rao Lower Bound (CRLB) or the Ziv-Zakai Lower Bound (ZZLB), etc., or to use the standard deviation estimate obtainable based on the so-called 1D autocorrelation method (disclosed later). Furthermore, performing the observation of the displacement vector (strain tensor) can increase the spatial resolution of images (e.g., ultrasound echo images, etc.) obtained from wave signals in a reflection or transmission fashion. For instance, temporally successive frames of plural wave signal frames, etc. (e.g., ultrasound echo data frames) or other images obtained from the wave signal frames can be phase-matched by the present invention, or the motion prediction based on the Markov model can be used for the phase matching. As the results, it is made possible to stochastically fuse them (multiplexing and separating, etc.) by superposing (compounding) or signal separating such as the ICA, etc. Moreover, various superresolutions (e.g., nonpatent document 38, etc.) can be efficiently performed. It is also possible to perform the fusion after performing the superresolution. Although the block matching can also be performed for the phase matching for the processings, particularly the high precise phase matching based on the phase rotation id effective.

And the so-called compressed sensing can also be performed. Similarly, the DAS processing can also be used. Similarly to the three superresolutions mentioned above, the superposing of plural waves can also be used. Although the three superresolutions mentioned above requires a fewer calculations, the combinations, including the compressed sensing, can also be performed.

Here, examples of DAS processings that can be performed in the present invention are summarized. Ones of the present invention, the method DII, etc. are included. Below, the processing of a real time sequence signal or an analytic signal is described and in addition, the processing can be used for signals obtained by various processings described in the present invention as well.

DAS Processing that is Performed for a Conventional Digital Diagnosis Equipment (Method D1)

In order to perform a reception dynamic focusing, for reading out the digital ultrasound signals from the memories of respective channels that store the digital ultrasound signals obtained via analogue-to-digital (AD) conversion, the signals stored in the memories with addresses meaning the digital reception times corresponding to the distances of the reception element positions of respective channels form respective points of interest are read out (i.e., delays). And, the signals read out are summed within the effective aperture (i.e., summation). Since this method yields errors for the delay processing, determined by the sampling frequency of reception signals, the sampling frequency should be as high as possible, even if the frequency is satisfied with the Nyquist theorem. This method has a feature that the processing is fast. Also, the signals to be processed cannot be digital real signals obtained by AD conversions but analogue or digital analytic signals. The processing (calculation) can also be performed with an exclusive circuit or a conventional CPU and below the examples of calculation protocol is described. The time or the spatial coordinate (discrete number) of samplings can be considered as the indices of arrays of a program (cording) or addresses of memories by which the digital signals are stored. This is also the same for other examples.

For instance, for the DAS processing for the point of interest A or the sampling position i=I expressed by the discrete number, the real signal or the analytic signal $$r(I), \quad (DAS1)$$

is added by the real signal or the analytic signal, each of other reception signals obtained by other elements, expressed by using the discrete number $\Delta i$, i.e., $$r'(I+\Delta i), \quad (DAS1')$$

in which the $\Delta i$ is calculated as follows for each of other reception signals r' by discretizing the analogue $\Delta x$ expressing the difference in signal position between the point of interest A and the same signal position I as that of r (i.e., the difference in a propagation distance between the point of interest A and the reception elements): when the sampling interval is expressed by sampx in a distance, $\Delta i$ is calculated by using a discretization function or the corresponding calculation such as $\Delta i = n\ int(\Delta x/sampx)$ using n int(x) expressing the function for rounding off to the nearest discrete number, or $\Delta i = int\ a(\Delta x/sampx)$ using int a (x) expressing the function for rounding up to the nearest discrete number, or $\Delta i = int\ d(\Delta x/sampx)$ using int d(x) expressing the function for rounding down to the nearest discrete number, etc. (When performing a transmission or outward way beamforming as well in the DAS processing such as in a synthetic aperture in a reflection case, $\Delta x$ includes the difference in an outward way propagation distance as well as that in a return path propagation distance.). Since the discrete number $\Delta i$ is desired to be the one making $\Delta i \times sampx$ the nearest to the analogue $\Delta x$, the function 'n int' is the best in the above illustrated functions (not limited to these). Within the effective aperture width with respect to respective positions to be beamformed, all the digital reception signals obtained by the reception elements are processed and summed up as described above. Under the assumption of a constant wave propagation speed, the propagation time can be used similarly instead of the propagation distance for the explanation of calculations. Or, the signal value of the position different by $\Delta x$ can also be calculated with approximate interpolations. There exist various interpolation methods for a digital signal such as a bilinear interpolation, a high order interpolation, the Laglange interpolation, the spline interpolation, etc. and not limited to these.

DAS Processing that is an Improved Version of Method D1 for an Accuracy (Method D2)

For DAS processing performed based on Method D1, in order to increase the accuracies of delay processings, analytic signals a(t) that are calculated via Hilbert transform from the digital reception signals are multiplied by the complex exponential functions to perform phase rotations, i.e., by implementing delays to that can be smaller than the sampling interval sampt onto the digital signals. The summations are performed for the high-accuracy delayed signals.

$$a(t+t_0) = a(t)\exp[j\omega_0(t)t_0], \quad (DAS2)$$

where j is an imaginary unit, t is a sampling time expressed by $t = i \times sampt$ (discrete number, i=0 to N), and $\omega_0(t)$ is the nominal angular frequency, the 1st moment angular frequency of local or global spectra, or the instantaneous angular frequency at the sampling time (position) t. Eq. (DAS2) achieves an approximate calculation of the signal at the time (position) shifted by the analogue distance to in a positive direction of the sampling coordinate with respect to the sampling time (position) t. In the DAS processing at the sampling time (position) expressed by a discrete number, i=I, i.e., a point of interest A itself or a position nearest to the point of interest A, similarly to the method D1, used should be an analytic signal a(t)=a((I+Δi)×sampt) at the sampling time (position) I+Δi expressed by using Δi calculated, for instance, as Δi=n int(Δt/sampt), based on the analogue delay value Δt to be implemented for the corresponding sampling time (position) i=I. When performing a transmission or outward way beamforming as well in the DAS processing such as in a synthetic aperture in a reflection case, the Δt includes the difference in an outward way propagation time as well as that in a return path propagation time. Thus, used should be the signal at the sampling time (position) t nearest to the ideal analogue time (position) T=I×sampt+Δt. When T>t, a positive value $t_0$=T−t=Δt−Δi×sampt is used; and when T<t, a negative value $t_0$=T−t is used. Within the effective aperture width with respect to respective positions to be beamformed, all the digital reception signals obtained by the reception elements are processed and summed up as described above.

Although the accuracy of this method is higher than Method D1, this processing is still approximate one using the frequency $\omega_0(t)$ of the respective sampled times (positions). That is, this processing suffers from the effects of frequency modulations such as by an attenuation or a scattering, etc. Similarly to Method D1, the sampling frequency should be as high as possible. This processing is also fast.

When the sampling signal is expressed not by a time but a discrete position x (=i×sampx, where i is a discrete number, 0 to N−1) obviously, eq. (DAS2) can be expressed using the wavenumber $k_0$ (=$\omega_0$/c=$2\pi f_0$/c=$2\pi/\lambda$, where c is a wave propagation speed, $f_0$ is the nominal frequency, the 1st moment frequency of local or global spectra or the instantaneous frequency, and $\lambda$ is the wavelength) by $$a(x+x_0)=a(x)\exp[jk_0(x)x_0]. \quad \text{(DAS2')}$$

Similarly, in the DAS processing at the sampling position expressed by a discrete number, i=I, i.e., a point of interest A itself or a position nearest to the point of interest A, used should be an analytic signal a(x)=a((I+Δi)×sampx) at the sampling position I+Δi expressed by using Δi calculated, for instance, as Δi=n int(Δx/sampx), based on the analogue distance difference Δx to be implemented for the corresponding sampling position i=I. When performing a transmission or outward way beamforming as well in the DAS processing such as in a synthetic aperture in a reflection case, the Δx includes the difference in an outward way propagation distance as well as that in a return path propagation distance. Thus, used should be the signal at the sampling position x nearest to the ideal analogue position X=I×sampx+Δx. When X>x, a positive value $x_0$=X−x=Δx−Δi×sampx is used; and when X<x, a negative value $x_0$=X−x is used.

Or, in eqs. (DAS2) and (DAS2'), instead that the phase rotations are respectively implemented for the digital signals of the sampling time (position) t and position x nearest to the ideal analogue time (position) T and position x, the following processings can be performed. Considering each sampling position i satisfies x=i×sampx for every generated beam or wave as each point of interest A; and using the above-described delay Δt and distance difference Δx which each reception element position within the effective aperture width has with respect to each point of interest A as the digital data Δt(i) and Δx(i) with respect to each point of interest i, the digital analytic signal a(i) of each reception signal received within the effective aperture width for a beam or a wave is multiplied by a complex exponential function as follows:

$$a(i)\exp[j\omega_0(i)\Delta t(i)] \quad \text{(DAS2'')}$$

or $$a(i)\exp[jk_0(i)\Delta x(i)], \quad \text{(DAS2''')}$$

and the result is summed up about each point of interest i.

DAS Processing that is an Improved Version of Method D2 (Method DII)

Method D2 is an approximate processing in that a frequency or a wavelength of a sampling position is used for an analytic signal. In contrast, Method DII, i.e., a present invention, allows a high-speed calculation without using the frequency nor the wavelength at a sampling position similarly.

The 1st moment (center) frequency of the amplitude spectrum S(i) in a discrete frequency domain of which frequency coordinate is expressed by a natural number i with the discrete Fourier transform, which has zero spectra for a non-positive frequency, is calculated by $$M_0=\Sigma iS(i)/\Sigma S(i), \quad \text{(DASII1)}$$

which is an analogue value for the discrete frequency i and of which amplitude spectrum S(i) (i=0 to N−1) is calculated as a squared root of the multiplication of the conjugate of the discrete Fourier transform of a digital spatial signal r(x) (the sampling position x=i×sampx) and the discrete Fourier transform itself. The addition range i of Σ in the equation is 0 to N/2.

Thus, the wavenumber $k_0$ is expressed by $$k_0=(2\pi M_0)/(N\times sampx). \quad \text{(DASII2)}$$

Here, the analytic signal a(x) is considered as $$a(x) = A(x)\exp\{jk_0(x)x\} \quad \text{(DASII3)}$$
$$= A(x)\exp\{jk_0(x)\times(i\times sampx)\}.$$

Considering each sampling position i satisfies x=i×sampx for every generated beam or wave as each point of interest A; and using the distance difference Δx which each reception element position within the effective aperture width has with respect to each point of interest A as the digital data Δx(i) with respect to each point of interest i, the digital analytic signal a(i) of each reception signal received within the effective aperture width for a beam or a wave is multiplied by a complex exponential function as follows:

$$a(i)\exp\{j(2\pi\Delta x(i)/sampx)/(N\times sampx)\times(i\times sampx)\}=a(i)\exp\{j(2\pi\Delta x(i))/(N\times sampx)\times i\}. \quad \text{(DASII4)}$$

The processing yields an effectiveness that with the larger x (or i) coordinate, the DAS-processed signal has a larger bandwidth (a higher spatial resolution) in the direction orthogonal to the x axis. In eq. (DASII4), instead of i (=0 to N), $$N-i (i=0 \text{ to } N-1) \quad \text{(DASII5)}$$

can also be used. In this case, with the smaller x (or i) coordinate, the DAS-processed signal has a larger bandwidth (a higher spatial resolution) in the direction orthogonal to the x axis. Setting the Δx(i) as a constant regardless the point of interest i allows performing an invariant frequency modulation in the i direction. That is, this processing is that every reception signal received within the effective aperture width is frequency-modulated with respect to the point of interest i by $$M_0+\Delta x(i)/\text{samp}x, \quad \text{(DASII6)}$$

and the result is summed up about each point of interest i. When the signal is expressed as not a digital spatial signal but a digital temporal signal r(t), similarly the analytic signal a(i) expressed using the instantaneous frequency $\omega_0(i)$ can be multiplied by the complex exponential function as follows:

$$a(i)\exp\{j(2\pi\Delta t(i)/\text{samp}t)/(N\times\text{samp}t)\times(i\times\text{samp}t)\}=a(i)\exp\{j(2\pi\Delta t(i))/(N\times\text{samp}t)\times i\}. \quad \text{(DASII4')}$$

This is also for other processings. It is also effective to perform a desired frequency modulation at a specific position or in a spatially uniform fashion. When the modulation wavenumber and modulation frequency are respectively $k_0'$ and $\omega_0'$ to be performed at the position x and time t, the modulation can be achieved by $$a'(x)=a(x)\exp[jk_0'(x)x] \quad \text{(DASII7)}$$

and $$a'(t)=a(t)\exp[j\omega_0'(t)t] \quad \text{(DASII7')}$$

respectively. Similarly, the discrete signals can be processed.

It is also effective to perform the superposing a non-modulated wave or modulated waves to increase the bandwidth (spatial resolution) or the accuracy of a measurement using a phase such as a displacement measurement, etc.

DAS Processing that is Theoretically the Most Accurate (Method D3)

Method D3 is a method previously developed by the present inventor (patent document 6, nonpatent document 15) The delay processing is achieved by multiplying in a frequency domain a complex exponential function to the spectra $A(\omega)$ of local signal including the signal of point of interest, i.e., by rotating the phase of the local signal.

$$A'(\omega)=A(\omega)\exp[j\omega t_0]$$

This processing is an interpolation processing that satisfies the Nyquist theorem. Although the accuracy is the highest theoretically, the long calculation time is required.

Fourier Beamforming (Method D4)

This is one of the basic beamformings of the present invention. This processing yields the same accuracy as that of Method D3 and however, with a much higher speed, by performing the digital wavenumber mapping with respect to the digital reception signal in a multi-dimensional frequency domain obtained using the fast Fourier transform. The processing does not require interpolation processing for the digital wavenumber mapping as a feature being different from other Fourier beamforming methods. If a higher speed is required for the beamforming, interpolation processing can also be performed. However, in that case, artifacts occur. For decreasing the lowering of an accuracy, a high sampling frequency is required.

For these beamforming processings, the analytic signals are not always processed. The calculation time can be decreased by omitting the calculations of analytic signals from reception signals. Although the processings that the complex exponential functions are multiplied to no analytic signals are incorrect theoretically and generate errors, the beamformed signals can be practically used for the imagings of signals themselves or various imagings obtained from the beamformed signals (e.g., elasticity imaging, etc., and among others).

The delay processings in the DAS processings (methods D1 to D3) are effective not only for the DAS processings but also other beamformings such as the Fourier beamforming, the adaptive beamforming, the minimum variance beamforming, etc., or shifting signals in the temporal and/or spatial coordinate system such as the phase aberration correction or the motion correction, the phase matching, the position matching, the position correction, etc. The applications are not limited to these described in the present invention. Similarly to the case of 1D analytic signals, the processings can be performed for the multi-dimensional signals expressed as a function of a position (x,y,z) and/or a time (t1,t2,t3). For instance, for the method D2, the following calculations can be performed in a 2D case, $$a(t1+t1_0,t2+t2_0)=a(t1,t2)\times\exp[j\{\omega1_0(t1,t2)t1_0+\omega2_0(t1,t2)t2_0\}] \quad \text{(2DAS2)}$$

and $$a(x+x_0,y+y_0)=a(x,y)\times\exp[j\{kx_0(x,y)x_0+ky_0(x,y)y_0\}], \quad \text{(2DAS2')}$$

and in a 3D case, $$a(t1+t1_0,t2+t2_0,t3+t3_0)=a(t1,t2,t3)\times\exp[j\{\omega1_0(t1,t2,t3)t1_0+\omega2_0(t1,t2,t3)t2_0+\omega3_0(t1,t2,t3)t3_0\}] \quad \text{(3DAS2)}$$

and $$a(x+x_0,y+y_0,z+z_0)=a(x,y,z)\times\exp[j\{kx_0(x,y,z)x_0+ky_0(x,y,z)y_0+kz_0(x,y,z)z_0\}]. \quad \text{(3DAS2')}$$

Here, $(\omega1_0,\omega2_0,\omega3_0)$ expresses the nominal angular frequencies, the 1st moment (center) angular frequencies and the instantaneous frequencies in the respective temporal directions at each time (t1,t2,t3); and $(kx_0,ky_0,kz_0)$ expresses the wavenumbers in the respective spatial directions at each position (x,y,z). The multi-dimensional signals expressed as a function of the combinations of a position (x,y,z) and a time (t1,t2,t3) can also be shifted similarly. That is, for a digital signal, an analogue-like shifting can be performed in the discrete coordinate system using the nominal angular frequencies, the 1st moment (center) angular frequencies, and the instantaneous frequencies in the respective temporal directions at each time or using the wavenumbers in the respective spatial directions at each position (When the higher accuracy is required, the sampling frequencies should be higher.). Similarly to the 1D case, the accuracy is higher than the method D1 (i.e., a block matching of the signals in a spatial and/or temporal domain), and the accuracy is lower than other methods (method D3 with phase matching based on the phase rotation in a frequency domain and method D4 with Fourier beamforming) and however, the calculation speed is faster. The usage of method D2 is proper when requiring a high-speed calculation.

Similarly to the 1D analytic signal, the modulation of method DII can also be performed for the multi-dimensional analytic signals expressed as a function of a position (x,y,z) and/or a time (t1,t2,t3).

For instance, the calculations can be performed in a 2D case, $$a'(x,y)=a(x,y)\exp[j\{kx_{0'}(x,y)x+ky_{0'}(x,y)y\}] \quad \text{(2DASII7)}$$

and $$a'(t1,t2)=a(t1,t2)\exp[j\{\omega1_{0'}(t1,t2)t1+\omega2_{0'}(t1,t2)t2\}], \quad \text{(2DASII7')}$$

and in a 3D case, $$a'(x,y,z)=a(x,y,z)\exp[j\{kx_{0'}(x,y,z)x+ky_{0'}(x,y,z)y+kz_{0'}(x,y,z)z\}] \quad \text{(3DASII7)}$$

and $$a'(t1,t2,t3)=a(t1,t2,t3)\exp[j\{\omega1_{0'}(t1,t2,t3)t1+\omega2_{0'}(t1,t2,t3)t2+\omega3_{0'}(t1,t2,t3)t3\}]. \quad (3DASII7')$$

Here, $(kx_{0'}, ky_{0'}, kz_{0'})$ expresses the modulation wavenumbers in the respective spatial directions at each position $(x,y,z)$; and $(\omega1_{0'}, \omega2_{0'}, \omega3_{0'})$ expresses the modulation frequencies in the respective temporal directions at each time $(t1,t2,t3)$. The multi-dimensional signals expressed as a function of the combinations of a position $(x,y,z)$ and a time $(t1,t2,t3)$ can also be processed similarly. Including the 1D case, the applications are not limited to the DAS processings.

Other delay processings can also be performed multi-dimensionally for a multi-dimensional signals.

The beamforming method related to other viewpoints of the present invention includes that for all beamformings including the Fourier beamformings above-described in methods (1) to (6) and (7), DAS processings and among others, by using at least more than two array-type aperture elements (≤2) being adjacent or not with not always a constant distance are used as one aperture (combined elements) by implementing the same delay or the same apodization of a transmission or a reception onto the physical elements, a higher intensity of wave can be used for the transmission and/or reception beamforming than that of wave generated by a single physical element transmission or reception, where the respective physical elements can also be driven independently and can also be used for obtaining reception signals independently, i.e., the respective physical elements can have independent channels for a transmission and a reception. This invention is effective when the intensity of a transmission or reception wave is small, for instance, when a physical element width or a physical element pitch (interval) is shorten to increase the spatial resolutions in the axial and lateral directions for a 1D-array-type transducer; when using a 2D or the higher dimensional array-type transducer with small physical elements (When the physical element width or the physical element pitch becomes shorter, the intensity further decreases.); and for an ultrasound, when increasing the frequency by making the element thickness small; when using PVDF, etc. having a smaller transmission intensity than PZT, etc. That is, by increasing the intensity of a transmission or reception wave, the SNR of reception signal received by the reception transducer can be increased. For instance, the processing is effective for performing a classical synthetic aperture (a monostatic or multistatic type). The scanning can be performed as follows: the effective aperture (width) can also be moved with a distance (an interval) being the same as one pitch, an arbitrary pitch or a changeable pitch of physical elements. For a multi-dimensional array-type transducer, different number of elements or different distances (intervals) can also be used for the scanning in different directions. The above-described adjacent or not physical elements to be used as one aperture (a combination) can also be changed during the scanning. Or, the effective aperture width can also be changed during the scanning similarly to conventional beamformings. The processings can be performed for various array-type transducers and the processings can be performed for an analogue instrument or a fusion of analogue and digital instrument (for instance, the transmission circuit including a transmission delay or a transmission apodization, etc. is analogue) as well as a digital instrument. In addition to the above-mentioned beamforming parameters or the above-mentioned wave parameters if required, the number of physical elements or their positions (combination) to be used for one transmission or reception aperture, or the effective transmission or reception aperture width, the moving distance (interval) of the effective transmission or reception aperture in the processings are similarly used for performing various applications described in the present invention. If required, plural effective apertures are used together for generating plural waves or beams (simultaneous transmissions, or transmissions at different times, however, at the same phase of the observation object). For a transmission or a reception for a classical synthetic aperture or conventional beamformings, at least within an effective aperture width, the physical elements (at least one physical element) used for one aperture (combination) can also be used for other apertures (combinations). When performing a mechanical scanning of the observation object with a high intensity wave generated by using a transducer with arrayed physical elements or a single physical aperture with large aperture widths (the transmission or reception position changes in a digital or analogue fashion), the beamforming can also be performed for transmissions or receptions performed densely or sparsely with respect to the physical aperture width.

When performing respective receptions with one or plural physical elements with respect to one physical element driving (firing), the addition of reception signals can also yield the same effect as that achieved by driving plural physical element simultaneously. With respect to the simultaneous plural physical element drivings (firings), performing respective receptions with one or plural physical elements and the addition processing with respect to the receptions can also yield the same effect similarly. Also for performing a transmission beamforming by driving the physical elements within the effective aperture width, various combinations of plural physical elements within the effective aperture width are respectively used to perform the simultaneous transmissions. The transmissions can also be performed from plural effective apertures (widths) simultaneously.

Performing the simultaneous transmissions from plural physical elements in various fashions as mentioned above is equivalent to increasing the transmission physical element width or pitch, which can generate grating lobes. Thus, as mentioned above, also the transmission element width (the combined or physical element width) is made large and the transmission pitch can be made smaller than the width. The physical element width or pitch can also be large (Mechanical scanning can allow correcting signals more densely than the physical element width or pitch.). These results depend on the wave's carrier frequency or steering angle (including zero degree) and the directions of grating lobes to be generated can also be estimated by geometrical calculations.

In the first place, side lobes can also be generated from the physical aperture element. Usually, to decrease the grating or side lobes leading to artifacts (virtual images), beamformings are performed with optimized, element width or pitch, element geometry, wave's carrier frequency, steering angle, apodization, etc. Although the sensitivities of a transmission and a reception are different in practice, the sensitivities can be considered to be same in many cases. Grating or side lobes can also be generated only for a reception beamforming similarly; and grating or side lobes can also be generated for both a transmission and a reception, and when using different elements or different combinations of elements for the transmission and reception, the grating or side lobes to be generated are different.

As the inventor of the present invention disclosed in the patent document 7 or nonpatent document 19, it is possible to separate waves with different steering angles in a frequency domain (also see the paragraph 0623). A steering angle or a wave propagation direction generated in practice can also be estimated from the 1st moments of spectra or the instantaneous frequencies of analytic signals corresponding to the spectra. It is also possible to estimate the refraction of wave. This method can also be used for separating or removing the grating or side lobes from the main lobes. Usually, the spectra corresponding to the grating or side lobes are being separate in a frequency domain and then, it is simple to specify or separate them (Only the noticed spectra can be extracted, or the spectra of other bandwidths can be exchanged by zero spectra.).

In fact, these grating or side lobes can be used in a raw fashion or after implementing some processing to yield the so-called lateral modulation (LM) to be performed for various applications such as a wave imaging or a displacement (vector) observation, etc. Usually, the LM wave is referred to as one generated by crossed waves, and the LM wave can be separated into the respective steered waves to perform the applications (Simultaneously, a weighting can also be performed.). For these, for instance, the separated waves can be respectively detected to yield images of the corresponding incoherent signals, and the superposition (compounding) of the generated incoherent signals can be performed to yield an image with suppressed speckles. Or, for a coherent signal, the corresponding spectra can also be divided into partial spectra of some bandwidths (or weighted) to synthesize new coherent signals. At least one new wave having at least one different parameter such as a steering angle, etc. can be generated, the respective waves can be detected to perform the imagings, or the images can also be superposed to perform the imaging similarly. Or, the respective coherent signals generated by these processings can also be used for observing a displacement, or the coherent signals can also be used simultaneously for holding simultaneous equations or an over-determined system to be solved for a displacement or displacement vector components. Some of waves corresponding to the grating or side lobes can have larger steering angles than the steering angle set for the beamforming and in such a case, totally the lateral frequency can become higher than that in a case where the grating or side lobes are not generated. Using such waves also increases the measurement accuracies of a lateral displacement (nonpatent document 19) and a displacement vector. The generated grating or side lobes can include those having larger or almost the same angle with respect to the steering angle set for the beamforming, all the corresponding waves can also be used together with the purposely beamformed wave. Since the grating or side lobes having the higher lateral frequencies have the lower signal intensity in the plurally generated grating or side lobes, the corresponding spectra can be disregarded by exchanging them by zero spectra in terms of the lower SNRs or the corresponding spectra can be used together with those having the lower lateral frequencies as wave components (i.e., a case not used solo). Similarly to a usual steered beamforming, a lateral frequency increasing, the frontal frequency decreases. For the displacement vector measurement, however, the increase in a measurement accuracy of a lateral displacement can overcome the decreasing of the frontal frequency, and the measurement accuracy of the displacement in the frontal direction can also increase.

The digital signal unit uses the plural waves generated using these processings to measure, with a high accuracy, a displacement vector expressing the object's displacement in an arbitrary direction (the multi-dimensional autocorrelation method or the multi-dimensional Doppler method, etc. for solving simultaneous equations on unknown displacement vector components (past inventions of the present invention's inventor, nonpatent document 13)) or a general one-directional displacement (high accuracy measurements can also be obtained by performing the least squares solution, the averaging of plural measurements obtainable or the increasing frequencies and bandwidths of signals owing to superposition of spectra on over-determined systems with the larger number of derived equations as that of unknown displacement components, patent document 5). From each generated wave, an equation is derived. The general Doppler method can also be implemented on a wave. The respective waves can also be superposed ones, the spectral-frequency-divided ones and the spectral processed ones. The respective waves are desired to be high frequencies and then, can also be the low-frequency-spectra disregarded ones; and besides when a high spatial resolution is also required, the waves are desired to be large bandwidths (nonpatent document 14). For the divisions and processings on spectra, windows allowing weighting the spectra can also be used. From the measured displacement (vector), a strain (tensor), a strain rate (tensor), a velocity (vector), an acceleration (vector) can be obtained by implementing partial derivative processings using spatial and/or temporal differential filters. These can also be used for calculating the (visco) shear modulus or viscosities, the mean normal pressure, the density, etc. As other displacement (vector) measurement methods such as the multi-dimensional cross-spectrum phase gradient method (one of block matching methods, patent document 6 or nonpatent document 15, etc.) or the digital demodulation method (patent document 7) can also be used for the measurements of a strain, etc. similarly. Using these methods, measurements of wave propagations such as a shear wave or low frequency vibrations can also be performed. The (visco) shear modulus, the shear wave propagation speed and/or direction, the displacement of a shear wave, the frequencies, the phase, the vibration amplitude, the vibration velocity and the vibration acceleration, etc. can be measured. These can also be calculated as distributions.

To increase the accuracies of the displacement measurements, previously the inventor of the present invention developed the implementing of the regularization. To determine the regularization parameters of penalty terms, for instance, the standard deviation (SD) of displacement (vector) measurements is estimated under the (local) stationary process and used a posteriori (patent document 6) or Ziv-Zakai Lower Bound (ZZLB: for instance, the lower bound of standard deviation (SD) shown in the nonpatent document 16) is estimated using the properties of the wave or beam, etc. and used a priori (for instance, nonpatent documents 17 and 18). It is also possible to use or perform the application of the standard deviation (SD) led for the 1D autocorrelation method being a 1-directional velocity measurement method (nonpatent document 20. The SD is used for the power Doppler.).

In the present invention, these standard deviations (SDs) or ZZLB can also be used for weighting the above-mentioned, derived Doppler equations to control the confidences of the respective equations when holding the simultaneous equations (A high confidence equation is weighted heavily and a low confidence equations is weighted lightly). That is, the weight values are calculated with respect to the above-mentioned respective waves or beams at respective position in an ROI and the equations, derived from the respective waves or beams at the positions, are correspondingly weighted using the weighted values and are solved. Using the least squares solutions, the weighted least squares solution (WLSQS) can be calculated a posteriori or a priori.

The simultaneous equations of the above-mentioned, derived Doppler equations are expressed as follows.

$$Au=b, \tag{A1}$$

where u is an unknown displacement vector of a position of interest or a local region including the position of interest, or the distribution; b is a change in a phase, generated between frames, of the point of interest or the local region including the position of interest, or the distribution; A is a matrix lexicographically comprising of frequencies of the point of interest or the local region including the position of interest, or the distribution. The components of A and b can be moving-averaged in a temporal or spatial direction. When the demodulations are performed at least in one direction, the equations are derived for Doppler equations about unknown displacement components in one or two directions with carrier frequencies.

The matrix W expressing the distribution of the reciprocals of SDs or ZZLBs, themselves, or the exponentiations or the distribution is used for weighting eq. (A1) and the following simultaneous equations are solved.

$$WAu=Wb \tag{A2}$$

Specifically, let's focus on one position of interest or one local region. With respect to one Doppler equation (or plural equations, i.e., simultaneous equations, derived using the cross-spectrum phase gradient method, comprising of equations hold regarding phase spectra in signal bandwidths calculated from the cross-spectra estimated for the local region or simultaneous equations, derived when performing the block matching using the multi-dimensional autocorrelation method or the multi-dimensional Doppler method, comprising of equations hold at respective positions in the local region) derived from one of waves or beams p (=1 to N), since the reciprocal of SD or ZZLB Wp calculated at the position or at the local region is that about the displacement in the beam direction, when the unknown displacement is a 3D vector $u=(Ux,Uy,Uz)^T$, the following equations hold.

$$Wp(AxpUx+AypUy+AzpUz)=Wpbp \tag{A3}$$

where Axp, Ayp and Azp (p=1 to N) are the frequencies in the x, y and z directions and they are components of the matrix A in eqs. (A1) and (A2); bp (p=1 to N) is the change in phase between the frames and it is components of the vector b; Wp is diagonal components of W in eq. (A2). When using the cross-spectrum phase gradient method (one of block matching methods) or the multi-dimensional autocorrelation method or the multi-dimensional Doppler method as block matching methods, all the simultaneous equations hold with respect to the local region are multiplied with Wp (i.e., with respect to one p, plural equations simultaneously hold and all the equations are multiplied with Wp).

For instance, according to the ZZLB mentioned in the nonpatent document 16, when the Cramer-Rao Lower Bound (CRLB) holds, the variance that is the square of CRLB is expressed as follows.

$$\sigma^2_{CRLB} = \frac{3}{2\pi^2 T(B_b^3 + 12 B_b f_{0b}^2)}\left\{\left(1+\frac{1}{SNR_c}\right)^2 -1\right\} \tag{A4}$$

where T is, for the multi-dimensional autocorrelation method or the multi-dimensional Doppler method, a moving-average width used for calculating the frequency or the change in phase, and for the block matching methods such as the multi-dimensional cross-spectrum phase gradient method, the multi-dimensional autocorrelation method or the multi-dimensional Doppler method, a length of local region used for the measurement (When T is same for simultaneous beams or equations, T is not required to be used and an arbitrary constant can be used.); $f_{Ob}$ is an ultrasound frequency in the beam direction; $B_b$ is a rectangular bandwidth in the beam direction; SNRc is a combined SNR by expressed using an echo SNR, SNRe, and a correlation SNR, SNRρ (a signal-to-noise ratio regarding the noise components generated by a decrease in echo correlation due to the distortion of signal wave caused by object's displacement or deformation itself):

$$SNR_\rho = \frac{\rho}{1-\rho} \tag{A5}$$

where ρ is correlation estimated at calculating a local cross-spectra between the frames or the local correlation estimated using the moving-average width, i.e., $$SNR_c = \frac{SNR_\rho SNR_e}{1+SNR_\rho + SNR_e} \tag{A6}$$

Thus, the SD can be estimated, for instance, as mentioned in the nonpatent document 17, by using T, $f_{Ob}$, $B_b$, SNRc, SNRe, SNRρ, ρ (including measured or estimated ones). Instead the measurements, an arbitrary constant or a typical value can also be used. $f_{Ob}$ is, as mentioned in the nonpatent document 19, an instantaneous frequency or the 1st order moment (i.e., weighted mean) that can be estimated, and $B_b$ is the square root of the 2nd order center moment that can be estimated.

$$f_{Ob}=\int f_b S(f_b) df_b \tag{S1}$$

and $$B_b = \sqrt{\int (f_b - f_{Ob})^2 S(f_b) df_b} \tag{S2}$$

where $f_b$ is a frequency in the beam direction, $S(f_b)$ is a spectrum of the frequency $f_b$.

$S(f_b)$ in eqs. (S1) and (S2) are normalized ones by the total energy calculated using a raw spectra and $f_b=1$ in eq. (S1) such that the total energy becomes 1. Or, the raw spectra $S(f_b)$ can be used for eqs. (S1) and (S2) and the calculation results can be respectively divided by the above-mentioned total energy, which require a fewer calculations totally. For $B_b$ calculated by eq. (S2), one converted from that of a practical spectral geometry or a practical transmission or reception pulse geometry to that of rectangular spectra can also be used (This is also when the 2nd order center moment is used as below). In the cases of the multi-dimensional signals, the calculations can also be performed using the two axes (i.e., 3D) or one axis (i.e., 2D) orthogonal to the beam direction as well and for instance, in the cases of 3D, $$f_{Ob}=\int f_b(f_x,f_y,f_z) S(f_x,f_y,f_z) df_x df_y df_z \tag{S1'}$$

and $$B_b = \sqrt{\int (f_b(f_x,f_y,f_z)-f_{Ob})^2 S(f_x,f_y,f_z) df_x df_y df_z}, \tag{S2'}$$

where $f_b(f_x, f_y, f_z)$ is a frequency in the beam direction at frequencies $(f_x, f_y, f_z)$ and $S(f_x, f_y, f_z)$ is a spectrum of the frequencies $(f_x, f_y, f_z)$; and in the cases of 2D, using a spectrum $S(f_x, f_y)$ of frequencies $(f_x, f_y)$ and in the cases of 1D, using a spectrum $S(f_x)$ of a frequency $(f_x)$, similarly the calculations can be performed.

Similarly, the spectra in eqs. (S1') and (S2') are normalized ones such that the total energy becomes 1. Or, similarly the raw spectra can be used for eqs. (S1') and (S2') and the calculation results can be respectively divided by the above-mentioned total energy, which require a fewer calculations totally. For $B_b$ calculated by eq. (S2'), one converted from that of a practical spectral geometry or a practical transmission or reception pulse geometry to that of rectangular spectra can also be used (This is also when the 2nd order center moment is used as below).

The echo SNRs, SNRe, can be statistically estimated by sampling echo data at the respective positions of interest iteratively from the object or calibration phantoms. On the basis of the object or the conditions, or experiences on the measurements, it is also possible to determine SNRe using typical values a priori. Alternatively, the correlation SNRs, SNRρ, can be estimated using the correlations p estimated locally at the respective positions of interest. How to calculate these is not limited to these. If some values cannot be used and then the SDs cannot be estimated absolutely, typical values can be used for the unknown values. When setting the regularization parameters, by judging whether the results obtained with changing an unknown constant to be multiplied to the SDs, ones calculated using available data, are good or not, the best constant can also be determined (regarding the regularizations, for instance, patent document 6 and nonpatent documents 17 and 18).

Or, for using or performing the application of a standard deviation (SD) led for the 1D autocorrelation method being a 1-directional velocity measurement method (nonpatent document 20. The SD is used for the power Doppler.), when the autocorrelation function is expressed for the slow-time-axis τ by $$R(\tau)=|R(\tau)|\exp\{i\emptyset(\tau)\} \quad (AUTO1)$$

the mean and the variance of a Doppler angular frequency ω are respectively expressed by $$\overline{\omega} = -i\frac{R'(0)}{R(0)} = \emptyset'(0) \quad (AUTO2)$$

and $$\sigma^2 = \overline{\omega^2} - \overline{\omega}^2 \quad (AUTO3)$$
$$= -\frac{R''(0)}{R(0)} + \left(\frac{R'(0)}{R(0)}\right)^2$$
$$= -\frac{|R(\tau)|''_{\tau=0}}{R(0)}$$
$$= -\frac{R''(0)}{R(0)} - (\emptyset'(0))^2$$

If the velocity in the beam direction is a constant within a period of a pulse repetition I, approximately the mean can be estimated by $$\overline{\omega} \approx \frac{\emptyset(I)}{I} \quad (AUTO2')$$

and further the pulse repetition period I is short, approximately the variance can be estimated by $$\sigma^2 \approx \frac{2}{I^2}\left[1 - \frac{|R(I)|}{R(0)}\right] \quad (AUTO3')$$

Here, R(0) can also be calculated form the integration of a signal energy or power spectra based on the Wiener-Khinchin theorem.

The above-described autocorrelation method is not explained using a spatial coordinate. Actually, the statistical estimations can be performed for 1D local region signals in a beam direction at a point of interest, or 2D or 3D local region signals at a point of interest, i.e., 1D, 2D or 3D moving-averaging can be performed as specifically described in nonpatent documents 13 and 19, for instance. For the 2D or 3D local region, the beam direction is not required to be the direction of an axis of the orthogonal coordinate system (a Cartesian or curvilinear coordinate) of the local region and the estimated mean and variance express those of a velocity in the beam direction of the local region or the point of interest.

Thus, the respective mean and variance of the displacement in the beam direction can be calculated by multiplying I and $I^2$ to eq. (AUTO2) or (AUTO2') and eq. (AUTO3) or (AUTO3'), respectively. Here, the measurement using an SD of a displacement for a weighting is shown and similarly, the measurement using an SD of a velocity or an acceleration for a weighting being also able to be estimated from a Doppler equation about the velocity or the acceleration can also be performed.

Here, when the 1st order moment or the 2nd order center moment in the beam direction is not directly estimated and instead, those in the respective directions are estimated (for instance, in the 3D cases of signals, the 1st order moment $f_{0x}$ and the 2nd order center moment $B_x$ are $$f_{0x}=\int f_x(f_x,f_y,f_z)S(f_x,f_y,f_z)df_xdf_ydf_z \quad (S1'')$$

and $$B_x=\sqrt{\int(f_x(f_x,f_y,f_z)-f_{0x})^2 S(f_x,f_y,f_z)df_xdf_ydf_z} \quad (S2'')$$

where $f_x(f_x, f_y, f_z)$ is a frequency in x-axis direction of frequencies $(f_x, f_y, f_z)$, and $S(f_x, f_y, f_z)$ is a spectrum; in the 2D cases, using the spectrum $S(f_x, f_y)$ at frequencies $(f_x, f_y)$ and in the 1D cases, using the spectrum $S(f_x)$ at a frequency $(f_x)$, the calculation can be performed similarly; and also in y- and z-axis directions, the calculations can be performed similarly), or other methods from the ZZLB are used and SD of the displacement in the beam direction is not directly estimated and instead, SDs of the displacement vector components in the respective directions are estimated, the following estimations can be performed. That is, under the assumption that the stochastic processes of the displacement component measurements are independent each other, the propagations of the respective measurement errors to the estimation error of the displacement in the beam direction are considered. For instance, when the respective means and SDs of 3D displacement vector components are estimated as (mx,σx), (my,σy) and (mz,σz), the mean $m_{beam}$ and SD $\sigma_{beam}$ of the displacement in the beam direction can be respectively estimated as follows.

$$m_{beam} = \sqrt{m_x^2 + m_y^2 + m_z^2} \tag{A7}$$

$$\sigma_{beam} = \sqrt{\frac{m_x^2 \sigma_x^2 + m_y^2 \sigma_y^2 + m_z^2 \sigma_z^2}{m_x^2 + m_y^2 + m_z^2}} \tag{A8}$$

Using the mean $m_{beam}$ and SD $\sigma_{beam}$, the SD of the displacement in the beam direction $\sigma_{CRLB}$ can be estimated.

When the parameters (T, $f_{0b}$, $B_b$, SNRc, SNRe, SNRρ) described in eqs. (A4) to (A6) are provided in the respective directions; and then the means of the displacements $f_{0x}$, $f_{0y}$ and $f_{0z}$ in the respective directions and the SDs of the displacements $\sigma_{CRLBx}$, $\sigma_{CRLBy}$ and $\sigma_{CRLBz}$ in the respective directions can be estimated, the SD of the displacement $\sigma_{CRLB}$ in the beam direction can be estimated using eq. (A8) as follows.

$$\sigma_{CRLB} = \sqrt{\frac{f_{0x}^2 \sigma_{CRLBx}^2 + f_{0y}^2 \sigma_{CRLBy}^2 + f_{0z}^2 \sigma_{CRLBz}^2}{f_{0x}^2 + f_{0y}^2 + f_{0z}^2}} \tag{A9}$$

When the unknown displacement at a position of interest is a 2D vector $u=(Ux,Uy)^T$, similarly the SD of the displacement in the beam direction can be calculated (When the unknown displacement is only a component and is a displacement U in an arbitrary direction or in a beam direction, the estimate of SD itself is used).

$$m_{beam} = \sqrt{m_x^2 + m_y^2} \tag{A7'}$$

$$\sigma_{beam} = \sqrt{\frac{m_x^2 \sigma_x^2 + m_y^2 \sigma_y^2}{m_x^2 + m_y^2}} \tag{A8'}$$

$$\sigma_{CRLB} = \sqrt{\frac{f_{0x}^2 \sigma_{CRLBx}^2 + f_{0y}^2 \sigma_{CRLBy}^2}{f_{0x}^2 + f_{0y}^2}} \tag{A9'}$$

When calculating the displacement at the respective positions of interest or at the respective local regions regarding the positions of interest, the simultaneous equations (A2) of the weighted Doppler equation (A3) [p=1 to N] holding at the positions of interest are solved. The number of waves or beams (i.e., the number of equations) N is required to be larger than the number of unknown displacement components. However, note that when performing the above-mentioned block matching, as mentioned above, plural equations of eq. (A3) holds on one wave or one beam p. Thus, compared with other displacement measurement methods, a fewer waves or beams can also be used for the measurements.

When performing the regularizations simultaneously, eq. (A2) of which unknown vector u is the displacement component distributions is obtained by simultaneously deriving all eqs. (A3) holding at the plural positions of interest or at the plural local regions set on the positions of interest in an ROI, and the regularized weighted least squares solution (RWLSQS) can be calculated. To set the regularization parameters, the SDs or the ZZLB can be used (values being proportional to the SDs or the exponentiations, etc.). Regarding the regularizations, for instance, see the patent document 6. The above-mentioned SDs of the displacements in the respective wave propagation directions or beam directions can also be used for setting the regularization parameters of the displacement components in all directions, and the SDs of the displacements in the respective wave propagation directions or beam directions can also be used for setting the regularization parameters of the displacement components in the respective directions. For instance, regarding the distribution of an unknown 3D displacement vector $(Ux,Uy,Uz)^T$, when calculating the unknown vector $U=(Ux,Uy,Uz)^T$ comprising of the partial unknown vector Ux, Uy and Uz being the distributions of the respective displacement components Ux, Uy and Uz in the x, y and z directions, the error energy, expressed using the matrix W comprising of the SDs Wp (p=1 to N) of the displacements in the respective beam directions at respective positions as diagonal components or using the matrices Wx, Wy and Wz respectively comprising of the SDs Wpx, Wpy and Wpz (p=1 to N) of the respective displacement components at respective positions as diagonal components, to be least-squares-minimized E(u) and the solution u are expressed as follows.

$$E(u) = \|b - Au\|^2 + \alpha_0 \|u\|_W^2 + \alpha_1 \|Du\|_W^2 + \alpha_2 \|D^T Du\|_W^2 = \tag{A10}$$
$$(b - Au)^T (b - Au) + \alpha_0 u^T W^T W u + \alpha_1 u^T D^T W^T W D u + \alpha_2 u^T D^T D W^T W D^T D u,$$

and then, $$(A^T A + \alpha_0 W^T W + \alpha_1 D^T W^T W D + \alpha_2 D^T D W^T W D^T D) u = A^T b$$

or $$E(u) = \|b - Au\|^2 + \alpha_{0x} \|u_x\|_{W_x}^2 + \alpha_{0y} \|u_y\|_{W_y}^2 + \alpha_{0z} \|u_z\|_{W_z}^2 + \alpha_{1x} \|Du_x\|_{W_x}^2 +$$
$$\alpha_{1y} \|Du_y\|_{W_y}^2 + \alpha_{1z} \|Du_z\|_{W_z}^2 + \alpha_{2x} \|D^T Du_x\|_{W_x}^2 + \alpha_{2y} \|D^T Du_y\|_{W_y}^2 + \alpha_{2z} \|D^T Du_z\|_{W_z}^2,$$

-continued and then, $$\left(A^T A + \begin{pmatrix} \alpha_{0x} W_x^T W_x & 0 & 0 \\ 0 & \alpha_{0y} W_y^T W_y & 0 \\ 0 & 0 & \alpha_{0z} W_z^T W_z \end{pmatrix} + \begin{pmatrix} \alpha_{1x} D^T W_x^T W_x D & 0 & 0 \\ 0 & \alpha_{1y} D^T W_y^T W_y D & 0 \\ 0 & 0 & \alpha_{1z} D^T W_z^T W_z D \end{pmatrix} + \begin{pmatrix} \alpha_{2x} D^T D W_x^T W_x D^T D & 0 & 0 \\ 0 & \alpha_{2y} D^T D W_y^T W_y D^T D & 0 \\ 0 & 0 & \alpha_{2z} D^T D W_z^T W_z D^T D \end{pmatrix}\right) \begin{pmatrix} U_x \\ U_y \\ U_z \end{pmatrix} = A^T b \quad (A10')$$

and in the respective equations where $\alpha_0$, $\alpha_1$, $\alpha_2$, $\alpha_{0x}$, $\alpha_{0y}$, $\alpha_{0z}$, $\alpha_{1x}$, $\alpha_{1y}$, $\alpha_{1z}$, $\alpha_{2x}$, $\alpha_{2y}$, and $\alpha_{2z}$ are regularization parameters; D is the gradient operator; $D^T D$ is the Laplacian operator. Here, in the 1st term of E (U) in eq. (A10) and eq. (A10'), the descriptions about the weighting processings using the reciprocal of a beam-directional displacement SD expressed in eq. (A2) and eq. (A3) are omitted. To distinguish the weighting matrix W (i.e., comprising of the reciprocals of displacement SDs) used in eq. (A2) and eq. (A3) from the different weighting matrix W used in eq. (A10), the matrix X is used for the matrix W of eqs. (A2) and (A3) instead as follows:

$$E(u) = \|b - Au\|_X^2 + \alpha_0 \|u\|_W^2 + \alpha_1 \|Du\|_W^2 + \alpha_2 \|D^T Du\|_W^2 =$$
$$(b - Au)^T X^T X (b - Au) + \alpha_0 u^T W^T W u +$$
$$\alpha_1 u^T D^T W^T W D u + \alpha_2 u^T D^T D W^T W D^T D u$$

and then, $$(A^T X^T X A + \alpha_0 W^T W + \alpha_1 D^T W^T W D + \alpha_2 D^T D W^T W D^T D)u = A^T X^T X b \quad (A10'')$$

or $$E(u) = \|b - Au\|_X^2 + \alpha_{0x}\|u_x\|_{W_x}^2 + \alpha_{0y}\|u_y\|_{W_y}^2 + \alpha_{0z}\|u_z\|_{W_z}^2 + \alpha_{1x}\|Du_x\|_{W_x}^2 +$$
$$\alpha_{1y}\|Du_y\|_{W_y}^2 + \alpha_{1z}\|Du_z\|_{W_z}^2 + \alpha_{2x}\|D^T Du_x\|_{W_x}^2 + \alpha_{2y}\|D^T Du_y\|_{W_y}^2 + \alpha_{2z}\|D^T Du_z\|_{W_z}^2$$

and then, $$\left(A^T X^T X A + \begin{pmatrix} \alpha_{0x} W_x^T W_x & 0 & 0 \\ 0 & \alpha_{0y} W_y^T W_y & 0 \\ 0 & 0 & \alpha_{0z} W_z^T W_z \end{pmatrix} + \begin{pmatrix} \alpha_{1x} D^T W_x^T W_x D & 0 & 0 \\ 0 & \alpha_{1y} D^T W_y^T W_y D & 0 \\ 0 & 0 & \alpha_{1z} D^T W_z^T W_z D \end{pmatrix} + \begin{pmatrix} \alpha_{2x} D^T D W_x^T W_x D^T D & 0 & 0 \\ 0 & \alpha_{2y} D^T D W_y^T W_y D^T D & 0 \\ 0 & 0 & \alpha_{2z} D^T D W_z^T W_z D^T D \end{pmatrix}\right) \begin{pmatrix} U_x \\ U_y \\ U_z \end{pmatrix} = A^T X^T X b. \quad (A10''')$$

It is also possible to perform only the regularizations as expressed by eq. (A10) and eq. (A10') without using the weighting matrix W in eq. (A2) and eq. (A3), i.e., the weighting matrix X in eq. (A10'') and eq. (A10'''). This processing is equivalent to the using of an identity matrix for the weighting matrix W in eq. (A2) and eq. (A3) and in such a way, only the regularization can be selectively performed. However, such a weighting matrix should not be used to decrease the calculations and actually, the weighting has also been used for achieving the spatially variant regularization.

The SDs or the ZZLB can also be used as the weights at respective positions for performing weighted averaging of measurement results of displacement components to be calculated by simultaneously holding selected Doppler equations. Using the reciprocal of SD Wp (p=1 to N) of the displacement in the beam direction or the reciprocals of SDs (Wpx,Wpy,Wpz) [p=1 to N] of the displacement components in the respective directions, the weighted averaging of displacements can be calculated at the respective positions as follows.

$$(Ux, Uy, Uz)^T = \frac{\sum_{p=1}^{N} W_p \times (U_{px}, U_{py}, U_{pz})^T}{\sum_{p=1}^{N} W_p} \quad (A11)$$

or $$(Ux, Uy, Uz)^T = \quad (A11')$$

$$\left( \frac{\sum_{p=1}^{N} W_{px} \times U_{px}}{\sum_{p=1}^{N} W_{px}}, \frac{\sum_{p=1}^{N} W_{py} \times U_{py}}{\sum_{p=1}^{N} W_{py}}, \frac{\sum_{p=1}^{N} W_{pz} \times U_{pz}}{\sum_{p=1}^{N} W_{pz}} \right)^T.$$

An SD can also be calculated not using the stationary processes or the ZZLB but using ensemble averaging under nonstationary processes. Specifically, calibration phantoms or the measurement object can also be used for estimating the SD. Thus, as mentioned above, the regularization parameters or the weight matrices can be determined. Or, on the basis of the object or the conditions, experiences of measurements, they can also be determined using typical values a priori and not limited to these.

Thus, the weights or the regularization parameters can be set with a spatial resolution and with a high accuracy and however, when the deformation of the object being small or the calculation amounts being decreased, SDs are estimated over a larger region than the point of interest or the local region (for instance, over an ROI or a partial region in the ROI such as one set at each position in the wave propagation range or at each depth in the observed object, etc.) or for the respective waves or beams, SDs can also be estimated globally and are used. The phase matching method (a past invention of the present invention's inventor) is required to be used for making them possible to perform the measurements and to increase the measurement accuracy (patent document 6 and nonpatent document 15). The stretching method, etc. mentioned in other literatures is also effective for increasing the measurement accuracy.

FIG. 19 shows for a 2D case a schematic of a motion compensation (phase matching) performed by moving a searching region set in the next frame with respect to a frame of interest by a displacement vector estimate obtained for a point of interest or a local region including a point of interest. Specifically, FIG. 19(a) shows the motion compensation for a translational motion, whereas FIG. 19(b) shows for a rotational motion included. In a 3D case, similar processings can be performed using a 3D or 2D, local or searching region.

When performing the translation processing in the phase matching (nonpatent documents 13 and 15), for instance, in an arbitrary coordinate system such as the Cartesian coordinate system to be used when using a linear-array-type transducer, etc., with respect to each point of interest or each local region including each point of interest in a frame of interest, a searching region or a region of interest including the point of interest or the local region including the point of interest (see FIG. 19(a)) is set in the next frame (referred to as a frame Ne). Similarly to the phase rotation of 1D signal (method D3 described in the paragraph 0384), the complex exponential function is multiplied to the spectra. For instance, in the 2D case, when the displacement vector of local signals is estimated as $(\Delta_1, \Delta_2)$ ('1' and '2' respectively express the axes of the 2D Cartesian coordinate system.), the complex exponential function $\exp\{i(k_1\Delta_1+k_2\Delta_2)\}$ is multi-plied to the 2D spectra $A(k_1,k_2)$ of the wave signals in the searching region to shift by $(-\Delta_1,-\Delta_2)$ (i.e., the inverse direction with respect to the displacement). In the 3D case, when the displacement vector of local signals is estimated as $(\Delta_1,\Delta_2,\Delta_3)$ ('1,' '2' and '3' respectively express the axes of the 3D Cartesian coordinate system.), the complex exponential function $\exp\{i(k_1\Delta_1+k_2\Delta_2+k_3\Delta_3)\}$ is multiplied to the 3D spectra $A(k_1,k_2,k_3)$ of the wave signals in the searching region to shift by $(-\Delta_1,-\Delta_2,-\Delta_3)$ (i.e., the opposite direction with respect to the displacement) (patent document 6, nonpatent document 15, etc.). That is, the inverse Fourier transform of the spectra by the multiplication yields at the same position local spatial (and temporal) signals phase-matched in the Cartesian coordinate system can be obtained. When shifting the local region in the direction of the displacement vector, the complex exponential function with an inverse sign of the kernel, $\exp\{-i(k_1\Delta_1+k_2\Delta_2)\}$ or $\exp\{-i(k_1\Delta_1+k_2\Delta_2+k_3\Delta_3)\}$, can be multiplied and however, in the digital signal processing, the circulatory of a digital signal becomes a problem as mentioned later. Thus, the wave signals in the searching region should be shifted.

When performing the rotation processing in the phase matching, for instance, in an arbitrary coordinate system such as the Cartesian coordinate system to be used when using a linear-array-type transducer, etc., similarly to the translational phase matching (nonpatent documents 13 and 15, see FIG. 19(a)), with respect to each point of interest or each local region including each point of interest in a frame of interest, a searching region or a region of interest including the point of interest or the local region including the point of interest (see FIG. 19(b)) is set in the next frame (referred to as a frame Ne). The Fourier transform (i.e., spectra) for a polar coordinate system (a center is each point of interest, or a position inside or outside region of interest) with respect to the signals in the searching region or the region of interest is calculated directly with no approximations via the Jacobi operation performed in the present invention.

In a 2D case, for instance, when $x=r \sin \theta$ and $y=r \cos \theta$, the Jacobi matrix is expressed by the inverse of that of the Fourier transform, eq. (22) (i.e., inverse function theorem), the polar Fourier transform is calculated by $$F(k_r, k_\theta) = \quad (22\text{Inv})$$

$$\iint f(x,y) e^{-i(k_r r + k_\theta \theta)} dr d\theta = \iint f(x,y) r^{-1} e^{-i(k_r r + k_\theta \theta)} dx dy$$

and in a 3D case, for instance, when $x=r \sin \theta \cos \psi$, $y=r \cos \theta$ and $z=r \sin \theta \sin \psi$, the Jacobi matrix is expressed by the inverse of that of the Fourier transform, eq. (27) (i.e., inverse function theorem), the polar Fourier transform is calculated by $$F(k_r, k_\theta, k_\varphi) = \quad (27\text{inv})$$

$$\iiint f(x,y,z) \exp\{-i(k_r r + k_\theta \theta + k_\varphi \varphi)\} dr d\theta d\varphi =$$

$$\iiint f(x,y,z)(r^2 \sin\theta)^{-1} \exp\{-i(k_r r + k_\theta \theta + k_\varphi \varphi)\} dx dy dz.$$

The origin of the spatial polar coordinate system is a singular point. The motion compensation can be achieved by performing the phase matching that the calculated polar Fourier transform (spectra) of the searching region or the region of interest in the frame Ne is multiplied in the polar Fourier domain by the complex exponential function (i.e., phase rotation) expressed using the estimates of displacements in the directions of a radius, a polar angle, an elevation angle, an azimuth angle which can be estimated using the displacement vector measurement method such as the multi-dimensional autocorrelation method or the phase gradient of local cross-spectra (cross-spectrum phase gradient method, nonpatent document 15) calculated from the two polar Fourier transforms (spectra) similarly directly calculated respective for signals of the point of interest or the local region including the point of interest and those of the same positions in the frame Ne. For instance, in the 2D case, when the displacement vector of local signals is estimated as $(\Delta_r,\Delta_\theta)$, the complex exponential function $\exp\{i(k_r\Delta_r+k_\theta\Delta_\theta)\}$ is multiplied to the 2D spectra $F(k_r,k_\theta)$ of wave signals in the searching region to shift the searching region in the opposite direction by $(-\Delta_r,-\Delta_\theta)$, whereas in the 3D case, when the displacement vector of local signals is estimated as $(\Delta_r,\Delta_\theta,\Delta_\varphi)$, the complex exponential function $\exp\{i(k_r\Delta_r+k_\theta\Delta_\theta+k_\varphi\Delta_\varphi)\}$ is multiplied to the 2D spectra $F(k_r,k_\theta,k_\varphi)$ of wave signals in the searching region to shift the searching region in the opposite direction by $(-\Delta_r,-\Delta_\theta,-\Delta_\varphi)$. That is, the phase-matched local signals can be obtained at the same position in the Cartesian or polar coordinate system by performing the inverse Fourier transform for the phase rotated polar Fourier transform of the searching region or the region of interest. That is, since in the 2D case $k_x=k_r \sin\theta'$ and $k_y=k_r \cos\theta'$, the respective local signals can be calculated by $$f(x,y) = \int\int F(k_r,k_\theta)e^{i(k_x x+k_y y)}dk_x dk_y = \qquad (22\text{InvINVD})$$
$$\int\int F(k_r,\theta')k_r e^{i(xk_r\sin\theta'+yk_r\cos\theta')}dk_r d\theta'$$

or $$f(r,\theta) = \int\int F(k_r,k_\theta)e^{i(k_r r+k_\theta \theta)}dk_r dk_\theta = \qquad (22\text{InvINVP})$$
$$\int\int F(k_r,\theta')e^{i(k_r r+\theta'\theta)}dk_r d\theta'$$

and since in a 3D case $k_x=k_r \sin\theta' \cos\psi'$, $k_y=k_r \cos\theta'$ and $k_z=k_r \sin\theta' \sin\psi'$, the respective local signals can be calculated by $$f(x,y,z) = \qquad (27\text{InvInvD})$$
$$\int\int\int F(k_r,k_\theta,k_\varphi)\exp\{i(k_x x+dk_y y+dk_z z)\}dk_x dk_y dk_z =$$
$$\int\int\int F(k_r,\theta',\varphi')r^2 \sin\theta' \exp\{i(xk_r\sin\theta'\cos\varphi' +$$
$$yk_r\cos\theta'+zk_r\sin\theta'\sin\varphi')\}dk_r d\theta' d\varphi'$$

or $$f(r,\theta,\varphi) = \qquad (27\text{InvInvP})$$
$$\int\int\int F(k_r,k_\theta,k_\varphi)\exp\{i(k_r r+k_\theta\theta+k_\varphi\varphi)\}dk_r dk_\theta dk_\varphi =$$
$$\int\int\int F(k_r,\theta',\varphi')\exp\{i(k_r r+\theta'\theta+\varphi'\varphi)\}dk_r d\theta' d\varphi'.$$

Figure 20:
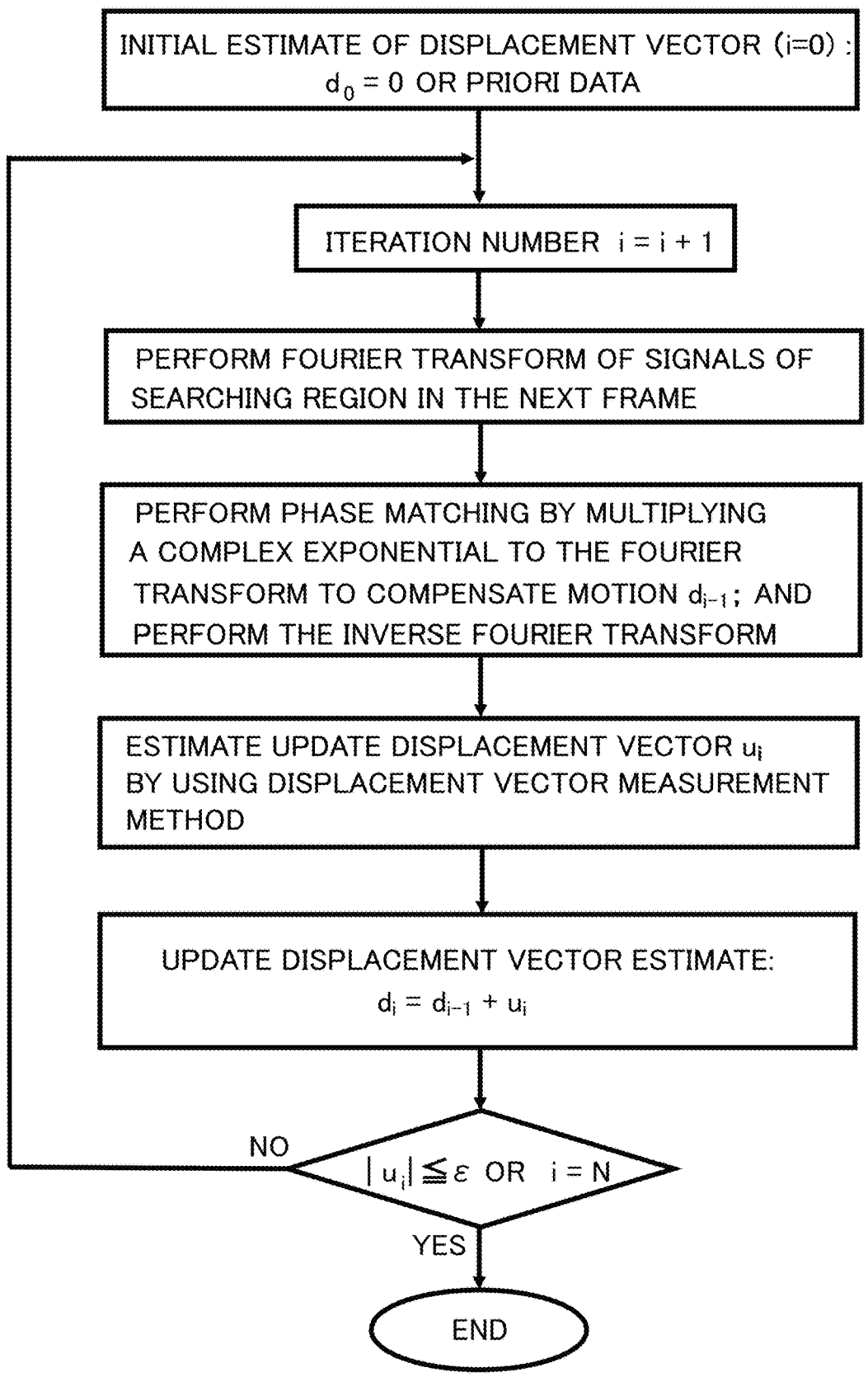
FIG. 20 shows a flow chart for illustrating a signal processing using the Fourier transform with the Jacobi operation.

The local region or the searching region is often centered on the point of interest. However, if the direction of a target displacement is known a priori, efficiently the latter can also be set toward the direction. It is also for the cases of a phase aberration correction or a motion compensation. The performing the displacement measurement methods except for the cross-spectrum phase gradient method such as the multi-dimensional autocorrelation method, e.g., the (analytic) signals of each frame are calculated in a polar coordinate system, for which the Fourier transform with the Jacobi operation is performed. Thus, the phase matching can be performed for the rotation with a high accuracy similarly to for the translation. When using the sector scan or the convex-type transducer, etc., performing the Fourier transform with the above-mentioned Jacobi operation permits the digital signals the discrete Fourier transform (discrete spectra) expressed in an arbitrary orthogonal coordinate system to be re-expressed in other arbitrary orthogonal systems (including different orthogonal coordinate systems such as the Cartesian orthogonal coordinate system, various curvilinear orthogonal coordinates, the same or different orthogonal coordinate systems with different origins or rotated) directly with no approximate processing (The strict interpolation using the phase rotation, described in the paragraphs 0026, 0132, 0214, etc. also yields the high accuracy and however, the processing requires more calculation times.). FIG. 20 shows a flow chart for illustrating a signal processing using the Fourier transform with the Jacobi operation, which the above-mentioned signal processing is not limited to.

For signals expressed in respective orthogonal coordinate systems, the phase matching is often performed for the translation at first, after which the phase matching is often performed for the rotation. The phase matching is not limited to the processing. The phase matching can also be performed interchangeably or in the inverse order. Or, the respective phase matchings can also be performed iteratively as disclosed in nonpatent document 13 and 15 (When the update displacement becomes smaller than the threshold set in advance, the iteration is terminated.). In the phase matchings, the processing of stretching or compressing can also be performed together.

Here, the shape of the local region or the searching region cannot always be a rectangle and instead, the shape can be others such as a circle (When the data are stored in a rectangular array such as square, rectangular, cubic or rectangular parallelepiped array, arrays corresponding to the outside of the practical circular or spherical region, etc. are padded by zeros.). The searching region must be properly larger than the local region such that circulated signals do not appear in the region of interest (the local region) to be obtained by multiplying the complex exponential function in a frequency domain (Setting the searching region too largely increases the calculations only and then, the size should be determined a priori using the magnitude of the observation object's displacement vector.). Here, if the radius displacement is zero and the observation object has only a rotational displacement, the size of searching region can be the same as that of the local region. With setting the radius displacement to zero, only the rotational displacement is calculated. Also, when the radius displacement is infinitesimal, under the assumption that the radius displacement is approximately zero, the rotational displacement can be sometimes estimated. Or, the searching region can also be set in the pre-frame. Or, when shortening the processing time, the phase matching can also be performed not by the multiplication of the complex exponential function but by a discrete shifting of the digital signals. In this case, the motion compensation must not always be performed for the searching region and instead, the phase matching can also be achieved by searching for the local region in the searching region in other frames directly (i.e., block matching).

In addition to the above-mentioned phase rotation processing in a polar coordinate system in a frequency domain, similarly to the shifting of the multi-dimensional signal based on the delay processings in the DAS processings described in the paragraph 0384 (i.e., method D1 with the interpolation processing or method D2 with shifting via performing the phase rotation for the analytic signal in a spatial and/or temporal domain), the phase matching can be performed for the multi-dimensional analytic signal expressed in a polar coordinate system (shifting in a radius direction or rotation processing). The above-mentioned phase rotation processing in a polar coordinate system in a frequency domain is based on the delay processing of method D3. These processings can also be used for the DAS processing in a polar coordinate system, and other beamformings such as the Fourier transform, the adaptive beamforming, the minimum variance beamforming in a polar coordinate system, etc., or shifting in the radius direction or rotating the signals in the temporal and/or spatial coordinate system such as the phase aberration correction or the motion correction, the phase matching (including new processing methods), the position matching, the position correction, etc.

For instance, the following calculations can be performed in a 2D case, $$f(r+r_0,\theta+\theta_0)=f(r,\theta)\times\exp[j\{k_r(r,\theta)r_0+k_\theta(r,\theta)\theta_0\}], \quad (2DASr)$$

and in a 3D case, $$f(r+r_0,\theta+\theta_0,\varphi+\varphi_0)=f(r,\theta,\varphi)\times\exp[j\{k_r(r,\theta,\varphi)r_0+k_\theta(r,\theta,\varphi)\theta_0+k_\varphi(r,\theta,\varphi)\varphi_0\}]. \quad (3DASr)$$

Here, $(k_r,k_\theta,k_\varphi)$ expresses the wavenumbers in the respective spatial directions at each position (x,y,z). That is, for a digital signal, an analogue-like shifting can be performed in the discrete coordinate system using the wavenumbers in the respective spatial directions at each position (When the higher accuracy is required, the sampling frequencies should be higher.). Similarly to the 1D case, the accuracy is higher than the method D1 (i.e., a block matching of the signals in a spatial and/or temporal domain), and the accuracy is lower than other methods (method D3 with phase matching based on the phase rotation in a frequency domain and method D4 with Fourier beamforming) and however, the calculation speed is faster. The usage of method is proper when requiring a high-speed calculation.

As for these processings, an attention is required for the fact that simultaneously the point spread function is also shifted in a radius direction or rotated together with the observation object itself (a possible error source of the phase matching). These processings can also be performed for signals with no carrier frequencies (e.g., image processing, etc.).

As mentioned above, the Fourier transform or the inverse Fourier Transform via the Jacobi operation allows changing the orthogonal coordinate systems in spatial and frequency domains. It is useful for various measurements and imagings to change the coordinate system in a same domain with no approximate interpolations (being highly accurate). For instance, as the methods for measuring a displacement vector or a displacement, the multi-dimensional cross-spectrum phase gradient method, the multi-dimensional cross-correlation method, the multi-dimensional autocorrelation method, the multi-dimensional Doppler method, or the 1D versions are useful. Except for using the cross-correlation method, when performing the Fourier transform for calculating spectra or the inverse Fourier transform for calculating analytic signals, the Jacobi operation can be used for changing the coordinate system and the measurement results can be obtained in the coordinate system. When using the cross-correlation method, the coordinate system can be changed using the above-described method using the Jacobi operation and the measurement results can be obtained. The processings are useful for a temperature measurement and various property observations.

As Wp, the Wiener filter can also be used. The imaging of signals or the displacement measurements can be performed after weighting the signals directly in a temporal and/or spatial domain. The signals are r(x,y,z) before or after detections.

$$W_p(x,y,z) = \left( \frac{|r(x,y,z)|}{|r(x,y,z)| + \left|\frac{n(x,y,z)}{r(x,y,z)}\right|} \right)^q \quad (A12)$$

or $$W_p(x,y,z) = \left( \frac{|r(x,y,z)|^2}{|r(x,y,z)|^2 + \frac{|n(x,y,z)|^2}{|r(x,y,z)|^2}} \right)^q \quad (A13)$$

where n(x,y,z) is noise signals and q is an arbitrary positive value.

The noise signals n(x,y,z) can be statically estimated by iteratively acquiring echo data with respect to the object or the calibration phantoms. For instance, a standard deviation (SD) can be used and under the assumption of a stationary process, the SD can be estimated by performing summation averaging locally and also by performing ensemble averaging. The SD can also be set, on the basis of the object or the conditions, experiences of the measurements, using typical values a priori and not limited to these. For imaging the signals r(x,y,z) are detected by the envelope detection, the square detection, the absolute detection and at the moment, eqs. (A12) or (A13) can also be multiplied to signals at respective positions. When calculating the autocorrelation function via calculating power spectra by implementing the conjugate of analytic signal to the analytic signal, the weighting can be performed. As pre-processing, the weighting can be performed, i.e., on the signal used for the autocorrelation method or the Doppler method that uses the analytic signal, and the cross-spectrum phase gradient method or the cross-correlation method (that can be sued for others from the analytic signal), etc.

When the signals are 2D or 1D as well, instead of r (x,y,z) and n(x,y,z) in eqs. (A12) or (A13), r(x,y) and n(x,y), and r(x) and n(x) can be respectively used for performing the same processing. Eqs. (A12) or (A13) can also be calculated globally and used for the respective beams or an ROI scanned by the respective beams. Similarly, instead of eq. (A12) or (A13), eqs. (A4) to (A6) can also be used for directly weighting the echo data.

Particularly when using the multi-dimensional cross-spectrum phase gradient method (patent document 6 and nonpatent document 15), the Wiener filter can be used in a frequency domain as well as in a temporal and/or spatial domain. As mentioned above, on the respective waves or beams, to estimate, using the weighted least squares solution, the gradient of phase spectra $\theta(\omega x,\omega y,\omega z)$ [i.e., unknown 3D displacement vector] in a frequency domain $(\omega x,\omega y,\omega z)$ of the cross-spectra $H_p(\omega x,\omega y,\omega z)$ [p=1 to N], estimated for the signals acquired at pre- and post-displacements or deformations under the same condition, the following weightings can be performed.

$$W_p(\omega_x, \omega_y, \omega_z) = \tag{A12'}$$
$$\|H_p(\omega_x, \omega_y, \omega_z)\|^2 \left( \frac{\|H_p(\omega_x, \omega_y, \omega_z)\|}{\|H_p(\omega_x, \omega_y, \omega_z)\| + \sqrt{\frac{PW_{pn}(\omega_x, \omega_y, \omega_z)}{PW_{ps}(\omega_x, \omega_y, \omega_z)}}} \right)^q$$

or $$W_p(\omega_x, \omega_y, \omega_z) = \tag{A13'}$$
$$\|H_p(\omega_x, \omega_y, \omega_z)\|^2 \left( \frac{\|H_p(\omega_x, \omega_y, \omega_z)\|^2}{\|H_p(\omega_x, \omega_y, \omega_z)\|^2 + \frac{PW_{pn}(\omega_x, \omega_y, \omega_z)}{PW_{ps}(\omega_x, \omega_y, \omega_z)}} \right)^q$$

where PWpn($\omega x,\omega y,\omega z$) and PWps($\omega x,\omega y,\omega z$) are respectively power spectra of noises and signals and for PWps ($\omega x,\omega y,\omega z$), the squared magnitudes of the cross-spectra ($\|Hp(\omega x,\omega y,\omega z)\|^2$) can be used instead. q is an arbitrary positive value.

For instance, for eqs. (1) to (14') of the patent document 6, the squared magnitudes of cross-spectra ($\|H p(\omega x,\omega y,\omega z)\|^2$) themselves are used for the weightings and instead, Wp($\omega x,\omega y,\omega z$) can be used for the weightings (For Wp, as mentioned above, the SDs of the displacements in the beam direction or the ZZLB can also be used). The weights are evaluated on the respective waves or beams (p=1 to N) at the respective positions and the weighted least squares minimization is performed once at the positions.

The power spectra PWpn($\omega x,\omega y,\omega z$) of noises can be statically estimated by iteratively acquiring echo data with respect to the object or the calibration phantoms. The PWpn($\omega x,\omega y,\omega z$) can also be set, on the basis of the object or the conditions, experiences of the measurements, using typical values a priori and not limited to these.

Or, n(x,y,z)/r(x,y,z) expressed in eq. (A12) or (A13), or PWpn($\omega x$, $\omega y$, $\omega z$)/PWps($\omega x,\omega y,\omega z$) expressed in eq. (A12') or (A13') can be set on the basis of the reciprocal of the above-mentioned echo SNR (SNRe) or that of the combined SNR (SNRc expressed using the SNRe and the correlation SNR$\rho$). Eq. (A12') or (A13') is calculated with a spatial resolution or globally estimated on the respective beams or on the ROI scanned by the respective beams and similarly to eq. (A12), (A13), (A4) to (A6), and Eq. (A12') or (A13') is used for weighting echo data directly (for imaging or displacement measurement). When performing the detections (envelope detection, square detection, absolute detection, etc.) of signals r(x,y,z) for performing imaging, eq. (A12) or (A13) can be used, and in the cases, L2-norms of the first spectra Hp($\omega x,\omega y,\omega z$) [spectra of local signals or signals over the ROI] in the equations cannot be used. This is also when performing the calculation of the autocorrelation function signal via calculating the power spectra by multiplying the conjugate of the local spectra Hp($\omega x,\omega y,\omega z$) to the spectra Hp($\omega x,\omega y,\omega z$).

When the unknown displacement is a 2D vector u=(Ux, Uy)$^T$ or one displacement in the beam direction, in eqs. (A12') and (A13'), for the cross-spectra H ($\omega x,\omega y$) or H ($\omega x$) estimated for signals acquired at pre- and post-displacements or deformations instead of H($\omega x,\omega y,\omega z$), similarly the respective Wiener filters are used to obtain weights and the weights are used Moreover, when implementing the regularizations, according to eq. (1) or (10'), the above-mentioned SDs, etc. can be used to set the regularization parameters similarly.

When using the cross-spectrum phase gradient method or other block matching methods, a single wave or beam can also be used for calculating a displacement vector at least having two directional components and even which using the single wave or beam, over-determined system can be realized.

All in the above-mentioned displacement measurements, the measurements can also be performed without making over-determined systems and also in the cases, the above-mentioned weighting or regularizations can be performed.

A displacement can be measured at least for two signals and when the above-described displacement measurement is large (a displacement of a point of interest or a local region including the point of interest), the instantaneous phase change (the multi-dimensional or 1D autocorrelation method or the multi-dimensional or 1D Doppler method, nonpatent document 13) or the local phase difference (the multi-dimensional or 1D cross-spectrum phase gradient method, nonpatent document 15) expressed in the equations as phase terms can be inverted and then, instead of the phase unwrapping, the phase matching (spatial shifting or phase rotating by the multiplication of a complex exponential function) can be performed as explained above (Originally, the phase matching method is innovative in that the method allows achieving the tissue displacement/strain measurement, for instance, C. Sumi et al, World Congress of Ultrasound in Medicine and Biology, Sapporo, 1994). In the paragraph 0405, for a polar coordinate system, the spatial shifting in the radius and rotation directions using the same processing is also explained. In addition, various shifting processings such as ones to be used for the delay processing for the DAS processing described in the paragraphs 0384 and 0405 are also effective. For the large displacement measurement, the multi-dimensional or the 1D cross-correlation method (In this case, the block matching is effective.) or cross-spectrum phase gradient method (The processing is performed with making the sampling intervals coarse.), which can be used for a large displacement measurement is used to estimate the target displacement coarsely and the estimate is used for the phase matching (The phase matching can be performed iteratively.). After completing the coarse phase matching, the fine estimate is performed using the above-described methods (Similarly the fine phase matching can be performed iteratively and for the cross-spectrum phase gradient method, the sampling intervals can be reset to the original fine sampling intervals.). The phase matching can also be used for the phase aberration correction as explained above.

Based on these processings, the deformations can be performed for various processings (e.g., the demodulation method, etc. described in the patent document 7). Basically, the autocorrelation method uses the phase of a complex autocorrelation function. To stabilize the estimate, Method Ai performs a temporal or spatial moving averaging for the instantaneous phase calculated by implementing the inverse of tangential function onto the imaginary part/real part of the complex autocorrelation function (based on the Euler formula), whereas Method Aii uses the phase calculated as the inverse tangential function of the imaginary part/real part of the moving-averaged complex autocorrelation function. In the Doppler method, the subtraction of the instantaneous phase of an analytic signal is used and to stabilize the estimate, the instantaneous phase calculated by implementing the inverse tangential function onto the imaginary part/ real part of the analytic signal or the subtraction of the instantaneous phase is similarly moving-averaged (Method D). The cross-spectrum phase gradient method uses the cross-spectrum phase of local signals.

In these, in the case where the processing is performed based on Method Ai or Method D, and the phase matching (spatial shifting) is performed using a coarse estimate of a displacement obtained using the cross-correlation method, when the temporal or spatial moving-average is performed on a spatially discontinuous, instantaneous phase distribution, the displacement cannot be calculated correctly (The errors occur and the final result of the phase matching becomes discontinuous displacement distribution.). Then, after the phase matching (spatial shifting), for instance, when in the 3D observation case the equation is expressed as fx ux+fy uy+fz uz=θ using the instantaneous frequencies (fx,fy,fz), the unknown displacement (ux,uy,uz) to be used for updating the coarse estimate (dx0,dy0,dz0), and the instantaneous phase θ that can be spatially discontinuous before being moving-averaged, with respect to the phase θ, θ'=θ+fx dx0+fy dy0+fz dz0 is calculated using the coarse estimate (dx0,dy0,dz0) for performing the phase matching that the phase corresponding to the coarse estimate (dx0, dy0,dz0) is added (corresponding to the phase rotation) and by solving fx dx+fy dy+fz dz=θ" expressed using the phase θ", i.e., obtained by performing the moving-averaged for θ', the estimate of a target displacement (dx,dy,dz) can be directly obtained (new phase matching). In the calculations, the instantaneous frequencies (fx,fy,fz) can be moving-averaged or not. By the new phase matching, the incorrect estimate of (ux,uy,uz) is not added to the coarse estimate (dx0,dy0,dz0). Or, with no moving-averaging of the instantaneous phase θ' obtained with the phase matching, instead of θ", the equation expressed for θ' can also be directly solved for the target displacement (dx,dy,dz). Thus, the same result as that obtained by adding the update displacement estimate (ux,uy,uz) to the coarse estimate (dx0,dy0,dz0) can be obtained. These can also be performed for the 2D and 1D observations similarly.

Alternatively, in the case where the processing is performed based on Method Aii, when performing the phase matching (spatial shifting) using a coarse estimate of a displacement obtained using the cross-correlation method similarly, since the temporal or spatial moving-average is not performed on a spatially discontinuous, instantaneous phase distribution, and the discontinuity possibly in an instantaneous phase (moving-averaged one) causes no problem. That is, for instance, in the 3D observation case, by calculating a phase θ'''=θ"+fx dx0+fy dy0+fz dz0 for the moving-averaged phase θ" obtained after the phase matching (spatial shifting) using the coarse estimate (dx0,dy0, dz0), i.e., by obtaining the phase θ''' with performing the phase matching that the phase corresponding to the coarse estimate (dx0,dy0,dz0) is added, and the target displacement (dx,dy,dz) can be directly estimated by solving the equation $f_x$ dx+$f_y$ dy+$f_z$ dz=θ''' (new phase matching). Or, as originally, instead of θ''', the equation fx ux+fy uy+fz uz=θ" using θ" can also be solved for the update displacement (ux,uy,uz), and the estimate can be added to the coarse estimate (dx0,dy0,dz0) to calculate the target displacement. In the calculations, the instantaneous frequencies (fx,fy,fz) can be moving-averaged or not. These can also be performed for the 2D and 1D observations similarly.

Or, when performing the processing based on Method D, when performing the phase matching (spatial shifting) using a coarse estimate of a displacement obtained using the cross-correlation method similarly, the cross-spectrum phase characteristics (frequency properties) can have a spatially discontinuous distribution and however, since the moving-averaging is not performed for the distribution, no problem occurs (At each local region, the phase frequency properties cannot be discontinuous.). The equations about the displacement can be held at the 1st moment frequency or the neighborhoods (In the 1D, 2D and 3D cases, at least one, two and three frequencies must be used.), or an over-determined system can also be held within a signal bandwidth. Also in this case, after the phase matching (spatial shifting), for instance, when in the 3D observation case the equation is expressed as Fx ux+Fy uy+Fz uz=α using the frequencies (fx,fy,fz) in the signal bandwidth, the unknown displacement (ux,uy,uz) to be used for updating the coarse estimate (dx0,dy0,dz0), and the cross-spectrum phase α of the respective frequencies, with respect to the phase α,α'=α+Fx dx0+Fy dy0+Fz dz0 is calculated using the coarse estimate (dx0,dy0,dz0) for performing the phase matching that the phase corresponding to the coarse estimate (dx0,dy0,dz0) is added (corresponding to the phase rotation) and by solving Fx dx+Fy dy+Fz dz=α' expressed using the phase α', the estimate of a target displacement (dx,dy,dz) can be directly obtained (new phase matching). Or, as originally, instead of α', the equation Fx ux+Fy uy+Fz uz=α using a can also be solved for the update displacement (ux,uy,uz), and the estimate can be added to the coarse estimate (dx0,dy0, dz0) to calculate the target displacement. These can also be performed for the 2D and 1D observations similarly.

By generating plural waves with different wave parameters or beamforming parameters at the same position (including physically generated ones, quasi-waves generated by superposing such plural waves or by dividing spectra, etc.), and by leading to one equation from one wave, totally the same number of equations as that of the unknown target displacement vector components are led from the waves, or totally larger number of equations than the unknown target displacement vector components are led to yield an over-determined system. Also, the equations held at other positions can also be used in the system of equations and in the case, the above-described new phase matching that yields a spatially continuous phase distribution can also be performed.

Particularly when the optimization processings (paragraphs 0402, 0403, etc.) and other optimization processings to stabilize the displacement measurement (estimation) accuracy, the above-described new phase matching that yields a spatially continuous phase distribution should be performed. At first, if the phase data include the above-described errors, using the temporal or spatial local means, variances or covariances estimated under the assumption of a locally stationary about the above-described phase of a complex autocorrelation function, the above-described instantaneous phase subtraction of analytic signals, or local cross-spectrum phase causes errors. For instance, this is a case where the maximum likelihood estimation is performed (being the maximum a posteriori (MAP) estimation or not). Here, the normal or over-determined system is expressed as $$FD=\theta, \quad (LM1)$$

where F is a matrix comprising of frequencies; D and e are vectors respectively comprising unknown displacements (dx0,dy0,dz0) and the above-described spatially continuous phase distribution data yielded by the new phase matching. Assuming that there exists in eq. (LM1) the noise $$n=\theta-FD \quad (LM2)$$

obeying the Gaussian distribution and then, the likelihood function is $$p(\theta|D) = \frac{1}{\sqrt{\det(2\pi S)}} \exp\left\{-\frac{1}{2}(\theta - FD)^T S^{-1}(\theta - FD)\right\}, \quad (LM3)$$

where S is a covariance matrix of θ components expressed using the expectation operator E[•]:

$$S = E[(\theta - E[\theta])(\theta - E[\theta])^T], \quad (LM4)$$

where T is a transpose. Eq. (LM4) expresses S calculated through an ensemble averaging and however, S can also be calculated based on an additional averaging under the assumption of a locally stationary. Thus, the logarithm of likelihood (L) is expressed by implementing the logarithm onto eq. (LM3) as $$L = -\ln\left(\sqrt{\det(2\pi S)}\right) - \frac{1}{2}(\theta - FD)^T S^{-1}(\theta - FD). \quad (LM5)$$

To obtain D maximizing L, the partial derivative of eq. (LM5) is set to zero, and the following equation can be obtained:

$$F^T S^{-1} FD = F^T S^{-1} \theta. \quad (LM6)$$

Incidentally, as a superresolution, when solving the system of equations FO=B, expressed by using the matrix F expressing the blur function (being considered as a point spread function (PSF) for the linear spatio-temporal invariant system or linear spatio-temporal variant system) and the vectors O and B respectively expressing the original image (target) and the blurred image B, for O, the likelihood estimation can be similarly achieved by solving $$F^T S^{-1} FO = F^T S^{-1} B. \quad (LM7)$$

where S is a covariance matrix of B, and when the signal is expressed using the complex signal, Hermitian transpose H is used instead of the transpose T as follows:

$$F^H S^{-1} FO = F^H S^{-1} B. \quad (LM8)$$

where S is a covariance matrix of B:

$$S = E[(B - E[B])(B - E[B])^T],$$

$$S = E[(B - E[B])(B - E[B])^H] \quad (LM9)$$

$$\text{or } S = E[BB^T] \text{ or } S = E[BB^H]. \quad (LM9')$$

when the wave signal does not include a direct current, instead of eq. (LM9), as like in eq. (LM9'), the mean value can be set to zero. It is cautious that it requires time to complete the calculations for the superresolution or restoration itself, and the covariance matrix.

The processing to be performed in a spatio-temporal domain is effective for the spatio-temporal variant system. The point spread function at each distance from a physical aperture can be effectively estimated as a mean of the estimations obtained at different positions with the same distance (1D autocorrelation function in the axial or lateral direction, or multi-dimensional autocorrelation function, nonpatent documents 35 and 36). With no averaging, the point spread function estimated at the point of interest itself can also be used. For the spatio-temporal processing, for instance, the conjugate gradient method can be used. When performing the maximum likelihood estimation, the below-described MAP (maximum a posteriori, for instance, non-patent document 42) is effective and the method using the EM algorithm is also reported (nonpatent document 31). For these processing results, it is also effective to perform the shaping-filtering that a desired point spread function is used for the convolution in a spatio-temporal domain or equivalently the corresponding frequency response can be multiplied in a frequency domain.

In the case of a spatio-temporal processing, when the spatio-temporal invariant can be assumed for the point spread function, the deconvolution is to be performed. In terms of the calculation speed, for the deconvolution, the inverse filtering processing should be performed in a frequency domain as described in the present patent document. In such a case, the point spread function is averaged in a region where the point spread function is spatio-temporal invariant. This corresponds to the case where the spatial resolution is approximately homogeneous such as when performing the synthetic aperture or the combination of transmission of a plane wave and reception with a dynamic focusing, etc. Occasionally, even in a spatio-temporal variant case such as when a focused beam is generated, under the assumption of a spatio-temporal invariant, the same processing can also be performed in a frequency domain.

Similarly, for these processing results, it is effective to perform the shaping-filtering that a desired point spread function is used for the convolution in a spatio-temporal domain or equivalently the corresponding frequency response can be multiplied in a frequency domain.

As for the displacement measurement, the variance estimated a posteriori from the displacement measurements can be used to set a regularization parameter such that the regularization parameter becomes proportional to the variance (the regularization, nonpatent document 18), or the reciprocal of the variance can be used as weights (confidences of respective equations) for a weighted least squares estimation. When the displacement measurement includes errors caused by the above phase errors, the estimation errors also occur.

Furthermore, statistics will be used for the equations about the update displacement (ux,uy,uz) with respect to the coarse estimate (dx0,dy0,dz0). Thus, the standard deviation led for the 1D autocorrelation method for a one-direction velocity measurement (which is used for the so-called power Doppler, nonpatent document 20), the standard deviation led for the multi-dimensional autocorrelation method based on that of the 1D autocorrelation method, and the Ziv-Zakai Lower Bound (ZZLB) can be estimated a priori and with no assumption of the stationary about the displacement measurements and however, similarly errors occur. When performing this kind of optimization processing, all the displacement measurement methods require the above-described new phase matching that yields spatially continuous phase distribution as a pre-processing (During the phase matching, the update displacement (the residual displacement) itself or the corresponding phase data cannot be moving-averaged nor optimized.). Or, this new phase matching allows performing, even if not required, obtaining plural estimation results (measurements) with several different optimization methods and the results can be used for obtaining a final result by the integration or judgement; although the calculations increase, the results can afford benefits.

Here, the MAP estimation being effective additionally to the maximum likelihood estimation is described, and further the similarity to the regularization is mentioned (nonpatent document 42).

The MAP estimation of D in eq. (LM1) can be performed by maximizing the a posteriori stochastic density function about D:

$$p(D|\theta) = \frac{p(\theta|D)p(D)}{p(\theta)}, \quad \text{(MAP01)}$$

where p (θ|D) is the a posteriori stochastic density function about θ (the same equation as the likelihood function), LM3) and p(D) is a stochastic density function about D:

$$p(D) = \frac{1}{\sqrt{\det(2\pi C_D)}} \exp\left\{-\frac{1}{2}(D-E[D])^T C_D^{-1}(D-E[D])\right\}. \quad \text{(MAP02)}$$

This MAP estimation is equivalent to the minimization of the cost function of the weighted least squares method $$\text{Cost}(u) = \frac{1}{2}(\theta - FD)^T S^{-1}(\theta - FD) + \frac{1}{2}(D - E[D])^T C_D^{-1}(D - E[D]), \quad \text{(MAP1)}$$

where CD is a covariance matrix of unknown displacement components D and E [•] is an expectation operator yielding a vector comprising the expectations of the components of a vector •. Thus, the solution is obtained by solving $$(F^T S^{-1} F + C_D^{-1})D = (F^T S^{-1}\theta + C_D^{-1} E[D]). \quad \text{(MAP2)}$$

For calculating $S^{-1}$, the LU decomposition can be used and not limited to this. Actually, $C_D$ and E[D] can be estimated through an ensemble averaging or an additional averaging under the assumption of a locally stationary (i.e., to be processed for obtained plural sampled data such as estimates obtained not with the MAP but the maximum likelihood or the least squares estimation, etc.), or estimated a priori using the standard deviation estimated for the autocorrelation function described in the present patent (For the conventional one-direction displacement observation, the 1D moving-averaging can be used, whereas for the displacement vector observation, the multi-dimensional moving-averaging should be performed.), the Ziv-Zakai Lower Bound (ZZLB), or the Cramer-Rao Lower Bound (CRLB), etc. The estimation is not limited to these and based on the experience, the data can also be set a priori.

Alternatively, when performing the regularization for the lest squares estimation about eq. (LM1), the following system of equations similar to eq. (MAP2) are to be solved:

$$(F^T F + \lambda P)D = (F^T\theta + \lambda PE[D]) \quad \text{(REG1)}$$

where P is a regularization operator, and X is a hyper regularization parameter. This system of equations can also be obtained from eq. (MAP1) by using the weight matrix W' of which diagonals are the variances of 9 obtained by the above-described new phase matching or the variances about the subtraction of the left- and right-hand of eq. (LM1) instead of the covariance matrix S; and by further using the multiplication of the regularization operator P and the regularization parameter λ instead of $C_D^{-1}$ about D. For the regularization operator P, an identity matrix can be used and, in this case, the regularization parameter λ can be spatially variant (nonpatent document 17). The regularization parameter is an all-band-pass filter and then, the result of D can have a smaller magnitude than the original. As other regularization operator P, a high-pass filter or a differential filter (the Laplacian operator $G^T G$ using the gradient operator G, or the n-power norm), etc. can also be used. In this case, although the error with a high frequency is effectively suppressed, the original high frequency components can be lost (But, the regularization can also be used for the restoration from a blurred image or the superresolutions). Plural regularization parameters can also be used simultaneously. Being different from eq. (REG1) led for the regularization, conventionally a typical value can be used for the regularization parameter λ, or λ is set to be proportional to the variance of θ obtained using the new phase matching or the variance of subtraction of left- and right-hand of eq. (LM1) or D (With the larger regularization parameter, the effect increases.). Or, in the weighted least squares estimation for eq. (A2) using the weight matrix W, the reciprocals of variance of D is used for $W^T W$ (weighting more largely the high accuracy equations having smaller standard deviations about D to be more important).

In terms of the similarity between the eqs. (MAP2) and (REG1), it is effective to mix the equations to be used. In these, if E[D] is not a zero vector, conventionally it is regarded as a zero vector for the calculations.

As for the restoration of a blurred image or a superresolution, applying the maximum likelihood estimation to the above-described system FO=B leads eqs. (LM7) to (LM9) to be solved. Or similarly to the above-described displacement measurement, the MAP estimation can also be performed (Although E [B] is not a zero vector, conventionally it can be regarded as zero.) and the EM algorithm can also be used. Or, it is also effective to perform the processing as a spatio-temporal invariant system in a frequency domain. Similarly to the above-described displacement measurement method, it is also effective to regularize the spatio-temporal system and to solve it stably (nonpatent document 43). As disclosed in the nonpatent document, the processing can also be performed in a frequency domain with a higher speed:

$$(|F^*F|+\lambda|P^*P|)O=F^*B, \quad \text{(REG2)}$$

where * denotes the conjugate and here, the frequency responses of respective spatial distributions expressed by the matrix and vectors are expressed using the same characters. In the nonpatent document, it is reported that the regularization is more effective than the conventional Wiener filtering. In the present invention, performed can be the applications of the Winer filtering described in the present patent document (including changed types) or the spatio-temporal variant regularization (The regularization parameter is spatio-temporally variant.). Or, the shaping filtering can also be performed as described above.

For the signal processings in the cases where the reception signal has a low SNR, the signals have different wave parameters or beamforming parameters, the sensed signals are physically different, etc., this regularization can become effective such as with the smoothing processing and then decreasing the spatial resolution as compensation.

As others, for instance, for the inverse analysis described in the paragraph 0377 or various other inverse analyses (The system is expressed as Ax=b.), the optimizations can also be performed similarly such as the maximum likelihood estimation, the MAP estimation, the regularizations, the Bayes estimation and among others. When the observation target is a vector such as a displacement vector or a current density vector, etc., for the respective direction components, different regularization operators and parameters can also be used (nonpatent document 17).

The new phase matching processing (method) can be effectively used for the beamforming processings such as for generating plural waves with different wave parameters or beamforming parameters at the same position (in addition to the physically generated ones, quasi-waves generated by the spectral frequency divisions, etc.) and for generating quasi-waves by superposing such waves (with increased bandwidths and spatial resolutions via the coherent summation), or the phase aberration correction to be performed at the beamforming processings, for which the signal separation can be effectively performed by using the ICA (Independent Component Analysis) processing (A higher effect can be obtained for the multiple processing than the additional averaging.) or the superresolution such as using the nonlinear processing, etc. When performing the phase aberration correction, if there exists a tissue motion, the motion compensation can also be performed simultaneously. For instance, for the reception signals in a single frame or plural sequential frames received during the object obviously moves, the phase aberration correction can be performed during or after the beamformings or the superresolution can be performed similarly (Superposed waves can be superresolutioned or superresolutioned waves can be superposed, etc.). Or, these processings can also be performed for different sensed signals such as the MRI, the ultrasound, the X-ray CT, the OCT, the terahertz, etc. When performing the processings of such plural frame data, the accuracy of phase matching to be performed between the plural frame data decreases due to the large displacement/deformation of object, the lacking of signal data by the object's uncontrollable, spontaneous displacement (For instance, the object can go out form the 1D, 2D or 3D region of interest), the physical action such as a thermal treatment, etc. or chemical action such as a chemotherapy, etc. Thus, the optimizations such as the regularization and the maximum likelihood estimation, etc. are effective for the displacement measurement described in the present patent document and the new phase matching is also effective in such cases. Speckle signals as well as specular signals can be processed and if required, extracting or enhancing the edges, and the tissue tracking using features (for instance, for a human, the tissue structure such as a blood vessel bifurcation position, etc.), etc. Or, according to a signal, in the above-described regularizations, the target is made smoothed much, or the above-described processings can also be effectively performed for envelope-detected signals.

Thus, the new phase matching processing is effective for the phase matching required during the displacement measurements, etc., the DAS processing described in the paragraph 0384, the estimation and the implementation of delays for the beamformings such as the Fourier beamforming, the adaptive beamforming, the minimum variance, etc. (phase aberration correction), the phase aberration correction during the beamforming described in the paragraph 0372, the tissue motion compensation, the matching of position for plural data, the estimation for the shifting amount of signal in the temporal, spatial or spatio-temporal coordinate in which positions are corrected, etc.

Various techniques such as a detection of object motion and the imaging on the basis of observed waves can be used and for instance, in the field of a medical ultrasounds, on the basis of a mean velocity and variance, etc., displayed regarding blood flow, or tissue displacement or deformation, are information about the velocity, moving or not, the complexity, etc. An agent (micro bubbles) can be positively used for performing measurement imaging with increased intensity of waves from bloods in vessels or hearts. Such an agent is effective for a functional measurement as well as a geometrical observation. A typical example of a self-emanating type agent is a radioisotope used for PET (Positron Emission Tomography) and the observation is performed on the basis of counting the generation of a positron or a radioactive ray. This is a type to be dealt with as a passive instrument of the 2nd embodiment. For instance, magnetic substances (that can have an affinity with a target such as cancerous diseases, etc.) are injected into a vein and mechanical vibrations can be applied to generate magnetic fields. In this case, mechanical stimuli are applied using the transmission transducer and as the responses, electromagnetic waves are observed by the reception transducer. The above-mentioned photoacoustics, etc. can also be performed. For instance, a representative PET agent used for the early detection of cancer for a whole body, $^{18}$FDG ($^{18}$F-Fluoro-deoxy-glucose, a glucose labelled by a positron emission nuclide) being more taken in a cancer cell than the normal cell (3 to 20 times), can also be used as a photoacoustic agent by receiving the generated ultrasound waves. Similarly to the PET, an accumulation mechanism of $^{18}$FDG by metabolic trapping is used: $^{18}$FDG is taken in through the glucose transporter of the cell membrane like a glucose and is metabolized by an enzyme hexokinase but remains in a cell without advancing to the glycolytic pathway unlike a glucose. The photoacoustic diagnosis can be performed with the PET or not. The photoacoustic processing is based on the reception beamforming of arrived and acquired ultrasounds (transmission waves) using the laser radiation timing as a trigger. The application of photoacoustics has an advantage for tissues to be diagnosed in that a higher spatial resolution measurement/imaging can be achieved than the PET having a low spatial resolution. The PET is based on the mechanism that a positron is released from a positron emission nuclide (positron nuclide) by $\beta^+$ collapse and next, the positron is drawn with an electron and become extinct by the combination with the electron after a few millimeter movement, by which an extinction radiation is generated (2 gamma beams, i.e., 2 photons, released in the approximately opposite direction) and is observed. Thus, similarly to the PET, the photoacoustics can be used for the early detection of cancers, i.e., the existence of cancer can be confirmed by the observation of $^{18}$FDG accumulation; the malignancy and the progress, etc. can be diagnosed from the intensity of photoacoustic signal (a malignant tumor cell aggravates the glucose metabolism and then, a high accumulation). In addition to the D-type glucose existing in a human body, learned from "The application of the characteristic that a cancer lesion specifically takes L-type glucose to a fluorescence L-type glucose (oral or intravenous injection), researched now by associate professor, Dr. Katsuya Yamada's research group," the L-type glucose can also be used. Or, for instance, the brain has the most prosperous glucose metabolism in a human body, and the Alzheimer's dementia is accompanied by a metabolism abnormality from an early stage. When an ischemia progresses, the glucose metabolism aggravates (positive), whereas when the myocardium necrotizes, the glucose metabolism is not performed. The photoacoustics can also be used for the observations. The laser or an ultrasound can also be radiated from the neighborhood of the disease, for instance, for the brain, via opening the head, for a deeply situated abdomen organs, via opening the abdomen or using a laparoscope or a catheter, etc. For these applications, while a spectroscopy (a light absorption frequency properties) about many agents are measured and known, the frequency variance of photoacoustic signals (about the laser radiation and the generation of a photoacoustic signal itself) can also be used. That is, as described below the generated ultrasounds can be observed in a wideband fashion or with a specific bandwidth with respect to the laser radiated in a wideband fashion or with a specific bandwidth. Or, similarly the generated ultrasounds can be respectively observed with respect to the laser radiations with different bandwidths, and the plurally observed ultrasound signals can be superposed for realizing a case using a wideband laser radiation virtually. Or, the same light sources or the same ultrasound sensors of a wideband or a specific bandwidth can be arrayed in 1D, 2D or 3D arrays. Similarly, different light sources or different ultrasound sensors can also be arrayed (for instance, locally successively, interchangeably, or periodically). The light sources and the ultrasound sensors can also be installed into separated bodies or one body. Or, the light source or the ultrasound sensor can also be exchanged by others (Other sources or sensors can be used at the same positions.). The imaging is not always performed and instead, only the quantitative observation using numerical values can also be performed. The light source aperture such as the steering wheel fiber, the fiber array or the LED, etc. can also be spatially fixed with respect to the observation object together with the ultrasound sensors, and the frequency or the bandwidth of the laser radiation and of the reception signal can also be changed or controlled at the instrument bodies or by exchanging the instruments. Occasionally, the steering wheel fiber, the fiber array or the LED can also be exchanged by ones with a proper frequency/bandwidth. As mentioned above, the glucose concentration can also be observed for the diagnosis of a blood glucose level or the imaging. As PET agents, other than the glucose are also used, i.e., an oxygen, a water, an amino acid, a nucleic acid, a neurotransmitter, etc. labelled by a positron emission nuclide, i.e., $^{11}$C-methionine, $^{11}$C-acetic acid, $^{11}$C-Colin, $^{11}$C-methyl spiperone, $^{13}$N-ammonia, $^{15}$O-water, $^{15}$O-oxygen gas, $^{18}$F-Fluorodopa, etc. Other agents developed for the photoacoustics or other modalities, etc. can also be used. Using these agents or not, the Doppler measurements (including vector one) can also be performed for a blood, a urine, a body fluid. Also, soft tissues or stiff tissues can also be dealt with such as for the measurements of the displacements or deformations, or the visco-elasticities (including for various treatments as well as the diagnosis and examination). The usefulness of the indocyanine green (ICG) fluorescent imaging is well known, and it is often used for the angiography, or observing the blood vessel, the blood flow, the microcirculation, the lymphatic vessel, the lymph flow, the sentinel lymph node, the hepatic segmentation, etc. Since the ICG has a high light absorption property, it can be used as the agent for the photoacoustics and similarly to such observations. When exposed to a radiation, prevention of being exposed is required, or the quantity of being exposed is made less than the safety level as usual. The agents can also have the effects of treatment. Conversely a therapeutic drug can have the effect of the agents.

Various agents can also be used simultaneously or not. A reception-wideband ultrasound sensor is often used and the received wideband photoacoustic signals obtained at once can be used for the above-described applications, etc. Or, the analogue- or digital-filtered signals can also be used with the bandwidth selection for the above-described applications (including the imaging of photoacoustic signals themselves). The above application results using the respective frequencies or bandwidths of photoacoustic signals can also be used with superposing or averaging. For the imaging, the numeric values of the observed data to be displayed can also be assigned by different colors or displayed can also be a light and a shade in the same color (i.e., a resolution yielded about the numeric values). The processing yields a spatial resolution in the image. The observed results of the respective frequencies or the respective bandwidths can also be imaged, and the results can also be superposed for the imaging. In such a case, the observed results of the respective frequencies or the respective bandwidths can also be assigned by different colors or displayed can also be a light and a shade in the same color (i.e., a resolution yielded about the numeric values). If what agents or substances of the observation object yields the respective bandwidths of photoacoustic signals are known (It is also important to measure the variances of photoacoustic signals and however, for instance, the light absorption data ranging 400 nm to 25 µm about the human tissues or diseases, and materials related to them are much, which are to be references.), particularly the photoacoustic signals with the bandwidths corresponding to the targets can also be used or not (Radiated are the lights with the bandwidths generating the photoacoustic signals for at least one originally existing in an observation object, at least one included from the outside of an observation object, the both existing, plural markers being mixed, no marker with no consideration about a marker, etc.). The photoacoustic signals obtained can also be used for the imaging as described above, for observing the displacement or the temperature (for heating, thermal treatment, temperature rising due to the exposure to light for the photoacoustics), and for the inverse analysis (observation) using the observations. Moreover, as described in the present patent document, the photoacoustic signals can be separated to those of the respective or different markers with the signal processings such as the spectral analysis (analogue or digital filtering), ICA, etc. including the cases where the phase aberration correction is performed or not, respective which can be used variously. Or, the image processings can also be used for the signal separations, for instance, by using the image patterns deterministically or stochastically as indexes. It is also effective to use the difference of a signal intensity or a magnitude of spectra (an effective value). The processings themselves can become the analyses of a marker. In such a case, both the photoacoustic signals respectively obtained when such agents are used and not can also be processed simultaneously. As described above, similarly the separated photoacoustic signals can also be used for the imaging, observing the displacement or the temperature (for heating, thermal treatment, temperature rising due to the exposure to light for the photoacoustics), and the inverse analysis (observation) using the observations. For instance, when imaging the static fluid or with a slow speed flow in the medium such as a blood, etc., or observing the motion, the Doppler observation can be performed for the photoacoustic signal or the ultrasound (echo) signal to be often used together, and it is effective to directly separate the flow (motion) or to specify the blood flow position (region) for performing the separation using the clutter rejection filter conventionally used for the blood flow Doppler observation, or using the difference in a signal intensity. Off course, also when performing the observation with adopting the frequencies or bandwidths of lights to the target fluid, the processing is effective. Or, it is also effective to perform the Doppler observations simultaneously using other optical instruments (light pulse or electromagnetic pulse) such as the OCT, etc. of which frequencies or bandwidths are adopted to the target fluid or not. The important matter is that it also becomes possible to perform the specific evaluations of the surrounding media of the separated fluid (displacement or temperature, inverse analysis, etc.). These processings also become effective methods for couple analyses, examinations, syntheses.

For the photoacoustic signals (reception signals), in addition to the widely known beamforming methods, various beamforming methods and signal processings described in this invention document can be used. Thus, as described above, the applications include the imagings of photoacoustic signals themselves. For the detection processings, in addition to the widely known methods, the methods described in the present patent document can be used. For instance, as a simple beamforming processing, as described in the paragraph 0098, etc., the conjugate of the frequency response of the observed wave is multiplied to the frequency response (for instance, for the respective 3D, 2D and 1D frequency responses of the same dimensional signals, $S(\omega 1, \omega 2, \omega 3)$, $S(\omega 1, \omega 2)$ and $S(\omega 1)$, the auto-spectra $S(\omega 1, \omega 2, \omega 3)$ $S^*(\omega 1, \omega 2, \omega 3)$, $S(\omega 1, \omega 2)S^*(\omega 1, \omega 2)$ and $S(\omega 1)S^*(\omega 1)$ can be calculated in a frequency domain), to which performing the inverse Fourier transform yields the autocorrelation function in a spatio-temporal domain (The autocorrelation function can be directly calculated with performing the convolutional processing in a spatio-temporal domain and however, regarding the calculation speed, the processing is effective only when the signal length is short.). That is, calculating the autocorrelation function without normalizing the maximum to 1 can yield a point spread function (a pressure shape) at every point of interest in the region of interest. By superposing the calculated point spread functions in the region of interest, the beamforming in the region of interest can be achieved. The conjugate product has an effect of matched filtering to be used for the signal detection and then, yields a high accuracy result. The photoacoustic wave (ultrasound) often has a smaller intensity and then a lower SNR than the ultrasound wave received with respect to the ultrasound transmission. Moreover, when the ultrasound array is multi-dimensional (2D or 3D), the transmission wave and the reception signals have a smaller intensity and then a lower SNR than the 1D array. The processing is effective for various waves. Also the processing can also be performed for various beamformed data (including the results of the synthetic aperture processing), only transmission beamformed data and no beamformed data (i.e., raw reception data for the synthetic aperture processing). The patent document 11 is disclosing that the point spread function of an arbitrary wave such as an ultrasound, a shear wave, a thermal wave, etc. or the wave source can be estimated at the point of interest. From the estimated point spread function, the wavelength can be estimated at the spatial coordinate system including the fast-time-axis in the depth (range) direction and the lateral axis orthogonal to the fast-time-axis. The frequency of the wave observed based on the Doppler method can be estimated by the signal processing in the slow-time-axis direction. Thus, the propagation velocities of waves can be estimated.

For the displacement or temperature measurement, etc., the multi-dimensional cross-spectrum phase gradient method, the multi-dimensional cross-correlation method, the multi-dimensional autocorrelation method, the multi-dimensional Doppler method, the corresponding 1D methods, and the demodulation method, etc. can be used for various beamformed data (including the results of the synthetic aperture processing), only transmission beamformed data and no beamformed data (i.e., raw reception data for the synthetic aperture processing). These displacement measurement methods include performing the above-described beamforming and then, yielding a high accuracy measurement effectively for not only the photoacoustic wave, but also the conventional transmission ultrasound and ultrasound echo, and other waves. The photoacoustic signal can have a lower SNR than the conventional transmission ultrasound and ultrasound echo. Both the photoacoustic signal and ultrasound signal can have extremely large intensity signals with respect to the surrounding and then, the coarse estimate obtained using the multi-dimensional cross-spectrum phase gradient method or the multi-dimensional cross-correlation method can include a sudden measurement error and in such a case, the fine estimate should be performed via the phase matching using the coarse estimate of which sudden measurement error is removed by implementing the median filter or the low-pass filter to the coarse estimate. This is same for other waves. The averaging can be implemented onto the observation results respectively obtained using the transmission ultrasound or the ultrasound echo, and the photoacoustic signal. Or, to display an observation data, the weighting averaging can also be performed for the observation results using the confidence data evaluated by the methods described in the present patent or the methods for determining what data is considered to be important, etc. Or, system of equations led from the respective ultrasound signals and photoacoustic signals can also be solved in a least squares sense, the weighted least squares estimation can also be performed for the system of equations using the confidence data evaluated by the methods described in the present patent or the methods for determining what data is considered to be important, etc., or the optimizations can also be performed for the system of equations such as the regularization, the maximum likelihood estimation, the Bayes estimation, and other methods described in the present patent document, etc. The a priori or a posteriori optimization can be performed. The superposition of the transmission ultrasound, the ultrasound echo, and the photoacoustic wave can also be processed, similarly using the confidence data evaluated by the methods described in the present patent or the methods for determining what data is considered to be important, etc., the respective signal intensities (or the amplitude gains) can be controlled to yield the superposed image (The indicator of the device possesses a graphical interface or the console may possess an adjustment device such as knobs.). These processing can also be performed in a digital fashion, i.e., the digitized signals can be signal-processed in a hardware or in a software. Or, the analogue processing using an analogue delay (a delay line, etc.) or amplifier can also be performed.

For the signal separation, various signal processing methods such as the ICA, etc. described in the present patent document can be used. For instance, spectra can also be divided before and/or after the beamformings. When dividing the angular spectra (i.e., spectra before beamforming), in addition to the Fourier beamforming, various beamformings such as the DAS processing, etc. can be performed. For the superposing of wave signals, the superposing can be performed coherently or incoherently. Particularly by performing the beamforming methods or the signal processing methods described in the present patent document, a small intensity signals can also be processed and then, highly precise, detailed observation is possible. Fundamentally, the photoacoustic signal has a wideband and then, a high spatial resolution observation can be achieved (including the above-described applications, etc.). Also, a photoacoustic microscope can also be realized and one with a handy-type ultrasound sensor as well. In this case, the above-described applications, etc. can also be performed. As for the light radiation, a laterally large region can also be radiated at once using a plane wave, a spherical wave, a cylindrical wave, etc., whereas mechanical or electric scanning with a light beam can also be performed. The latter radiation allows a higher spatial resolution observation than the former.

When the reception property of an ultrasound sensor has a narrow bandwidth, the respective reception signals (photoacoustic signals) obtained using the plural ultrasound sensors with different reception bandwidths can also be processed as described above or used together.

These observed photoacoustic signals can be processed instead of the ultrasound echo similarly, and various signal processings (including the inverse analyses) described in the present patent document can be performed, which can be variously used. For instance, the mechanical reconstruction based on the Doppler observation, and the thermal reconstruction based on the temperature observation, etc. can be performed and not limited to these. Thus, the photoacoustic instrument realized by using a light source with the ultrasound instrument yields various applications. The various images obtained from the photoacoustic signals can be displayed, being superposed onto the transmission or echo ultrasound image (For instance, one is colored and the other can be gray-scaled, and both can be transparent and can be simultaneously displayed). Thus, at least the ultrasound transmission and the light radiation are performed interchangeably and iteratively, ultrasounds respectively received for them are processed. The photoacoustic wave (ultrasound) often has a smaller intensity and then a lower SNR than the ultrasound wave received with respect to the ultrasound transmission. Moreover, when the ultrasound array is multi-dimensional (2D or 3D), the transmission wave and the reception signals have a smaller intensity and then a lower SNR than the 1D array. For these, to increase the SNR, it is effective to perform the additional averaging onto the plural reception signals (ultrasound or photoacoustic wave) obtained for the same temporal phase of the observation object. In these cases, the ultrasound transmission and the light radiation can also be interchangeably or iteratively simply, the respective continuous transmissions or radiations can also be performed iteratively. Under the condition or the assumption of the same temporal phase for the observation object, the digitized signals can also be additionally averaged in a hardware or a software. Or, the analogue processing using an analogue delay (a delay line, etc.) can also be performed.

Irregularly, only the photoacoustic imaging is performed, and in this case, the ultrasound instrument can have no transmit device.

For instance, the transmission unit 31 and the reception unit 32 shown in FIG. 2 generates, for the reception signals obtained at the respective temporal phases, wave signal data by superposing non-normalized autocorrelation functions calculated locally at respective positions of interest in the region of interest; the digital signal processing unit 33 can perform the imaging of the wave signal data of the respective temporal phases or calculate a displacement vector or a displacement component. Here, the reception signals used for calculating the autocorrelation signals at respective temporal phases can also be superposed ones at respective temporal phases.

The waves can be separated before performing the last inverse Fourier transform and then the separated waves can be detected (square detection or envelope detection), the waves separated after performing the last inverse Fourier transform can be detected, or originally separated waves can be detected before or after performing the Fourier transform (nonpatent document 1). The imaging of the distributions of the respective wave intensities are imaged or incoherent signals obtained by the detections are superposed to enhance the deterministic signals (for instance, reflection signals or specular signals) and decrease the stochastic signals (for instance, scattering signals or speckle signals), by which the spatial variations of structures of an object or media are imaged effectively (a past invention of the present invention's inventor).

Coherent signals corresponding to superposed waves are detected and the distribution of intensities can also be imaged. Also non-detected, coherent signals can be imaged to display the wave vibrations themselves, images of signal phase distributions can be displayed together with those of the signal intensities (magnitudes). A single wave can also be displayed similarly.

The way to display is generally and popularly on the basis of a gray-scaled or color image and if the quantitativeness is required, the numerical data displayed in a gray or color format can also be displayed with a bar. Or, displaying using bird's-eye-views, etc. can also be performed, and CG can also be used. The images can be display as static or dynamic images, and the dynamic images can also be displayed in a frozen condition, both images can also be displayed in a real-time or via off-line processings. Wave data or image data can also be read out from the storage devices (or storage media) to display the data. Temporal changes in arbitrary numerical data can also be displayed in graph formats.

Or, for instance, using the bandwidths of microwaves or infrared rays, or terahertz waves allows measuring the temperature distributions of measurement objects. The transmitted waves are demodulated by the radiations from the objects and the modulations are detected (Using passive-type instruments according to the 2nd embodiment allow the measurements of temperature distributions of objects by using the radiated waves themselves). Similarly to other waves, not using continuous waves but using pulse waves or burst waves and beamformings generate a spatial resolution. The infrared-ray can be used to observe the temperature distributions of the surfaces of objects mainly (it can also be considered that the measurements are limited to object surfaces), whereas using the microwaves or terahertz waves allows the measurements of internal temperature distributions. On the basis of the observed physical or chemical quantities, high order processings such as approaches of an inverse problem, etc. can be performed to calculate visco elastic moduli or elastic moduli, viscosities (patent document 9), thermal properties (patent document 10), electric properties (patent document 8, a conductivity or a permittivity (dielectric constant)), a permeability, wave propagation speeds (a light speed or a sound speed), an attenuation, a scattering (forward or backward scatterings, etc.), a transmission, a reflection, a refraction, a diffraction wave, a surface wave, wave sources (which can also be used as a diffraction source), etc. with their variances. In patent documents 8 to 10, methods for reconstructing a distribution of physical properties related to the observed physical quantity in a region of interest which is one of physical quantities is disclosed. Or, in another case, distributions of physical properties can be directly estimated from a wave directly sensed by a sensor. In the medical applications, when using the ultrasound or MRI, etc., for cancerous diseases, the diseases during treatments using warming and heating, and inflammation parts after the thermal treatments or surgeries, observations or monitorings of visco-elastic moduli as well as the temperatures or thermal properties can also be performed. Also the body temperature observations (including in morning, at noon and at night, with a metabolism, growth, aging, before or after meat, before or after smoking, when adding loads to peripheral systems, electrophysiological nervous control, etc.) or physical loads on various organs, etc. can be performed similarly. The observings and monitorings are not limited to such medical applications, other organic substances or non-organic substances, mixed substances can also be object to be observed and on the diagnoses, restorations and applications, various observations or monitorings can be performed in conjunction with. The applications of terahertz are not limited to the measurements and similarly to other waves, performed can be the imagings of the transmission wave, reflection wave, refraction wave, diffraction wave, etc., and the Doppler measurement, etc. As a feature, similarly to an X-ray, observing of inorganic substances can also be performed. Although other waves can also be used for the organic and inorganic substances, fusions can also be performed by using other waves simultaneously.

The measured physical quantities such as displacements or temperatures, etc. can be displayed similarly, the measurements can also be displayed with superposed on the geometrical images simultaneously obtained. When displaying these distributions, the quantitativeness is often required and then, the numerical data corresponding to the displayed brightness or color can also be displayed using bars. Or, displaying using bird's-eye-views, etc. can also be performed, and CG can also be used. The images can be display as static or dynamic images, and the dynamic images can also be displayed in a frozen condition, and both images can also be displayed in a real-time or via off-line processings. Wave data or image data can also be read out from the storage devices (or storage media) to display the data. Temporal changes in arbitrary numerical data can also be displayed in graph formats.

From other devices, additional information about the object to be observed can be provided via the input devices, or other observed data such as physical or chemical quantities can also be provided. In the cases, the digital signal processing unit can perform, in addition to the above-mentioned processings, high order processings such as data mining, independent signal separation (independent component analysis), signal separations using principle component analysis, coding, multi-dimensional spectrum analysis, MIMO, SIMO, MUSIC and identification of the object using parametric methods, or superresolutions that can use these methods together or ISAR (Inverse synthetic aperture), etc.

The passive-type instruments according to the 2nd embodiment performs these processings and then, the cases are mentioned there in detail. Being different from the passive-type instruments, since the active-type instruments according to the present embodiment performs the transmissions of waves and the scanning, the position of interest can be specified on the received reception signals. And, when performing the transmission focusing or multi-focusings, the conditions or the functions of focused positions can be understood and if there exist wave sources at the focus positions, the wave sources can be understood by demodulating the waves with high spatial resolutions and with modulated by the information of the wave sources. By using waves that can be categorized in the same types of plane waves (flat array), cylindrical waves (ring-type array) or spherical waves (spherical kernel array), it is possible to perform the understanding speedy, i.e., with high frame rates.

On the applications on communications, the positions to be communicated can be targeted (focused on) and the, the energy saving can be enhanced as well as the security can be increased. When composing the measurement system to perform the observation, the degree of free is high. By using the processings on the basis of the system theory, it is possible to identify the point spread functions (PSFs) to be generated or according to the purposes, it is simple to control the PSFs. It is also possible to use plural transmission transducers and/or plural reception transducers (that can also work as the transmission transducers). The waves to be transmitted or received can be a same kind or not and occasionally, plural instrument bodies exclusive for the plural transducer to be driven synchronizedly can also be used, and the passive-type instrument according to the 2nd embodiment can also be used together. These can also be connected with other instruments (including the instruments that control these) via exclusive or general networks and the instrument body can also have a control function of the networks.

On the basis of the various types of observation data, in conjunction with, other instruments can also work such as manufacturing machines of materials or structures, instruments for performing the treatments or restorations, machines that uses the data such as robots, etc. And the instruments are not limited to these. These measurements and the high order processings using the waves can also be performed by other instruments by using the wave data, etc. stored in the detachable storage devices (storage media), or the data are stored into the common (same) type storage devices (storage media) and can also be used by other instruments.

When the received reception signals stored in the memories or storage devices (storage media) include harmonic waves components generated by an object or in media, prior to performing beamformings, the signals can be separated into a fundamental wave and harmonic waves (only the 2nd harmonic wave or when the higher order harmonic waves are not ignored, plural harmonic waves) and the beamformings (general phasing and summing) can be implemented on the respective separated signals, or after implementing the beamforming on the stored reception signals, the separations can be performed. The separations can be implemented on the spectra of reception signals in a frequency domain and however, there exists the cases where the bandwidths of the spectra corresponding to the plural waves can overlap. Then, in the field of medical ultrasound, the so-called pulse inversion method is performed, i.e., at the same phase of the object, the wave of a polarity being inverted to that of the original wave is generated and the respective reception signals with respect to the wave transmissions are superposed before or after the beamforming, the 2nd harmonic wave component as well as the fundamental wave (separated waves) can be obtained at each stage.

Alternatively, the separation method using a polynomial expression is also known. The instrument of the present embodiment can perform the 1D processings in the wave propagation direction or multi-dimensional processings for the cases where the lateral modulation is performed or with strictly considering the changing of the wave propagation directions at respective positions, and the processing can be performed before or after the beamformings. However, note that when performing the beamformings after separating the reception waves, since the beamformings are implemented on the respective fundamental wave and harmonic waves, the total calculation time can increase and then, the parallel processing is to be performed. Basically, the separation after performing the beamforming requires a short time.

Alternatively, when the waves transmitted from the respective transmission apertures are encoded, prior to performing the beamforming, the reception signals received by the respective reception aperture elements are separated, by performing the signal detections on the basis of the matched filtering, into the wave components to be generated with respect to the transmissions with the respective transmission aperture elements; and in the cases where dynamic focusing can be performed on the transmission as well as the reception, which is well known. The method is also effective for the high-speed transmission(s) using the plane wave(s) and in the cases where focused beams and steerings are generated as well.

Also when plural waves or beams are simultaneously transmitted, for instance, the respective waves, etc. with above-mentioned plural different frequencies or plural different steering angles can be encoded and transmitted. In the cases, the receptions signals are similarly decoded, by which the receptions are separated into the reception signals generated with respect to the respective transmission waves or beams. Thus, the ability for separating the signals can be increased. This is effective, for instance, when the bandwidths of the respective waves overlap or the propagation directions of the waves become same due to the refraction, reflection, transmission, scattering, diffraction, etc. These are on the basis of the idea that the waves to be separated are encoded using independent codes. Under using the same physical parameters, the coding can also be simply performed.

In these processings, although simultaneous equations can also be solved, the matched filtering has its effect and rather the processing can be achieved with a high speed. Codes proper to the object or media are also developed. However, the number of elements to be used increases, the required lengths of codes must be longer and although the signal energy can be increased (the effect can also be effectively used and important), in a contrary, for instance, when the object or media deforms, the accuracy decreases and becomes not proper. The similar problems also occur when the chirp signal compression is performed.

In communications, the waves transmitted from the respective aperture elements are encoded using the codes correspondingly to the information to be conveyed, and transmitted (As beamformings, for instance, a plane wave, a cylindrical wave or a spherical wave is used to send the information widely, or by performing focusings, which can be performed at plural positions, the accuracy of information is ensured at the positions, the security is ensured regarding the local communications or the communications with specific objects, or the energy saving is performed), and beamformings are performed with respect to the reception signals and the results are decoded. The applications of the coding using the instrument of the present embodiment are not limited to these (The digital signal processing unit, which can include memories, using the memories or the storage devices (storage media) perform these processings).

Always or occasionally, or with determined temporal intervals, beamforming parameters can be optimized such as a transmission intensity, transmission and reception apodizations, transmission and reception delays, steering angles, transmission and reception time intervals (scan rates), a frame rate, scanning lines, the number of, the geometries, the areas and the directions of the faces of effective apertures, the geometries, the areas and the directions of the faces of aperture elements, the direction of the face of a physical aperture or polarization modes, etc.) on the basis of the physical quantities (a magnitude or a direction of a displacement, a velocity, an acceleration, a strain, a strain rate, etc. or a temperature, etc.) or chemical quantities, additional information, observed by the instrument of the present embodiment or provided by others, or visco elastic moduli, elastic moduli, viscosities, thermal properties, electric properties (a conductivity or a permittivity), a permeability, a wave propagation velocity (light velocity or sound velocity, etc.), an attenuation, a scattering, a transmission, a reflection, a refraction, a diffraction, a surface wave, wave sources, materials, structures, their variances, and among others, related to waves and obtained by the above-mentioned high order processings such as approaches of an inverse problem (patent documents 8 to 10), etc. Thus, optimized beamformings can be performed such that spatially uniform qualities (a spatial resolution, a contrast, a scanning rate) can be generated; high qualities (a spatial resolution, a contrast, a scanning rate) can be generated at the positions where some targets are detected (using the geometries, materials, structures, properties of motions, temperature, moisture, etc.) or at the related positions; scattering waves (forward or backward scattering waves), transmission waves, reflection waves, refraction waves, diffraction wave or surface waves can be properly evaluated according to the object motion, the compositions and structures; observing can be performed with respect to rather wide directions mostly.

The wave propagation speeds are determined by the physical properties of media, of which physical properties depend on the environment conditions such as a pressure, a temperature and a moisture, etc. Moreover, the physical properties are inhomogeneous in the media and then, the propagation speeds are also inhomogeneous. The propagation speeds can also be measured in a real-time or on the basis of the calibration data regarding the environment conditions, the propagation speeds can also be calculated. The instrument according to the present embodiment is further equipped with the phase aberration correction unit for correcting the inhomogeneity in propagation speed; and in practical, the above-mentioned transmission delays of the respective channels themselves can also be used at the transmissions for performing the phase aberration corrections as well by adjusting the amounts of correction delays as well. In addition, after performing the receptions, to correct the inhomogeneity in propagation speed on the propagation path between the transmission and reception positions, the above-mentioned digital signal processing unit can perform the corrections by multiplying complex exponential function in a frequency domain. Alternatively, the corrections can also be implemented at the calculations of the above-mentioned Fourier transform or inverse Fourier transform directly. The confidence of the measured propagation speeds can be confirmed, with respect to the measurement object or the reference existing or set in the neighborhood of the object, by generating image signals, of which image formation conditions, spatial resolutions, signal intensities, contrasts, etc. can be used as indices. Moreover, using these, the corrections can be further performed. In the 2nd embodiment disclosed later, after performing the receptions, the phase aberration corrections can be performed for transmission and/or reception.

Waves diverges during the propagations with effected by an attenuation, a scattering, a transmission, a reflection, a refraction, a diffraction, etc. and then, basically the wave intensities become small as the waves propagate. Thus, the instrument of the present embodiment is equipped with the function for performing the corrections with respect to the effects of an attenuation, on the basis of the Lambert's law, with respect to the signals before or after the beamforming. Or, equipped with can be also the function that an operator can adjust the corrections for the attenuations at the respective positions or the respective distances by using the input device. Similarly, as mentioned above, equipped with can be also the function for performing optimized corrections before or after the beamforming according to the object. In these processings, not the digital processings but analogue processings using analogue devices or circuits can also be performed to make much of the speedy of the processings although the degree of freedom is lower.

In the above-mentioned processings, the superposing and the spectral frequency division are linear processings, whereas at or after performing the generations of waves using the above-mentioned methods (1) to (6), nonlinear processings can be implemented to generate new signals with other wave parameters. In the process of the beamforming, when the reception signals are analogue, analogue signal processings can be performed using the analogue circuits (diodes or transistors, amplifiers, exclusive nonlinear circuits, etc.), whereas when the reception signals are digital, as the digital signal processing to be performed using the digital signal processing unit, exponentiation or multiplication and other nonlinear processings can be implemented on the reception signals. In a frequency domain, nonlinear processing can also be performed with respect to spectra.

Alternatively, as modifications of DAS, DAM (Delay and Multiplication) processing, that is an invention of the present invention's inventor, can also be performed in a frequency domain using the instrument of the present inventions. The multiplications using the exponentiations or multiplications in a spatial domain can be calculated using the convolution integrals in a frequency domain. It is possible to increase the frequencies or bandwidths, generating quasi-signals of the above-mentioned harmonic waves generated during the wave propagations, etc. Regarding the steered waves, signals that are detected at least in one direction or to all directions can be generated, for instance, as the results, imagings of the waves generated can be performed, and a displacement vector can also be performed using a general one-directional displacement measurement method.

In addition, using virtual source, image signals can also be generated. As far, reported were the virtual sources that set behind physical apertures or at transmission-focused positions. Previously, the inventor of the present inventions reported virtual receivers as well as virtual sources that can be set at arbitrary positions, and also physical wave sources or detectors that can be set at arbitrary positions of proper scatters or diffraction gratings, etc. (patent document 7, nonpatent document 8). The present inventions can be performed using the virtual sources or the virtual receivers as mentioned above. It is also possible to increase a spatial resolution or make the field of vision (FOV) large. In addition, when performing beamformings of transmissions or receptions, or both the transmissions and receptions on reception signals obtained with respect to the transmissions using at least one aperture element (cases where the beamformings are performed or not, i.e., SA transmissions and receptions), by using at least one different parameter within the plural parameters of waves, those of beamformings and those of transducers (a shape and a size of element, a configuration, a number, an effective aperture width, an element material, etc.), plural beams or waves with different properties or features can be generated (including the cases where plural results are generated from same reception signal) and the over-determined systems can also be generated. Similarly, the over-determined systems can also be generated using the virtual sources or the virtual receivers, of which positions or distributions (geometries or sizes, etc.) are changed. Also in the cases, from same reception signals, plural beams or waves with different properties or features can also be generated. As the features of over-determined systems, increasing SNRs and spatial resolutions can be achieved by performing the coherent superposing as well as reducing speckles can be achieved by superposing of coherent signals obtained via the detections, etc.; these have effects in performing imagings. In addition, the effects for increasing accuracies of various measurements such as displacement measurements, temperature measurements, etc. can also be obtained. In addition to the virtual sources and the virtual receivers, at least one parameter within the plural wave parameters, plural beamforming parameters and plural transducer parameters can also be set different (for instance, steering angles, etc. can be changes physically on the basis of electric and electrical engineering or mechanics or in a software fashion).

According to arbitrary wave sources, the transmission waves can be generated on coordinate systems expressed by rotating, using an arbitrary position as the center, the coordinate system determined by a reception aperture element array or spatially shifting (for instance, a coordinate determined by axial and lateral axes of the transmission aperture and then the generated coordinate system is different from that determined by those of the reception aperture). In the cases, after the correction of a coordinate system is implemented on the reception signals, the beamformings can be performed. For instance, when image signals are to be generated directly on the coordinate system, that is expressed by rotating, using the origin as a center, the above-mentioned 2D Cartesian coordinate system (x,y) by an angle $\theta$, eq. (29) can be multiplied to the analytic signals expressed by the first temporal Fourier transform. The processings can yield image signals without losing the high speediness inherently achievable by the present inventions, i.e., with higher speeds than the calculations using the rotating the wavenumber vector $(k_x, \sqrt{(k^2-k_x^2)})$ and the coordinate system (x,y) together with the Jacobi calculation.

$$\exp(isk \tan \theta x) \tag{29}$$

Note that s=2 for reflection waves, and s=1 for transmission waves. In practical, only for the correction about the transmission, s=1 is used. The spatial shifting (parallel translation) can also be performed in a frequency domain by performing complex exponential function. The above-mentioned method using the rotations of the wavenumber vector $(k_x, \sqrt{(k^2-k_x^2)})$ and the coordinate (x,y) together with the Jacobi calculation can perform transmission beamforming with converted to the coordinate system determined by the reception aperture element array (s=1), after which the reception beamforming (s=1) can be performed, i.e., yielding a low speed.

In the active-type instruments according to the present embodiment, similarly to the passive-type instruments according to the 2nd embodiment, other analogue devices can also be used such as lens, reflectors (mirrors), scatters, deflectors, polariscopes, polarizers, absorbent bodies (attenuators), multipliers, conjugators, phase delay devices, adders, differentiators, integrators, matchers, filters (spatial or temporal, frequencies), diffraction gratings (holes), spectroscopes, collimators, splitters, directional couplers, nonlinear media, special devices such as amplifiers of waves, etc. Particularly when using lights, in addition, used can be polarizing filters, ND filters, blockers, optical waveguides, optical fibers, optical Kerr effect devices, nonlinear optical fibers, mixing optical fibers, modulation optical fibers, optical trapping (or confinement) devices, optical memories, dispersion shift optical fibers, band-pass filters, temporal inverters, encoders using optical masks, etc. and for controlling (conversions of wavelengths, switchings, routings) such devices, optical node technologies, optical cross connects (OXC), optical add-drop multiplexers (OADM), optical multiplexers or separators, optical switching devices and also as devices, optical transmission networks or optical networks themselves, and not limited to these. These can be incorporated into the transducers or instrument bodies, etc. On the beamformings, all these can be optimally controlled together with the instruments artificially or naturally with the above-mentioned various mechanisms. In a frequency domain, nonlinear processings can also be implemented on.

Under such various combinations, the instrument of the present inventions can also be used in general instruments using waves. In medical instruments, for instance, such instruments are ultrasound diagnosis instruments (reflection or echo methods and transmission-types, etc.), X-ray CT (agents increasing the attenuation effects can also be used), X-ray roentgens, angiographies, mammographies, MRI (Magnetic Resonance Imaging, agents can also be used), OCT (optical Coherent Tomography), PET (Positron Emission Tomography, corresponding to the 2nd embodiment), SPECT (Single Photon Emission Computed Tomography), endoscopes (including capsule types), laparoscopes, catheters equipped with various types of sensing functions, terahertz instruments, various types of microscopies, various types of radiotherapy instruments (chemotherapies can also be performed together to increase the treatment effects), SQUID meters, electroencephalographs, electrocardiograms and HIFUs (High Intensity Focus Ultrasounds), etc. Particularly, MRI is an originally digital instrument and including the capability, the application range is very large. For instance, using electromagnetic observations and inverse problems, etc. which the inventor of the present inventions has been conducting allow the applications on all the reconstructions (measurements) of electric current distributions and electric property distributions, observing of displacements or mechanical wave propagations, reconstructions (measurements) of mechanical properties, observing of temperature distributions or thermal waves and reconstructions (measurements) of thermal properties (patent documents 8 to 10). In patents 8 to 10, methods for reconstructing the distributions of observed physical properties related to a physical quantity which is one of physical quantities in a 1D, 2D or 3D region of interest. The observed physical quantity can also be a surface wave (an electromagnetic wave, an elastic wave, a thermal wave, etc.) or a physical quantity provided at a boundary and based on the observation, the physical properties can also be reconstructed. When using a terahertz modality, an electric field, an electric current density or electric properties, etc. can be observed. Doppler measurement using the terahertz is also important. Or, in another case, distributions of physical properties can be directly estimated from a wave directly sensed by a sensor. For the applications, in addition to the MRI, an ultrasound can also be used. As other works, for instance, using OCT, on the basis of the infrared spectroscopy, allows the measurements of absorption spectra and for instance, imagings of an oxygen concentration or a glucose concentration of a skin's basal cell carcinoma or blood can be performed. It is also possible to apply the OCT to general Near Infrared (NIR) and the distribution evaluations can be performed with higher spatial resolutions than the general NIR-based reconstructions. Also on them, instruments of ultrasound sensor (including microscope-types) can be equipped with the OCT or laser instruments, by which photoacoustics can also be performed, and not limited to these. Alternatively, using the laser or OCT instruments will allow detecting and imaging tissue fluctuations with high sensitivities with no mechanical stimuli (The surface wave can also be observed by Doppler observations, etc., and the applications can also be performed.). Alternatively, responses with respect to every possible (mechanical) stimuli including due to laser lights, etc. can also be made target of imagings (including the uses of lights for observing the dynamics generated by the lights themselves, etc.). For other imagings, chemical sensors, etc. can also be used. Combinations of waves are not limited these. In addition to physical sensors, chemical sensors, etc. can also be used together. The instruments according to the present inventions can also be used for various types of radars, sonars and optical system devices, etc. For waves, continuous waves as well as pulse waves or burst waves can also be used. Such digital processings with a high degree of freedom can also be realized using analogue circuits with a high operation speeds, and vice versa. These exists various types of instruments in respective fields such as resource explorations, non-destructive examinations, communications. On them, the instruments according to the present inventions can also be used. The instruments of the present inventions can be used as instruments (or devices) in general instruments (or devices) regarding the operation modes (for instance, imaging modes, Doppler modes, measurement modes, communication modes, etc.), and not limited the modes or other above-mentioned modes).

When arbitrary plural beams or waves such as above-mentioned fixed focusing beams, multi-focusing beams, plane waves and others are physically transmitted simultaneously, if a large region can be integrated over an ROI, a high frame rate can be achieved. The simultaneous transmissions in plural directions can also be performed using a same effective aperture, and the simultaneous transmissions in a same direction or in different directions can also be performed using different effective apertures. On the beamformings, in addition to such same or different steering angles or focus positions, etc., beamforming parameters such as ultrasound frequencies or bandwidths (those of a beam direction or a propagation direction, directions orthogonal to them), a pulse shape, a wavenumber, an aperture geometry or apodizations, etc. that determine a beam shape, etc. and transducer parameters such as an element geometry or an element size, array element configurations, etc. being same or different can also be used simultaneously.

When physically performing the plural transmissions, if the used parameters are different, the followings can be considered as representative cases.

(A1) Performing same software steering on the all.
(A2) Performing plural different software steerings (For instance, the same steering is performed in a software fashion every different physical steering angle).

Also, when physically performing the plural transmissions, if the used parameters are same, the followings can be considered as representative cases.

(B1) Performing a software steering.
(B2) Performing plural software steerings.

However, note that some combinations of them can also be performed. Being dependent on the existences of obstacles or effects of scatterings or attenuations (those can be dependent on a frequency) during the wave propagation process, so-called adaptive beamformings can also be performed. In these cases, when the combinations of the software transmission and reception steerings or apodizations are same, superposed reception signals can be processed at once. When the different combinations are used, every same combination, superposed reception signals can be processed at once and next, the calculated spectra are superposed prior to performing the final inverse Fourier transform.

In cases (A1) and (B1), reception echo signals received as the superposition of the echo signals with respect to the respective transmission ultrasounds are software-processed once.

In case (A2), the reception echo signals received as the superposition of the echo signals with respect to the respective transmission ultrasounds are separated to be superpositions to be same software-processed; and the respective superpositions are software-processed once and next, the calculated spectra are superposed prior to performing the final inverse Fourier transform. The signal separation can be performed using the above-mentioned various type methods, and not limited to them.

In case (B2), plural different software processings are performed on angular spectra of all superposed reception signals and next, the calculated spectra are superposed prior to performing the final inverse Fourier transform.

Alternatively, when such plural beams or waves are not physically transmitted simultaneously, if the plural transmissions and receptions are performed under the condition or the assumption that the phase of the object is same, the same processing as those of the above-mentioned simultaneous transmissions can be performed. In these cases, when the combinations of the software transmission and reception steerings or apodizations are same, superposed reception signals can be processed at once. When the different combinations are used, every same combination, superposed reception signals can be processed at once and next, the calculated spectra are superposed prior to performing the final inverse Fourier transform. The reception signals received with respect to the simultaneous transmissions or transmissions with different times can also be processed similarly under the same condition or under the same assumption. The parameters used for the physical transmissions can be known in advance; or can also be calculated to be used by analyzing the beams or waves. These are also in the cases of passive-types mentioned later.

By performing the plural transmissions of beams or waves simultaneously or at different times, high frame rates, or a same focusing or plural foci can be generated. In addition, the same processings including the superposing processings allows yielding beams or waves with new parameters (for instance, increasing bandwidths and improving spatial resolution, etc.). Using together the spectral frequency division method also allows yielding beams or waves with new parameters. By separating the generated beams or waves into those with same parameters, of respective which can also be used (For instance, displacements in directions of generated beams or waves can be measured as well as a displacement vector measurement). Nonlinear processings or increasing bandwidths via nonlinear processings mentioned later can also be performed on the superposed signals, signals of which spectra are divided ones, or separated signals. The superposed signals, signals of which spectra are divided ones, separated signals or such signals on which the nonlinear processings are implemented, etc. can be used for the displacement measurement, etc. The respective signals can also be detected for performing the imagings, the detected signals can also be superposed for imagings (For instance, speckle reduction can be performed). The applications are not limited to these and as mentioned above, various and not limited.

<Simulation Results>

Below, when the waves to be processed are ultrasounds and mainly, the representative results obtained for the above-mentioned beamforming methods (1) to (7) in simulations, performed to confirm the feasibilities, are shown (image signal generations using plane wave transmission, steered monostatic SA, multistatic SA, fixed focusing; and those on the Cartesian coordinate system for transmission and reception performed on the polar coordinate system; and migration).

Figure 21:
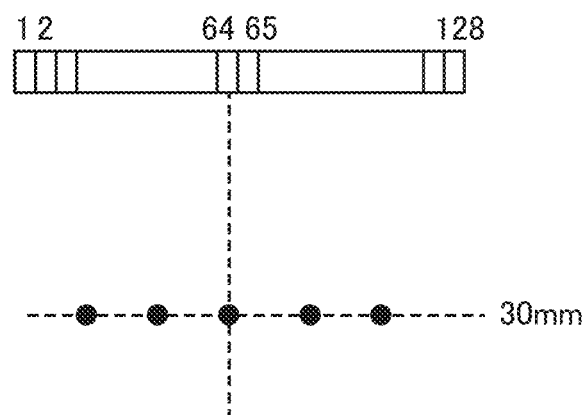
FIG. 21 shows a schematic of a numerical phantom used in simulations.

FIG. 21 shows a schematic of a numerical phantom used in simulations. The numerical phantom has 5 point scatters at a 30 mm depth with a lateral interval, 2.5 mm, in anechoic and non-attenuate media. To generate the echo signals, Field II (nonpatent document 21) is used. Here, the depth and lateral directions are expressed using the z and x axes, respectively.

Figure 22:
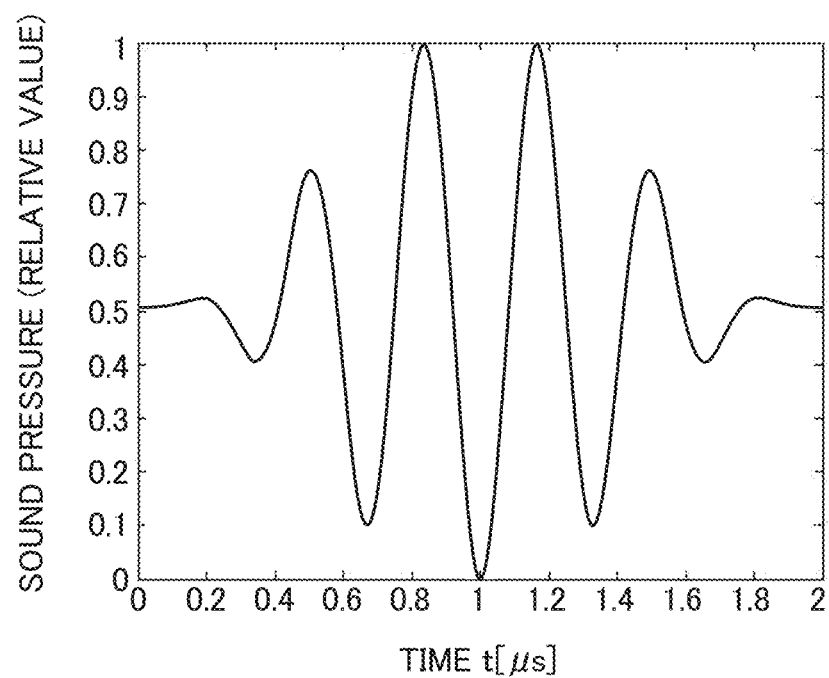
FIG. 22 shows a schematic of a shape of an acoustic pressure pulse wave used in simulations.

For the plane wave transmission and the migration method, and the monostatic SA, a 1D linear-type array transducer (128 elements; an element width, 0.1 mm; kerf, 0.025 mm; an elevational width, 5 mm) is used, whereas for the fixed focusing and the multistatic SA, a 1D linear-type array transducer (256 elements; an element width, 0.1 mm; kerf, 0.025 mm; an elevational width, 5 mm; an effective aperture width, 33 to 129 elements) is used. For the transmission and reception on the polar coordinate system, a convex-type transducer (128 elements; an element width, 0.1 mm; kerf, 0.025 mm; an elevational width, 5 mm; a curvature radius, 30 mm) is used. The center frequency of the transmitted ultrasound pulses is 3 MHz, and the pressure shape is shown in FIG. 22. The steering angle is defined with respect to the depth direction (the direction of the face of aperture) and expressed as $\theta$ below.

(1) Transmission of Plane Wave

FIGS. 23A(a) to 23A(d) respectively show the simulation results obtained using the method (1) for steered plane wave transmissions with steering angles $\theta$=0, 5, 10, 15°. Moreover, FIG. 23B show the results obtained, when $\theta$=0°, by performing approximate interpolations on the wavenumber matching. These results are obtained using the same reception steering angles as those of the transmission steering angles. The horizontal and vertical axes of FIGS. 23A and 23B respectively express the lateral (x) and depth (z) positions ([mm]), respectively. As shown in FIG. 23A, it can be confirmed that the echo images with image formations are obtained and the steerings can also be performed. All the images are obtained via down-sampling from 100 MHz to 10 MHz (the paragraph 0208 and 0209) and the imaging data are obtained with a spatial interval in the depth direction corresponding to the sampling frequency 25 MHz (also for other image data).

Alternatively regarding the results obtained, when $\theta$=0°, via performing the approximate interpolations on the wavenumber matchings, FIG. 23B(e) shows for the sampling frequencies 100 (left) and 25 MHz (right), the results obtained by using neighborhood spectra for the wavenumber matching, whereas FIG. 23B(f) shows for the sampling frequencies 100 (left) and 25 MHz (right), those obtained by performing linear approximate interpolations for the wavenumber matching. Although the higher sampling frequency and performing not the replacing of spectra but the linear approximations yield the images with higher stability, the results does not reach the stability of the no approximate result [FIG. 23A(a)]. Performing non-zero steering yields less stability when performing the approximate wavenumber matchings.

Figures 24, 25:
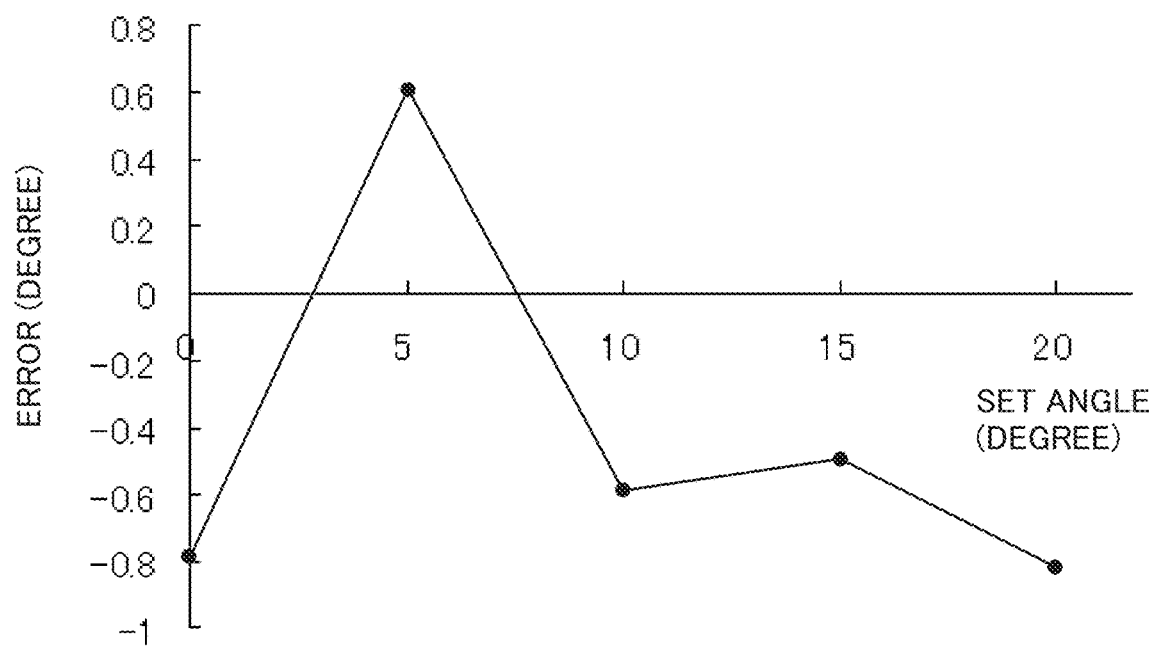
FIG. 24 shows a table summarizing for the steered plane wave transmissions with method (1), the obtained steering angles and the errors with respect to the set steering angles.
FIG. 25 shows a figure exhibiting errors of steering angles obtained for steered plane wave transmissions with method (1)

FIGS. 24 and 25 show the results calculated for the generated steering angles, ones estimated from the spectra of the generated image signals. To perform the estimation with a stability, the scatters in the numerical phantom is increased by positioning 300 scatters randomly in the depth range, 0 to 40 mm. The reflection coefficient of the respective scatters is set to −1 to 1. Regardless the steering angles, the errors ranging from 0.5 to 0.8° are confirmed. The errors depend on the positions of the scatters with respect to the generated waves. Increasing the number of scatters improves the accuracy of estimation (omitted).

Figure 27:
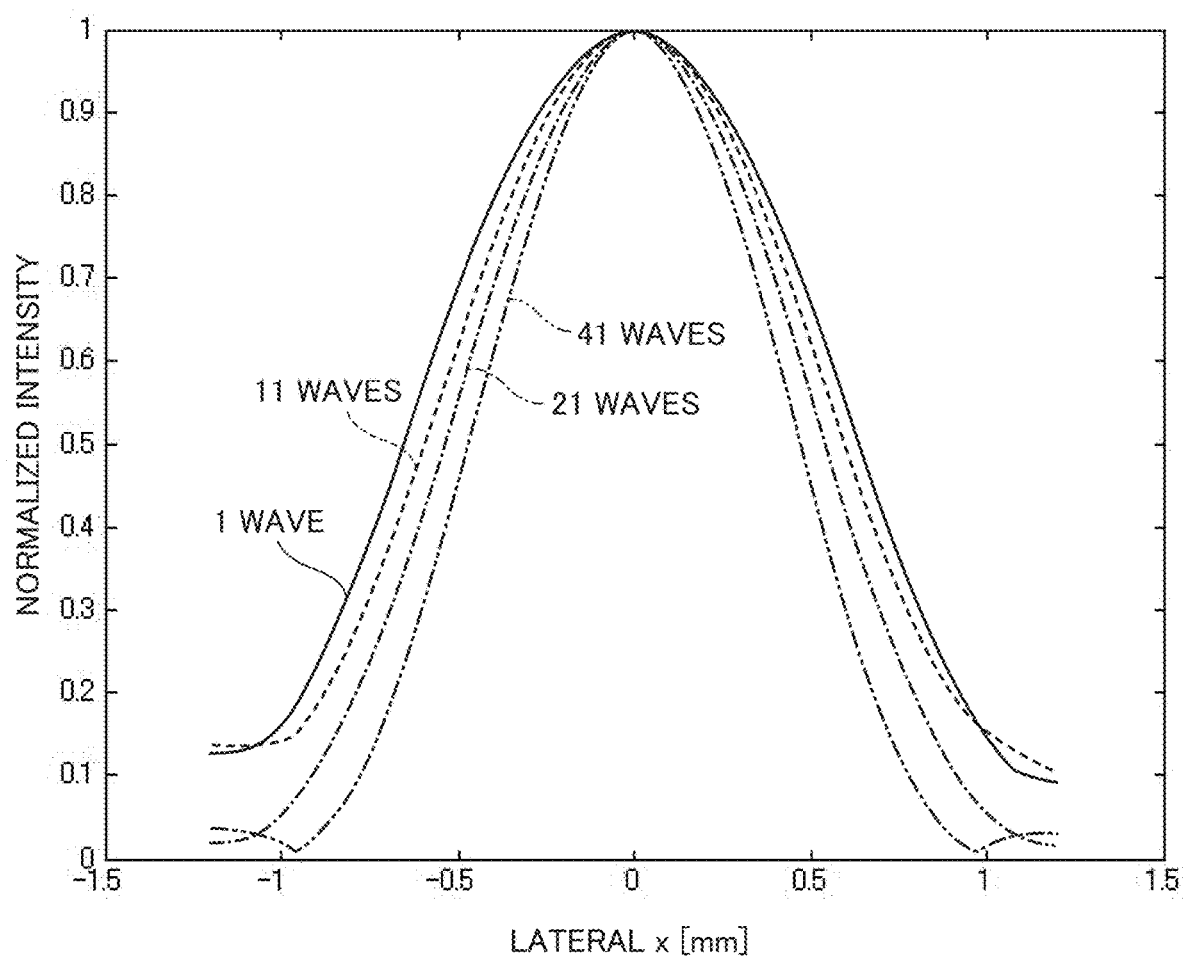
FIG. 27 shows point spread functions (PSFs) generated for steered plane wave transmissions and method (1)

FIG. 26 shows images obtained by superposing the image signals generated for the respective steering angles. The steering angles are increased with respect to the 0° (one wave) by the interval of 1°; and the results are obtained for 11 waves (−5° to 5°), 21 waves (−10° to 10°), 41 waves (−20° to 20°). FIG. 27 shows the lateral profiles of the point spread functions (PSFs) estimated from the generated image signals, of which the horizontal axis expresses the lateral (x) position ([mm]) and the vertical axis expresses the relative brightness. As shown in FIG. 27, increasing the number of superposing improves the lateral resolution.

Migration Method [Method (6) Applied to the Same Plane Wave Transmissions]

FIG. 28 shows the images obtained by using the migration method for the same steered plane wave transmissions as those of FIG. 23A. The steering angles are θ=0, 5, 10, 15° Unstable results obtained for cases with approximate wavenumber matchings are omitted.

(2) Monostatic SA

FIG. 29 shows the simulation results obtained by performing the steered monostatic SA. Similarly to FIG. 23A, performed steering angles are θ=0, 5, 10, 15°. As shown in FIG. 29, the image formations are obtained and the performed steerings can also be confirmed.

(3) Multistatic SA

FIG. 30 shows the simulation results obtained by performing the steered multistatic SA. FIG. 30(a) shows the low-resolution image generated using the received signals using the same elements for the receptions as those for the transmissions only (i.e., one set). That is, it is the same result as that of monostatic SA. FIG. 30(b) shows the results obtained by using the monostatic data together with 16 elements of the respective left and right sides with respect the transmission element for the reception, i.e., superposing of the results of 33 sets. FIGS. 30(c) and 30(d) are respectively the results obtained using the superposing of 65 sets (monostatic data and those of left and right 32 elements with respect to the transmission element) and 129 sets (monostatic data and those of left and right 64 elements with respect to the transmission element). As shown in FIG. 30, the successful image formations can be confirmed.

Figure 31:
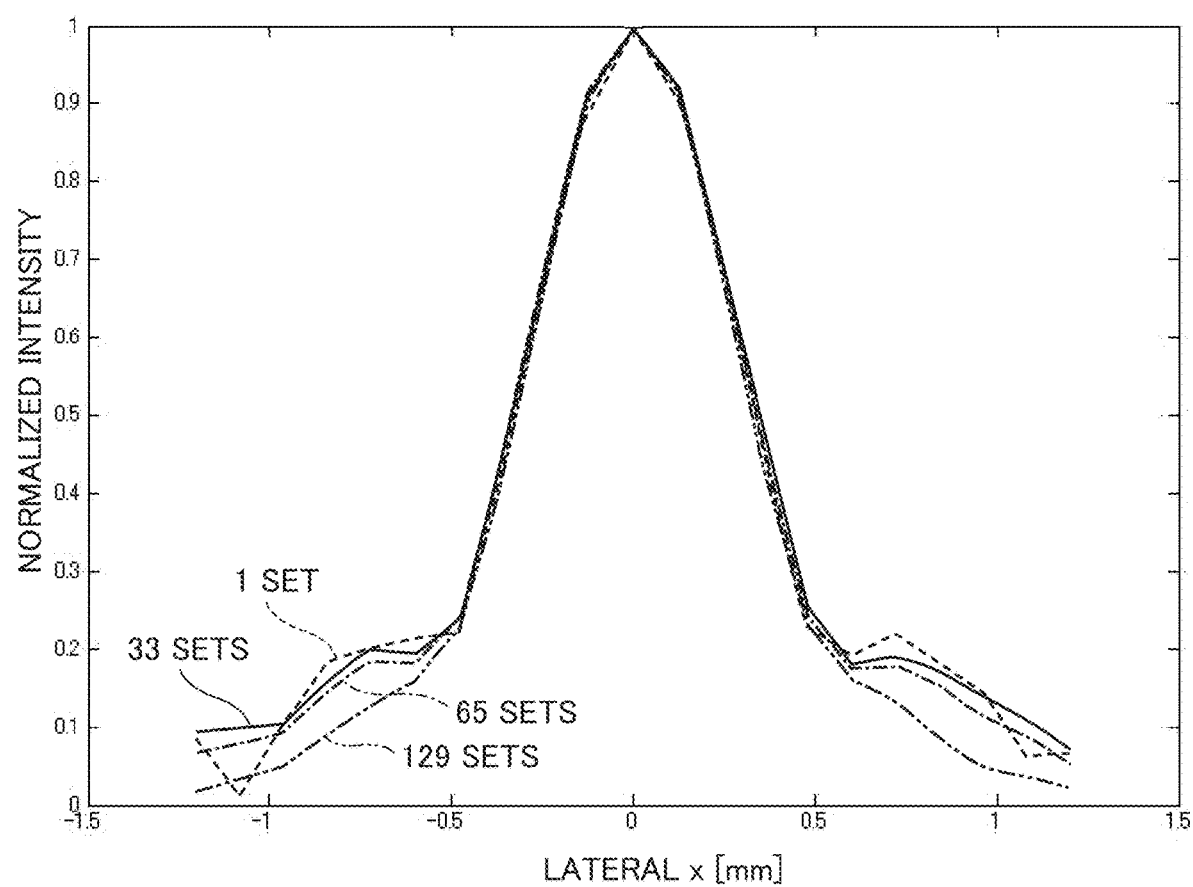
FIG. 31 shows point spread functions (PSFs) generated using method (3), i.e., multistatic SA.

FIG. 31 shows the lateral profiles of the PSFs. As shown in FIGS. 30 and 31, increasing the number of superposing suppresses the sidelobes and improves the lateral resolution.

(4) Fixed Focusing

FIG. 32 shows the results obtained for the focusing transmissions. Here, the method (1) is used. FIG. 32(a) shows the result obtained by implementing the method (1) once onto the superposing of the echo signals received on the respective transmission effective apertures as the respective reception effective apertures (method 4-1); FIG. 32(b) shows the result obtained by superposing the results of low-resolution image signals generated on the respective effective apertures (method 4-2); FIG. 32(c) shows the result obtained by superposing the results generated on the respective sets comprising of echo data of the same relationships about the positions between the transmission and reception elements similarly to the multistatic SA (method 4-3). As shown in FIG. 32, all methods successfully yield the image formations and there exists no particular differences. The method used for obtaining the result of FIG. 32(a) [method (4-1)] yields a higher speed calculation than other two methods and then effective. The result also shows that reception beamformings can also be performed on the reception signals received with respect to plural beams or all beams to be transmitted simultaneously ideally (Reception signals generated by transmitted beams with interferences can also be processed to yield a high frame rate). The processing can also be implemented on plural transmissions of all kinds of waves (including combinations of different type waves) as well as the fixed focusing transmissions. That is, the plural waves can also include ones generated by different transmission beamformings, by beamformed and not beamformed, different kinds of waves (electromagnetic waves or mechanical waves, thermal waves, etc.), nonlinear processings or detections, superresolutions or adaptive-beamformings, minimum variance processings, separations, processings such as filtering, weighting or dividing of spectra, etc. During the beamformings, the processings can also be performed. Off course, reception signals with respect to the respective transmissions can also be superposed to be processed. However, also in these wavenumber matchings, approximate interpolation processings can be performed.

(5) Image Signal Generation on Cartesian Coordinate System with Respect to Transmission and Reception on the Polar Coordinate System (5-1) Cylindrical Wave Transmission FIG. 33(a) shows the result obtained by performing the signal processings on reception signals in a frequency domain with respect to a cylindrical wave transmission performed by exciting all the convex-type array elements simultaneously. In fact, as mentioned in the method (5-1'), at the transmission and the reception, a plane wave or a virtual linear array is generated at the depth, 30 mm. As shown in FIG. 33(a), the image formations can be obtained on the scatters.

(5-1') Cylindrical Wave Transmission Using Linear-Type Array

Next, shown is the results of echo signals generated with respect to a cylindrical wave transmitted using a linear-type array and a virtual source (FIG. 8A(a)) set behind the array. FIG. 33(b) shows the result obtained using a virtual source behind the array at a distance, 30 mm, and the method (1) disclosed in the method (5-1'); FIG. 33(c) shows the result obtained using a virtual source behind the array at a distance, 60 mm, and the method (2) disclosed in the method (5-1'). The image formations can be obtained on the scatters.

On the using the linear-type array transducer and the method (1) disclosed in the method (5-1'), the case where a cylindrical wave is generated using a virtual source behind the array at a distance, 30 mm, is applied to generate a plane wave or a virtual linear-type array transducer with an extended lateral width (FIG. 8B(g)) at the distance, 30 mm. The result is shown in FIG. 33(d).

(5-2) Foxed Focusing

Using a convex-type array, fixed focusing is performed at a distance, 30 mm, from the respective elements (FIG. 14(a)). The results obtained by processing the reception signals are shown in FIGS. 34(a) and 34(b): FIG. 34(a) shows the result obtained by performing the echo signal generation processing once on the superposition of received signals of the respective effective apertures; and FIG. 34(b) shows the result obtained by superposing the low-resolution image signals generated with respect to the respective transmissions. Although omitted to show is the result obtained by superposing echo data generated with respect to the respective sets comprising of reception signals acquired at the same distances between the transmission and reception elements (similarly to the multistatic SA), these three calculation results are almost same similarly to in using the method (4). Alternatively, FIG. 34(c) shows the result obtained for the fixed focusing at a depth, 30 mm (FIG. 14(b)), by performing the echo signal generation processing once on the reception signals. The image formations can be obtained on the scatters.

These results are obtained similarly to the method (4). The result also shows that reception beamformings can also be performed on the reception signals received with respect to plural beams or all beams to be transmitted simultaneously ideally (Reception signals generated by transmitted beams with interferences can also be processed to yield a high frame rate). The processing can also be implemented on plural transmissions of all kinds of waves (including combinations of different type waves) as well as the fixed focusing transmissions. That is, the plural waves can also include ones generated by different transmission beamformings, by beamformed and not beamformed, different kinds of waves (electromagnetic waves or mechanical waves, thermal waves, etc.), nonlinear processings or detections, super-resolutions or adaptive-beamformings, minimum variance processings, separations, processings such as filtering, weighting or dividing of spectra, etc. During the beamformings, the processings can also be performed. Off course, reception signals with respect to the respective transmissions can also be superposed to be processed. However, also in these wavenumber matchings, approximate interpolation processings can be performed.

It is demonstrated that the beamformings performed via above simulations according to the present invention, using the digital Fourier transform, allows performing arbitrary beamforming processings on arbitrary orthogonal coordinate systems, with no approximate interpolations and with high accuracies, on the basis of the proper using the complex exponential functions and Jacobi calculations. Although all the beamformings achieved by the present invention can also be performed using DAS(Delay and Summation) method, owing to the differences in the lateral wavenumber matchings and the lateral Fourier transforms, all the beamformings achieved by the present invention achieves high speeds in calculations. For instance, when using the 1D array and a general PC, the calculations to be performed are at least 100 times as fast as the DAS methods. When the aperture elements distribute in a 2D or 3D space or comprise a 2D or 3D multi-dimensional array, the above methods can be multi-dimensional simply and the present invention efficiently solve the problem that it takes more processing times in the multi-dimensional processings than in the 1D processings, i.e., the increasing the speediness of beamforming becomes more efficient. Cases where superposing of plane wave transmissions with different steerings, etc. becomes effective are also demonstrated. High contrasts owing to suppressions of sidelobes as well as high spatial resolutions can be achieved with high speeds.

On the above examples, it is confirmed that arbitrary focusings (including no focusing) and steerings can be performed using arbitrary array-type aperture geometries and further, it is confirmed that arbitrary beamforming processings can be performed on arbitrary orthogonal coordinate systems with no approximate interpolations and high accuracies as well as with high speeds. The time can be shortened, required for obtaining the high order measurement results such as a displacement measurement, etc. on the basis of using the image signals generated and further, the measurement accuracy also become high. However, on the present invention, as disclosed in the methods (1) to (7), arbitrary beamformings can also be performed via implementing approximate interpolations on the wavenumber matchings; and then much higher processings can be achieved. To increase the accuracies of the approximate wavenumber matchings, proper over-samplings of reception signals are required in return an increased calculation amount. In the cases, being different from in the cases where image signals of arbitrary positions can be generated when no approximate interpolations are performed, it is cautious that the number of data to be used for the Fourier transforms increases.

At first, explained are examples of the 1st embodiment of the present invention using the representative transducers, the reception sensors, the transmission unit and the reception unit, the control unit, the output unit and the external storage devices, etc. The confirmed feasibilities of the method (1) to (7) demonstrate that arbitrary beamformings that are on the basis of the focusing and the steering can be performed on arbitrary orthogonal coordinate systems, and beamformings and the applications achieved by the instruments of the present invention are not limited these including other beamformings and applications mentioned above.

2nd Embodiment

Next, the compositions of the measurement and imaging instrument or the communication instrument according to the second embodiment of the present invention are explained. FIG. 1 shows a schematic representation (block map) of compositions for the active-type of instrument according to the first embodiment of the present invention; and FIG. 2 shows the specific schematic representation (block map) of compositions of a body of instrument shown in FIG. 1. In the second embodiment of the present invention, passive-type of instruments are used. Thus, at least the instruments according to the second embodiment are equipped with no transmission transducers and neither wire lines nor wireless lines for transferring drive signals from the control unit to the transmission transducers.

Regarding the active-type instrument according to the first embodiment, referring to FIGS. 1 and 2 showing a schematic representation (block map) of compositions of instrument, the compositions of the units and the devices are specifically explained. Absolutely active-type instruments use transmission and reception transducer array devices with arbitrary aperture geometries (including a case where a transducer can be used for both transmission and reception at least), whereas passive-type instruments do not use the transmission transducer array devices on them.

That is, the basic compositions of instrument according to the second embodiment are the reception transducers (or reception sensors) 20, the body of instrument 30, the input devices 40, the output devices (or display devices) 50, the external storage devices 60. The body of instrument 30 is equipped with the reception unit 32, the digital signal processing unit 33, the control unit 34 and not shown storage unit (memories, storage devices or storage media) mainly. The body of instrument 30 can also be equipped with the transmission unit 31. The explanations about the compositions performed on the first embodiment can also be adopted to the second embodiment.

Similarly to the first embodiment, the respective devices or the respective units in the body of instrument can also be set at different positions. The body of instrument 30 is conventionally referred to one comprised of such plural units. Similarly to the first embodiment, the reception transducer 20 can also be mechanical scanned to perform the receiving signals. No array-type transducer generally referred to as can also be used to perform almost same processings as those of array-type transducer.

However, being different from the instruments according to the first embodiment, the instruments according to the second embodiment has the functions for sensing the timings of wave generations as explained in detail below. It is possible to generate a timing signal by receiving the wave, that arrives at from an arbitrary wave source, to be observed. Or, a timing signal is generated via other process and the timing signal is sensed by the control unit via a wire or wireless line. The timing signals are used as trigger signals for the reception unit to start the acquisition of data (AD converters and writing into memories of the respective reception channels).

A way how to sense the timing signals that informed the control unit of the generations of waves is, when the waves arrive at from the wave sources themselves are used as the timing signals, to use the reception signals received by the reception aperture elements 20$a$ of the reception transducers (or reception sensors) according to the present embodiment themselves or to use the timing signals received by the exclusive receiving devices that can be equipped with the body of instrument 30.

In this case, the signals received by the reception aperture elements 20$a$ (that can be all elements, elements existing at an edge or a center, etc., or sparsely used) or the exclusive receiving devices (the reception channels can be plural at least) are temporally, continuously detected and for instance, information about reception signals such as a signal intensity, a frequency, a bandwidth or codes, etc. are set on the control unit 34 itself (internal memories) or the analogue judging circuit (in this case, can be non-variable in a software or hardware fashion and can also be fixed in a hardware fashion) via above-mentioned various types of input means. Or, the sensing of the timings of wave generations can also be performed on the basis of by collating the received signals by the reception aperture elements 20$a$ or the exclusive receiving devices with the judging data such as thresholds or values, or databases about features of waves to be observed, etc. recorded by the memories or storage devices (storage media).

When judging the received signals in an analogue fashion, exclusive analogue circuits equipped with can be used and only when the received signals are judged as signals to be observed, the trigger signals are generated for starting the data acquisitions, i.e., the reception signals are AD converted and stored into memories or storage devices (storage media); and beamforming processings can be performed.

When judging the received signals in a digital fashion, the received signals are temporally, continuously AD converted and stored into the memories or storage devices (storage media) and always or occasionally (when the command is given via the input means, etc.) or at the specified temporal intervals (can be set via the input means, etc.), the stored signals are read out by the digital signal processing unit 33 and further judged on the basis of by collating with the judging data. Only when the signals are judged as the signals to be observed, beamformings can be performed.

Since the storage capacity of the memories or storage devices (storage media) is finite, when the digital judging is performed, if the signals to be observed are not detected within a specified time (that can be set via the input means, etc.), the memory address can be initialized. Although it is not effective for energy saving, occasionally the beamformings are performed to yield image signals with high accuracies and on the basis of using the generated image signals for collating with the judging data, the wave signals can be judged. Also when the waves of general communication purposes are observed, the processings can be performed similarly.

The exclusive receiving devices can be set at different positions from other devices or units, for instance, positions in the neighborhoods of wave sources to be observed, positions where the reception environments with respect to the timing signals are favorable, etc. Waves (to be the timing signals) that propagate with higher speeds than the reception signals received by the reception apertures can be used, the timing signals can be transferred to the control unit in the body of instrument via the exclusive receiving devices. Exclusive lines (wire or wireless) that can use repeaters can also be used. In this case, the timing signals are used as the trigger signals for performing the acquisitions of reception signals (AD converting, storing into the memories or storage devices, storage media) and beamformings.

After the waves to be observed are received by the instruments of the present invention, the timing signals of the wave generations can arrive at. That is, the propagation speed is slow, or such a mechanism is employed. Such a case also occurs consequently. To cope with such cases, the acquisitions of reception signals are always, continuously performed to make it possible to retroactively reading out the corresponding reception signals stored into the memories or storage devices (storage media), and beamformings can be performed. In the cases, information about the waves obtained by other observers or observing instruments can be added onto the timing signals as additional information at repeaters, etc.; and the timing signals with the additional information are transferred; and information including the additional information are read out by the exclusive receiving devices; and the information read out can be used by other instruments as well as the instruments of the present invention. The lines to be used are not limited to exclusive lines and general networks can also be used. Also when the waves of general communication purposes are observed, the similar timing signals can also be used. The additional information can also be transferred using other waves or signals from the timing signals.

Together with the generations of waves to be observed, waves being different from the timing signals with higher or lower propagation speeds than the waves received at the reception aperture elements are generated before, at or after the generations of the waves to be observed; and the exclusive receiving devices or lines can be similarly set and used. In the cases, information about the waves to be observed can also be added to timing signals; and at repeaters, etc., information about the waves obtained by other observers or observing instruments can also be added to the timing signals as additional information and the timing signals with the additional information are transferred; and information including the additional information are read out by the exclusive receiving devices; and the information read out can be used by other instruments as well as the instruments of the present invention. The lines to be used are not limited to exclusive lines and general networks can also be used. Also when the waves of general communication purposes are observed, the similar timing signals can also be used. The additional information can also be transferred using other waves or signals from the timing signals.

As these exclusive receiving devices, exclusive sensing devices are used such that the timing signals can be sensed or the additional information can be read out. Arbitrary observers or arbitrary observing instruments (arbitrary active- or passive-types of observing devices or the similar observing devices, etc. and others such as arbitrary active- or passive-types of observing devices or the similar observing devices, etc. related to other phenomena or waves that can be the presages of the target wave generations, other phenomena or waves simultaneously generated related to the target waves, or other phenomena or waves generated after the target wave generations, etc.) can also be used. Irregularly, the exclusive receiving devices can perform only the reception of timing signals, reading out the additional information can also be performed by the digital signal processing unit using the control unit in exclusive devices or the body of instrument.

In the cases where the active- or passive-types of instruments themselves can also be used as the sensing devices for the timing signals, similarly, the additional information can be read out by the digital signal processing unit 33. The timing signals can also be generated by the sensing devices equipped with. When the time or the place, or both the time and the place the waves are generated are unknown, the generations of timing signals are important for increasing the efficiencies about the data acquisition operations and beamforming processings, saving the electric power, saving the memories or storage devices (storage media). On the basis of the clock signals of the control unit 34, the data acquisitions and the beamformings are performed. When the wave sources are temporally digital, the synchronizing should be performed with respect to the clocks of the control unit. On the basis of the digital receptions of waves to be observed, the instruments can work with high clock frequencies and high sampling frequencies. When the timing signals are digital, the synchronizing is performed in the body of instrument and this is also when the timing signals are analogue.

The objects to be observed are waves generated by self-emanating type wave sources themselves, the features of wave sources (magnitudes, types of sources, etc.), the positions where or the times when the sources work, etc. The source can also be processed as a diffraction source. Similarly to when the instruments are active-type, temperatures (distributions) of objects can also be calculated from the spectra of waves, or distributions such as of a displacement, a velocity, an acceleration, a strain, a strain rate, etc. can also be measured. Also, the properties of media in which the waves propagate (a propagation speed, physical properties related to waves, an attenuation, a scattering, a transmission, a reflection, a refraction, a diffraction, etc. or their frequency variances, etc.) can be observed; and further the structures or compositions of the objects can also be clarified. For instance, radioactive substances (isotopes used for PET, etc.), substances with nonzero thermodynamic temperature, earthquake sources, nervous activities, celestial astronomical observations, weathers, arriving bodies, moving bodies, communication instruments including mobile communication instruments, reactors with respect to physical or chemical stimuli, electric sources, magnetic sources, radioactive sources, or various types of energy sources, etc. can also be observed and the observation objects are not limited to these.

Via multiphysics and multichemistries using reception transducers or reception sensors with respect to plural different types of waves, the fusion of measurement results or the data mining can also be performed. Off course, a single transducer or sensor can also be used for the observations (For instance, for medical ultrasonic imaging, strains expressing tissue deformations and blood flows, and tissue properties related to these can also be imaged selectively with being simultaneously superposed with different colors, etc. onto an echo image, and by using a wideband transducer, plural photoacoustic waves with respect to different markers can also be imaged simultaneously with different colors, etc., where according to the magnitudes of physical quantities and physical properties, and the directions of physical quantities, the colors can also be changed and the depths of colors can also be changed, etc.). With respect to multi-functions or a function on the basis of physical or chemical properties, or ones that effect the surrounding in other states, etc., by observing the behaviors of a systemic of object (for a human, a whole body) or of a local is performed in a multi-faceted fashion, newly or specifically the behaviors of the systemic of object (for a human, a whole body) or the local can also be understood. For instance, on living things, various nervous controls (body temperatures, blood flows, metabolisms, etc.) performed for a short or long time, effects (radiation exposures, nutrient intakes), etc. performed for a short or long time can be observed to be used for developing artificial organs or cultured tissues that contribute to a longevity or lengthening-life, the hybrids, medicines or supplements, etc. and for monitoring their actions or operations.

It is important that the developed country reaches aged society including Japan, and therefore the QOL must be improved and medical expenses must be decreased. For the many diseases of adult diseases, which are increasing, such as human cancerous diseases including a liver cancer, a pancreatic cancer, a renal cancer, a thyroid cancer, a prostate cancer, a breast cancer, etc. (more than 1.5 million people in Japan; one of two people suffers; and the cause of death of one of three people), a uterine myoma, brain disease including a brain tumor, a cerebral hemorrhage, cerebral infarction, etc., (more than approximately 1.3 million people), ischemic heart diseases including a myocardial infarction, an angina pectoris (more than 1.7 million people), an arteriosclerosis/a clot (the cause of death of one of four people), a hyperlipidemia (more than 2.06 million people), diabetes (more than 10 million people), the inventor of the present invention focuses on the networks of a nerve, a blood stream and a lymph in the linkage of the organs/diseases. The present invention can open up the innovative, integration image diagnosis systems, techniques and clinical styles (including the examination) for achieving a simple and inexpensive, early noninvasive differential diagnosis with a high precision.

Almost metastasis cancers are, in addition to those to the lymph nodes which attract a lot flows of the lymph fluid (lymphogenous metastases), those to tissues which are rich about the blood flows such as the lung, liver, brain, bone, etc. (hematogenous metastases). Currently, about the lymphoma, when the swelling and stiffness are detected at first, next the expansion (the stage of a disease) and a whole-body state are diagnosed. Various cancers are known to metastasize between organs through the blood flows, for instance, a pancreatic cancer, a breast cancer, a stomach cancer, a lung cancer, and a colon cancer respectively metastasize to a liver and a peritoneum, etc., a liver, a lung and a brain, etc., a lung, a liver, a kidney, a pancreas, etc., a liver, a kidney, a brain, etc., a liver, a lung, a brain, etc. As for the metastasis cancers having the characteristics of primary cancers, it is vital to identify the primary cancers in order to provide appropriate treatments. Of course, for instance, for the case of the primary hepatocellular carcinoma, it is important to perform the detections of a hepatitis, a viral chronic hepatitis, a cirrhosis, etc. causing it (outbreak mechanism itself). In addition, since it had been clarified that there exist many feeding arteries around an early cancer tumor and lot intratumoral blood flows in an advanced cancer tumor; if a bloodstream is poor, the probability of the prostatic disease and the uterine myoma is high; if a blood pressure is high, the probability of the arteriosclerosis is high; for the clot, the high fat blood and the blood sugar, a viscosity is large; the probability to suffer from a cancer rises 1.2 to 1.3 times much by yes or no of the diabetes past; a coronary heart disease onset risk becomes higher to 3 times in a diabetes group; the diabetes and dyslipidemia (20-50% of diabetes) turn worse mutually, and they promote the arteriosclerosis; the temperature rise by heating increases the bloodstream (perfusion); the kidney controls the number of red blood cells (an oxygen content) and the blood pressure, etc., the present invention for observing with a high precision in a real-time the conditions of diseases, nerve controls, hemodynamics simultaneously. It is also desirable that the hemodynamic measurement accuracy increases, i.e., for the clot for after the art, and for the pacemaker user (the welfare) for the everyday life.

For instance, with the above-mentioned approach focusing on the networks of nerves, blood flows and lymphs, using a single instrument such as an MRI (magnetic resonance imaging), a SQUID (superconducting quantum interference device), (photo) ultrasound instrument, OCT (optical interference tomography) or the fusion instrument is used and using the new high accuracy but simple real-time 3D in vivo image diagnosis techniques based on the inverse problems for the three fundamental physics of electromagnetics, mechanics and thermology (paragraph 0377, etc.) allows performing integrated early imaging techniques about the conditions of the linked organs/tissues (simultaneous observations or fusion imagings focusing on the relationships (linkages) by the simultaneous plural observations about the same or plural organs/tissues) Moreover, As low invasive treatment means of a cancer, and brain and heart diseases, the fusions of the high intensity focus ultrasound (HIFU), electromagnetic thermal coagulation treatment, chemotherapy, pharmacy therapy, various radioactive therapy, etc., can also be made possible and revolutionarily a high precision but inexpensive, early differential diagnosis and low invasive, early treatment can also be made possible. Thus, an innovative clinical style can be opened up such that the thermal treatment can be performed immediately after the the short time, early stage diagnosis is performed.

(1)<Electromagnetics base> Imagings of an electric current density vector and electric properties using MRI and SQUID: The neural network in a brain is visualized by imaging the 3D distributions of the electric current field and the electric properties (a conductivity and a permittivity (dielectric constant)) based on the magnetic field measurements (to be superposed onto the diffusion imaging of MRI for the displaying). They are respectively the inverse problem of Bio-Savart's law and the differential-type inverse problem using the observed current density vector data. For instance, the controlling of perfusion can be monitored for the below-described (6) fusion with the HIFU thermal treatment.

(2)<Mechanical base> Imagings of a blood flow and a blood pressure and a shear viscosity using MRI, (photo) ultrasound, OCT: Using the MRI based on the distribution imaging such as of a hydrogen, a carbon, and a phosphorus, etc., the ultrasound echo technique, and the (photo) ultrasound technique (under the differentiation of artery and the vein, using a D- or L-form glucose which is well taken in a cancer cell, of which latter is special as reported recently, a sugar due to a diabetes, and an LDL and HDL cholesterol and an acyl glycerol due to a dyslipidemia as a contrast agent or a marker), the 3D distributions of the 3D flow velocity vector and the 3D strain rate tensor are imaged using the multi-dimensional Doppler method (being different from the conventional Doppler, only directing the sensor to the object allows observing the vector in an arbitrary direction). Moreover, the 3D distributions of the blood pressure or the cardiocavity pressure, the shear viscosity and the density are imaged based on the differential-type inverse problem using the observed flow velocity data. As for the MRI, in the intracranial brain, as for the ultrasonic echo technique, in the cardiocavity, the abdominal organs (liver, pancreas, kidney, prostate, uterus) and in the superficial tissues (breast, thyroid gland, eyes, skin), and as for the (photo) ultrasound or OCT, the organs in an opened body, the eyes, the skin (the eyes in conjunction with diabetes), the blood flows are observed. Thus, finally, the blood flow network is observed. The ischemic heart diseases (myocardial infarction and angina), the cerebropathys (brain tumor, cerebral hemorrhage, cerebral infarction), the arterioscleroses, the clots are diagnosed with paying attentions to the dyslipidemia and the blood sugar by the quantifications of the blood pressure, intracavity pressure, viscosity. For (5) integration imaging, (3) the simultaneous observations of the soft tissues are performed. Or, (6) the monitoring of the perfusion at the HIFU thermal treatment is performed.

(3)<Mechanical base> Imagings of mechanical dynamics and a (visco) shear modulus for soft tissues using MRI, (photo) ultrasound, OCT: As for the ultrasound echo technique and the (photo) ultrasound (the soft tissue ingredients are focused on, and novelly the wideband observations of an irradiation light and photoacoustic wave with or no contrast media and marker are performed), the 3D distributions of the 3D displacement vector and 3D strain tensor of soft tissues are imaged using the same multi-dimensional Doppler method as that of (2). Moreover, the 3D distributions of the intra-body pressure (intra-tissue pressure or eye pressure), (visco) shear (stiffness), density, mechanical source (radiation force or HIFU) are imaged in situ from the observed displacement data based on the differential-type inverse problem. As for the MRI, the intracranial brain tissue and the lymph network, as for the ultrasonic echo technique, the heart tissue (myocardium and each valve), the abdominal organs (liver, pancreas, kidney, prostate, uterus), the superficial tissues (breast, thyroid gland, eyes, skin), the lymph network, and as for the photoacoustics and OCT, the organs in an opened body, the eyes, the diseases of skin (tissue conditions) are diagnosed. For (5) the integration imaging, (2) the simultaneous imagings of blood flow are performed. Or, (6) the monitoring of the effects (tissue degeneration such as a coagulation, etc.) of the HIFU thermal treatment is performed.

(4)<Thermal base> Imagings of a temperature and thermal properties of soft tissues using MRI, (photo) ultrasound, OCT: For monitoring of the metabolism and (6) the HIFU thermal treatment, in addition to the observations using the chemical shift of Larmor frequency of MRI and the temperature dependency of (photo) acoustic propagation speed and the volume, the temperature dependency of (3) the (visco) shear modulus is used for observing the in situ 3D temperature distribution, which realizes a practical observation being robust to the tissue displacement. The terahertz and infra-red measurements can also be performed. To increase the temperature measurement accuracy, the observations can also be performed simultaneously, and further the temperature dependency data used in other measurement methods being calibrated based on the high accuracy temperature measurement can also be used, or a target temperature can also be obtained from every temporal temperature measurements or temporal changes. Furthermore, the 3D distributions of the thermal properties (thermal conductivity, thermal capacity. thermal diffusivity), the perfusion (applicable of (2) blood flow), and the thermal source (HIFU) are imaged based on the differential-type inverse problem, which can be applied to the planning of thermal treatment of (6) HIFU thermal treatment.

(5)<Integration imaging> Simultaneous, plural observations of plural organs based on (1) to (4): By performing the 3D imaging of tissue properties based on the electromagnetism, mechanics, and thermology, the integration image diagnosis for simultaneously observing one organ or plural organs from plural aspects is performed with mainly performing the observations of the networks of a nerve, a blood flow/perfusion, and a lymph (i.e., linkage between organs and diseases). The short time diagnosis with a simplicity can be performed.

(6)<Fusion of integration imaging and treatment> The HIFU thermal treatment control (automatic treatment) using (5) the integration imaging: To complete the treatment low-invasively in a short time, used is the sequential-update-type automatic thermal treatment planning that performs the prediction of a temperature distribution to be generated by calculating the temperature distribution via a the temperature calculation simulator utilizing (2) the blood flow data, and (4) the observed data of temperature and thermal properties and HIFU thermal database and also uses the monitoring data of the treatment effects (degenerations) performed by (3) the (visco9 shear modulus imaging. Under performing the phase aberration correction, the controllings are performed about the HIFU beam focusing (heating) position, the beam shape, the beam intensity, the radiation duration, the radiation interval. By increasing the treatment accuracy, confidence, safety, treated can also be other diseases from the prostate cancer and the myoma of uterus with no obstacles such as a bone that are treated widely since the HIFU applicator can be set in the neighborhood of the disease.

The treatment means should be low-invasive and not limited to these as mentioned above. The present invention allows providing the aged society with simple and high QOL, but inexpensive techniques. By this, the examinations leading to the early detections and the preventions spread in the society, and the much shorter treatment means to be performed simultaneously ideally can also be realized (a major candidate for theranosis). The above-described imagings and treatments can be performed not only from a body surface but also during the surgery (The organ in an opened body can be treated directly or via organs.), under the operation of laparoscope art, through a mouth, a nasal hole, a gate or a vagina.

These include the cases equipped with replacements or complements of various sensors equipped with living tissues, or new sensors. When the objects are living tissues, a small size and wearable, and geometries and materials to be familiar to the living tissues can also be demanded. The contents of proceedings to be performed are also various, for instance, when plural mechanical waves such as compressible waves or shear waves arrive at simultaneously, similarly to in the first embodiment, the waves can be separated on the basis of the modes, frequencies, bandwidths, codes, propagation directions, etc. using analogue exclusive devices or the digital signal processing unit; and beamformings can be performed. When there exist plural electromagnetic wave sources, plural electromagnetic waves with different features can be being superposed, the separations can be performed similarly. Or, even if plural waves arriving at, high accuracy image signals can be generated owing to the effects of the phasings and summings in beamformings (for instance, the media include scatters).

Off course, after performing the beamformings, signals can also be separated on the basis of the same processings. To obtain the effects of phasings and summings, the arrival directions of waves or the positions of wave sources are required to be calculated; and the beamformings can be performed with steering in the calculate directions and with focusing at the calculated positions. On performing the reception beamformings, the fixed focusings as well as the dynamic focusing are useful. To calculate the data, the first moments of the multi-dimensional spectra or the instantaneous frequencies of waves received at the reception aperture element array, the bandwidths, the so-called MIMO, SIMO or MUSIC, the independent components analysis, encoding, or various types of parametric methods, etc. can also be used. After performing the beamformings, the same processings can also be performed. Particularly, after performing the beamformings at plural positions, waves can also be observed using geometrical information. The processing methods are not limited to these, for instance, methods are performed under the approaches of inverse problems, etc.

For instance, the propagation directions of arriving waves can be calculated on the basis of the analysis of multi-dimensional spectra (a past patent of the patent invention's inventor). Furthermore, using the instruments of the present invention, even when the information of propagation times cannot be obtained using plural transducers or reception effective apertures set at different positions (generally, using the times when the waves are observed at plural positions are used to calculate the position of the wave source and the distance to the source), it is possible to calculate the position and the distance geometrically. If the wave is not a pulse wave nor a burst wave but a continuous wave, the wave source can be observed. When the arrival direction of the wave is confirmed using an arbitrary processing, by performing the reception steering and the reception focusing in the direction where the wave source exists (monostatic or multistatic SA), the wave source can also be observed in detail. If necessary, using the active-type instruments of the first embodiment, the transmission beamformings can also be performed. In these processings, by interrogating the directions with high possibilities of the existence of wave source mainly by performing the reception beamformings with changing the steering angle, the direction of the wave source can also be specified via observing the obtained images or image formations, spatial resolutions, contrasts, signal intensities, etc. or performing the multi-dimensional spectra analyses. The steering can also be automatically controlled.

Performing superresolutions, the spatial resolutions of image signals can be increased. The descriptions about the processings are also performed in the paragraphs 0009 and 0425. As the effects of the superresolutions, it becomes simple to measure the wave sources, or the sizes, intensities, positions, etc. of scatters or reflectors in measurement objects or in media. Although the bandwidths of targets are absolutely limited by the physically generated wave fields, the representative superresolution implements the inverse filtering onto the bandlimited data to increase the bandwidths and restore the original wave sources or signals. Generally, the waves are suffered from the frequency-dependent attenuations, out of focusings, motion artifacts (when the wave sources can be moving), disturbances possible in media existing between the transducers and the objects. To compensate these effects, such a superresolution can also be performed. As mentioned in the paragraph 0383, not only the increasing the bandwidth but also the performing the filtering such that the desired point spread function can be generated is effective and for various superresolutions, performing the combination of the filtering and the inverse filtering in a frequency or spatio-temporal domain is one of features of the present invention.

Also, when the measurement object, etc. moves during performing the transmission and/or reception to generate an image signal, the motion compensation is required to be performed. There is often that the PSF is unknown and in the cases, blind convolution can be performed including the cases where the above-mentioned signal separation processing (particularly, blind separation) is performed together. The methods, etc. mentioned in the paragraph 0425 are well known. Or, there are various other methods such as the maximum likelihood, etc. (e.g., nonpatent documents 39-41, etc.). The PSF is estimated using some ways such as via the estimation of an autocorrelation function and ideally, the PSF is desired to be coherent. However, including the cases where a spectra distribution geometry or a bandwidth is estimated with respect to incoherent signals, inverse filtering can be performed. Also in this case, performing together the filtering to yield the desired point spread function is useful.

If the PSF cannot be estimated when the PSF is required to be observed, for instance, data-base prepared in advance, comprising the data on the PSF estimated when the estimation can be achieved, should be used. One of the effective methods performing inverse filterings is to weight the spectra of the observed signals such that the amplitude spectra (strictly, effective values) distribution becomes the same as those of the desired PSF or the desired echo distribution. The amplitude spectra distribution of the desired PSF or the desired echo distribution can also be set analytically; using simulations; or via optimization, etc.; or by performing the beamforming using desirable parameters with respect to the measurement object and specifically, by performing the estimation once with performing the beamforming once, by calculating an ensemble mean with performing the beamforming plural times or by performing the additional averaging under the locally stationary assumption (which has a long history, for instance, nonpatent documents 35 and 36); by similarly performing the estimations with respect to calibration phantoms. A 1D point spread function in the direction of a wave propagation or the orthogonal direction can be estimated from the corresponding 1D autocorrelation function; and a multi-dimensional point spread function can be estimated from the corresponding multi-dimensional autocorrelation function (nonpatent documents 8 and 14). The autocorrelation functions are respectively equivalent to the corresponding 1D spectra in the direction of the wave propagation and the orthogonal direction, and the corresponding multi-dimensional spectra (i.e., auto-spectra). These can be used for estimating the wavelength of a wave, the geometry of a mechanical source, the spatial resolution of a wave (patent document 11, etc.), or superresolutions. For instance, the spatial resolution of low-resolution signals generated by performing a plane wave transmission that allows high-speed receptions with a Gaussian-type apodization (nonpatent document 15) can be increased by using a desired, high spatial resolution PSF or echo distribution generated using a fixed focusing or a dynamic focusing with an exponentiation-type apodization (nonpatent document 15). The using a plane wave transmission is proper for achieving a high accuracy measurement of a rapid object motion or a shear wave propagation and then, the simultaneous using the beamforming and the superresolution realizes the high spatial ultrasound imaging as well as the measurement. Or, the spectra of the signals themselves can be used for performing the inversion. The processing can be performed onto the angular spectra obtained before the wavenumber matching or the spectra obtained after the wavenumber matching. That is, using the angular spectra or the spectra of a signal distribution such as a desired PSF or echo distribution, etc. to those of the reception signal can yield the spatial resolution. On the weighting processing, it is cautious that various type noises filled in the reception signals should not be amplified, i.e., not by dividing the object spectra with zero or small spectra, and as mentioned above, the regularization (suppressing the extra amplifications of high frequency components) or the Wiener filter (suppressing the amplifications of low SNR frequency components), singular-value-decomposition (small singular values and spectra are disregarded and the corresponding frequency signal components are not used), the maximum likelihood (being the MAP or not), etc. are effective to cope with the problem.

Also on the processes of the above-mentioned digital wave signal processings in the methods (1) to (7), the inverse filtering can be performed. The spatial resolution of the correspondingly obtained image signals can be increased; and regarding the quantitativeness (numerical data), the same effects can also be obtained and then, when the numerical data are display as images, the same effects can also be obtained. Effects such that blurred images can be restored or focusings are yielded can be obtained. The inverse filtering can also be implemented on incoherent signals. However, it is effective to implement it on the coherent signals and particularly, the effects can be confirmed on the understanding of the spatial distributions of physical properties. The superresolution can also be implemented on superposed image signals or spectral frequency divisions; and the applications of the superresolutions are not limited to these.

In the present invention, it is also possible to perform new superresolutions. One is on the basis of the nonlinear processings disclosed later, whereas another is the instantaneous phase imaging.

The signal, obtained using a single wave or beam with the propagation direction t (coordinate axis) at the position coordinate t=s, is expressed as follows.

$$r(s)=A(s)\cos\{\int_{t=0}^{t=s}\omega(t)dt+\theta(s)\} \quad (30\text{-}1)$$

where $$\theta(s)=\int_{t=0}^{t=s}\delta\theta(t)dt \quad (30\text{-}2)$$

and t=0 is the reference position of the t-axis direction, i.e., the position of the wave source and $\delta\theta(t)$ expresses the change in phase generated at the position coordinate t due to the reflection or scattering.

On the basis of the signal model, the instantaneous angular frequency ω(t) and the instantaneous phase θ(s) etc. along the propagation direction t are calculated and imaged. The propagation direction t directs in the facial direction when not performing a steering, whereas the direction t has a steering angle (nonzero) when performing a steering. The ROI can also be 3D, 2D or 1D. As disclosed in the nonpatent document 19, the propagation direction of the wave or beam can be measured with a spatial resolution (the 1st moments or the instantaneous frequencies can be used) together with the frequency in the propagation direction. Thus, the frequency in the direction of an integration path (tangential direction) set on the spatial integration processing of a frequency disclosed later can be calculated with a high accuracy. For instance, the integration path can be set as a straight line using the steering direction (expressed by an angle) set at performing the transmission or using the global estimate of a steering direction (an angle) of the generated wave or beam similarly. To simplify the processings, the nominal frequency or simultaneously obtained global frequency estimate in the globally estimated direction can also be used. It is not impossible to perform the integration in the propagation direction estimated with a spatial resolution, however, since the interpolation processing is required, it is not practical.

Here, A(s), being an amplitude, expresses the reflection intensity or the scattering intensity at the position coordinate t=s and for instance, can be calculated by performing the envelope detection (square root of summing of squared IQ signal components) via the quadrature detection of eq. (30-1). Or, the quadrature signal component $$r'(s)=A(s)\sin\{\int_{t=0}^{t=s}\omega(t)dt+\theta(s)\} \quad (31)$$

is generated by Hilbert transform using Fourier transform; and using the in-quadrature signal component eq. (30-1) together, A(s) can be calculated (patent document 7 or nonpatent document 14). The latter calculation method is proper to the digital signal processing particularly.

Using eqs. (30) and (31), the complex analytic signal can be expressed as follows (patent document 6 or nonpatent document 7).

$$r(s)=A(s)\exp[i\{\int_{t=0}^{t=s}\omega(t)dt+\theta(s)\}] \quad (32)$$

To calculate the instantaneous phase θ(s), at first, the instantaneous angular frequency is calculated. As the usual practice, using the methods disclosed in the patent document 6 and the nonpatent document 7, assuming is performed that the instantaneous frequency at the position coordinate t=s equals to that at the next sampling position coordinate t=s+Δs, however, the instantaneous phase at the position coordinate t=s does not equal to that at the next sampling position coordinate t=s+Δs (δθ(t) is a random change in phase determined by the random scattering intensity or reflection and with respect to t, the change can be large).

$$\omega(s)\approx\omega(s+\Delta s) \quad (33)$$

$$\Delta\theta(s)=\theta(s+\Delta s)-\theta(s)=\int_{t=s}^{t=s+\Delta s}\delta\theta(t)dt \quad (34)$$

(random and the value can be small)
Under the assumptions, the signal at the position coordinate t=s+Δs is expressed as $$r(s+\Delta s)=A(s+\Delta s)\exp[i\{\int_{t=0}^{t=s+\Delta s}\omega(t)dt+\theta(s+\Delta s)\}], \quad (35)$$

and under the assumptions of eqs. (33) and (34), the production of eqs. (32) and (35) is expressed as follows.

$$R(s) = r(s+\Delta s)r^*(s) \quad (36)$$
$$\approx A(s+\Delta s)A(s)\exp[i\{\omega(s)\Delta s+\Delta\theta(s)\}]$$

Thus, the instantaneous frequency at the position coordinate t=s can be estimated as follows.

$$\omega(s) \approx \frac{\tan^{-1}\frac{Imag\{R(s)\}}{Real\{R(s)\}}}{\Delta s} \quad (37)$$

As disclosed in the patent document 6 or the nonpatent document 7, in practice, since noises are filled in the signal r(s) and assuming eqs. (33) and (34), the moving-average processing is performed in the s-axis direction or including the orthogonal two or one direction to increase the accuracy of estimate. This moving-average processing can also be performed on eq. (36) and the estimate is calculated according to eq. (37):

$$\overline{\omega}(s) \approx \frac{\tan^{-1}\frac{Imag\{\overline{R(s)}\}}{Real\{\overline{R(s)}\}}}{\Delta s} \quad (38\text{-}1)$$

or the moving-average processing is also performed on eq. (37) itself:

$$\overline{\omega}(s) \approx \overline{\frac{\tan^{-1}\frac{Imag\{R(s)\}}{Real\{R(s)\}}}{\Delta s}} \quad (38\text{-}2)$$

It was previously confirmed that for a displacement (vector) measurement, eq. (38-1) yields a higher accuracy than eq. (38-2) itself:

Using these moving-averaged instantaneous frequencies, detection can be performed on the instantaneous frequency at the respective position coordinate. Since the estimate of the instantaneous frequency is unbiased, in the digital signal processing cases, the following equation $$demf(s)=\exp[-i\{\int_{t=t'}^{t=s}\overline{\omega}(t)dt\}] \quad (39)$$

is multiplied to eq. (32) and under the assumption that the instantaneous phase θ(s) is the integral of a random change in phase determined by the random scattering intensity or reflection (i.e., random), the estimate can be obtained.

$$\theta'(s) = \tan^{-1}\left[\frac{Imag\{r(s)demf(s)\}}{Real\{r(s)demf(s)\}}\right] \quad (40)$$

Instead the moving-averaged instantaneous frequencies calculated by eqs. (38-1) and (38-2), the 1st moment of spectra (i.e., a weighted mean) (×2π) can also be used. The expression is given as eq. (S1).

The t in the expression of the above-mentioned observed signal being 0 (t=0) expresses the reference position of the t-axis direction, i.e., the position of the wave source. With respect to this, the reference position t=t' in eq. (39) can also be set to 0 (i.e., t'=0, the position of the wave source) and in the cases where the θ'(s) calculated as a distribution regarding the position coordinate t=s is the estimate of the instantaneous phase [eq. (30-2)] itself, expressed as the integration of the change in phase due to the reflection and scattering. The averaged instantaneous frequency is used and then, the calculated θ'(s) is an estimate obtained under the condition.

When due to the effects of window lengths used for the moving-average processings or calculations of spectra, the instantaneous frequencies cannot be estimated from the position of the wave source (t=0) to t=s' (not zero and not equal to s as well), using t'=0 and an angular frequency $\omega_0$ that is a nominal frequency or a measurement/estimate obtained in advance, $$\overline{\omega}(t) - \omega_0 \ 0 \leq t \leq s' \quad (41)$$

in eq. (39), which is calculated. Or, using t'=s' (not zero, but not equal to s as well) in eq. (39) is possible and however, in the cases the following bias error is generated in the estimate θ'(s).

$$\theta_{bias} = \int_{t=0}^{t=s'} \overline{\omega}(t) dt \quad (42)$$

However, when the change in the instantaneous phase Δθ(s) between at the position coordinate t=s and the next sampling position coordinate t=s+Δs (i.e., sampling interval is Δs) is estimated on the basis of eqs. (30-2) and (34), the bias becomes no problem. The estimate result can be obtained as follows.

$$\Delta \theta'(s) = \tan^{-1} \left[ \frac{Imag[\{r(s+\Delta s) demf(s+\Delta s)\}\{r(s) demf(s)\}^*]}{Real[\{r(s+\Delta s) demf(s+\Delta s)\}\{r(s) demf(s)\}^*]} \right] \quad (43)$$

For eq. (36), the conjugate product with a complex exponential having ω(s)Δs as a kernel can also be calculated. In the above eqs. (34), (36) (43), etc., the subtraction of phase is calculated using the finite forward difference and instead, the backward difference can also be performed. And, in eqs. (37), (38-1), (38-2), the calculation of differentiation of phase is approximated by dividing the above-mentioned phase difference by the sampling interval and instead, a differential filter with a high cutoff frequency can also be used for the differential processing. And, for the integration of the estimate of an instantaneous frequency in eq. (39), known various integration operations such as a trapezoidal method can be performed.

The estimate of the instantaneous phase [eq. (30-2)] including no phase rotation, expressed by eq. (40), can also be obtained using an alternative method: at first, arctan (i.e., inverse of tangent) is implemented on imaginary part/real part of the analytic signal expressed by eq. (32) to calculate the kernel of the cosine expressed by eq. (30-1) (i.e., instantaneous phase including the phase rotation), which is directly subtracted by the phase rotation calculated by the integration eq. (42) with s'=s on the moving-averaged instantaneous frequency or on the 1st moment of spectra. Note that since the arctan's direct calculation results are ranging −π to π, the calculate results are required to be unwrapped prior to perform the subtraction. Since the instantaneous phase including the phase rotation monotonically increases, if the arctan's result changes to be negative, the unwrapping can be performed by adding 2πm, where m is a positive natural number expresses the number of times to be counted when the arctan's result becomes negative in the propagation direction of the beam or wave. Similarly to the above-mentioned calculations, eq. (41) can also be used, and there exists the cases where the bias error expressed by the eq. (42) is generated. When estimating the change in the instantaneous phase Δθ(s) between at the position coordinate t=s and the next sampling position coordinate t=s+Δs (i.e., sampling interval is Δs), that is with no bias error, instead of eq. (43), the difference of the estimates of instantaneous phases including no phase rotations at the neighboring two position coordinates can be directly calculated by the subtraction.

Images regarding the phase expressed by Eq. (40) or Eq. (43) has an increased bandwidths, this is a kind of the superresolution. The phase itself can also be displayed, or cosine or sine function of the phase can also be displayed and furthermore, the envelope-weighted cosine or sine function can also be displayed. Also note that regarding the analytic signal of which phase is expressed by eq. (40), the square root of the summing of squared real and imaginary parts is equivalent to the envelope detection. Thus, squared detection, absolute detection, raw signals ideally with no broken wave oscillations (sign of signal values, phase) should be imaged (as a gray or color image). Mainly, the images exhibit the phase or change in phase together with the signal amplitude that determined by the reflection or scattering. Alternatively, the calculated instantaneous frequency can also be imaged to display the effect of attenuations or scatterings (as a gray or color image).

The above-mentioned Hilbert transform is performed based on the (fast) Fourier transform (nonpatent document 13), and the original calculations of Hilbert transform can also be performed. Also, differentiation can also be performed for real signals to yield signals with a phase leading by 90 degrees, and the imaginary parts (signals) of Hilbert transform can be generated by multiplying −1 onto the signals, although the accuracy decreases when noises are filled in the target real signals. The multiplication of the angular frequency due to the differentiation can be corrected using the estimate of angular frequency obtained by performing (i) a finite difference approximation (using the so-called forward, backward, central difference, etc., i.e., summation of numerical values multiplied by 1 and −1, respectively, or subtraction) or a differentiation onto the phases calculated for the signals of the region including the position and the adjacent or surrounding positions by performing the inverse cosine or inverse sine onto the real signals, and (ii) a division by the distance between the positions.

For instance, when performing the differentiation for an arbitrary signal expressed by eq. (30-1), under the condition or the assumption that the spatial derivative (spatial variant) of A(s) is smaller than the instantaneous frequency ω(s), or by performing the moving-average for eq. (30-1) or the result of spatial derivative over the multidimension including the direction of the partial derivative or in the direction of the partial derivative, the following approximation is performed.

$$\frac{\partial}{\partial s} r(s) \approx -\omega(s) A(s) \sin\left\{ \int_{t=0}^{t=s} \omega(t) dt + \theta(s) \right\} \quad (30\text{-}1')$$

The moving-average cannot be performed for the signals themselves. Or, the ω(s) can also be estimated as below. Further the differentiation for eq. (30-1') leads the following approximation under the condition or the assumption that the spatial derivative of ω(s) is small in addition to the condition, the assumption and the processing mentioned above.

$$\frac{\partial^2}{\partial s^2} r(s) \approx -\omega(s)^2 A(s) \cos\left\{ \int_{t=0}^{t=s} \omega(t) dt + \theta(s) \right\} \qquad (30\text{-}1'')$$

The moving-average cannot be performed for the signals themselves. The $\omega^2(s)$ can be estimated by dividing eq. (30-1") by eq. (30-1) and multiply (−1) to the result. However, since the estimate can become negative, such an estimate can be exchanged by the neighboring positive estimate over the multidimension including the direction of the partial derivative s or in the direction of the partial derivative s, the similar interpolation obtained only using positive estimates, the similar result of a median filtering, the similar result of a moving-average, or the combination of these processings. The median filtering can remove the sudden large estimation errors particularly. Or, $\omega(s)$ can be estimated as a median-filtered or moving-averaged, squared-root of a positive estimate $\omega(s)^2$. Through these processings, $\omega(s)$ can be estimated. By dividing eq. (30-1') by $\omega(s)$ and multiplying −1 to the result, the imaginary part of analytic signal of eq. (30-1) can be obtained. That is, the analytic signal can be estimated. The 2nd derivatives can also be estimated by using the differential filter or the finite difference approximation twice for eq. (30-1), or by using the 2nd differential filter or the 2nd finite difference approximation (using the so-called central difference, i.e., summation of numerical values multiplied by 1, −2 and 1, respectively, which is divided by the squared, distance between the data position). Or, for the differentiation, a differential filter generated using an OP amp can also be used, or a digital differential filter or an approximate differentiation based on a subtraction can also be used for a digital circuit or a digital signal processing. Since the differential processing is a kind of a high pass filtering, the differential processing can also be performed with a high cutoff frequency or moving-average processing can also be performed for the differential results. Or, for the above-mentioned instantaneous frequency $\omega(s)$, to make the calculation simple, a nominal frequency or a globally estimated frequency (the 1st moment, etc.) can also be used. These detection processings are much faster than other detection processings. These processings can also be used for an envelope imaging of r(s) (the magnitude of analytic signal), or measurements of a displacement, a velocity, an acceleration, a strain, a strain rate, a temperature, etc. The measurement accuracy is almost the same as that obtained by performing the (fast) Fourier transform and however, the inventor of the present invention has confirmed that the echo image generated can become to have a higher intensity at a deep region than that obtained by performing the (fast) Fourier transform. This Hilbert transform method is faster than that using a Fourier transform (nonpatent document 13) and then, the new method is effective when plural beams or waves with different wave parameters or different beamforming parameters are generated at every temporal phase (increase of reception signals received by a reception transducer leads the increase of the number of beamformings and Hilbert transforms). The new method is also effective when performing the transform at once for superposed, plurally beamformed signals as one beamformed signal (The instantaneous frequency calculated via the differentiations corresponds to a synthesized frequency in the differential direction with respect to the superposed, beams or waves.). The instantaneous phase imaging mentioned above can also be performed with respect to the superposed ones similarly. For the measurements, plural waves/beams or quasi-waves/quasi-beams obtained via the spectral frequency division, etc. are respectively used for obtaining simultaneous Doppler equations (it can be an over-determined system). In the cases, eq. (30-1) expresses each wave/beam or each quasi-wave/quasi-beam, of which an analytic signal is similarly calculated and used. When the observed signals are also multi-dimensional, i.e., the carrier frequencies exist in plural coordinate axes (e.g., when performing the lateral modulation or steering, etc.), the instantaneous frequencies can be estimated similarly (mentioned later).

Figure 35:
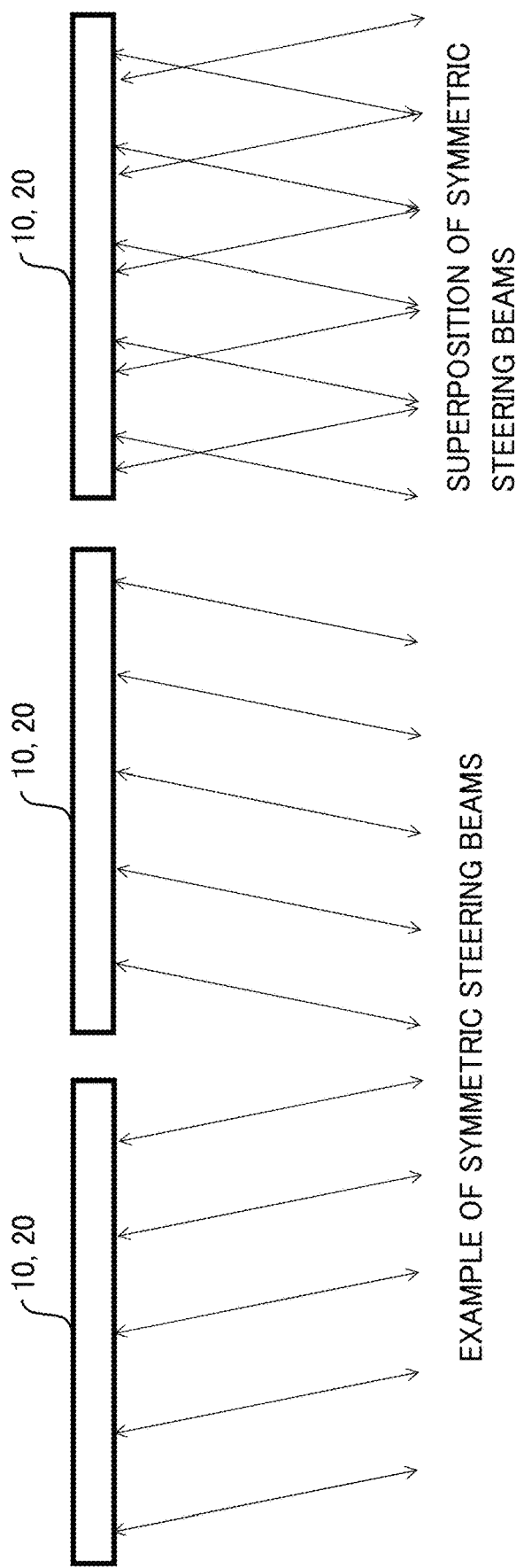
FIG. 35 shows an illustration in a 2D case, two steering beams and a lateral modulation yielded by superposing the two steering beams.

FIG. 35 shows an example of a 2D case with two steering beams and a lateral modulation generated by superposing the two steering beams, and FIG. 36 shows an example of a 3D case with four steering beams and a lateral modulation generated by superposing the four steering beams (when using three steering beams, three steering beams of four beams shown in FIG. 36 can be used and Or, three beams all symmetric with respect to the axial direction can also be generated, of which figure is omitted). Other arbitrary geometric array apertures from the linear-type 1D and 2D array apertures shown in FIGS. 35 and 36 can also be used, and arbitrary orthogonal coordinate systems can also be used. Regardless the geometry of an array aperture and an orthogonal coordinate system, for the respective 2D and 3D lateral modulations, the beams (or waves) are crossed by steerings such that the waves are symmetric with respect to the axial direction or the lateral direction orthogonal to the axial direction of the orthogonal coordinate system to be used for the observation (the axial and lateral axes, respectively) or the areas including the axial axis and the lateral direction orthogonal to the axial axis (i.e., All waves are to be symmetric with respect to the axial direction.). When the beams (or waves) are not symmetric, the coordinate system can also be translated or rotated to be symmetric and as described in other paragraphs, the nonsymmetric beams (or waves) can also be processed directly. Here, the steered waves are referred to as steered beams, arbitrary steered waves can be used and a non-steered wave can be included (i.e., with a steering angle of zero degree). In the lateral modulation case, for instance, in the 2D case, as shown in FIG. 35, the crossed, two steered waves can be processed under the conditions of being separate or superposing, and in the 3D case, as shown in FIG. 36, similarly the crossed, three or four steered waves can be processed under the conditions of being separate or superposing. Similarly, performed steerings are also processed when signals are processed as multi-dimensional ones. As disclosed in the nonpatent document 19, the propagation direction of the wave or beam can be measured with a spatial resolution (using the 1st moments or the instantaneous frequencies) and simultaneously, the frequency in the direction can also be measured. Thus, the frequency in the direction of an integration path (tangential direction) set on the spatial integration processing of a frequency can be calculated with a high accuracy. For instance, on the above 1D signal case, the integration path can be set as a straight line using the steering direction (expressed by an angle) set at performing the transmission or using the global estimate of a steering direction (an angle) of the generated wave or beam similarly and in this multi-dimensional signal case, the integration path can be arbitrarily set in the multi-dimensional space theoretically. However, in practice, important is that the integration calculation is performed using integration paths properly set on the coordinate system used for performing the beamforming and for instance, straight lines, arcs or the connections are often used. To simplify the processings, the nominal frequency or simultaneously obtained global frequency estimate can also be used (to be projected onto the integration path). It is not impossible to perform the integration in the propagation direction estimated with a spatial resolution, however, since the interpolation processing is required, it is not practical. Now, the signal in an ROI is expressed by $$r(s_1,s_2,s_3)=A(s_1,s_2,s_3)\cos\{\int_c[\omega_1(t_1,t_2,t_3),\omega_2(t_1,t_2,t_3),\omega_3(t_1,t_2,t_3)]\cdot(dt_1,dt_2,dt_3)^T+\theta(s_1,s_2,s_3)\}, \quad (30'\text{-}1)$$

where $$\theta(s_1,s_2,s_3)=\int_c\delta\theta(t_1,t_2,t_3)(dt_1,dt_2,dt_3)^T \quad (30'\text{-}2)$$

and $\delta\theta(t1, t2, t3)$ expresses the change in phase generated at the position coordinate $(t_1,t_2,t_3)$ due to the reflection or scattering and the integration path c denotes an arbitrary path from the starting position 0, i.e., the reference position expressing the position with a zero instantaneous phase, to the position of interest $(s_1,s_2,s_3)$. If there exist plural positions with zero instantaneous phases in an ROI (for instance, respective positions of aperture elements in an array possible), they have the same mean. Thus, imaging is performed via calculating the instantaneous angular frequencies $[\omega_1(t_1, t_2, t_3), \omega_2(t_1, t_2, t_3), \omega_3(t_1\ t_2, t_3)]$ and the instantaneous phase $\theta(t1, t_2,t_3)$ etc. When the ROI is 2D, $$r(s_1,s_2)=A(s_1,s_2)\cos\{\int_c[\omega_1(t_1,t_2),\omega_2(t_1,t_2),\omega_3(t_1,t_2)]\cdot(dt_1,dt_2)^T+\theta(s_1,s_2)\} \quad (30''\text{-}1)$$

where $$\theta(s_1,s_2)=\int_c\delta\theta(t_1,t_2)(dt_1,dt_2)^T \quad (30''\text{-}2)$$

and the integration path c denotes an arbitrary path from the starting position 0, i.e., the reference position expressing the position with a zero instantaneous phase, to the position of interest $(s_1,s_2)$ similarly to in eqs. (30'-1) and (30'-2). Below, the processings are performed similarly to in the 3D case.

Here, $A(s_1,s_2,s_3)$, being an amplitude, expresses the reflection intensity or the scattering intensity at the position coordinate $(s_1,s_2,s_3)$ and for instance, can be calculated by performing the envelope detection (square root of summing of squared IQ signal components) via the quadrature detection of eq. (30'-1). Or, the quadrature signal component $$r'(s_1,s_2,s_3)=A(s_1,s_2,s_3)\sin\{\int_c[\omega_1(t_1,t_2,t_3),\omega_2(t_1,t_2,t_3),\omega_3(t_1,t_2,t_3)]\cdot(dt_1,dt_2,dt_3)^T+\theta(s_1,s_2,s_3)\} \quad (31')$$

is generated by Hilbert transform using Fourier transform; and using the in-quadrature signal component eq. (30'-1) together, $A(s_1,s_2,s_3)$ can be calculated (patent document 7 or nonpatent document 14). The latter calculation method is proper to the digital signal processing particularly.

Using eqs. (30') and (31'), the complex analytic signal can be expressed as follows (patent document 6 or nonpatent document 7).

$$r(s_1,s_2,s_3)=A(s_1,s_2,s_3)\exp[i\{\int_c[\omega_1(t_1,t_2,t_3),\omega_2(t_1,t_2,t_3),\omega_3(t_1,t_2,t_3)]\cdot(dt_1,dt_2,dt_3)^T+\theta(s_1,s_2,s_3)\}] \quad (32')$$

To calculate the instantaneous phase $\theta(s_1,s_2,s_3)$, at first, the instantaneous angular frequencies are calculated. As the usual practice, using the methods disclosed in the patent document 6 and the nonpatent document 7, assuming is performed that the instantaneous frequency in the $t_1$ direction at the position coordinate $(s_1,s_2,s_3)$ equals to that at the next sampling position coordinate in the $t_1$ direction, $(s_1+\Delta s_1,s_2,s_3)$, however, the instantaneous phase at the position coordinate $(s_1,s_2,s_3)$ does not equal to that at the next sampling position coordinate $(s_1+\Delta s_1,s_2,s_3)$ ($\delta\theta(t_1,t_2,t_3)$ is a random change in phase determined by the random scattering intensity or reflection and with respect to $(t_1,t_2,t_3)$, the change can be large).

$$\omega_1(s_1,s_2,s_3) \approx \omega_1(s_1+\Delta s_1,s_2,s_3) \quad (33')$$

$$\Delta\theta_1(s_1,s_2,s_3) = \theta(s_1+\Delta s_1,s_2,s_3) - \theta(s_1,s_2,s_3)$$
$$= \int_{t_1=s_1}^{t_1=s_1+\Delta s_1} \delta\theta(t_1,s_2,s_3)dt_1$$

(random and the value can be small) $\quad (34')$

Under the assumptions, the signal at the position coordinate $(s_1+\Delta s_1,s_2,s_3)$ is expressed as $$r(s_1+\Delta s_1,s_2,s_3)=A(s_1+\Delta s_1,s_2,s_3)\exp[i\{\int_{c_1}[\omega_1(t_1,t_2,t_3),\omega_2(t_1,t_2,t_3),\omega_3(t_1,t_2,t_3)]\cdot(dt_1,dt_2,dt_3)^T+\theta(s_1+\Delta s_1,s_2,s_3)\}] \quad (35')$$

where the integration path $c_1$ is an arbitrary path from the starting position 0, i.e., the reference position expressing the position with a zero instantaneous phase in eq. (32'), via an arbitrary path to the position of interest $(s_1,s_2,s_3)$ (on the processings, conventionally the same path as that of eq. (32') can also be used) and further from the position of interest $(s_1,s_2,s_3)$ to the neighboring sampling position in the $s_1$ direction by the sampling interval $\Delta s_1$, i.e., $(s1+\Delta s_1,s_2,s_3)$. And, under the assumptions of eqs. (33') and (34'), the conjugate product of eqs. (32') and (35') is expressed as follows.

$$R_1(s_1,s_2,s_3) = \quad (36')$$
$$r(s_1+\Delta s_1,s_2,s_3)r^*(s_1,s_2,s_3) \approx A(s_1+\Delta s_1,s_2,s_3)A(s_1,s_2,s_3)$$
$$\exp[i\{\omega_1(s_1,s_2,s_3)\Delta s_1 + \Delta\theta_1(s_1,s_2,s_3)\}]$$

Thus, the instantaneous frequency $\omega_1(s_1,s_2,s_3)$ in the $s_1$ direction at the position coordinate $(s_1,s_2,s_3)$ can be estimated as follows.

$$\omega_1(s_1,s_2,s_3) \approx \frac{\tan^{-1}\frac{Imag\{R_1(s_1,s_2,s_3)\}}{Real\{R_1(s_1,s_2,s_3)\}}}{\Delta s_1} \quad (37')$$

As disclosed in the patent document 6 or the nonpatent document 7, in practice, since noises are filled in the signal $r(s_1,s_2,s_3)$ and assuming eqs. (33') and (34'), the moving-average processing is performed in the $s_1$-axis direction or including the orthogonal two or one direction to increase the accuracy of estimate. This moving-average processing can also be performed on eq. (36') and the estimate is calculated according to eq. (37'):

$$\overline{\omega_1}(s_1,s_2,s_3) \approx \frac{\tan^{-1}\frac{\overline{Imag\{R_1(s_1,s_2,s_3)\}}}{\overline{Real\{R_1(s_1,s_2,s_3)\}}}}{\Delta s_1} \quad (38'\text{-}1)$$

or the moving-average processing is also performed on eq. (37') itself:

$$\overline{\omega_1}(s_1,s_2,s_3) \approx \overline{\frac{\tan^{-1}\frac{Imag\{R_1(s_1,s_2,s_3)\}}{Real\{R_1(s_1,s_2,s_3)\}}}{\Delta s_1}} \quad (38'\text{-}2)$$

It was previously confirmed that for a displacement (vector) measurement, eq. (38'-1) yields a higher accuracy than eq. (38'-2). Similarly, the instantaneous frequencies in the $s_1$ and $s_3$ directions can also be calculated via calculating $R_2(s_1,s_2,s_3)$ and $R_3(s_1,s_2,s_3)$, respectively.

Using these moving-averaged instantaneous frequencies, detection can be performed on the instantaneous frequencies at the respective position coordinate. Since the estimates of the instantaneous frequencies are unbiased, in the digital signal processing cases, the following equation $$demf(s_1,s_2,s_3) = \exp[-i\{\int_{c'}[\overline{\omega}_1(t_1,t_2,t_3),\overline{\omega}_2(t_1,t_2,t_3),\overline{\omega}_3(t_1,t_2,t_3)]\cdot(dt_1,dt_2,dt_3)^T\}] \quad (39')$$

where the integration path c' is an arbitrary path from the starting position, which can be set at an arbitrary position except for the position of interest $(s_1,s_2,s_3)$ in an ROI possibly including a reference position 0 with a zero instantaneous phase, to the position of interest $(s_1,s_2,s_3)$, which is regardless the integration path c in eq. (32'), however, on the processings, the same path as that of eq. (32') or the part can also be used conventionally. If there exist plural positions with zero instantaneous phases in an ROI (for instance, array element positions), since they have the same mean, the position of distance to the respective positions of interest $(s_1,s_2,s_3)$ being short can be used as the stating position 0. The integration path can also be set along the coordinate axes, which does not require interpolations of instantaneous frequencies. That is, the axes of integration directions can be changed at the positions of the sampling positions, (39') is multiplied to eq. (32') and under the assumption that the instantaneous phase $\theta(s_1,s_2,s_3)$ is the integral of a random change in phase determined by the random scattering intensity or reflection (i.e., random), the estimate can be obtained.

$$\theta'(s_1, s_2, s_3) = \tan^{-1}\left[\frac{Imag\{r(s_1, s_2, s_3)demf(s_1, s_2, s_3)\}}{Real\{r(s_1, s_2, s_3)demf(s_1, s_2, s_3)\}}\right] \quad (40')$$

Instead the moving-averaged instantaneous frequencies calculated by eqs. (38'-1) and (38'-2), the 1st moments of spectra (i.e., weighted means) ($\times 2\pi$) can also be used. The expression of moment in the x-axis, one axis of 3D orthogonal coordinate system, is given as eq. (S1"). Moments in other axes can also be calculated similarly, and also in the 2D case.

The integration path c, expressed in the equation of the above-mentioned observed signal, denotes an arbitrary path from the starting position 0, i.e., the reference position expressing the position with a zero instantaneous phase, to the position of interest $(s_1,s_2,s_3)$. The 0 expresses the position of the wave source. With respect to this, the stating position of the integration path c' in eq. (39') can also be set to 0 (the wave source position) and in the cases where the $\theta'(s_1,s_2,s_3)$ calculated as a distribution regarding the position coordinate $(t_1,t_2,t_3)=(s_1,s_2,s_3)$ is the estimate of the instantaneous phase [eq. (30'-2)] itself, expressed as the integration of the change in phase due to the reflection and scattering. The averaged instantaneous frequencies are used and then, the calculated $\theta'(s_1,s_2,s_3)$ is an estimate obtained under the condition.

When due to the effects of window lengths used for the moving-average processings or calculations of spectra, the instantaneous frequencies cannot be estimated from the position of the wave source 0 to $(t_1,t_2,t_3)=(s_1',s_2',s_3')$ (not the wave source position and not equal to $(s_1,s_2,s_3)$ as well), using the 0 as the starting position of the integration path c' and angular frequencies $(\omega_{0x}, \omega_{0y}, \omega_{0z})$ that are nominal frequencies or measurements/estimates obtained in advance, $$(\overline{\omega}_1(t1,t2,t3),\overline{\omega}_2(t1,t2,t3),\overline{\omega}_3(t1,t2,t3)) \equiv (\omega_{01},\omega_{02},\omega_{03})$$

$$(t1,t2,t3) \in c' \text{ (interval from the wave source position}$$
$$0 \text{ to } (t_1,t_2,t_3)=(s_1',s_2',s_3')) \quad (41')$$

in eq. (39'), which is calculated. Or, using $(t_1,t_2,t_3)=(s_1',s_2',s_3')$ as the starting position of the integration path c' (not the wave source position and not equal to $(s_1,s_2,s_3)$ as well) in eq. (39') is possible and however, in the cases the following bias error is generated in the estimate $\theta'(s_1,s_2,s_3)$.

$$\theta_{bias} = \int_{c''}[\overline{\omega}_1(t_1,t_2,t_3),\overline{\omega}_2(t_1,t_2,t_3),\overline{\omega}_3(t_1,t_2,t_3)]\cdot(dt_1,dt_2,dt_3)^T, \quad (42')$$

where c" denotes an arbitrary integration path from the wave source position 0 to $(t_1,t_2,t_3)=(s_1',s_2',s_3')$.

However, for instance, when the change in the instantaneous phase $\Delta\theta'(s_1,s_2,s_3)$ between at the position coordinate $(s_1,s_2,s_3)$ and the next sampling position coordinate $(s1+\Delta s_1, s_2,s_3)$ (i.e., sampling interval is $\Delta s_1$) is estimated on the basis of eqs. (30'-2) and (34'), the bias becomes no problem. The estimate result can be obtained as follows.

$$\Delta\theta_1'(s_1, s_2, s_3) = \tan^{-1}\left[\frac{Imag\left[\frac{\{r(s_1+\Delta s_1, s_2, s_3)demf(s_1+\Delta s_1, s_2, s_3)\}}{\{r(s_1, s_2, s_3)demf(s_1, s_2, s_3)\}^*}\right]}{Real\left[\frac{\{r(s_1+\Delta s_1, s_2, s_3)demf(s_1+\Delta s_1, s_2, s_3)\}}{\{r(s_1, s_2, s_3)demf(s_1, s_2, s_3)\}^*}\right]}\right] \quad (43')$$

For eq. (36'), the conjugate product with a complex exponential having $\omega(s_1,s_2,s_3)\Delta s_1$ as a kernel can also be calculated. The changes in the instantaneous phases in the respective $t_2$ and $t_3$ directions, $\Delta\theta_2(s_1,s_2,s_3)$ and $\Delta\theta 3(s_1,s_2,s_3)$, between at the position coordinate $(s_1,s_2,s_3)$ and the next sampling position coordinates $(s_1,s_2+\Delta s_2,s_3)$ and $(s_1,s_2,s_3+\Delta s_3)$ (i.e., the respective sampling intervals are $\Delta s_2$ and $\Delta s_3$), can also be estimated similarly. In the above eqs. (34'), (36') (43'), etc., the subtraction of phase is calculated using the finite forward difference and instead, the backward difference can also be performed. And, in eqs. (37'), (38'-1), (38'-2), the calculation of differentiation of phase is approximated by dividing the above-mentioned phase difference by the sampling interval and instead, a differential filter with a high cutoff frequency can also be used for the differential processing. And, for the integration of the estimates of instantaneous frequencies in eq. (39'), known various integration operations such as a trapezoidal method can be performed. The estimate of the instantaneous phase [eq. (30'-2)] including no phase rotation, expressed by eq. (40'), can also be obtained using an alternative method: at first, arctan (i.e., inverse of tangent) is implemented on imaginary part/real part of the analytic signal expressed by eq. (32') to calculate the kernel of the cosine expressed by eq. (30'-1) (i.e., instantaneous phase including the phase rotation), which is directly subtracted by the phase rotation calculated by the integration eq. (42') with $(s_1',s_2',s_3')=(s_1,s_2,s_3)$ on the moving-averaged instantaneous frequencies or on the 1st moments of spectra. Note that since the arctan's direct calculation results are ranging $-\pi$ to $\pi$, the calculate results are required to be unwrapped prior to perform the subtraction. Since the instantaneous phase including the phase rotation monotonically increases, if the arctan's result changes to be negative, the unwrapping can be performed by adding $2\pi m$, where m is a positive natural number expresses the number of times to be counted when the arctan's result becomes negative in the propagation direction of the beam or wave. Similarly to the above-mentioned calculations, eq. (41') can also be used, and there exists the cases where the bias error expressed by the eq. (42') is generated. When estimating the change in the instantaneous phase $\Delta\theta_1'(s_1,s_2,s_3)$ between at the position coordinate $(s_1,s_2,s_3)$ and the next sampling position coordinate $(s1+\Delta s_1,s_2,s_3)$ (i.e., sampling interval is $\Delta s_1$), that is with no bias error, instead of eq. (43'), the difference of the estimates of instantaneous phases including no phase rotations at the neighboring two position coordinates can be directly calculated by the subtraction. The changes in the instantaneous phases in the respective $t_2$ and $t_3$ directions, $\Delta\theta_2'(s_1,s_2,s_3)$ and $\Delta\theta_3'(s_1,s_2,s_3)$ between at the position coordinate $(s_1,s_2,s_3)$ and the next sampling position coordinates $(s_1,s2+\Delta s_2,s_3)$ and $(s_1,s_2,s_3+\Delta s_3)$, can also be estimated similarly.

Images regarding the phase expressed by Eq. (40') or Eq. (43') has an increased bandwidths, this is a kind of the superresolution. The phase itself can also be displayed, or cosine or sine function of the phase can also be displayed and furthermore, the envelope-weighted cosine or sine function can also be displayed. Also note that regarding the analytic signal of which phase is expressed by eq. (40'), the square root of the summing of squared real and imaginary parts is equivalent to the envelope detection. Thus, squared detection, absolute detection, raw signals ideally with no broken wave oscillations (sign of signal values, phase) should be imaged (as a gray or color image).

The above mentioned Hilbert transform is performed based on the multi-dimensional (fast) Fourier transform [nonpatent document 13; Although the crossed beams or waves can be processed regardless being spatially superposed or not (i.e., separate), since the former processing allows performing a Fourier transform at once of all the reception signals (waves) and requires a fewer calculations, the separate signals (waves) can also be processed after being superposed, as confirmed later.], and similarly to the 1-dimensional (1D) case, the original calculations of Hilbert transform can also be performed.

Also, similarly to the 1D case, differentiation can also be performed for real signals to yield signals with a phase leading by 90 degrees, and the imaginary parts (signals) of Hilbert transform can be generated by multiplying −1 onto the signals, although the accuracy decreases when noises are filled in the target real signals. The multiplication of the angular frequency due to the differentiation can be corrected using the estimate of angular frequency obtained by performing a finite difference approximation (the so-called forward, backward, central difference, etc.) or a differentiation onto the phases calculated for the signals of the region including the position and the adjacent or surrounding positions by performing the inverse cosine or inverse sine onto the real signals, and (ii) a division by the distance between the positions. However, as shown in FIGS. 35 and 36, for the lateral modulation, the methods described in this paragraph can be used only when the steered waves are separate or separated. The method can also be used directly for a single steered wave (this paragraph). For signals being superposed, one method is described at the end of this paragraph; and other two methods are described in the next paragraphs.

For instance, when performing the partial differentiation for an arbitrary signal expressed by eq. (30'-1), etc. in one of directions $s_1, s_2$ and $s_3$. Under the condition or the assumption that the spatial derivative (spatial variant) of $A(s_1,s_2,s_3)$ is smaller than the instantaneous frequency in the derivative direction, $\omega_1(s_1,s_3)$, $\omega_2(s_1,s_2,s_3)$ or $\omega_3(s_1,s_2,s_3)$, or by performing the moving-average for eq. (30'-1) or the result of spatial derivative over the multidimension including the direction of the partial derivative or in the direction of the partial derivative, the following approximation is performed. For instance, in the case where the partial derivative is performed in the direction of $s_1$, $$\frac{\partial}{\partial s_1}r(s_1,s_2,s_3) \approx \qquad (30'\text{-}1') $$
$$-\omega_1(s_1,s_2,s_3)A(s_1,s_2,s_3)\sin\left\{\int_c [\omega_1(t_1,t_2,t_3), \omega_2(t_1,t_2,t_3),\right.$$
$$\left.\omega_3(t_1,t_2,t_3)]\cdot(dt_1,dt_2,dt_3)^T + \theta(s_1,s_2,s_3)\right\}$$

The moving-average cannot be performed for the signals themselves. For instance, for the lateral modulation (LM), an instantaneous frequency of some direction can be smaller than that or those of other directions and in such a case, it may be also possible to set the direction of a partial differentiation in the direction. However, if the direction corresponds to that of steering, since the sampling interval can be coarse, it is cautious for the approximate calculations. Or, the $\omega_1(s_1,s_2,s_3)$ can also be estimated as below. Further the same directional differentiation for eq. (30'-1') leads the following approximation under the condition or the assumption that the spatial derivative of $\omega_1(s_1, s_2, s_3)$ is small in addition to the condition, the assumption and the processing mentioned above.

$$\frac{\partial^2}{\partial s_1^2}r(s_1,s_2,s_3) \approx \qquad (30'\text{-}1'') $$
$$-\omega_1^2(s_1,s_2,s_3)A(s_1,s_2,s_3)\cos\left\{\int_c [\omega_1(t_1,t_2,t_3), \omega_2(t_1,t_2,t_3),\right.$$
$$\left.\omega_3(t_1,t_2,t_3)]\cdot(dt_1,dt_2,dt_3)^T + \theta(s_1,s_2,s_3)\right\}$$

The moving-average cannot be performed for the signals themselves. The $\omega_1^2(s_1,s_2,s_3)$ can be estimated by dividing eq. (30'-1'') by eq. (30'-1) and multiply (−1) to the result. However, since the estimate can become negative, such an estimate can be exchanged by the neighboring positive estimate over the multidimension including the direction of the partial derivative or in the direction of the partial derivative, the similar interpolation obtained only using positive estimates, the similar result of a median filtering, the similar result of a moving-average, or the combination of these processings. The median filtering can remove the sudden large estimation errors particularly. Or, $\omega_1(s_1,s_2,s_3)$ can be estimated as a median-filtered or moving-averaged, squared-root of a positive estimate $\omega_1^2(s_1,s_2,s_3)$. Through these processings, $\omega_1(s_1,s_2,s_3)$ can be estimated. By dividing eq. (30'-1') by $\omega_1(s_1,s_2,s_3)$ and multiplying −1 to the result, the imaginary part of analytic signal of eq. (30'-1) can be obtained. That is, the analytic signal can be estimated. The 2nd derivatives can also be estimated by using the differential filter or the finite difference approximation twice for eq. (30'-1), or by using the 2nd differential filter or the 2nd finite difference approximation (the so-called central difference). Also, when the partial derivatives are performed in other directions $s_2$ and $s_3$ from $s_1$, similarly the $\omega_2(s_1,s_2,s_3)$ and $\omega_3(s_1,s_2,s_3)$ can be calculated and then, the analytic signal can be calculated. However, as mentioned above, the partial derivative direction should be selected properly.

However, for instance, the inventor of the present invention has confirmed for a 2D case using beams with steering angles, ±20°, that there can exist no large difference in a measurement accuracy between when the partial derivative direction is set in the depth and lateral directions. Although for formulating an image, there exists a difference with respect to the Hilbert transform performed by the multi-dimensional (fast) Fourier transform (nonpatent document 13) and the echo intensity can become larger at a deep position, the measurement accuracy of displacement vector can become almost the same as that obtained by the Hilbert transform performed by the multi-dimensional (fast) Fourier transform. Or, for the differentiation, a differential filter generated using an OP amp can also be used, or a digital differential filter or an approximate differentiation based on a subtraction can also be used for a digital circuit or a digital signal processing. Since the differential processing is a kind of a high pass filtering, the differential processing can also be performed with a high cutoff frequency or moving-average processing can also be performed for the differential results. Or, for instantaneous frequencies such as $\omega_1(s_1,s_2,s_3)$, to make the calculation simple, a nominal frequency or a globally estimated frequency (the 1st moment, etc.) can also be used. These detection processings are much faster than other detection processings. These processings can also be used for an envelope imaging of $r(s_1,s_2,s_3)$ (the magnitude of analytic signal), or measurements of a displacement (vector), a velocity (vector), an acceleration (vector), a strain (tensor), a strain rate (tensor), etc. For the measurements of a vector or a tensor, plural waves/beams or plural quasi-waves/quasi-beams obtained via the spectral frequency division, etc. are respectively used for obtaining simultaneous Doppler equations (it can be the LM or over-determined system). In the cases, eq. (30'-1) expresses each wave/beam or each quasi-wave/quasi-beam, of which an analytic signal is similarly calculated and used. Or, the calculated analytic signal can also be used for the temperature measurement, etc. similarly.

This Hilbert transform method is faster than that using a Fourier transform (nonpatent document 13) and then, the new method is effective when plural beams or waves with different wave parameters or different beamforming parameters are generated at every temporal phase because the increase of reception signals received by a reception transducer leads the increase of the number of beamformings and Hilbert transforms (the steered directions can also be same and the steered directions cannot always be symmetric with respect to an axial direction). The new method is also effective when performing the transform at once for superposed, plurally beamformed signals as one beamformed signal, i.e., eq. (30'-1) (The instantaneous frequencies calculated via the differentiations correspond to synthesized frequencies in the differential directions with respect to the superposed, beams or waves.). The instantaneous phase imaging mentioned above can also be performed with respect to the superposed ones similarly. The method effectiveness increases in terms of the high-speed calculation achievable when physical aperture elements comprise a 2D or 3D distribution or a multi-dimensional array because further effectively the new method can solve the problem that a long processing gets being required.

Also, for echo signals of a lateral modulation (LM) performed by using crossed beams or by superposing crossed waves, the following processing can be directly performed (FIGS. 35 and 36 for the 2D and 3D cases, respectively). For the respective 2D and 3D lateral modulations, the processings are explained for the case where the waves are crossed by steerings such that the waves are symmetric with respect to the axial axis or the lateral axis orthogonal to the axial axis of the orthogonal coordinate system to be used (the axial and lateral axes, respectively) or the areas including the axial axis and the lateral direction orthogonal to the axial axis (i.e., All waves are to be symmetric with respect to the axial direction.). When the waves are not symmetric, the orthogonal coordinate is required to be set such that the waves are symmetric. In this case, interpolation processings are required or the Fourier imaging is properly performed.

In a 2D case with echo signals laterally modulated by crossing two waves, the following processing can be directly performed. When the echo signals are expressed by $$r(s_1,s_2)=A(s_1,s_2)\cos\{\omega_1(s_1,s_2)s_1\}\cos\{\omega_2(s_1,s_2)s_2\}, \quad (30A\text{-}1)$$

the 1st and 2nd partial derivatives with respect to $s_1$ are respectively, $$\frac{\partial}{\partial s_1}r(s_1,s_2) \approx -\omega_1 A(s_1,s_2)\sin\{\omega_1(s_1,s_2)s_1\}\cos\{\omega_2(s_1,s_2)s_2\} \quad (30A\text{-}2)$$

and $$\frac{\partial^2}{\partial s_1^2}r(s_1,s_2) \approx -\omega_1^2 A(s_1,s_2)\cos\{\omega_1(s_1,s_2)s_1\}\cos\{\omega_2(s_1,s_2)s_2\}. \quad (30A\text{-}3)$$

From Eqs. (30A-1) and (30A-3), similarly the instantaneous frequency $\omega_1(s_1,s_2)$ can be calculated and using eq. (30A-2), $$A(s_1,s_2)\sin\{\omega_1(s_1,s_2)s_1\}\cos\{\omega_2(s_1,s_2)s_2\} \quad (30A\text{-}4)$$

can be calculated. Here, in eq. (30A-1), instantaneous phases with no phase rotation in the $s_1$ and $s_2$ directions to be expressed in the cosine functions are omitted. In addition, since the partial derivative of eq. (30A-2) with respect to $s_2$ leads $$\frac{\partial}{\partial s_1 \partial s_2}r(s_1,s_2) \approx \quad (30A\text{-}5)$$
$$\omega_1\omega_2 A(s_1,s_2)\sin\{\omega_1(s_1,s_2)s_1\}\sin\{\omega_2(s_1,s_2)s_2\},$$

the instantaneous frequency $\omega_2(s_1,s_2)$ calculated from eq. (30A-1) by the 1st and 2nd spatial derivatives with respect to $s_2$ and the above-calculated instantaneous frequency $\omega_1(s_1,s_2)$ can be used for calculating $$A(s_1,s_2)\sin\{\omega_1(s_1,s_2)s_1\}\sin\{\omega_2(s_1,s_2)s_2\}. \quad (30A\text{-}6)$$

For the calculation of eq. (30A-6), eq. (30A-1) can be partially differentiated with respect to $s_1$ after $s_2$ and in the case, $$A(s_1,s_2)\cos\{\omega_1(s_1,s_2)s_1\}\sin\{\omega_2(s_1,s_2)s_2\} \quad (30A\text{-}7)$$

can also be calculated. Addition and subtraction of eqs. (30A-1), (30A-4), (30A-6) and (30A-7) lead an analytic signals, $$A(s_1,s_2)[\cos\{\omega_1(s_1,s_2)s_1+\omega_2(s_1,s_2)s_2\}+j\sin\{\omega_1(s_1,s_2)s_1+\omega_2(s_1,s_2)s_2\}] \quad (30A\text{-}8)$$

or $$A(s_1,s_2)[\cos\{-\omega_1(s_1,s_2)s_1-\omega_2(s_1,s_2)s_2\}+j\sin\{-\omega_1(s_1,s_2)s_1-\omega_2(s_1,s_2)s_2\}] \quad (30A\text{-}8')$$

and $$A(s_1,s_2)[\cos\{\omega_1(s_1,s_2)s_1-\omega_2(s_1,s_2)s_2\}+j\sin\{\omega_1(s_1,s_2)s_1-\omega_2(s_1,s_2)s_2\}] \quad (30\text{A-9})$$

or $$A(s_1,s_2)[\cos\{-\omega_1(s_1,s_2)s_1+\omega_2(s_1,s_2)s_2\}+j\sin\{-\omega_1(s_1,s_2)s_1+\omega_2(s_1,s_2)s_2\}]. \quad (30\text{A-9'})$$

Applying a displacement measurement method such as the multi-dimensional autocorrelation method or the multi-dimensional Doppler method (nonpatent document 13), the demodulation method (patent document 7), etc. to the two independent analytic signals to perform a displacement vector measurement, or the respective envelope detections can also be obtained and used for imaging. The plurally calculated envelope detection results can also be used for imaging via superposing (a speckle reduction can also be performed). The detection is not limited to the envelope detection and others such as a squared detection, etc. can also be performed. The real and/or imaginary parts of the analytic signal can be used, and the respective can be used for imaging, the results of plural detections can also be used via the superposing for imaging (a speckle reduction can also be performed).

Since the practical calculation result of eq. (30A-6) becomes different if the order of partial derivatives is exchanged, two data can be obtained for eq. (30A-6), which can be used for the calculations of eqs. (30A-8), (30A-8'), (30A-9) and (30A-9') and two data obtained for an analytic signal expressed by the same equation can be averaged by superposing and can also be used for displacement measurement and imaging. Or, an over-determined system can also be generated for unknown displacement vector components (displacement measurement and imaging). Plural envelope detection results can also be used for imaging via superposing (a speckle reduction can also be performed).

Or, since the echo signals laterally modulated by superposing two crossed waves can also be expressed by one of $$r(s_1,s_2)=A(s_1,s_2)\sin\{\omega_1(s_1,s_2)s_1\}\sin\{\omega_2(s_1,s_2)s_2\}, \quad (30\text{A-1'})$$

$$r(s_1,s_2)=A(s_1,s_2)\sin\{\omega_1(s_1,s_2)s_1\}\cos\{\omega_2(s_1,s_2)s_2\}, \quad (30\text{A-1''})$$

and $$r(s_1,s_2)=A(s_1,s_2)\cos\{\omega_1(s_1,s_2)s_1\}\sin\{\omega_2(s_1,s_2)s_2\}, \quad (30\text{A-1'''})$$

similarly the same procedure performed for eq. (30A-1) can be used for calculating analytic signals or over-determined systems. Here, in eqs. (30A-1'), (30A-1'') and (30A-1'''), similarly to eq. (30A-1), instantaneous phases with no phase rotation in the $s_1$ and $s_2$ directions to be expressed in the cosine or sine functions are omitted.

In a 3D case with echo signals laterally modulated by crossing three or four waves, when the echo signals are expressed by $$r(s_1,s_2,s_3)=A(s_1,s_2,s_3)\cos\{\omega_1(s_1,s_2,s_3)s_1\}\cos\{\omega_2(s_1,s_2,s_3)s_2\}\cos\{\omega_3(s_1,s_2,s_3)s_3\}, \quad (30\text{B-1})$$

similarly to in the 2D case, partial derivatives lead an analytic signal:

$$A(s_1,s_2,s_3)[\cos\{\omega_1(s_1,s_2,s_3)s_1+\omega_2(s_1,s_2,s_3)s_2+\omega_3(s_1,s_2,s_3)s_3\}+j\sin\{\omega_1(s_1,s_2,s_3)s_1+\omega_2(s_1,s_2,s_3)s_2+\omega_3(s_1,s_2,s_3)s_3\}] \quad (30\text{B-2})$$

or the totally same number of independent analytic signals as that of crossed waves (three or four). Thus, led can be simultaneous equations comprising of at least three equations or over-determined system comprising four equations, since the number of unknown displacement components is three. Here, in eq. (30B-1), instantaneous phases with no phase rotation in the $s_1$, $s_2$ and $s_3$ directions to be expressed in the cosine functions are omitted. Similarly to the 2D case, 3D echo imaging can also be performed. The envelope or squared detection, etc. can be performed the for respective signals for imaging. The results can also be used via the superposing for imaging (a speckle reduction can also be performed). Similarly to in the 2D case, exchanging the order of partial derivatives yields plural data for an analytic signal expressed by the same equation, which can be used for yielding an over-determined system for a displacement measurement and an imaging (a speckle reduction can also be performed).

Or, since the echo signals laterally modulated by superposing crossed waves can also be expressed by one of $$r(s_1,s_2,s_3)=A(s_1,s_2,s_3)\sin\{\omega_1(s_1,s_2,s_3)s_1\}\cos\{\omega_2(s_1,s_2,s_3)s_2\}\cos\{\omega_3(s_1,s_2,s_3)s_3\} \quad (30\text{B-1'})$$

$$r(s_1,s_2,s_3)=A(s_1,s_2,s_3)\cos\{\omega_1(s_1,s_2,s_3)s_1\}\sin\{\omega_2(s_1,s_2,s_3)s_2\}\cos\{\omega_3(s_1,s_2,s_3)s_3\} \quad (30\text{B-1''})$$

$$r(s_1,s_2,s_3)=A(s_1,s_2,s_3)\cos\{\omega_1(s_1,s_2,s_3)s_1\}\cos\{\omega_2(s_1,s_2,s_3)s_2\}\sin\{\omega_3(s_1,s_2,s_3)s_3\} \quad (30\text{B-1'''})$$

$$r(s_1,s_2,s_3)=A(s_1,s_2,s_3)\sin\{\omega_1(s_1,s_2,s_3)s_1\}\sin\{\omega_2(s_1,s_2,s_3)s_2\}\cos\{\omega_3(s_1,s_2,s_3)s_3\} \quad (30\text{B-1''''})$$

$$r(s_1,s_2,s_3)=A(s_1,s_2,s_3)\sin\{\omega_1(s_1,s_2,s_3)s_1\}\cos\{\omega_2(s_1,s_2,s_3)s_2\}\sin\{\omega_3(s_1,s_2,s_3)s_3\} \quad (30\text{B-1'''''})$$

$$r(s_1,s_2,s_3)=A(s_1,s_2,s_3)\cos\{\omega_1(s_1,s_2,s_3)s_1\}\sin\{\omega_2(s_1,s_2,s_3)s_2\}\sin\{\omega_3(s_1,s_2,s_3)s_3\} \quad (30\text{B-1''''''})$$

$$r(s_1,s_2,s_3)=A(s_1,s_2,s_3)\sin\{\omega_1(s_1,s_2,s_3)s_1\}\sin\{\omega_2(s_1,s_2,s_3)s_2\}\sin\{\omega_3(s_1,s_2,s_3)s_3\} \quad (30\text{B-1'''''''})$$

similarly the three or four analytic signals, or ones obtained by exchanging the order of partial derivatives can be used. Here, in eqs. (30B-1'), (30B-1''), (30B-1'''), (30B-1''''), (30B-1'''''), (30B-1'''''') and (30B-1'''''''), similarly to eq. (30B-1), instantaneous phases with no phase rotation in the $s_1$, $s_2$ and $s_3$ directions to be expressed in the cosine or sine functions are omitted.

In the cases where the respective waves have different carrier frequencies (including cases where sensors with different carrier frequencies are used or different driving frequencies are used, etc.) and where the frequency demodulations, etc. occur during the propagations and then the waves are not generated symmetrically in practice (including a case where since the waves are not generated symmetrically strictly and then increasing the measurement accuracy), etc., for the 3D and 2D lateral modulations, etc., in order to make the coordinate systems $(s_1,s_2)$ and $(s_1,s_2,s_3)$ the orthogonal coordinate systems by making the instantaneous frequencies, or local or global 1st moment frequencies of all waves themselves (i.e., in the 3D case, $\sqrt{(\omega_1(s_1,s_2,s_3)^2+\omega_2(s_1,s_2,s_3)^2+\omega_3(s_1,s_2,s_3)^2)}$ and in the 2D case, $\sqrt{(\omega_1(s_1,s_2)^2+\omega_2(s_1,s_2)^2)}$) a same by using ratio values for normalizing the respective frequencies of all waves or the same as the frequency of one of the waves by using ratio values for normalizing the respective frequencies of other waves, etc. The ratio values are also used for normalizing the respective instantaneous phases (expressed in the 3D case, $\theta=\omega_1(s_1,s_2,s_3)s_1+\omega_2(s_1,s_2,s_3)s_2+\omega_3(s_1,s_2,s_3)s_3$ and in the 2D case, $\theta=\omega_1(s_1,s_2)s_1+\omega_2(s_1,s_2)s_2$) or the changes. By these, the coordinate systems can be regenerated as the orthogonal coordinate systems (It can be confirmed that the processing is required to generate a strict lateral modulation.). There exist various methods for performing the normalization and not limited to this. It's important not to destroy the phase information of a wave signal set as the target of normalization.

As the next processing, to generate new coordinates $s_1$, $s_2$ and $s_3$ and an area including at least one coordinate axis which are used as a symmetric axis or area with respect to the plural waves generated in practice, the wave signals are re-expressed in the new coordinate system through implementing interpolations (The coordinate system is translated or rotated to make the waves symmetric.), and the analytic signals can be obtained by the above-mentioned approximate calculations based on the partial differentiations in the new orthogonal coordinate system and finally, the results obtained can be re-expressed in the original coordinate system. However, the approximate interpolations decrease the accuracy, although the calculation speed is high. Instead, although no approximate signal shifting by the multiplication of a complex exponential function can also be performed to yield a high accuracy, the processing requires a calculation time. Thus, as another method, with no performing the interpolations, the above-described approximate calculations based on the partial differentiations in the original orthogonal coordinate system. However, the frequencies approximately calculated by the partial differentiations are not the frequencies of the coordinate directions of the original orthogonal coordinate system, i.e., data to be expressed as projections of the approximate frequencies of the new coordinate system above-referred to as (i.e., comprising of existing symmetric axes or symmetric axes expressing the symmetric areas) onto the original orthogonal coordinate system (axes). Since the angle (rotational angle) between the original and new orthogonal coordinate systems can be calculated, the directly calculated data can be re-expressed as the approximate frequencies in the new coordinate system. When the directivity of the sensor includes a bias and when the waves are intentionally generated non-symmetrically with respect to the frontal direction of the aperture due to the existence of an obstacle, etc., the processing can be performed similarly. Also in this case, to generate an orthogonal coordinate system for the lateral modulation and to obtain an accuracy, the above-described normalization processing about the instantaneous frequencies or the 1st moment frequencies (and processing about instantaneous phases) are effective.

However, for performing the normalization processing, since the Fourier transform is to be performed to calculate the wave frequencies, it is desired to directly calculate the analytic signals of respective waves by performing the inverse Fourier transform of single quadrant or octant spectra obtained through zero spectra padding.

Or, in the lateral modulation case using the superposition of crossed waves (FIGS. 35 and 36 for the 2D and 3D cases, respectively), being different from the Hilbert transform using the multi-dimensional (fast) Fourier transform (nonpatent document 13) and using the partial differentiation (the former paragraphs), it is also possible to perform the Hilbert transform using a 1-dimensional (fast) Fourier transform.

In the 2D case, when the 2D echo signal, a superposition of crossed waves, is expressed by eq. (30A-1), the 1D Fourier transforms are respectively performed for $s_1$ and $s_2$; and by performing the 1D inverse Fourier transforms after padding zero spectra in the respective half bandwidths (negative frequency bandwidths), the following signals can be calculated:

$$A(s_1,s_2)[\cos\{\omega_1(s_1,s_2)s_1\}\cos\{\omega_2(s_1,s_2)s_2\}+j\sin\{\omega_1(s_1,s_2)s_1\}\cos\{\omega_2(s_1,s_2)s_2\}] \quad (30C\text{-}1)$$

and $$A(s_1,s_2)[\cos\{\omega_1(s_1,s_2)s_1\}\cos\{\omega_2(s_1,s_2)s_2\}+j\cos\{\omega_1(s_1,s_2)s_1\}\sin\{\omega_2(s_1,s_2)s_2\}]. \quad (30C\text{-}2)$$

Moreover, for eq. (30C-1) or (30C-2), similarly the 1D processings are performed for the coordinate of cosine function of the imaginary part (i.e., $s_2$ and $s_1$), the following signal can be calculated:

$$A(s_1,s_2)[\cos\{\omega_1(s_1,s_2)s_1\}\cos\{\omega_2(s_1,s_2)s_2\}+j\sin\{\omega_1(s_1,s_2)s_1\}\sin\{\omega_2(s_1,s_2)s_2\}] \quad (30C\text{-}3)$$

Using the real parts (common) and the imaginary parts of these eqs. (30C-1), (30C-2) and (30C-3), analytic signals of eqs. (30A-8), (30A-8'), (30A-9) and (30A-9') can be calculated; and applying a displacement measurement method such as the multi-dimensional autocorrelation method or the multi-dimensional Doppler method (nonpatent document 13), the demodulation method (patent document 7), etc. to the two independent analytic signals to be calculated of the four analytic signals to perform a displacement vector measurement. In addition, for the two independent analytic signals, the respective detections such as envelope detections, square detections, etc. can also be obtained (a speckle reduction can also be performed). Regarding calculations, a total number of the 1D Fourier transforms and the 1D inverse Fourier transforms is the same as that of the method using the 2D Fourier transforms and the 2D inverse Fourier transforms (nonpatent document 13), i.e., totally the number for six directions.

For the 3D case, when the 3D echo signal, a superposition of three or four crossed waves, is expressed by eq. (30B-1), similarly to a 2D case, the analytic signal of eq. (30B-2) and other independent analytic signals totally with the same number of crossed waves (three or four) can be obtained through the 1D Fourier transforms and the 1D inverse Fourier transforms. Thus, led can be simultaneous equations comprising of at least three equations or over-determined system comprising four equations, since the number of unknown displacement components is three. Similarly to in the 2D case, 3D echo imaging can also be performed. Regarding calculations, a total number of the 1D Fourier transforms and the 1D inverse Fourier transforms is the same as that of the method using the 3D Fourier transforms and the 3D inverse Fourier transforms (nonpatent document 13), i.e., totally the number for 12 directions when the number of crossed waves is three; totally the number for 15 directions when the number of crossed waves is four.

In these cases, a displacement vector measurement is performed. In addition, the envelope or squared detection, etc. can be performed the for respective signals for imaging. The results can also be used via the superposing for imaging (a speckle reduction can also be performed). Also for the over-determined system, a displacement measurement or an imaging can be performed (a speckle reduction can also be performed).

As far, new fast Hilbert transforms are disclosed for the echo signals laterally modulated by superposing crossed waves. The superposed, crossed waves can be obtained when the transmissions are simultaneously performed or when the reception signals obtained for the respective transmissions are superposed. In contrast, in the cases where the crossed waves are separated (i.e., the reception signals obtained for the respective transmissions or the separated signals obtained by separating the reception signals with respect to simultaneous transmissions), for instance, in the 2D case where the two crossed waves are separated, the two independent wave signals [a real signals of eq. (30A-8) or eq. (30A-8') and eq. (30A-9) or eq. (30A-9')] are expressed by $$A(s_1,s_2)[\cos\{\omega_1(s_1,s_2)s_1+\omega_2(s_1,s_2)s_2\} \quad (30\text{A-}8'')$$

and $$A(s_1,s_2)[\cos\{\omega_1(s_1,s_2)s_1-\omega_2(s_1,s_2)s_2\} \quad (30\text{A-}9'')$$

to respective of which the 1D Fourier transforms and the inverse 1D Fourier transforms are performed in the two directions (i.e., the 2D Fourier transform and the inverse 2D Fourier transform once) and totally eight directional transform processings are required. As disclosed in nonpatent document 13 or as mentioned above, a fewer calculations are required by superposing separate reception wave signals or by receiving plural waves simultaneously. This is the same for the 3D case (the 1D transform processings in totally 18 directions when the number of crossed waves is three; and in totally 24 directions when the number of crossed waves is four: as the 3D transform processings, totally 6 and 8 times, respectively).

Mainly, the images obtained by the methods exhibit the phase or change in phase together with the signal amplitude that determined by the reflection or scattering. Alternatively, the calculated instantaneous frequency can also be imaged to display the effect of attenuations or scatterings (as a gray or color image). The existence of the above-mentioned instantaneous phase decreases the measurement accuracies of the above-mentioned displacement measurement methods on the basis of the Doppler method or classical measurement methods when using the methods solo even if the target displacement (vector) is infinitesimal. The inventor of the present invention previously solves the problem by developing the phase matching method to be performed on the successive frames (for instance, nonpatent document 15). Also another method for stretching or compressing the signals expressing a tissue deformation can be also effective, when rather high intensity and random signals are used, for instance, on the tissue displacement or strain measurement, etc., the phase matching method should be used absolutely (A translation or a rotation can be performed.). Generally, blood flow is measured using narrowband signals and however, the present invention opens up new high spatial resolution measurement and viscoelastic measurements, etc. The multi-dimensional vector and tensor can also be measured. For a blood flow measurement, a precise examination can be performed by performing the phase matching.

The above-mentioned envelope detection methods are usual in practice for being implemented on the generated image signals and however, it is also effective to implement processing using the conjugate product on the angular spectra or spectra and further on the respective wavenumber (frequency) components prior to the summing processing (one of nonlinear processings according to the present inventions). Also for the amplitude detection, in addition to the above-mentioned method, square detection or absolute detection, etc. can be implemented. Also in the present invention, implementing multi-dimensional Fourier transform on the image signals generated by beamforming (i.e., focusing or steering realized by implementing delays or apodizations) generates spectra and further when implementing beamforming on the beamformed, image signals, implementing multi-dimensional Fourier transform on the image signals generated angular spectra. That is, after generating image signals, further some beamforming can be performed on the generated image signals. The results obtained by the beamforming processing as well as other processing (weighting spectra (processing on spectra), nonlinear processing, inverse filtering, etc., others) including superresolutioned images can also be used for the above-mentioned coherent superposition (compounding) as well as incoherent superposition (compounding). The targets to be superposed are different or same signals (obtained at before or after beamformings), signals implemented by other processings, or their raw signals, etc. The coherent superposition is proper for increasing the bandwidths (spatial resolutions) or the SNRs, whereas the incoherent superposition is for reducing the speckles as well as increasing the SNRs. For the reduction of speckles, often the decreasing in spatial resolution also occurs. However, the processings including the superresolutions can allow for coping with the problem and yielding high spatial resolution results. The incoherent superposition is performed on positive values converted to from wave signals by some detections (including exponentiation detections). The above-mentioned detections except for the envelope detection yields detected signals, however, with remaining coherencies (At least, the oscillations of waves can be confirmed). Although the envelope detection is useful, the detections being able to leave the coherencies in detected signals are also useful not to lose a spatial resolution. In comparison, the envelope detection allows the decreasing the spatial resolutions simply.

The operation modes can be set by the commands (signals) inputted into the instrument. When additional information is provided regarded the waves to be observed (kinds, features, properties, intensities, frequencies, bandwidths, codes, wave sources (diffractions), etc.) or objects or media in which waves propagate (propagation velocities, physical properties related to waves, attenuations, scatterings, transmissions, reflections, refractions, diffractions, etc. or their frequency variances, etc.) are given, the instrument can also perform analogue or digital processings properly. The properties or features of generated image signals (intensities, frequencies, bandwidths or codes, etc.) can also be analyzed. The data acquired by the instruments according to the present embodiment can also be used by other instruments. The instruments according to the present embodiment can also be used as one of network devices and then, can also be controlled by the control instruments (devices). Or, the instruments can also work as the control instruments (devices) for controlling networks. Local networks can also be controlled by the instruments.

When using the passive-type instrument according to the present embodiment as the active-type instrument, the transmission transducer (or applicator) 10 is connected to the transmission unit 31 equipped with in the instrument body 30. One of the following formations can be realized: when the transmitter 31a is an analogue type and has an input terminal for a trigger signal, the trigger signal generated by the control unit 34 is inputted; when the transmitter 31a is a digital type and has a mode for working according to external clock signals, clock signals generated by some unit or the control unit 34 are provided; or whole the instrument body works according to the clocks of the transmitter 31a. When the transmitter 31a is a digital type, on the either formation, clocks of the transmission and the reception are synchronized. This is significant on the generation of an image signal on the basis of plural transmissions. If the synchronizing cannot be performed, the errors can be decreased by increasing the clock frequency and the sampling frequency.

Thus, arbitrary beamformings can be performed by digital processings such as FFT with no approximate interpolations.

In practical, arbitrary focusings and arbitrary steerings can be performed using arbitrary aperture geometries. However, in the present invention, as mentioned in the method (1) to (7), approximate interpolations can also be performed in the wavenumber matchings of arbitrary beamformings and then, the faster beamforming can also be achieved. For performing approximate wavenumber matchings with high accuracies, reception signals must be over-sampled properly and in return, the calculation amounts increase. In the cases, being different from in cases where image signals of arbitrary positions can be generated when no approximate interpolations are performed, it is cautious that the number of data to be used for the Fourier transforms increases. The 2nd embodiment can also be performed using general instruments regarding the instrument and the operation mode (for instance, imaging mode, Doppler mode, measurement mode, communication mode, etc.) and not limited to these or above-mentioned ones.

On the above 1st and 2nd embodiments, waves such as electromagnetic wave, vibration waves (mechanical waves) including acoustic waves (compressible waves), shear waves, ballistic waves, surface waves, etc., thermal waves, etc. (including a surface wave, a guided wave, etc.) are used to perform arbitrary beamformings with high speeds and with no approximate interpolations on the basis of digital processings, i.e., and with high accuracies such as the transmission and the reception focusings, the transmission and the reception steerings, the transmission and the reception apodizations including performing or not, those when the coordinate systems of transmissions and/or receptions are different from those where beamformed signals are obtained. Increasing of the frame rate for imaging the beamformed signals as well as increasing the image qualities such as a spatial resolution and a contrast can be achieved. Furthermore, using the beamformed signals increases the measurement accuracies such as of a displacement, a deformation, a temperature, etc. However, in the present invention, as mentioned in the method (1) to (7), approximate interpolations can also be performed in the wavenumber matchings of arbitrary beamformings and then, the faster beamforming can also be achieved. For performing approximate wavenumber matchings with high accuracies, reception signals must be over-sampled properly and in return, the calculation amounts increase. In the cases, being different from in cases where image signals of arbitrary positions can be generated when no approximate interpolations are performed, it is cautious that the number of data to be used for the Fourier transforms increases. The high-speed beamformings performed on the superposing and/or spectral frequency division on the waves or beams generated by the high-speed beamformings, or the superposing and/or spectral frequency division on the reception signals prior to the reception beamformings yield various applications and the present invention is not limited to these. The high-speed processings provides a great effects on the use of a multi-dimensional array for multi-dimensional imaging. The Fourier transforms and the inverse Fourier transforms performed on the above-mentioned calculation algorithms are desired to be FFTs and IFFTs including the exclusive ones. The present invention is not limited to the above embodiments and much transformation is possible in technical thought of the present invention by a person having normal knowledge in the technical area concerned.

The measurement objects are various such as organic and inorganic substances or matters, solids, liquids, gases, rheology matters, living things, celestial objects, an earth, environments, etc., the application range is prominently widespread. The present invention contributes to nondestructive evaluations [As recent topics, the examinations of metals or plastics, etc. (particularly, Fiber-Reinforced Plastics using a carbon fiber or a glass fiber, etc.) are often performed by using cheap and simple ultrasounds, and the inventor of the present invention is also proposing to perform an ultrasonic observation for a rubber (material) having a large attenuation property with respect to an ultrasound.], diagnoses, resource explorations, growth and manufacturing of substances and structures, monitoring of physical and chemical restorations and treatments, applications of clarified functions and physical properties, etc., where a high measurement accuracy can be achieved without generating turbulences under the conditions of a noninvasiveness, a low invasiveness, no observable blood, etc. Ideally, the measurement objects can be observed at their original positions in situ. For instance, when a 3D wave can be observed, a 3D displacement in an arbitrary direction can be measured in a Doppler manner by directing the sensor toward the measurement object, although a conventional Doppler method requires to set the wave propagation direction toward the direction of the measurement object's displacement to measure the displacement (e.g., ultrasonic echo technique). The operational technique using a hand can also be simplified. For instance, for observing a strain tensor, a strain rate tensor and a shear wave propagation in an eye ball, and for reconstructing the viscoelasticity and the eye pressure based on the mathematical inverse problem, an ultrasound technique can be used when an eyelid closes and via a water when an eyelid opens, or an OCT can be used when an eyelid opens. An intracardiac, intravascular or ocular fundus' and retina's blood vector flow can also be observed in an ultrasonic Doppler manner and a viscosity, an intravascular pressure, a blood pressure can also be reconstructed, etc. Or, an ultrasound as well as a light can be used for various biometrics authentications such as a fingerprint judgement (authentication) or iris authentication, etc. (including observations of functions related to dynamics or a temperature, etc. or various physical properties). Or, the observation object under a working condition can also be observed in situ. For instance, for a neural network or an electric-electronic circuit under a working condition, the electric property distributions such as of an electric conductivity or a permittivity (dielectric constant) can be reconstructed by observing an electric current density vector distributions based on the electromagnetic field (distribution) observations; the thermal property distributions can be reconstructed by observing the temperature distributions; for a tire of a moving car, a rubber pipe which the fluid flows through, an isolation rubber of the electric wire which the electric current flows through, etc., the internal distribution of a visco-elasticity or a pressure can be reconstructed by observing an internal strain tensor or a strain rate tensor using an ultrasonic Doppler technique, or the internal distribution of thermal properties, a heat generation, or a perfusion can be reconstructed by observing an internal temperature; for a human muscle under an exercise, a visco-elasticity or a tissue pressure can be reconstructed by observing a motion vector, etc. Or, monitorings of growths and manufacturings of substances can be performed without changing physical conditions, etc. for the observations. In paragraph 0094, the observation method of an elastic wave for observing an anisotropy of elasticity is described (ultrasound, MRI, ICT, etc. can be used) and similarly, other anisotropies of various physical properties can also be observed by observing waves (various electromagnetic waves, mechanical waves, thermal waves, etc.) related to the respective physical properties. That is, the positions and the number of sources, and the directivities, etc. can be controlled for observing the superpositions of waves being observation objects (electromagnetic waves, lights, radiation waves, audible sounds, ultrasounds, elastic waves, thermal waves) or the respectively observed waves can be superposed for controlling the propagation direction. Or, the positions and the number of sources, and the directivities, etc. can be controlled for generating plural independent waves and increasing the reconstruction accuracies of physical properties (an over-determined system can be generated.). For instance, designing of devices (media, sources, etc.) generating various surface waves or guided waves can be performed well. The observation objects are not only waves but also static or quasi-static fields (a strain tensor distribution, a potential distribution, an electric current density vector distribution, a temperature distribution, etc.) and static physical properties can also be reconstructed.

When the SNRs of directly sensed waves for observing the waves or the fields are low, the superposing and the additional averaging of waves are effective. For instance, when observing the electric current density vector is observed by observing brain magnetic fields of a human being or an animal with a SQUID meter, since the signal with a very small intensity is usually buried in ambient magnetic fields, the electric current density vector distribution can be reconstructed with a high accuracy from the superposed (additionally averaged), evoked brain magnetic fields with respect to stimuli (visible, audible, somatosensory) and further the electric properties can also be reconstructed. From the respectively evoked magnetic fields, the electric current density distributions are observed, which are superposed (additionally averaged) and the electric properties can also be reconstructed. In addition, when the observation object is idiopathic such as an epilepsy, the observed magnetic fields can also be superposed and the time series can also be integrated for performing the reconstructions. Or, for observing with a terahertz (electric field measurement), the additional averaging can be performed to increase the SNR, by which the electric properties can also be reconstructed. When the superposition (additional average) or the integration includes plural signals of phenomena, the accumulations can be observed simultaneously and random noises can be suppressed. Also using such superposed signals allows performing the reconstructions of distributions of an electric current density vector and/or electric properties and for instance, neural networks (running nerves) that worked during the observations can be visualized.

Observation with changing a wave frequency or generating a wide-band wave allows reconstructing the frequency variance of a physical property.

Measurement objects can also be treated or restored owing to the actions of the waves themselves. Simultaneously, the processes can also be observed by performing the beamforming using the responses from the objects. The Beamformings can also be performed on satellite communications, radars, sonars, etc. to achieve accurate communications under saving energies by realizing informationally safe environments. In ad hoc communication instruments and mobile instruments, the present invention is effective. The present invention can also be used for sensor networking. When the objects are dynamic and real time characteristics is demanded, the present invention also make it possible to perform digital beamformings with high speeds, i.e., in short times as well as with high accuracies.

3rd Embodiment

Being dependent on a frequency, a bandwidth, an intensity or a mode, etc., the waves such as electromagnetic waves, lights, mechanical vibrations, acoustic waves or thermal waves exhibit different behaviors. As far, many transducers for various type waves are developed and the waves themselves, the waves' transmission waves, reflection waves, refraction waves, diffraction waves or scattering waves are used for imaging. For instance, it is well known that on non-destructive examinations, medicines or sonars, ultrasounds, i.e., acoustic waves with higher frequencies, are used. Also on radars, electromagnetic waves with proper frequencies with respect to observation objects are used such as microwaves, terahertz waves, infrared rays, visible waves or radioactive rays such as an X-ray, etc. These are also for other waves.

On the imagings using such waves, amplitude data obtained via the quadrature detection, the envelope detection or the square detection are displayed in a gray or color scale in a 1D, 2D or 3D. Alternatively, on the Doppler measurements using such waves, raw coherent signals are processed (ultrasound Doppler, radar Doppler, Laser Doppler, etc.). Moreover, it is well known that in the fields of image measurements, object motions are observed using incoherent signals obtained via the detections (cross-correlation processing or optical flow, etc.). On the medical ultrasounds or sonars, the imagings are also carried out using harmonic waves, and chord and different tone waves generated physically.

In such fields, for instance, the present inventor develops ultrasonic imaging techniques for a differential diagnosis of lesions such as cancerous diseases, sclerosis, etc. of human tissues. The present inventor increases a spatial resolution in echo imaging and an accuracy in measurement and imaging of a tissue displacement; and the present inventor also increases a spatial resolution and an efficiency of HIFU (High Intensity Focus Ultrasound) treatment; and the present inventor also promotes those imagings based on the reception of the echo with respect to the HIFU radiation. Those imagings are based on performing appropriate beamformings and also, proper detection methods or displacement measurement methods are demanded, etc.

For instance, the inventor of the present invention developed as the beamforming methods, the lateral modulation method using crossed beams, the spectral frequency division method, one using many crossed beams and over-determined systems, etc.; and as the detection methods, the quadrature detection, the envelope detection and the square method, etc.; and as the displacement vector measurement methods, the multi-dimensional autocorrelation method, the multi-dimensional Doppler method, the multi-dimensional cross-spectrum phase gradient method and the phase matching method, etc. In addition, the inventor of the present invention reported the techniques for reconstructing a (visco) shear modulus distribution or a thermal property distribution on the basis of the measurements of a displacement or a strain (nonpatent documents 13 and 30). In practice, several methods and techniques in the developments are used clinically. Many recent reports by the inventor of the present invention are performed at ITECs (International Tissue Elasticity Conferences), IEEE Trans. on UFFC, IEICE ultrasound meetings, ASJ acoustical imaging meetings, etc.

Related to these, the inventor of the present invention focuses on nonlinear imaging. Today on the medical ultrasounds, so-called harmonic imaging is performed, i.e., nonlinear imagings on the basis of the results of physical actions during the ultrasound propagations. Below, mentioned are applications of nonlinear ultrasounds to the diagnosis and the treatment, particularly.

The harmonic imaging is to image the harmonic wave components generated during the wave propagations due to the fact that the wave propagation speeds of high intensity sound pressures are large (generally, it is explained that a bulk modulus is large with respect to a high intensity sound pressure). For this harmonic imaging, the contrast media (ultrasound agents) can also be used to increase nonlinear effects generated during the ultrasound propagation.

Long time has passed since the effectiveness was recognized in clinics, such as a capability for imaging a blood flow in capillary, etc. (nonpatent document 22). The Doppler measurement using the nonlinear components (harmonic components) is also possible and then, the results obtained using the multi-dimensional vector measurements in such a case will be presented in the near future. In the nonpatent document 23, the so-called pulse inversion method is used to separate harmonic waves from a fundamental wave signal.

Alternatively, the tissue imaging was performed in advance to the blood flow imaging historically. At the initial applications, the harmonic components are separated by filterings (nonpatent document 24) and in the historical present, the above-mentioned pulse inversion method is used to separate them. When the transmission signal is wideband, the bandwidths of the fundamental wave and the harmonic waves filled in the generated wave are to be overlapped, the use of the filtering is limited. Or, there is a report that the fundamental wave and the harmonic waves are separated in a least squares sense by expressing the observed wave using a polynomial expression comprised of the respective exponentiation terms corresponding to the waves to be separated (nonpatent document 25).

Recently, on the ultrasound microscope (nonpatent document 26) or the radiation force imaging (nonpatent document 27), the applications of the harmonic components or chords are also reported. There exist deep relationships between the nonlinear propagations and the thermal absorptions and in the applications of HIFU, high intensity ultrasounds are focused on the focus position and including the cases where cavitations are generated (nonpatent document 28). When an ultrasound is converted into the energy of a shear wave (or the wave mode is converted to other energy), the generated high frequency shear wave is well absorbed in the neighboring tissues during the propagation (Girke). For instance, shear phenomena are caused by a scattering or an ultrasound to be a slanted incident wave into a boundary such as between a soft tissue and a bone.

The contrast media to be used for increasing the nonlinear effects on the HIFU treatment can also be considered to be effective on these points (nonpatent document 29 etc.). On the treatment of cancerous diseases, the inventor of the present invention referred to, 17 years ago, the effects of blocking the feeding artery by coagulating the blood at the position and the inventor of the present invention considers that such effects can also be acquired using the contrast media. Recently, it becomes possible to cheaply introduce applicators having the same bandwidths as those of diagnostic transducers and then, the inventor of the present invention considers that the exclusive contrast media should be developed. The inventor of the present invention considers that both destructive and nondestructive properties are attractive and then, the diagnostic contrast media with both the properties or some mixed several type contrast media can be used proximately.

A wave is effected by attenuations during the propagation and then, the wave energy becomes smaller with the propagation distance. A diverging wave are also effected by the diverging. In the cases, since the transmission wave, the reflection wave, the refraction wave, the scattering wave or the diffusion wave reflects a change in impedance, the or existence of a reflector or a scatter, the waves are used for imaging them or the Doppler measurements. On the imagings, the signal is desired to have high frequency components and to be wideband whenever possible and on the Doppler measurements they are also similar.

However, generally, the high frequency signal components are effected by attenuations, the energies are lost with the propagation distance; causing the signal to be low frequency and narrow band. That is, the imaging at far position from a wave source become to have a low signal-to-noise ratio (SNR) and a low spatial resolution. Accordingly, the accuracy of Doppler measurement decreases. To decrease the effects due to the attenuations is of extreme importance in an engineering sense.

It also becomes possible to perform higher spatial resolution imaging and higher accuracy Doppler measurement if a high frequency signal being not able to be generated by a single wave source can be generated. It is acceptable that a high frequency signal is generated simply. Generally, the attenuations are intense on the high frequency components and then, for instance, the microscope being well suffered from the attenuations is desired to allow observing positions as deeply as possible using the high frequency. Also it is useful if low frequency imagings or measurements using low frequency signals can be performed. It is also useful if a low frequency signal being not able to be generated by a single wave source can be generated. For instance, it is possible to deform at a deep position with a low frequency. On the applications of medical ultrasounds, MRIs, OCTs and lasers, deeply situated tissues are deformed in a low frequency using plural signal sources (Tissue Elasticity).

For instance, vibrations are applied to in plural directions to generate lower frequency vibrating waves than the respective applied vibrations; or plural ultrasound beams are crossed at their same focus position, etc. to yield a low frequency mechanical source for generating low frequency vibrating waves. The generated vibrating waves may be ultrasounds (longitudinal waves). Or, the generated vibrating waves are shear waves (transverse waves), which can be observed using ultrasounds. It is useful if the propagation directions of the generated waves can be controlled. If these signals can be generated theoretically or on the basis of calculations, the generated waves can be controlled, which is useful. Moreover, detection methods, which allows simply performing detections in short times instead of a general quadrature detection and a general enveloped detection, or the square detection, are also important.

Then, in consideration of the above-mentioned points, the 2nd purpose of the present invention is to provide imaging instrument that allows increasing the spatial resolution and the measurement accuracy by increasing or newly generating high frequency components with the generally relatively small intensities or lost on arbitrary waves propagating from an inside of measurement object. The imaging instrument can be used for increasing or imitating the nonlinear effects in the measurement object, or for newly generating nonlinear effects when there exist no nonlinear effects in the measurement object, or virtually realizing and imaging nonlinear effects. And the 3rd purpose of the present invention is to allow generations of high frequency signals, which cannot be generated by using a single wave source. And the 4th purpose of the present invention is to realize detection methods, which can be performed simply in short times.

To solve the above-mentioned problems, the imaging instrument according to one aspect of the present invention is equipped with a nonlinear reception processing unit that performs at least one of the three processings with respect to arbitrary waves propagating form the inside of measurement object, i.e., (i) after implementing nonlinear processings at arbitrary positions on the propagation path, generating reception signals is performed by receiving using a transducer; (ii) generating analogue reception signals is performed by receiving using a transducer, after which analogue nonlinear processings are implemented; (iii) generating analogue reception signals is performed by receiving using a transducer, after which digital nonlinear processings are implemented onto the digital reception signals obtained by performing digital sampling with respect to the generated analogue reception signals; and further equipped with image signal generation unit that generates image signals exhibiting the image of the measurement object.

According to one of viewpoints of the present invention, implementing nonlinear processings, on arbitrary waves arriving from the inside of measurement object, with respect to signals having frequencies that do not cause serious problems regarding attenuations makes it possible to increase or newly generate high frequency components with the generally relatively small intensities or lost on arbitrary waves propagating from an inside of measurement object and further to improve the spatial resolution and the measurement accuracy. With respect to arbitrary coherent signals generated by detecting, by a transducer, waves arriving from signal sources of arbitrary waves such as electromagnetic waves, lights, mechanical vibrations, acoustic sounds or thermal waves, etc. or the waves themselves generated from the signal sources, the transmission waves, the reflection waves, the diffraction waves or the scattering waves, implementing effects of multiplications or exponentiations during the wave propagations or performing processings including their analogue or digital calculations allows increasing nonlinear effects in the measurement object. These can also be used for the wave sources (diffractions). Or, the similar effects can also be imitated or newly generated or virtually realized. These can be used for the imagings.

For instance, on the imagings or the Doppler measurements using the coherent signals, compared with imagings using the raw signals, high spatial resolution imagings can be realized utilizing widebanded signals including the high frequency components and compared with Doppler measurements using the raw signals, high accuracy measurements of a displacement, a velocity, an acceleration, a strain or a strain rate can be realized. With respect to incoherent signals, the similar processings can be performed on the similar problems. For the hardwares, general devices can be used. Off course, analogue processings (circuits) is faster than digital processings (circuits). For performing calculations including high order calculations and at the point of a large degree of freedom, used can be calculators or devices having calculation functions such as FPGA and DSP, etc.

Particularly, it is robust to the effects of attenuations during the wave propagations and it is also possible to generate high frequency components that cannot be generated using a single signal source; yielding high spatial resolution imagings and high accuracy Doppler measurements. For instance, using plural 100 MHz ultrasound transducers, physically the same times as the number of used transducers as high frequency ultrasounds as that of the single transducer used can be generated, i.e., high frequencies being not able to be generated by a general transducer can be generated. It is also useful for generating a high frequency simply. The present invention can also generate high frequencies by performing calculations. Thus, it is also possible to generate high frequency waves or signals that cannot be generated physically. Similarly, low frequency imagings or measurements using low frequency signals can also be performed similarly. Also, it is possible to generate low frequency signals that cannot be generated by a single signal source physically. The generated waves can also be controlled by realizing these signals theoretically or on the basis of calculations.

For instance, on the ultrasonic microscope, ultrasounds with a higher frequency than the frequency determined by the ultrasound sources can be generated using high frequency ultrasounds (signals) with several hundred MHz and since the generated ultrasounds are robust to the attenuations, a special ultrasonic microscope allowing high spatial resolutions imagings and high accuracy Doppler measurements can be realized. Also, low frequency imagings or measurements using low frequency signals can also be performed. Also, when performing the measurements of tissue deformation, for instance, deeply situated tissues can be deformed in low frequencies. On the applications of medical ultrasounds, MRIs, OCTs, lasers, etc., deeply situated tissues can be deformed using plural signal sources. These are also for other imaging instruments or other Doppler instruments. Or, it is also possible to increase the spatial resolutions for performing warming, heating, cooling, freezing, welding, thermal treatment, washing or restorations. The same effects can be obtained on incoherent signals obtained by various type detections.

On the technical aspects of signal processings, it is also possible to perform the quadrature detection and envelope detection simply. For instance, when the present invention is applied to the steered beams or waves, the IQ signals, i.e., results of quadrature detections performed on all coordinate axes, can be obtained and the envelope detection becomes simple. Moreover, when applying the present invention to the crossed beams, the IQ signals, i.e., results of quadrature detections performed on the respective coordinate axes, can be obtained and then, only implementing the Doppler signal processings on the respective directions makes it possible to measure a displacement vector, a velocity vector, an acceleration vector, a strain tensor or a strain rate tensor. Off course, on the imagings, the square detection can also be performed.

On the radars, sonars, non-destructive examinations or diagnose, imagings and Doppler measurements using arbitrary coherent signals generated by detecting, by a transducer, waves arriving from signal sources of arbitrary waves such as electromagnetic waves, lights, mechanical vibrations, acoustic sounds or thermal waves, etc. or the transmission waves, the reflection waves, the refraction waves, the scattering waves or the diffraction waves with respect to the waves generated from the signal sources, are widely used for respective various media with proper frequencies. Waves generated from signal sources are also applied to the heating, the cooling, the freezing, the welding, the thermal treatment, the washing or the restorations. The same effects can be obtained on incoherent signals obtained by various type detections. Moreover, recently, the image measurements using incoherent signals are performed such as motions, etc., and various imagings or measurements are performed on the basis of the image processings and signal processings. The present invention brought effects on these all, and the usability and the market potential of the present invention are prominently high.

Figure 37:
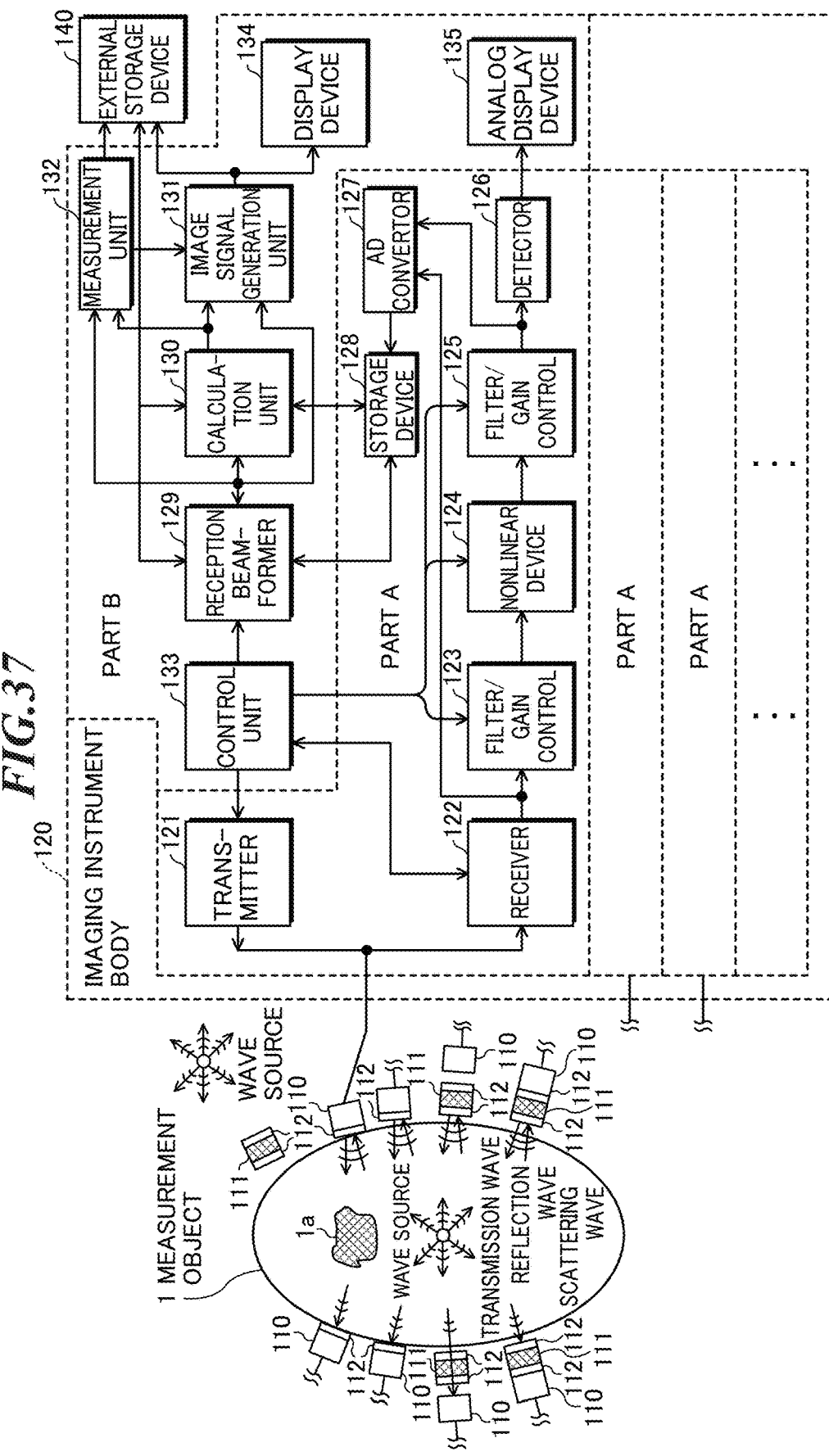
FIG. 37 shows schematic representation (block map) of compositions of a measurement and imaging instrument according to the third embodiment of the present invention and the modification.

FIG. 37 shows schematic representation (block map) of the compositions of imaging instrument according to the third embodiment of the present invention. This imaging instrument performs imagings of measurement objects or measuring of physical quantities such as displacements in measurement objects nondestructively on the basis of arbitrary waves such as electromagnetic waves, lights, mechanical vibrations, acoustic sounds or thermal waves, etc. arriving from the measurement objects.

As shown in FIG. 37, the imaging instrument includes at least one transducer 110 and the imaging instrument body 120. The transducer 110 can be able to generate or receive arbitrary waves such as electromagnetic waves, lights, mechanical vibrations, acoustic waves or thermal waves, etc. In the cases, the transducer 110 can be used for transmitting arbitrary waves to the measurement object 1 and for receiving reflected waves or scattered waves generated in the measurement object 1. For instance, when arbitrary waves are ultrasounds, ultrasound transducers can be used to perform the transmissions of ultrasounds according to the drive signals and the receptions of ultrasounds for generating reception signals. It is well known that according to the applications, ultrasound elements (PZT, PVDF, etc.) are different as well as the structures of the transducers.

In the medical applications, for blood flow measurement, a narrowband ultrasound is used historically. First in the world, the inventor of present invention has been realizing to use a wideband echo imaging transducer for measurements of soft tissues' displacement or strain (including static cases), shear wave propagation (speed), etc. Also for HIFU treatment, although a continuous wave can be used, in order to realize a high spatial resolution treatment, the inventor of the present patent has been developing new applicators using devices in a wideband type. As one of applications of a high intensity ultrasound, as mentioned above, tissues are stimulated by generating mechanical sources in the measurement object 1 with no thermal effects, for which echo imaging transducer can also be used. In addition to the thermal treatments and generations of mechanical sources, echo imagings can also be performed simultaneously. This is also for using of other wave sources and transducers. There exists for the transducers, contact and noncontact types, which are used by properly performing the respective wave impedance matchings.

Or, as the transducers 110, transmission transducer used for generating arbitrary waves and reception transducer (sensor) used for receiving arbitrary waves can be able to be used. In the cases, the transmission transducers can transmit arbitrary waves to the measurement object 1 and the sensor can receive reflected waves, refracted waves, scattered waves, diffracted waves or transmission waves, etc. generated in the measurement object.

For instance, when the arbitrary waves are thermal waves, thermal sources being not intentionally generated such as a sunlight, an illumination or a metabolism in vivo in a body can be used, whereas a stationary thermal source such as an infrared warmer or a heater, etc., an ultrasound transducer that transmits ultrasounds for heatings, often driven by a drive signal (that can be able to generate a mechanical source in the measurement object 1), an electromagnetic transducer or a laser, etc. can also be used. An infrared sensor generating reception signals by receiving thermal waves, a pyroelectric sensor, detectors of microwaves or terahertz waves, a temperature sensor such as using optical fibers, etc., an ultrasound transducer (that detects a change in temperature using the dependencies of changes in a sound speed or a volume on the temperature) or a nuclear magnetic resonance signal detector (that uses a chemical shift of nuclear magnetic resonance signal) can be used. A proper reception transducer can be used.

The transducer 110 can also be used positively for generating waves including harmonic waves according to drive signals. For instance, the transducer 110 generate the waves according to the wave sources and the nonlinearities of the circuit of transmitter 121 that drive the transducer 110. The transducer 110 can have a transmission aperture or a reception aperture, or plural transmission or reception apertures. The transmission aperture of transducer 110 also can be equipped with a nonlinear device 111 that implements nonlinear processings on the generated arbitrary waves. The reception aperture of transducer 110 can also be equipped with a nonlinear device 111 that implements nonlinear processings on arbitrary waves arriving from an inside of the measurement object 1. The nonlinear device 111 are not always to be contacted on the transmission apertures or the reception apertures of transducer 110, the device 111 can also be set at arbitrary positions on the propagation paths of arbitrary waves.

Between the measurement object 1 and the transmission or reception apertures of transducer 110, operation devices 112 such as filters (spectroscopes, etc.), blockers, amplifiers or attenuators, etc. can also be set. When using a nonlinear device 111, the operation devices 112 can also be set in front of, behind or both sides of the nonlinear device 111. The transducer 110, the nonlinear device 111 and the operation device 112 can be separated or incorporated in into a body.

FIG. 37 also shows the case where a wave source(s) exists in the measurement object 1, and the direct control of the wave source(s) by the controller 133 can be possible. By using the lens, etc., the focusing can be performed on the waves generated by the transducer 110 or by using plural transducers 110, focused transmissions can be performed, etc., which can generate a wave source(s) (including sources of mechanical waves or thermal sources, new generations of electromagnetic waves, for instance, with respect to magnetic substances, etc. that can be contrast media, or controlling of the wave intensity or the wave propagation direction by physical actions between waves or stimuli on physical properties, etc.).

Off course, a wave source(s) can exist in the measurement object originally (for instance, an electric current source(s) expresses the electric activities of brain or cardiac and the cardiac can also work as a mechanical source). There exist the cases where the wave source(s) can be controlled or not, the measurement object 1 is observed in situ, or such wave sources can be an imaging or measurement object themselves. Or, such a wave source(s) can exist outside the measurement object 1 and similarly dealt with, which can also be a measurement object(s). Between the wave source (s) and the measurement object 1, the nonlinear device 111 or the operation device 112 can also be set properly.

Moreover, to obtain nonlinear effects in the measurement object 1 or to increase nonlinear effects in the measurement object positively, contrast media such as microbubbles (increasing nonlinearities) 1a, etc. can be injected at least into a part of the measurement object 1. The contrast media 1a can have affinities for diseases or fluids, which are targets, etc. in the measurement object 1. Thus, to the transducer that receives a wave, waves generated by plural wave sources can be arrived at.

The transducer 110 is provided with a drive signal from the imaging instrument body 120 via wire lines or wireless and/or the transducer 110 outputs received signals into the imaging instrument body 120. When wireless is used, the transducer 110 is equipped with a wireless receiver and/or a wireless transmitter; and wireless transmitter and receiver are set in the imaging instrument body 120.

The imaging instrument body 120 can include, in the part A, a transmitter 121, a receiver 122, a filter/gain control unit 123, a nonlinear element 124, a filter/gain control unit 125, a detector 126, an AD (Analogue-to-digital) convertor 127 and a storage device 128. Also, the imaging instrument 120 can include, in the part B, a reception beamformer 129, a calculation unit 130, an image signal generation unit 131, a measurement unit 132, a control unit 133, a display device 134, an analogue display device 135. The control unit 133 controls the respective units or devices in the imaging instrument body 120.

When using the plural transducers 110, the same number of part A as that of the transducers 110 (the number of channels) can be set. Below, also explained is the case where an array is comprised of the plural transducers. As shown in FIG. 37, when plural numbers (channels) of part A are set, reception signals outputted from storage devices 128 of the respective parts A can be provided to the reception beamformer 129 of the part B. Or, parts B can also be connected with respect to the respective parts A in a cascade fashion and the received signals can be processed independently. In the case, the received signals outputted from the storage devices of the respective parts A are provided to the reception beamformers 129 of the parts B of the respective channels. The plural transducers 110 can include ones for other different type waves and in the cases, nonlinear effects of different type waves can also be observed simultaneously, and not nonlinear effects of the same type waves but those generated between different type waves can also be observed.

On the part A, the transmitter 121 to the detector 126 can also be comprised of analogue circuits and at least partially it can also be comprised of digital circuits. On the part B, the reception beamformer 129 to the control unit 133 can also be comprised of digital circuits, or the CPU (central processing unit) and the storage media in which softwares for making the CPU to perform respective type processings are recorded. As the storage media, a hard disk, a flexible disk, an MO, an MT, a CD-ROM or a DVD-ROM, etc. can be used. At least partially the reception beamformer 129 to the control unit 133 can be comprised of analogue circuits.

The transmitter 121 includes a signal generator such as a pulser that generates a drive signal according to a trigger signal provided by the control unit 133 etc. The control unit 133 can control the frequency or the carrier frequency, the bandwidth, the transmission signal intensity (apodization), the wave shape or the geometry of a pulse wave or a burst wave, etc. The control unit 133 can set timings of trigger signals or the delay times on the respective channels. Or, the transmitter 121 can also include delay devices for adding delays to the respective trigger signals (channels) according to the delay times set by the control unit 133 and for all the channels, the timings of trigger signals outputted from the control unit 133 is set at a constant, The transmitter 121 provides a generated drive signal to the transducer 110 and makes the transducer 110 to generate an arbitrary wave. For instance, the transmitter 121 can include an amplifier for working on the drive signal (and being able to work as an apodization) to control the wave intensity to be transmitted or the harmonic wave intensities to be generated and furthermore, the transmitter 121 can also include a delay device of which delay time is set by the control unit 133. A drive signal including harmonic waves can also be generated and can be used. Not a resonance but an apodization can be performed, or in the cases where forcedly vibrating is performed, various waves including a chirp wave, etc. can be generated and can be used. When drive signals generated by a transmitter 121 with plural channels are provided to plural transducers 110, according to the delay times set by the control unit 133, the beam transmission with a focusing or a steering and the plane wave transmission can be performed (Since the plane wave transmission yields a narrow band in the direction orthogonal to the propagation direction and it is also effective to be wide banded in the direction).

Furthermore, the transmitter 121 can also include nonlinear devices to which nonlinear effects are similarly set (analogue devices such as a transistor, a diode or a nonlinear circuit, etc. or digital devices such as a nonlinear calculators (processors), etc.). Frequencies or carrier frequencies, bandwidths, apodizations, delays and nonlinear effects to be used are prepared in advance, which can also be controlled via the control unit 133 by an operator. Or, they can also be determined adaptively by the calculation unit 130 according to the observed states and can be controlled.

When driving the plural transducers 110, the frequencies or the carrier frequencies, the bandwidths, the apodizations, the delay devices and nonlinear devices of the transmitters of respective channels can be controlled and specifically, the prepared patterns of them in advance can also be used, the pattern can also be controlled via the control unit 133 by an operator, or the pattern can also be determined adaptively according to the observed states by the calculation unit 130 and can be set.

The receiver 122 can include, for instance, an amplifier for amplifying or an attenuator for attenuating reception signals (that can be possible in working as an apodization or a filter) and furthermore, the receiver 122 can also include a delay device of which delay time is set by the control unit 133. Furthermore, the receiver 122 can also include a nonlinear device to which nonlinear effects are similarly set (analogue devices such as a transistor, a diode or a nonlinear circuit, etc. or digital devices such as a nonlinear calculators (processors), etc.). In cases where waves are received by plural transducers 110, they can be set similarly to those of the transmitter 121. The receiver 122 amplifies the reception signals generated from arbitrary waves received by the transducer 110, and the amplified reception signals can be outputted to the filter/gain control unit 123 and the AD convertor 127.

The filter/gain control unit 123 is a filter to limit the bandwidth of reception signals or includes an amplifier or an attenuator for controlling the gain of reception signals. The filter/gain control unit 123 can control the bandwidth or the gain of reception signals and can output the reception signals to the nonlinear element 124.

The nonlinear element 124 can include, for instance, analogue devices such as a transistor, a diode or a nonlinear circuit, etc. and implements analogue nonlinear processings on the reception signals. The nonlinear processings can be an exponentiation calculation at least on one frequency component signals included in the reception signals or a multiplication calculation on plural frequency component signals included in the reception signals (A Hall effect device, etc. can be used).

The filter/gain control unit 125 is a filter to limit the bandwidth of reception signals or includes an amplifier or an attenuator for controlling the gain of reception signals. The filter/gain control unit 125 can control the bandwidth or the gain of reception signals and can output the reception signals to the detector 126 and the AD convertor 127.

The above-mentioned filter/gain control units 123 and 125 and the nonlinear element 124 can also be set on the prepared ones in advance, they can also be controlled via the control unit 133 by an operator, or they can also be determined adaptively according to the observed states by the calculation unit 130 and can be set. When driving the plural transducers 110, their respective channels can be controlled independently, the prepared patterns in advance can also be used, the pattern can also be controlled via the control unit 133 by an operator, or the pattern can also be determined adaptively according to the observed states by the calculation unit 130 and can be set.

For instance, when not performing the reception beamformings, the detector 126 generates analogue signals by implementing the envelope detection or the square detection, etc. Or, the displacement measurement can also be performed via the quadrature detection. On the basis of the image signals or the measurements generated by the detector 126, the analogue display device 135 displays the images of the measurement object 1 or the wave sources.

The AD convertor 127 selects the reception signals outputted by the filter/gain control unit 125 and by the receiver 122 when the analogue nonlinear processings are implemented onto the reception signals and not, respectively. The AD convertor 127 can convert the analogue signals into the digital signals by digital samplings. The digital reception signals generated the AD convertor 127 are outputted to the storage device 128. The storage device 128 are comprised of memories such as RAM for instance, and the reception signals are stored.

The reception signals stored by the storage device 128 are provided to the reception beamformer 129. While the signal processings are performed by the reception beamformer 129, the signals under being processed are be stored in the storage device 128 or the external storage device 140 temporally and if required, the stored signals are read out. When using a single or plural transducers 110, the reception beamformer 129 can perform the pulse inversion method or the separation of harmonic waves, etc. using the polynomial fitting method, etc. (The calculation unit 130 can also be possible to perform the same processings).

When using the plural transducers 110, the reception beamformer 129 performs the reception beamformings with respect to the reception signals provided by the storage devices 128 of plural channels. For instance, after the reception beamformer 129 performs the delays via implementing the delays onto the reception signals of plural channels according to the delay times set by the control unit 133, the reception beamformer 129 synthesizes the receptions signals to generate new reception signals with focusing by implementing the summing or the multiplication.

Or, when the respective receivers 122 of plural channels include the delay devices, the receivers 122 can implement delays onto the respective reception signals according to the delay times set by the control unit 133. The reception beamformer 129 synthesizes the reception signals by implementing the summing and the multiplications onto the reception signals of plural channels. On the reception beamforming, the reception beamformer 129 can also perform the apodizations.

Or, by the (multi-dimensional) fast Fourier transformer being equipped with the imaging instrument body 120, the spectra of the reception signals are obtained and on the basis of the spectral analysis, the properties of filterings, or beams or waves can be controlled such as a frequency or a carrier frequency, a bandwidth, a frequency or a carrier frequency of at least one of directions, a bandwidth of at least one of directions, a shape, a beam geometry, a steering direction or a propagation direction, etc. By performing the spectral frequency division (nonpatent document 30), plural reception signals can be obtained from a single reception signal, etc. (corresponding to plural quasi-beamformings) and furthermore, the nonlinear processings can also be implemented on these signals. With respect to the signals to which the nonlinear processings are implemented on, these processings can also be performed.

On this imaging instrument, the above-mentioned plural wave signals generated by the single or plural transducers (nonlinear processed or not processed) are stored into the storage device 128 or the external storage device 140. The reception beamformer 129 or the calculation unit 130 reads out the results and performs the summation (superposing, linear processing) or the multiplication (nonlinear processing), which can be used for the imaging or various measurements. In the cases, the phasings are properly performed.

The calculation unit 130 can perform, mainly, digital nonlinear processings onto the digital reception signals outputted by the reception beamformer 129. The nonlinear processings can be an exponentiation calculation at least on one frequency component signals included in the reception signals or a multiplication calculation on plural frequency component signals included in the reception signals. The calculation unit 130 can also work as the beamformer 129 as mentioned above. Including the case, while the signals are processed, the signals under being processed can be stored into the storage device 128 or the external storage device 140 temporally and if required, the signals are read out.

Here, the transducer 110 to the operation device 112 and the receiver 122 to the calculation unit 130 composes the nonlinear reception processing unit that implements the nonlinear processings onto arbitrary waves arriving from the inside of measurement object 1 or the reception signals obtained by receiving the arbitrary waves. On the nonlinear reception processing unit, at least one of the nonlinear device 111, the nonlinear element 124 and the calculation unit 130 implements the nonlinear processings onto the arbitrary waves arriving from the inside of measurement object 1 or the reception signals obtained by receiving the arbitrary waves. There are also other ways to obtain such nonlinear effects as mentioned above.

That is, the nonlinear reception processing unit performs at least one of the three processings with respect to arbitrary waves propagating form the inside of measurement object 1, i.e., (i) after implementing nonlinear processings using the nonlinear devices 111 at arbitrary positions on the propagation path, generating reception signals is performed by receiving using a transducer 110; (ii) generating analogue reception signals is performed by receiving using a transducer 110, after which analogue nonlinear processings are implemented using the analogue nonlinear elements 124; (iii) generating analogue reception signals is performed by receiving using a transducer, after which digital nonlinear processings are implemented using the digital nonlinear devices 130 onto the digital reception signals obtained by performing digital sampling with respect to the generated analogue reception signals; and further equipped with image signal generation unit that generates image signals exhibiting the image of the measurement object. As mentioned above, there also exists other ways to obtain nonlinear effects.

The image signal generation unit 131 and the measurement unit 132 select the reception signals outputted by the calculation unit 130 and by the reception beamformer 129 when the digital nonlinear processings are implemented onto the reception signals and not, respectively.

The image signal generation unit 131 generates the image signals expressing the measurement object 1 on the basis of the reception signals generated by the nonlinear reception processing unit. Or, the image signal generation unit 131 can generate image signals on the basis of the reception signals obtained by the nonlinear processings and not together. The image signal generation unit 131 can also select the reception signals obtained in the cases of no implementation of the nonlinear processings and can generate the image signals expressing the measurement object 1. For instance, the image signal generation unit 131 generates image signals by implementing the envelope detection processing or the square detection processing, etc. The display device 134 generates the image signals expressing the measurement object 1 on the basis of the image signals generated by the image signal generation unit 131.

The measurement unit 132 can perform the measurement of a displacement, etc. in the measurement object 1 using at least one of the plural signals obtained by the nonlinear processings. For instance, on the observing the propagations of mechanical or electromagnetic waves, the measurement unit 132 measures a particle displacement and a particle velocity generated by arbitrary wave propagations of the wave itself or other waves on the basis of the measured displacement. In the cases, the image signal generation unit 131 generates image signals expressing the wave propagations on the basis of the particle displacement or the particle velocity measured by the measurement unit 132. When plural waves arrive at, the waves can also be separated in advance, or the measurements can also be performed via separating processing on the waves by analogue or digital processings after the receiving the waves.

Or, on the measurements of thermal wave propagations, the measurement unit 132 uses, as the transducer 110, an infrared sensor or a pyroelectric sensor, detectors of microwaves or terahertz waves, a temperature sensor such as using optical fibers, etc., an ultrasound transducer (that detects a change in temperature using the dependencies of changes in a sound speed or a volume on the temperature) or a nuclear magnetic resonance signal detector (that uses a chemical shift of nuclear magnetic resonance signal) for measuring the thermal waves. In the cases, the image signal generation unit 131 generates image signals expressing the thermal wave propagations on the basis of the thermal waves measured by the measurement unit 132. The image signals generated by the image signal generation unit 131 and the measurement data obtained by the measurement unit 132 can be stored in the external storage device 140.

The above-mentioned nonlinear reception processing unit can obtain the results of exponentiation calculations by the nonlinear processings with respect to the arbitrary waves arriving from the inside of the measurement object 1, or when the nonlinear processings are the exponentiation calculations, with respect to the arbitrary waves, as the results of the chord and different tone waves and harmonic tone waves, reception signals with an increased or decreased frequency can be obtained compared to the corresponding signals obtained when the nonlinear processings are not implemented on. The nonlinear processings can also be multiplication calculations. The nonlinear processings can also be high order nonlinear processings and as the effects, mainly the results of the exponentiation calculations and the multiplication calculations can also be obtained.

Thus, when the arbitrary waves have plural different frequency components, the nonlinear processings generate wideband reception signals compared to the corresponding signals obtained when the nonlinear processings are not implemented on. The reception signals generated with the increased frequency are harmonic wave signals with an increased frequency, an increased spatial resolution, a decreased sidelobes or an increased contrast compared to the corresponding signals obtained when the nonlinear processings are not implemented on. In addition, the reception signals generated with the decreased frequency are the signals with the direct currents approximately obtained by implementing the quadrature detections on the generated harmonic wave signals. The image signal generation unit 131 generates image signals on the basis of at least one of signals obtained by the nonlinear processings.

Also, when plural arbitrary waves arriving from the inside of the measurement object 1 have at least one different value about the propagation direction, the steering angle, the frequency, the carrier frequency, the pulse shape, the beam geometry, the frequency or the carrier frequency in one of three directions or the bandwidth in one of three directions from others in the measurement object 1, with respect to the superposed plural arbitrary waves arriving at, the nonlinear reception processing unit can perform at least one processing of the above-mentioned (i) to (iii). The image signal generation unit 131 generates image signals on the basis of the reception signals obtained by the nonlinear reception processing unit.

Prior to the reception of plural arbitrary waves, the nonlinear reception processing unit let the plural arbitrary waves to pass at least through the analogue delay device or the analogue storage device as the operation device 112 such that the plural arbitrary waves can be superposed at respective positions in the measurement object 1. This is the so-called phase aberration correction.

The nonlinear reception processing unit can obtain the results of exponentiation calculations by the nonlinear processings with respect to the superposition of arbitrary waves arriving from the inside of the measurement object 1, or when the nonlinear processings are the exponentiation calculations, with respect to the superposition of arbitrary waves, as the results of the chord and different tone waves and harmonic tone waves, reception signals with an increased or decreased frequency can be obtained compared to the corresponding signals obtained when the nonlinear processings are not implemented on. By this, the above-mentioned similar effects can be obtained. The image signal generation unit 131 generates image signals on the basis of at least one of signals obtained by the nonlinear processings.

Also, when plural arbitrary waves arriving from the inside of the measurement object 1 have at least one different value about the propagation direction, the steering angle, the frequency, the carrier frequency, the pulse shape, the beam geometry, the frequency or the carrier frequency in one of three directions or the bandwidth in one of three directions from others in the measurement object 1, with respect to the superposed plural arbitrary waves arriving at, the nonlinear reception processing unit can not only perform at least one processing of the above-mentioned (i) to (iii) but also perform, at arbitrary timing after receiving the plural arbitrary waves, the separating the reception signals into plural signals on the basis of the analogue or digital signal processings using the analogue or digital device. The image signal generation unit 131 generates image signals expressing the image of above-mentioned measurement object on the basis of one of the separated plural signals obtained by the nonlinear reception processing unit. By performing the nonlinear calculations (processings), the effects of multiplication calculation can be obtained. Also, after performing the analogue or digital phase aberration correction and the signals are superposed again, the effects of exponentiation calculation can also be obtained.

Also, when plural arbitrary waves arriving from the inside of the measurement object 1 have at least one different value about the propagation direction, the steering angle, the frequency, the carrier frequency, the pulse shape, the beam geometry, the frequency or the carrier frequency in one of three directions or the bandwidth in one of three directions from others in the measurement object 1, with respect to at least one of the not superposed plural arbitrary waves arriving at, the waves not superposed by blocking using the operation device 112, and waves separated by using the device (analogue or digital) or the analogue or digital signal processing, the nonlinear reception processing unit can perform at least one processing of the above-mentioned (i) to (iii). The image signal generation unit 131 generates image signals on the basis of the reception signals obtained by the nonlinear reception processing unit.

Prior to the reception of plural arbitrary waves, the nonlinear reception processing unit lets the plural arbitrary waves at least to pass through the analogue delay device or the analogue storage device as the operation device 112 such that the plural arbitrary waves can be superposed at respective positions in the measurement object 1. This is the so-called phase aberration correction.

Also, the nonlinear reception processing unit lets the analogue reception signals at least to pass through the analogue delay device and the analogue storage device, or implements delays on the digital reception signals by digital processings, or lets the digital reception signals to pass through the digital storage device, such that the plural arbitrary waves can be superposed at respective positions in the measurement object 1.

Also, the nonlinear reception processing unit can obtain the results of exponentiation calculations by the nonlinear processings with respect to the respective arbitrary waves arriving from the inside of the measurement object 1, or when the nonlinear processings are the exponentiation calculations, with respect to the respective arbitrary waves, as the results of the chord and different tone waves and harmonic tone waves, reception signals with an increased or decreased frequency can be obtained compared to the corresponding signals obtained when the nonlinear processings are not implemented on. By this, the above-mentioned similar effects can be obtained. The image signal generation unit 131 generates image signals on the basis of at least one signals obtained by the nonlinear reception processing unit.

Also, the nonlinear reception processing unit can obtain the results of multiplication calculations by the nonlinear processings with respect to the respective arbitrary waves arriving from the inside of the measurement object 1, or when the nonlinear processings are the multiplication calculations, with respect to the respective arbitrary waves, as the results of the chord and different tone waves and harmonic tone waves, reception signals with an increased or decreased frequency can be obtained compared to the corresponding signals obtained when the nonlinear processings are not implemented on.

Thus, when the arbitrary waves have plural different frequency components, the nonlinear processings generate wideband reception signals compared to the corresponding signals obtained when the nonlinear processings are not implemented on. Also, the reception signals generated with the increased or decreased frequency are signals, having direct currents due to (approximate) quadrature detections at least in one direction as well as having bandwidths of harmonic waves at least in other one direction, with an increased spatial resolution, a decreased sidelobes or an increased contrast compared to the corresponding signals obtained when the nonlinear processings are not implemented on. The image signal generation unit 131 generates image signals on the basis of at least one of signals obtained by the nonlinear processings.

To generate image signals, the image signal generation unit 131 can also implement an arbitrary detection processings onto at least one of the plural signals generated by the nonlinear processings or implement onto the superposed plural signals or implement onto the plural signals and the implemented signals are superposed.

4th Embodiment

Figure 38:
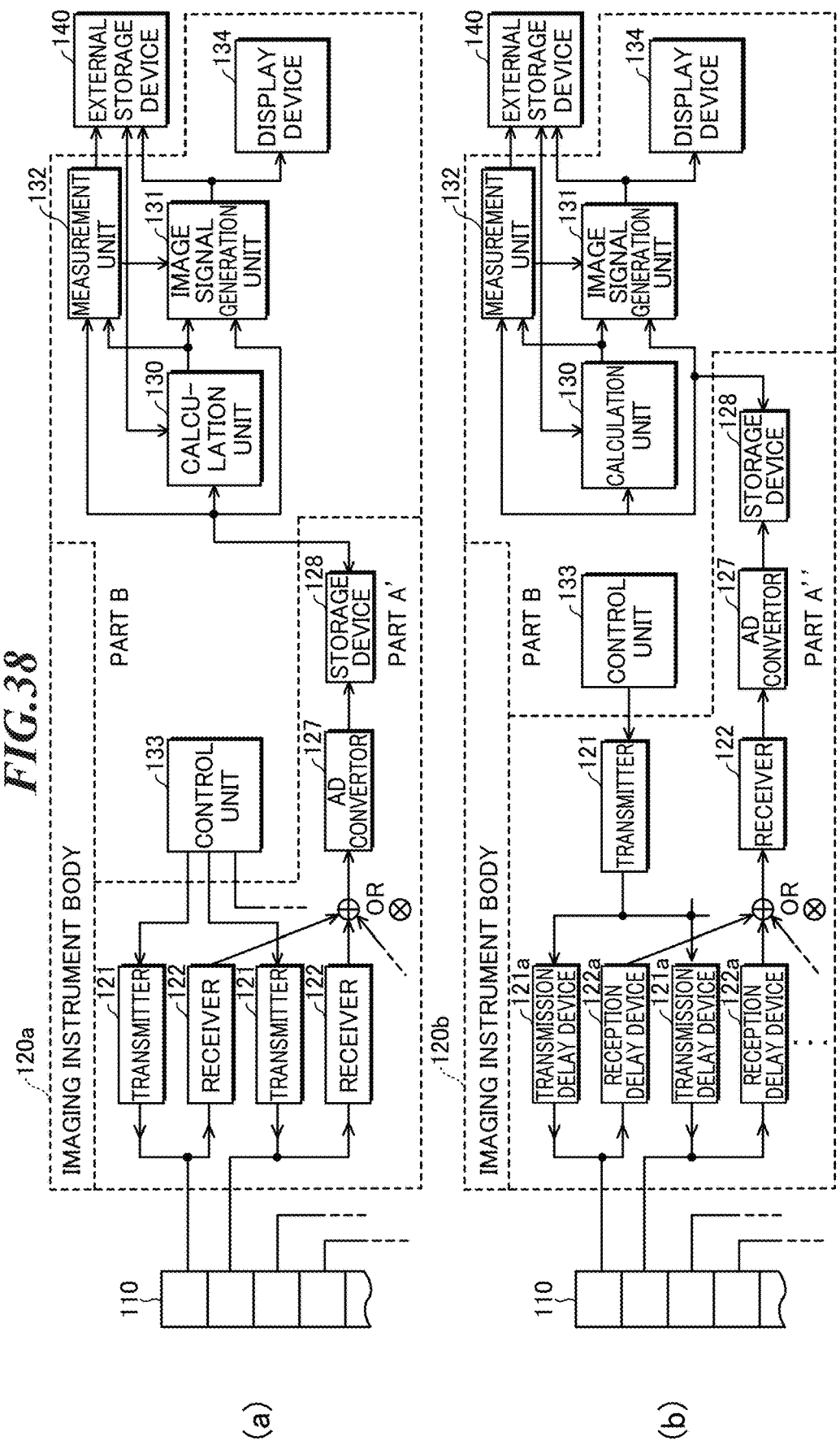
FIG. 38 shows schematic representation (block map) of compositions of a measurement and imaging instrument according to the fourth embodiment of the present invention and the modification.

Next, explained is the 4th embodiment of the present invention. FIG. 38 shows schematic representation (block map) of compositions of imaging instrument according to the fourth embodiment of the present invention and the modifications. The imaging instruments according to the 4th embodiment and the modifications are instruments that generate waves by driving plural transducers 110 or a transducer array or receive waves for performing imagings (FIG. 38 shows a transducer array). As composition elements, the same capabilities as the compositions of the 3rd embodiment can be used.

On the imaging instrument according to the 4th embodiment and shown in FIG. 38(*a*), the plural transducers 110 or the transducer array elements are respectively connected to the plural transmitters 121 and receivers 122 similarly to the cases where the imaging instrument (FIG. 37) according to the 3rd embodiment uses plural transducers 110 or a transducer array. On the imaging instrument body 120*a*, plural transmitters 121 or receivers 122 are set in a part A'.

Analogue reception signals from the plural transducers 110 or the transducer array are phased by using the delay devices in the receiver 122, or analogue reception signals not phased, are summed (linear analogue processing) by the sum processing unit or multiplied (nonlinear analogue processing, Hall effect devices, etc. can be used) by the multiplication processing unit. Thus, the reception beamforming is performed and on the part B, the reception beamformer 129 (FIG. 37) is not required.

Moreover, the reception digital signals obtained via the AD convertor 127 are stored in the storage device 128. The part B of the imaging instrument body 120*a* performs the imaging or the measurement imaging, similarly to the 3rd embodiment, by making the control unit 133 to control the respective units or devices to obtain all the nonlinear effects that are obtainable by the 3rd conduct on the basis of the reception signals. In FIG. 38, wires connections from the control unit 133 to the receiver 122 etc. are omitted.

Also on the 4th embodiment, similarly to the transmitters and receivers of the 3rd embodiment, delays can be added onto the drive signals for the respective transducers or the reception signals and then, the transmission or the reception focusing or steering, etc. can also be performed. Compared with the 3rd embodiment that requires the same number of AD convertors 128 and storage devices 128 as the channel number, on the 4th embodiment, one AD convertor 127 and one storage device 128 are required and then the instrument can be simpler.

Alternatively, on the imaging instrument according to a modification of the 4th embodiment, shown in FIG. 38(b), in the part A" in the imaging instrument body 120b, the transmission delay devices 121a and the reception delay devices 122a are set outside the transmitter 121 and the receiver 122. Being different from in the imaging instrument shown in FIG. 38(a), in the imaging instrument shown in FIG. 38(b), the phasing is performed on the analogue reception signals by the reception delay devices 122a or the phasing is not performed on, and the sum processing unit performs the summing (linear analogue processing) or the multiplication processing unit performs the multiplication (nonlinear analogue processing) and the receiver 122 received the results. Thus, one transmitter 121 and one receiver 122 are required and then, the instrument can be prominently simpler and however, the same nonlinear effects as those of the 3rd embodiment can also be obtained.

The imaging instrument according to the 3rd embodiment shown in FIG. 37, the imaging instrument according to the 4th embodiment shown in FIG. 38(a), the imaging instrument according to the modification of the 4th embodiment shown in FIG. 38(b), other type imaging instruments and their composition elements can also be used simultaneously. For instance, the respective coherent or incoherent image signals, or measurement results obtained by using plural type instruments can also be displayed, or simultaneously they can also be displayed in parallel, or their superpositions or the multiplications can also be displayed. Basically, reception signals of the same time or the same phase can be processed. On one imaging instrument, when plural image signals or measurement results can be obtained using reception signals received at the same time or the same phase, the same processings can also be performed. The signals to be processed is analogue or digital signals after the phasing is performed, the summings and the multiplications are performed by analogue (Hall effect elements, etc. can be used) or digital (calculators or computing units) processing.

The imaging instrument of the 1st or 4th embodiment of the present invention basically implements the nonlinear processings on the signals using analogue calculators of various type devices, digital calculators, computers or devices like these (FPGA or DSP, etc.). As mentioned later in detail, the nonlinear processings are mainly to obtain the effects of exponentiation or multiplication, and the calculations themselves are not limited to these and the calculations can also be high order calculations including other nonlinear properties. Through the polynomial fitting, the spectral analysis, the pulse inversion method, the numerical calculations, or signal processings, etc., such effects can also be extracted or separated. The nonlinear processing can be implemented on not only the signals but also the waves and prior to performing the reception, a wave can also be extracted or separated using wave devices (filters on a time or a space, or their frequencies or spectroscopy, etc.). Exclusive devices can also be used.

As mentioned above, the imaging instrument is equipped with the nonlinear device 111, the nonlinear element 124 or the calculation unit 130 together with the transducer 110 for an arbitrary wave, the transmitter 121 and the receiver 122. If necessary, a data storage device (a memory, a hard disk, a photograph, a CD-RW or other storage media) or a display device, etc. can also be equipped with. The imaging instrument can also be comprised of the respective general devices, which can be realized by building up them. To existing instruments without the nonlinear devices 111, the nonlinear elements 124, the calculation unit 130 or other nonlinear devices, the devices performing the nonlinear processings of the present invention can also be added to perform the nonlinear processings.

The waves transmitted from the transmitter 121 (wave source) or the transducer 110 are a pulse wave, a burst wave or a coded wave (phase-modulated, etc.) and then imaging or measurement can be performed with spatial resolutions. However, if the spatial resolution is not required on the measurement, the waves are not limited to these and a continuous wave can also be used.

The generated waves are determined by the transducer properties of the electric signals (drive signals) to the waves on the transducer 110 and then the device and the drive signals properly designed can be used. For instance, for lights, various light sources (coherent or incoherent, light emitting diode (LED), mixed LED, laser (variable wavelength) or optical oscillator, etc.) can be used and for acoustic waves, an electroacoustic transducer or a vibrator, etc. can be used. For the oscillatory waves, an actuator-based oscillation source can be used and for thermal waves, a thermal source, etc. can be used. Thus, on the present embodiment, transducers 110 that generated various type waves can be used.

For the transducer 110 to be used for processing the above-mentioned respective type waves, representative transducers can be used and also special transducers having nonlinear properties that are not used generally can be used positively. In general, if high voltages are applied to the ultrasound elements, ultrasounds including harmonic waves are generated by the nonlinear phenomena and however, mainly the so-called harmonic imaging using the extractions of nonlinear components generated during the wave propagations in the media is performed. And then, only the fundamental wave can also be performed by filtering out the harmonic wave components.

On the present conduction, such nonlinear waves positively generated can be used. That is, when nonlinear properties can be obtained at the transmissions, the nonlinear properties can be effectively used on the present invention. Alternatively, by generating with no nonlinear components, nonlinear phenomena occurring in the measurement object can also be explored.

When the waves including the nonlinear components, such harmonic waves can also be effected by nonlinear phenomena. When transmitted waves have harmonic waves originally or crossed plural waves (or other wave parameters except for the propagation direction or the steering angle are different such as a frequency or a carrier frequency, a pulse shape, a beam geometry, or frequencies, carrier frequencies or bandwidths in respective directions), as mentioned later, analogue processings such as the pulse inversion method, the temporal or spatial filtering, the spectral filtering, or the polynomial fitting or digital processings such as those corresponding the analogue processings or signal processings, etc. are used to separate the waves and the present invention can also be performed, or the present invention can also be performed under the waves are not separated. Also, using blockers such as obstacles, filter devices or spectroscopies (on a time or a space, or their frequencies) or physical stimuli for changing the refraction of media (optical switch, etc.), etc. during the wave propagation, the receptions of the respective waves separated in advance can also be performed. When it is possible to control the respective wave sources, the respective waves can also be generated independently and the respective observations can be performed.

Also, after generating the waves using the transducer 110, prior to the propagations of waves propagating in the measurement object, by using the devices for directly generating nonlinear phenomena on the waves, waves including the nonlinear components can be propagated into the measurement object. Also, during or after the wave propagations in the measurement object, it is possible to use devices for generating the nonlinear phenomena. By coupling waves or signals or mixing them, etc. can also performed to yield multiplication effects.

For instance, on lights, used can be (i) nonlinear optical elements (for instance, optical harmonic generation device used for the wavelength conversion of laser light to the short wavelength region), (ii) optical mixing devices, (iii) devices for generating optical parametric effects such as optical parametric generation, stimulated Raman scattering, coherent Raman scattering, stimulated Brillouin scattering, stimulated Compton scattering or four wave mixing, etc., (iv) devices for generating multiphoton transitions such as general Raman scattering (spontaneous emission), etc., (v) devices for generating nonlinear refraction index change and (vi) devices for generating electric field dependence refractive index change, etc. Couplers or optical fibers, etc. can also be effectively used. Observations of plural positions (multi-channels) can also be performed and are suited to performing the signal processings.

When using lights, there exists deep relationships with wide areas such as optical electronics, nonlinear optical effects or laser engineering, etc. on the generation, the control or the measurement of lights. The optical devices to be used generally can also be used as the operation devices 112 or nonlinear devices 111, and exclusively developed devices can also be used. For these, an optical amplifier (a photon multitube, etc.), an absorber (an attenuator), a reflector, a mirror, a scatter, a diffraction grating, a collimator (variable focus), a lens, a deflector, a polariscope, a polarizing filter, an ND filter, a polarized beam splitter (a separator), a blocker, an optical waveguide (using photonics crystal, etc.), an optical fiber, an optical Kerr effect device, a nonlinear optical fiber, a mixing optical fiber, a modulation optical fiber, an optical trapping (or confinement) device, an optical memory, a coupler, a directional coupler, a distributor, a mixed distributor, a spectrometer, a dispersion shift optical fiber, a band-pass filter, a phase conjugator (using degenerate four-wave mixing or photorefractive effects, etc.), a switch using optical control of ferroelectric semiconductors, a phase delay device, a phase correction device, a temporal invertor, an optical switch or an encoder using optical masks, etc., etc. can be used solo or together, and not limited to these. Under optical controls (wavelength conversion, switching, routing), an optical node technology, an optical cross connect (OXC), an optical add-drop multiplexer (OADM), an optical multiplexer or separator or an optical switching element are used as well as an optical transmission network or an optical network itself as a device, and optical signal processings can also be performed.

For detectors, a CCD camera, a photodiode, a mixed-type photodiode or a virtual source (as a wave source as well) disclosed in the present invention can also be used. For optical signal processings, a temporal or spatial filter, a correlation calculation, a matched filtering processing, an extracting of signal, a heterodyne or superheterodyne (obtained low frequency signals can be AD converted and can also be demodulated) and homodyne, etc. can be used. Also, electromagnetic wave detectors can also be used.

Particularly for nonlinear media, for instance, there are a great variety of media such as a carbon bisulfide, a sodium vapor, a semiconductor on the basis of silicone, gallium arsenide, etc., a quantum well and an organic dye such as a fluorescein, an erythrosine, etc. On crystals such as a barium titanate, self-pumped four wave mixing can also be used without an externally provided pumped wave.

On visible lights, infrared rays, microwaves or terahertz waves and other waves such as radioactive rays, etc., the respective general devices can also be used and also the exclusive devices can also be used. Not only SAW but also other devices that have relationships between oscillation systems and electromagnetic systems are also useful. Also, nonlinear devices can be used. On thermal transfers, nonlinearities are variously exhibited such as by a synthesis between alumina and zirconium, a solder and a layered cobalt oxide. A heat acts on optical devices and can yield nonlinearities, the applications can also be considered.

For a transducer 110, there are contact and contactless types with respect to the measurement object. It is possible to be required to use impedance matching devices on the respective waves. It is also between the devices in an instrument or an electric circuit as well as in a measurement space. When observing living tissues using ultrasounds, a gel or water, etc. is used as a matching material. On the ultrasonic microscopes, in general, the specimens are observed on the stage and however, an array-type or a mechanical type (an element or an element array is mechanically moved to perform the scan in housing filled with a matching material such as water, etc.) can also be realized and used and then, the setting is simpler with respect to the specimens (the observation direction can be determined freely, etc.), or the developing a handy type can make it possible to be used for performing direct observing of the measurement object in situ or in vivo without cutting and carrying the specimens off (in vitro). Almost the ultrasound microscopes have fixed focusing determined by the used lens and then, particularly such elements or the element array can be used favorably. Thus, the mechanical scanning can be performed in the wave propagation direction as well as the lateral and elevational directions. With respect to the RF waves, antennas are used. And for observing the potential of magnetic field of living tissues, electrolyte gels and electrodes, or SQUID meters can be used. According to the size of measurement object, miniaturized devices can be used (microscopes, etc.). The weak signals can have no nonlinearity, and in the cases, quasi-nonlinearities can be generated, or nonlinearities can be generated virtually. When nonlinear signals are so weak to be observed, the nonlinearities can also be increased.

The nonlinear devices and the transmitter 121 or the transducer 110 can also be installed into one body. Also, the nonlinear devices can be built up respectively and used. Thus, the nonlinear devices can increase the frequency and the bandwidth and can also implement nonlinear processings (calculations) onto the waves themselves by using the nonlinear devices at arbitrary positions as well as onto the reception signals.

Also, when observing waves passively including the cases where the wave sources cannot be controlled, the present invention can be used. The present invention can also be used after obtaining a signal source position or an arrival direction, a signal intensity, a size of wave source or the source distribution using various methods or devices, or the present invention can also be used for obtaining a signal source position or an arrival direction, a signal intensity, a size of wave source or the source distribution. In the cases, a signal source position or an arrival direction, a signal intensity, a size of wave source or the source distribution can be obtained on separated waves or signals; or after obtaining a signal source position or an arrival direction, etc., the waves or signals can also be separated; or both can be performed simultaneously. Obtaining the wave source or the arrival direction increases the accuracy of beamforming. Onto the signals, signal processings such as the analogue or digital processings, etc. can be implemented; and onto the waves, temporal or spatial filters, the frequency filters or spectrometer, etc. can be used.

On using a transducer for receiving waves that propagated in media including the measurement object, the transducer used for the wave transmission can also be used for the reception (The reflection signals are observed). Alternatively, the reception transducer can also be different from a transmission transducer. In the cases, the transmission transducer and the reception transducer can have neighboring positions (for instance, a case where reflected waves are observed) or different (far) positions (for instance, transmission or refraction waves, etc. are observed).

The transducer 110 can have a single aperture; or the plural transducers 110 can be used in an array fashion (1D, 2D or 3D array) with densely and adjacently positioned, in a sparse array fashion or in a far positioned fashion simultaneously. The geometries of the apertures are various (a circular, a rectangular, a flat, a concave and a convex) and accordingly, the directivities of the apertures are also various. Every element can also have plural apertures facing different directions in a body and then at every position, the plural directivities can be obtained. Not only scalar measurements such as potentials or pressures, or temperatures, etc. but also vector measurements such as magnetic waves or electric waves can also be performed. Polarization can also be performed. Off course, element materials or structures are various with respect to one wave. Also, the configurations using them are also various and for instance, there exists one having plural apertures facing to different directions, etc.

FIG. 39 shows illustrations of configurations of plural transducers. FIG. 39(a1) shows plural transducers 110 arrayed densely in a 1D array state; FIG. 39(b1) shows plural transducers 110 arrayed sparsely in a 1D array state; FIG. 39(a2) shows plural transducers 110 arrayed densely in a 2D array state; FIG. 39(b2) shows plural transducers 110 arrayed sparsely in a 2D array state; FIG. 39(a3) shows plural transducers 110 arrayed densely in a 3D array state; FIG. 39(b3) shows plural transducers 110 arrayed sparsely in a 3D array state.

By using lens, etc. at the part of the transducer aperture, a beam can be generated or controlled in an analogue fashion. Using the drive signals mentioned above can also control beams. Also, the imaging instrument according to the present embodiment can be equipped with a mechanical scanning device having 6 freedoms at a maximum (rigid motions in three directions and rotations in three directions) and then, the mechanical scanning device mechanically can also move at least one transducer 110 or at least one transducer array at least in one direction to perform the scanning, controlling the focus positions or steerings with respect to the measurement object 1.

Alternatively, when using plural transducers 110, the same number of channels of transmitters 121 as that of the transducers 110 are equipped with to generate the same number of drive signals as that of the transducer 110 to be driven. Or, using delay elements, plural drive signals can also be generated from a limited number of generated signals to perform desired beamformings (with a desired focus position or a desired steering direction).

Also, general analogue or digital beamformer can also be used. By performing the above-mentioned beamformings (including only reception beamformings) in a parallel fashion, the real-time processings of the scanning the measurement object can also be improved.

Also, by driving the plural transducers 110 at the same time, the plural beamformings can also be performed simultaneously. Or, there are cases where the transmitters 121 are switched and used and within the time allowed to receive the signals of the same phase of the measurement object, using different transducers 110 at different times can also be used for performing plural beamformings. Using the same transducer to be used for mechanical scanning can also make it possible to perform the plural beamformings.

On the respective beamformings including the cases where the mechanical scan is performed, the classical SA can also be performed, in which a general delay-and-summation (DAS) processing or the delay-and-multiplication (DAM) processing on the basis of the present invention can be performed (both processing can be realized in monostatic and multistatic types). For the transmissions, with no focusings, plane waves can also be generated. In the cases, a large region can also be observed at once in a short time. At the times, the plane waves can also be steered. Waves can also be received as plane waves and also dynamic focused (When performing transmission focusing, the receptions should also perform the steerings). The respective plane waves are narrow band in the directions orthogonal to the propagation direction and then, increasing the bandwidths is effective.

FIG. 40 shows figures that explain various wave formations obtained using 1D transducer array. On FIG. 40, (a) shows a focusing of wave and at respective transmission and reception, a wave beam with a focus position determined by delay times are formed; (b) shows a steering of wave and the respective transmission and reception, a steered wave beam with a steering direction determined by delay times are formed; (c) shows a transmission or reception of plane wave and the plane wave steered to the direction determined by delay times are formed. The plane wave is narrow band in the direction orthogonal to the propagation direction and then, increasing the bandwidths is effective.

Prior to performing the reception by the transducer 110, by letting the plural waves pass through at least one of the analogue delay device and the analogue storage device such that the plural waves can be superposed at respective positions in the measurement object 1. Also, after performing the reception by the transducer 110, by letting the plural waves pass through at least one of the analogue delay device and the analogue storage device, or after performing digital sampling of the received signals, by implementing digital delays onto the sampled digital signals via digital processings or by passing the digital signals into the digital storage device such that the plural waves can be superposed at respective positions in the measurement object 1. The so-called phase aberration correction can be performed in the above-mentioned fashion or in conjunction with the phasing in the above-mentioned beamformings as well. There are various devices, for instance for lights, an optical fiber can also become a delay line; and an optical trapping (or confinement) device can also become a delay device or a storage device.

Alternatively, with respect to the measurement object, as the results of the waves propagating in the measurement object, the signals effected by nonlinear effects can also be observed or inversely, nonlinear components cannot be obtained. In general, when the intensity of a wave is strong, the nonlinear phenomena can be observed well whereas when the intensity is weak, the nonlinear phenomena cannot be observed well. For both cases, the present invention can be performed. The reception signals can also be processed by the present invention after separating the signals via proper signal processings, etc.

For the signal separations, analogue devices of various type waves (temporal or spatial filter, their frequency filters, or spectroscopies) can also be used or on the basis of the signal processings, the analogue or digital processings can also be performed (the above-mentioned decoding processing with respect to the coding processing, calculations of the 1st moments of spectra via spectral analysis, calculations of the instantaneous frequencies using calculated analytic signals, MIMO, SIMO, MUSIC or independent signal separation processing, etc.). In the passive cases, the present invention can also be used after obtaining a signal source position or an arrival direction, a signal intensity, a size of wave source or the source distribution using various methods or devices, or after using the present invention, a signal source position or an arrival direction can also be obtained. Or, simultaneously with the beamformings, a signal source position or an arrival direction, a signal intensity, a size of wave source or the source distribution can also be obtained. As mentioned later, after expressing the target waves with harmonic waves, etc. via nonlinear processings, the signal separations can also be accurately performed. Concretely, by performing the exponentiation calculations, after increasing frequencies and bandwidths (when the orders are larger than 1) and decreasing frequencies and bandwidths (when the orders are smaller than 1), the processing can be performed in a frequency domain with a high accuracy. The restorations of the separated signals can be simply performed using the exponentiation calculations with the reciprocals of the used orders.

FIG. 41 shows illustrations of a beam direction, an angle of a direction of arriving wave (arrival direction) and the first moments of spectra in spatial and frequency domains in a 2D measurement case. In FIG. 41, (a) shows for a position of interest (x,y) in a spatial domain, the direction angles of beams 1 and 2 are expressed by $\theta_1$ and $\theta_2$. (b) shows in a frequency domain, the 1st moments of spectra of beams 1 and 2, and the instantaneous frequencies (fx,fy) In the present invention, a vector comprising of the instantaneous frequencies or the 1st moments of local or global spectra in the independent frequency axes can be used as an instantaneous frequency vector or a 1st moment frequency vector and in the 3D case, expressed as (fx,fy,fz). In a spatial domain, the wave signals are expressed in the 2D or 3D Cartesian orthogonal coordinate system, polar coordinate system, or orthogonal curvilinear coordinate system and then, the spectra calculated by the Fourier transform in the respective orthogonal coordinate system are expressed, in the frequency domain, in the Cartesian orthogonal coordinate system, polar coordinate system, or orthogonal curvilinear coordinate system comprising of the frequency coordinates corresponding to the spatial coordinates. Thus, the instantaneous frequencies or the 1st moment frequency vector to be used are expressed in the respective frequency coordinates. The Fourier transform or the inverse Fourier Transform via the Jacobi operation described in the paragraph 0405 allows changing the orthogonal coordinate systems in spatial and frequency domains. It is useful for various measurements and imagings to change the coordinate system in a same domain with no approximate interpolations (being highly accurate). As described at other parts, in addition to the arrival direction of a wave, the direction or the position of an existing wave source, the propagation direction of a generated wave or beam, the steering angle of a transmission and/or reception, etc. can be calculated. The beams 1 and 2 can also correspond to waves of grating or side lobes. As the methods for measuring a displacement vector or a displacement, the multi-dimensional cross-spectrum phase gradient method, the multi-dimensional cross-correlation method, the multi-dimensional autocorrelation method, the multi-dimensional Doppler method, or the 1D versions are useful. Except for using the cross-correlation method, when performing the Fourier transform for calculating spectra or the inverse Fourier transform for calculating analytic signals, the Jacobi operation can be used for changing the coordinate system and the measurement results can be obtained in the coordinate system. When using the cross-correlation method, the coordinate system can be changed using the above-described method using the Jacobi operation and the measurement results can be obtained.

Here, when an element pitch of an array-type sensor is coarse, the reception signals with an aliasing in the direction of the element array direction (originally, a digital domain) can be used for the beamforming, the signal components of the aliased bandwidth or bandwidths should be filtering out from the angular spectra of raw reception signals or the signals obtained after the beamforming. By shortening the element pitch by making the element width small as mentioned above, the lateral bandwidth increases, which can be confirmed from the angular spectra. By this, a laterally large bandwidth signals can be generated by a beamforming and however, if the aliasing occurs, the similar processing is required. These processings are required for all beamforming processings. Since the beamformed signals can be generated within the signal bandwidth of angular spectra of raw reception signals, it is possible to confirm the maximum steering angle to be generated using the element array.

Basically, beamformings are performed on waves in an analogue fashion or when using plural transducers 110, beamformings (focusing or steering) are performed. As mentioned above, after performing the signal separations, the beamformings can be performed and also after performing the beamformings, the signal separations can also be performed.

Also, when performing the SA, from the same reception signal set, plural focused signals with plural different focus positions or plural steered signals with plural different steering angles can be generated (Delay-and-summation or the delay-and-multiplications on the basis of the present invention). The present invention can also be implemented on the generated signals. The transmitter 121 and the receiver 122 can be installed into a body or not (a separated type).

As the nonlinear elements 124, there are various elements. For the electric analogue signals after receiving by the transducer 110, a diode or a resistor can be used. Any nonlinear elements used in circuits, leading nonlinear phenomena to signals including applications of superconducting phenomena, etc., can also be used. Also, nonlinear elements for distributed parameter system can also be used. According to the frequencies of waves (signals), proper elements are used. Using various type amplifiers, the gains of waves or signals can also be controlled properly.

Prior to performing the receiving using the transducer 110, nonlinear processings (calculations) can also be performed by using the nonlinear devices for directly generating nonlinear phenomena on the waves. For instance, on lights, used can be (i) nonlinear optical elements, (ii) optical mixing devices, (iii) optical parametric effects, (iv) multiphoton transitions such as general Raman scattering (spontaneous emission Raman scattering), etc., (v) nonlinear refraction index change and (vi) electric field dependence refractive index change, etc. The nonlinear devices and the transducer 110 can also be installed into a body and also the nonlinear devices can be built up respectively and used. Also, nonlinear phenomena occurring at the conversion from a wave to electric signal by the transducer 110 (i.e., at the reception of the wave) can also be used.

In all the above cases, the analogue nonlinear processing can be performed onto the waves themselves or signals after receptions, whereas after AD conversions of signals, nonlinear processings can also be performed on signals using the digital processings or calculators, or devices like these (FPGA or DSP, etc.).

Regarding the imaging instrument according to an embodiment of the present invention, when calling the instrument as an analogue type, the processings are performed by analogue processings as mentioned above. And then, for instance, analogue signals effected by the nonlinear phenomena can be displayed using display devices such as a Braun tube display or an oscilloscope (an analogue or digital one), etc. If required, the signals are recorded by storage media such as a photograph (an analogue or digital one) or a holography, etc. Or, the signals are digitized via AD conversions and if required, the signals can be recorded by digital data storage media such as a memory, a hard disk or a CD-RW, etc. and can also be displayed using display devices.

Alternatively, when calling the instrument as a digital type, the analogue signals are AD converted after proper analogue processings (gain control or filtering) and there also exists the cases where the digitized signals are stored into storage media such as a memory or a hard disk, etc., and the digital nonlinear calculation processings are performed on the digital signals. And if required, the data are stored into data storage devices (the above-mentioned photograph or digital storage media, etc.) and displayed on display devices.

On the above-mentioned compositions, in the cases where the effects of nonlinear phenomena occurred in the measurement object are included in the reception signals, the above-mentioned analogue or digital instrument can also be used for increasing the nonlinear effects, whereas in the cases where the effects are not included in the reception signals, the instrument can newly generate, imitate or virtually realize nonlinear effects. Also, separations of the nonlinear effects (harmonic wave components) occurred in the measurement object, the nonlinear components generated by signal sources (harmonic wave components) and effects of nonlinear processings can also be performed. Exceptionally, including the cases where the nonlinear processings are not performed, the above-mentioned devices or signal processings can be used to separate the preceding two nonlinear effects (nonlinear components).

On the above explanations about the imaging instrument, the cases where transducers for waves to be observed are used are mentioned. However, for instance, the propagations of vibration waves can also be observed optically on the basis of the laser Doppler or the optical image processings and also the propagation of a shear wave that is a dominant low frequency vibration wave in human tissues can be observed using a same vibration, i.e., the ultrasound Doppler effect The propagations of the audible sound or the ultrasound, etc. can also be captured optically. The optical processing means the processings of generally called electromagnetic waves and then, radioactive rays such as an X-ray are also included. The audible sound can also be observed using an ultrasound. Regarding thermal waves, an infrared camera on the basis of a radiation, a microwave, a terahertz wave, an ultrasound using changes in a sound speed or a volume, a nuclear magnetic resonance using a chemical shift or an optical fiber, etc. can be used to achieve the observations. The observations are enabled by the coherent signal processings or by the incoherent processings such as image processings, etc. The case examples about the observations of waves of interest using other waves are not limited to these, and the measurement results are analogue or digital signals in any case. Thus, the present invention can also be implemented onto the observed waves (signals). In addition to the Doppler effects, it can be grasped that the physical properties of media are modulated by the target waves and then, the waves to be used for sensing the target waves are modulated. On these, the detection processings for waves to be effected by the Doppler effects or the modulations are effective. Particularly, on the uses of electromagnetic waves, the polarization can be used to simply observe waves propagating in various directions and also to simply capture the structures with various directions. Alternatively, as mentioned in the document of the present invention, acoustic waves can also allow various measurements on the basis of the divergence. The radiation measurement is also important. Using the microwaves, in addition to the temperature distribution measurement, various remote sensing can be performed, for instance, measuring scatterings or attenuations allows the measurements of distributions of raindrops or moistures, atmospheric pressures, etc. In this situation, performing the beamformings mentioned in the document of the present invention and various other processings are effective for generating high spatial resolutions and particularly for observing the desired positions with high speeds. The effects such as a directness and a high speediness in observing arbitrary surfaces or regions and spaces regardless the image processings after generating images.

On the above explanations about the imaging instrument, mentioned are nonlinear processing devices of electromagnetic waves, vibrations including acoustic waves, thermal waves or the corresponding signals. However, it is also possible to increase, imitate and virtually realize nonlinear effects between different kind (type) physical energies (i.e., in addition to cases where nonlinear effects are generated physically, chemically, or biologically, cases where nonlinear effects cannot be generated are included) and in the cases, the present invention can also be performed by that devices regarding the plural kind (type) waves to be processed are simultaneously used to receive the waves or at the same phase of the measurement object, the waves can be received at different times. That is, it is possible for the present invention to process the cases where plural kind (type) waves are generated simultaneously as well as the cases single kind (type) waves are generated solo.

On the respective electromagnetic waves, vibrations including acoustic waves and thermal waves, the waves with different frequencies exhibit different dominant behaviors being dependent on the respective measurement objects (media) and then, the names are different. In this situation, the waves can also be considered to be different types. For instance, on the electromagnetic waves, there are a microwave, a terahertz wave, a radioactive ray such as an X-ray, etc. and on the vibration waves, for instance, in human soft tissues, a shear wave cannot propagate as a wave in a Mega Hertz bandwidth and an ultrasound is dominant, whereas a property of an incompressibility is intense and a shear wave is dominant in a low frequency range such as 100 Hz, etc.

The present invention increases, imitates and virtually realizes nonlinear effects between such waves that exhibit different behaviors. In the cases, the present invention can also be performed by that devices regarding the plural kind (type) waves to be processed are simultaneously used to receive the waves or at the same phase of the measurement object, the waves can be received at different times. Off course, since the phenomena such as attenuations, scatterings, reflections, refractions, diffractions, etc. have variances, there is a limitation that the waves must be properly used with considerations about the SNRs of reception signals. However, since high frequency components, which cannot be physically generated or captured, can be generated, the application range of the present invention is prominently broad.

Investigating the nonlinear effects occurring in the measurement object can also be performed by switching the uses of cases where the observation of the nonlinear effects occurring in the measurement object is positively performed and the implementing of the present invention is performed; or by using both cases simultaneously and by using the nonlinear processing or calculations positively.

Next, using the above-mentioned compositions of the imaging instrument, one embodiment that the present invention is applied to ultrasound echo signals is explained. The generation of harmonic waves during the ultrasound propagations can be expressed by the multiplication or the exponentiation. Particularly, the chord and different tone waves are expressed by the multiplications between the waves with different propagation directions or frequencies (nonpatent document 27), whereas in general, the harmonic tone waves are expressed by the exponentiations of the same frequency waves (nonpatent document 25). As physical phenomena, when the wave intensity is large, the phenomena occur well. Also, there are effects that for high intensity wave components, the wave components' distortions become larger with increasing the propagation distance and however, being more suffered from the attenuations than the fundamental waves during the propagations. Alternatively, when the waves' intensities are not so large, as an interference of the waves, only the superpositions (summations and subtractions) can be observed well. The application of the interference is the lateral modulation previously developed by the inventor of the present invention (nonpatent documents 13 and 30 etc.).

Figure 42:
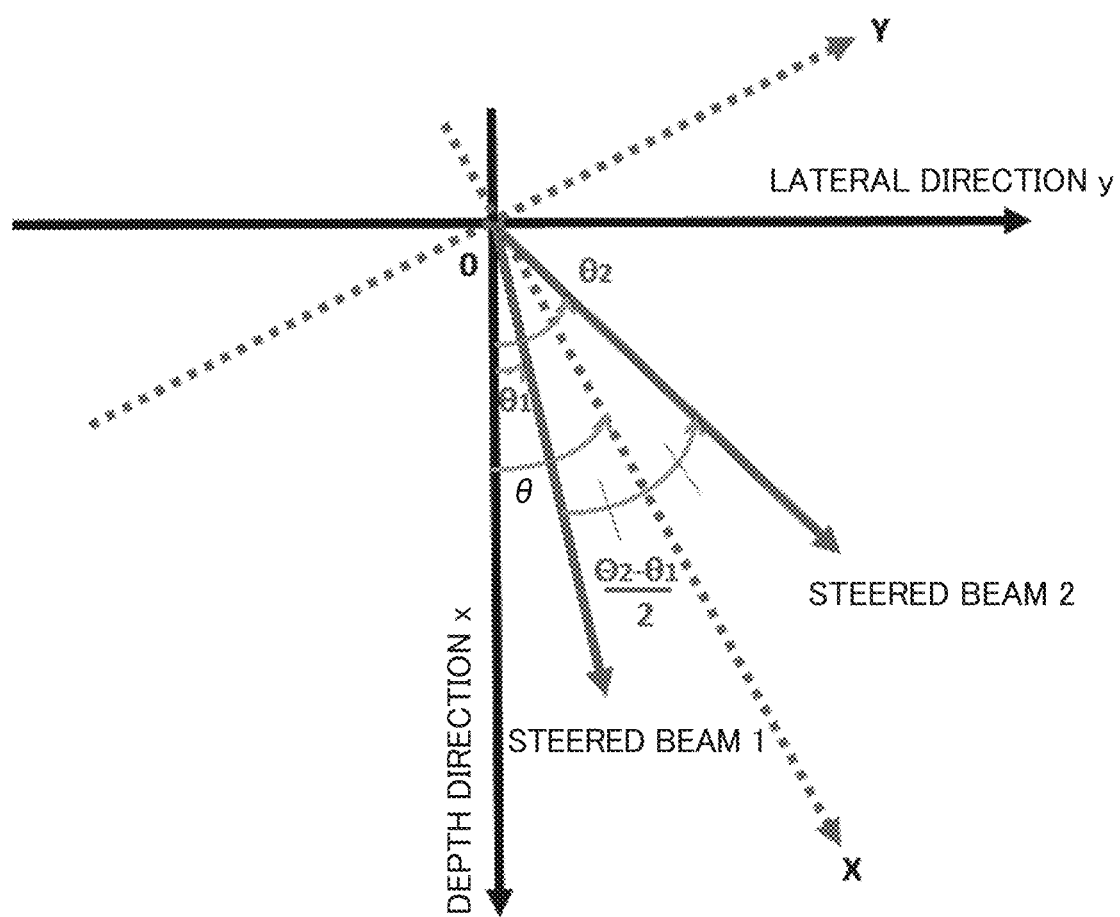
FIG. 42 shows an illustration for the lateral modulation, of two steered beams in a 2D spatial domain.

FIG. 42 shows an illustration for the lateral modulation, of two steered beams in a 2D spatial domain. In FIG. 42, the horizontal and vertical axes respectively show the lateral and axial positions y and x. Here, as representative examples, in two cases where the beamforming is performed in an arbitrary direction (the direction of angle θ in the figure) and the lateral modulation is performed with respect to an arbitrary direction as an axis (X-axis), respectively, the effects of nonlinear processings performed after the reception beamformings are confirmed. The calculations can be extended to a 3D case simply and also it is possible to confirm that the same effects can be obtained in a 3D space. Below, λ is a wavelength corresponding to the 1st moment of an ultrasound. The distances in the depth and lateral directions x and y respectively express the distances between the origin, where the ultrasound is transmitted, and an arbitrary position, where the ultrasound is reflected, i.e., if the time t is required for the round trip, the distance of the ultrasound propagation generated during the time t/2.

<0> Lateral Modulation: Superposition of Two Beams or Waves (Plane Waves, Etc.) with Steering Angles $\theta_1$ and $\theta_2$ (Simultaneous Transmissions and Receptions or Superposition of the Respective Transmissions and Receptions).

The superposition (addition, i.e., summation) of two RF echo signals having a same carrier frequency, a same instantaneous frequency, a local or global 1st moment of spectra is expressed as the next equation.

$$A(x,y)\cos[2\pi(2/\lambda)(x\cos\theta_1+y\sin\theta_1)]+A'(x,y)\cos[2\pi(2/\lambda)(x\cos\theta_2+y\sin\theta_2)] \quad (50')$$

Here, assuming $A(x,y)=A'(x,y)$ (i.e., the reflections and scatterings of two waves are equal), the superposition of the two RF echos can be expressed by the next equation on the coordinate system (X,Y), of which X-axis expresses the central direction between the propagation directions of the two waves and Y-axis expresses the direction orthogonal to X-axis.

$$A(x,y)\cos\{2\pi(2/\lambda)\cos[(1/2)(\theta_2-\theta_1)]X\}\times\cos\{2\pi(2/\lambda)\sin[(1/2)(\theta_2-\theta_1)]Y\} \quad (50)$$

Thus, on the coordinate (X,Y), the lateral modulation is realized. To generate independent frequencies in the orthogonal X and Y directions for the lateral modulation, two waves having a same carrier frequency, a same instantaneous frequency, a local or global 1st moment of spectra are required to be generated. However, for the displacement vector measurement, the two waves can also have different frequencies. For instance, in below <2> and <3>, nonlinear processing is implemented onto the lateral modulation. In a 3D space, there are two directions to be laterally modulated and then, at least three crossed beams are required to be generated similarly (nonpatent documents 13 and 30).

<1> Exponentiation Calculation of One Beam or One Wave Steered in One Direction (Steering Angle, θ)

The RF echo signal is expressed as the next equation.

$$A(x,y)\cos[2\pi(2/\lambda)(x\cos\theta+y\sin\theta)]$$

In this case, for instance, the 2nd order exponentiation (2nd power) of the RF echo can be expressed as the next equation (51).

$$(1/2)A^2(x,y)\times\{1+\cos[2\pi(2\cdot 2/\lambda)(x\cos\theta+y\sin\theta)]\} \quad (51)$$

Thus, the 2nd harmonic wave component can be simultaneously generated with the direct current component and therefore, a base-banded signal can also be obtained simultaneously (The envelope signal can also be directly obtained). The calculated squared echo signal has spectra with a wider bandwidth than the basic signal owing to the multiplication effects between the signals with different frequencies within the basic signal bandwidth; yielding high spatial resolutions both in the wave propagation direction and the direction orthogonal to the propagation direction by generating a shorter pulse length and a narrower beam width.

As a simpler example, for instance, when an RF echo signal has two frequency $f_1$ and $f_2$ components at a depth position x, the squared signal obtained by the square calculation can be expressed as the next equation.

$$e_I(x;f_1,f_2)^2=e_{II}(x;0,2f_1,2f_2,f_1+f_2,f_1-f_2)$$

Thus, the squared signal had a direct current (frequency zero) and frequency $2f_1$, $2f_2$, $f_1+f_2$ and $f_1-f_2$ components.

That is, if the wave has different frequency signal components, the signals generated by the exponentiation calculations (processings) have wider bandwidths in the directions, in which the wave has the different frequency components, than the reception wave to be received when the nonlinear processings are not implemented; and a generated harmonic wave obtains at least one of effects such as increasing in frequencies, increasing in spatial resolutions, decreasing in sidelobes, increasing in contrasts with respect to the reception wave to be received when the nonlinear processings are not implemented; and a signal generated in a bandwidth including a direct current (a base-banded signal) is a signal obtained by implementing approximate quadrature detection onto the generated harmonic wave; and at least on the basis of one of signals generated by the nonlinear processing, the corresponding wave can be imaged.

Performing the higher order exponentiation calculations (processings), for instance, n-order (n>2), yields the n-fold high frequency signal components and the higher spatial resolutions. Also, strictly, the generated base-banded signal is different from the results of quadrature detection of the 2nd harmonic wave (the general base-band signal) since the generated base-banded signal has a generated pure direct current. Then, if the detection processing is not implemented on the 2nd harmonic signal, a higher spatial resolution image can also be obtained than the original echo image. The direct current generated by the nonlinear processing can be calculated by the intensities of high frequency wave, low frequency wave or harmonic wave, etc. generated simultaneously and basically, the direct current components to be filled in the base-banded signal are removed. Occasionally, when omitting the calculations, all the direct current components can also be removed. By performing the processings, without performing the brightness control to be dependent on the depth, the imaging can be performed with respect to the deeper position than the imaging including the direct current components.

The harmonic wave signals or low frequency signals are expressed in various fashions (four arithmetic operations about sine wave or cosine wave, etc.) on the basis of the double angle or the arcminute theorem, if required, the calculations can be performed via the digital Hilbert transform (nonpatent document 13). The actual measured harmonic waves can also be processed. These are calculated nonlinear signals at respective positions with respect to arbitrary intensity waves and differs from the nonlinear components physically accumulated and effected by the attenuations during the propagations, which realizes new harmonic wave or low frequency imagings.

<2> Exponentiation Calculation of Lateral Modulation Echo Signal

For instance, the square of eq. (50) is expressed by the next eq. (52).

$$A(x,y)^2 \times \cos^2\{2\pi(2/\lambda)\cos[(1/2)(\theta_2-\theta_1)]X\} \times \cos^2\{2\pi(2/\lambda)\sin[(1/2)(\theta_2-\theta_1)]Y\} = A(x,y)^2 \times [1+\cos\{2\pi(2\cdot 2/\lambda)\cos[(1/2)(\theta_2-\theta_1)]X\} + \cos\{2\pi(2\cdot 2/\lambda)\sin[(1/2)(\theta_2-\theta_1)]Y\} + \cos\{2\pi(2\cdot 2/\lambda)\cos[(1/2)(\theta_2-\theta_1)]X\} \times \cos\{2\pi(2\cdot 2/\lambda)\sin[(1/2)(\theta_2-\theta_1)]Y\}] \quad (52)$$

Thus, obtained can be a direct current (corresponding to the above-mentioned base-banded signal), the two signals of the 2nd harmonic waves detected in different one direction, and the signal of the 2nd harmonic waves' lateral modulation. Similarly to <1>, increasing in a spatial resolution is performed. The base-banded signal or other high order harmonic wave signals can also be calculated similarly to <1>.

As a simpler example, for instance, when crossed echo signals at a position (x,y) are respectively expressed as $e_1((x,y); (f_0,f_1))$ and $e_2((x,y); (f_0,f_2))$ and are symmetric in the y direction, the squared signal of the superposition can be expressed as the next equation.

$$[e_1((x,y);(f_0,f_1))+e_2((x,y);(f_0,f_2))]^2 = e_1((x,y);(f_0,f_1))^2 + 2e_1((x,y);(f_0,f_1))e_2((x,y);(f_0,f_2))+e_2((x,y);(f_0,f_2))^2 = e_{1'}((x,y);(0,0),(2f_0,2f_1))+e_{12'}((x,y);(2f_0,0),(0,2f_1),(0,2f_2))+e_{2'}((x,y);(0,0),(2f_0,2f_2))$$

Thus, it can be grasped that the squared signal of the superposition has frequency (0,0), $(2f_0,2f_1)$, $(2f_0,2f_2)$, $(2f_0, 0)$, $(0,2f_1)$ and $(0,2f_2)$ components.

That is, the signals generated by the exponentiation calculation are the harmonic wave signals of the respective signals to be linearly superposed (corresponding to the crossed waves) and base-banded signals (having bandwidths at least including direct currents in one direction), and if the wave has different frequency signal components, the signals generated by the exponentiation calculations (processings) have wider bandwidths in the directions, in which the wave has the different frequency components, than the reception wave to be received when the nonlinear processings are not implemented; and the generated harmonic waves obtain at least one of effects such as increasing in frequencies, increasing in spatial resolutions, decreasing in sidelobes, increasing in contrasts with respect to the corresponding waves to be received when the nonlinear processings are not implemented; the and base-banded signals are signals obtained by implementing the quadrature detection or approximate quadrature detection onto the generated harmonic waves in the respective directions or plural directions; and at least on the basis of one of signals generated by the nonlinear processing, the corresponding wave can be imaged. When the crossed waves or beams have different frequencies or are not symmetric with respect to the axis, the exponentiation processings yield the chord and different tone waves in a multi-dimensional space and similarly, the generated signals can be used for the imaging or measurements. When other parameters are different on plural waves used, they can also act on the nonlinear processing results.

As mentioned above, in a 3D space, the lateral modulation requires the generations of three crossed beams at least and in the cases, the obtained base-banded signals are a signal of the approximately quadrature-detected harmonic waves of the respective beams (a signal having a direct current) and signals of the harmonic waves quadrature-detected in arbitrary one or two directions. That is, since with respect to an axis (or an area) set with respect to the two beams such that the two beams become symmetric, the polarities of the frequencies in the symmetric direction is inverse, the addition is zero. All the waves or beams can also be generated symmetrically with respect to the coordinate axes and however, not limited to the case. The frequencies or other parameters can also be different on the plural beams or waves.

<3> Multiplication Calculation of Lateral Modulation Echo Signals

For instance, since the two waves expressed in eq. (0') can be used separately and on the consideration about the multiplication, to hold a simplified equation, let the propagation directions equal two directions symmetric with respect to the x axis, i.e., $\theta_1=-\theta_2$. In the case, the multiplication (production) of the two RF echo signals can be expressed by the next eq. (53).

$$A(x,y)\cos[2\pi(2/\lambda)(x\cos\theta_1+y\sin\theta_1)] \times A'(x,y)\cos[2\pi(2/\lambda)(x\cos\theta_1-y\sin\theta_1)] = A(x,y)A'(x,y) \times \{\cos[2\pi(2\cdot 2/\lambda)\cos\theta_1 x]+\cos[2\pi(2\cdot 2/\lambda)\sin\theta_1 y]\} \quad (53)$$

Thus, the two signals of the 2nd harmonic waves detected in different one direction can be obtained. These signals are the same signal components as those obtained in eq. (52).

As a simpler example, when crossed echo signals at a position (x,y) are respectively expressed as $e_1((x,y);(f_0,f_1))$ and $e_2((x,y);(f_0,f_2))$ and are symmetric in the y direction, the multiplication of the signals can be expressed as the next equation.

$$e_1((x,y);(f_0,f_1)) \times e_2((x,y);(f_0,f_2)) = e_{12}'((x,y);(2f_0,0),(0,2f_1),(0,2f_2))$$

Thus, it can be grasped that the multiplication of the signals has frequency $(2f_0,0)$, $(0,2f_1)$ and $(0, 2f_2)$ components.

That is, the signals generated by the multiplication calculation are base-banded signals (having bandwidths at least including direct currents in one direction) correspondingly obtained from the respective signals to be linearly superposed (corresponding to the crossed waves), and if the wave has different frequency signal components, the signals generated by the multiplication calculations (processings) have wider bandwidths in the directions, in which the wave has the different frequency components, than the reception wave to be received when the nonlinear processings are not implemented; and the base-banded signals are signals obtained by implementing the quadrature detection onto the harmonic waves in the respective directions or plural directions, of which harmonic waves will obtain at least one of effects such as increasing in frequencies, increasing in spatial resolutions, decreasing in sidelobes, increasing in contrasts with respect to the respective waves to be received when the nonlinear processings are not implemented; and at least on the basis of one of signals generated by the nonlinear processing, the corresponding wave can be imaged. When the crossed waves or beams have different frequencies or are not symmetric with respect to the axis, the exponentiation processings yield the chord and different tone waves in a multi-dimensional space and similarly, the generated signals can be used for the imaging or measurements. When other parameters are different on plural waves used, they can also act on the nonlinear processing results.

As mentioned above, in a 3D space, the lateral modulation requires the generations of three crossed beams at least and in the cases, the obtained base-banded signals are signals of the harmonic waves quadrature-detected in arbitrary one or two directions. That is, since with respect to an axis (or an area) set with respect to the two beams such that the two beams become symmetric, the polarities of the frequencies in the symmetric direction is inverse, the addition is zero. All the waves or beams can also be generated symmetrically with respect to the coordinate axes and however, not limited to the case. The frequencies or other parameters can also be different on the plural beams or waves.

Similarly to the above-mentioned crossed beams, in addition to the propagation directions or the steering angles of the respective beams or waves, other parameters can be different, for instance, the frequency or the carrier frequency, the pulse geometry, the beam geometry, the frequencies, the carrier frequencies or the bandwidths in the respective directions. Also, being different from the cases where for performing the lateral modulations, two and four (can be three) crossed waves or beams are respectively generated in 2D and 3D cases, more waves or beams can be used in the respective dimensions. Particularly, performing the transmissions of plane waves, cylindrical waves or spherical waves allows high-speed transmissions and receptions and then, such using of plural waves can achieve beamformings with higher speeds than the general imaging. Also, since when using focusing beams, the superposed reception signals can also be processed by the high-speed beamformings using the FFT, particularly included when performing the simultaneous transmissions of plural beams, the high-speed processing can be performed similarly (as mentioned above, on the wavenumber matching, approximate interpolations can also be performed). For stabilizing the nonlinear processings, it is also effective to superpose (additional averaging) the plural transmissions and receptions performed under using the same parameters. The above-mentioned same processings can also be implemented on the reception signals obtained when performing the so-called pulse inversion transmissions, specifically, the same processings can be implemented onto the harmonic wave obtained by superposing the reception signals received by the pulse transmissions with different polarities; or the same processings can be implemented onto the respective reception signals prior to performing the superposition. These superpositions (i.e., additions) yield harmonic waves with a frequency being even number times of the frequency of the fundamental wave and instead of the additions, performing the subtractions yield harmonic waves with a frequency being odd number times of the frequency of the fundamental wave. It is also important to use these harmonic waves for imagings (Even the simple subtraction on the reception signals with the pulse inversion transmissions yields the 3rd harmonic wave mainly). When superposition of harmonic wave signals is obtained using the present invention with respect to the reception signals band-limited by the transducer's bandwidth or by implementing an analogue or digital filter onto, the harmonic waves can be separated by using filterings (analogue or digital), or by performing signal processings (analogue or digital) using various superpositions or the basic signal. Also, not using a pulse inversion method, signals with phase differences except for 180 degree can be transmitted and, in such cases, these processings can be performed. Summarizing, on beams or waves with at least one different parameter, when the beams or waves are being superposed, being separated or being not superposed, etc., the same nonlinear effects can also be obtained and can also be used effectively. It can be grasped that waves or beams to be generated by the nonlinear effects as well as the linear effects can be designed (parameters of beams or waves such as a propagation direction, etc.) via theories and calculations and can also be controlled.

The harmonic wave signals, the chord or different tone waves, or harmonic tone waves, etc. generated by these nonlinear processings (calculations) improve the qualities of echo imagings owing to their above-mentioned properties. There are no effects due to the attenuations, which causes effects on the general harmonic imagings. The present invention is also effective for generating nonlinear components at the respective positions virtually or interpreting the nonlinear signals physically generated. Also, the present invention is effective for non-observable cases due to the weak intensities of the waves. Furthermore, on a displacement measurement, the increasing frequency is received enthusiastically because the phase rotation speed increases and the displacement measurement accuracy will become high. However, in the below shown phantom experiment, although the spatial resolution improved, only the high spatial resolution measurement tends to increase the measurement noises.

In this situation, the regularization (for instance, non-patent document 18) or the above-mentioned weighted least squares solution method or weighted averaging processing via statistical evaluations becomes effective. For instance, using the general one-directional displacement measurement methods onto the two signals of the 2nd harmonic waves detected in different one direction obtained in processings <2> and <3> allows the measurements of the displacement components in the respective directions. Specifically, for measuring a displacement or a displacement vector generated during the different temporal phases of the measurement object, on the signals with a carrier frequencies in arbitrary one direction, at each position of interest, the instantaneous phase change generated during the temporal phases is divided by the instantaneous frequency, the 1st moment frequency or a nominal frequency, etc. to measure the displacement in the direction; and furthermore on the basis of the measurements of different directions, a displacement vector can be synthesized. At past, it requires more calculations than the autocorrelation method (nonpatent document 13) and however, to make a displacement vector measurement using the general one-directional displacement measurement methods possible, a digital demodulation method for a lateral modulation echo signal is disclosed (calculating the product and conjugate product on analytic signals: nonpatent document 30, etc.). According to the present invention, the lateral modulation echo signal can be demodulated using remarkably fewer memories and calculations and moreover, the obtained signals are harmonic wave signals. For decreasing noises, it is effective when the same waves can be acquired plural times under the same conditions, additional averaging can also be performed on the raw reception signals or the nonlinear-processing-implemented signals after the reception of the raw signals and Or, integration processing, etc. can also be performed on them. Also, instead of the exponentiation or the multiplication, it is also possible to calculate a squared norm or an inner product and, in the cases, the spatial resolution is determined by the signal length to be used for the calculations. These methods can also be effective for imagings, etc. except for of the displacement measurements.

The inventor of the present invention developed the digital demodulation method disclosed in the nonpatent document 30, concretely in which the phases determined by the displacement components in the respective directions are derived to calculate the respective displacement components and as below, for instance, when performing the measurement of a 2D displacement vector (dx,dy), since the instantaneous phase difference (change) between the two different temporal phase of an arbitrary position in a 2D ROI is expressed as the phases of complex autocorrelation signals exp[j(fxdx+fydy)] and exp[j(fxdx−fydy)] (the multi-dimensional complex autocorrelation signal used in the multi-dimensional autocorrelation method described in nonpatent document 13, or possibly the multi-dimensional complex signal used in the multi-dimensional Doppler method described in nonpatent document 13, which can also be referred to as the complex autocorrelation function signal or simply complex signal, hereafter), that can also be expressed as independent two single quadrant spectra generated by the respective two crossed beams or waves, by calculating the product (multiplication) or the conjugate product (conjugate multiplication) of them, exp[j(2fxdx)] and exp[j(2fydy)] are obtained and then, by dividing the instantaneous phases differences 2fxdx and 2fydy in the respective directions using the instantaneous frequencies 2fx and 2fy in the respective directions, the unknown displacement vector (dx, dy) can be obtained (As shown in FIG. 8b in the patent document 7, there exist other combinations of independent two single quadrant spectra.). When performing the 3D displacement vector (dx,dy,dz) measurement, four or at least three complex autocorrelation signals exp[j(fxdx+fydy+fzdz)], exp[j(fxdx+fydy−fzdz)], exp[j(fxdx−fydy+fzdz)], exp[j(fxdx−fydy−fzdz)] (the multi-dimensional complex autocorrelation signal used in the multi-dimensional autocorrelation method described in nonpatent document 13, or possibly the multi-dimensional complex signal used in the multi-dimensional Doppler method described in nonpatent document 13, and also hereafter), which are calculated using four or at least three crossed beams or waves, are used and similarly the displacement vector can also be calculated (Similarly, there exist other combinations of independent three or four single octant spectra.). The method for estimating the instantaneous frequencies from the wave signals, which is based on the autocorrelation method or the Doppler method, is specifically described in the nonpatent document 13. In the case based on the autocorrelation method, for the complex analytic signals of at least more than two different temporal phases (single quadrant or octant spectra) for at the position of interest, after calculating the instantaneous phase subtraction (a difference or a change) about the signal of the same position of the next temporal phase with respect to the signal of the temporal phase of interest (i.e., the signal of interest) in the slow-time-axis (which is usually phase-matched coarsely using the cross-correlation method or the cross-spectrum phase gradient method), and further after calculating the respective direction instantaneous frequencies of the same signal of interest by dividing the respective direction subtractions (forward differences) about the instantaneous phase subtractions (differences) about the signals of the same position and the forward adjacent positions (e.g., the next forward sampling positions) in the respective directions of the next temporal phase with respect to the signal of interest by the respective distances of the adjacent positions in the respective directions. Or, instead of the next temporal phase signal, the last temporal phase signal can also be used, or for the calculations of instantaneous frequencies, instead of the forward adjacent position signal, the backward adjacent position signal can also be used (corresponding to a backward subtraction). Or, in the case based on the Doppler method, for the complex analytic signal of each temporal phase (single quadrant or octant spectra), the instantaneous frequencies can be calculated by dividing the instantaneous phase subtractions about the signals of the respective adjacent positions in the respective directions with respect to the signal of interest by the respective distances in the respective directions. The instantaneous phase subtraction between the two complex signals can also be calculated by implementing the inverse tangential function onto the imaginary part/real part of the conjugate product of the signals, or by subtracting the instantaneous phases calculated for the respective signals as the inverse tangents of the imaginary part/real part of the respective signals. To stabilize the estimates of the instantaneous frequencies, the calculated raw data can also be moving-averaged in the temporal, spatial (multi-dimensional processing is effective), or spatio-temporal directions (multi-dimensional processing is effective). When performing the multi-dimensional moving-averaging, implementing the inverse tangent onto the imaginary part/real part of the conjugate product of the two signals corresponds to implementing the inverse tangent onto the imaginary part/real part of the inner product of local multi-dimensional complex signals (one of the signals being made conjugate), or directly implementing the inverse tangent onto the imaginary part/ real part of the respective complex signals corresponds to performing the moving-average onto the subtraction of the calculated instantaneous phases. The wave for performing the moving-averaging is specifically described in the nonpatent document 13 and however, the estimation methods for the instantaneous frequencies is not limited to these. For instance, in the case where each spatial direction instantaneous frequency is estimated based on the autocorrelation method, for at the position of interest at least more than two different temporal phases, in addition to the instantaneous phase subtraction about the signal of the next and/or last temporal phase with respect to the signal of the temporal phase of interest (signal of interest), with more than two instantaneous phase subtractions about the signals of the forward or backward positions in each direction of the same next and/or last temporal phase with respect to the signal of interest, the least squares estimation can also be performed onto the instantaneous phase subtraction distribution in each direction to estimate the gradient of the 1st order linear function with an intercept. Or, in the case based on the Doppler method, at each temporal phase, in addition to the instantaneous phase of the signal of interest, more than two instantaneous phases are calculated for the signals at the forward and/or backward positions, and the least squares estimation can also be performed on the instantaneous phase distribution to estimate the gradient of the 1st order linear function with an intercept. In these processings, the moving-averaging to be performed can also include that in the temporal direction.

For instance, the digital signal processing unit 33 shown in FIG. 2 calculates in the 3D orthogonal coordinate system case the 3D displacement vector by using at least three steering waves with different steering angles including zero or non-zero degree generated by the transmission unit 31 or the reception unit 32, or in the 2D orthogonal coordinate system case the 2D displacement vector by using at least two steering waves with different steering angles including zero or non-zero degrees generated by the transmission unit 31 or the reception unit 32 as follows: the respective instantaneous phase changes generated at least during two different temporal phases for the newly generated waves that propagates in the orthogonal directions are divided by the respective instantaneous frequencies or the corresponding 1st moments (frequencies) of spectra in the orthogonal propagation directions to calculate the displacement vector components in the respective orthogonal propagation directions, where (1) the respective instantaneous phase changes can be calculated at least for two different temporal phases with respect to the waves newly generated by the respective multiplication and the conjugate multiplication of the two analytic signals obtained from the single octant or quadrant spectra corresponding to the same, distinct steering waves used for the scanning, or (2) the same instantaneous phase changes are calculated by the respective multiplication and the conjugate multiplication of the two complex signals obtained at least for two different temporal phases with respect to the two analytic signals obtained from the single octant or quadrant spectra corresponding to the same, distinct steering waves. As described in the paragraph 0623, the instantaneous frequency vector or the 1st moment frequency vector, (fx,fy) or (fx,fy,fz), comprising of the instantaneous frequencies, or the 1st moment frequencies of local or global spectra expresses the wave propagation direction (FIG. 41 or 42). That is, the above-described wave signals or the complex analytic signals such as ones with different steering angles, or the complex autocorrelation signals expressing the instantaneous phase change at least between the two different temporal phases or the production or the conjugate product of complex signals have the relations to the respective waves of which propagation directions are expressed by the respective instantaneous frequency vectors or the 1st moment (frequency) vectors expressed in the respective kernels. This is the same as that of the nonlinear processings.

With respect to arbitrary waves crossed in arbitrary directions, since these digital demodulations or nonlinear processings <2> or <3> yields waves with carrier frequencies in the respective directions of the symmetric (central) axis and the axis orthogonal to the symmetric (central) axis (waves with detected in one or two directions), by making the waves to avoid passing to an obstacle or a blocker, etc. related to the waves and by crossing the waves behind the obstacle or a blocker, etc. in such a fashion, waves with carrier frequencies in arbitrary directions can be generated behind the obstacle or blocker, etc. Such waves cannot be directly generated through the obstacle or blocker, etc. Thus, such configurations allow the imaging or the displacement measurement behind an obstacle or a blocker, etc., which is difficult in general. For instance, cases where such waves with carrier frequencies in the depth and lateral directions are generated behind an obstacle or a blocker, etc. are equivalent to cases where the obstacle or blocker is looked through from the frontal direction and also the object motion in an arbitrary direction behind the obstacle and blocker can be measured. The imaging and the displacement measurement can also be performed on from an arbitrary direction, and not limited to from the frontal direction of the obstacle or blocker, etc. In these cases, using at least one mirror allows the observing of behind of the obstacle and blocker, etc. by generating a reflection wave. For instance, crossed waves can also be generated behind the obstacle or blocker, etc. by generating the reflection waves using mirrors set in the directions of the steered waves from the frontal direction of the obstacle or blocker, etc. There can exist wave sources in other directions from the frontal direction of the obstacle or blocker, etc. Various combinations can be generated for the steering angles and carrier frequencies, considering the necessity of obtaining effects of a complex production and a complex conjugate, the methods dealing with simultaneous equations are not limited regarding the combinations and the calculations are a fewer.

On the digital demodulation method, or the nonlinear processings <2> or <3>, since the frequencies of the two-fold instantaneous frequencies of the respective directions are generated, the beamformings are to be performed in advance with a sufficiently wide bandwidth on the basis of the Nyquist theorem, the number of beams are to be interpolated in a space, or the bandwidth is to be increased in a frequency domain by padding zero spectra (interpolation of data). Thus, the so-called aliasing cannot be generated (This is about the single quadrant or octant spectra since the complex analytic signal is processed.). These processings also fall in a variety of signal separations.

Figure 43:
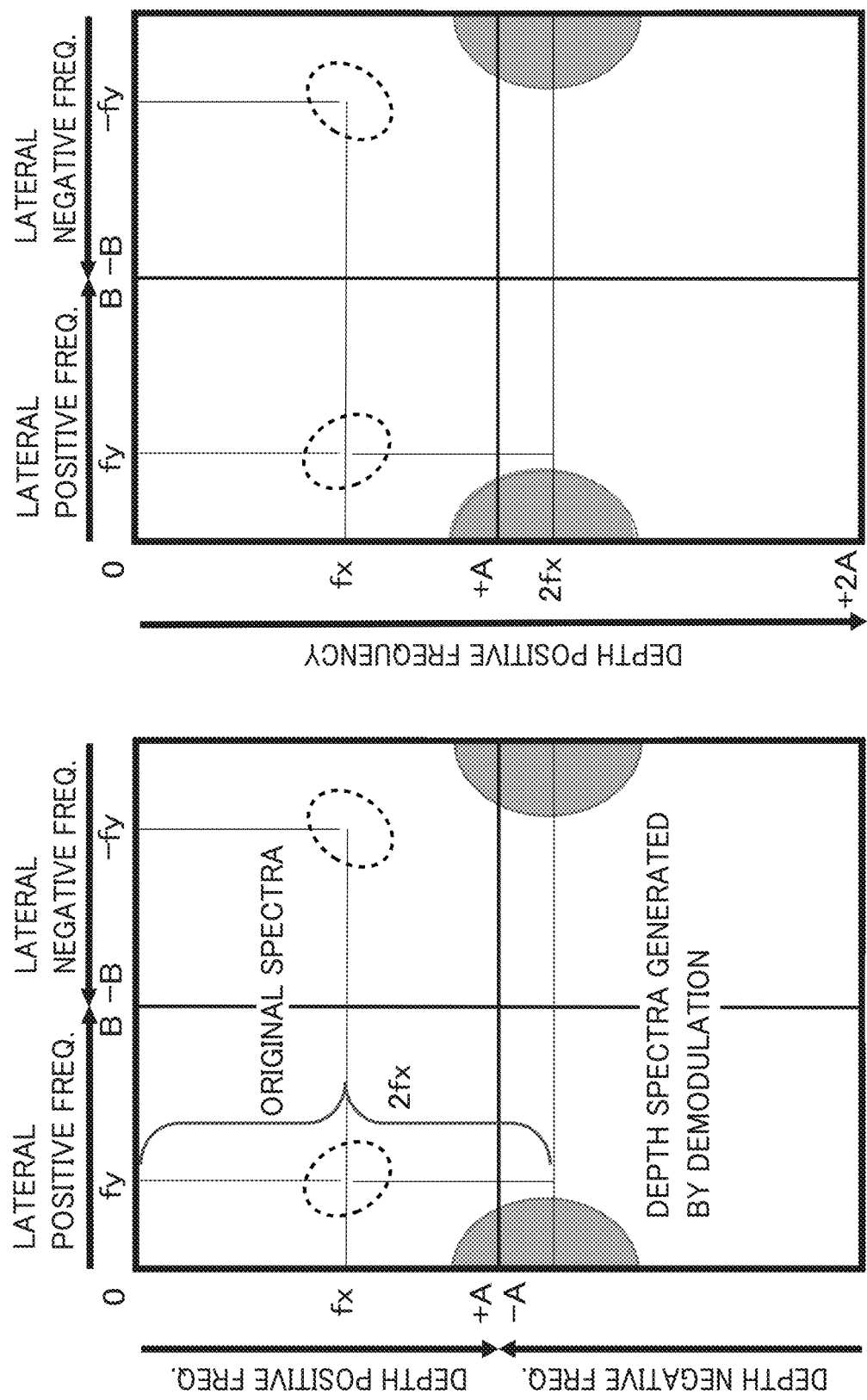
FIG. 43 shows an illustration for the demodulation for the 2D lateral modulation, of resetting the depth frequency coordinate axis, when an aliasing occurs in the depth frequency coordinate axis with respect to spectra with the depth bandwidth 2A.
Figure 44:
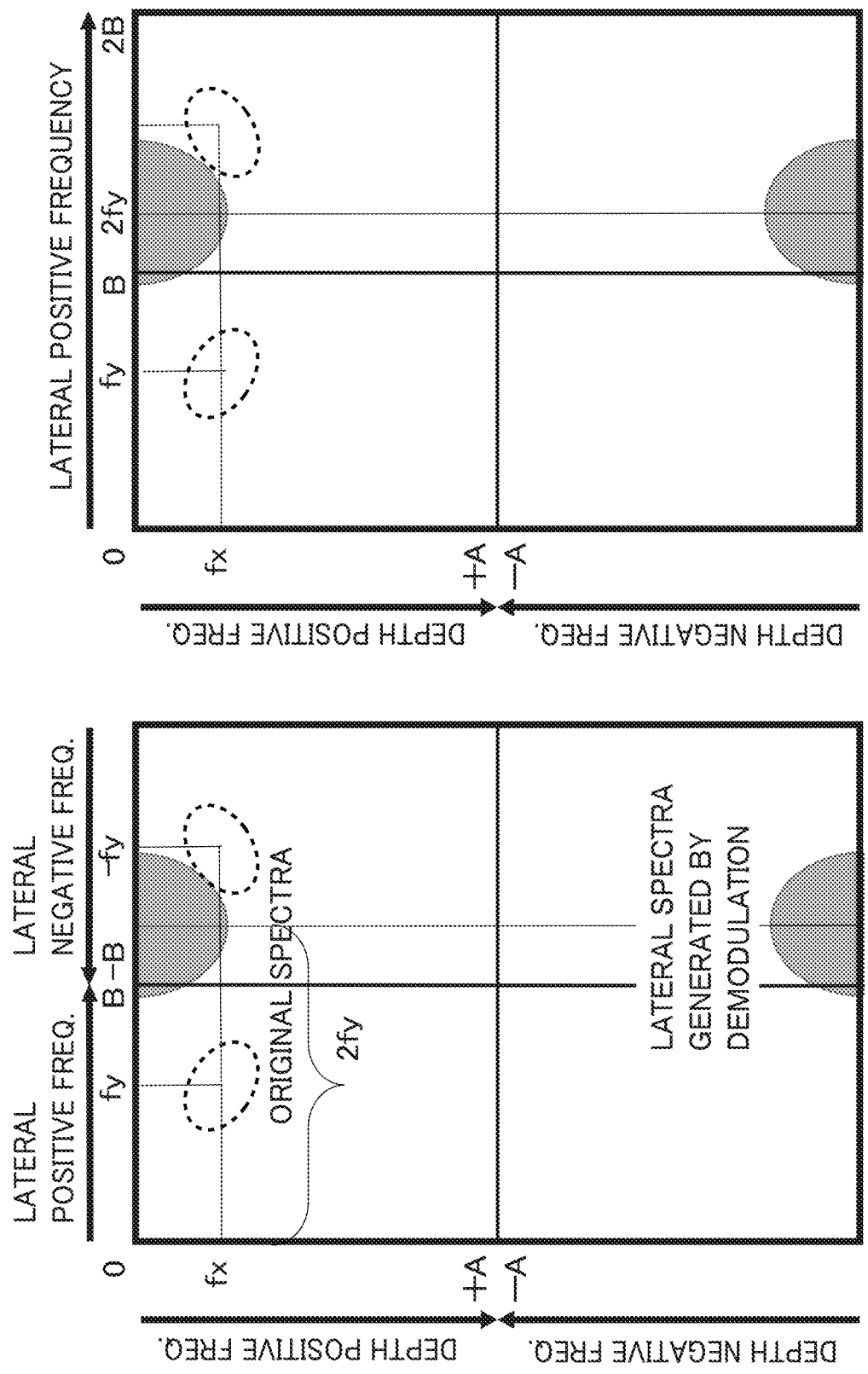
FIG. 44 shows an illustration for the demodulation for the 2D lateral modulation, of resetting the lateral frequency coordinate axis, when an aliasing occurs in the lateral frequency coordinate axis with respect to spectra with the lateral bandwidth 2B.

Or, these demodulation methods, or nonlinear calculation <2> or <3> can also be performed without increasing the signal bandwidth. Under the condition, the original signals before being processed are satisfied with the Nyquist theorem, the same processings can be performed to calculate the instantaneous phase differences (changes) in the respective directions, i.e., 2fxdx, 2fydy and 2fzdz; and dividing them with the corresponding twofold instantaneous frequencies that are calculated from the original signals, i.e., fx, fy and fz. Without increasing the bandwidth, the measurements can be achieved with a higher speed with a fewer calculations and memories. Instead of the twofold frequencies, the summation of the instantaneous frequencies in the respective directions estimated from the respective waves/beams can also be used. In these cases, instead of the instantaneous frequencies, the twofold 1st moment or the center frequency of local or global spectra of original signal can also be used. Or, without calculating them, the twofold nominal frequency or the twofold typical values provided in advance, etc. can also be used. Or, as shown for schematics of spectrum distributions in FIG. 43 and FIG. 44, when the aliasing occurs, the way the frequency domain of a frequency coordinate of which the aliasing occurs is read by a positive or negative half bandwidth can also be changed to allow the direct calculation of the twofold frequency from the 1st moment of the spectrum distributions (Since before the processings, the signals are satisfied with the Nyquist theorem, the twofold frequency can be calculated absolutely.). The spectrum distribution can be calculated for echo signals within a region of interest, some region, or a local region including each point of interest. FIG. 43 shows the illustration of the processing after changing the way the frequency coordinate is read when the aliasing occurs for the 2D spectrum with an axial bandwidth 2A (−A to A) by the demodulation for a 2D lateral modulation, whereas FIG. 44 shows the illustration of the processing after changing the way the frequency coordinate is read when the aliasing occurs for the 2D spectrum with a lateral bandwidth 2B (−B to B) by the demodulation for a 2D lateral modulation. There are various combinations of independent analytic signals. FIG. 43 shows for two analytic signals with instantaneous (or 1st moment) frequencies of (fx,fy) and (fx,−fy) the illustration for the enabled calculation of the axial 1st moment of spectra as 2fx when the aliasing occurs in the axial direction, whereas FIG. 44 shows for the same two analytic signals the illustration for the enabled calculation of the lateral 1st moment of spectra as 2fy when the aliasing occurs in the lateral direction. The axial and lateral aliasings can occur simultaneously. Alternatively, when using the instantaneous frequencies, since the instantaneous frequencies are calculated as ones are expressed in the positive or negative half bandwidth, the frequency coordinates having aliasings can be corrected using the value of a bandwidth determined by the sampling frequency. For instance, when the respective spectra of the product or the conjugate product (demodulations) become to have more spectra in the negative bandwidth compared to the conditions shown in FIGS. 43 and 44, since the corresponding signals are to have a minus frequency, the instantaneous frequency can be corrected by the summation of the directly estimated instantaneous frequency and the bandwidth value. When using the 1st moment (frequency) of spectra is used, the same processing can be performed (i.e., the directly estimated negative frequency is added by the bandwidth value). Alternatively, when using a negative frequency signal is used as the complex analytic signal, since such a signal is estimated to have a positive instantaneous frequency or a positive 1st moment (frequency) of spectra, in such a case the estimated positive frequency is subtracted by the bandwidth. The processing is equivalent to the above-described changing the way the frequency coordinate is read. Also in the 3D case, when the aliasing occurs, the way the frequency domain of a frequency coordinate of which the aliasing occurs is read by a positive or negative half bandwidth can also be changed to allow the direct calculation of the twofold frequency from the 1st moment of the spectrum distribution. Or, when the aliasing occurs, the way the frequency domain of a frequency coordinate of which the aliasing occurs is read by a positive or negative half bandwidth is changed similarly and subsequently a frequency domain of a half bandwidth of zero spectra can also be added to increase the bandwidth such that the analytic signals obtained by the inverse Fourier transform are satisfied with the Nyquist theorem (At this timing of increasing the bandwidths or performing the signal interpolations, it is also possible to perform the calculations of instantaneous frequencies and changes of instantaneous phases, which can decrease calculations compared to the cases where the bandwidths are increased or the signals are interpolated in advance. However, the calculations are more than the case where the bandwidth is not increased.). If these demodulation methods, or nonlinear calculation <2> or <3> can also be performed without generating the aliasings, the instantaneous phase differences (changes) can be divided by the directly calculated twofold or summation's, instantaneous frequencies or 1st moment frequencies of spectra without changing the way the frequency coordinate is read nor increasing the bandwidth. When using the instantaneous frequency, similarly to in the 2D case, the correction using the bandwidth value can be performed. Or, without performing the calculations, the twofold nominal frequency or typical value (provided one in advance), etc. can also be used. Within the changing the way the frequency coordinate is read, no problem occurs. The processing with the increasing the bandwidth by the zero spectra padding or the performing the signal interpolation can lead the lowering of a measurement accuracy as well as the increasing calculations and then, the processing with no increasing the bandwidth is effective in these senses. For the wide-banded or no wide-banded cases, if necessary, the regularization processing can also be performed.

Figure 45:
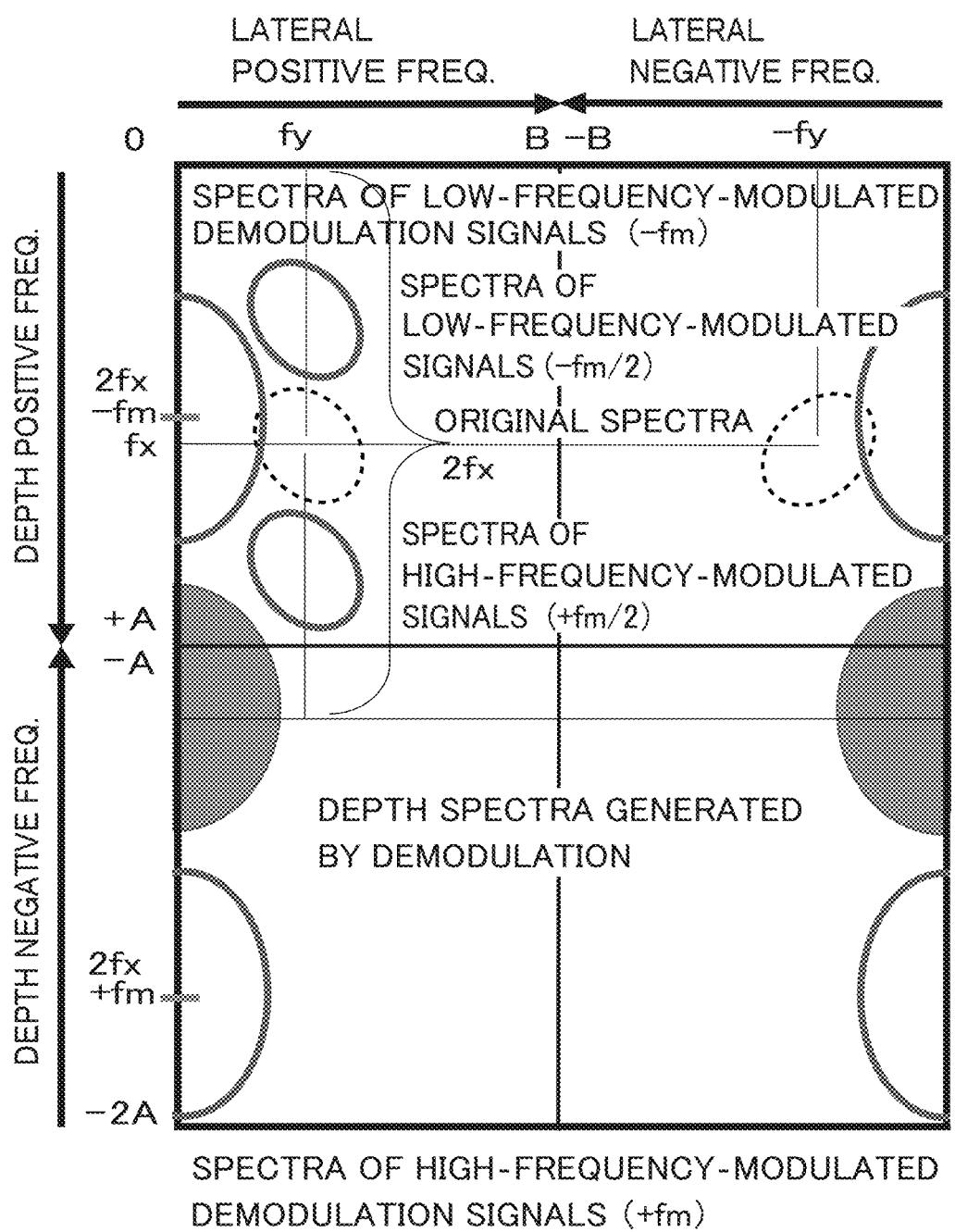
FIG. 45 shows an illustration of frequency-modulation for a demodulation.

Or, a frequency modulation can be effectively used to cope with the aliasing. By implementing the frequency modulation onto the received, reception wave signals (realtime signals), the complex analytic signals, the complex autocorrelation signals (or complex signals), the signals obtained as the product or the conjugate product such that the above-described aliasing does not occur for the product and the conjugate product, or by generating the aliasing for the product and the conjugate product through such frequency modulations and in the case using the 1st moment (frequency) of spectra, as described above, the way the frequency coordinate is read is changed, and in the case using the 1st moment of spectra or the instantaneous frequency, as above-described, the bandwidth value is used for the summation or the subtraction to calculate the frequencies, onto which the frequency correction can be implemented by adding or subtracting the modulation frequency in the respective cases when the frequency is lowered or heightened. For the illustration of the demodulation by multiplication shown in FIG. 43, FIG. 45 shows the illustration where the frequency modulation with ±fm is performed. The frequency demodulation can also be implemented onto the demodulated signals and the signals prior to the demodulation processings can also be frequency-modulated in advance (FIG. 45 shows the case with the modulation frequency of ±fm/2). Or, with no calculations, the twofold values such as of a nominal frequency or a typical value obtained in advance can also be used. These are same for the demodulation using the conjugate product shown in FIG. 44. For the instantaneous phase difference (change) or the corresponding phase data, ones to be directly calculated from the frequency-modulated signals can also be used, or ones calculated from non-frequency-modulated signals can also be used. Thus, the respective direction displacements can be obtained by dividing the instantaneous phase difference (change) or the corresponding phase data by the corrected instantaneous frequencies or the 1st moments (frequencies) of spectra. Also when performing the frequency modulation with using the 1st moment (frequency) of spectra, as described above, the locally estimated 1st moment can also be used equivalently to an instantaneous frequency, or globally estimated one can also be used.

As usually, the frequency modulation can be performed as follows: when the signal to be processed is a real (time) signal, the multiplication of a cosine or sine function with a frequency being the multiplication of the modulation frequency and (+1) or (−1) is performed for the signal, when the signal is a complex analytic signal or a complex autocorrelation signal (a complex signal), the complex exponential function with a frequency being the multiplication of the modulation frequency and (+1) or (−1), or for both cases, the spectra obtained by the Fourier transform are frequency-shifted in a frequency domain by the frequencies being the multiplication of the modulation frequency and (+1) or (−1). The point is to perform processings for the complex analytic-type signals finally (i.e., single quadrant or octant spectra to be processed). When performing the frequency modulation by the multiplication of the cosine or sine function to the real (time) signal, both signals of which frequency is heightened and lowered are obtained, one of which is extracted and used usually. For the processing, a low-pass or high-pass filtering is to be performed for the frequency-modulated signal, if the original signal is wideband or the modulation frequency is small, it is cautious that the modulated signals are overlapped in a frequency domain and cannot be separated by the filtering. Alternatively, when the complex exponential function is multiplied to the complex analytic signal, the complex autocorrelation signal (or the complex signal) and the spectra of the real (time) signal or such complex signals are frequency-shifted, one of them can be obtained. These frequency modulations can be performed at the digital signal processing unit or the data processing unit after outputting the reception signals by sensors, which can be realized by digital signal processings or by analogue signal processings using a mixer (multiplicator) or a filter, etc. Although the explanation is performed here under the assumption that the demodulation is performed by digital signal processings, all can also be performed by analogue processings with a high speed.

Above, the practical examples of the displacement vector measurement are explained under the assumption that the reception signals themselves are satisfied with the sampling theorem. These processings being effective in the cases where the aliasings occur by the demodulations are also effective for reception signals that are not satisfied with the sampling theorem. In the cases, in addition to the demodulation method, to perform the multi-dimensional displacement vector measurement methods such as the multi-dimensional cross-spectrum phase gradient method, the multi-dimensional autocorrelation method, the multi-dimensional Doppler method, etc. and the corresponding 1D processings (one direction measurement methods) and among others is made possible.

For instance, in the cases where the wave signals, the complex analytic signals, or the complex autocorrelation signals or the complex signals that express the instantaneous phase changes generated between two different temporal phases at least, or the multiplications or the conjugate multiplications of them have aliasings, when a displacement vector or a displacement is calculated using the instantaneous phase change and the instantaneous frequencies or the 1st moments (frequencies) of spectra, the digital signal processing unit 33 shown in FIG. 2 can perform the corrections for the erroneous instantaneous frequencies or the 1st moments (frequencies) of spectra calculated from the aliased signals by adding or subtracting the erroneous frequencies by the bandwidth values determined by the sampling frequencies.

Or, in the same cases where the aliasings occur for the signals, when a displacement vector or a displacement is calculated using the instantaneous phase change and the instantaneous frequencies or the 1st moments (frequencies) of spectra, the digital signal processing unit 33 shown in FIG. 2 can perform the frequency modulations for the signals to make the signal frequencies lower such that the aliasings do not occur or to make the signal frequencies higher and in the cases using the 1st moments (frequencies) of spectra, the frequency coordinate of the half bandwidth is re-read (i.e., changing the way the coordinate is read as mentioned above), or in the case using the 1st moments (frequencies) of spectra or the instantaneous frequencies, the frequencies are corrected by the additions or subtractions of the bandwidth values; and finally the digital signal processing unit 33 demodulates the signal frequencies by the additions and the subtractions of the modulation frequencies for the two frequency modulation cases. Here, the frequency modulation performed by the data processing unit can be a detection processing.

The above-described demodulation methods, or nonlinear calculation <2> or <3> can be made more accurate by the below-described improvements. For instance, the explanation is performed for the above-described 2D displacement vector measurement (dx,dy). Since the instantaneous phase difference (change) between the two different temporal phase of an arbitrary position in a 2D ROI is expressed as the phases of complex autocorrelation signals exp[j(fxdx+fydy)] and exp[j(fxdx−fydy)], that can also be expressed as independent two single quadrant spectra generated by the respective two crossed beams or waves, by calculating the product or the conjugate product of them, exp[j(2fxdx)] and exp[j(2fydy)] are obtained and then, by dividing the instantaneous phases differences 2fxdx and 2fydy in the respective directions using the instantaneous frequencies 2fx and 2fy in the respective directions, the unknown displacement vector (dx,dy) can be obtained (As shown in FIG. 8b in the patent document 7, there exist other combinations of independent two single quadrant spectra.). However, in the 2D orthogonal coordinate system used for the observation, although the two beams or waves are steered such that they become symmetric with respect to the symmetric axis, practically the two beams or waves do not become symmetric and the frequencies (absolute values) in the propagating directions of the waves do not become same strictly. For instance, this is because the main directivity of a physical aperture or an aperture array element can direct in others from the frontal direction, the propagation speed can be inhomogeneous, the frequency modulation can occur during the propagation due to an attenuation or a scattering in the medium, errors can occur for the digital or analogue delays, etc. The above-described method achieves the measurement under the assumption that the frequencies are same and then, measurement errors occur in practice. Actually, as mentioned above, the products or conjugate products such as about the reception real (time) signal, the complex analytic signal, the complex autocorrelation signal (or complex signal) generate waves with carrier frequencies in the symmetric axis about arbitrary waves crossed in an arbitrary direction and in the direction orthogonal to the symmetric axis and then, the above-described assumption causes errors.

Figure 46:
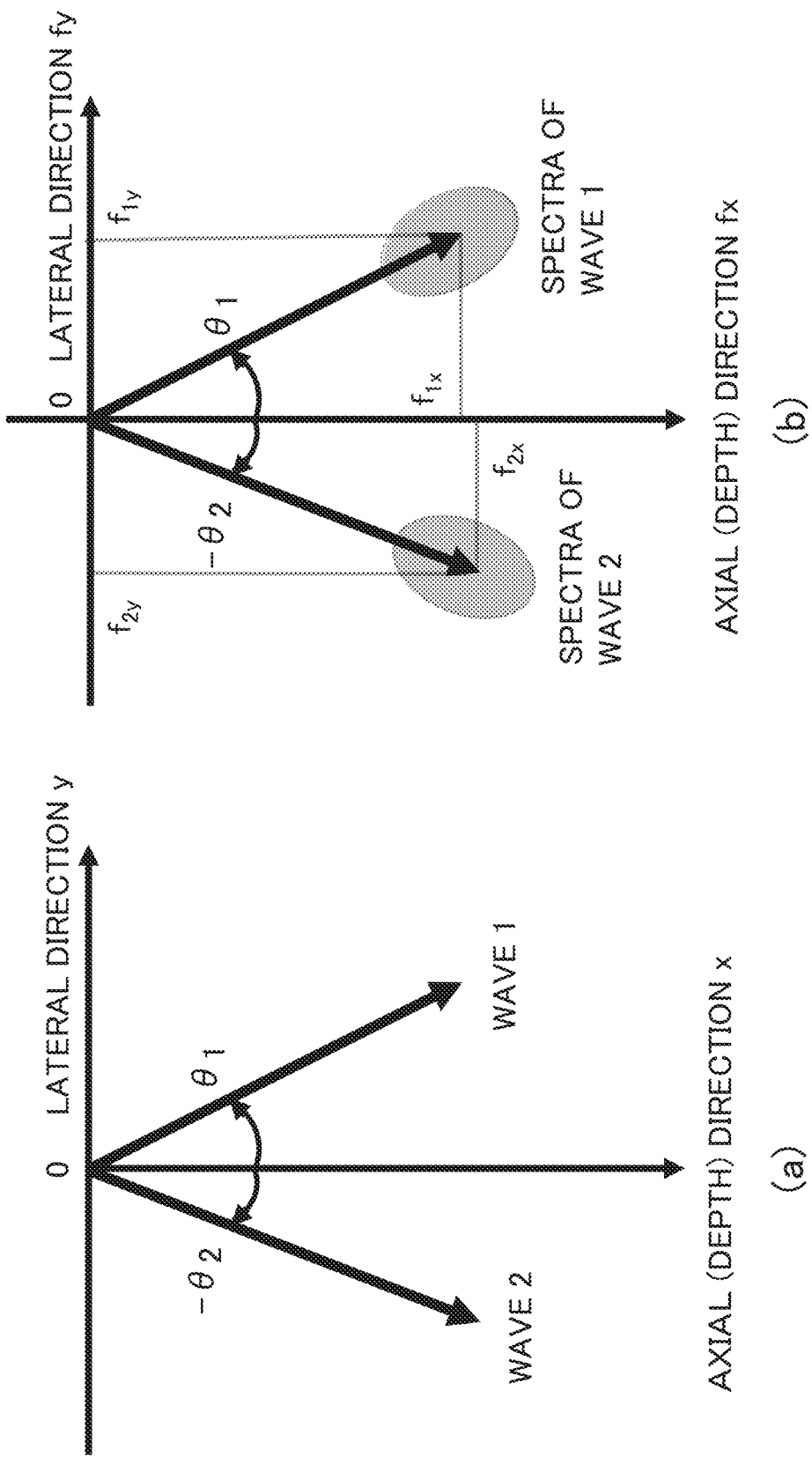
FIG. 46 shows for a 2D coordinate system schematics of two generated waves and the corresponding spectra.
Figure 47:
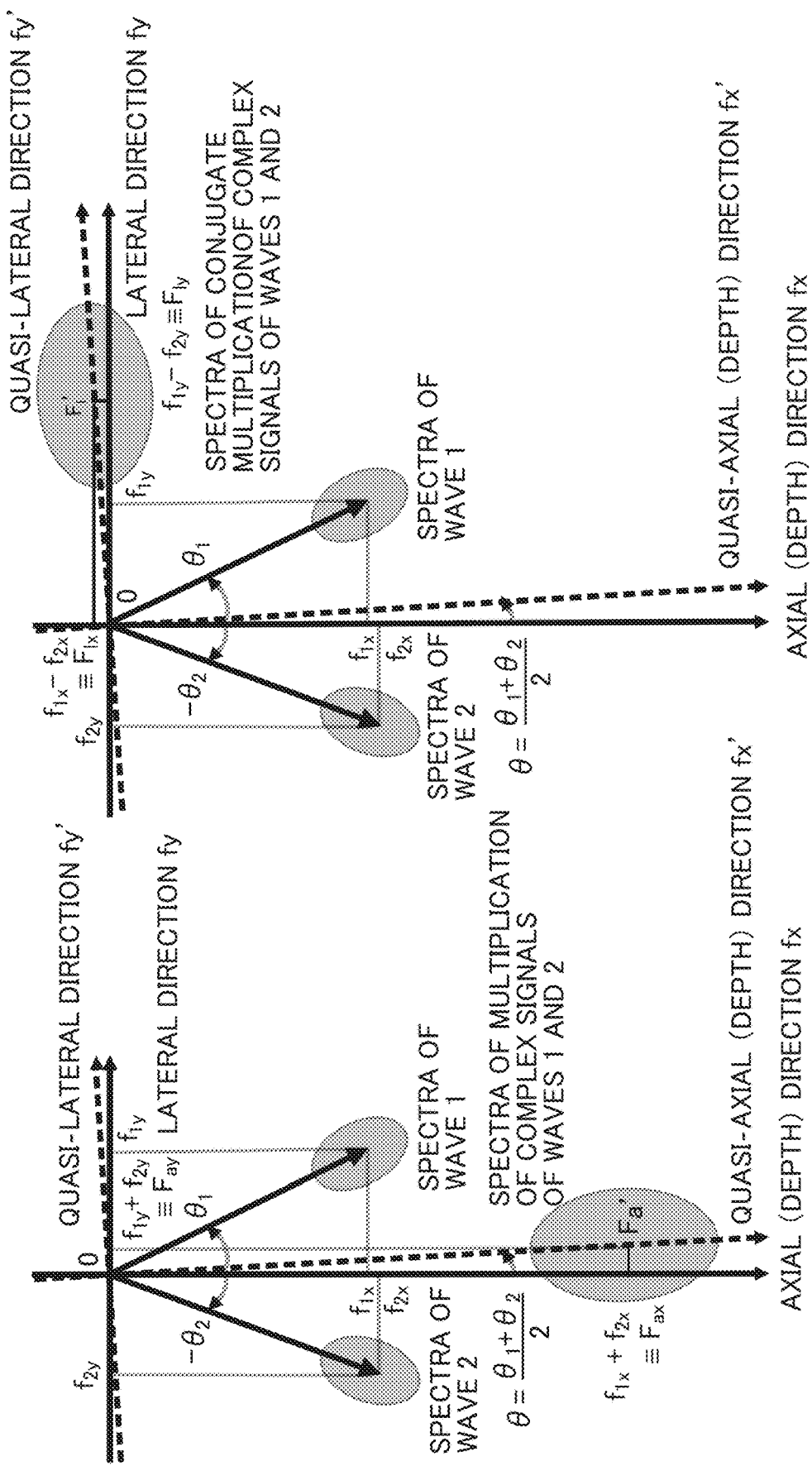
FIG. 47 shows for a 2D coordinate system schematics of spectra of product (multiplication) and conjugate product (conjugate multiplication) of complex autocorrelation signals of two waves.
Figure 48:
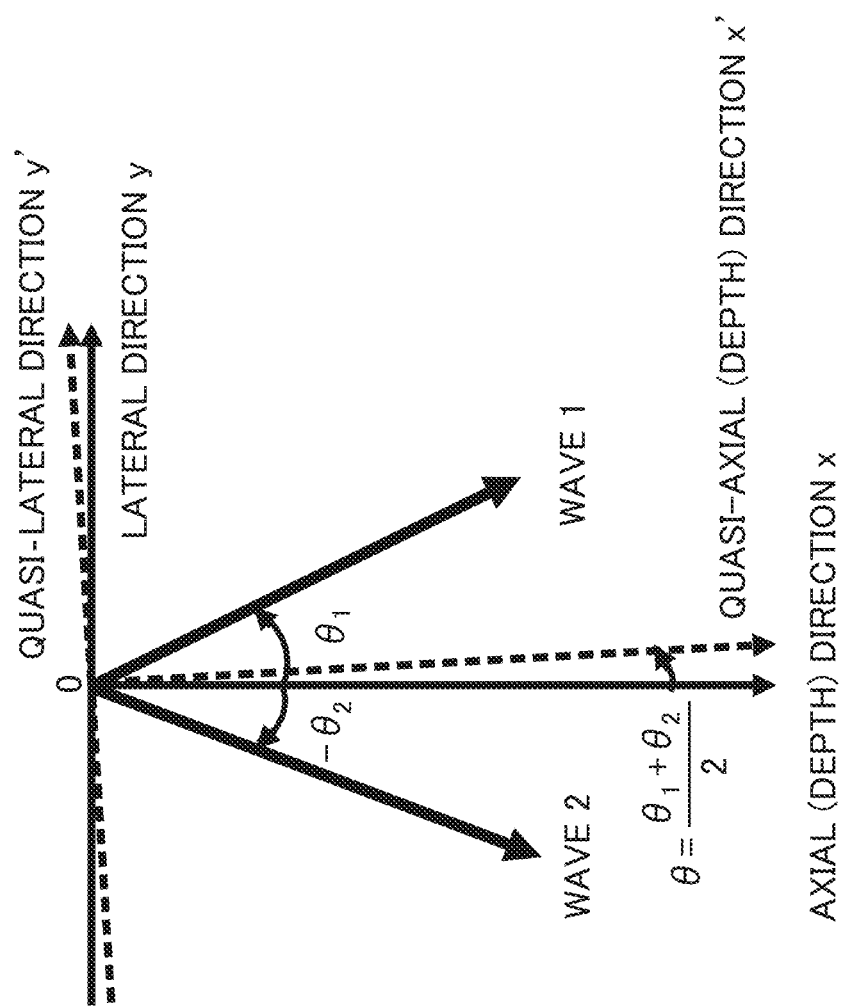
FIG. 48 shows for a schematic of two nonsymmetric waves generated in a 2D coordinate system the spatial coordinate axes of a quasi-axial direction and a quasi-lateral direction orthogonal to the quasi-axial direction.

As shown in FIG. 46(a), in the 2D coordinate system (x,y) to be used for the displacement vector measurement, the steering angles of two waves 1 and 2 are respectively regarded as $\theta_1$ and $-\theta_2$; and the respective instantaneous frequencies or 1st moments (frequencies) of spectra are regarded as $(f_{1x},f_{1y})$ and $(f_{2x},f_{2y})$ (i.e., the instantaneous frequency vectors or the 1st moment (frequency) vectors). And, FIG. 46(b) shows for the 2D coordinate system (x,y), the corresponding frequency coordinate system (fx,fy) with the schematics of the two waves' spectra. In FIG. 46, the axial and lateral directions are regarded as x and y directions. Here, as often observed when $|\theta_1|>|\theta_2|$, the frequencies (absolute values) of waves generated at an arbitrary position in a 2D region of interest are satisfied with $|f_{1y}|>|f_{2y}|$ and $|f_{1x}|<|f_{2x}|$. Since the instantaneous phase difference (change) between the two different temporal phases are expressed as the phases of the complex autocorrelation signals, $\exp[j(f_{1x}dx+f_{1y}dy)]$ and $\exp[j(f_{2x}dx+f_{2y}dy)]$, the product and the conjugate product are calculated as $\exp[j\{(f_{1x}+f_{2x})dx+(f_{1y}+f_{2y})dy\}]$ and $\exp[j\{(f_{1x}-f_{2x})dx+(f_{1y}-f_{2y})dy\}]$. Thus, under the assumptions of $f_{1x}=f_{2x}=f_x$ and $f_{1y}=-f_{2y}=f_y$, the phases of approximately expressed $\exp[j2f_xdx]$ and $\exp[j2f_ydy]$ can be divided by $2f_x$ and $2f_y$, respectively, or under the assumptions of $f_{1y}=-f_{2y}=f_y$ and $f_{1x}=f_{2x}=f_x$, the phases of approximately expressed $\exp[j\{(f_{1x}+f_{2x})dx\}]$ and $\exp[j\{(f_{1y}-f_{2y})dy\}]$ can be divided by $f_{1x}+f_{2x}$ and $f_{1y}-f_{2y}$, respectively. Through the nonlinear processing <2> or <3>, similarly the approximate calculations can be performed. The spectra of the product and the conjugate product of the complex autocorrelation signals of waves 1 and 2 shown in FIGS. 46(a) and 46(b) are schematically shown in FIG. 47. Similarly the spectra can also be calculated through the nonlinear processing <2> or <3>. Alternatively, without the assumption, calculated are $\exp[j\{(f_{1x}+f_{2x})dx+(f_{1y}+f_{2y})dy\}]$ and $\exp[j\{(f_{1x}-f_{2x})dx+(f_{1y}-f_{2y})dy\}]$, of which phases are respectively denoted as $\alpha_a$ and $\alpha_1$ here. Thus, by dividing the phases $\alpha_a$ and $\alpha_1$ by the frequencies $F_a'$ and $F_1'$, respectively, which are the frequencies of the direction of a quasi-axis fx' (quasi-axial frequency) that positions the two waves symmetrically and a quasi-axis fy' (quasi-lateral frequency) orthogonal to the quasi-axis fx', respectively, the displacements of the quasi-axial direction x' and the quasi-lateral direction y' in the 2D orthogonal coordinate system (x',y') shown in FIG. 48 corresponding to the 2D frequency coordinate system expressed as (fx',fy'). That is, in the newly defined spatial 2D orthogonal coordinate system (x',y') that positions the two waves 1 and 2 symmetrically with respect to the x'-direction, the displacement vector can be observed:

$$\begin{pmatrix} \alpha_a \\ \alpha_1 \end{pmatrix} = \begin{pmatrix} F_a' & 0 \\ 0 & F_1' \end{pmatrix} \begin{pmatrix} dx' \\ dy' \end{pmatrix}, \quad \text{(demodu0)}$$

where the frequencies $F_a'$ and $F_1'$ respectively expressed as $\sqrt{(F_{ax}^2+F_{ay}^2)}=\sqrt{\{(f_{1x}+f_{2x})^2+(f_{1y}+f_{2y})^2\}}$ and $\sqrt{(F_{1x}^2+F_{1y}^2)}=\sqrt{\{(f_{1x}-f_{2x})^2+(f_{1y}-f_{2y})^2\}}$ can be calculated using $(f_{1x},f_{1y})$ and $(f_{2x},f_{2y})$ or using the instantaneous frequencies or the 1st moments (frequencies) of spectra about the product and the conjugate product of the complex autocorrelation signals, $(F_{ax},F_{ay})$ and $(F_{1x},F_{1y})$ (i.e., the magnitudes of instantaneous frequency vectors or 1st moment (frequency) vectors).

Since the 2D orthogonal coordinate system to be used for the observation is (x,y), the displacement vector (dx',dy') calculated in the 2D orthogonal coordinate system (x',y') is angle-corrected such that the measurement is expressed in the 2D orthogonal coordinate system (x,y). The angle difference (rotation angle) between the 2D orthogonal coordinate system (x,y) and (x',y'), $\theta=(\theta_1+\theta_2)/2$, can be calculated as a mean about the two waves' steering angles, $\theta_1=\tan^{-1}(f_{1y}/f_{1x})$ and $\theta_2=\tan^{-1}(f_{2y}/f_{2x})$, using $\tan^{-1}(F_{ay}/F_{ax})=\tan^{-1}\{(f_{1y}+f_{2y})/(f_{1x}+f_{2x})\}$ calculated using $(f_{1x},f_{1y})$ and $(f_{2x},f_{2y})$, $90°+\tan^{-1}(F_{1y}/F_{1x})=90°+\tan^{-1}\{(f_{1y}-f_{2y})/(f_{1x}-f_{2x})\}$ when $F_{1x}<0$ or $\tan^{-1}(F_{1y}/F_{1x})=\tan^{-1}\{(f_{1y}-f_{2y})/(f_{1x}-f_{2x})\}$ when $F_{1x}>0$, or similarly calculated from the 1st moments (frequencies) of spectra or the instantaneous frequencies of the product and the conjugate product of the complex autocorrelation signals, $(F_{ax}, F_{ay})$ and $(F_{1x}, F_{1y})$.

For the angle correction, there exists two methods. One of them is that the rotation matrix is implemented onto the calculated (dx',dy') to obtain the observation result (dx,dy), i.e., $$\begin{pmatrix} dx \\ dy \end{pmatrix} = \begin{pmatrix} \cos\theta & -\sin\theta \\ \sin\theta & \cos\theta \end{pmatrix} \begin{pmatrix} dx' \\ dy' \end{pmatrix}. \quad \text{(Rot1)}$$

Or, the rotation matrix is implemented onto the instantaneous frequency vectors or the 1st moment(frequency) vectors expressed in the 2D orthogonal coordinate system (x',y') about the product and the conjugate product, $(F_a',0)$ and $(0,F_1')$, respectively, i.e., $$\begin{pmatrix} F_{ax} \\ F_{ay} \end{pmatrix} = \begin{pmatrix} \cos\theta & -\sin\theta \\ \sin\theta & \cos\theta \end{pmatrix} \begin{pmatrix} F_a' \\ 0 \end{pmatrix} \quad \text{(Rot2-1)}$$

and $$\begin{pmatrix} F_{1x} \\ F_{1y} \end{pmatrix} = \begin{pmatrix} \cos\theta & -\sin\theta \\ \sin\theta & \cos\theta \end{pmatrix} \begin{pmatrix} 0 \\ F_1' \end{pmatrix}. \quad \text{(Rot2-2)}$$

Using the calculated instantaneous frequency vectors or the 1st moment (frequency) vectors $(F_{ax},F_{ay})$ and $(F_{1x},F_{1y})$ in the 2D orthogonal coordinate system (x,y), or $(f_{1x}+f_{2x},f_{1y}+f_{2y})$ and $(f_{1x}-f_{2x},f_{1y}-f_{2y})$ that can be calculated as $(F_{ax},F_{ay})$ and $(F_{1x},F_{1y})$ using $(f_{1x},f_{1y})$ and $(f_{2x},f_{2y})$ as described above, the equations can be led with respect to the respective phases, $\alpha_a$ and $\alpha_1$, of the complex exponential functions $\exp[j\{(f_{x1}+f_{x2})dx+(f_{y1}+f_{y2})dy\}]$ and $\exp[j\{(f_{x1}-f_{x2})dx+(f_{y1}-f_{y2})dy\}]$:

$$\begin{pmatrix} \alpha_a \\ \alpha_1 \end{pmatrix} = \begin{pmatrix} F_{ax} & F_{ay} \\ F_{1x} & F_{1y} \end{pmatrix} \begin{pmatrix} dx \\ dy \end{pmatrix}, \quad \text{(Rot2-3)}$$

which can be solved as the system of equations for the target displacement (dx,dy).

Similarly, as shown in FIG. 49(a), when the symmetric axis x' about the waves 1 and 2 are much different from the axis x of the 2D orthogonal coordinate system (x,y) to be used for the observation, by performing the same processings, the respective displacements of the quasi-axial direction x' and the quasi-lateral direction y' in the 2D orthogonal coordinate system (x',y') shown in FIG. 49(b) corresponding to the 2D frequency coordinate system expressed as (fx',fy') of which quasi-axis fx' (quasi-axial frequency) positions the two waves symmetrically and quasi-axis fy' (quasi-lateral frequency) orthogonal to the quasi-axis fx'. That is, in the newly defined spatial 2D orthogonal coordinate system (x',y') that positions the two waves 1 and 2 symmetrically with respect to the x'-direction, the displacement vector (dx',dy') can be observed. Thus, similarly to the above-described case, by directly using eq. (Rot1), or performing the angle-correction using eqs. (Rot2-1), (Rot2-2) and (Rot2-3), the result (dx,dy) can be obtained in the observation coordinate system (x,y). Such an observation is useful, for instance, when performing the measurement for a human tissue with respect to ultrasonic transmission or reflection signals acquired such that the symmetric axis is steered in others from the direction of an obstacle such as a bone, etc. As far, if required, the inventor of the present invention has performed the lateral modulation in the desired direction in addition to the lateral direction aligned to the sensor arrays and has performed the multi-dimensional cross-spectrum phase gradient method, the multi-dimensional autocorrelation method, the multi-dimensional Doppler method, etc., for a displacement vector measurement. In such a case, to perform the demodulation method is made possible. That is, the demodulation method allows performing the displacement vector measurement even if the generated waves do not become symmetric with respect to the axis of the coordinate system to be used for the observation, similarly to other displacement vector measurement methods.

Moreover, for any displacement vector measurement method as mentioned above and others, for instance, the displacement vector can be observed (calculated) using not only the orthogonal coordinate system used for generating the waves but also other orthogonal coordinate systems by using the above-described angle-correction method. i.e., by correcting the displacement vector itself or frequencies of equations. For instance, for the target displacement vector (dx,dy), the system of equations is led in the 2D orthogonal coordinate system (x,y) using the multi-dimensional cross-spectrum phase gradient method, the multi-dimensional autocorrelation method, the multi-dimensional Doppler method, the demodulation method, i.e., $$\begin{pmatrix} \alpha_1 \\ \alpha_2 \end{pmatrix} = \begin{pmatrix} F_{1x} & F_{1y} \\ F_{2x} & F_{2y} \end{pmatrix} \begin{pmatrix} dx \\ dy \end{pmatrix}, \quad \text{(Rot2-4)}$$

where the subscripts '1' and '2' expresses the two waves; $F_x$ and $F_y$ are respectively the frequencies in the x and y directions (instantaneous frequency vectors or 1st moment (frequency) vectors). After calculating (dx,dy), by using eq. (Rot1) for rotating the 2D orthogonal coordinate system by a desired angle θ, the displacement vector (dx",dy") expressed in the new 2D coordinate system can be observed. Or, eq. (Rot2-4) can be rewritten using the instantaneous frequency vectors or the 1st moment (frequency) vectors ($F_{1x}''$,$F_{1y}''$) and ($F_{2x}''$,$F_{2y}''$) to be calculated by rotating the corresponding frequency vectors ($F_{1x}$, $F_{1y}$) and ($F_{2x}$,$F_{2y}$) by the same angle θ using eqs. (Rot2-1) and (Rot2-2):

$$\begin{pmatrix} \alpha_1 \\ \alpha_2 \end{pmatrix} = \begin{pmatrix} F_{1x}'' & F_{1y}'' \\ F_{2x}'' & F_{2y}'' \end{pmatrix} \begin{pmatrix} dx'' \\ dy'' \end{pmatrix}. \quad \text{(Rot2-5)}$$

By solving the equations, the displacement vector (dx",dy") can be directly calculated.

Also in the 3D case, by using independent three or four single octant spectra corresponding to the three or four crossed beams or waves and the 3D rotation matrix, the above processings can be performed similarly. In the 3D case, basically the waves are steered such that the waves become symmetric with respect to the axial direction and an area including the axial axis and the lateral direction orthogonal to the axial direction (i.e., all waves to be symmetric with respect to the axial direction). Similarly to in the 2D case, the waves cannot be symmetric with a high accuracy or intentionally the waves can be made asymmetric. Thus, the waves can be processed with a quasi-axis and a quasi-area including the quasi-axis and quasi-lateral direction orthogonal to the quasi-axis (i.e., all waves to be symmetric with respect to the quasi-axis or the quasi-area) similarly.

Figure 50:
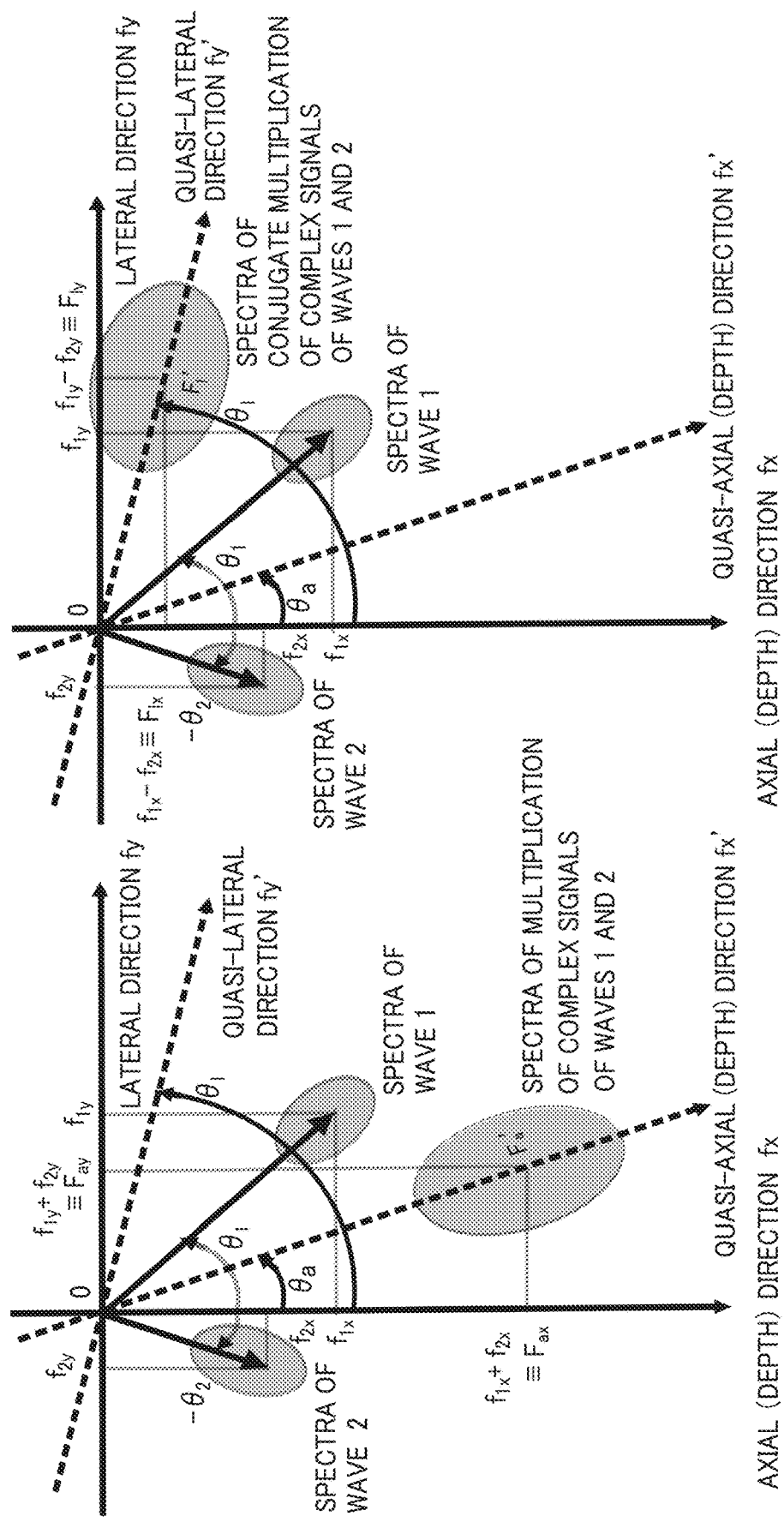
FIG. 50 shows schematics of no orthogonal quasi-axial and quasi-lateral directions.

Here, the above-described new demodulation method is explained under the assumption that the frequencies (absolute values) of waves generated at an arbitrary position in a 2D region of interest are satisfied with $|f_{1y}|>|f_{2y}|$ and $|f_{1x}|<|f_{2x}|$ as often observed when $|\theta_1|>|\theta_2|$. However, the frequency modulation due to the attenuation or the scattering, the condition $|f_{1y}|>|f_{2y}|$ and $|f_{1x}|>|f_{2x}|$ can be generated. Also when the wave frequencies themselves differ each other, the condition can occur. In these cases, the quasi-axial direction x' and the quasi-lateral direction y' are not orthogonal, which causes a problem. That is, the demodulation methods described above and in the nonpatent document 30 and the patent document 7 yields an accurate measurement strictly when the two waves themselves' instantaneous frequencies or the local or global 1st moments (frequencies) of spectra (i.e., the magnitudes of the instantaneous frequency vectors or the local or global 1st moment (frequency) vectors), $\sqrt{(f_{1x}^2+f_{1y}^2)}$ and $\sqrt{(f_{2x}^2+f_{2y}^2)}$, are same, i.e., when the coordinate system (x',y') is an orthogonal coordinate system. In fact, even if $(f_{1x}^2+f_{1y}^2)$ and $(f_{2x}^2+f_{2y}^2)$ are approximately same, the coordinate system does not become an orthogonal one and an error occurs strictly (paragraph 0640). That is, the correction using eq. (Rot1) cannot be performed. Alternatively, also in this case, eq. (Rot2-3) is effective as explained later. FIG. 50 shows the schematic of the quasi-axial direction fx' and quasi-lateral direction fy' in a frequency domain. The directions fx' and fy', and the corresponding spatial coordinates x' and y' cannot become the symmetric axis of the waves.

Thus, as a fundamental processing (pre-processing) for the demodulation methods described above and in the non-patent document 30 and the patent document 7, to make the two waves' magnitudes of instantaneous frequency vectors or that of the local or global 1st moment (frequency) vectors $\sqrt{(f_{1x}^2+f_{1y}^2)}$ and $\sqrt{(f_{2x}^2+f_{2y}^2)}$ same, the correction is performed for one of waves by multiplying a constant value to all frequencies expressed in the 2D orthogonal coordinate system (x,y) to be used for the observation and the instantaneous phase difference (change) as well (That is, the complex autocorrelation signals with the corrections in such a way are used.). Or, for the each wave, the normalizing can be performed by dividing all the frequencies in the x- and y-directions and the instantaneous phase difference by the magnitude of the instantaneous frequency vector or that of the local or global 1st moment (frequency) vector $\sqrt{(f_{1x}^2+f_{1y}^2)}$ or $\sqrt{(f_{2x}^2+f_{2y}^2)}$ of each wave (That is, the complex autocorrelation signals with the normalizations in such a way are used.). Other equivalent processings can also be performed such as one making the magnitude of the instantaneous frequency vector or the local or global 1st moment (frequency) vector some same value, which can be realized by normalizing the frequencies in the respective directions and the instantaneous phase difference (change) as well, etc. This is one of inventions for the demodulation processing described above and described in the nonpatent document 30 and the patent document 7. All the demodulation processings are made highly accurate.

Or, without performing such a pre-processing, after calculating the angles $\theta_a$ and $\theta_1$ of the quasi-axial direction x' and the quasi-lateral direction y' generated in practice, instead of the angle correction described in the paragraph 0661, the target displacement vector expressed in the 2D orthogonal coordinate system (x,y) to be used for the observation can be calculated using the respective direction displacements $d_a$ and $d_l$ together. Since the axial direction x' and the lateral direction y' are not orthogonal obviously, here the respective direction displacements are denoted using other characters, $d_a$ and $d_l$, being different from the respective direction displacements, dx' and dy', used for the above-described case where the axial direction x' and the lateral direction y' are orthogonal or approximately orthogonal:

$$\begin{pmatrix} d_a \\ d_l \end{pmatrix} = \begin{pmatrix} \cos\theta_a & \sin\theta_a \\ \cos\theta_1 & \sin\theta_1 \end{pmatrix} \begin{pmatrix} d_x \\ d_y \end{pmatrix} \quad \text{(Synv0)}$$

where the respective $\theta_a$ and $\theta_1$ can be calculated as $\tan^{-1}(F_{ay}/F_{ax}) = \tan^{-1}\{(f_{1y}+f_{2y})/(f_{1x}+f_{2x})\}$, and $180°+\tan^{-1}(F_{1y}/F_{1x}) = 180°+\tan^{-1}\{(f_{1y}-f_{2y})/(f_{1x}-f_{2x})\}$ when $F_{1x}<0$ or $\tan^{-1}(F_{1y}/F_{1x}) = \tan^{-1}\{(f_{1y}-f_{2y})/(f_{1x}-f_{2x})\}$ when $F_{1x}>0$ using $(f_{1x}, f_{1y})$ と $(f_{2x}, f_{2y})$, or similarly calculated from the 1st moments (frequencies) of spectra or the instantaneous frequencies of the product and the conjugate product of the complex autocorrelation signals, $(F_{ax}, F_{ay})$ and $(F_{1x}, F_{1y})$. Or, using eq. (demodu0) and eq. (Synv0) leads $$\begin{pmatrix} \alpha_a \\ \alpha_1 \end{pmatrix} = \begin{pmatrix} F'_a & 0 \\ 0 & F'_1 \end{pmatrix} \begin{pmatrix} d_a \\ d_l \end{pmatrix} = \quad \text{(Synv1)}$$

$$\begin{pmatrix} F'_a & 0 \\ 0 & F'_1 \end{pmatrix} \begin{pmatrix} \cos\theta_a & \sin\theta_a \\ \cos\theta_1 & \sin\theta_1 \end{pmatrix} \begin{pmatrix} d_x \\ d_y \end{pmatrix} = \begin{pmatrix} F_{ax} & F_{ay} \\ F_{1x} & F_{1y} \end{pmatrix} \begin{pmatrix} d_x \\ d_y \end{pmatrix}.$$

Thus, eq. (Rot2-3) holding in the orthogonal coordinate system can also hold for the non-orthogonal case. Eq. (Synv1) can be solved.

Also in the case of observing a 3D displacement vector, as the fundamental processing (pre-processing) for the demodulation methods described above, or in the nonpatent document 30 and the patent document 7,similarly, to make the three or four waves' magnitudes of instantaneous frequency vectors or that of the local or global 1st moment (frequency) vectors $\sqrt{(f_{1x}^2+f_{1y}^2+f_{1z}^2)}$, $(f_{2x}^2+f_{2y}^2+f_{2z}^2)$, $\sqrt{(f_{3x}^2+f_{3y}^2+f_{3z}^2)}$ and $\sqrt{(f_{4x}^2+f_{4y}^2+f_{4z}^2)}$ same, the correction is performed for one of waves by multiplying a constant value to all frequencies expressed in the 3D orthogonal coordinate system (x,y,z) to be used for the observation and the instantaneous phase difference (change) as well (That is, the complex autocorrelation signals with the corrections in such a way are used.). Or, for the each wave, similarly the normalizing can be performed by dividing all the frequencies in the x-, y- and z-directions and the instantaneous phase difference by the magnitude of the instantaneous frequency vector or that of the local or global 1st moment (frequency) vector $\sqrt{(f_{1x}^2+f_{1y}^2+f_{1z}^2)}$, $\sqrt{(f_{2x}^2+f_{2y}^2+f_{2z}^2)}$, $\sqrt{(f_{3x}^2+f_{3y}^2+f_{3z}^2)}$ or $\sqrt{(f_{4x}^2+f_{4y}^2+f_{4z}^2)}$ of each wave (That is, the complex autocorrelation signals with the normalizations in such a way are used.). Other equivalent processings can also be performed such as one making the magnitude of the instantaneous frequency vector or the local or global 1st moment (frequency) vector some same value, which can be realized by normalizing the frequencies in the respective directions and the instantaneous phase difference (change) as well, etc. Or, without performing such a pre-processing, after calculating the angles of the quasi-axial direction x', the quasi-lateral direction y' and the quasi-elevational direction z' generated in practice, instead of the angle correction described in the paragraph 0661, the target displacement vector expressed in the 3D orthogonal coordinate system (x,y,z) to be used for the observation can be calculated using the respective direction displacements together (similarly to eq. (Synv0) in the 2D case). Or, together with the instantaneous phase differences (changes) of the axial direction x', lateral direction y' and elevational direction z', the instantaneous frequency vectors or the 1st moment (frequency) vectors expressed in the orthogonal coordinate system to be used for the observation can also be used similarly to eq. (Synv1).

The measurement and imaging related to the embodiment of the present invention can also apply the orthogonalization of waves being pre-processing of the displacement vector measurement described above to the imaging of the waves themselves. As described in the paragraph 0641, for generating the lateral modulation imaging signal having independent frequencies in the orthogonal directions, two, three or four waves with the same carrier frequency, instantaneous frequency, or local or global 1st moment (frequency) in the respective waves' propagation directions are required to be generated (i.e., the same magnitude for the instantaneous frequency vectors or the local or global 1st moment (frequency) vectors).

For instance, the control unit 34 shown in FIG. 2 controls the transmission unit 31 and the reception unit 32 such that the wave signal data can be generated at least two temporal phases by scanning the observation object laterally at least with three steered waves generated electrically or mechanically with different steering angles each other (zero or non-zero) in the 3D orthogonal coordinate system having three axes of the depth direction, the lateral direction orthogonal to the depth direction, and the elevational direction orthogonal to the depth and lateral directions, or at least with two steered waves generated electrically or mechanically with different steering angles each other (zero or non-zero) in the 2D orthogonal coordinate system having two axes of the depth direction, and the lateral direction orthogonal to the depth direction.

Or, when the digital signal processing unit 33 shown in FIG. 2 uses complex analytic signals having waves' instantaneous phases as kernels, obtained from single octant or quadrant spectra corresponding to the wave signal data generated by scanning the measurement object with a single steered wave at least at two temporal phases, or complex autocorrelation signals or complex signals having the instantaneous phase change generated at least between the two temporal phases as kernels to calculate 3D and 2D displacement vectors in the cases of 3D and 2D orthogonal coordinate systems, respectively, to make the magnitudes of the instantaneous frequency vectors or the 1st moment (frequency) vectors of the complex analytic signals, complex autocorrelation signals, or complex signals of all waves same, the instantaneous frequency vectors' components or the 1st moment (frequency) vectors' components, and the instantaneous phases or the instantaneous phase changes of the complex analytic signals, complex autocorrelation signals, or complex signals of the respective waves can be multiplied by the respective constants or can be respectively normalized, and the corrected, corresponding wave signal data of all the waves, which are symmetric with respect to the axis of the 3D or 2D orthogonal coordinate system or the rotated one with respect to the origin, are superposed for the imaging. Further, this processing can include yielding the product and the conjugate product for two complex analytic signals, two complex autocorrelation signals, or two complex signals, which express new two waves with the orthogonal propagation directions.

For the above-described displacement vector measurement and the imaging of a wave itself, in addition to the above-described plurally generated waves, various other waves can be used. For instance, the transmission unit 31, the reception unit 32, or the digital signal processing unit 33 shown in FIG. 2 generated plural waves, which includes at least new one generated (A) by superposing at least two waves, (B) by dividing at least original or (A) superposed one, (C) by using (B) for superposing with another wave.

Thus, the demodulation method of the present invention allows the high accuracy observation of a displacement vector in various cases even where the propagation directions (steering directions) of plural waves do not have the coordinate axis of the orthogonal coordinate system used for the observation (observation coordinate system) as the symmetric axis, or even where the frequencies in the propagation directions of plural waves are different each other, etc. as described above. That is, similarly to the multi-dimensional autocorrelation method, the multi-dimensional Doppler method, the multi-dimensional cross-spectrum phase gradient method, etc., generating independent waves with different steering angles or different frequencies, of which number is the same as that of unknown displacement vector components allows the high accuracy observation of the displacement vector. Or, particularly when generating a laterally wideband wave, similarly to other measurement methods, it is also effective to generate independent quasi-waves of which number is the same as that of the unknown displacement vector components by spectral frequency division, or it is also effective to make the lateral frequency higher by disregarding the lateral low frequency spectra (The generated quasi-waves can also be processed similarly to in the case where plural waves are directly generated.). Or, solved can also be over-determined system about the unknown displacement vector in the observation coordinate system generated by more waves or quasi-waves than the number of unknown displacement vector components via processings such as the generation of plural waves or the spectral frequency division, etc. (The generated quasi-waves can also be processed similarly to in the case where plural waves are directly generated.). The processings of generation of plural waves and the spectral frequency division can also be performed simultaneously (The generated quasi-waves can also be processed similarly to in the case where plural waves are directly generated.). For increasing the bandwidth of a wave, it is effective to perform the coherent addition (coherent superposing or compounding) with respect to plural waves generated simultaneously with different frequencies or steering angles, or plural waves generated at different times but at the same temporal phase. For such an over-determined system, it is useful to perform the weighted least squares estimation described in the paragraphs 0391 and 0392, etc., or various optimization methods described in the present inventions and not limited to these. For the optimizations, the phase matching described in the paragraph 0416 is useful. In the case, the phase matching can also be performed for the system of equations about the unknown update displacement vector expressed in the observation coordinate system by using the coarse measurement result obtained in the observation coordinate system, or the phase matching can also be performed for the system of equations about the unknown update displacement expressed in the quasi-coordinate-axis by using the coarse measurement result obtained in the quasi-coordinate-axis directly or indirectly from the coarse measurement result obtained in the observation coordinate system. When not performing the optimizations, based on the original phase matching method (patent document 6 or nonpatent document 15, etc.), the coarse measurement result obtained in the observation coordinate system can also be added to the fine result (update displacement) calculated by the demodulation method in the observation coordinate system, or the coarse measurement result expressed in the quasi-coordinate-axis can also be added to the update displacement calculated by the demodulation method in the quasi-coordinate-axis. Other modified methods can also be performed. For the calculation of the multi-dimensional analytic signal, in addition to the method using the Fourier transform (nonpatent document 13, etc.), the approximate processing method about the Hilbert transform, using the differential processing, described in the paragraph 0506 to 0508, etc. is also useful. Although the explanation is performed mainly in the case where the complex autocorrelation signal is used, as described above, the complex signal led based on the multi-dimensional Doppler methods can also be used (expressing the relation between the instantaneous frequencies and the instantaneous phase difference), and the case where the nonlinear signal processing <2> or <3> is performed can also be processed similarly.

As far, several examples are presented, where the present invention is applied to the ultrasonic imagings or the ultrasonic measurements. The present invention can be used for other waves from the ultrasound similarly to other processing methods. When the bandwidth of the signal components generated (calculated) using the present invention overlaps that of other signal, it is impossible to separate them in a frequency domain. In the cases, the pulse inversion method or the separation using polynomial terms can be used. Alternatively, the inventor of the present invention processes the superposed spectra and for instance, the spectra can also be divided (nonpatent document 30). On the present invention, included cases where spectra overlaps, the way how to separate the waves with a high accuracy is to obtain an effect that the overlapped spectra can be distinguished well in a frequency domain by performing the exponentiation processings (calculations) as the nonlinear processings onto the superposed waves, and the waves shown as the wide-banded harmonic waves are to be separated in a frequency domain. Inversely, a high frequency signal can be changed by a low frequency signal; a wide-band signal can be changed by a narrow-band signal; they can also be displayed or processed. The separation can also be performed with a high accuracy in a frequency domain after performing decreasing the frequencies and the bandwidths (the order less than 1) as well as the increasing the frequencies and the bandwidths (the order larger than 1) using the exponentiation processings (calculations). The propagation direction can be calculated using the estimates of the 1st moments of spectra of the harmonic wave generated (local direction, i.e., with a spatial resolution, or macro direction with low or no spatial resolution) or the instantaneous frequencies (having a spatial resolution) estimated from the analytic signals. Or, using the exponentiation order implemented can allow the inverse calculations about the wave parameters such as frequencies or bandwidths, etc. of the original waves, and the restoration can also be allowed to be performed in a separated state (It is simple to restore the waves after separating the harmonic waves, i.e., by implementing the exponentiation processings (calculations) using the reciprocals of the order used). In such situations, it is also possible to measure the signal source positions or the signal arrival directions, the signal source intensities, the sizes of single sources or the distributions. When generating higher frequency signals than the original signal, in advance to the processings (calculations), it is required to increase the bandwidth such that the processings can be achieved. For that, the spectral zero padding is effective with no approximations (nonpatent document 30), whereas the sampling intervals can also be shorter directly on the basis of the temporal or spatial approximate interpolations.

Recently, it becomes possible to perform simulations on the nonlinear propagations with low costs. Therefore, the nonlinear calculations of the present invention or such simulation technologies can also be implemented onto not beamformed signals (plane wave, etc.) or SA echo signals (data set) to generate nonlinear signals. Also, on the basis of these, the nonlinear signals measured in practical can also be analyzed using an inverse problem approach (inverse analyses) and can be used for the tissue diagnoses.

For instance, when using ultrasounds for living tissues, for performing the tissue characterization, estimations about the acoustic propagation speed, the bulk modulus, the acoustic impedance, the reflection, the Rayleigh scattering, the back scattering, the multiple scattering or the attenuation can be performed and can be used for diagnoses. Also on other waves, it becomes possible to perform the inverse analyses about the phenomena or physical properties related to (On lights, Mie scattering, scatterings on radioactive rays or Compton scattering, etc.).

On the treatments using heating or warming, it is required to be clarified the object's reception properties of heat (for instance, properties with respect to the pressure of a high intensity ultrasound, or effects of agents or contrast media, etc.) and the characteristics of increase in a temperature, which is required to understand generally or at clinical sites. In such situations, the calculations including the nonlinear calculations become effective. Also on the treatment, it is effective that the effects are evaluated and used on the basis of the imagings of nonlinear effects using the present invention. Or, it is also possible to perform echo imagings or tissue displacement measurements using the present invention on the reception signals physically effected by the nonlinearities or the separated base-banded signals and plural harmonic waves.

The present invention relates to imaging instruments that increases the frequencies, the bandwidths and contrasts of signals by implementing nonlinear processings such as the multiplications or the exponentiations onto coherent signals of arbitrary waves such as electromagnetic waves, lights, radioactive rays, mechanical vibrations, acoustic waves except for the ultrasounds, and thermal waves, etc. in addition to the ultrasounds. Using the present invention, increasing, imitating, newly generating the harmonic waves can be performed. Furthermore, the harmonic waves can be virtually realized.

Also, with fewer calculations than the general detection processings, a signal of a base-band and detected signals, in an arbitrary direction, of the harmonic wave signals can also be simultaneously obtained. As the results, for instance, increasing the frequencies and bandwidths, and contrasts or suppressing the sidelobes can be achieved and also high SNR nonlinear imagings become possible. Also, using the general one-directional displacement measurement methods, the measurement of a displacement vector become possible to be performed simply with fewer calculations. From the viewpoint of the generating the chord or different tone waves, or the harmonic tone waves, high or low frequency signals can be obtained including the cases where the frequencies or carrier frequencies, the steering directions or the propagation directions, etc. are different and then, these can also be effectively used for imagings or measurements. The waves or beams to be generated by the nonlinear effects as well as the linear effects can be designed (parameters of beams or waves such as a propagation direction, etc.) via theories and calculations and can also be controlled.

Alternatively, in the area of an image measurement, it is well known that observations of motions are performed by using incoherent signals (the results are displayed using images) generated by implementing various type detections (including simply absolute values being evaluated on signals, etc.) on coherent signals. Methods equivalent to the cross-correlation method, the optical flow or the SAD (Sum and Difference) method, etc. can be used. Also, implementing the present invention onto incoherent signals increases the bandwidths (spatial resolution). Also, used can be the above-mentioned high spatial resolution detection signals obtained using the present invention. High density data via increasing the bandwidths are proper to the processings and then, the measurement accuracies of the motions also increase. The above-mentioned method can also be used for the coherent signals and also in the cases, the increasing the bandwidths is effective for increasing the measurement accuracy. That is, the present invention can be used both for arbitrary coherent signals and arbitrary incoherent signals.

Or, on the warming, the heating, the cooling, the freezing, the welding, the restoration, the thermal treatment of cancerous diseases (thermal therapy) or the cryotherapy or the washing such as of arbitrary objects (glasses, etc.) performed using waves (laser, ultrasound or high intensity focus ultrasound), the present invention can increase the effects and the spatial resolution via the nonlinear phenomena or the prediction about the effects (for instance, the exponentiation effects by the thermal treatment using the high intensity focus ultrasound, the increases the effects using the crossed beams, i.e., the increasing the frequencies and the spatial resolutions by the multiplication as well as the increasing the spatial resolutions by the addition, etc.).

On the thermal treatment, etc. using the high intensity focus ultrasound, since the harmonic waves are generated owing to the tissue nonlinear effects and the harmonic waves are high frequencies, the absorption effects as a thermal energy are strong. Thus, it is simple to understand the heat building up in tissues and it is also possible to predict it. Form the same viewpoint, for the treatment, it is effective to transmit a high frequency signal, a wideband signal or a harmonic wave, or to generate superposed beams or crossed beams and also, the understanding and the prediction becomes simply possible. Concretely, a sound pressure geometry or a PSF (point spread function) can be estimated on the basis of the simulation on the sound field or the estimation of autocorrelation function on a system allowable to receive reception signals and then, it is effective that the harmonic wave signals are evaluated directly or the nonlinear processings (calculations) are also implemented onto the fundamental wave signal. This is similar for other waves.

Also, the present invention is also effective in obtaining nonlinear effects even under the physical conditions that physically the nonlinear effects cannot be obtained (For instance, the wave intensity cannot be increased with respect to the measurement object or due to a high frequency of the wave, a high intensity of the wave cannot be obtained, etc.). In contrary, for instance, for the ultrasound echo imaging, the displacement measurement or the treatment, it is possible to perform the present invention under the condition that the nonlinear effects are enhanced by using contrast agents such as microbubbles, etc. The tissues with the agents diffused through can also be processed and the agents are also proper to the measurements or imagings on bloods in the vessels or in a heart. That is, the present invention can increase, imitate, newly generate the nonlinear effects. Furthermore, the present invention can also virtually realize the nonlinear effects. As mentioned above, it is possible to perform the evaluations of the nonlinear effects. The contrast agents can also be used for increasing the effects of the thermal treatments. These are similar for other waves.

Also, when high frequency signals are generated, which cannot be realized by using a single signal source, it becomes possible to perform higher spatial resolution imagings and higher accuracy Doppler measurements. In general, the effects of attenuations are intense on high frequency components and for instance, it is desired that on microscopes that is suffered from the attenuations, the deep region can be observed using high frequency waves. For instance, when using plural 100 MHz ultrasound transducers, physically the same times as the number of used transducers as high frequency ultrasounds as that of the single transducer used can be generated, i.e., high frequencies being not able to be generated by a general transducer can be generated. It is also useful for generating a high frequency single (a chord tone wave) simply. By using the present invention, such high frequency waves can also be generated through processings or calculations. Thus, the present invention can also generate high frequency waves or signals that cannot be generated physically. Similarly, it is also possible to perform the low frequency imagings or measurements using the low frequency signals (for instance, a different tone wave). Also, it is possible to generate low frequency signals that cannot be generated by a single signal source. The generated waves can also be controlled by realizing these signals theoretically or on the basis of calculations.

Below, to demonstrate the effects of the present invention, explanation is performed about experimental data, simulation results and material data such as photographs, etc. These are ultrasonic simulations and agar phantom experiments used for demonstrating the effectiveness of the present invention on the ultrasonic echo imagings and measurement imagings. The present invention can also be used for arbitrary signals except for the ultrasonic echo method (familiar signals by lasers, light waves, OCT signals, electric signals, magnetic signals, radioactive rays such as an X-ray and thermal waves, etc.) and can also be used between different type signals. These can be used for raw coherent signals or incoherent signals obtained after signal processings.

With respect to the echo signals obtained by performing the frontal beamforming and lateral modulation beamforming (a lateral modulation frequency, 3.5 MHz) using the SA echo data (a linear-type array transducer, 7.5 MHz) obtained from an agar phantom disclosed in the nonpatent document 30, the above-mentioned processings <1> to <3> are performed.

Figure 51:
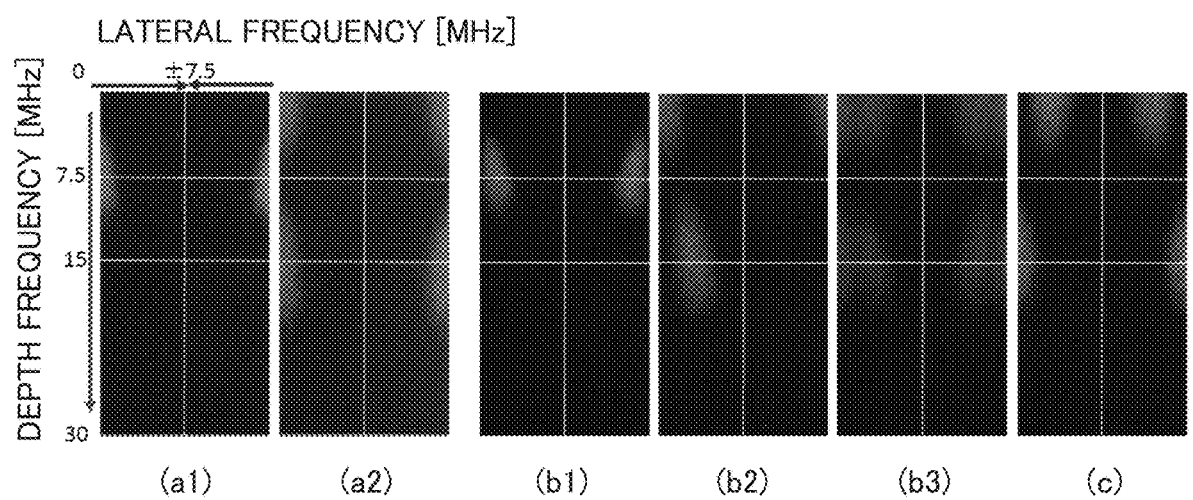
FIG. 51 shows varieties of spectra of echo signals obtained via an embodiment of the present invention.

FIG. 51 shows varieties of spectra of echo signals obtained via an embodiment of the present invention. In FIG. 51, the horizontal and vertical axes respectively express the lateral frequency [MHz] and the depth frequency [MHz]. In FIG. 51, (a1) and (a2) respectively show for the no steering case, spectra of the original echo signals and squared echo signals. (b1), (b2) and (b3) respectively show for the lateral modulation, spectra of the original echo signals, squared echo signals steered only in one direction and squared lateral modulation echo signals. (c) shows the spectra obtained by the multiplication of echo signals of the crossed, steered beams. From FIG. 51, the spectra derived in the above-mentioned theory for the respective signals can be confirmed. For all the echo signals, as the results of the square or the multiplication, the spectra of the 2nd harmonic waves are generated of which bandwidths become wider than the original spectra.

Figure 52A:
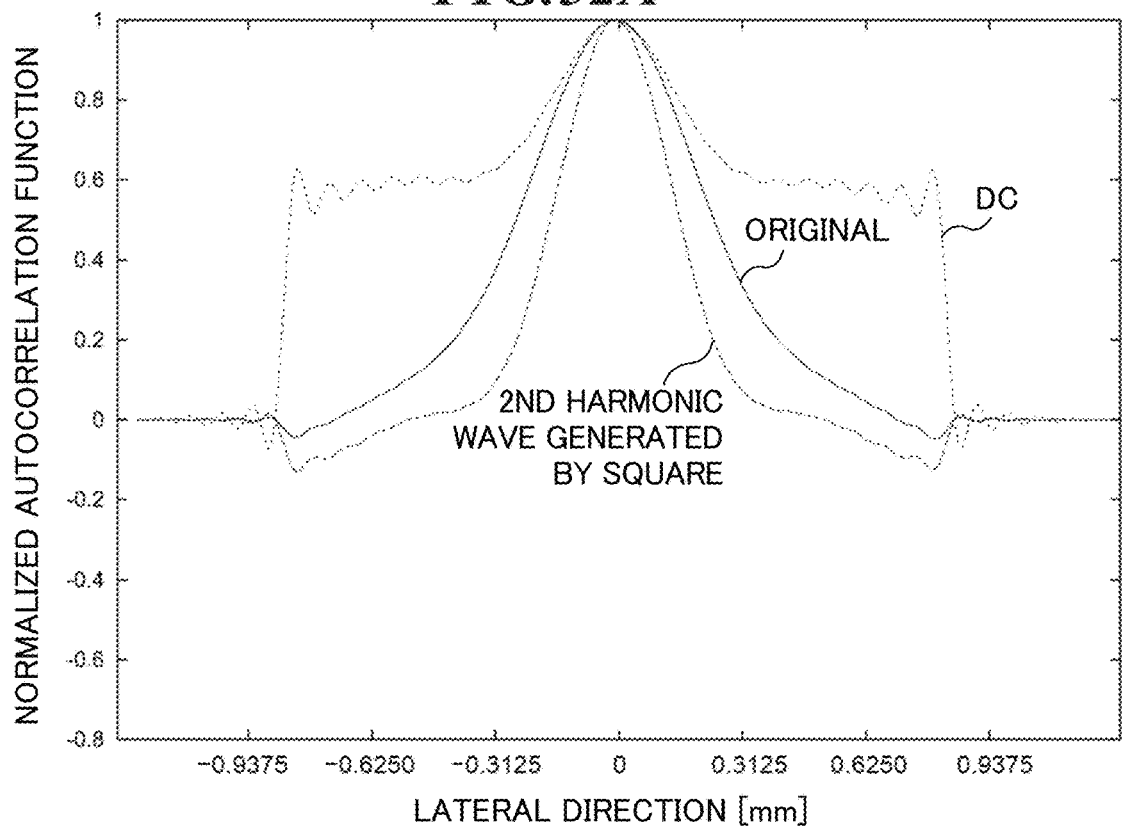
FIGS. 52A to 52C show varieties of autocorrelation functions of echo signals obtained via an embodiment of the present invention.
Figure 52B:
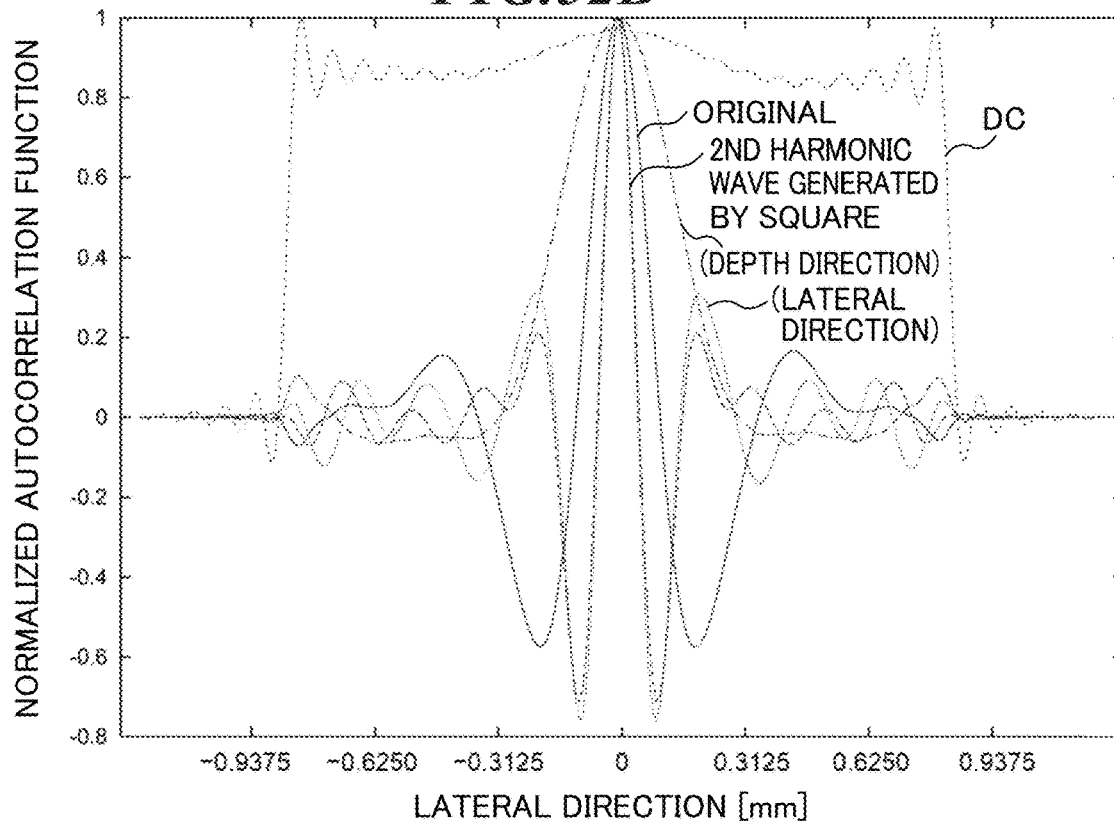
Figure 52C:
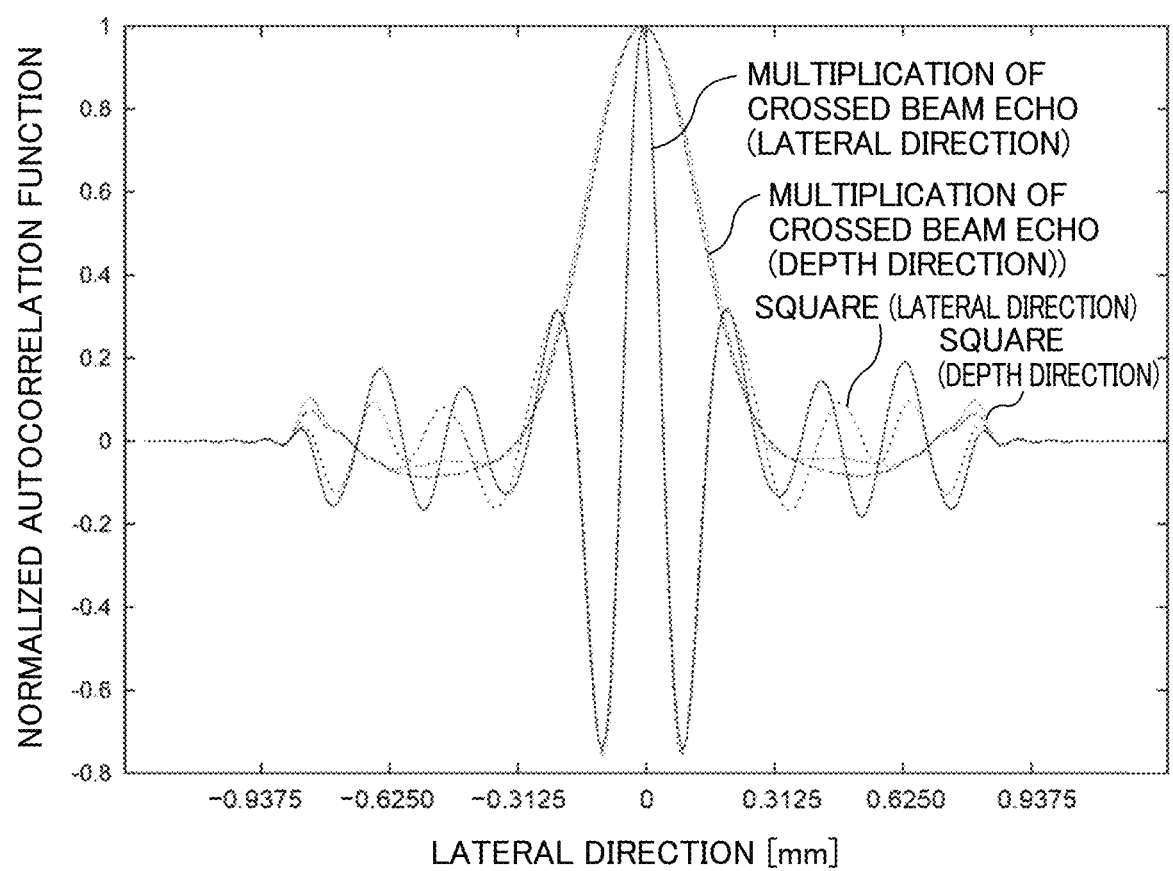

FIGS. 52A to 37C show varieties of autocorrelation functions of echo signals obtained via an embodiment of the present invention. Here, the lateral and vertical axes respectively show the lateral position [mm] and the normalized autocorrelation function. FIG. 52A shows for the no steering case, comparison about the normalized autocorrelation functions between the original echo signal and the 2nd harmonic wave obtained from the squared echo signal. FIG. 52B shows for the lateral modulation case, comparison about the normalized autocorrelation functions between the original lateral modulation echo signal and the 2nd harmonic waves obtained from the squared lateral modulation echo signal. FIG. 52C shows for the multiplication of crossed beam echo signals and the squared lateral modulation echo signal, the normalized autocorrelation functions of the lateral components and depth components. On the basis of the autocorrelation functions, the lateral profile of the sound pressure or the point spread function (PSF) can be evaluated (in the case of depth, 19.1 mm, i.e., at a centered depth in the ROI). Although omitted here, with respect to the 2D echo signals, calculation of the 2D autocorrelation function allows the evaluation of a 2D distribution of the sound pressure or the PSF, whereas with respect to a 3D echo signals, a 3D autocorrelation function can be used.

FIGS. 53 to 55 show varieties of B-mode echo images obtained via an embodiment of the present invention. The depth of these echo images ranges from the depth, 10.0 to 28.1 mm, and the lateral width is 20.7 mm. In the agar phantom, a cylindrical inclusion (dia.=10 mm) is centered on the ROI (depth, 19 mm) of which shear modulus is 3.29 times as large as that of the surrounding.

In FIGS. 53 to 55, (a1), (a2) and (a3) respectively show for the no steering case, echo images obtained on the basis of the original echo signal, the base-banded signal, the 2nd harmonic wave obtained from the squared echo signals. In the cases where there exist two images at the left and right sides, the left and right images respectively show the results obtained on the basis of the envelope and squared detections.

(b1), (b2), (b3), (b4) and (b5) respectively show for the lateral modulation case, echo images obtained on the basis of the original lateral modulation echo signal, the base-banded signal, the 2nd harmonic wave obtained from the squared lateral modulation echo signal, the lateral component of the 2nd harmonic wave obtained from the squared lateral modulation echo signal and the depth component of the 2nd harmonic wave obtained from the squared lateral modulation echo signal.

Also, (c1) and (c2) respectively show for the 2nd harmonic waves obtained by the multiplication of the crossed beam echo signals, echo images obtained on the basis of the lateral components and the depth components. When there exist plural waves, the inventor of the present inventor also disclosed the detection to be implemented on a superposition of coherent signals at past and however, the results of a superposition of the respective detection signals are shown here.

It can be confirmed that corresponding to the increasing in bandwidths as the spectra shown in FIG. 51, the spatial resolutions increase as shown in FIGS. 52A to 52C and FIGS. 53 to 55. Here, the direct current in the base-banded data is not cut off. The direct current or if required, the remarkedly low frequency spectra in the depth and lateral directions are cut off by filtering, etc., the lines running in the vertical direction with the high and low brightness (vertical stripes) can be removed completely (the results omitted). From FIGS. 52A to 52C, it can be confirmed that the sidelobes are suppressed. Corresponding to these, From FIGS. 53 to 55, the increasing in a contrast can also be confirmed (It is worthy of note the strong scatter, etc.). Since the attenuations are not corrected on the original echo signals, due to the increasing in a contrast under the no correction, the images obtained from the signals after implementing the nonlinear processing onto have much lower signal intensities at the deep region than the shallow region compared to the original signal images.

On the imagings using the original signals, the so-called attenuation correction with respect to the wave propagation is implemented onto the coherent signals or the incoherent signals obtained by the detection, whereas on the present instrument, the nonlinear processings can also be implemented onto the coherent signals obtained by implementing the attenuation correction onto the original coherent signals in advance, or the coherent or incoherent signals obtained by implementing the nonlinear processings onto are corrected. Similarly to the general correction processing, on the present invention, the correction processing itself can also be implemented mainly on the basis of the signal intensities before or after performing the reception beamformings or after generating the images. According to the Lambert's law, the correction can also be performed.

In the cases, a mean attenuation coefficient can also be used simply, whereas for performing accurate corrections, the attenuation coefficients of respective positions on the waves or beams propagation paths can also be calculated by the calculation unit 130 via signal processings or in an inverse problem approach and can be used. That is, the correction can be adaptively or automatically performed. Or, the operator can adjust the intensities at the respective depths within the specified range via the control unit 133 with referring to the generated images. According to the measurement object, patterns to be selected can also be prepared.

The gain control can be performed by the receiver 122, the amplifier or the attenuator installed into the filter/gain control unit 123 or 125, the amplifier, the attenuator installed into or the digital processings performed by the reception beamformer 129, or the analogue or digital processings performed by the calculation unit 130. On the transmitter 121, the intensities of beams or waves to be transmitted can also be adjusted. Also, as the operation device 112, an amplifier or an attenuator can be used and then, the wave intensities themselves can also be adjusted. It is cautious that the use of the contrast agent 1a has prominent effects on the determinations.

On the square calculation on the lateral modulation echo signal (processing <2>) of the above-mentioned experiments, since the laterally detected spectra (one of two spectra that can also be obtained by detecting the 2nd harmonic waves in different one direction) overlaps with those of the simultaneously generated 2nd harmonic waves, the inventor of the present invention divided them by the visual estimation. Although the results are compared with those of the multiplication of the two waves of the lateral modulation echo signals (processing <3>) on the estimated autocorrelation functions (FIG. 52C), there is no difference except for that the harmonic frequency becomes lower slightly.

In addition to these experiments, using the multi-dimensional autocorrelation method, a displacement vector measurement, a strain tensor measurement and a shear modulus reconstruction are performed. In the results obtained, here shown in FIG. 56 are the results obtained using the processing <3>, i.e., the two signals of the 2nd harmonic waves detected in different one direction, for the measurements of displacement components in respective two directions.

Figure 56:
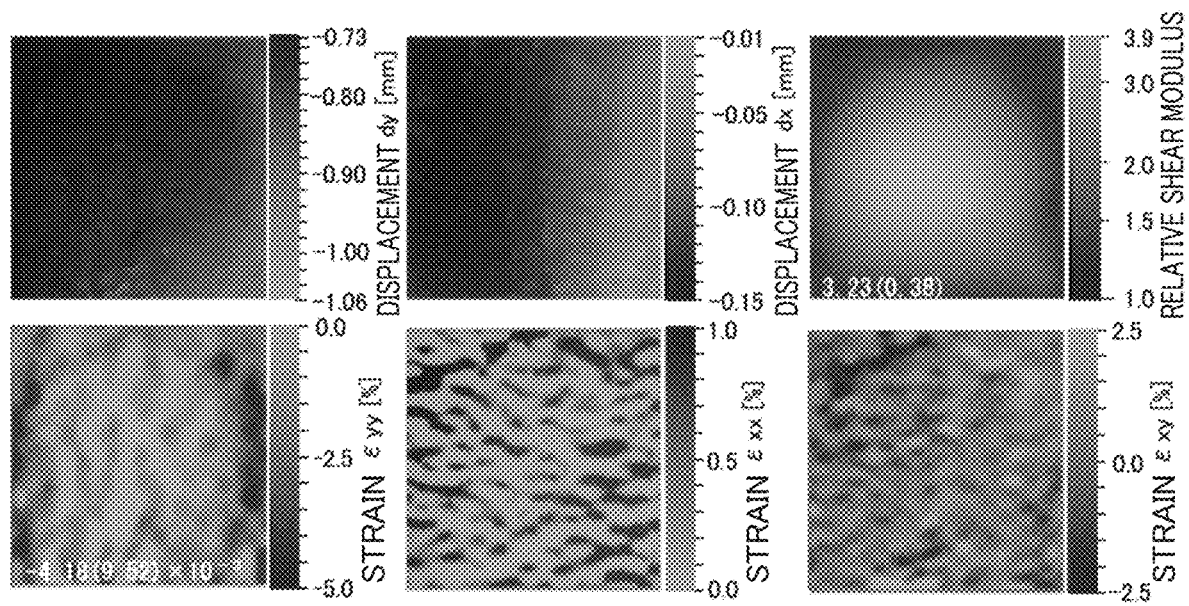
FIG. 56 shows images of a displacement vector, a strain tensor and a relative shear modulus measured on an agar phantom via an embodiment of the present invention.

FIG. 56 shows images of a displacement vector, a strain tensor and a relative shear modulus measured on an agar phantom via an embodiment of the present invention. The parts of FIG. 56 also show the means and the standard deviations (SDs) estimated on the center of the inclusion in the parentheses. Compared with the results obtained by performing the digital demodulation onto the same lateral modulation echo data, the noise intends to increase (SD of the lateral (y) strain increased from $3.08 \times 10^{-3}$ to $9.52 \times 10^{-3}$) and however, the spatial resolution becomes the two-fold and on the shear modulus reconstruction, the accuracy is also improved with performing the regularization (the means changes from 3.37 to 3.23).

Here, although the results are omitted, as mentioned in the paragraph 0655, with respect the generated plural beams or waves, the nonlinear processings can also be implemented onto the superposition, or after the nonlinear processings are implemented onto the respective beams or waves, the superposition can also be performed on them. As mentioned at others, the nonlinear processings can also be implemented onto raw reception signals (no reception-beamformed signals: only transmission beamforming or SA cases). Although plural waves or beams generated under using same wave or beamforming parameters can also be processed, those obtained under using different parameters can also be processed.

To increase the spatial resolution, the superresolution on the above-mentioned linear model is effective and then, such a superresolution can also be used for these plural waves or beams. That is, the superresolutions can also be implemented onto the superposition, or after the superresolutions are implemented onto the respective beams or waves, the superposition can also be performed on them. Both can be mixed and can also be processed. Superposition performed under the same parameters (additional averaging) with the noises to be reduced can also be processed. With respect to the original signals (including the cases where the signals are harmonic waves), prominently high spatial resolutions can be realized. Various type superresolutions are mentioned. For instance, as mentioned in the paragraph 0363, when the inverse filtering is performed using a desired PSF or spectra of a desired signal distribution such as a desired echo distribution, etc. as a target, similarly to as mentioned together with the displacement measurement in the paragraph 0390 to 0415, the Wiener filter can be used as the weights for the imagings of signals themselves. Particularly, for instance, when the weights on the basis of the Wiener filter used for eq. (A12') or eq. (A13') (the first squared norms of signal spectra are respectively removed) are used, the weighted norm of the inverse filter $$\frac{G_p(\omega_x, \omega_y, \omega_z)}{H_p(\omega_x, \omega_y, \omega_z)}, \quad \text{(AA1)}$$

where the respective $H_p(\omega_x, \omega_y, \omega_z)$ and $G(\omega_x, \omega_y, \omega_z)$ are the spectra of the signal to be processed and the target, being $$W_p(\omega_x, \omega_y, \omega_z) = \qquad (AA2)$$

$$\left\| \frac{G_p(\omega_x, \omega_y, \omega_z)}{H_p(\omega_x, \omega_y, \omega_z)} \right\| \left( \frac{\|H_p(\omega_x, \omega_y, \omega_z)\|}{\|H_p(\omega_x, \omega_y, \omega_z)\| + \sqrt{\frac{PW_{pn}(\omega_x, \omega_y, \omega_z)}{PW_{ps}(\omega_x, \omega_y, \omega_z)}}} \right)^q$$

or $$W_p(\omega_x, \omega_y, \omega_z) = \qquad (AA3)$$

$$\left\| \frac{G_p(\omega_x, \omega_y, \omega_z)}{H_p(\omega_x, \omega_y, \omega_z)} \right\| \left( \frac{\|H_p(\omega_x, \omega_y, \omega_z)\|^2}{\|H_p(\omega_x, \omega_y, \omega_z)\|^2 + \frac{PW_{pn}(\omega_x, \omega_y, \omega_z)}{PW_{ps}(\omega_x, \omega_y, \omega_z)}} \right)^q$$

where PWpn ($\omega_x$, $\omega_y$, $\omega_z$) and PWps ($\omega_x$, $\omega_y$, $\omega_z$) are respectively the power spectra of the noise and the signal. q is an arbitrary positive value. can be used for the processings. Also for other superresolutions on the linear model mentioned above, the Wiener filter can be used to decrease the amplification of noise. When, with no the Wiener filter, the norm of eq. (AA1) itself is implemented, only the frequency spectra having a larger than the $\in$-fold ($\in$<1) norm (maximum norm, $L_2$-norm, $L_1$-norm, etc.) of the signal spectra Hp($\omega_x$, $\omega_y$, $\omega_z$) can also be processed (Results of other frequency spectra are set to zero). On these, anomalistically, not the norm of eq. (AA1) but eq. (AA1) itself can also be used and the phase can also be matched. In the case, Gp($\omega_x$,$\omega_y$,$\omega_z$) can often have phase information about the measurement object.

Or, these weighting processings can also be performed on the blind convolution. When performing the whitening by implementing the inverse filtering using an another calculated PSF or system transfer function, when multiplying the conjugate of such PSFs, the system transfer functions or eq. (AA1) or when they are performed onto the pre- or post-beamformed signals (the state of only the transmission beamforming performed or reception signals acquired for SA), these weightings are useful. Particularly, on the inverse filterings, the regularizations can also be implemented. Or, the maximum likelihood (being MAP or not) can also be implemented.

With respect to the signals obtained by implementing the superresolution using these linear models, above-mentioned nonlinear processings can also be implemented. The spatial resolutions increase further and the contrasts increase further. As the results of the superresolutions using these linear models, the followings can be used, i.e., the superresolution-implemented original signal (that can also be a harmonic wave and also below), the superposition of the plural super-resolution-implemented signals, the superresolution-implemented, superposed plural original signals, their mixed and processed, etc. Also, when there exist plural original signals, the superresolutions are implemented onto the respective signals under the linear models and subsequently, the non-linear processings are implemented onto the respective results and superposed. They can also be mixed and processed.

Also, as mentioned above, with respect to the nonlinear processing-implemented signals, the superresolutions using the linear models can also be used. Although the spatial resolution can increase and however, the contrast can decrease. As the results of the superresolutions using the nonlinear processings, the followings can be used, i.e., the nonlinear-processings-implemented original signal (that can also be a harmonic wave and also below), the superposition of the plural nonlinear-processings-implemented signals, the nonlinear-processings-implemented, superposed plural original signals, their mixed and processed, etc.

Also, when there exist plural original signals, the nonlinear processings are implemented onto the respective signals and subsequently, the superresolutions using the linear models are implemented onto the respective results and superposed. They can also be mixed and processed.

When implementing these nonlinear processings onto the plural signals (expressing beams or waves and not limited to a fundamental wave and can be harmonic waves) at a position of interest, if the intensities of original signals before being processed are different due to the effects by the directivities of apertures, or the scatterings or attenuations in the object (including a case where they depend on the frequency), the differences can be increased and particularly when high order harmonic waves are generated, the differences becomes prominent. The differences can be positively imaged or can also be quantitatively confirmed on the spectral images (The frequency characteristics can be increased and confirmed). Alternatively, to decrease the differences for imagings, before or after implementing the nonlinear processings, the energies of signals or specific frequency spectra can also be weighted and can be used for the imagings. The plural signals superposed can also be imaged. The signal spectra or energies can also be estimated at a local region including a position of interest or over the ROI. Off course, regardless implementing the nonlinear processings or not, the weighting can also be performed similarly at performing the linear superposition.

Also, due to the effects of attenuations or reflections/scatterings during the propagations, the signal intensities become weak in a propagation direction and however, for instance, the degree of attenuation of a plane wave is weaker than that of a focused beam. Particularly for a higher order, the implementation of the nonlinear processings increases the effects. Thus, as mentioned above, before or after performing the nonlinear processings, the signal intensities can also be corrected (Also when not performing the non-linear processings, the correction can also be performed). The processings can also be performed before or after performing the detections.

There also exists various other superresolutions, one of which can be used together on the same or a different signal for performing the coherent addition to be used. As mentioned above, the superresolutions can also be performed for the superposed signals. Instead, inherent addition can also be performed to reduce speckles. Often the incoherent addition via the superresolutions does not make the spatial resolutions low as mentioned above.

Also, being dependent on the single intensities or SNRs, or the spatial resolutions on the respective processings of the superresolutions, spatially nonuniform addition can also be performed. That is, being dependent on them at the respective positions, the parameters of the respective methods can be variable. The cases where the spectra are processed are as above-mentioned and for instance, in the cases of the nonlinear processings, the parameters are the order of the exponentiation or the number of multiplications, etc. And when performing the additions of the coherent signals or the incoherent signals. The parameters are the number of additions or the weight values, etc. Off course, spatially uniform processes can also be performed.

As the effects of increasing contrasts by the nonlinear processings, scatters, reflectors or diffractions within a wave source or an observation object (tissue, etc.) can also be visualized particularly well. Increasing the order of exponentiation or the number of multiplications can also generate an effect that the difference in signal intensity (brightness for a gray image) becomes prominent. For instance, it can also become simple to detect the calcifications after the necrosises of living tissues. Or, for instance, being dependent on the signal intensities, coloring can be performed, which can be displayed with the superposing onto the general gray images or Doppler images, power Doppler images, contrast agent images, etc. After correcting the intensities of the signal distribution, the processings can also be performed. For instance, after performing the correction on the intensity of a signal (before or after detection) received from the ROI such that the signal intensity become uniform in the ROI, the nonlinear processings can be implemented to visualize the scattering intensity distribution or the scattering intensities of plural scatters, or the reflection intensity distribution or the difference in reflection intensity of reflectors. To count the number of the reflectors or scatters, the processings can also be performed. Except for a focused beam or SA, using a plane wave or a spherical wave, or cylindrical wave yields a low spatial resolution and also in such situations, various superresolutions such as the nonlinear processings are useful and particularly when performing the nonlinear processings, scattered waves or reflected waves can be visualized remarkedly well at the generated positions. For instance, when generating crossed waves, a cross-type wave shape can be enhanced and displayed as a scattered wave at the scatter position. The diffraction source can also be a target.

The PSF is calculated in a simulation for using one or two concave aperture HIFU applicators (simulation: frequency, 5 MHz; an aperture diameter, 12 mm; a focus depth, 30 mm) and also the exponentiation and the multiplication of the PSF. As mentioned above, this type calculation is effective in performing the considerations about the thermal effects. By collecting experimental data, it is possible to formulate the relationship among the sound pressure (PSF), the sound pressures of harmonic waves and reception properties of a heat, etc. and then, the formulation can be useful for increasing the efficiency of thermal treatment via designing the applicator or a radiated acoustic pressure (ultrasound parameter), etc. These are also for using other waves.

FIG. 57 shows varieties of acoustic pressures obtained using a concave HIFU applicator via an embodiment of the present invention. In FIG. 57, (a1) and (a2) shows for using one aperture the acoustic pressure image obtained from the original signal and the acoustic pressure images obtained from the squared signal (left including a direct current as well; right showing only the generated harmonic wave), respectively. (b1) and (b2) shows for using the two apertures (the crossed angles are ±5° with respect to the lateral direction) the acoustic pressure image obtained from the original signal and the acoustic pressure images obtained from the multiplied signals (left including a direct current as well; right showing only the generated harmonic wave), respectively. The images are obtained by the envelope detection and the image size is 3.8×12.8 mm². It can be confirmed that on the 2nd harmonic wave components respectively obtained by the square and the multiplication, the acoustic pressures concentrate on the desired regions and the contrast increases. Thus, the estimation of the intensity (i.e., power) of a fundamental wave and the acoustic pressure distribution geometry of the generated harmonic wave (with the 2nd order and over) can be performed. Also, the power consumed from the harmonic wave (intensity) can also be estimated. On the harmonics to be observed in practical, the similar estimations can be performed.

As far, regarding the imaging instrument according to an embodiment of the present invention, the nonlinear processing device of mainly the electromagnetic waves, mechanical vibrations including sounds, thermal waves, or the corresponding signals are mentioned. However, it is also possible to increase, imitate and virtually realize nonlinear effects between different kind (type) physical energies (i.e., in addition to cases where nonlinear effects are generated physically, chemically, or biologically, cases where nonlinear effects cannot be generated are included) and in the cases, the present invention can also be performed by that devices regarding the plural kind (type) waves to be processed are simultaneously used to receive the waves or at the same phase of the measurement object, the waves can be received at different times. That is, it is possible for the present invention to process the cases where plural kind (type) waves are generated simultaneously as well as the cases single kind (type) waves are generated solo.

On the respective electromagnetic waves, vibrations or thermal waves, the waves with different frequencies exhibit different dominant behaviors being dependent on the respective measurement objects (media) and then, the names are different. For instance, on the electromagnetic waves, there are a microwave, a terahertz wave, a radioactive ray such as an X-ray, etc. and on the vibration waves, for instance, in human soft tissues, a shear wave cannot propagate as a wave in a Mega Hertz bandwidth and an ultrasound is dominant, whereas a property of an incompressibility is intense and a shear wave is dominant in a low frequency range such as 100 Hz, etc. The present invention increases, imitates and virtually realizes nonlinear effects between such waves that exhibit different behaviors.

In the cases, the present invention can also be performed by that devices regarding the plural kind (type) waves to be processed are simultaneously used to receive the waves or at the same phase of the measurement object, the waves can be received at different times. Off course, since the phenomena such as attenuations, scatterings, reflections, refractions, diffractions, etc. have variances, there is a limitation that the waves must be properly used with considerations about the SNRs of reception signals. However, since high or low frequency components, which cannot be physically generated or captured, can be generated, the application range of the present invention is prominently broad.

Also mentioned are regarding imagings of the nonlinear processings or the nonlinear effects in the measurement object or applications to other measurements, where harmonic waves can be positively propagated in the measurement object as well as the original fundamental wave can also be positively used together in the situations. Also, over-determined systems can also be generated. The fundamental wave can also be processed similarly to the harmonic waves.

Furthermore, an arbitrary detection processing can be implemented onto at least one of plural signals generated via the nonlinear processings, or superposition can be performed after an arbitrary detection processing is implemented onto the plural signals that can include the basic signal, or an arbitrary detection processing can be implemented onto the superposition of plural signals that can include the basic signal to perform the imagings or measurements such as a displacement, etc. Regarding the superposition, the incoherent addition (incoherent compounding) is effective in performing a speckle reduction and if the generated high frequency signals are used, the spatial resolution does not become small. The problem of a low spatial resolution generation often caused by the general speckle reduction does not occur. Using the low frequency signals can also be useful, although the spatial resolution decreases.

Alternatively, the coherent addition (coherent compounding) can increase the signal bandwidths, i.e., spatial resolution. Particularly, when a high frequency signal is generated and used, the frequency increases, whereas when a low frequency signal is generated and used, the frequency decreases. Consequently, the spatial resolutions of imagings can also increase as well as the measurement accuracies such as a displacement and others can also increase. As mentioned above, the generated plural beams or waves, and signals obtained by the spectral frequency division can also be processed by these including the nonlinear processings.

The displacement measurements can be used as mentioned above, for instance, for radars, sonars and environmental measurements, etc. The application range is not limited. In addition to the displacement, a temperature can also be measured, for instance. Temperature sensors can directly also used for sensing a temperature, whereas the dependency of wave propagation properties on a temperature can also be detected to measure a temperature distribution, for instance, when using an ultrasound, thermal strains generated by the dependency of a sound speed and a volume change on a temperature are measured by the exclusive signal processings. Also, a chemical shift of magnetic resonance frequency can also be detected by using the signal processings. When measuring thermal waves, the nonlinearities can be imaged and can also be used for achieving a high efficiency of thermal treatments.

Investigating the nonlinear effects occurring in the measurement object can also be performed by switching the uses of cases where the observation of the nonlinear effects occurring in the measurement object is positively performed and the implementing of the present invention is performed; or by using both cases simultaneously and by using the nonlinear processing or calculations positively. That is, by skillfully using the nonlinearities of signal sources or contrast media, or the analogue or digital nonlinear processings, the nonlinear effects in the measurement object can be measured with a high accuracy and can also be imaged.

The above-mentioned imagings and measurements are on the basis of the performing proper beamformings, and proper detection methods and tissue displacement vector measurement methods, etc. are also important. As past, the present inventor developed particularly as the detection methods for multi-dimensional signals, the square detection, etc. in addition to the quadrature detection or the envelope detection; as the beamforming methods, the lateral modulation methods using crossed beams (nonpatent documents 13 and 30), the spectral frequency division method (nonpatent 30), the controlling the wave or beam geometries using spectral filtering, the using plural crossed beams and the over-determined system method, etc.; as the displacement vector measurement methods, the multi-dimensional autocorrelation method, the multi-dimensional Doppler method, the multi-dimensional cross-spectral phase gradient method and the phase marching method, etc. (nonpatent documents 13 and 30); and others, on the basis of the displacement or the strain measurement, the (visco) shear modulus distribution or the thermal property distributions can be reconstructed and imaged. With respect to not only the original waves or beams but also the superposition of plural waves or signals, or the waves or signals generated by the nonlinear processings being implemented onto (which can also include imitations), the spectral frequency division can yield quasi-waves or quasi-beams can be generated, and the spectral filtering can control the wave or beam geometries.

With respect to the superposition of plural signals that can include a fundamental wave or at least one of plural signals that can include a fundamental wave, signals obtained by implementing the spectral division or the filtering in a frequency domain (nonpatent document 30), the original signals that not there-processings-performed, or the using them together can also be used for generating the over-determined systems to perform the imagings or the other measurements such as a displacement, etc. as mentioned above, As mentioned above, the present invention for the coherent signals obtained by the sensors by detecting the transmission waves, the reflection waves, the refraction waves, the scattering waves or diffraction waves of arbitrary waves, the nonlinear responses with respect to a high intensity of a wave during the propagation or the nonlinear effects (generations of a harmonic wave or a chord tone wave, a different tone wave, etc.) such as the multiplication or the exponentiation generated on the superposing of waves can be obtained by implementing the analogue processings or the digital processings using the calculator and then, compared to the imagings using the original signals, imaging with a high frequency, a broad band, a high contrast and a high spatial resolution can be achieved. Not imaging with the increased frequency but with the decreased frequency can also be performed. Under the same effects, compared to the Doppler measurements using the original signals, measurements on the displacement, the velocity, the acceleration, the strain or the strain rate can be achieved with high spatial resolutions and with high accuracies.

The superposing of waves means one that generated among waves during the physical beamformings, or physically beamformed waves, physically nonbeamformed waves, etc. When the wave intensity is weak, mainly the superposition theorem on the basis of the linear principle can be observed, whereas when the wave intensity is strong, signals effected by the nonlinear effects such as the multiplication or the exponentiation (i.e., harmonic waves, chord tone waves, different tone waves) can be observed in addition to the superposition. The present invention focuses on the latter phenomena. The present invention also has one feature that the present invention can be used all these wave components and the superposed waves regardless the intensities. Off course, the present invention can be used for the fundamental wave or the waves including harmonic waves artificially radiated or generated during the wave propagation. As the harmonic waves generated during the wave propagation, for instance, there are ultrasound harmonic signals, etc.

With respect to this, for instance, with respect to beams generated by the beamformings (physical apodizations, delay processings or summing, or their calculations), the waves themselves not beamformings-performed (plane waves, reception signal sets for SA, etc.), or arbitrary waves such as the transmission waves, the reflection waves, the refraction wave, the scattered waves, the diffraction waves, etc., the present invention allows the high accuracy measurements or imitations of the nonlinear effects such as the multiplication or the exponentiation, etc. generated by the nonlinear effects owing to the high intensity of wave or the superposing of plural waves propagating in a same direction or in different directions (the same waves of the same physical quantities and however only with different propagation directions, waves of the same physical quantities with different parameters, waves of different type physical quantities), for instance, by positively using the analogue or digital processing device after the transducer(s) detects the signals for implementing the nonlinear processings onto, i.e., harmonic waves, chord tone waves or different tone waves with increased bandwidths can be obtained. Also, in addition to the cases where nonlinear effects are generated physically, chemically or biologically, the present invention also allows the increasing of the nonlinear effects, or when no nonlinear effects can be observed or no nonlinear effects are not generated, the present invention also allows the generating nonlinear effects. Also, plural detected signals can also be obtained simultaneously. In addition, the using the base-banded signals generated by the physical actions is also included in the present invention (The harmonic waves calculated from reception signals by using the pulse inversion method or the filtering method, etc. can be removed, or using the estimated signals obtained by the above-mentioned processings or calculations, etc.).

At past, the inventor of the present invention disclosed the lateral modulation method on the basis of the linear theorem using the crossed waves (plane waves, etc.) or crossed beams (there exists the carrier frequencies both in the depth and lateral directions) and using the present invention allows yielding the effects of exponentiation can also be obtained on the lateral modulation as well as the effects of multiplication between the crossed waves. Also, although the effects of exponentiation and multiplication can be obtained in general by increasing the wave intensities, the present invention allows yielding the nonlinear effects regardless the wave intensities.

Also, the present invention allows yielding the base-banded signals by using the new detection processing to be performed with fewer calculations instead of the general quadrature detection or the envelope detection; and the effects can be obtained for the echo imagings and the Doppler measurement. However, note that the detected signals are different from a base-band signal referred to as in general in that the direct current is included. Then, the base-banded signals can be directly used or used after removing the direct current via analogue or digital processings. In addition, the using the base-banded signals obtained by the physical actions is also included in the present invention. The signals generated by the processings to have base-band bandwidths are also referred to as the base-banded signals.

For instance, in the area of medical ultrasounds or sonars, although the so-called harmonic echo imaging is clinically used, where harmonic waves are generated by nonlinear phenomena during the ultrasound propagations in living tissues (for a higher pressure, the acoustic propagation speed is higher since the bulk modulus acts higher and then, the wave shape distorts and the effects are accumulated during the propagation), it is not disclosed to use the physically generated base-banded signals. It is also not disclosed to use base-banded signals physically generated by other nonlinear phenomena. The base-band signals, base-banded signals and incoherent signals obtained using the envelope detection and the square detection, etc. can also be included in the processing objects of the present invention.

Particularly, on the Doppler measurements, the inventor of the present invention makes it possible to measure a displacement vector, a velocity vector or an acceleration vector in an arbitrary direction, or a strain tensor or a strain rate tensor with high accuracies by using the multi-dimensional signals being different from the performing of a general Doppler measurement that allows the measurement of a displacement in the wave propagation direction. Being different from the general detections, the present invention can yield signals of the harmonic waves quadrature-detected in arbitrary one direction (base-banded signals) from the multi-dimensional signals simultaneously and then, general one-directional displacement measurement methods can be used to simply perform the measurements with fewer calculations and in short times. In this situation, it is also possible to perform the echo imagings using the harmonic waves or above-mentioned base-banded signals simultaneously obtained. In addition, the suppressing the sidelobes and then the increasing the contrast are possible. Also, as mentioned above, the temperature measurements can also be performed.

There exists the base of the present invention in that chord tone waves and different tone waves are generated by performing the multiplication between the sine waves or cosine waves with a different single frequency; implementing the exponentiation calculation on a wave yields the order-fold frequency of the wave (both the double angle and the arcminute theorem can be performed); implementing the nonlinear processings onto a signal having plural frequency components (distortion wave) yields an increased bandwidths. In addition, the effect of the suppressed sidelobes can also be obtained and then, the contrast increases. Although these effects can be often observed as the effects obtainable particularly for high intensity waves during the propagations, regardless the wave intensities, the present invention allows increasing, imitating or newly generating the nonlinear effects by implementing analogue or digital processings onto an arbitrary signals. It is also possible to virtually realize the nonlinear effects. Not limited to the cases where the spatial resolutions exist, similarly with respect to the continuous waves, the harmonic waves or the detected signals can also be generated physically or artificially. If the physically generated base-banded signals can be understood under the present invention, the applications also become useful in an engineering sense. For instance, the measurements of a displacement or a displacement vector components can be performed (General one-directional displacement measurement methods can be used). Also, the observed harmonic waves can also be used for performing the measurements of a displacement or a displacement vector (The above mentioned various multi-dimensional displacement vector measurement methods can be used), and also the over-determined systems can be generated for performing the imagings (high SNRs, high spatial resolutions, speckle reductions, etc.) and the displacement component measurements (high accuracies), etc. similarly to the cases using the nonlinear processings of the present invention. In these cases, the contrast agents can be positively used for effectively increasing the nonlinear effects.

Or, on the warming, the heating, the cooling, the freezing, the welding, the restoration, the thermal treatment of cancerous diseases (thermal therapy) or the cryotherapy or the washing such as of arbitrary objects (glasses, etc.) performed using waves (laser, ultrasound or high intensity focus ultrasound, etc.), the present invention can increase the effects and the spatial resolution via the nonlinear phenomena or the prediction about the effects (for instance, the exponentiation effects by the thermal treatment using the high intensity focus ultrasound, the increases the effects using the crossed beams, i.e., the increasing the frequencies and the spatial resolutions by the multiplication as well as the increasing the spatial resolutions by the addition, etc.). On these, continuous waves can also be used and similar effects can be obtained.

The present invention is also effective in obtaining nonlinear effects even under the physical conditions that physically the nonlinear effects cannot be obtained (For instance, the wave intensity cannot be increased with respect to the measurement object or due to a high frequency of the wave, a high intensity of the wave cannot be obtained, etc.). In contrary, for instance, for the ultrasound echo imaging, the displacement measurement or the treatment, it is possible to perform the present invention under the condition that the nonlinear effects are enhanced by using contrast agents such as microbubbles, etc. That is, the present invention can increase, imitate, newly generate the nonlinear effects. Furthermore, the present invention can also virtually realize the nonlinear effects. Also, the present invention can be used for the purposes of purely increasing the spatial resolutions, the accuracies and the efficiencies on the imagings, displacement measurements and treatments, etc.

Similarly to the harmonic imaging, the present invention allows increasing the frequencies, the bandwidths and the contrast, or suppressing the sidelobes and then, high SNR nonlinear imagings can be performed. In addition, required memories and calculations are fewer and the analogue and digital detections can be performed simultaneously.

The effectiveness of the present invention was demonstrated by performing ultrasonic simulations and agar phantom experiments on the ultrasonic echo imagings and measurement imagings. The present invention can also be used for arbitrary signals except for the ultrasonic echo method (familiar signals by lasers, light waves, OCT signals, electric signals, magnetic signals, radioactive rays such as an X-ray and thermal waves, etc.) and can also be used between different type signals. Signals including incoherent signals obtained by analogue processings (for instance, energy detection on reception signals using a sensor or using nonlinear elements, etc.) or digital processings can be processed together with the coherent signals.

Alternatively, in the area of an image measurement, it is well known that the observations of motions are performed by using incoherent signals (the results are displayed using images) generated by implementing various type detections (physical phenomena or general signal processings) on coherent signals. Also, implementing the present invention onto incoherent signals increases the bandwidths (spatial resolution). Also, used can be the above-mentioned high spatial resolution detection signals obtained using the present invention. The measurement accuracies of the motions also increase. That is, the present invention can be used both for arbitrary coherent signals and arbitrary incoherent signals.

Long time has passed since the imagings and the measurements of motions, etc. using the above-mentioned coherent or incoherent signals are to be performed in various areas including the above-mentioned examples, etc. In such situations, it is useful and effective to perform the imagings, with high or low frequencies, with broad bandwidths and high spatial resolutions, and with high contrasts as well as to measure a displacement, etc. with high accuracies using the nonlinear effects obtained by the present invention. It is also effective to perform the multi-dimensional signal processings themselves and also in an engineering sense. Also, on other applications such as the treatments as mentioned above, it is effective and useful to evaluate and use the treatment effects on the basis of the nonlinear effect imagings.

On the imaging instrument, using the harmonic wave components and base-banded signals (the above-mentioned new detection signals) generated by implementing the multiplication and the exponentiation is useful for generating the image signals and not limited to the multiplication and the exponentiation, implementing high order nonlinear processings can also yield the same effects. In view of the costs, the present invention and the existing technology can be selectively employed or used together.

The present invention is not limited to the above embodiments and much transformation is possible in technical thought of the present invention by a person having normal knowledge in the technical area concerned. With respect to the waves such as the electromagnetic waves, vibration waves (mechanical waves) such as sounds (compressible waves), shear wave, surface wave, etc., or the thermal wave, etc., for the reflection waves, the transmission waves, the scattering waves (forward or backward scatterings, etc.), the refraction waves, the diffraction waves, the surface waves, the ballistic waves, the waves generated by self-emanating wave sources, the waves transmitted from moving bodies, or the waves arrived from unknown wave sources, etc., to be observed, proper digital processing algorithms implemented on digital circuits or softwares, or analogue or digital hardwares for the displacement (vector) measurement or the temperature measurement, etc., are used.

Various measurement methods disclosed in the patent documents 5 to 7 and 11 about the displacement measurements (e.g., high accuracy and high specific measurement of an object's displacement, or particle or medium displacement, etc. in addition to the propagation direction of the sensing wave, or a wave propagation, etc.) or in others are often disclosed by using illustrations with a reflection method or an echo method mainly and however, the above-mentioned various waves including the transmission waves, etc., can also be used, and not limited to these. In addition, to increase the processing speed, the analogue processing can also be performed instead the digital processing.

INDUSTRIAL APPLICABILITY

The present invention can be utilized on beamforming methods that use arbitrary waves arrival from a measurement object for performing the beamformings and on measurement and imaging instruments and communication instrument using such beamforming methods.

These days, the signal generations of a radar or a sonar, other optical type waves or an acoustic wave, a thermal wave, etc. are usually performed using digital instruments and also for the purposes of the signal applications, the digital instruments are also required to be equipped with a capability of performing the high order processings or calculations at least. The increasing the dimensionality of various instruments will increase the importance of the present invention. The measurement objects are various such as solids, fluids, rheology matters, inorganic and organic substances, living things, environments, etc., the measurement range is immeasurable and will be prominently widespread. Henceforth, the down sizings will be carried out on the respective devices in the instruments; and calculators with sufficiently high capabilities, however cheap, will be able to be built up together; and then it can be expected to that many useful, real-time instruments will be realized. Furthermore, not only wave imaging instruments but the applications through the measurements using waves will also be developed enthusiastically and the application range will also be prominently widespread. The more various type instruments will become digital henceforth, in the situations, the demands for performing on the basis of the present invention, the high-speed, real-time beamformings with high accuracies will increase. Especially, in addition to that the processings are high speed, it is not required to perform approximate interpolations at all, which was required at past. However, when the higher speediness is more considered, also on the present invention, the approximate interpolations will be able to be performed, although the accuracies decrease. The instruments are also effective for a general communication and a sensor network. The availability and marketability of the digital beamformings according to the present invention on the basis of the digital signal processings are sufficiently high. In addition, to increase the processing speed, the analogue processing can also be performed instead the digital processing.

The invention claimed is:

1. An imaging instrument comprising:
   at least one transducer configured to receive at least one wave arriving from an observation object to generate a reception signal;
   a nonlinear processor configured to
   generate a band-widened and sidelobe-reduced reception signal due to a nonlinear effect based on at least one of (i) processing on a propagation path of said at least one wave, (ii) analogue signal processing on said reception signal generated by said at least one transducer, and (iii) digital signal processing on a digital reception signal obtained by sampling said reception signal generated by said at least one transducer; and
   an image signal generator configured to generate an image signal representing said observation object based on said band-widened and sidelobe-reduced reception signal generated by said nonlinear processor,
   wherein said band-widened and sidelobe-reduced reception signal includes at least one of a frequency-increased component and a frequency-decreased component in comparison with said reception signal as a result of generation of at least one harmonic tone wave by an effect of exponentiation of a same frequency component or generation of chord and different tone waves by an effect of multiplication of plural different frequency components in at least one direction different from a propagation direction of said at least one wave in a multi-dimensional space when said at least one wave has plural different frequency components in said at least one direction through obtaining the effect of the exponentiation or the multiplication due to the nonlinear effect for said at least one wave or implementing a calculation of the exponentiation or the multiplication onto said reception signal or said digital reception signal.

2. The imaging instrument according to claim 1, wherein in a case where plural waves arrive from said observation object simultaneously or within a time when said observation object is in a substantially same phase, said plural waves are different from one another in at least one of a propagation direction, a steering angle, a frequency, a carrier frequency, a pulse shape, a beam profile, and a bandwidth in one direction, and at least one wave of said plural waves includes a same frequency component or plural different frequency components in at least one direction different from a propagation direction of said at least one wave in the multi-dimensional space and arrives without being superposed onto the other wave or is shield from the other wave so as not to be superposed onto the other wave or is separated from the other wave by being blocked with an analogue or digital device or analogue or digital signal processing, said nonlinear processor generates the band-widened and sidelobe-reduced reception signal due to a nonlinear effect based on at least one of (i) processing on a propagation path of said at least one wave of said plural waves, (ii) analogue signal processing on said reception signal generated from said at least one wave of said plural waves, and (iii) digital signal processing on a digital reception signal obtained by sampling said reception signal generated from said at least one wave of said plural waves.

3. The imaging instrument according to claim 1, wherein said nonlinear processor generates at least one of a frequency-decreased signal and a band-narrowed signal through obtaining the effect of the exponentiation with an order less than 1 due to the nonlinear effect for said at least one wave or implementing the calculation of the exponentiation with an order less than 1 onto said reception signal or said digital reception signal.

4. The imaging instrument according to claim 1, wherein said nonlinear processor increases or decreases a dynamic range or a spatial change of said at least one wave, said reception signal, or said digital reception signal.

5. The imaging instrument according to claim 1, wherein said nonlinear processor generates the band-widened and sidelobe-reduced reception signal representing at least one of a high frequency wave and a low frequency wave that cannot be generated physically, or in a case where a nonlinear component cannot be generated or observed, said nonlinear processor increases a nonlinear component or generates a nonlinear component artificially or virtually.

6. The imaging instrument according to claim 1, wherein said nonlinear processor obtains an effect of a complex production or a conjugate production due to the nonlinear effect for said at least one wave or the corresponding spectra or implements a calculation of a complex production or a conjugate production onto said reception signal, said digital reception signal or the corresponding spectra.

7. The imaging instrument according to claim 1, wherein said nonlinear processor changes a sampling interval or performs predetermined signal processing in a case where a frequency or a bandwidth of a signal changes through obtaining the effect of the exponentiation or the multiplication due to the nonlinear effect for said at least one wave or implementing the calculation of the exponentiation or the multiplication onto said reception signal or said digital reception signal.

8. The imaging instrument according to claim 1, wherein in a case where plural waves arrive from said observation object, said nonlinear processor causes said plural waves or corresponding analogue signals to pass through an analogue delay device or an analogue storage device, or implements digital delays onto corresponding digital signals or causes corresponding digital signals to pass through a digital delay device before or after obtaining the effect of the exponentiation or the multiplication due to the nonlinear effect for said at least one wave or implementing the calculation of the exponentiation or the multiplication onto said reception signal or said digital reception signal such that said plural waves are superposed with one another at each position in said observation object.

9. The imaging instrument according to claim 1, wherein in a case where plural waves arrive from said observation object, said plural waves include at least one of an electromagnetic wave, a mechanical wave, a sound wave, a thermal wave, a longitudinal wave, a transverse wave, a transmission wave, a reflection wave, a scattering wave, a refraction wave, a diffraction wave, a surface wave, and a guided wave.

10. The imaging instrument according to claim 1, wherein:
    said nonlinear processor separates said reception signal into plural signals, implements filtering onto said reception signal, or divides spectrum of said reception signal by using an analogue or digital device or performing analogue or digital signal processing at a predetermined stage; and said image signal generator generates the image signal representing said observation object based on at least one signal generated by said nonlinear processor.

11. The imaging instrument according to claim 1, wherein in a case where plural same waves arrive from said observation object with a same phase, said nonlinear processor reduces a noise by implementing additional averaging onto said reception signal, said digital reception signal, or said band-widened and sidelobe-reduced reception signal.

12. The imaging instrument according to claim 1, wherein said band-widened and sidelobe-reduced reception signal includes at least one of a frequency-increased signal, a spatial-resolution-increased signal, a contrast-increased harmonic tone signal, a quadrature detection signal generated in at least one direction and corresponding to said contrast-increased harmonic tone signal, said quadrature detection signal including a direct current component.

13. The imaging instrument according to claim 1, wherein at least one of a nonlinear device, a material, and a contrast agent is used at an observation position or in a medium so as to increase the nonlinear effect.

14. The imaging instrument according to claim 1, wherein said at least one transducer generates a harmonic wave when receiving said at least one wave.

15. The imaging instrument according to claim 1, further comprising:

at least one of an amplifier and an attenuator configured to control an intensity of said at least one wave before receiving said at least one wave or an intensity of a signal at a predetermined stage after receiving said at least one wave, and compensate an attenuation enhanced nonlinearly with increasing a propagation distance.

16. The imaging instrument according to claim 1, further comprising:

a transmitter configured to generate a driving signal,
wherein said at least one transducer not only receives said at least one wave but also transmits a transmission wave according to the driving signal generated by said transmitter, or said imaging instrument further comprises at least one other transducer configured to only transmit a transmission wave according to the driving signal generated by said transmitter.

17. The imaging instrument according to claim 16, wherein when said at least one transducer or said at least one other transducer transmits the transmission wave according to the driving signal generated by said transmitter, said transmission wave is generated in accordance with a nonlinearity of said at least one transducer, said at least one other transducer, or a driving circuit of said transmitter.

18. The imaging instrument according to claim 16, further comprising:

a mechanism configured to perform a transmission beamforming, or control or adjust said transmission wave in a linear or nonlinear fashion with respect to an intensity, focusing, multi-focusing, a propagation direction, a steering angle, a waveform in a propagation direction or a different direction therefrom, a beam profile, a frequency, a bandwidth, a ratio of magnitudes of a mainlobe and a sidelobe, a signal component, or a crossing angle when plural transmission beams are generated in different directions at a same time or not.

19. The imaging instrument according to claim 16, wherein said transmitter transmits plural transmission waves toward said observation object with a same phase by using driving pulse-type signals with inverted phases, and said nonlinear processor performs a pulse-inversion method or performs filtering with a polynomial fitting, a MIMO (multiple-input and multiple-output), a SIMO (single-input and multiple-output), a MUSIC (multiple signal classification), an independent component analysis, or a principal component analysis or uses an analogue or digital device to separate said reception signal into fundamental and harmonic waves or nonlinear components generated in said observation object and said at least one transducer or said at least one other transducer.

20. The imaging instrument according to claim 1, wherein when implementing signal processing onto said reception signal or said digital reception signal, said nonlinear processor uses a virtual transmission or reception transducer.

21. The imaging instrument according to claim 1, wherein said nonlinear processor includes a reception beamformer configured to implement reception beamforming onto at least one set of reception signals generated by plural transducers, and a calculation of an addition, the exponentiation, or the multiplication is implemented before, during, or after said reception beamforming.

22. The imaging instrument according to claim 21, wherein said reception beamformer performs plural reception steerings in different directions, or generates plural signals by filtering or dividing a spectrum of a beamformed signal with respect to said at least one set of reception signals.

23. The imaging instrument according to claim 1, further comprising:

a mechanism configured to perform a reception beamforming, or control or adjust said at least one wave in a linear or nonlinear fashion with respect to an intensity, focusing, multi-focusing, a propagation direction, a steering angle, a waveform in a propagation direction or a different direction therefrom, a beam profile, a frequency, a bandwidth, a ratio of magnitudes of a mainlobe and a sidelobe, a signal component, or a crossing angle when plural reception beams are generated in different directions.

24. The imaging instrument according to claim 1, wherein said nonlinear processor includes a reception beamformer configured to implement a reception beamforming onto one set of reception signals generated by plural transducers, and spatial-resolution-increased signals are used to estimate a wave source position or an arrival wave direction of said at least one wave, or separate wave sources, or arrival waves.

25. The imaging instrument according to claim 24, wherein said reception beamformer is further used for reperforming a reception beamforming including at least a focusing or a steering based on estimation of said wave source position or said arrival wave direction of said at least one wave, or with respect to at least one of said separate wave sources, or at least one of said arrival waves or when said reception beamformer also has a function for transmission beamforming or a transmission beamformer is used, a transmission beamforming includes at least a focusing or a steering based on the estimation of said wave source position or said arrival wave direction of said at least one wave, or with respect to at least one of said separate wave sources, or at least one of said arrival waves.

26. The imaging instrument according to claim 1, wherein in a case where plural waves are received, said nonlinear processor performs a coherent compounding of at least two band-widened and sidelobe-reduced reception signals, at least one band-widened and sidelobe-reduced reception signal and at least one original reception signal, or original reception signals to generate a more wide-banded and high-spatial-resolutioned signal.

27. The imaging instrument according to claim 1, wherein said nonlinear processor generates plural band-widened and sidelobe-reduced reception signals, and said nonlinear processor implements an arbitrary detection onto at least one of the plural band-widened and sidelobe-reduced reception signals and a coherent compounding of the plural band-widened and sidelobe-reduced reception signals, or compounds arbitrary-detected plural band-widened and sidelobe-reduced reception signals or an arbitrary-detected original signal together, or implements a predetermined nonlinear calculation onto an arbitrary-detected signal.

28. The imaging instrument according to claim 1, further comprising:
a measurement unit configured to perform a measurement of displacement generated within said observation object, wherein at least one band-widened and sidelobe-reduced reception signal is used or an original reception signal is also used.

29. The imaging instrument according to claim 1, further comprising:
a measurement unit configured to observe a thermal wave by using, as said transducer, at least one of an infrared ray sensor, a pyroelectric sensor, an ultrasound sensor, and a sensor for measuring a chemical shift of a nuclear magnetic resonance frequency.

30. The imaging instrument according to claim 1, wherein said nonlinear processor uses said band-widened and sidelobe-reduced reception signal for performing an imitation or an inverse analysis about a nonlinear phenomenon or a generation process of a nonlinear wave, or an action process of the nonlinear phenomenon of a wave onto an observation target.

* * * * *